US011345702B1

(12) United States Patent
Rai et al.

(10) Patent No.: US 11,345,702 B1
(45) Date of Patent: May 31, 2022

(54) PGDH INHIBITORS AND METHODS OF MAKING AND USING

(71) Applicant: Myoforte Therapeutics, Inc., Menlo Park, CA (US)

(72) Inventors: Roopa Rai, San Carlos, CA (US); Robert Booth, Los Altos Hills, CA (US); Michael J. Green, Half Moon Bay, CA (US)

(73) Assignee: MYOFORTE THERAPEUTICS, INC., Menlo Park, CA (US)

( * ) Notice: Subject to any disclaimer, the term of this patent is extended or adjusted under 35 U.S.C. 154(b) by 0 days.

(21) Appl. No.: 17/484,398

(22) Filed: Sep. 24, 2021

Related U.S. Application Data

(63) Continuation of application No. PCT/US2021/014783, filed on Jan. 22, 2021.

(60) Provisional application No. 62/965,062, filed on Jan. 23, 2020, provisional application No. 63/007,755, filed on Apr. 9, 2020, provisional application No. 63/029,184, filed on May 22, 2020, provisional application No. 63/092,116, filed on Oct. 15, 2020, provisional application No. 63/110,803, filed on Nov. 6, 2020, provisional application No. 63/133,965, filed on Jan. 5, 2021.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ............................. C07D 471/04; C07D 519/00
USPC ..................................................... 514/210.16
See application file for complete search history.

(56) References Cited

U.S. PATENT DOCUMENTS 8,426,401 B2 * 4/2013 Bian ........................ A61P 13/10
514/210.18
2009/0264414 A1 10/2009 Andersen et al.

FOREIGN PATENT DOCUMENTS

| WO | WO-2015065716 A1 | 5/2015 |
| WO | WO-2016144958 A1 | 9/2016 |
| WO | WO-2018102552 A1 | 6/2018 |
| WO | WO-2018145080 A1 | 8/2018 |
| WO | WO-2018187810 A1 | 10/2018 |
| WO | WO-2019010482 A1 | 1/2019 |
| WO | WO-2021151014 A1 | 7/2021 |

OTHER PUBLICATIONS

Ahmad et al.: The PGE2 EP2 receptor and its selective activation are beneficial against ischemic stroke. Exp Transl Stroke Med 2(1):12, pp. 1-8 doi:10.1186/2040-7378-2-12 (2010).

Barnthaler et al.: Inhibiting eicosanoid degradation exerts antifibrotic effects in a pulmonary fibrosis mouse model and human tissue. J Allergy Clin Immunol. 145(3):818-833.e11 doi:10.1016/j.jaci.2019.11.032 (2020).

Chemtob et al.: Deficiency in prostaglandin E2 (PGE2) receptors, mainly EP2 subtype, on brain synaptosomes in early development: implications on cerebral metabolism. Semin Perinatol. 18(1):23-29 (1994).

Collier et al.: Inhibition of 15-PGDH Increases Early Callus Size and Mineralization in a Murine Model of Fracture Repair. ORS 2017 Annual Meeting Paper No. 0190 (2017).

Colombe et al.: Prostaglandin metabolism in human hair follicle. Exp Dermatol. 16(9):762-769 doi: 10.1111/j.1600-0625.2007.00586.x (2007).

Echeverria et al.: Stimulation of PGE receptors EP2 and EP4 protects cultured neurons against oxidative stress and cell death following beta-amyloid exposure, ur J Neurosci. 22(9):2199-2206 doi:10.1111/j.1460-9568.2005.04427.x (2005).

Hao et al.: Physiological regulation of prostaglandins in the kidney. Annu Rev Physiol. 70:357-377 doi:10.1146/annurev.physiol.70.113006.100614 (2008).

Kawaguchi et al.: The role of prostaglandins in the regulation of bone metabolism. Clin Orthop Relat Res. (313):36-46 (1995).

Keller et al.: Short-term effect of local application of PGE2 on callus in rabbit osteotomy. Eur J Exp Musculoskeletal Res 1:86-92 (1992).

Konturek et al.: Prostaglandins and ulcer healing. J Physiol Pharmacol. 56 Suppl 5:5-31 (2005).

McCullough, et al., Neuroprotective Function of the PGE2 EP2 Receptor in Cerebral Ischemia, The Journal of Neuroscience, 2004, 24(1): 257-268.

Michelet et al.: Expression of NAD+ dependent 15-hydroxyprostaglandin dehydrogenase and protection of prostaglandins in human hair follicle. Exp Dermatol. 17(10):821-828 doi:10.1111/j.1600-0625.2008.00706.x (2008).

PCT/US2021/014783 International Search Report and Written Opinion dated Jun. 2, 2021.

Porter: Contrast-associated nephropathy. Am J Cardiol. 64(9):22E-26E doi:10.1016/0002-9149(89)90730-3 (1989).

PUBCHEM-SID: 104018957: 1-(4-Phenoxymethyl-benzyl)-piperidine; compound with oxalic acid. Deposit Date: Jan. 19, 2011, pp. 1-6 (2011).

PUBCHEM-SID: 17386203: 2-bromophenyl 4-(1-piperidinylcarbonyl)benzyl ether. Deposit Date: Nov. 13, 2006, pp. 1-8 (2006).

PUBCHEM-SID: 318704914: 1,4,4-Trimethyl-1,2,3,4-tetrahydroquinoline-6-yl(1-piperidinyl)methanone. Deposit Date: Nov. 21, 2016, pp. 1-6 (2016).

PUBCHEM-SID: 4249877: 1-(3-methylphenyl)-5-(piperidin-1-ylcarbonyl)-1H-benzimidazole. Deposit Date: Aug. 16, 2005, pp. 1-8 (2005).

Smith et al.: Therapeutic Targeting of 15-PGDH in Murine Idiopathic Pulmonary Fibrosis. bioRxiv 2019.12.16.878215, pp. 1-28 doi:https://doi.org/10.1101/2019.12.16.878215 (2019).

(Continued)

*Primary Examiner* — Niloofar Rahmani
(74) *Attorney, Agent, or Firm* — Wilson Sonsini Goodrich & Rosati

(57) ABSTRACT

Disclosed herein are compounds that can inhibit 15-hydroxyprostaglandin dehydrogenase. Such compounds may be administered to subjects that may benefit from modulation of prostaglandin levels.

20 Claims, 1 Drawing Sheet

(56) References Cited

OTHER PUBLICATIONS

Wallace: Prostaglandins, NSAIDs, and gastric mucosal protection: why doesn't the stomach digest itself? Physiol Rev. 88(4):1547-1565 doi:10.1152/physrev.00004.2008 (2008).

Yang et al.: Altered hippocampal long-term synaptic plasticity in mice deficient in the PGE2 EP2 receptor. J Neurochem. 108(1):295-304 doi:10.1111/j.1471-4159.2008.05766.x (2009).

Zhang, et al. Inhibition of the prostaglandin-degrading enzyme 15-PGDH potentiates tissue regeneration. Science 348.6240 (2015).

* cited by examiner

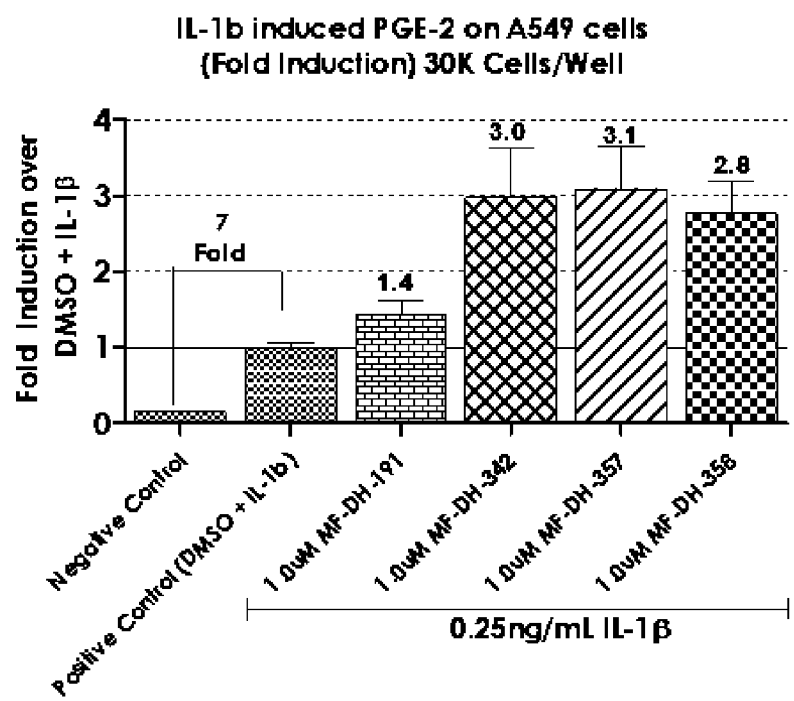
- Negative Control (No compounds, No IL-1beta): Basal level of PGE2 in untreated cells
- Positive Control (DMSO+IL-1 beta, No Compounds): Level of PGE2 in cells after IL-1 beta stimulation

PGDH INHIBITORS AND METHODS OF MAKING AND USING

This application is a continuation of PCT International Application No. PCT/US2021/014783 filed on Jan. 22, 2021, which claims the benefit of U.S. Provisional Application No. 62/965,062, filed Jan. 23, 2020; U.S. Provisional Application No. 63/007,755, filed Apr. 9, 2020; U.S. Provisional Application No. 63/029,184, filed May 22, 2020; U.S. Provisional Application No. 63/092,116, filed Oct. 15, 2020; U.S. Provisional Application No. 63/110,803, filed Nov. 6, 2020; and U.S. Provisional Application No. 63/133,965, filed Jan. 5, 2021, each of which is incorporated herein by reference.

BACKGROUND OF THE INVENTION

Prostaglandins are a group of physiologically active lipid compounds with diverse biological effects including vasodilation, inhibition of platelet aggregation, bronchodilation, bronchoconstriction, immune responses, contraction and relaxation of gastrointestinal smooth muscles, gastric acid secretion, gastric mucus secretion, uterus contraction, lipolysis inhibition, neurotransmission, clotting, hyperalgesia, and pyrexia.

Treatment of diseases or disorders may require activation of prostaglandins, or inhibition of inactivation of prostaglandins. Hydroxyprostaglandin dehydrogenases, such as 15-hydroxyprostaglandin dehydrogenase (15-PGDH) are involved in the inactivation of prostaglandins. As such, diseases/disorders associated with prostaglandins can be prevented, treated and/or managed using inhibitors of hydroxyprostaglandin dehydrogenase such as inhibitors of 15-PGDH.

SUMMARY OF THE INVENTION

In one aspect, provided herein is a method of inhibiting 15-hydroxyprostaglandin dehydrogenase (15-PGDH) in a subject in need thereof, comprising administering to the subject a therapeutically effective amount of a compound of Formula I:

Formula I

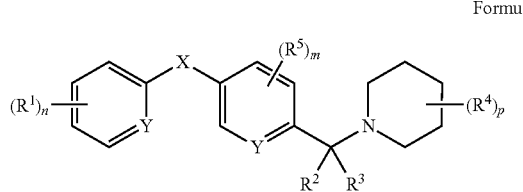

or a pharmaceutically acceptable salt thereof, wherein:
X is selected from —$OCH_2$—, —C(O)NH—, —NHC(O)—, —C(O)NMe-, —NMeC(O)—, —$SCH_2$—, —S(O)$CH_2$—, —$SO_2CH_2$—;
each Y is independently selected from N and $CR^{11}$;
each $R^1$ is independently selected from halo, —$NR^6R^7$, —$OR^8$, —$C(O)R^8$, —$C(O)OR^8$, —$C(O)NR^6R^8$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
$R^2$ is H and $R^3$ is —$CF_3$; or
$R^2$ and $R^3$ are taken together to form oxo or thio;

each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
each $R^5$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
$R^6$ and $R^7$ are independently selected at each occurrence from H, $C_{1-6}$ alkyl, $C_{1-6}$ heteroalkyl, $C_{1-6}$haloalkyl, and $C_{3-10}$cycloalkyl;
each $R^8$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^{10}$ is independently selected from H, $C_{1-6}$alkyl, $C_{1-6}$haloalkyl, and $C_{3-10}$cycloalkyl;
each $R^{11}$ is independently selected from halo, —$NR^9R^{10}$, —$OR^1$, —$C(O)R^1$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
n is 0, 1, 2, 3, 4, or 5;
m is 0, 1, 2, 3, or 4; and
p is 0, 1, 2, 3, 4, 5, 6, 7, 8, 9, or 10;
provided that the compound of Formula I is not

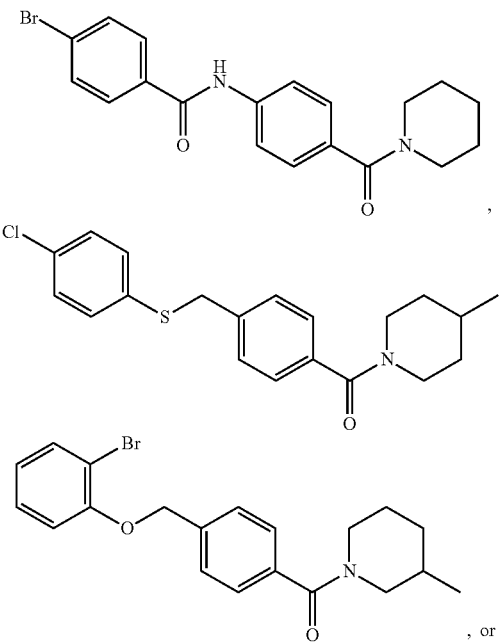

, or

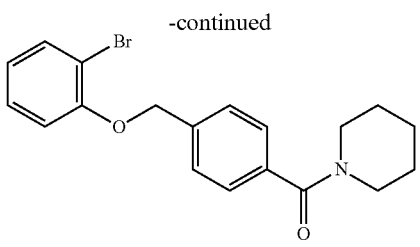

In some embodiments, the compound is a compound of Formula Ia:

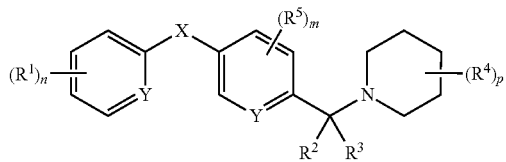

Formula Ia or a pharmaceutically acceptable salt thereof.

In some embodiments, the compound is a compound of Formula Ib:

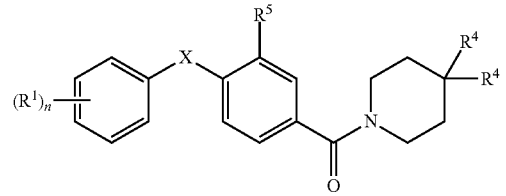

Formula Ib or a pharmaceutically acceptable salt thereof.

In another aspect, provided herein is a method of inhibiting 15-hydroxyprostaglandin dehydrogenase (15-PGDH) in a subject in need thereof, comprising administering to the subject a therapeutically effective amount of a compound of Formula II:

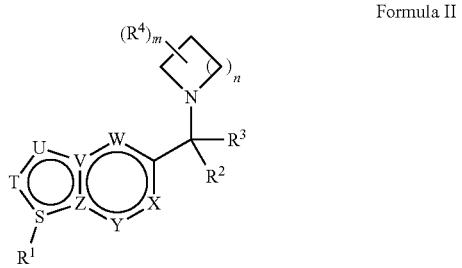

Formula II or a pharmaceutically acceptable salt thereof, wherein:
T, U, W, X, and Y are independently selected from N and $CR^5$;
S, V, and Z are independently selected from N and C;
$R^1$ is selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; wherein the alkyl, cycloalkyl, aryl, or heteroaryl is optionally substituted with 1 to 3 substituents independently selected from halo, $-NR^6R^7$, $-OR^8$, $-C(O)R^8$, $-C(O)OR^8$, $-C(O)NR^6R^7$, $-SOR^9$, $-SO_2R^9$, $-SO_2NR^6R^7$, $-NR^{10}C(O)R^8$, $-NR^{10}C(O)NR^6R^7$, $-NR^{10}SO_2R^8$, $-NR^{10}SO_2NR^6R^7$, $C_{1-6}$alkyl, $C_{1-6}$heteroalkyl, $C_{1-6}$haloalkyl, $C_{3-10}$cycloalkyl, and 5- to 10-membered heteroaryl;

$R^2$ is H and $R^3$ is $-CF_3$; or
$R^2$ and $R^3$ are taken together to form oxo or thio;
each $R^4$ is independently selected from halo, $-NR^6R^7$, $-OR^8$, $-C(O)R^8$, $-C(O)OR^8$, $-C(O)NR^6R^7$, $-SOR^9$, $-SO_2R^9$, $-SO_2NR^6R^7$, $-NR^{10}C(O)R^8$, $-NR^{10}C(O)NR^6R^7$, $-NR^{10}SO_2R^8$, $-NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or two $R^4$'s are taken together with the carbon atoms to which they are attached and any intervening atoms to form a $C_{3-10}$cycloalkyl, and any remaining $R^4$'s are independently selected from halo, $-NR^6R^7$, $-OR^8$, $-C(O)R^8$, $-C(O)OR^8$, $-C(O)NR^6R^7$, $-SOR^9$, $-SO_2R^9$, $-SO_2NR^6R^7$, $-NR^{10}C(O)R^8$, $-NR^{10}C(O)NR^6R^7$, $-NR^{10}SO_2R^8$, $-NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;

each $R^5$ is independently selected from H, halo, $-NR^6R^7$, $-OR^8$, $-C(O)R^8$, $-C(O)OR^8$, $-C(O)NR^6R^7$, $-SOR^9$, $-SO_2R^9$, $-SO_2NR^6R^7$, $-NR^{10}C(O)R^8$, $-NR^{10}C(O)NR^6R^7$, $-NR^{10}SO_2R^8$, $-NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;

$R^6$ and $R^7$ are independently selected at each occurrence from H, $C_{1-6}$ alkyl, $C_{1-6}$ heteroalkyl, $C_{1-6}$haloalkyl, and $C_{3-10}$cycloalkyl;

each $R^8$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^{10}$ is independently selected from H, $C_{1-6}$alkyl, $C_{1-6}$haloalkyl, and $C_{3-10}$cycloalkyl; and n is 1, 2, 3, or 4; and
m is 0, 1, 2, 3, 4, 5, 6, 7, 8, 9, or 10;
provided that the compound of Formula II is not

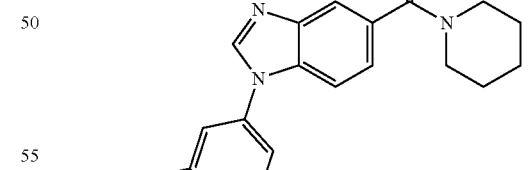

,

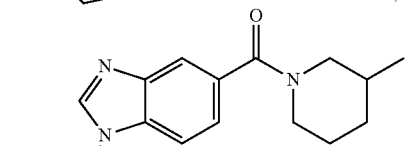

,

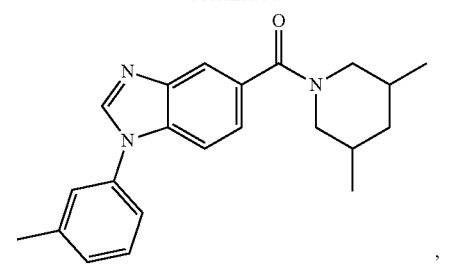
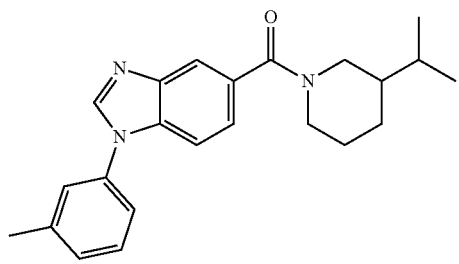
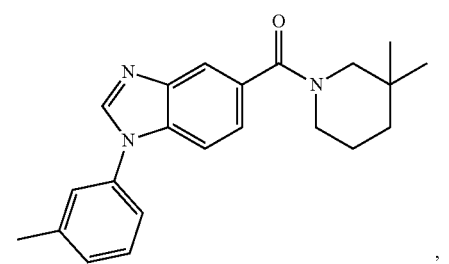
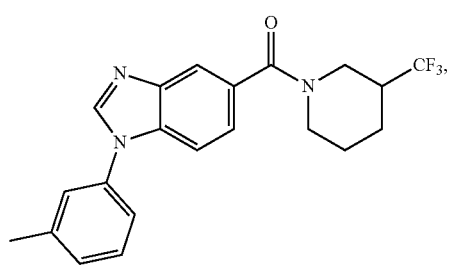
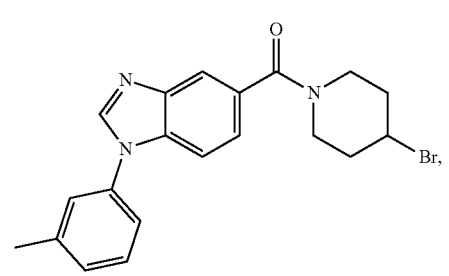
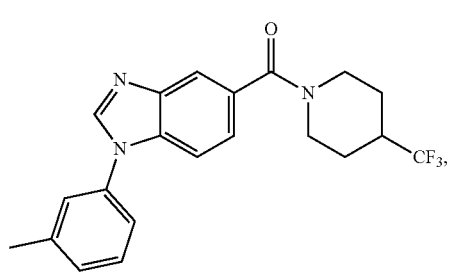
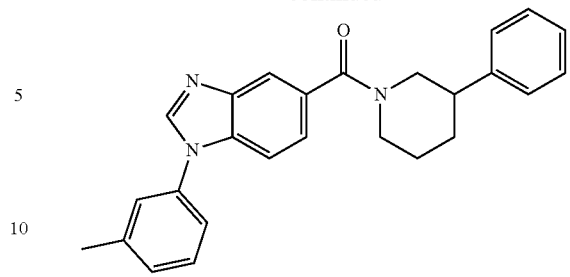
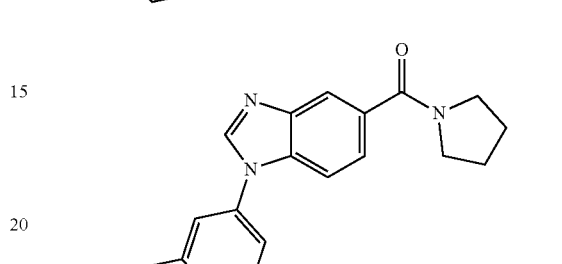
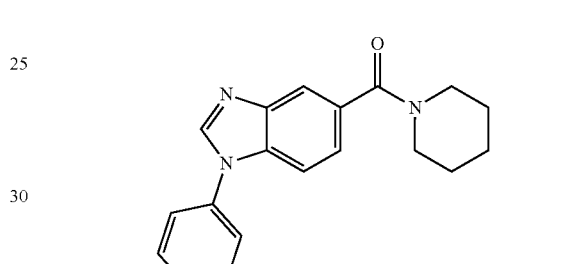
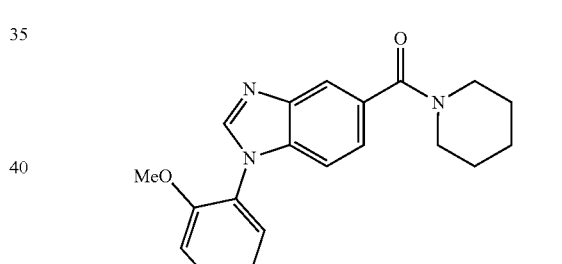
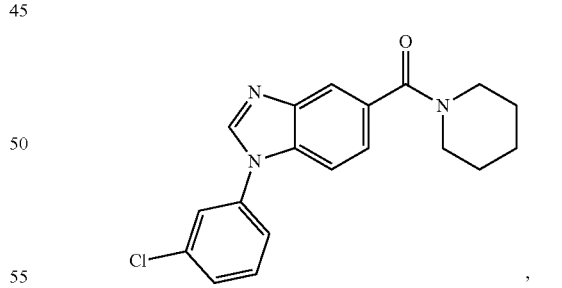
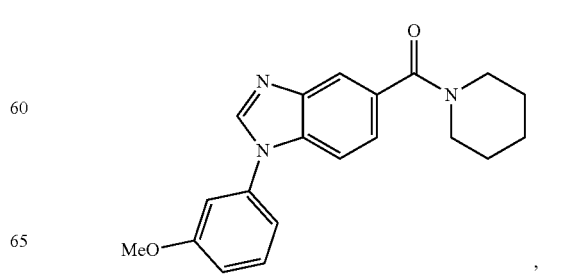

-continued
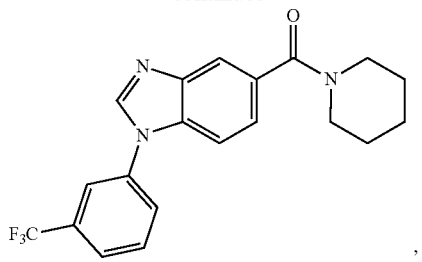
,
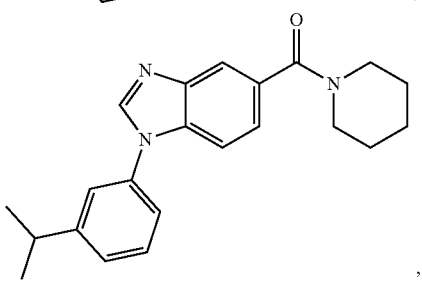
,
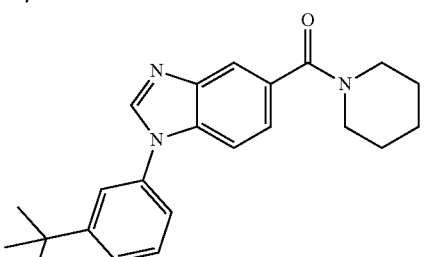
,
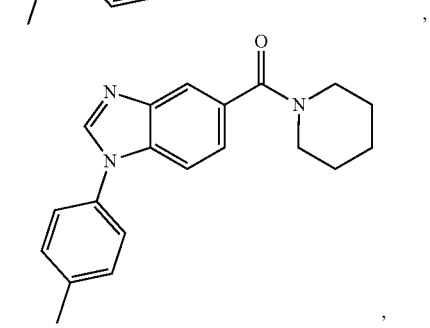
,
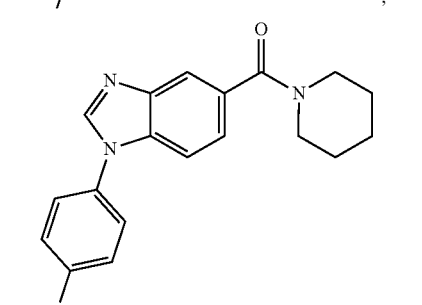
,
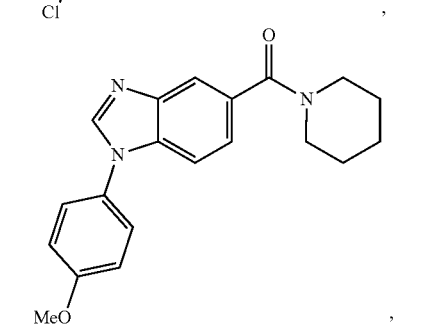
,
-continued
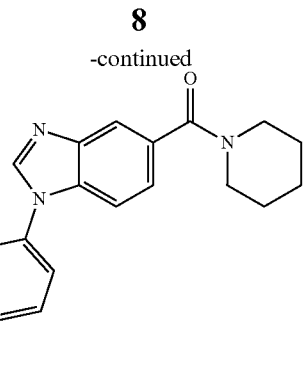
,
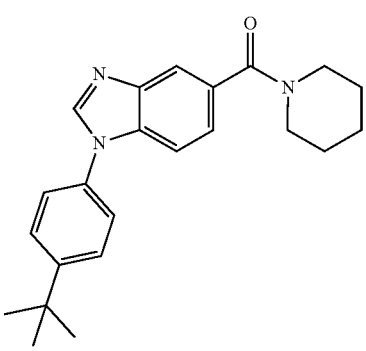
,
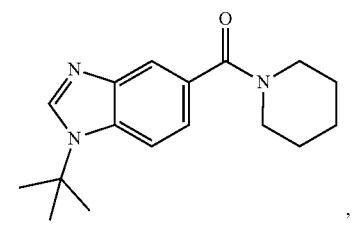
,
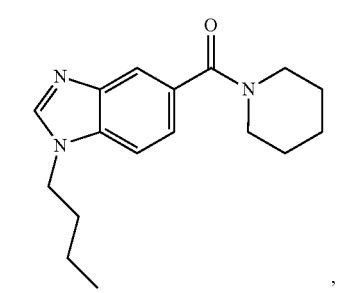
,
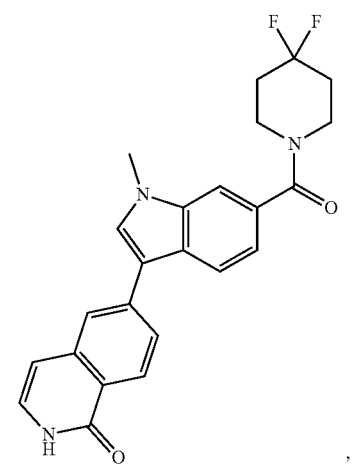
,

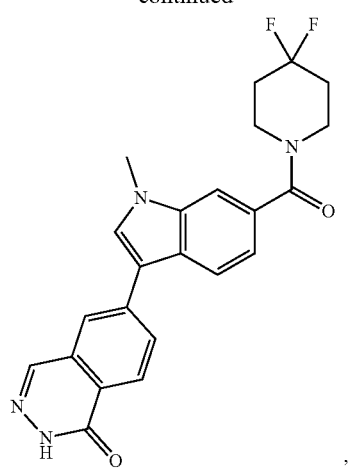
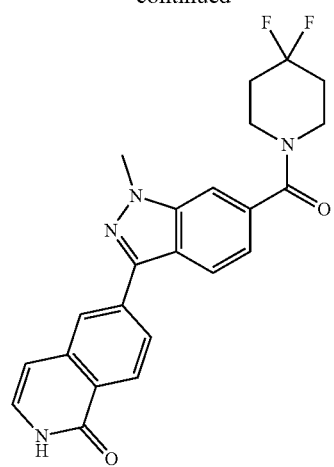
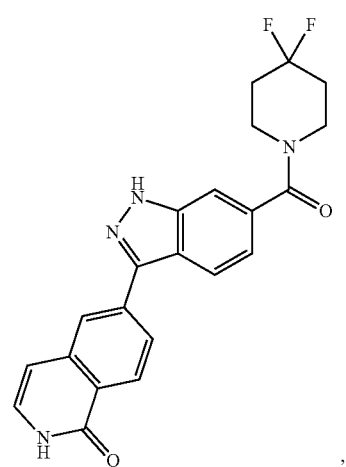 [SMILES: Cn1nc2cc(C(=O)N3CCC(F)(F)CC3)ccc2c1-c1ccc2c(=O)[nH]ccc2c1]
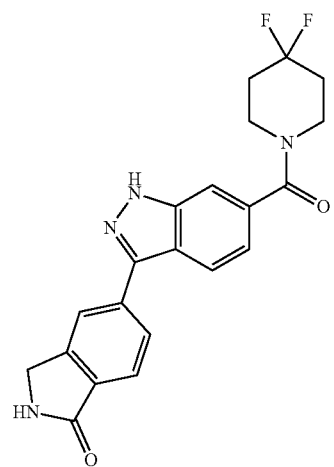
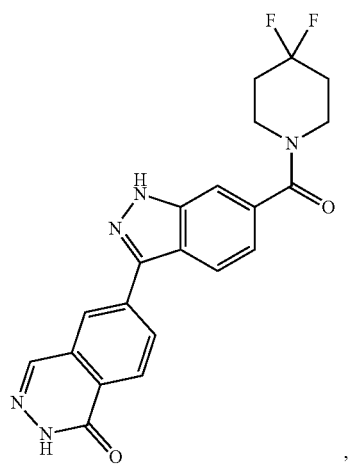
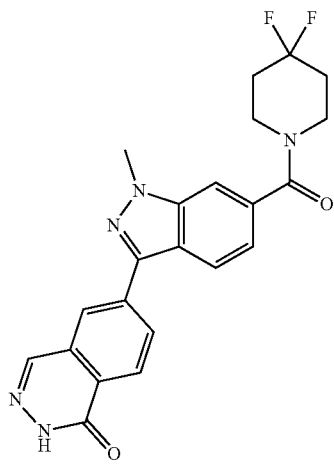

-continued

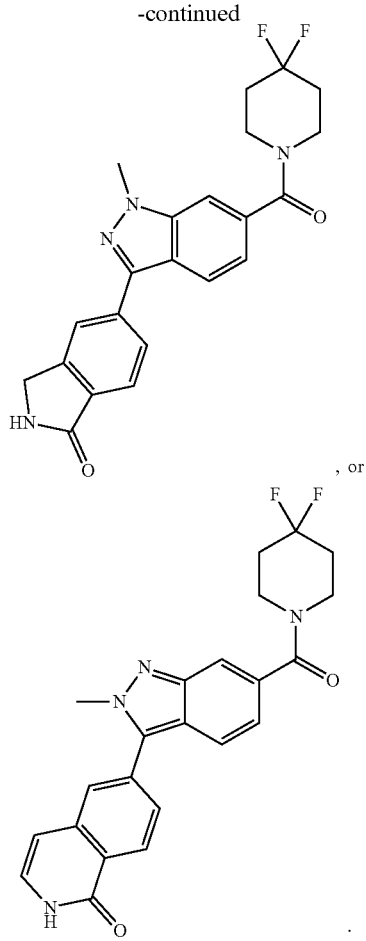

, or

In some embodiments, the compound is a compound of Formula IIa:

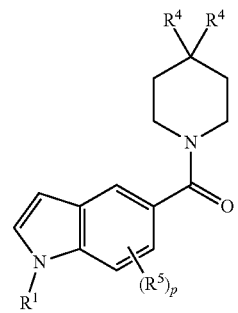

Formula IIa or a pharmaceutically acceptable salt thereof, wherein p is 0, 1, or 2.

In some embodiments, the compound is a compound of Formula IIb:

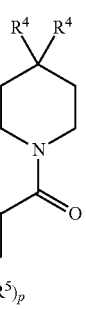

Formula IIb or a pharmaceutically acceptable salt thereof, wherein p is 0, 1, or 2.

In some embodiments, the compound is a compound of Formula IIc:

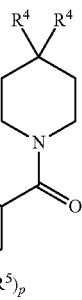

Formula IIc or a pharmaceutically acceptable salt thereof, wherein p is 0, 1, 2, 3, 4, or 5.

In some embodiments, the compound is a compound of Formula IId:

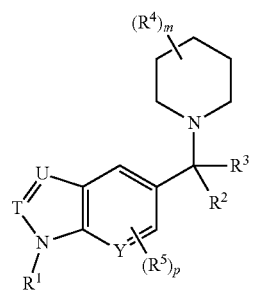

Formula IId or a pharmaceutically acceptable salt thereof, wherein p is 0, 1, 2, 3, or 4.

In some embodiments, the compound is a compound of Formula IIe:

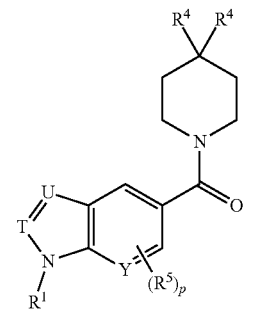

Formula IIe or a pharmaceutically acceptable salt thereof, wherein p is 0, 1, 2, 3, or 4.

In some embodiments, the compound is a compound of Formula IIf:

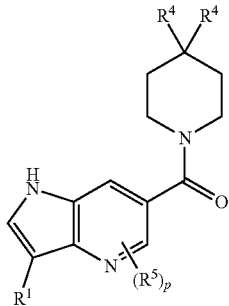

Formula IIf or a pharmaceutically acceptable salt thereof, wherein p is 0, 1, 2, or 3.

In some embodiments, the compound is a compound of Formula IIg:

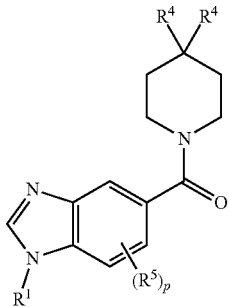

Formula IIg or a pharmaceutically acceptable salt thereof, wherein p is 0, 1, 2, 3, or 4.

In some embodiments, the compound is a compound of Formula IIh:

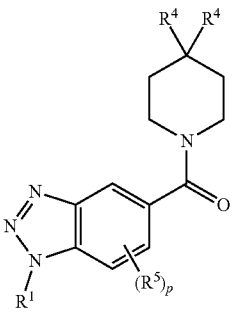

Formula IIh or a pharmaceutically acceptable salt thereof, wherein p is 0, 1, 2, or 3.

In some embodiments, the compound is a compound of Formula IIi:

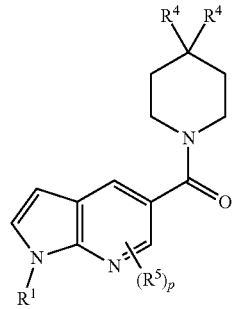

Formula IIi or a pharmaceutically acceptable salt thereof, wherein p is 0, 1, 2, 3, or 4.

In some embodiments, the compound is a compound of Formula IIj:

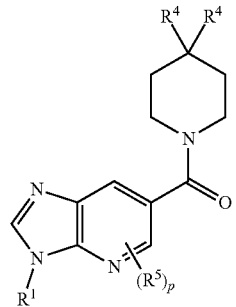

Formula IIj or a pharmaceutically acceptable salt thereof, wherein p is 0, 1, 2, or 3.

In some embodiments, the compound is a compound of Formula IIn:

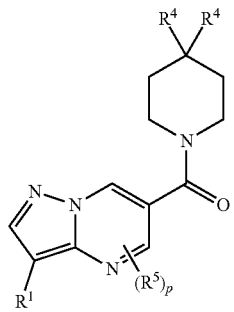

Formula IIn or a pharmaceutically acceptable salt thereof, wherein p is 0, 1, 2, or 3.

In some embodiments, the compound is a compound of Formula IIp:

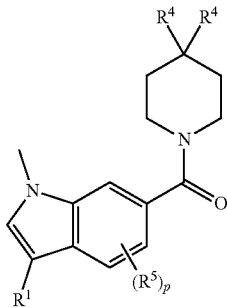

Formula IIp or a pharmaceutically acceptable salt thereof, wherein p is 0, 1, 2, 3, or 4.

In another aspect, provided herein is a method of inhibiting 15-hydroxyprostaglandin dehydrogenase (15-PGDH) in a subject in need thereof, comprising administering to the subject a therapeutically effective amount of a compound of Formula III:

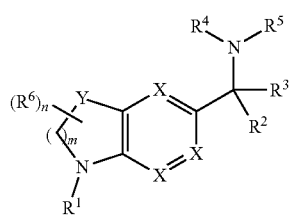

Formula III or a pharmaceutically acceptable salt thereof, wherein:
each X is independently selected from N and $CR^7$;
Y is selected from O, S, $SO_2$, and $C(R^8)_2$;
$R^1$ is selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; wherein the alkyl, cycloalkyl, aryl, or heteroaryl is optionally substituted with 1 to 3 substituents independently selected from halo, $—NR^9R^{10}$, $—OR^{11}$, $—C(O)R^{11}$, $—C(O)OR^{11}$, $—C(O)NR^9R^{10}$, $—SOR^{12}$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
$R^2$ is H and $R^3$ is $—CF_3$; or
$R^2$ and $R^3$ are taken together to form oxo or thio;
$R^4$ and $R^5$ are independently selected from $C_{1-6}$alkyl, $C_{1-6}$heteroalkyl, $C_{1-6}$haloalkyl, and $C_{3-10}$cycloalkyl; wherein each alkyl, heteroalkyl, haloalkyl, and cycloalkyl is independently optionally substituted with 1 to 3 substituents independently selected from halo, $—NR^9R^{10}$, $—OR^{11}$, $—C(O)R^{11}$, $—C(O)OR^{11}$, $—C(O)NR^9R^{10}$, $—SOR^{12}$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or
$R^4$ and $R^5$ are taken together, along with the nitrogen atom to which they are attached, to form a 3- to 10-membered heterocycloalkyl optionally substituted with 1 to 3 substituents independently selected from halo, $—NR^9R^{10}$, $—OR^{11}$, $—C(O)R^{11}$, $—C(O)OR^{11}$, $—C(O)NR^9R^{10}$, $—SOR^2$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^6$ is independently selected from halo, $—NR^9R^{10}$, $—OR^{11}$, $—C(O)R^{11}$, $—C(O)OR^{11}$, $—C(O)NR^9R^{10}$, $—SOR^{12}$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or
two $R^6$'s attached to the same carbon atom are taken together to form oxo, thio, or $C_{3-10}$cycloalkyl, and any remaining $R^6$'s are independently selected from halo, $—NR^9R^{10}$, $—OR^{11}$, $—C(O)R^{11}$, $—C(O)OR^{11}$, $—C(O)NR^9R^{10}$, $—SOR^{12}$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
each $R^7$ is independently selected from H, halo, $—NR^9R^{10}$, $—OR^{11}$, $—C(O)R^{11}$, $—C(O)OR^{11}$, $—C(O)NR^9R^{10}$, $—SOR^{12}$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
each $R^8$ is independently selected from H, halo, $—NR^9R^{10}$, $—OR^{11}$, $—C(O)R^{11}$, $—C(O)OR^{11}$, $—C(O)NR^9R^{10}$, $—SOR^{12}$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or
two $R^8$'s can be taken together to form a $C_{3-10}$cycloalkyl optionally substituted with 1 to 3 substituents independently selected from halo, $—NR^9R^{10}$, $—OR^{11}$, $—C(O)R^{11}$, $—C(O)OR^{11}$, $—C(O)NR^9R^{10}$, $—SOR^{12}$, $—SO_2R^{12}$, $—SO_2NR^9R^{10}$, $—NR^{13}C(O)R^{11}$, $—NR^{13}C(O)NR^9R^{10}$, $—NR^{13}SO_2R^{11}$, $—NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
$R^9$ and $R^{10}$ are independently selected at each occurrence from H, $C_{1-6}$alkyl, $C_{1-6}$heteroalkyl, $C_{1-6}$haloalkyl, and $C_{3-10}$cycloalkyl;
each $R^{11}$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^{12}$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^{13}$ is independently selected from H, $C_{1-6}$alkyl, $C_{1-6}$haloalkyl, and $C_{3-10}$cycloalkyl;
m is 1 or 2; and
n is 0, 1, 2, 3, or 4.

In some embodiments, the compound is a compound of Formula IIIa:

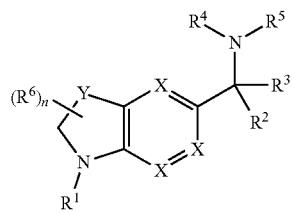

Formula IIIa or a pharmaceutically acceptable salt thereof.

In some embodiments, the compound is a compound of Formula IIIb:

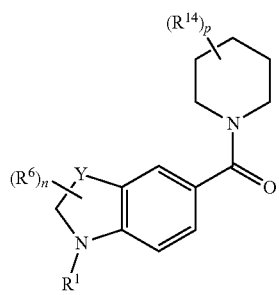

Formula IIIb or a pharmaceutically acceptable salt thereof, wherein:
each $R^{14}$ is independently selected from halo, —$NR^9R^{10}$, —$OR^{11}$, —$C(O)R^1$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; and
p is 0, 1, 2, or 3.

In some embodiments, the compound is a compound of Formula IIIc:

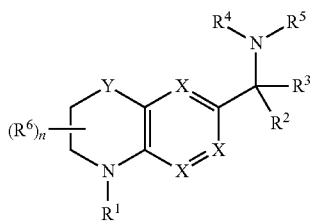

Formula IIIc or a pharmaceutically acceptable salt thereof.

In some embodiments, the compound is a compound of Formula IIId:

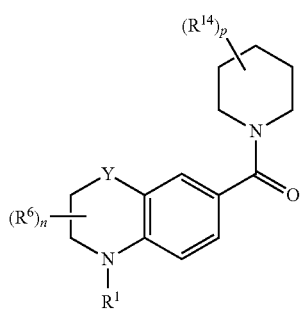

Formula IIId or a pharmaceutically acceptable salt thereof, wherein:
each $R^{14}$ is independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; and
p is 0, 1, 2, or 3.

In another aspect, provided herein is a compound of Formula IIk:

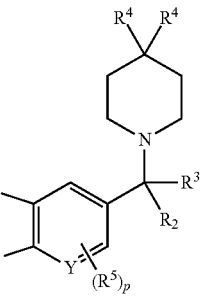

Formula IIk or a pharmaceutically acceptable salt thereof, wherein:
T, U, and Y are independently selected from N and $CR^6$, provided that when U is N, at least one of T and Y is N;
$R^1$ is selected from $C_{6-10}$aryl and 5- to 10-membered heteroaryl; wherein the aryl or heteroaryl is optionally substituted with 1 to 3 substituents independently selected from halo, —$NR^7R^8$, —$OR^9$, —$C(O)R^9$, —$C(O)OR^9$, —$C(O)NR^7R^8$, —$SOR^{10}$, —$SO_2R^{10}$, —$SO_2NR^7R^8$, —$NR^{11}C(O)R^9$, —$NR^{11}C(O)NR^7R^8$, —$NR^{11}SO_2R^9$, —$NR^{11}SO_2NR^7R^8$, $C_{1-6}$alkyl, $C_{1-6}$heteroalkyl, $C_{1-6}$haloalkyl, $C_{3-6}$cycloalkyl, and 5- to 10-membered heteroaryl;
$R^2$ is H and $R^3$ is —$CF_3$; or
$R^2$ and $R^3$ are taken together to form oxo;
each $R^4$ is independently selected from H and halo;
$R^5$ is selected from halo, —$NR^7R^8$, —$OR^9$, —$C(O)R^9$, —$C(O)OR^9$, —$C(O)NR^7R^8$, —$SOR^{10}$, —$SO_2R^{10}$, —$SO_2NR^7R^8$, —$NR^{11}C(O)R^9$, —$NR^{11}C(O)NR^7R^8$, —$NR^{11}SO_2R^9$, —$NR^{11}SO_2NR^7R^8$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;
$R^6$ is selected from H, halo, —$NR^7R^8$, —$OR^9$, —$C(O)R^9$, —$C(O)OR^9$, —$C(O)NR^7R^8$, —$SOR^{10}$, —$SO_2R^{10}$, —$SO_2NR^7R^8$, —$NR^1C(O)R^9$, —$NR^{11}C(O)NR^7R^8$, —$NR^{11}SO_2R^9$, —$NR^{11}SO_2NR^7R^8$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;
$R^7$ and $R^8$ are independently selected at each occurrence from H, $C_{1-6}$alkyl, $C_{1-6}$heteroalkyl, $C_{1-6}$haloalkyl, and $C_{3-6}$cycloalkyl;
each $R^9$ is independently selected from H, $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;
each $R^{10}$ is independently selected from $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;
each $R^{11}$ is independently selected from H, $C_{1-6}$alkyl, $C_{1-6}$haloalkyl, and $C_{3-6}$cycloalkyl; and
p is 0, 1, or 2.

In another aspect, provided herein is a compound of Formula IIm:

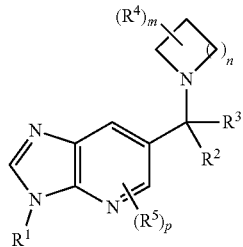

Formula IIm or a pharmaceutically acceptable salt thereof, wherein:
$R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, and 5- to 10-membered heteroaryl;

$R^2$ is H and $R^3$ is —$CF_3$; or
$R^2$ and $R^3$ are taken together to form oxo;
each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; or
two $R^4$'s are taken together with the carbon atoms to which they are attached and any intervening atoms to form a $C_{3-10}$cycloalkyl, and any remaining $R^4$'s are independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$ haloalkyl, $C_{3-10}$cycloalkyl, $C_{6-10}$aryl, and 5- to 10-membered heteroaryl;

$R^5$ is selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;

$R^6$ and $R^7$ are independently selected at each occurrence from H, $C_{1-6}$alkyl, $C_{1-6}$heteroalkyl, $C_{1-6}$ haloalkyl, and $C_{3-10}$cycloalkyl;
each $R^8$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^{10}$ is independently selected from H, $C_{1-6}$alkyl, $C_{1-6}$haloalkyl, and $C_{3-10}$cycloalkyl;
n is 1, 2, 3, or 4;
m is 0, 1, 2, 3, 4, 5, 6, 7, 8, 9, or 10; and
p is 0, 1, 2, or 3.

In another aspect, provided herein is a compound of Formula IIq:

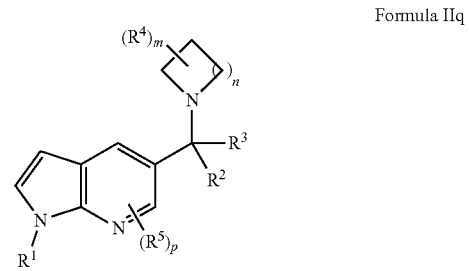

Formula IIq or a pharmaceutically acceptable salt thereof, wherein:
$R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, and 5- to 10-membered heteroaryl;

$R^2$ is H and $R^3$ is —$CF_3$; or
$R^2$ and $R^3$ are taken together to form oxo;
each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; or
two $R^4$'s are taken together with the carbon atoms to which they are attached and any intervening atoms to form a $C_{3-10}$cycloalkyl, and any remaining $R^4$'s are independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$ haloalkyl, $C_{3-10}$cycloalkyl, $C_{6-10}$aryl, and 5- to 10-membered heteroaryl;

$R^5$ is selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;

$R^6$ and $R^7$ are independently selected at each occurrence from H, $C_{1-6}$ alkyl, $C_{1-6}$ heteroalkyl, $C_{1-6}$haloalkyl, and $C_{3-10}$cycloalkyl;
each $R^8$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^{10}$ is independently selected from H, $C_{1-6}$alkyl, $C_{1-6}$haloalkyl, and $C_{3-10}$cycloalkyl;
n is 1, 2, 3, or 4;
m is 0, 1, 2, 3, 4, 5, 6, 7, 8, 9, or 10; and
p is 0, 1, 2, or 3.

In another aspect, provided herein is a compound of Formula IIIc:

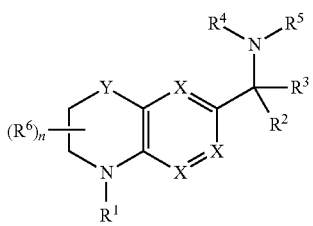

Formula IIIc or a pharmaceutically acceptable salt thereof, wherein:
each X is independently selected from N and $CR^7$;
Y is selected from O, S, $SO_2$, and $C(R^8)_2$;
$R^1$ is selected from $C_{6-10}$aryl and 5- to 10-membered heteroaryl; wherein the aryl or heteroaryl is optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^1$, $-NR^{13}C(O)NR^9R^{10}$, $-NR^{13}SO_2R^1$, $-NR^{13}SO_2NR^9R^{10}$, $C_{1-6}$alkyl, $C_{1-6}$heteroalkyl, $C_{1-6}$haloalkyl, $C_{3-6}$cycloalkyl, and 5- to 10-membered heteroaryl;
$R^2$ is H and $R^3$ is $-CF_3$; or
$R^2$ and $R^3$ are taken together to form oxo;
$R^4$ and $R^5$ are independently selected from $C_{1-6}$alkyl, $C_{1-6}$heteroalkyl, $C_{1-6}$haloalkyl, and $C_{3-6}$ cycloalkyl; wherein each alkyl, heteroalkyl, haloalkyl, and cycloalkyl is independently optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl; or
$R^4$ and $R^5$ are taken together, along with the nitrogen atom to which they are attached, to form a 3- to 10-membered heterocycloalkyl optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^2$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$ alkyl, $C_{1-6}$ heteroalkyl, $C_{1-6}$ haloalkyl, $C_{3-6}$cycloalkyl, $C_{6-10}$aryl, and 5- to 10-membered heteroaryl;
each $R^6$ is independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl; or
two $R^6$'s attached to the same carbon atom are taken together to form oxo, and any remaining $R^6$'s are independently selected from halo, $-NR^9R^{10}$, $-OR^{11}$, $-C(O)R^1$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;
each $R^7$ and $R^8$ is independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;

$R^9$ and $R^{10}$ are independently selected at each occurrence from H, $C_{1-6}$alkyl, $C_{1-6}$heteroalkyl, $C_{1-6}$haloalkyl, and $C_{3-6}$cycloalkyl;

each $R^{11}$ is independently selected from H, $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;

each $R^{12}$ is independently selected from $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;

each $R^{13}$ is independently selected from H, $C_{1-6}$alkyl, $C_{1-6}$haloalkyl, and $C_{3-6}$cycloalkyl; and n is 0, 1, 2, 3, or 4.

In another aspect, provided herein is a composition comprising a compound selected from the group consisting of:

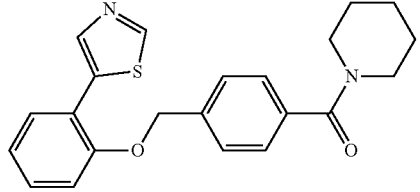

;


;

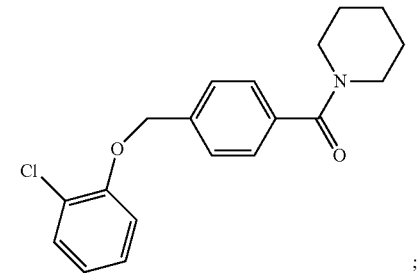

;

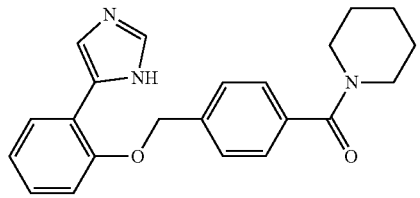

;

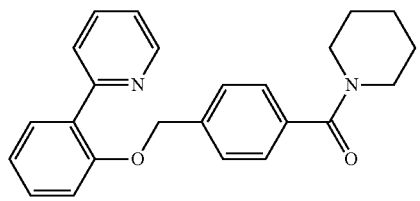

;

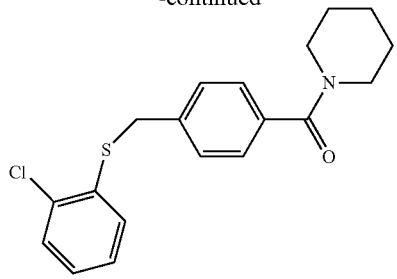
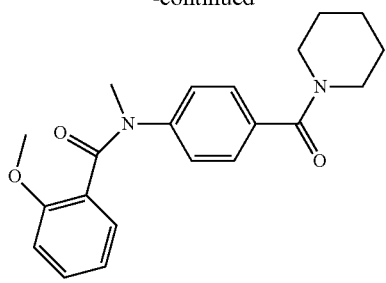
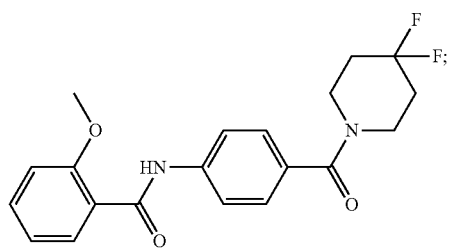
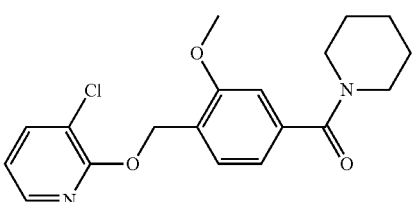
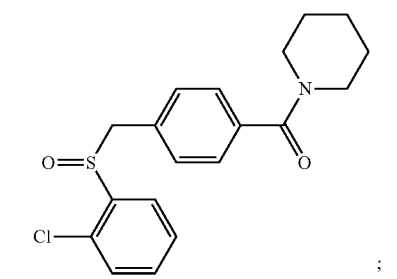
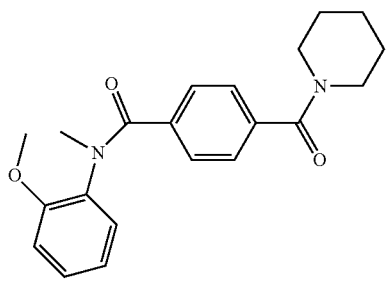
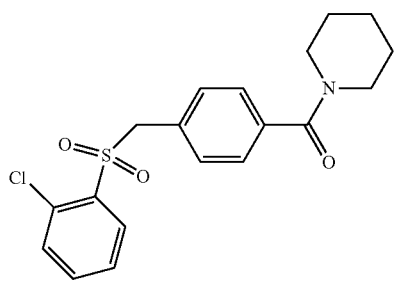
In another aspect, provided herein is a composition comprising a compound selected from the group consisting of:
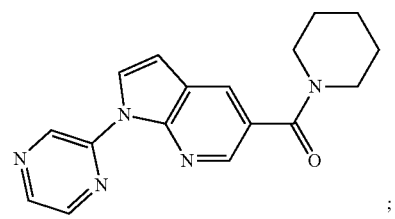
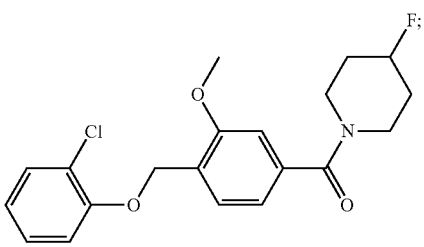
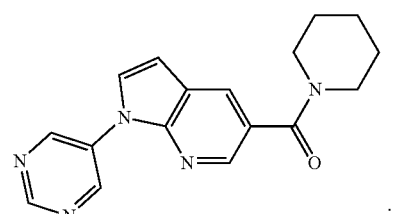
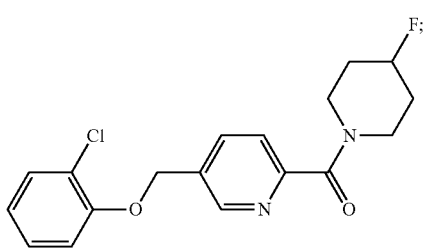
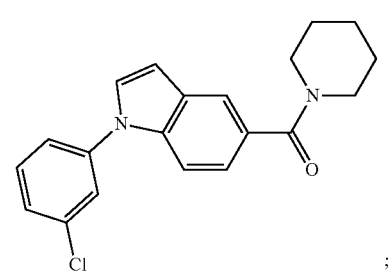

-continued
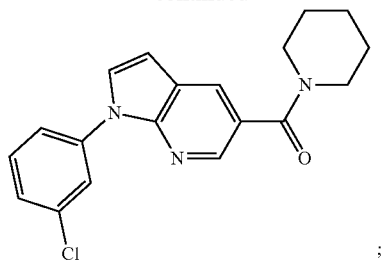
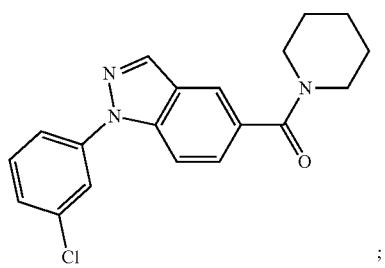
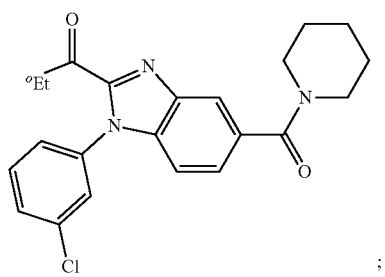
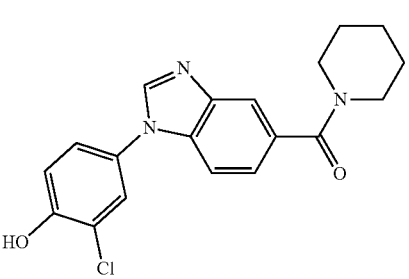
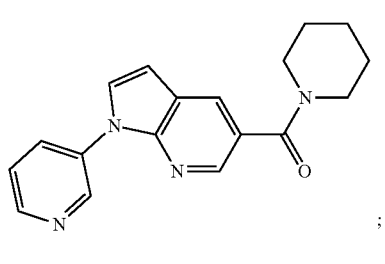
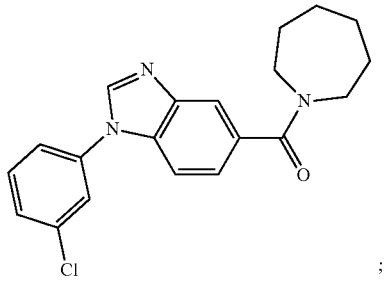
-continued
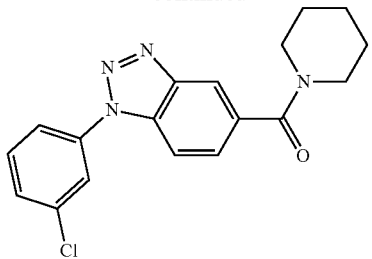
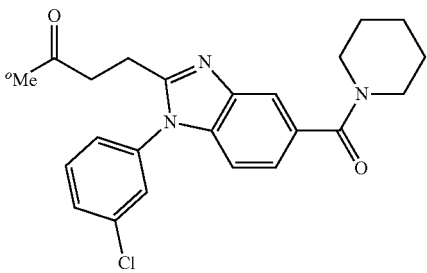
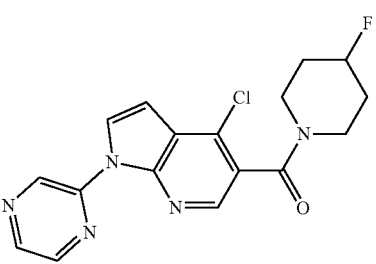
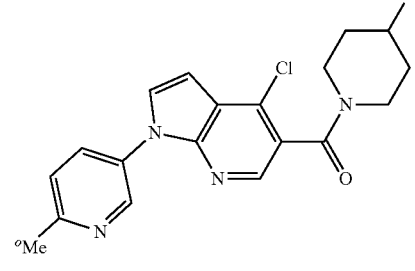
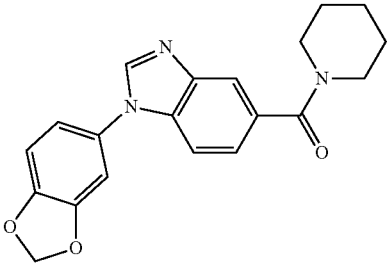
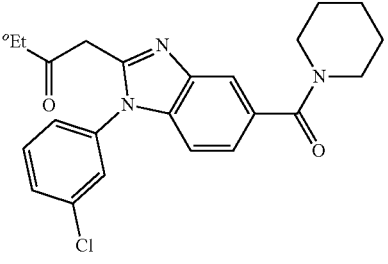

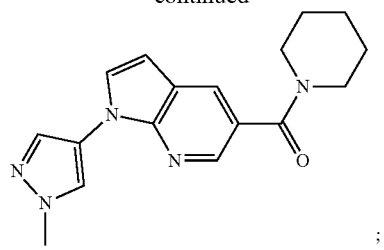;
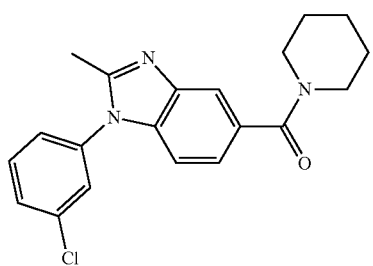;
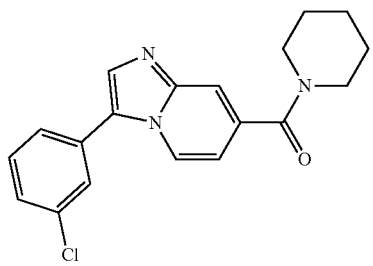;
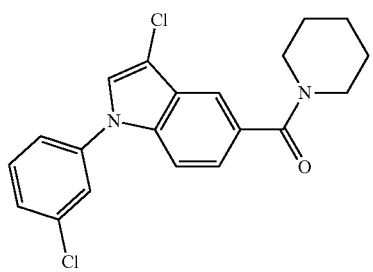;
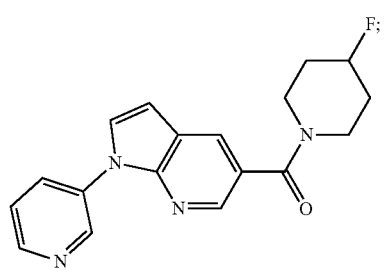;
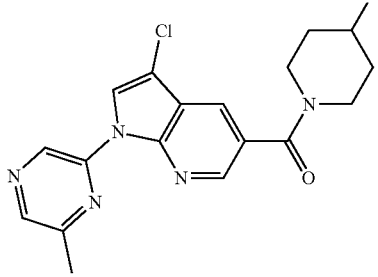;
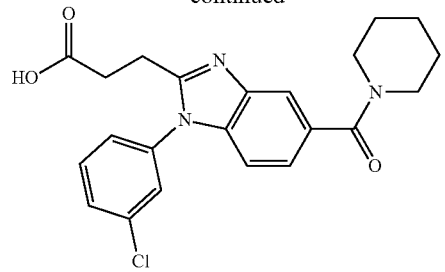;
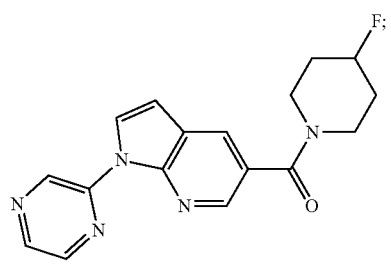;
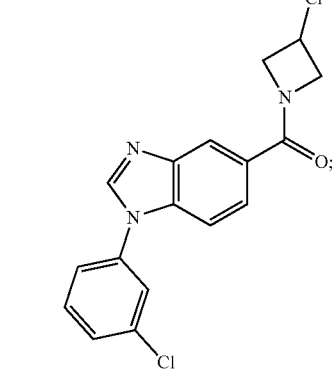;
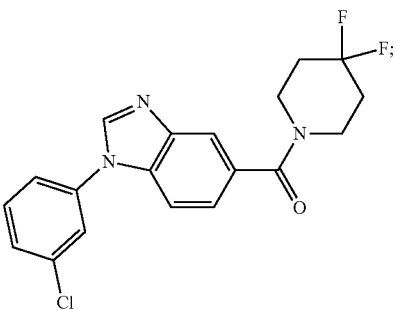;
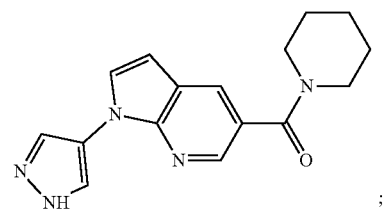;
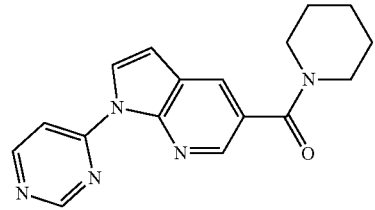;

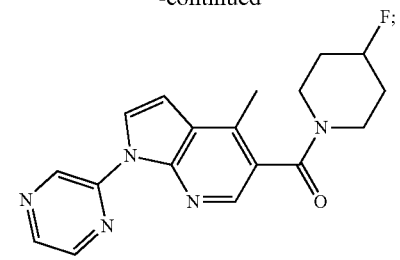
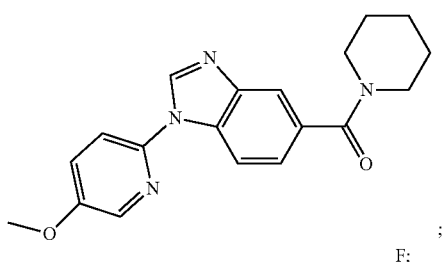
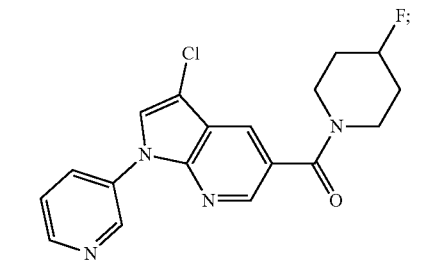
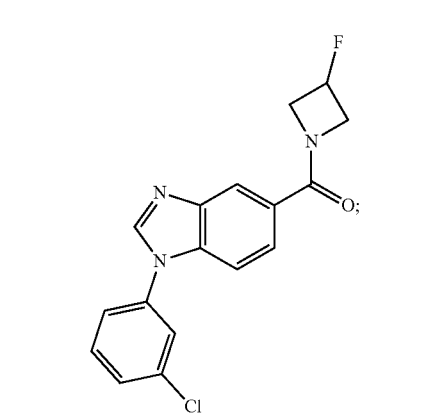
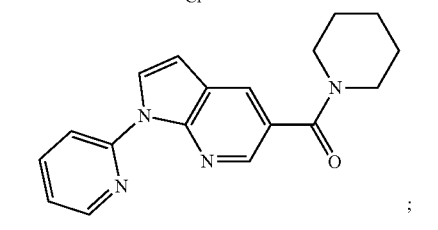
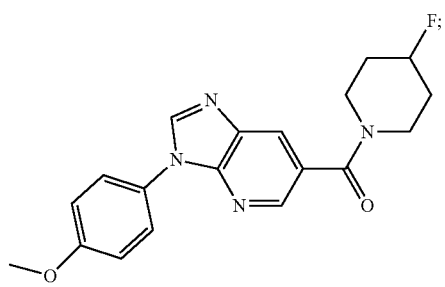
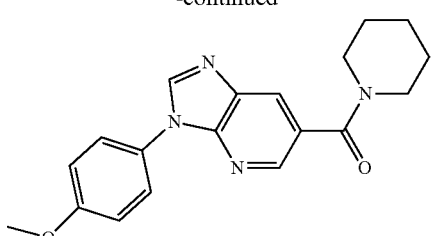
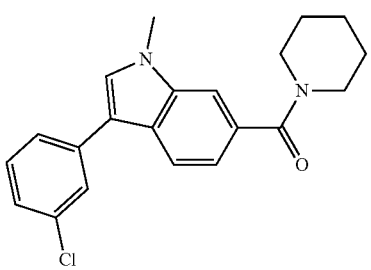
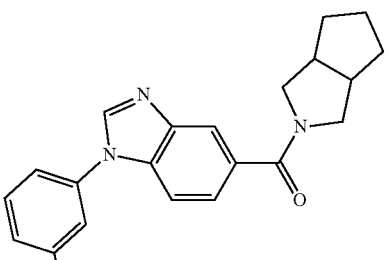
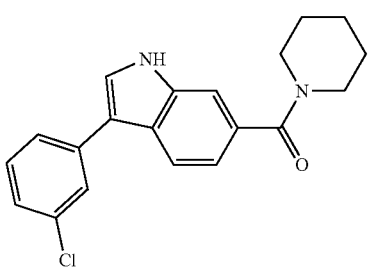
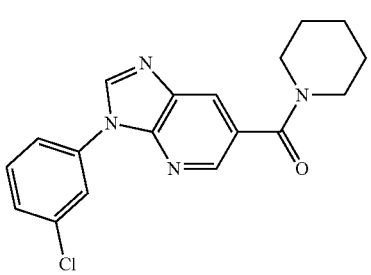
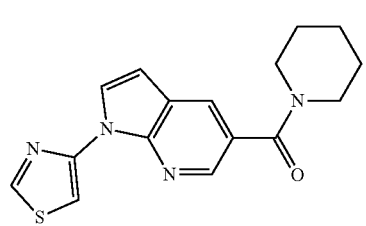

-continued
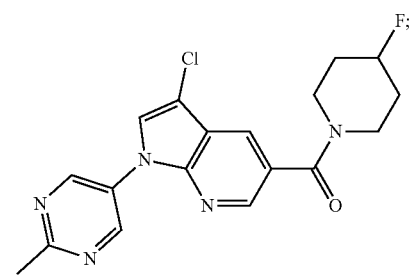
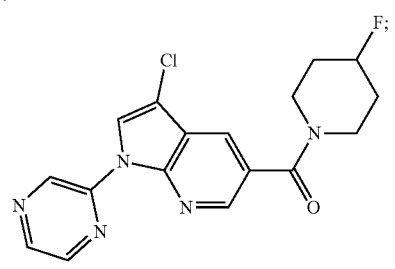
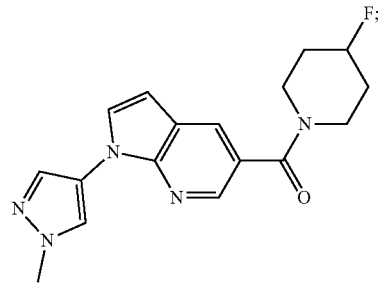
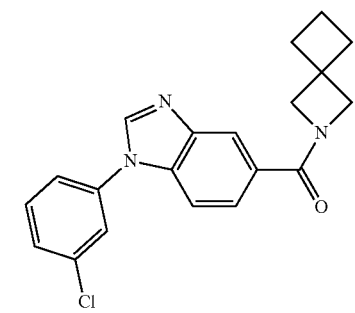
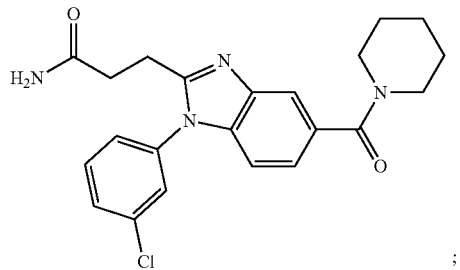
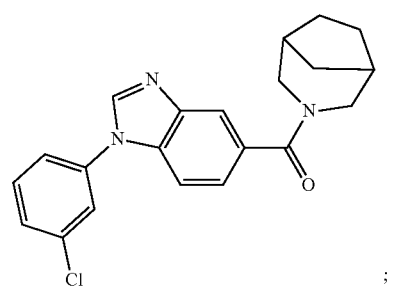
-continued
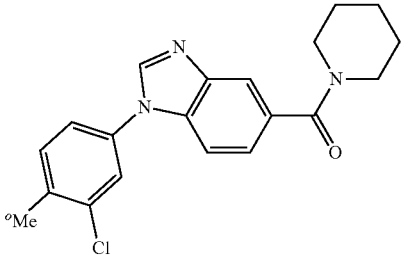
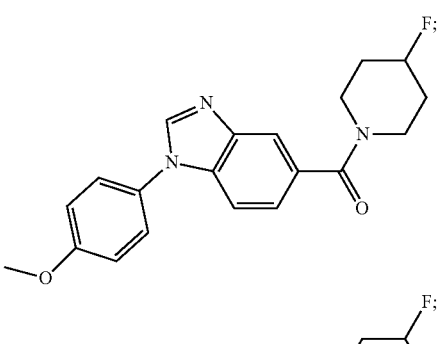
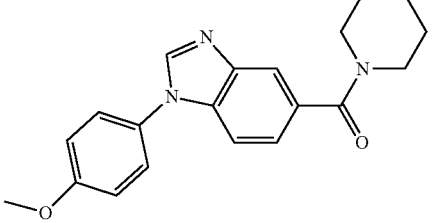
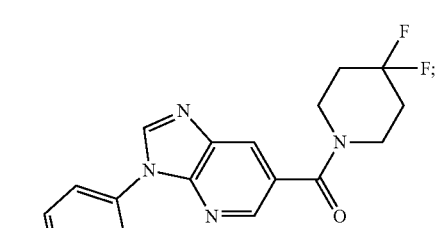
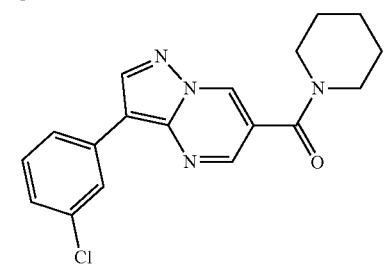
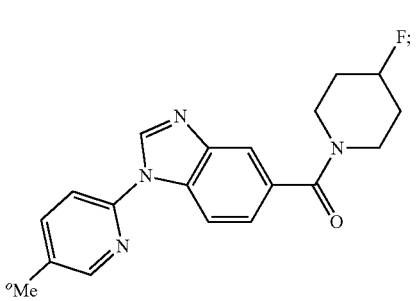

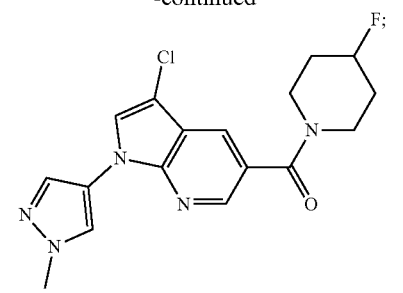
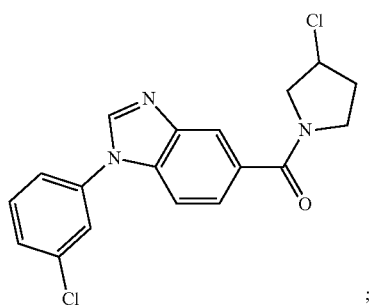
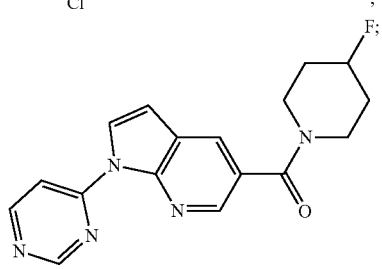
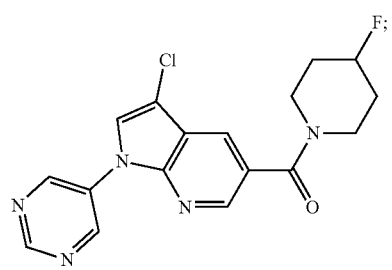
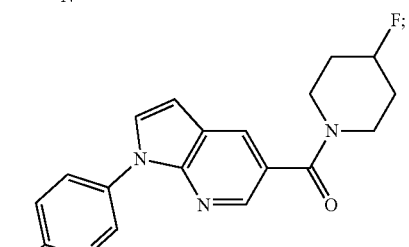
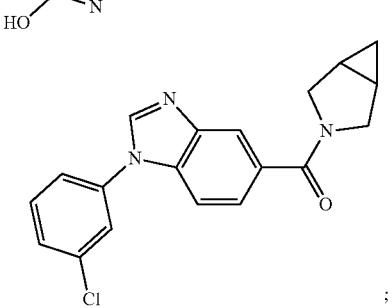
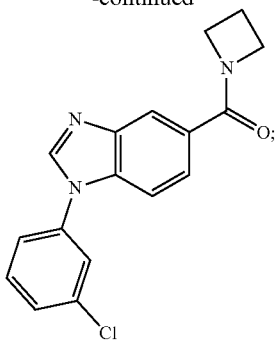
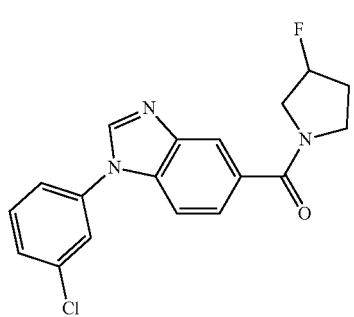
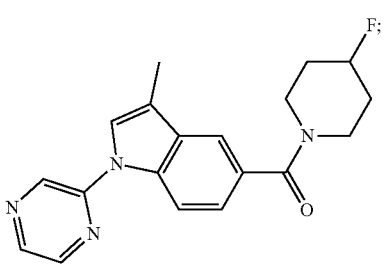
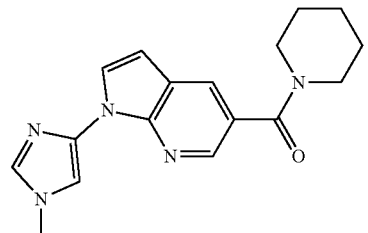
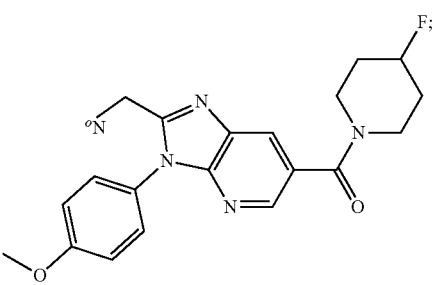

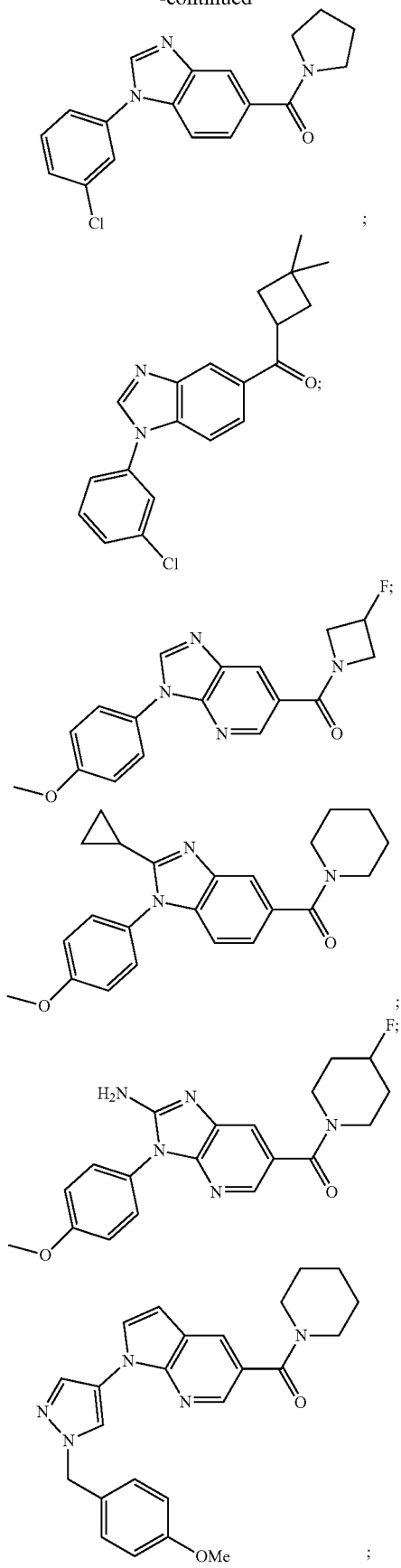
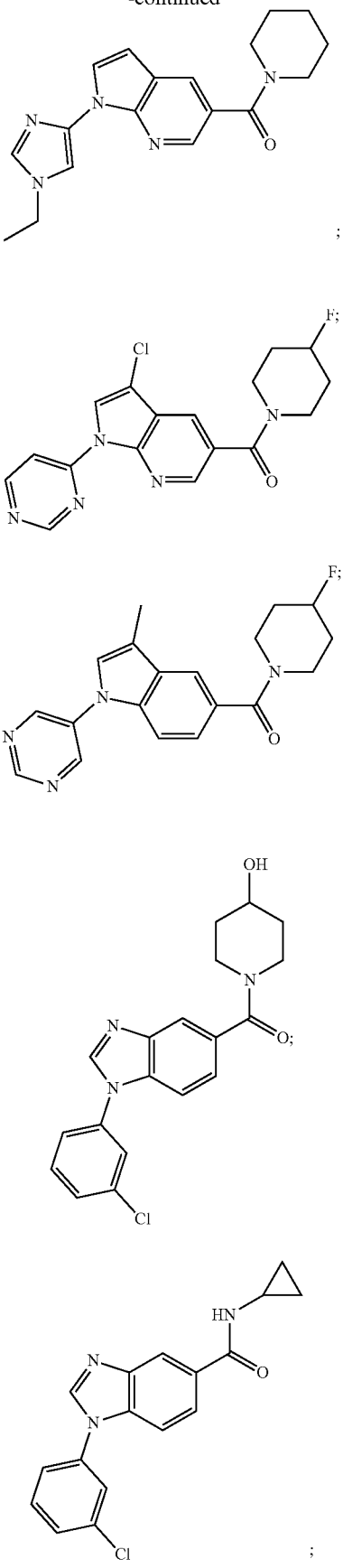

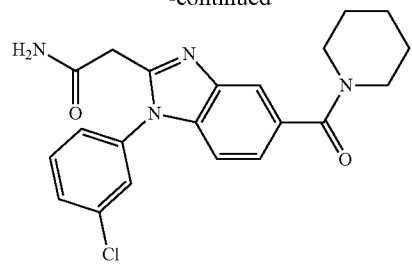
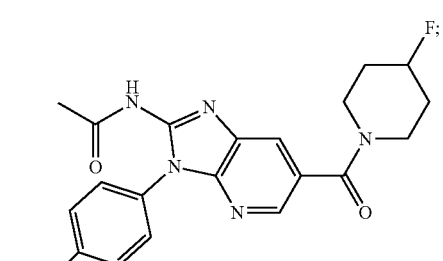
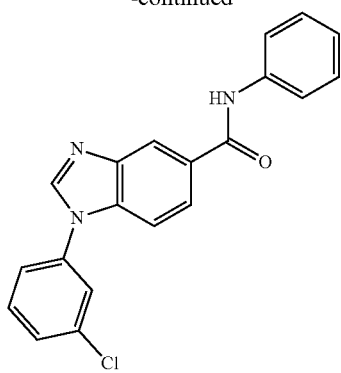
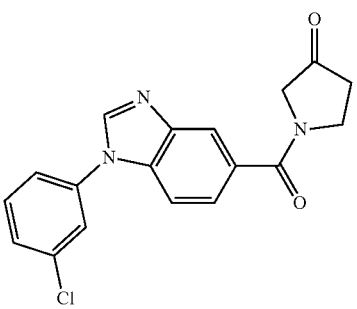
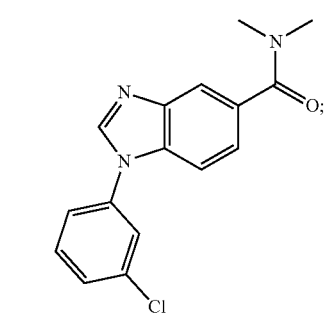
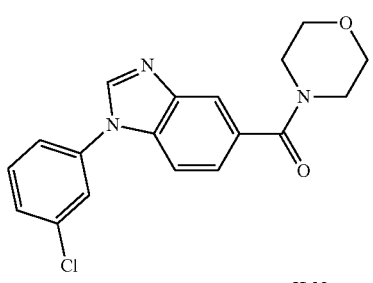
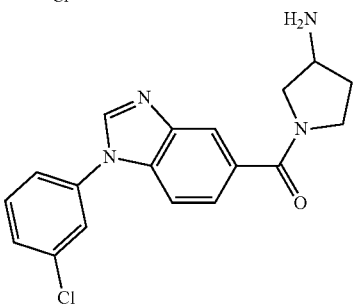

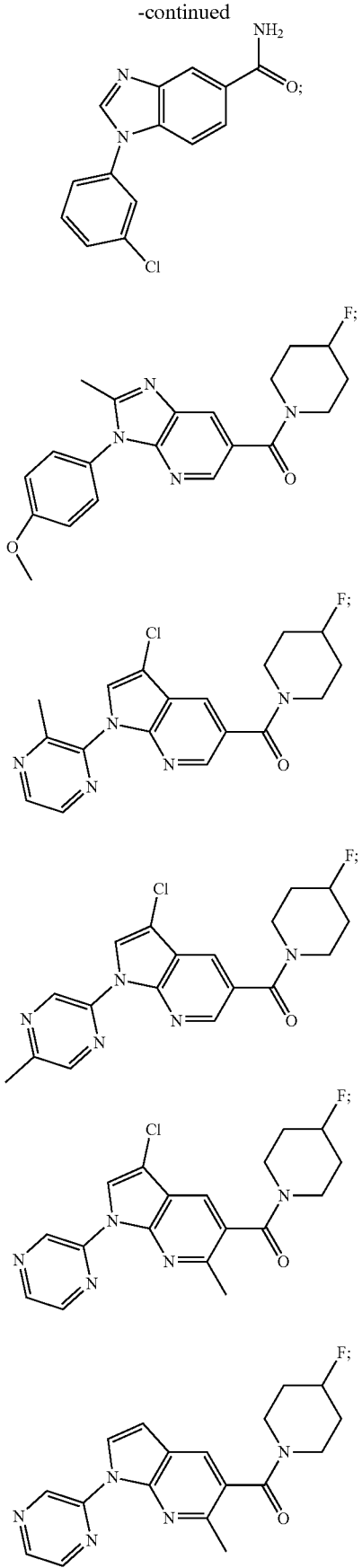
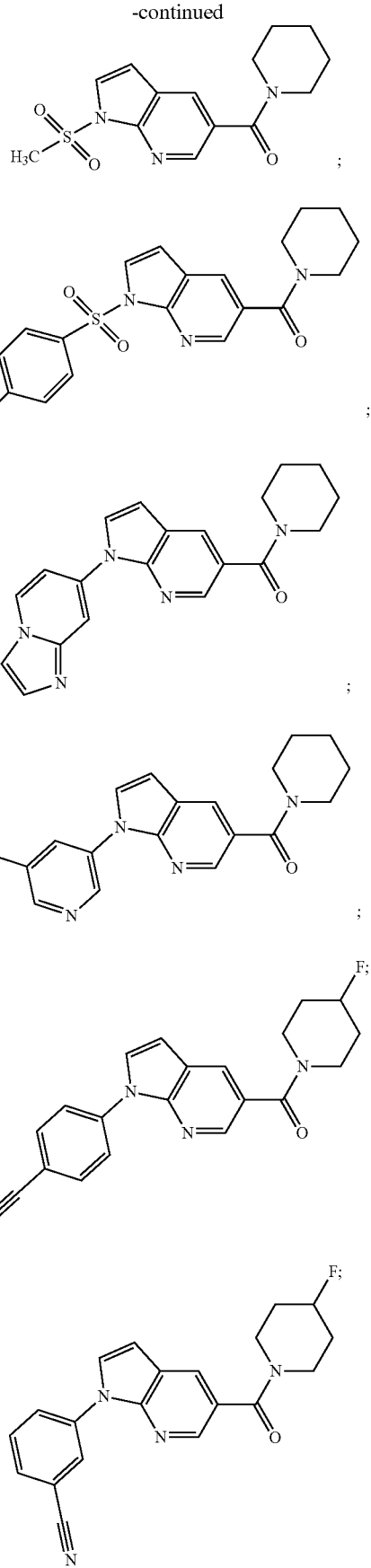

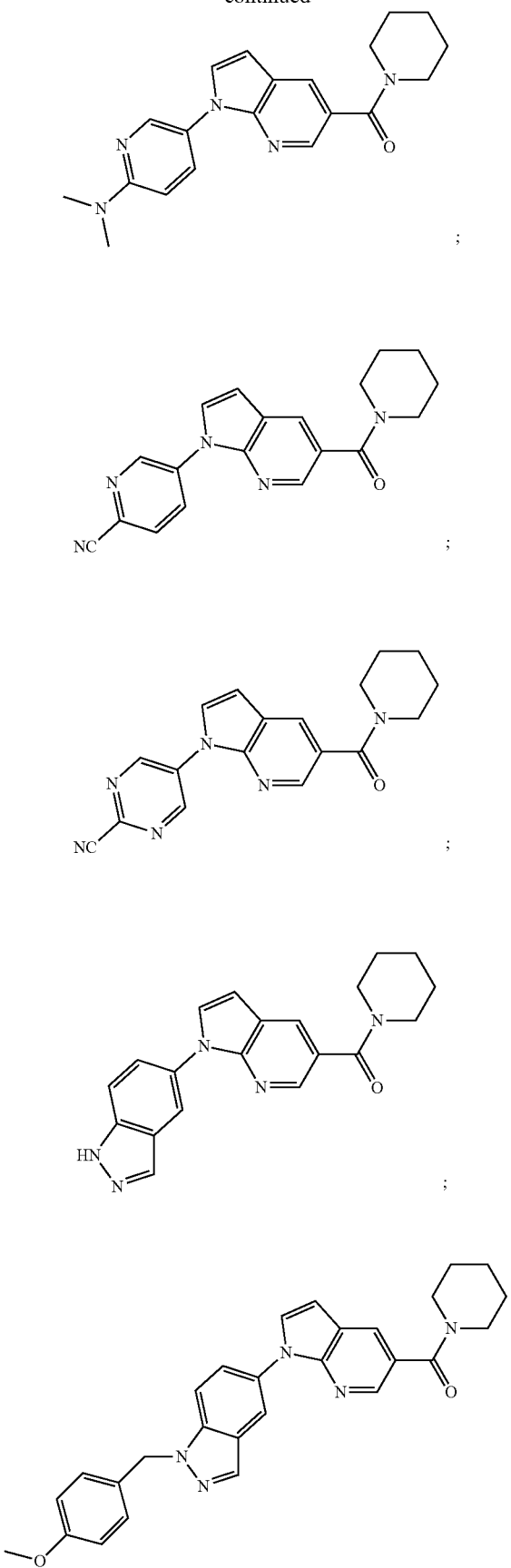

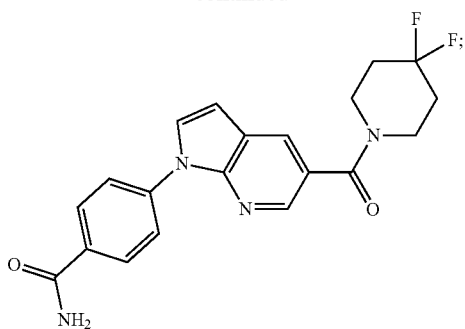
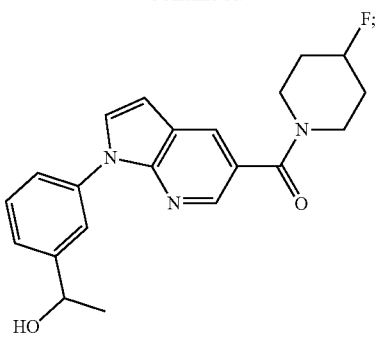

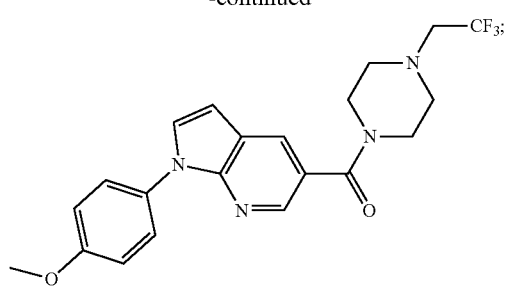
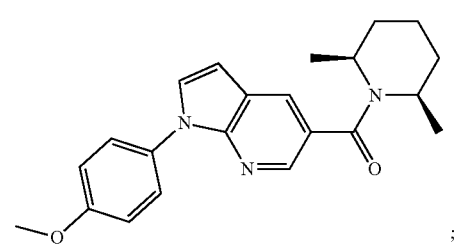
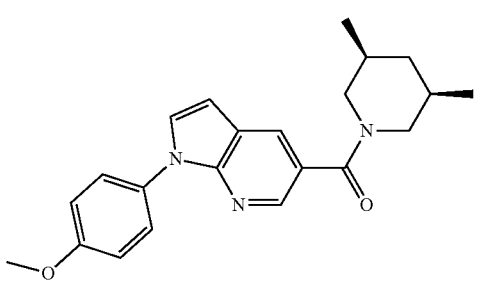
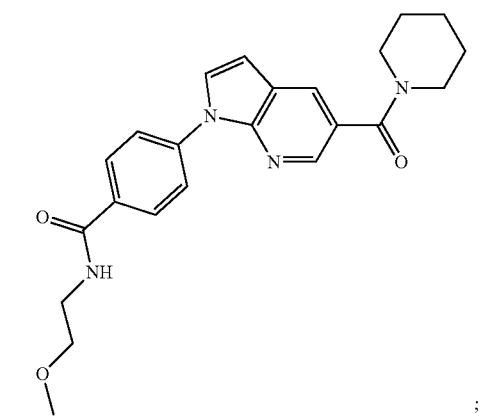
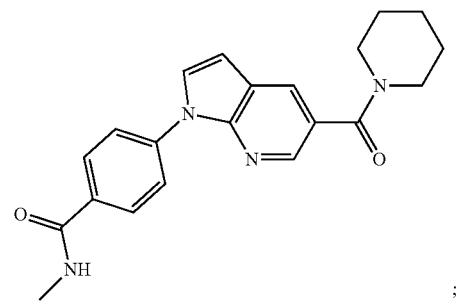
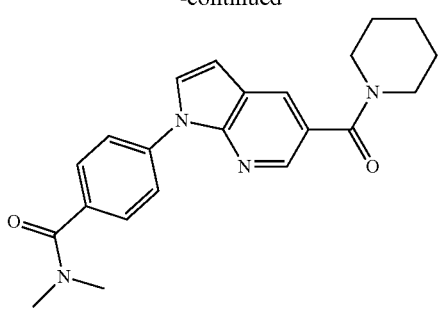
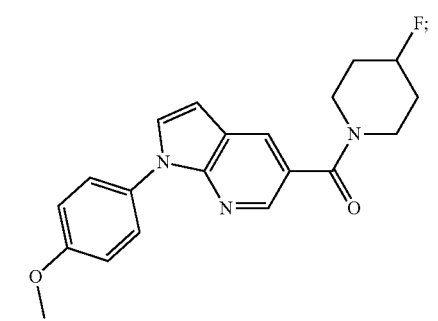
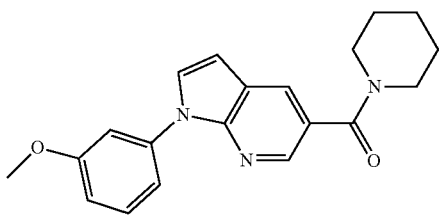
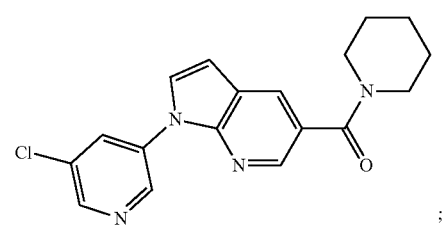
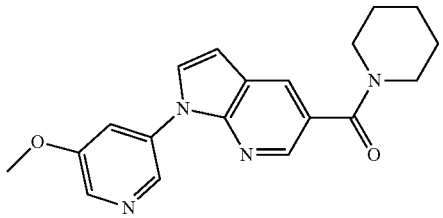
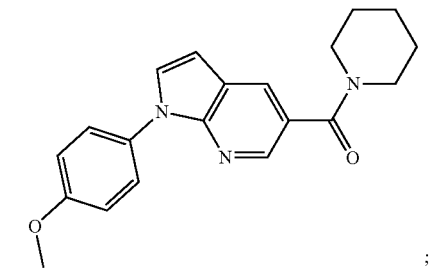

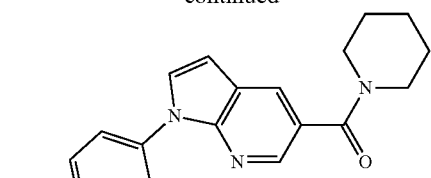;
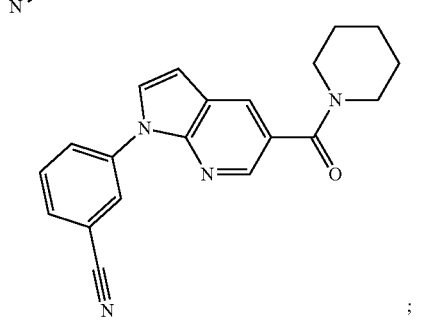;
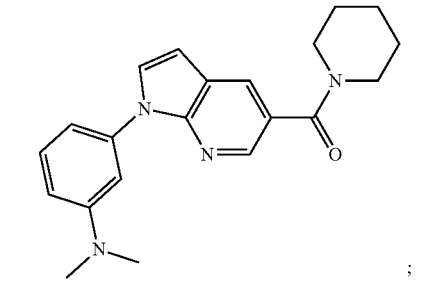;
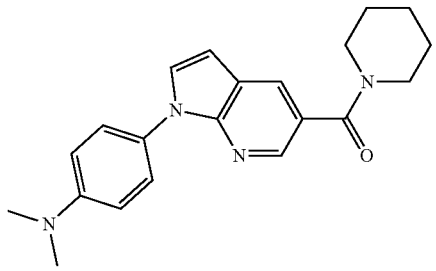;
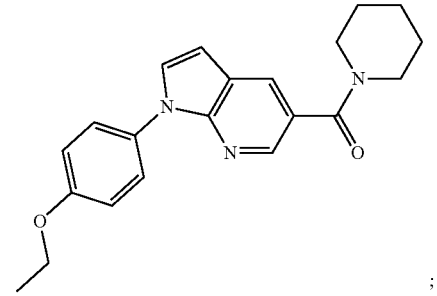;
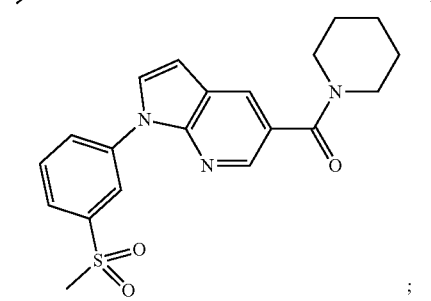;
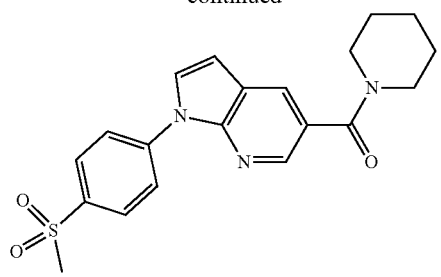;
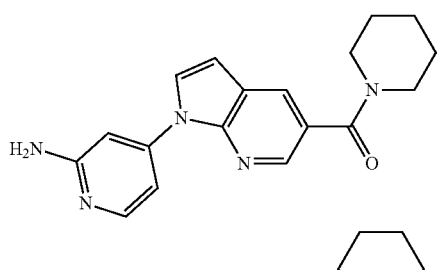;
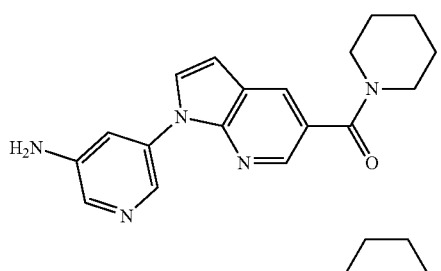;
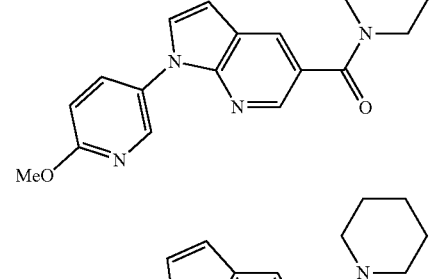;
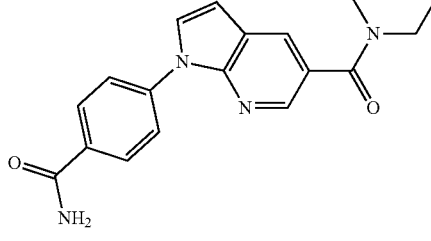;

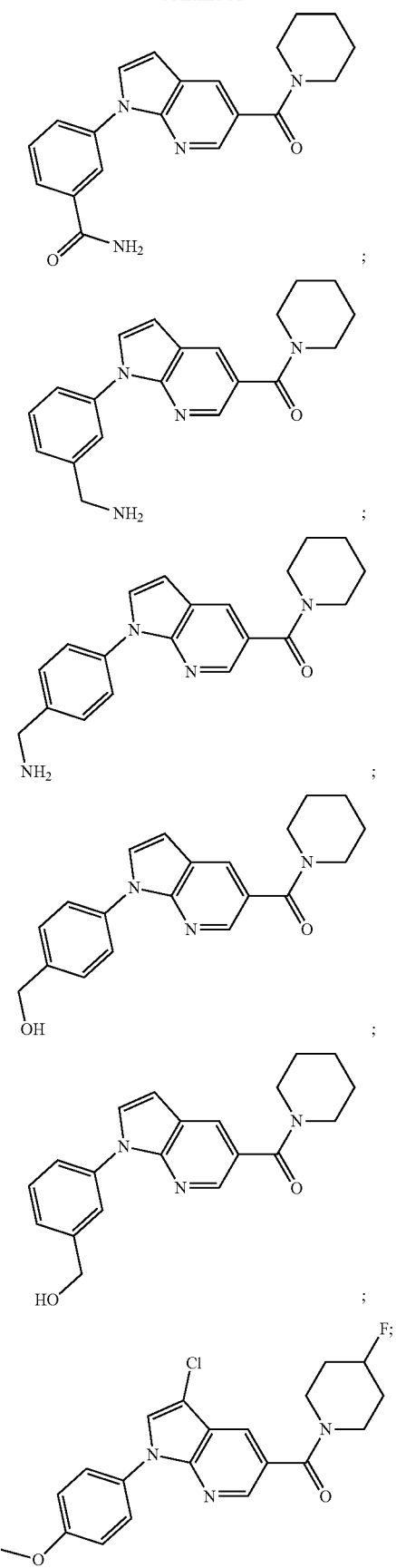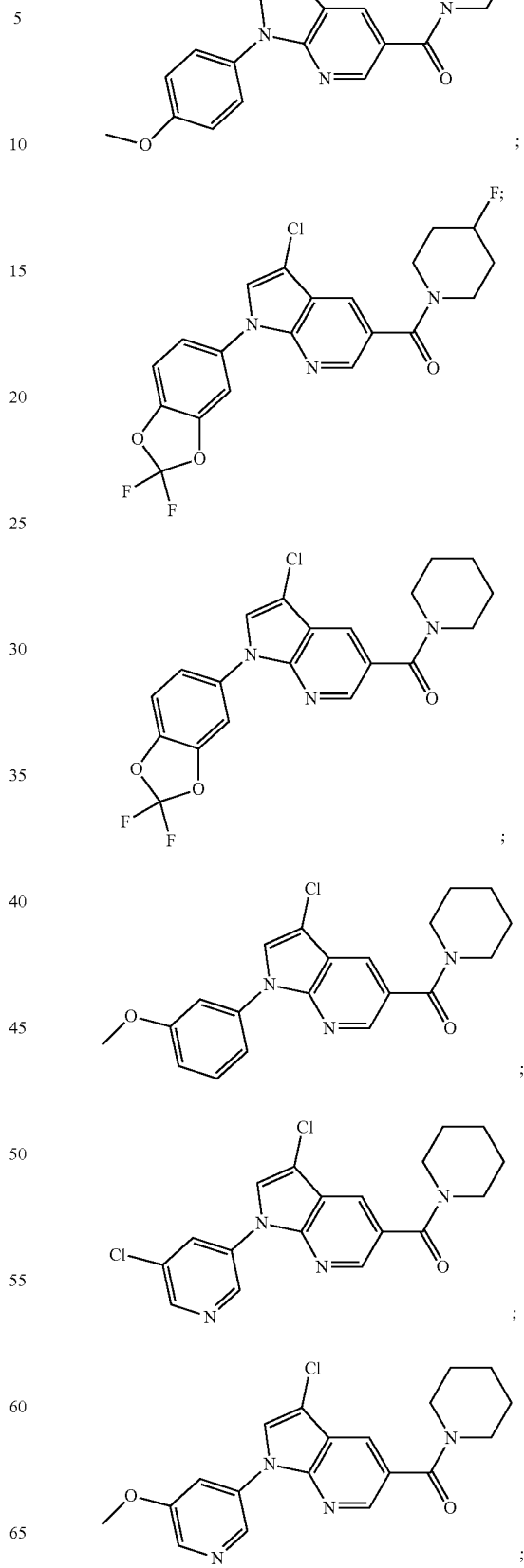

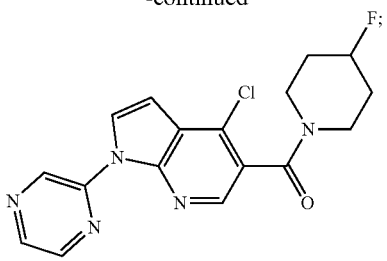
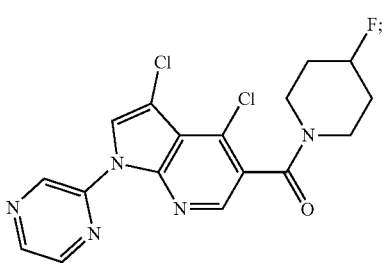
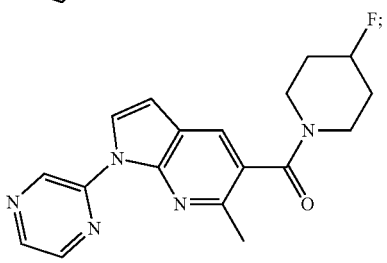
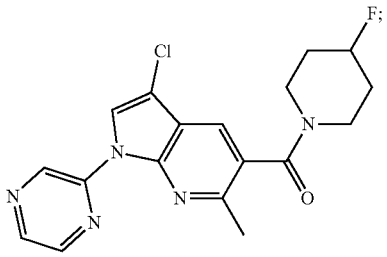
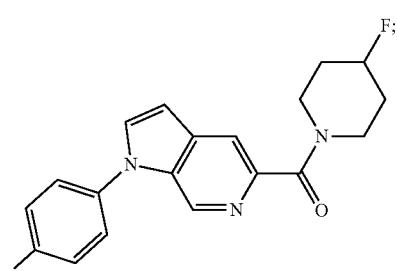
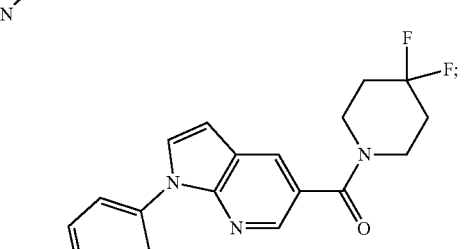
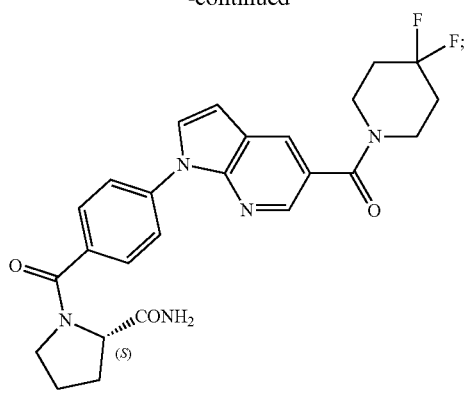
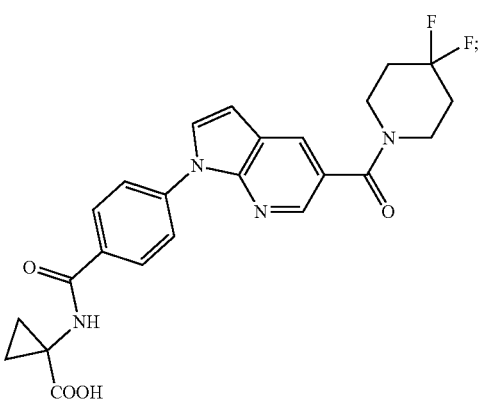
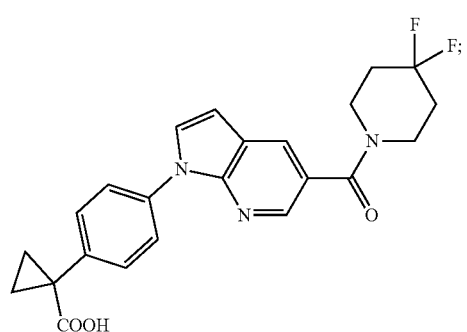
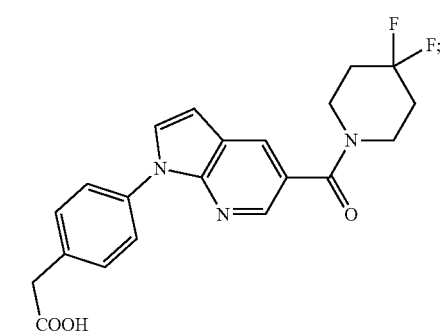

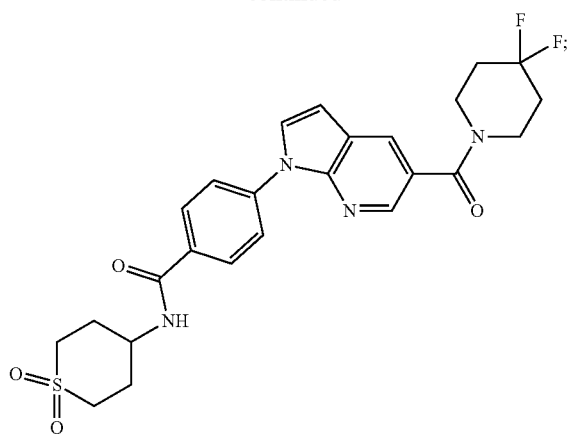
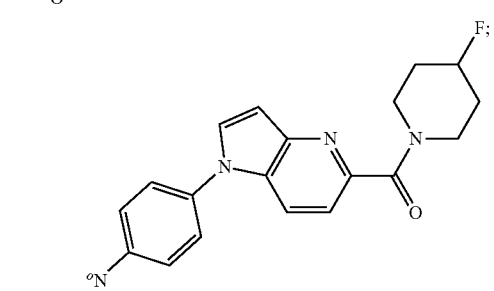
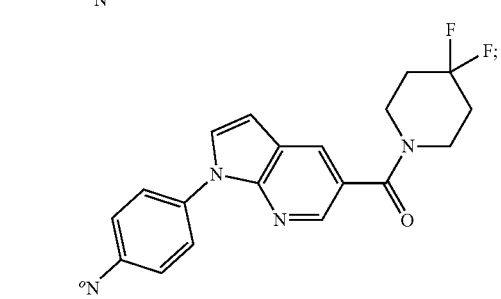
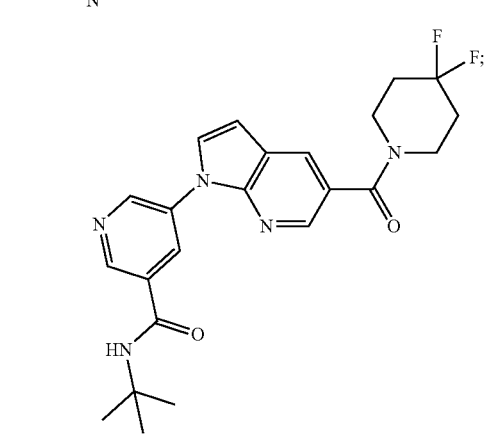
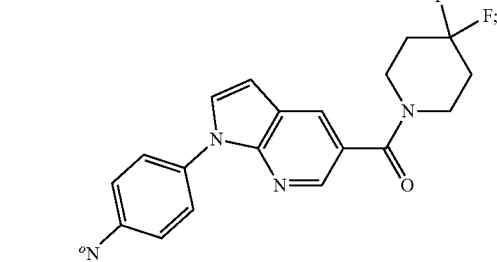
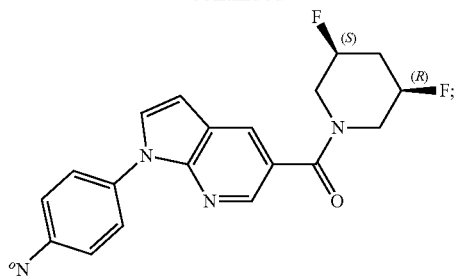
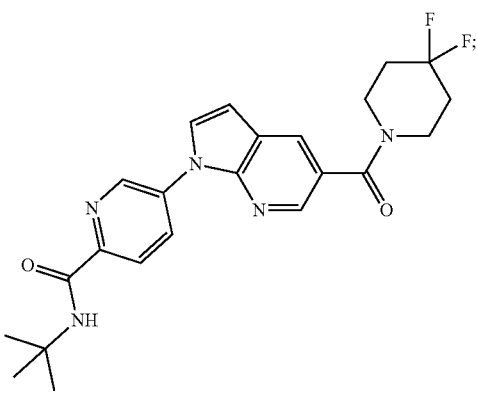
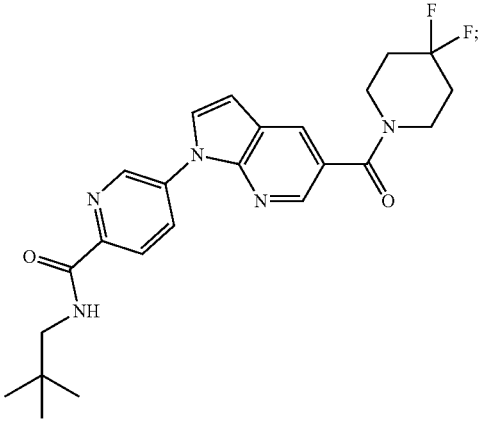

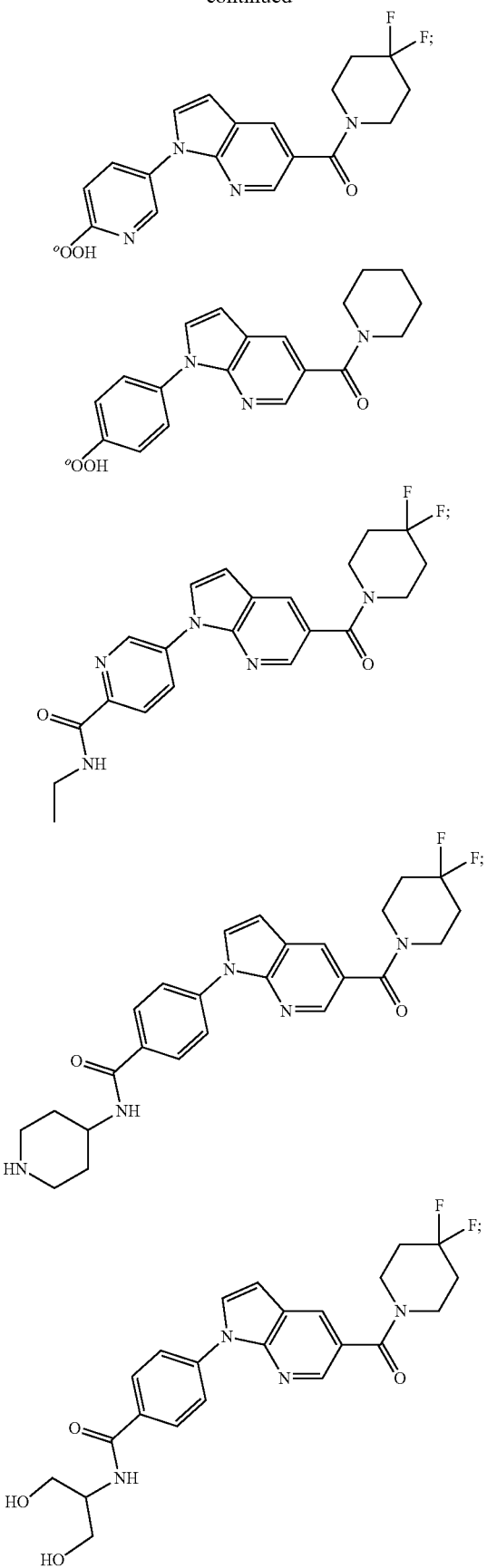
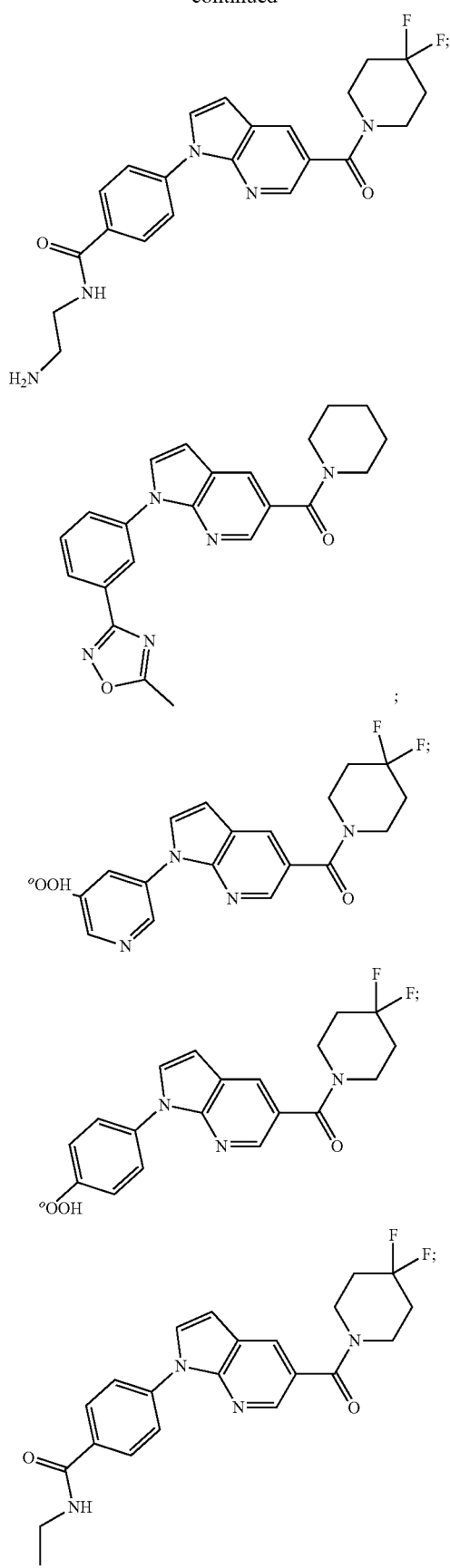

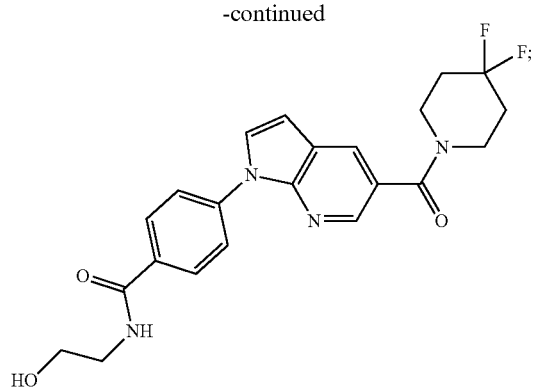
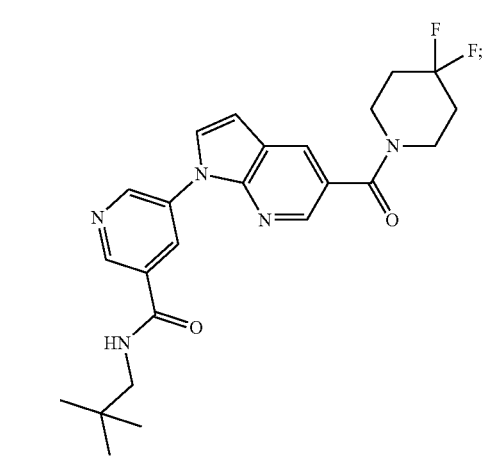
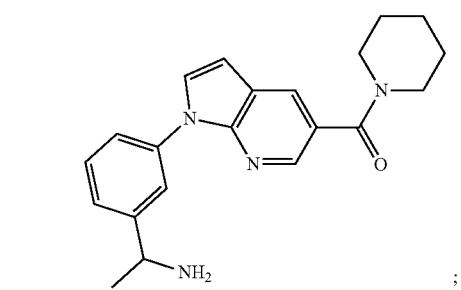
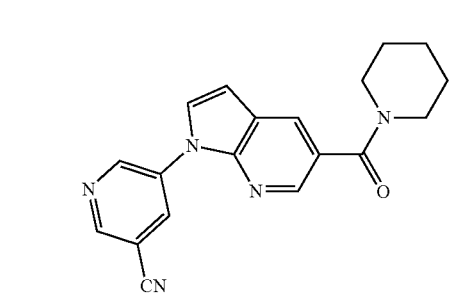
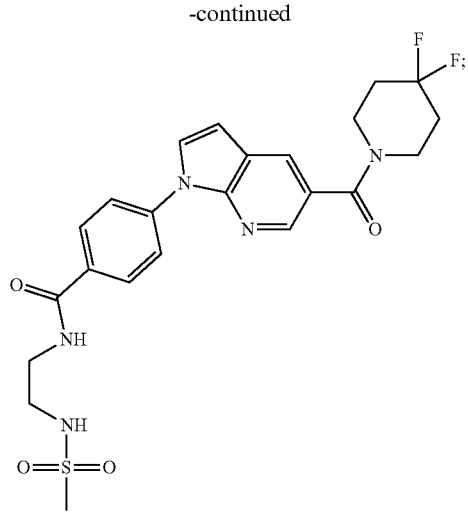
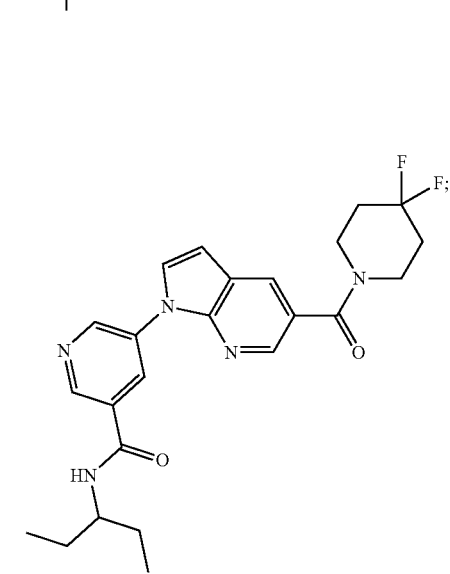
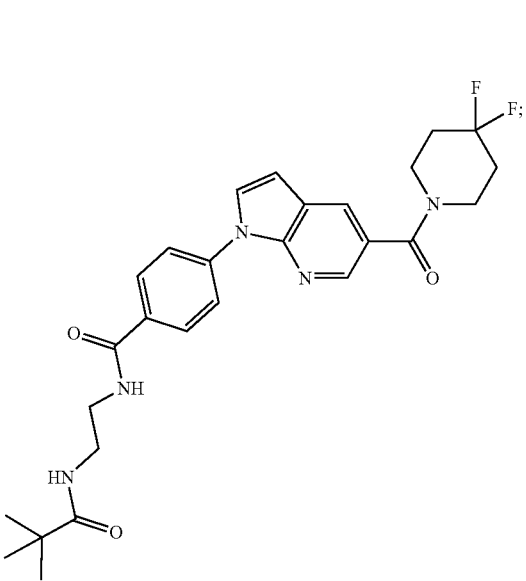

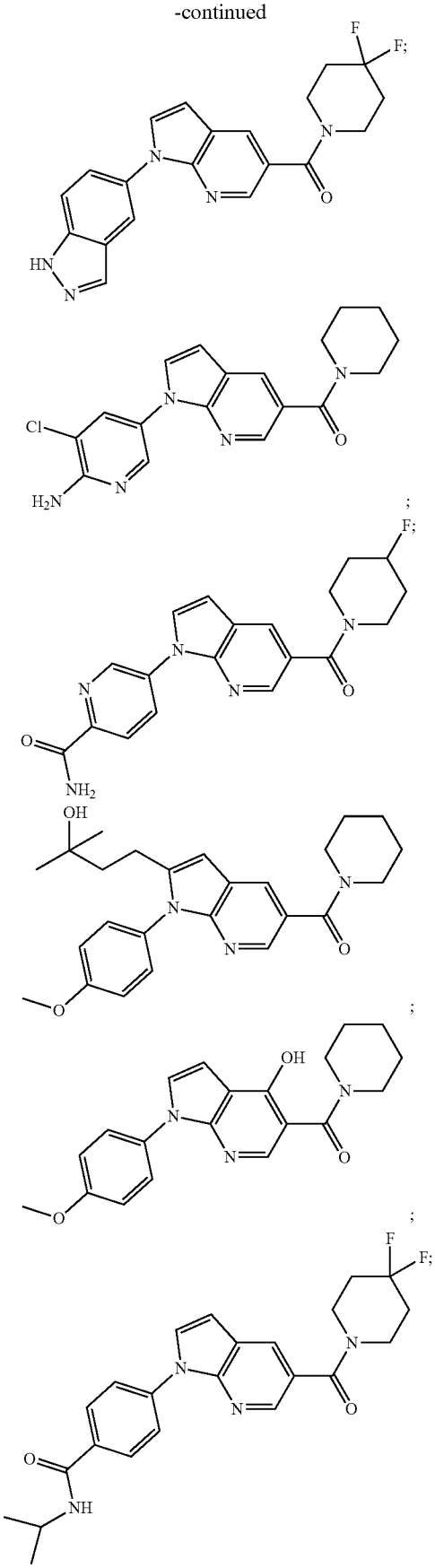
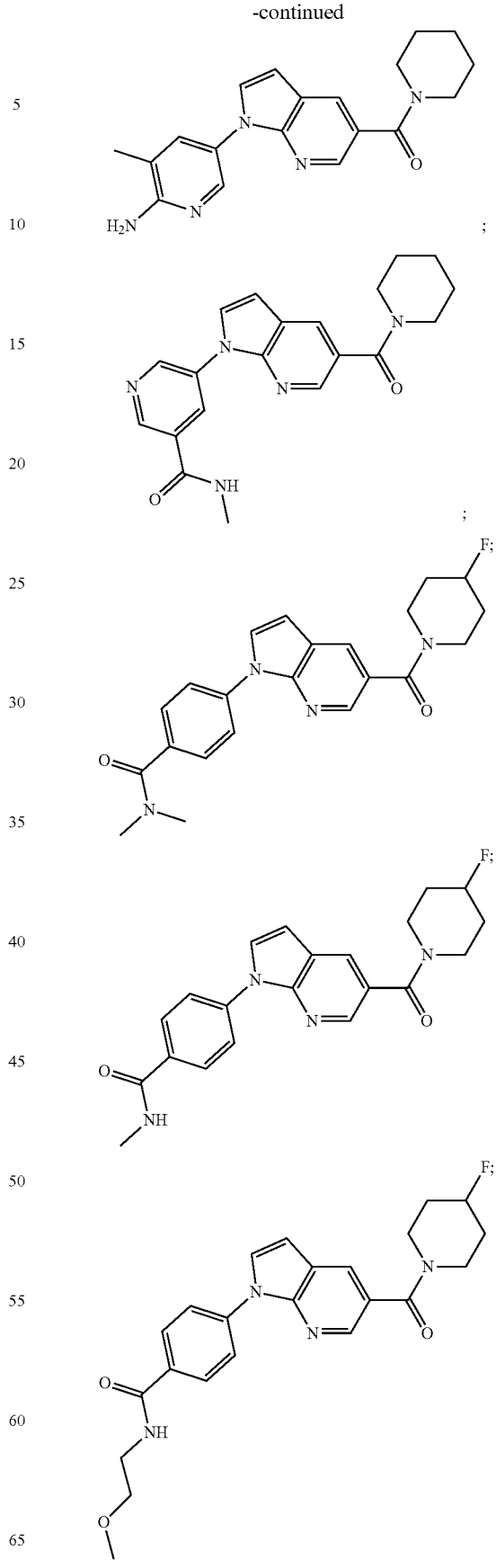

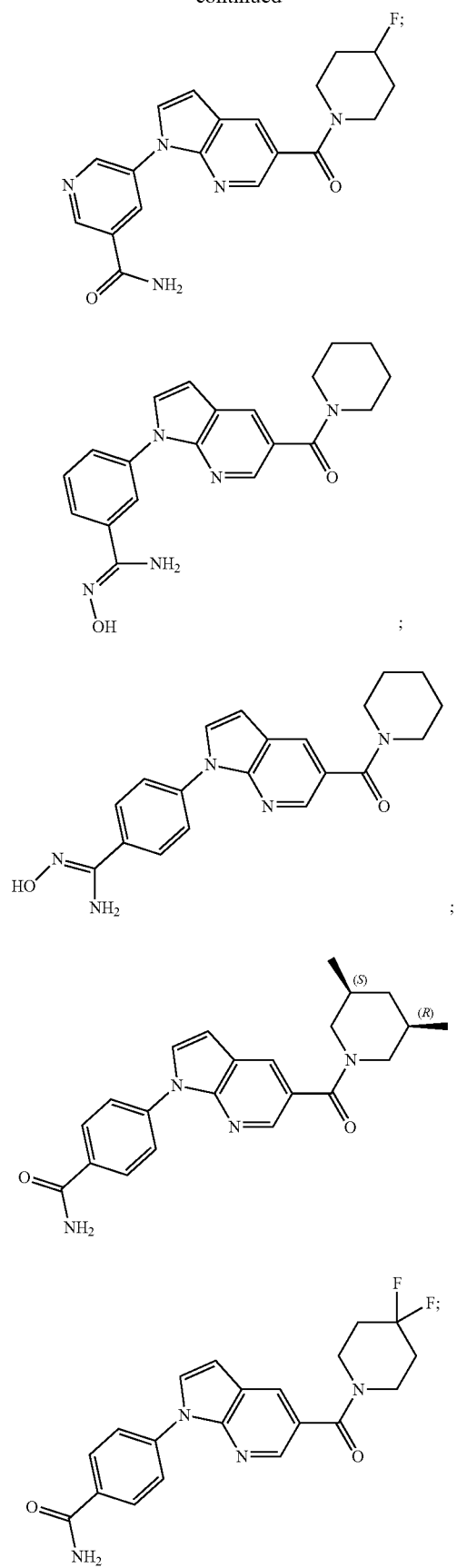
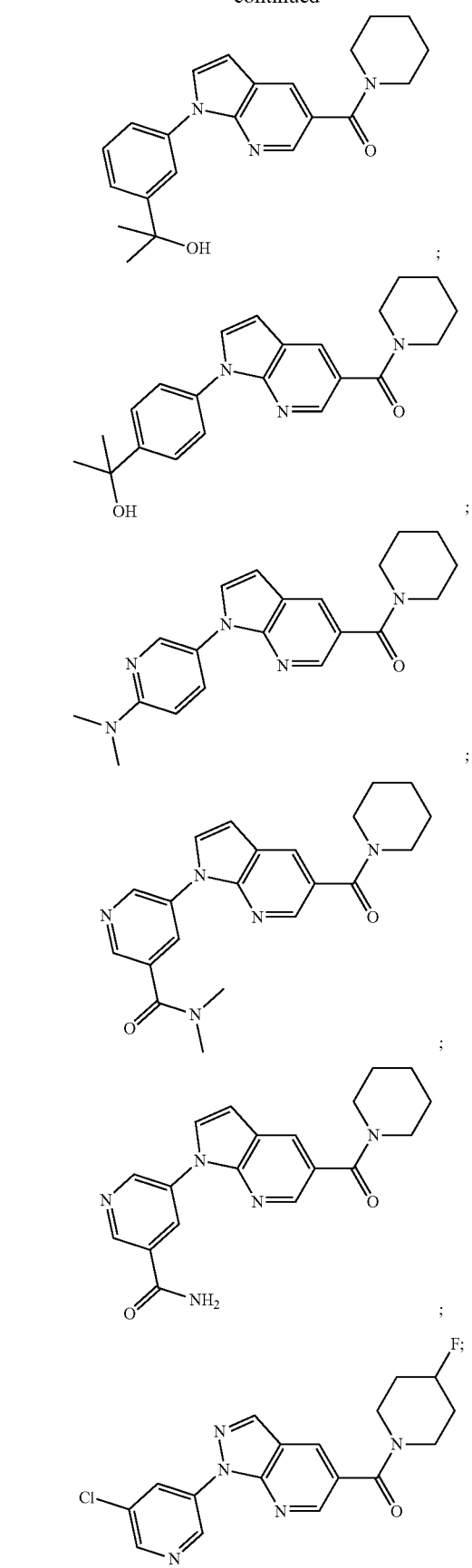

-continued
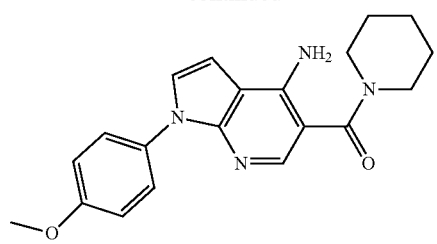
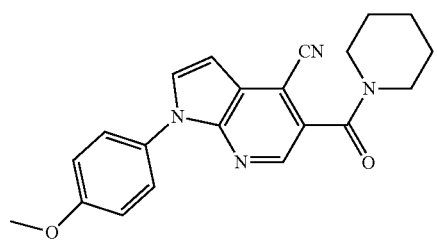
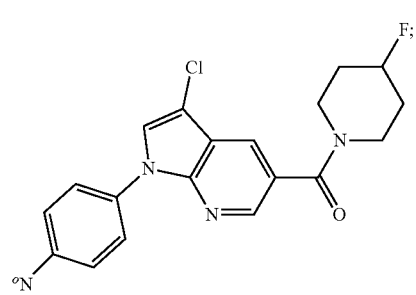
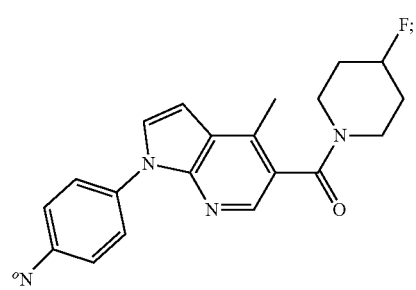
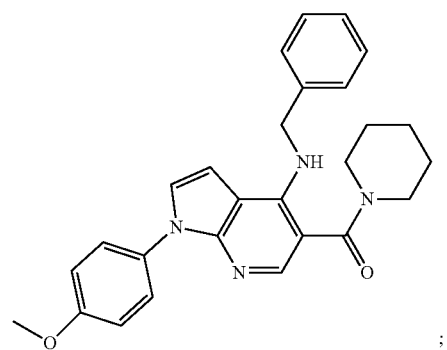
-continued
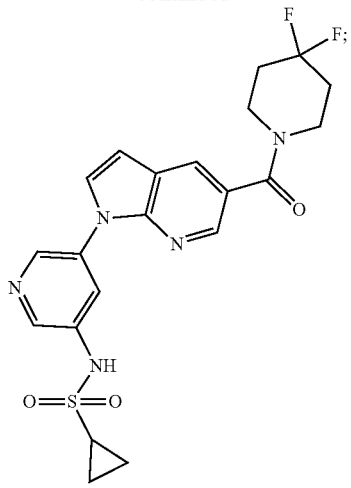
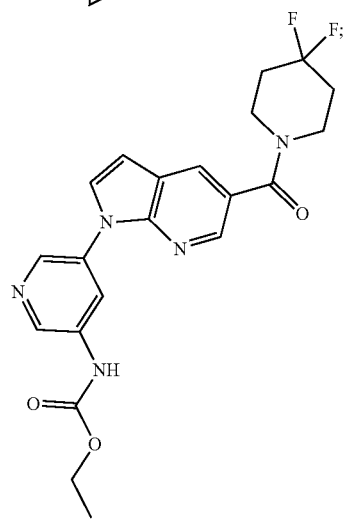
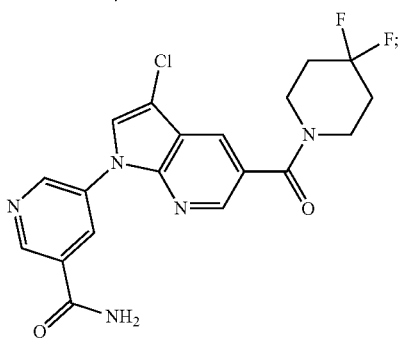
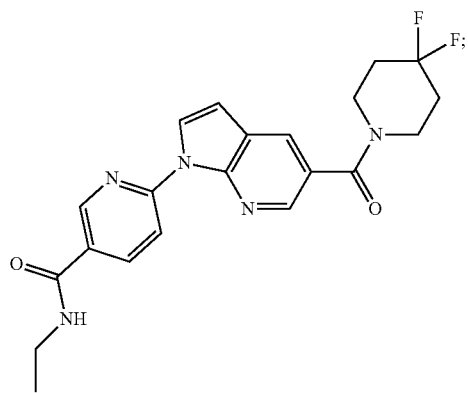

65
-continued
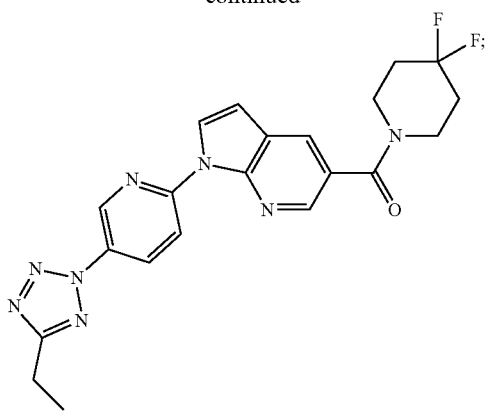
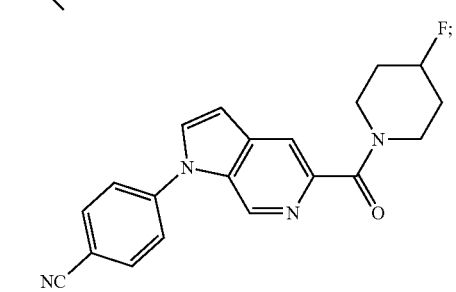
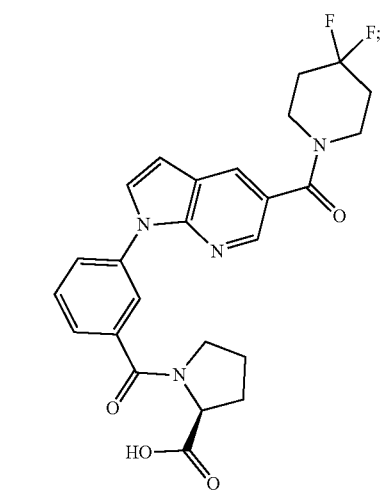
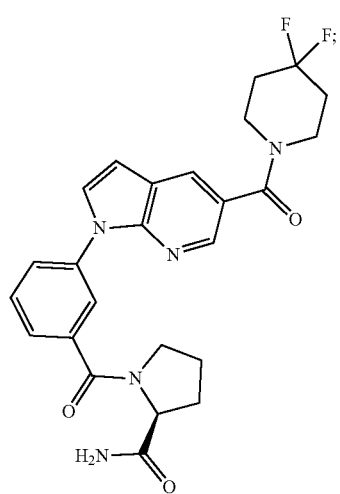
66
-continued
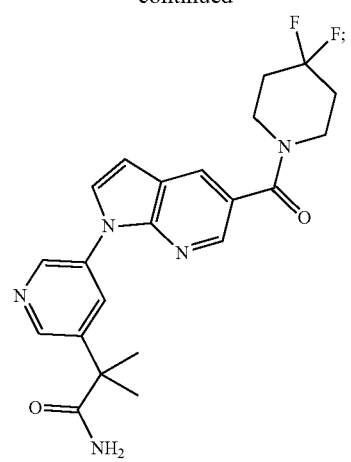
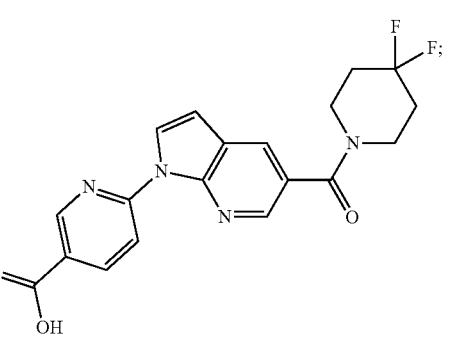
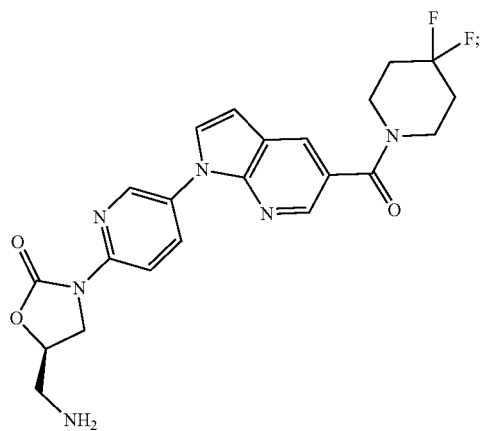
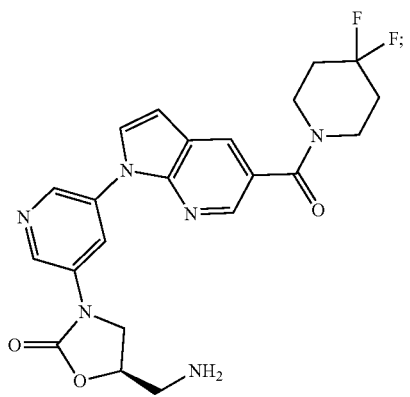

67
-continued
68
-continued
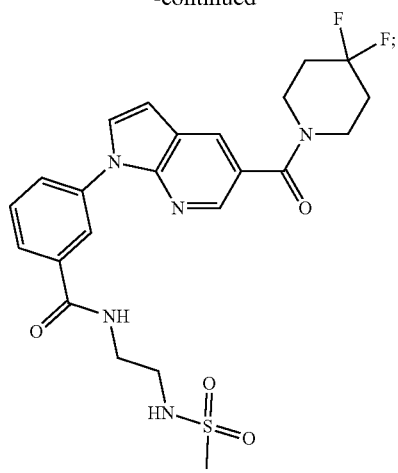
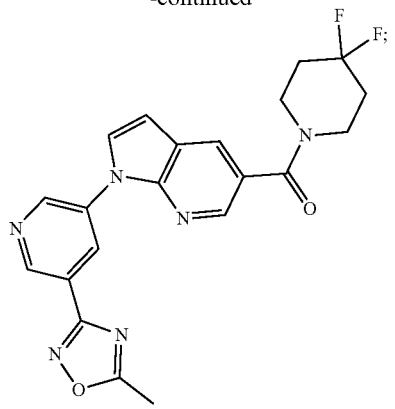

69
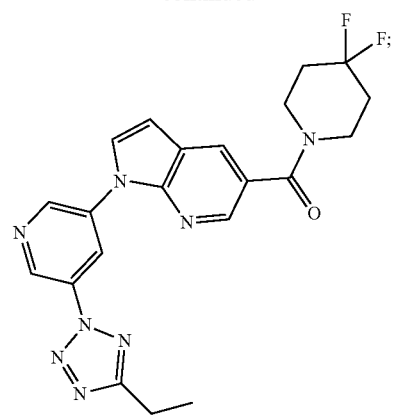
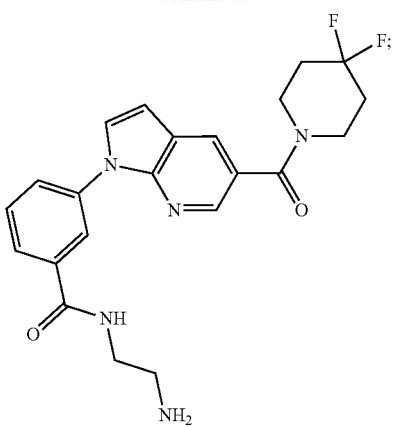
70
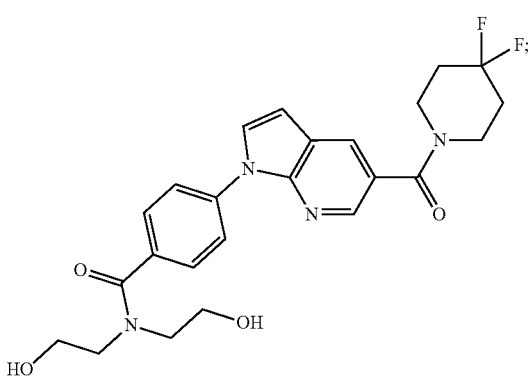
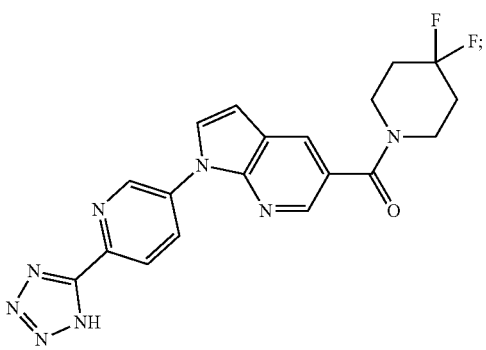
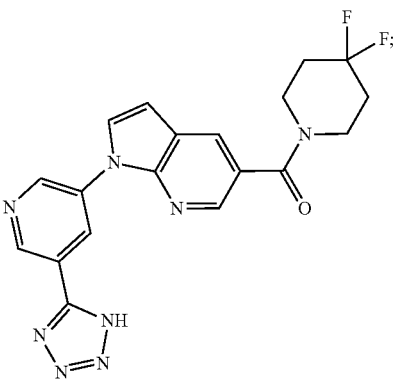

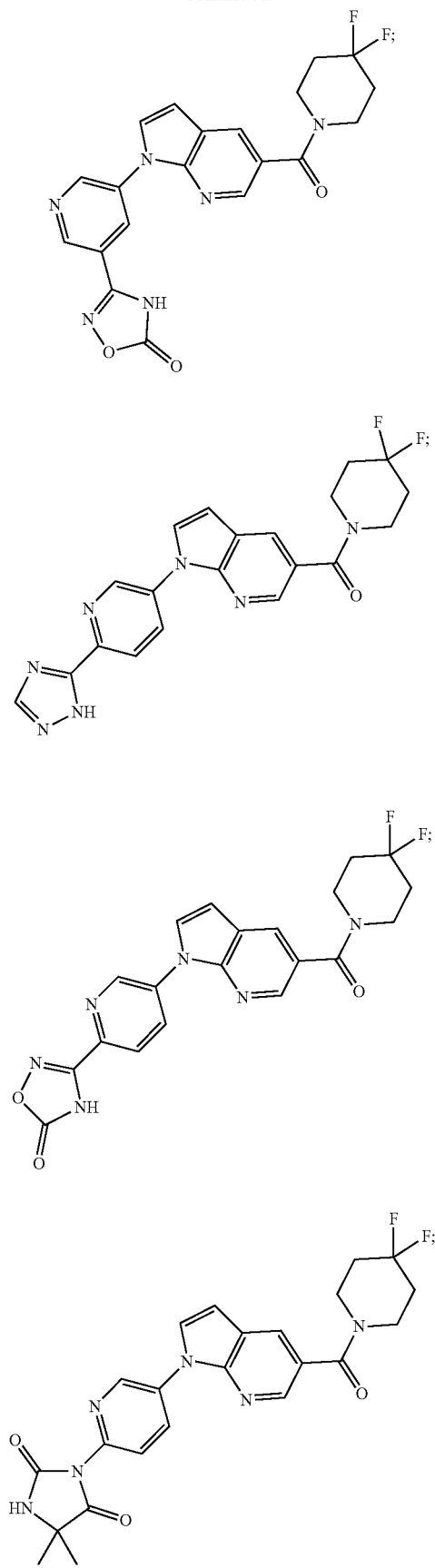
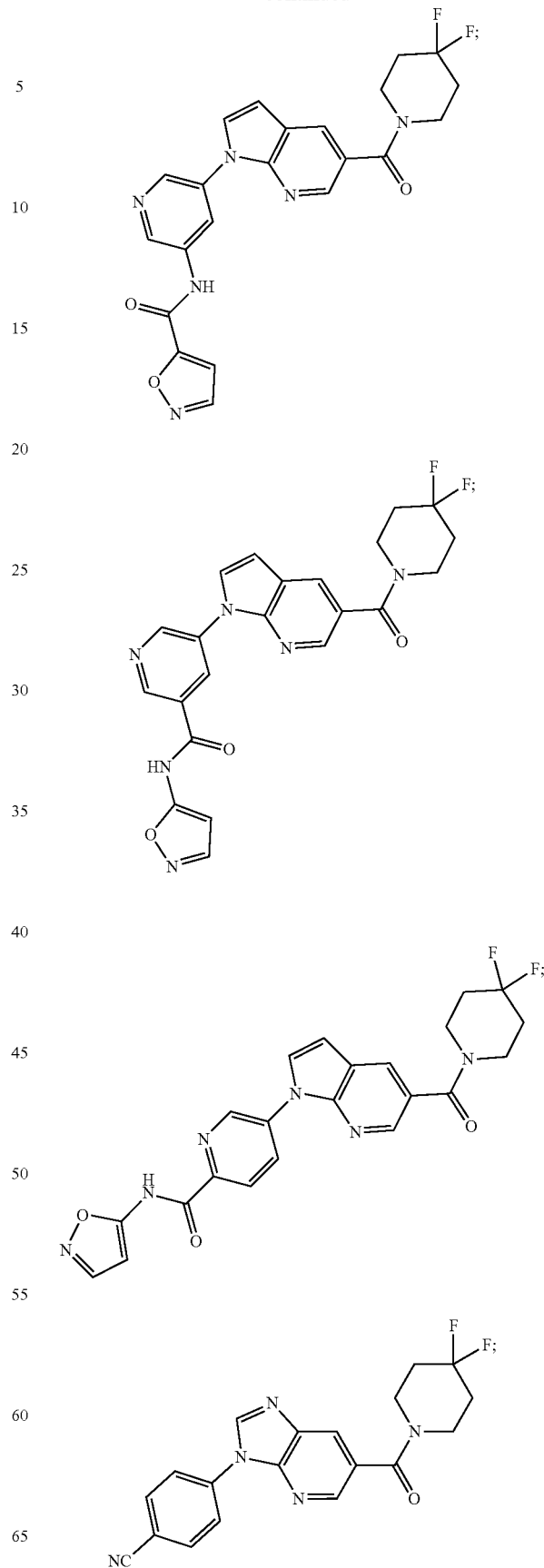

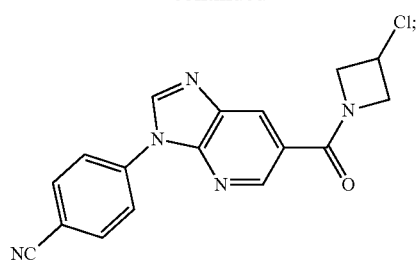
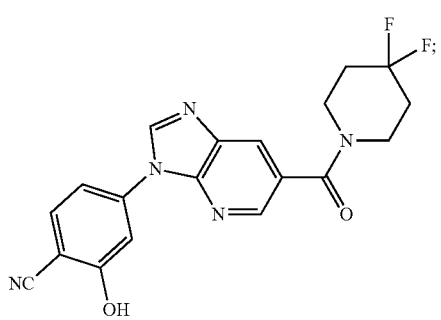
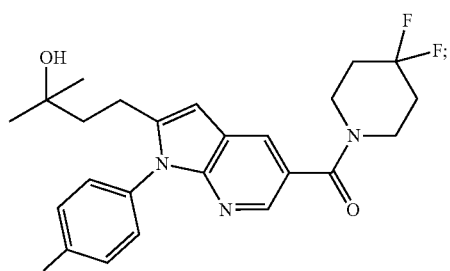
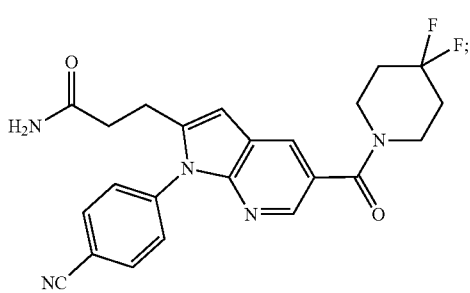
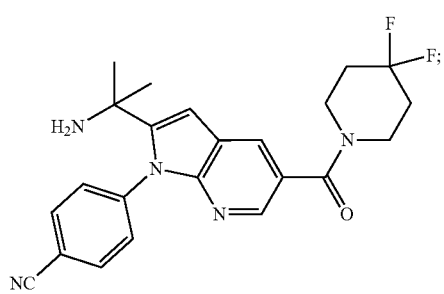
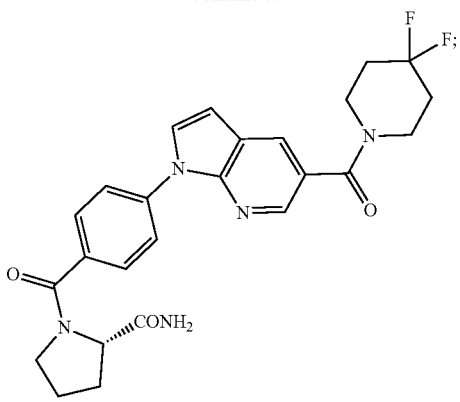
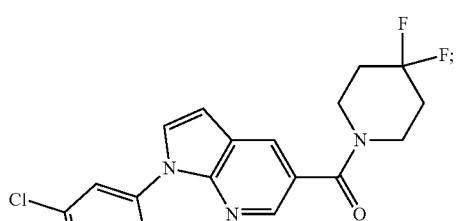
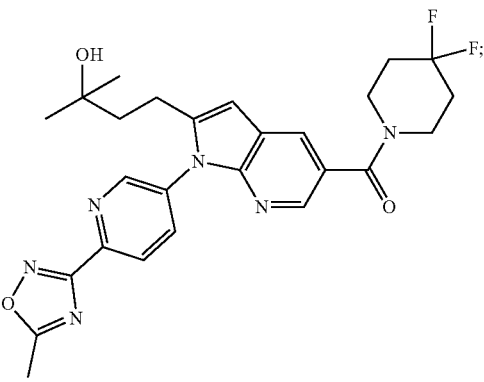
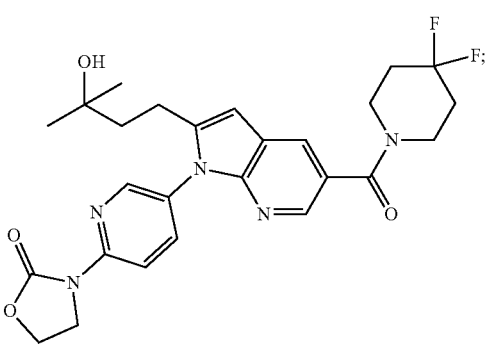

75
-continued
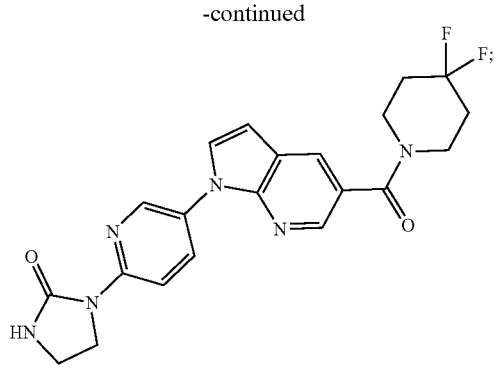
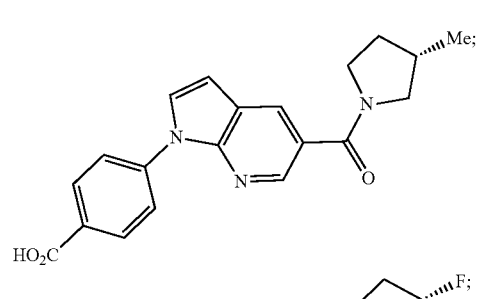
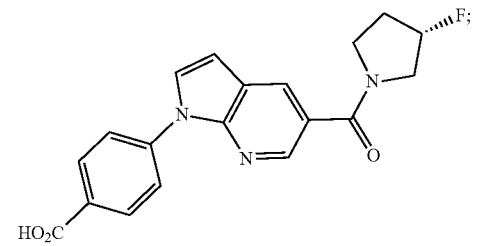
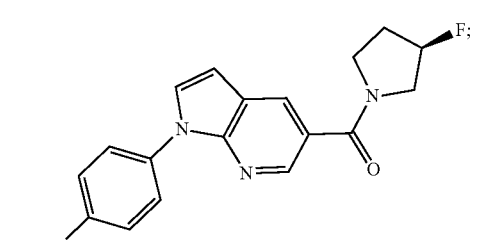
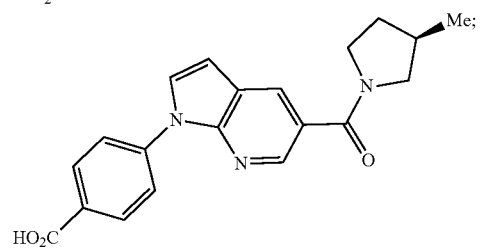
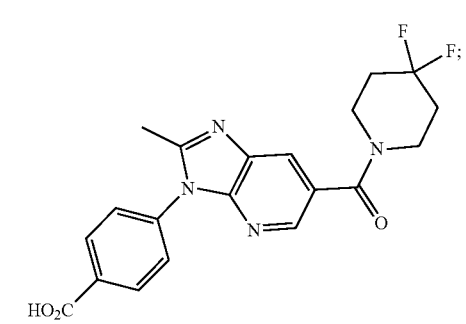
76
-continued
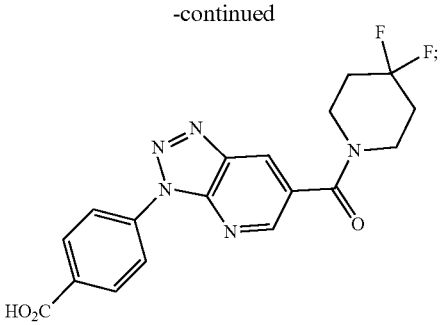
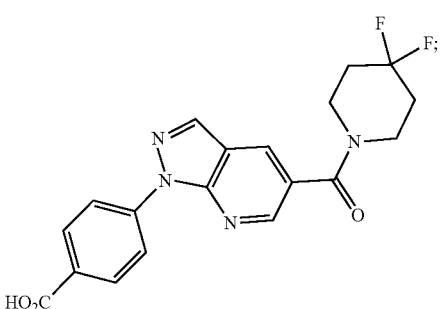
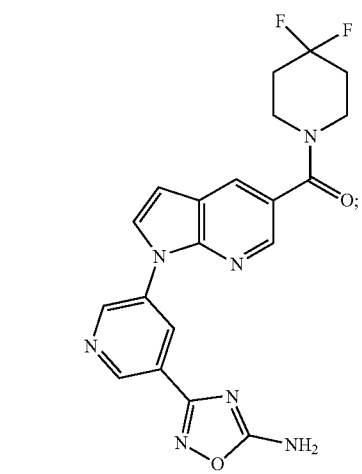
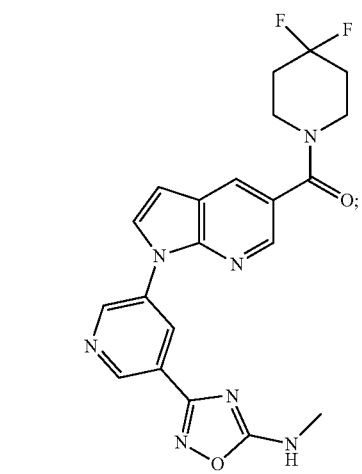

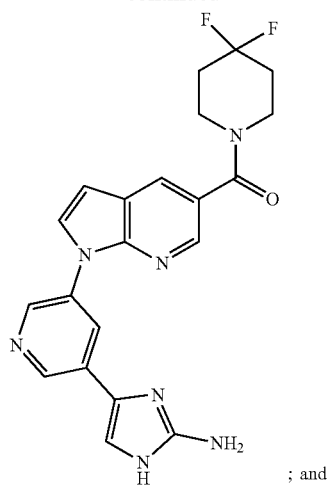
; and
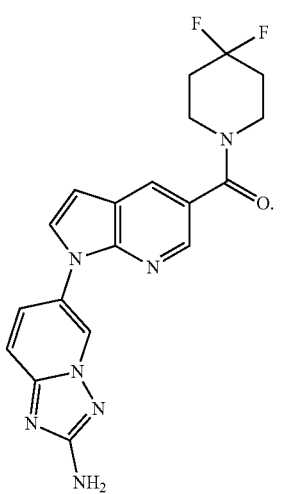 [SMILES: Nc1nc2ccc(-n3ccc4cc(C(=O)N5CCC(F)(F)CC5)cnc43)cn2n1]
In another aspect, provided herein is a composition comprising a compound selected from the group consisting of:
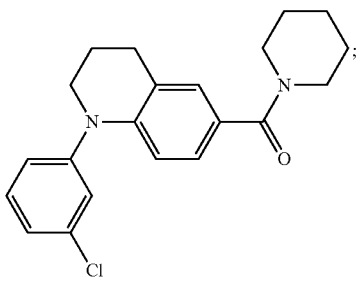
;
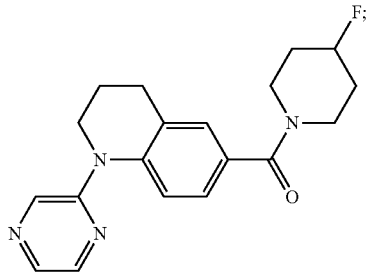
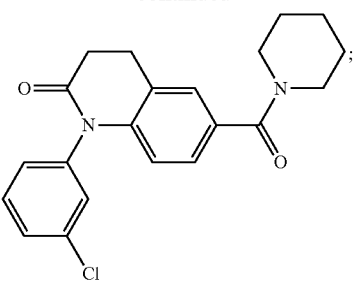
;
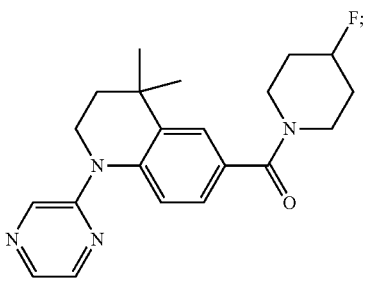
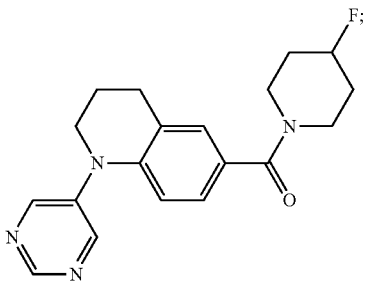
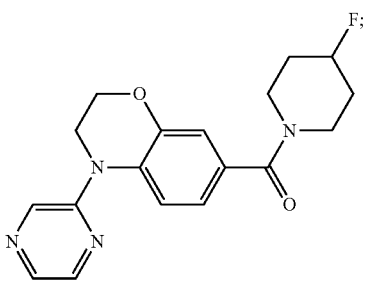

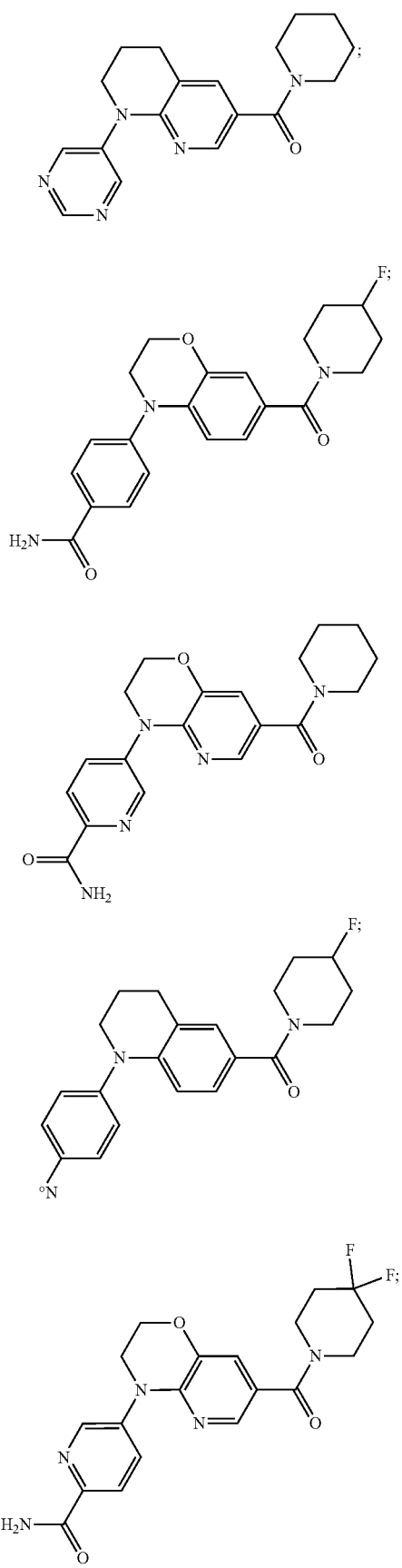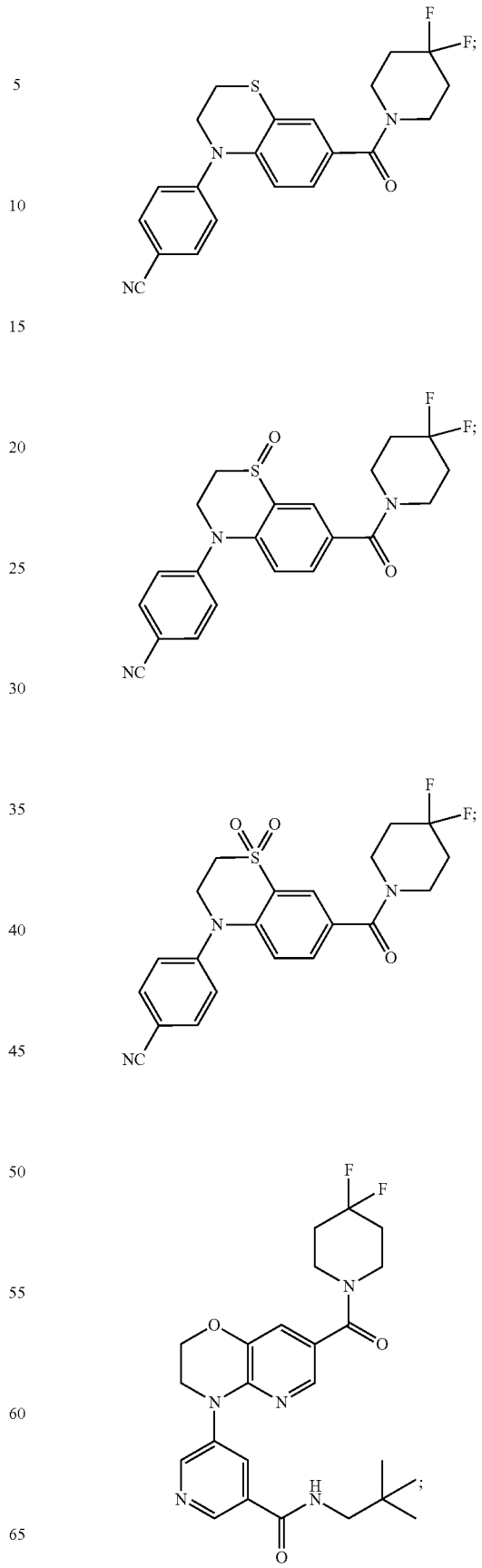

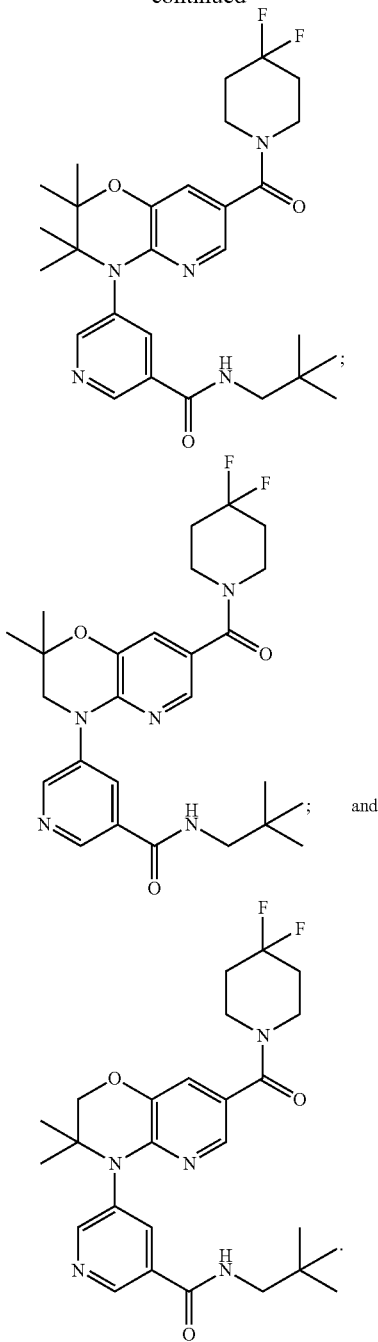

In another aspect, provided herein is a method of promoting and/or stimulation skin pigmentation, comprising administering one or more of the compositions described herein to a subject in need thereof.

In another aspect, provided herein is a method of inhibiting hair loss, comprising administering one or more of the compositions described herein to a subject in need thereof.

method of preventing and/or treating skin inflammation and/or damage, comprising administering one or more of the compositions described herein to a subject in need thereof.

In another aspect, provided herein is a method of preventing and/or treating vascular insufficiency, comprising administering one or more of the compositions described herein to a subject in need thereof.

In another aspect, provided herein is a method of preventing, treating, minimizing and/or reversing congestive heart failure, cardiomyopathy, comprising administering one or more of the compositions described herein to a subject in need thereof.

In another aspect, provided herein is a method of reducing cardiac ejection fraction, comprising administering one or more of the compositions described herein to a subject in need thereof.

In another aspect, provided herein is a method of preventing and/or treating a gastrointestinal disease, comprising administering one or more of the compositions described herein to a subject in need thereof.

In another aspect, provided herein is a method of preventing and/or treating renal dysfunction, comprising administering one or more of the compositions described herein to a subject in need thereof.

In another aspect, provided herein is a method of stimulation bone resorption and bone formation, comprising administering one or more of the compositions described herein to a subject in need thereof.

In another aspect, provided herein is a method of stimulating tissue regeneration by stimulating, comprising administering one or more of the compositions described herein to a subject in need thereof.

In another aspect, provided herein is a method of modulating cervical ripening, comprising administering one or more of the compositions described herein to a subject in need thereof.

In another aspect, provided herein is a method of promoting neuroprotection and/or stimulating neuronal regeneration, comprising administering one or more of the compositions described herein to a subject in need thereof.

In another aspect, provided herein is a method of treating and/or preventing a neurological disorder, a neuropsychiatric disorder, a neural injury, a neural toxicity disorder, a neuropathic pain, or a neural degenerative disorder, comprising administering one or more of the compositions described herein to a subject in need thereof.

In another aspect, provided herein is a method of treating and/or preventing fibrotic or adhesion disease, disorder or condition, comprising administering one or more of the compositions described herein to a subject in need thereof.

In another aspect, provided herein is a method of reducing and/or preventing scar formation, comprising administering one or more of the compositions described herein to a subject in need thereof.

In another aspect, provided herein is a method of treating and/or preventing muscle disorder, muscle injury and/or muscle atrophy, comprising administering one or more of the compositions described herein to a subject in need thereof.

In another aspect, provided herein is a method of treating and/or preventing fibrosis, comprising administering one or more of the compositions described herein to a subject in need thereof.

In another aspect, provided herein is a method of treating and/or preventing idiopathic pulmonary fibrosis, comprising administering one or more of the compositions described herein to a subject in need thereof.

In another aspect, provided herein is a method of treating and/or preventing kidney fibrosis, comprising administering one or more of the compositions described herein to a subject in need thereof.

In another aspect, provided herein is a method of stimulating muscle regeneration, comprising administering one or more of said compositions described herein to a subject in need thereof.

In another aspect, provided herein is a method of promoting organ fitness, comprising administering one or more of said compositions described herein to a subject in need thereof.

In another aspect, provided herein is a method of promoting wound healing, comprising administering one or more of said compositions described herein to a subject in need thereof.

In another aspect, provided herein is a method of treating acute kidney injury, comprising administering one or more of said compositions described herein to a subject in need thereof.

In another aspect, provided herein is a method of treating sarcopenia, comprising administering one or more of said compositions described herein to a subject in need thereof.

In another aspect, provided herein is a method of treating a neuromuscular disease, comprising administering one or more of said compositions of any of the preceding claims to a subject in need thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. An understanding of the features and advantages of the present invention may be obtained by reference to the following detailed description that sets forth illustrative embodiments, in which the principles of the invention are utilized, and the accompanying drawings of which:

FIG. 1 shows results of the cell-based assay for exemplary compounds.

DETAILED DESCRIPTION OF THE INVENTION

Definitions

Unless defined otherwise, all technical and scientific terms used herein have the same meaning as is commonly understood by one of skill in the art to which this disclosure belongs.

As used herein, the singular form "a", "an" and "the" includes plural references unless the context clearly dictates otherwise.

The term "$C_{x-y}$" when used in conjunction with a chemical moiety, such as alkyl, haloalkyl, or heteroalkyl, is meant to include groups that contain from x to y carbons in the chain. For example, the term "$C_{1-6}$ alkyl" refers to substituted or unsubstituted saturated hydrocarbon groups, including straight-chain alkyl and branched-chain alkyl groups that contain from 1 to 6 carbons. The term —$C_{x-y}$alkylene- refers to a substituted or unsubstituted alkylene chain with from x to y carbons in the alkylene chain. For example —$C_{1-6}$ alkylene- may be selected from methylene, ethylene, propylene, butylene, pentylene, and hexylene, any one of which is optionally substituted.

"Alkyl" refers to substituted or unsubstituted saturated hydrocarbon groups, including straight-chain alkyl and branched-chain alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Heteroalkyl" refers to a substituted or unsubstituted alkyl group which has one or more skeletal chain atoms selected from an atom other than carbon. Exemplary skeletal chain atoms selected from an atom other than carbon include, e.g., O, N, P, Si, S, or combinations thereof, wherein the nitrogen, phosphorus, and sulfur atoms may optionally be oxidized and the nitrogen heteroatom may optionally be quaternized. If given, a numerical range refers to the chain length in total. For example, a 3- to 8-membered heteroalkyl has a chain length of 3 to 8 atoms. Connection to the rest of the molecule may be through either a heteroatom or a carbon in the heteroalkyl chain. Unless stated otherwise specifically in the specification, a heteroalkyl group is optionally substituted by one or more substituents such as those substituents described herein.

"Aryl" refers to an aromatic ring wherein each of the atoms forming the ring is a carbon atom. Aryl groups can be optionally substituted. Examples of aryl groups include, but are not limited to, phenyl and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems wherein at least one of the rings in the ring system is aromatic, i.e., it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl is optionally substituted by one or more substituents such as those substituents described herein.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted.

The term "heterocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical may be partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. It is understood that when referring to the number of carbon atoms in a heterocloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, an oxo, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E-forms (or cis- and trans-forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that may induce a particular response in target cells, e.g., reduction of platelet adhesion and/or cell migration. The specific dose may vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein or enzyme. Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

Whenever a protein is referred to herein, it will be understood that a single protein can be referred to by different names. For example, "15-PGDH", "PGDH", and "hPGDH" all refer to the same protein, 15-hydroxyprostaglandin dehydrogenase.

Methods of Inhibiting 15-PGDH

Provided herein are methods of inhibiting 15-hydroxyprostaglandin dehydrogenase (15-PGDH).

In one aspect, provided herein is a method of inhibiting 15-hydroxyprostaglandin dehydrogenase (15-PGDH) in a subject in need thereof, comprising administering to the subject a therapeutically effective amount of a compound of Formula I:

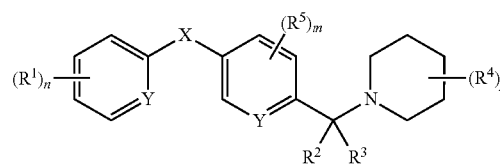

Formula I or a pharmaceutically acceptable salt thereof, wherein:
X is selected from —OCH$_2$—, —C(O)NH—, —NHC(O)—, —C(O)NMe-, —NMeC(O)—, —SCH$_2$—, —S(O)CH$_2$—, —SO$_2$CH$_2$—;
each Y is independently selected from N and CR$^{11}$;
each R$^1$ is independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, C$_{1-6}$haloalkyl, C$_{3-10}$cycloalkyl, C$_{6-10}$aryl, and 5- to 10-membered heteroaryl;
R$^2$ is H and R$^3$ is —CF$_3$; or
R$^2$ and R$^3$ are taken together to form oxo or thio;
each R$^4$ is independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl;
each R$^5$ is independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl;

$R^6$ and $R^7$ are independently selected at each occurrence from H, $C_{1-6}$ alkyl, $C_{1-6}$ heteroalkyl, $C_{1-6}$haloalkyl, and $C_{3-10}$cycloalkyl;

each $R^8$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^{10}$ is independently selected from H, $C_{1-6}$alkyl, $C_{1-6}$haloalkyl, and $C_{3-10}$cycloalkyl;

each $R^{11}$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;

n is 0, 1, 2, 3, 4, or 5;
m is 0, 1, 2, 3, or 4; and
p is 0, 1, 2, 3, 4, 5, 6, 7, 8, 9, or 10;
provided that the compound of Formula I is not

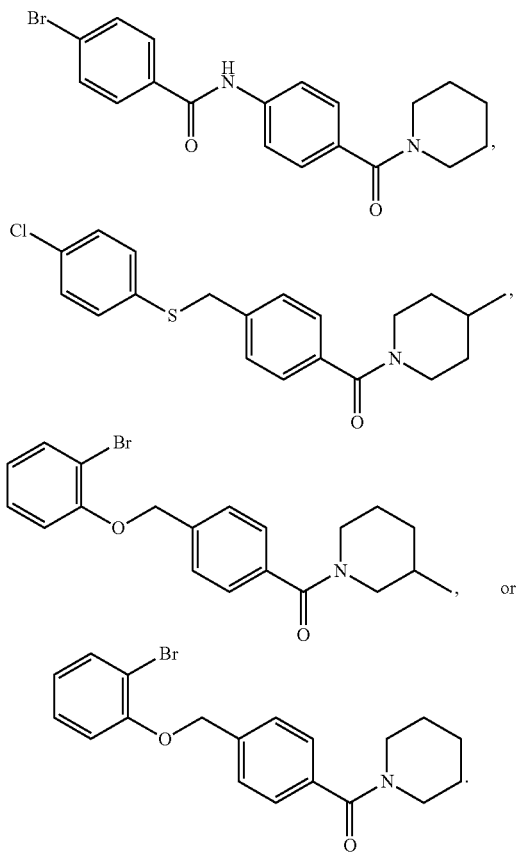

In some embodiments, X is selected from —$OCH_2$—, —$C(O)NH$—, —$NHC(O)$—, —$C(O)NMe$-, —$NMeC(O)$—, —$SCH_2$—, —$S(O)CH_2$—, and —$SO_2CH_2$—. In some embodiments, X is —$OCH_2$—. In some embodiments, X is —$C(O)NH$—. In some embodiments, X is —$NHC(O)$—. In some embodiments, X is —$C(O)NMe$-. In some embodiments, X is —$NMeC(O)$—. In some embodiments, X is —$SCH_2$—. In some embodiments, X is —$S(O)CH_2$—. In some embodiments, X is —$SO_2CH_2$—.

In some embodiments, each Y is independently selected from N and $CR^{11}$. In some embodiments, each Y is N. In some embodiments, each Y is $CR^{11}$. In some embodiments, one Y is N and the other Y is $CR^{11}$.

In some embodiments, each $R^1$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each $R^1$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^1$ is independently selected from halo, —$NR^6R^7$, —$OR^8$, —$C(O)R^8$, —$C(O)OR^8$, —$C(O)NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^1$ is independently selected from halo, —$NR^6R^7$, —$OR^8$, —$C(O)R^8$, and —$C(O)OR^8$.

In some embodiments, $R^2$ is H and $R^3$ is —$CF_3$. In some embodiments, $R^2$ and $R^3$ are taken together to form oxo. In some embodiments, $R^2$ and $R^3$ are taken together to form thio.

In some embodiments, each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^4$ is independently selected from halo, —$NR^6R^7$, —$OR^8$, —$C(O)R^8$, —$C(O)OR^8$, —$C(O)NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^4$ is independently selected from halo, —$NR^6R^7$, —$OR^8$, —$C(O)R^8$, and —$C(O)OR^8$.

In some embodiments, each $R^5$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, each $R^5$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^5$ is independently selected from halo, —$NR^6R^7$, —$OR^8$, —$C(O)R^8$, —$C(O)OR^8$, —$C(O)NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^5$ is independently selected from halo, —$NR^6R^7$, —$OR^8$, —$C(O)R^8$, and —$C(O)OR^8$.

In some embodiments, $R^6$ and $R^7$ are independently selected at each occurrence from H, $C_{1-6}$alkyl, $C_{1-6}$heteroalkyl, $C_{1-6}$ haloalkyl, and $C_{3-10}$cycloalkyl. In some embodiments, $R^6$ and $R^7$ are independently selected at each occurrence from H, $C_{1-6}$alkyl, $C_{1-6}$heteroalkyl, and $C_{1-6}$haloalkyl. In some embodiments, $R^6$ and $R^7$ are independently selected at each occurrence from H, and $C_{1-6}$alkyl.

In some embodiments, each $R^8$ is independently selected from H, $C_{1-6}$alkyl, $C_{1-6}$heteroalkyl, $C_{1-6}$ haloalkyl, $C_{3-10}$cycloalkyl, $C_{6-10}$aryl, and 5- to 10-membered heteroaryl. In some embodiments, each $R^8$ is independently selected from H, $C_{1-6}$alkyl, $C_{1-6}$heteroalkyl, $C_{1-6}$haloalkyl, and $C_{3-10}$cycloalkyl. In some embodiments, each $R^8$ is independently selected from H, $C_{1-6}$alkyl, $C_{1-6}$heteroalkyl, and $C_{1-6}$haloalkyl. In some embodiments, each $R^8$ is independently selected from H, and $C_{1-6}$ alkyl.

In some embodiments, each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each $R^9$ is independently selected from $C_{1-6}$alkyl, $C_{1-6}$heteroalkyl, $C_{1-6}$haloalkyl, and $C_{3-10}$cycloalkyl. In some embodiments, each $R^9$ is independently selected from $C_{1-6}$alkyl, $C_{1-6}$heteroalkyl, and $C_{1-6}$ haloalkyl. In some embodiments, each $R^9$ is independently selected from $C_{1-6}$alkyl.

In some embodiments, each $R^{10}$ is independently selected from H, $C_{1-6}$alkyl, $C_{1-6}$haloalkyl, and $C_{3-10}$cycloalkyl. In some embodiments, each $R^{10}$ is independently selected from H, $C_{1-6}$alkyl, and $C_{1-6}$haloalkyl. In some embodiments, each $R^{10}$ is independently selected from H and $C_{1-6}$alkyl.

In some embodiments, each $R^{11}$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, each $R^{11}$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^{11}$ is independently selected from halo, —$NR^6R^7$, —$OR^8$, —$C(O)R^8$, —$C(O)OR^8$, —$C(O)NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^{11}$ is independently selected from halo, —$NR^6R^7$, —$OR^8$, —$C(O)R^8$, and —$C(O)OR^8$.

In some embodiments, n is 0, 1, 2, 3, 4, or 5. In some embodiments, n is 0. In some embodiments, n is 1. In some embodiments, n is 2. In some embodiments, n is 3. In some embodiments, n is 4. In some embodiments, n is 5.

In some embodiments, m is 0, 1, 2, 3, or 4. In some embodiments, m is 0. In some embodiments, m is 1. In some embodiments, m is 2. In some embodiments, m is 3. In some embodiments, m is 4.

In some embodiments, p is 0, 1, 2, 3, 4, 5, 6, 7, 8, 9, or 10. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10.

In some embodiments, the compound is a compound of Formula Ia:

Formula Ia

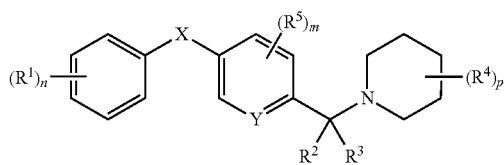

or a pharmaceutically acceptable salt thereof.

In some embodiments, the compound is a compound of Formula Ib:

Formula Ib

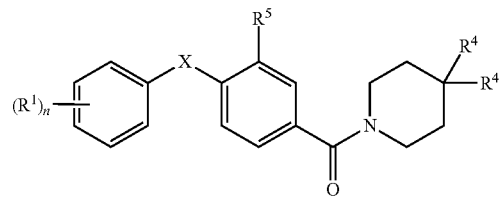

or a pharmaceutically acceptable salt thereof.

In another aspect, provided herein is a method of inhibiting 15-hydroxyprostaglandin dehydrogenase (15-PGDH) in a subject in need thereof, comprising administering to the subject a therapeutically effective amount of a compound of Formula II:

Formula II

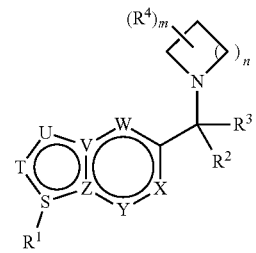

or a pharmaceutically acceptable salt thereof, wherein:

T, U, W, X, and Y are independently selected from N and $CR^5$;

S, V, and Z are independently selected from N and C;

$R^1$ is selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; wherein the alkyl, cycloalkyl, aryl, or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, and 5- to 10-membered heteroaryl;

$R^2$ is H and $R^3$ is —$CF_3$; or $R^2$ and $R^3$ are taken together to form oxo or thio;

each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or two $R^4$'s are taken together with the carbon atoms to which they are attached and any intervening atoms to form a $C_{3-10}$cycloalkyl, and any remaining $R^4$'s are independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$ haloalkyl, $C_{3-10}$cycloalkyl, 3- to 10-membered heterocycloalkyl, $C_{6-10}$aryl, and 5- to 10-membered heteroaryl;

each $R^5$ is independently selected from H, halo, $-NR^6R^7$, $-OR^8$, $-C(O)R^8$, $-C(O)OR^8$, $-C(O)NR^6R^7$, $-SOR^9$, $-SO_2R^9$, $-SO_2NR^6R^7$, $-NR^{10}C(O)R^8$, $-NR^{10}C(O)NR^6R^7$, $-NR^{10}SO_2R^8$, $-NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;

$R^6$ and $R^7$ are independently selected at each occurrence from H, $C_{1-6}$ alkyl, $C_{1-6}$ heteroalkyl, $C_{1-6}$haloalkyl, and $C_{3-10}$cycloalkyl;

each $R^8$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^{10}$ is independently selected from H, $C_{1-6}$alkyl, $C_{1-6}$haloalkyl, and $C_{3-10}$cycloalkyl; and n is 1, 2, 3, or 4; and m is 0, 1, 2, 3, 4, 5, 6, 7, 8, 9, or 10;

provided that the compound of Formula II is not

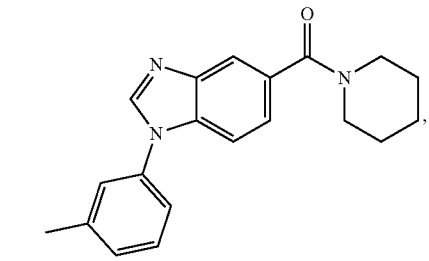

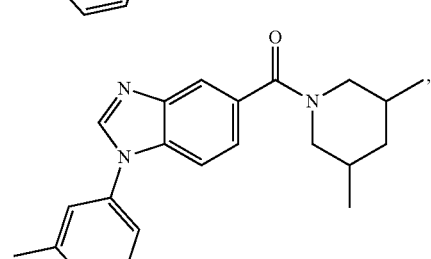

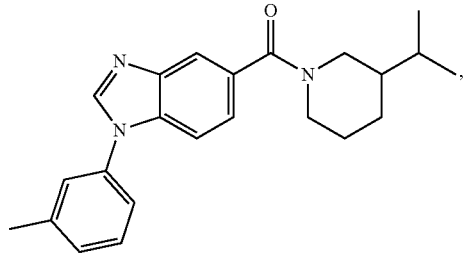

-continued

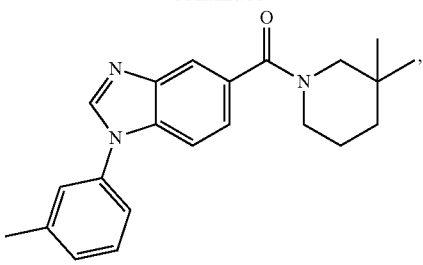

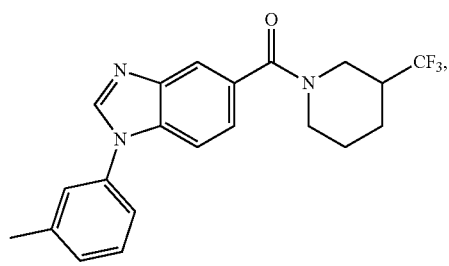

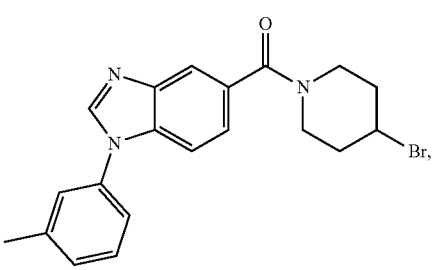

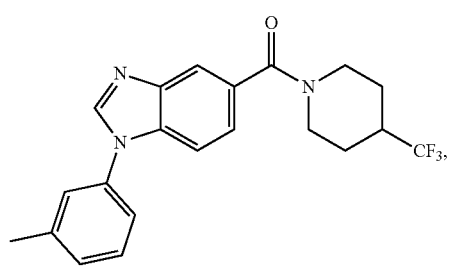

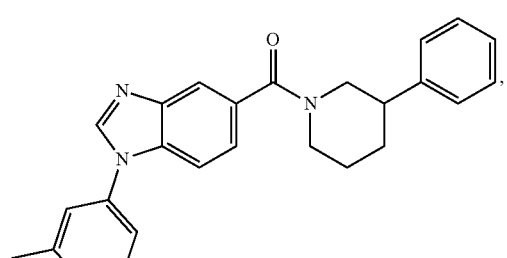

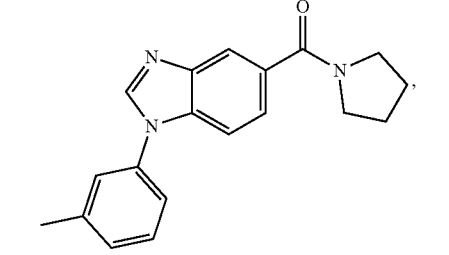

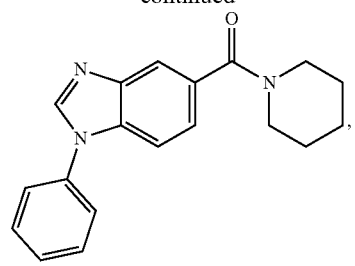
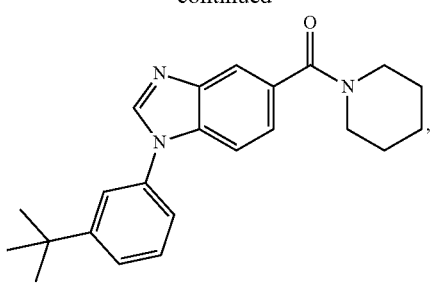
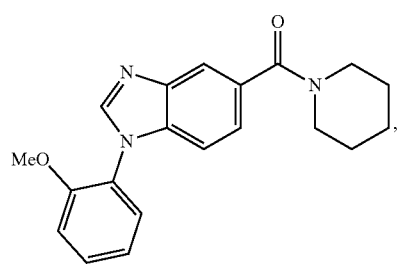
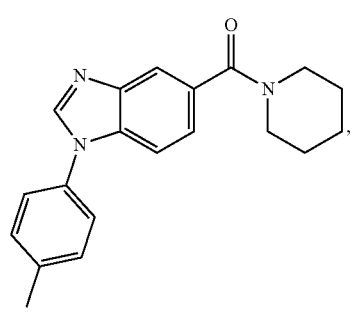
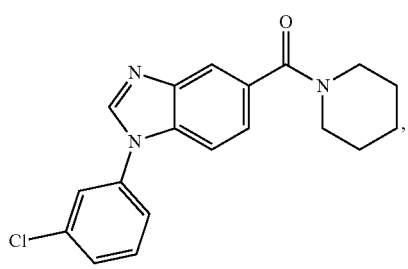
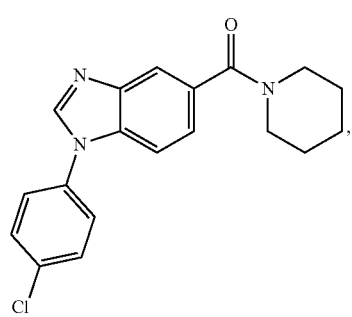
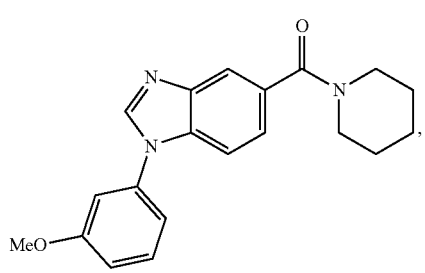
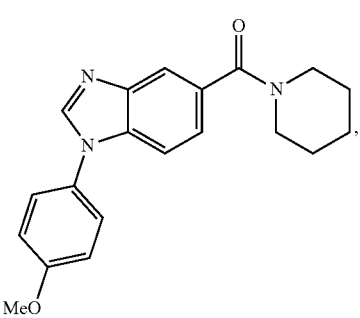
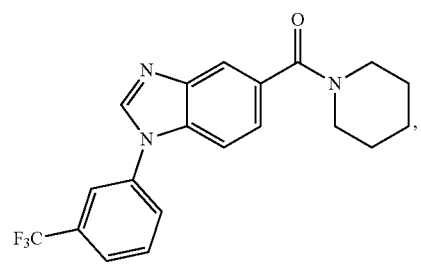
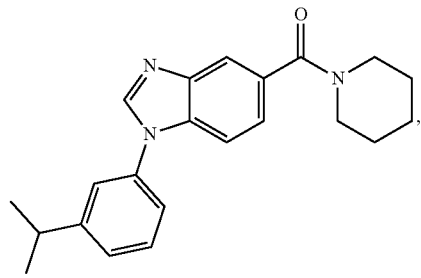
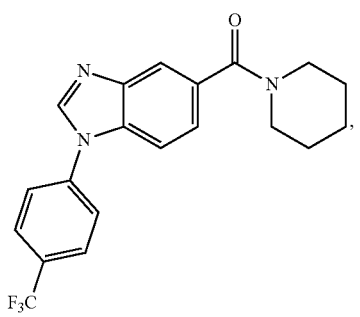

99
-continued
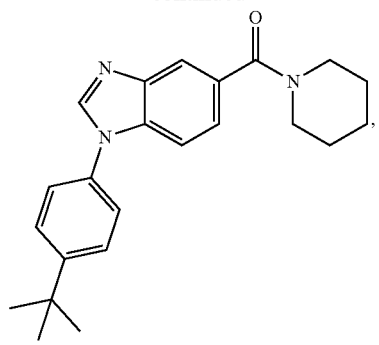
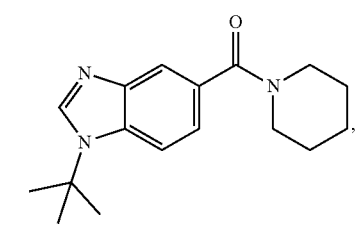
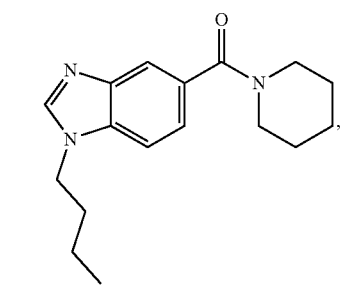
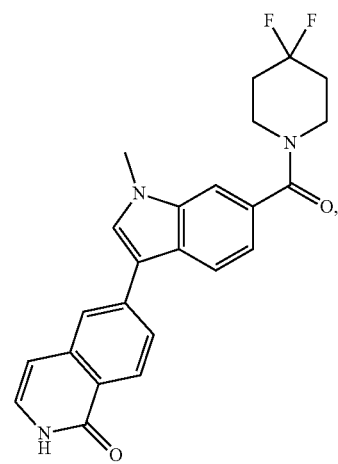 [SMILES: Cn1nc2cc(C(=O)N3CCC(F)(F)CC3)ccc2c1-c1ccc2c(=O)[nH]ccc2c1]
100
-continued
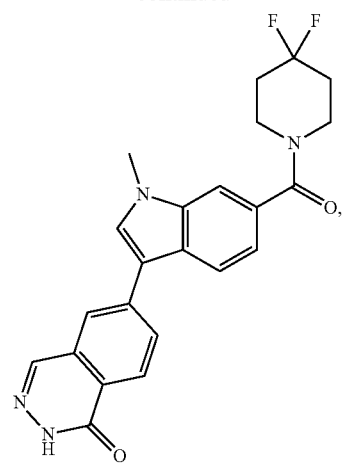
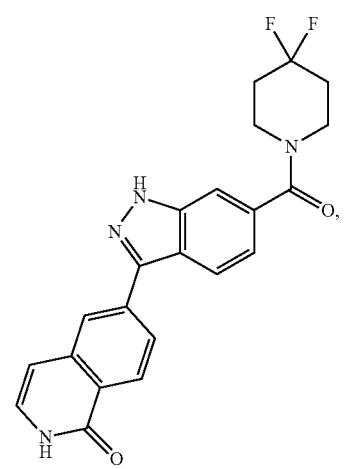
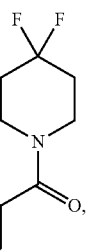

101
-continued

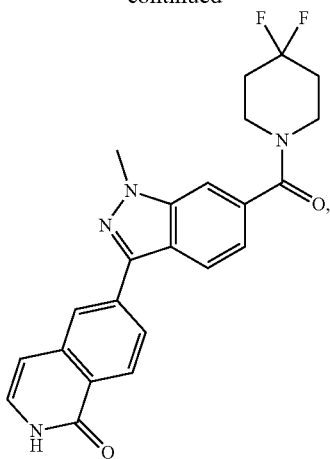

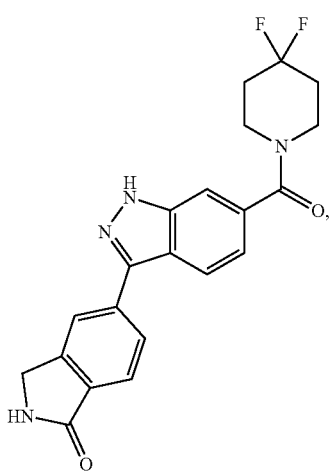

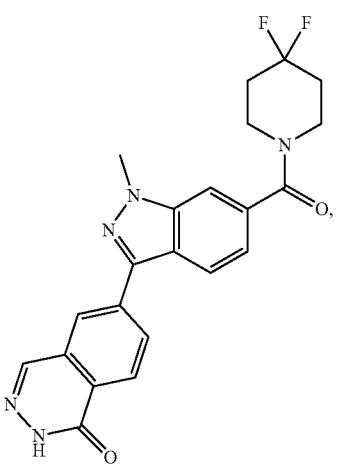

102
-continued

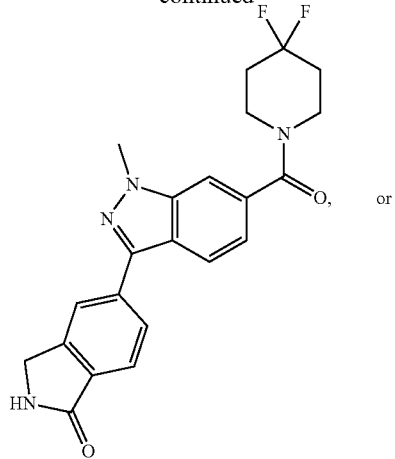

or

In some embodiments, T, U, W, X, and Y are independently selected from N and $CR^5$. In some embodiments, at least one of T, U, W, X, and Y is N and the rest are $CR^5$. In some embodiments, at least two of T, U, W, X, and Y are N and the rest are $CR^5$. In some embodiments, at least three of T, U, W, X, and Y are N and the rest are $CR^5$. In some embodiments, at least four of T, U, W, X, and Y are N and the rest are $CR^5$. In some embodiments, T, U, W, X, and Y are $CR^5$. In some embodiments, T, U, W, X, and Y are N.

In some embodiments, S, V, and Z are independently selected from N and C. In some embodiments, at least one of S, V, and Z is N and the rest are C. In some embodiments, at least two of S, V, and Z are N and the rest are C. In some embodiments, S, V, and Z are N. In some embodiments, S, V, and Z are C.

In some embodiments, $R^1$ is selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; wherein the alkyl, cycloalkyl, aryl, or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$ haloalkyl, $C_{3-10}$cycloalkyl, and 5- to 10-membered heteroaryl. In some embodiments, $R^1$ is selected from $C_{1-6}$alkyl, $C_{1-6}$heteroalkyl, $C_{1-6}$ haloalkyl, $C_{6-10}$aryl, and 5- to 10-membered heteroaryl; wherein the alkyl, aryl, or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, C$_{1-6}$haloalkyl, C$_{3-10}$cycloalkyl, and 5- to 10-membered heteroaryl. In some embodiments, R$^1$ is selected from C$_{6-10}$aryl and 5- to 10-membered heteroaryl; wherein the aryl or heteroaryl is optionally substituted with 1 to 3 substituents independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, C$_{1-6}$ haloalkyl, C$_{3-10}$cycloalkyl, and 5- to 10-membered heteroaryl. In some embodiments, R$^1$ is selected from C$_{6-10}$aryl and 5- to 10-membered heteroaryl; wherein the aryl or heteroaryl is optionally substituted with 1 to 3 substituents independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, and —NR$^{10}$SO$_2$NR$^6$R$^7$. In some embodiments, R$^1$ is selected from C$_{6-10}$aryl and 5- to 10-membered heteroaryl; wherein the aryl or heteroaryl is optionally substituted with 1 to 3 substituents independently selected from halo, —NR$^6$R$^7$, —OR$^8$, —C(O)R$^8$, —C(O)OR$^8$, and —C(O)NR$^6$R$^7$.

In some embodiments, R$^2$ is H and R$^3$ is —CF$_3$. In some embodiments, R$^2$ and R$^3$ are taken together to form oxo. In some embodiments, R$^2$ and R$^3$ are taken together to form thio.

In some embodiments, each R$^4$ is independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, each R$^4$ is independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, and C$_{1-6}$haloalkyl. In some embodiments, each R$^4$ is independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, and —NR$^{10}$SO$_2$NR$^6$R$^7$. In some embodiments, each R$^4$ is independently selected from halo, —NR$^6$R$^7$, —OR$^8$, —C(O)R$^8$, —C(O)OR$^8$, and —C(O)NR$^6$R$^7$. In some embodiments, each R$^4$ is halo. In some embodiments, each R$^4$ is fluoro.

In some embodiments, two R$^4$'s are taken together with the carbon atoms to which they are attached and any intervening atoms to form a C$_{3-10}$cycloalkyl, and any remaining R$^4$'s are independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$ heteroalkyl, C$_{1-6}$ haloalkyl, C$_{3-10}$cycloalkyl, 3- to 10-membered heterocycloalkyl, C$_{6-10}$aryl, and 5- to 10-membered heteroaryl. In some embodiments, two R$^4$'s are taken together with the carbon atoms to which they are attached and any intervening atoms to form a C$_{3-10}$cycloalkyl, and any remaining R$^4$'s are independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, and C$_{1-6}$haloalkyl. In some embodiments, two R$^4$'s are taken together with the carbon atoms to which they are attached and any intervening atoms to form a C$_{3-10}$cycloalkyl, and any remaining R$^4$'s are independently selected from halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, and —NR$^{10}$SO$_2$NR$^6$R$^7$. In some embodiments, two R$^4$'s are taken together with the carbon atoms to which they are attached and any intervening atoms to form a C$_{3-10}$cycloalkyl, and any remaining R$^4$'s are independently selected from halo, —NR$^6$R$^7$, —OR$^8$, —C(O)R$^8$, —C(O)OR$^8$, and —C(O)NR$^6$R$^7$. In some embodiments, two R$^4$'s are taken together with the carbon atoms to which they are attached and any intervening atoms to form a C$_{3-10}$cycloalkyl, and any remaining R$^4$'s are independently selected from halo. In some embodiments, two R$^4$'s are taken together with the carbon atoms to which they are attached and any intervening atoms to form a C$_{3-10}$cycloalkyl, and any remaining R$^4$'s are fluoro.

In some embodiments, each R$^5$ is independently selected from H, halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, each R$^5$ is independently selected from H, halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, —NR$^{10}$SO$_2$NR$^6$R$^7$, C$_{1-6}$alkyl, C$_{1-6}$heteroalkyl, and C$_{1-6}$haloalkyl. In some embodiments, each R$^5$ is independently selected from H, halo, —NR$^6$R$^7$, —OR$^8$, —C(O)R$^8$, —C(O)OR$^8$, —C(O)NR$^6$R$^7$, —SOR$^9$, —SO$_2$R$^9$, —SO$_2$NR$^6$R$^7$, —NR$^{10}$C(O)R$^8$, —NR$^{10}$C(O)NR$^6$R$^7$, —NR$^{10}$SO$_2$R$^8$, and —NR$^{10}$SO$_2$NR$^6$R$^7$. In some embodiments, each R$^5$ is independently selected from H, halo, —NR$^6$R$^7$, —OR$^8$, —C(O)R$^8$, —C(O)OR$^8$, and —C(O)NR$^6$R$^7$. In some embodiments, each R$^5$ is independently selected from H and halo.

In some embodiments, R$^6$ and R$^7$ are independently selected at each occurrence from H, C$_{1-6}$alkyl, C$_{1-6}$heteroalkyl, C$_{1-6}$ haloalkyl, and C$_{3-10}$cycloalkyl. In some embodiments, R$^6$ and R$^7$ are independently selected at each occurrence from H, C$_{1-6}$alkyl, C$_{1-6}$heteroalkyl, and C$_{1-6}$haloalkyl. In some embodiments, R$^6$ and R$^7$ are independently selected at each occurrence from H and C$_{1-6}$alkyl.

In some embodiments, each R$^8$ is independently selected from H, C$_{1-6}$alkyl, C$_{1-6}$heteroalkyl, C$_{1-6}$haloalkyl, C$_{3-10}$cycloalkyl, C$_{6-10}$aryl, and 5- to 10-membered heteroaryl. In some embodiments, each R$^8$ is independently selected from H, C$_{1-6}$alkyl, C$_{1-6}$heteroalkyl, C$_{1-6}$haloalkyl, and C$_{3-10}$cycloalkyl. In some embodiments, each R$^8$ is independently selected from H, C$_{1-6}$alkyl, C$_{1-6}$heteroalkyl, and C$_{1-6}$haloalkyl. In some embodiments, each R$^8$ is independently selected from H and C$_{1-6}$ alkyl.

In some embodiments, each R$^9$ is independently selected from C$_{1-6}$alkyl, C$_{1-6}$heteroalkyl, C$_{1-6}$haloalkyl, C$_{3-10}$cycloalkyl, C$_{6-10}$aryl, and 5- to 10-membered heteroaryl. In some embodiments, each R$^9$ is independently selected from C$_{1-6}$alkyl, C$_{1-6}$heteroalkyl, C$_{1-6}$haloalkyl, and C$_{3-10}$cycloalkyl. In some embodiments, each R$^9$ is independently selected from C$_{1-6}$alkyl, C$_{1-6}$heteroalkyl, and C$_{1-6}$ haloalkyl. In some embodiments, each R$^9$ is independently selected from C$_{1-6}$alkyl.

In some embodiments, each R$^{10}$ is independently selected from H, C$_{1-6}$alkyl, C$_{1-6}$haloalkyl, and C$_{3-10}$cycloalkyl. In some embodiments, each R$^{10}$ is independently selected from H, C$_{1-6}$alkyl, and C$_{1-6}$haloalkyl. In some embodiments, each R$^{10}$ is independently selected from H and C$_{1-6}$alkyl.

In some embodiments, n is 1, 2, 3, or 4. In some embodiments, n is 1. In some embodiments, n is 2. In some embodiments, n is 3. In some embodiments, n is 4.

In some embodiments, m is 0, 1, 2, 3, 4, 5, 6, 7, 8, 9, or 10. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, the compound is a compound of Formula IIa:

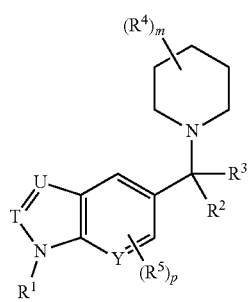

Formula IIa or a pharmaceutically acceptable salt thereof, wherein p is 0, 1, or 2.

In some embodiments, p is 0, 1, or 2. In some embodiments, p is 0. In some embodiments, p is 1. In some embodiments, p is 2.

In some embodiments, the compound is a compound of Formula IIb:

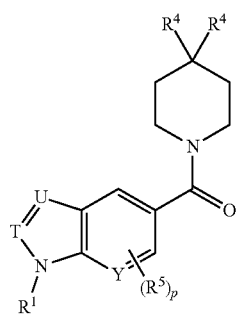

Formula IIb or a pharmaceutically acceptable salt thereof, wherein p is 0, 1, or 2.

In some embodiments, p is 0, 1, or 2. In some embodiments, p is 0. In some embodiments, p is 1. In some embodiments, p is 2.

In some embodiments, the compound is a compound of Formula IIc:

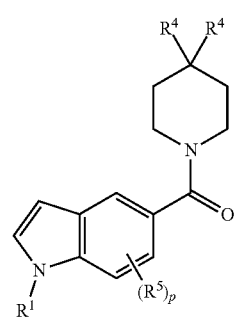

Formula IIc or a pharmaceutically acceptable salt thereof, wherein p is 0, 1, 2, 3, 4, or 5.

In some embodiments, p is 0, 1, 2, 3, 4, or 5. In some embodiments, p is 0. In some embodiments, p is 1. In some embodiments, p is 2. In some embodiments, p is 3. In some embodiments, p is 4. In some embodiments, p is 5.

In some embodiments, the compound is a compound of Formula IId:

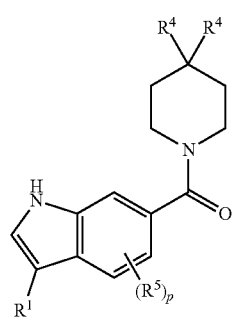

Formula IId or a pharmaceutically acceptable salt thereof, wherein p is 0, 1, 2, 3, or 4.

In some embodiments, p is 0, 1, 2, 3, or 4. In some embodiments, p is 0. In some embodiments, p is 1. In some embodiments, p is 2. In some embodiments, p is 3. In some embodiments, p is 4.

In some embodiments, the compound is a compound of Formula IIe:

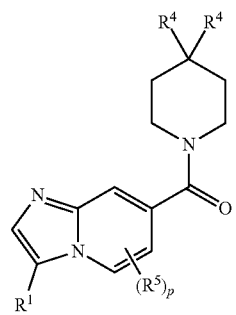

Formula IIe or a pharmaceutically acceptable salt thereof, wherein p is 0, 1, 2, 3, or 4.

In some embodiments, p is 0, 1, 2, 3, or 4. In some embodiments, p is 0. In some embodiments, p is 1. In some embodiments, p is 2. In some embodiments, p is 3. In some embodiments, p is 4.

In some embodiments, the compound is a compound of Formula IIf:

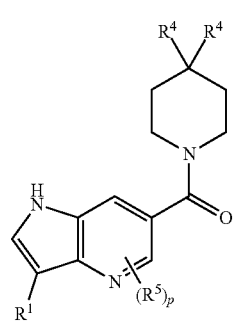

Formula IIf or a pharmaceutically acceptable salt thereof, wherein p is 0, 1, or 3.

In some embodiments, p is 0, 1, 2, or 3. In some embodiments, p is 0. In some embodiments, p is 1. In some embodiments, p is 2. In some embodiments, p is 3.

In some embodiments, the compound is a compound of Formula IIg:

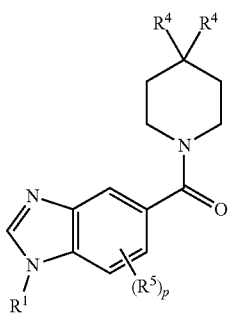

Formula IIg or a pharmaceutically acceptable salt thereof, wherein p is 0, 1, 2, 3, or 4.

In some embodiments, p is 0, 1, 2, 3, or 4. In some embodiments, p is 0. In some embodiments, p is 1. In some embodiments, p is 2. In some embodiments, p is 3. In some embodiments, p is 4.

In some embodiments, the compound is a compound of Formula IIh:

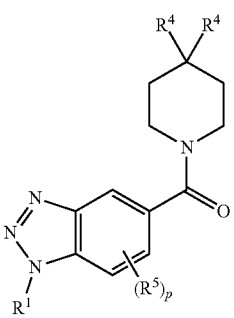

Formula IIh or a pharmaceutically acceptable salt thereof, wherein p is 0, 1, 2, or 3.

In some embodiments, p is 0, 1, 2, or 3. In some embodiments, p is 0. In some embodiments, p is 1. In some embodiments, p is 2. In some embodiments, p is 3.

In some embodiments, the compound is a compound of Formula IIi:

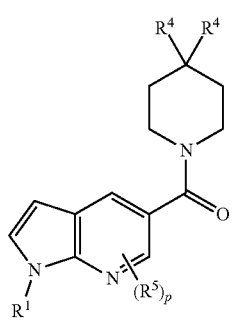

Formula IIi or a pharmaceutically acceptable salt thereof, wherein p is 0, 1, 2, 3, or 4.

In some embodiments, p is 0, 1, 2, 3, or 4. In some embodiments, p is 0. In some embodiments, p is 1. In some embodiments, p is 2. In some embodiments, p is 3. In some embodiments, p is 4.

In some embodiments, the compound is a compound of Formula IIj:

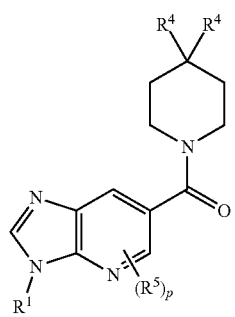

Formula IIj or a pharmaceutically acceptable salt thereof, wherein p is 0, 1, 2, or 3.

In some embodiments, p is 0, 1, 2, or 3. In some embodiments, p is 0. In some embodiments, p is 1. In some embodiments, p is 2. In some embodiments, p is 3.

In some embodiments, the compound is a compound of Formula IIn:

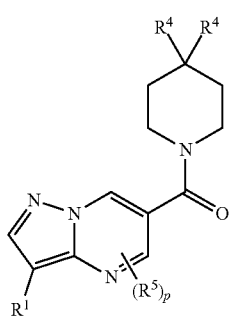

Formula IIn or a pharmaceutically acceptable salt thereof, wherein p is 0, 1, 2, or 3.

In some embodiments, p is 0, 1, 2, or 3. In some embodiments, p is 0. In some embodiments, p is 1. In some embodiments, p is 2. In some embodiments, p is 3.

In some embodiments, the compound is a compound of Formula IIp:

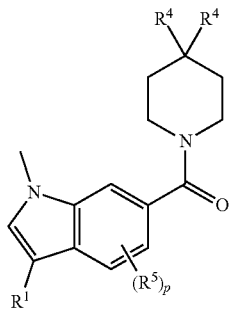

Formula IIp or a pharmaceutically acceptable salt thereof, wherein p is 0, 1, 2, 3, or 4.

In some embodiments, p is 0, 1, 2, 3, or 4. In some embodiments, p is 0. In some embodiments, p is 1. In some embodiments, p is 2. In some embodiments, p is 3. In some embodiments, p is 4.

In another aspect, provided herein is a method of inhibiting 15-hydroxyprostaglandin dehydrogenase (15-PGDH) in a subject in need thereof, comprising administering to the subject a therapeutically effective amount of a compound of Formula III:

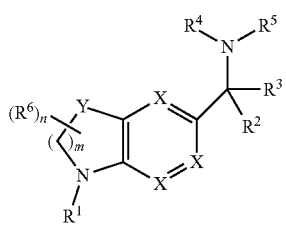

Formula III or a pharmaceutically acceptable salt thereof, wherein:
each X is independently selected from N and $CR^7$;
Y is selected from O, S, $SO_2$, and $C(R^8)_2$;
$R^1$ is selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; wherein the alkyl, cycloalkyl, aryl, or heteroaryl is optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
$R^2$ is H and $R^3$ is $-CF_3$; or
$R^2$ and $R^3$ are taken together to form oxo or thio;
$R^4$ and $R^5$ are independently selected from $C_{1-6}$alkyl, $C_{1-6}$heteroalkyl, $C_{1-6}$haloalkyl, and $C_{3-10}$cycloalkyl; wherein each alkyl, heteroalkyl, haloalkyl, and cycloalkyl is independently optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^1$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or
$R^4$ and $R^5$ are taken together, along with the nitrogen atom to which they are attached, to form a 3- to 10-membered heterocycloalkyl optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^2$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$ alkyl, $C_{1-6}$ heteroalkyl, $C_{1-6}$ haloalkyl, $C_{3-10}$cycloalkyl, $C_{6-10}$aryl, and 5- to 10-membered heteroaryl;
each $R^6$ is independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or
two $R^6$'s attached to the same carbon atom are taken together to form oxo, thio, or $C_{3-10}$cycloalkyl, and any remaining $R^6$'s are independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
each $R^7$ is independently selected from H, halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
each $R^8$ is independently selected from H, halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl; or
two $R^8$'s can be taken together to form a $C_{3-10}$cycloalkyl optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;
$R^9$ and $R^{10}$ are independently selected at each occurrence from H, $C_{1-6}$alkyl, $C_{1-6}$heteroalkyl, $C_{1-6}$haloalkyl, and $C_{3-10}$cycloalkyl;
each $R^{11}$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^{12}$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;
each $R^{13}$ is independently selected from H, $C_{1-6}$alkyl, $C_{1-6}$haloalkyl, and $C_{3-10}$cycloalkyl;
m is 1 or 2; and
n is 0, 1, 2, 3, or 4.

In some embodiments, each X is independently selected from N and $CR^7$. In some embodiments, at least one X is N and the rest are $CR^7$. In some embodiments, at least two X are N and the rest are $CR^7$. In some embodiments, each X is N. In some embodiments, each X is $CR^7$.

In some embodiments, Y is selected from O, S, $SO_2$, and $C(R^8)_2$. In some embodiments, Y is O. In some embodiments, Y is S. In some embodiments, Y is $SO_2$. In some embodiments, Y is $C(R^8)_2$.

In some embodiments, $R^1$ is selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; wherein the alkyl, cycloalkyl, aryl, or heteroaryl is optionally substituted with 1 to 3 substituents independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, $R^1$ is selected from $C_{3-10}$cycloalkyl, $C_{6-10}$aryl, and 5- to 10-membered heteroaryl; wherein the cycloalkyl, aryl, or heteroaryl is optionally substituted with 1 to 3 substituents independently selected from halo, $-NR^9R^{10}$, $-OR^{11}$, $-C(O)R^1$, $-C(O)$ $OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, $R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, $R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^1$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, and $C_{1-6}$haloalkyl. In some embodiments, $R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, and —$NR^{13}SO_2NR^9R^{10}$. In some embodiments, $R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^{11}$, —$C(O)OR^{11}$, and —$C(O)NR^9R^{10}$.

In some embodiments, $R^2$ is H and $R^3$ is —$CF_3$. In some embodiments, $R^2$ and $R^3$ are taken together to form oxo. In some embodiments, $R^2$ and $R^3$ are taken together to form thio.

In some embodiments, $R^4$ and $R^5$ are independently selected from $C_{1-6}$alkyl, $C_{1-6}$heteroalkyl, $C_{1-6}$haloalkyl, and $C_{3-10}$cycloalkyl; wherein each alkyl, heteroalkyl, haloalkyl, and cycloalkyl is independently optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, $R^4$ and $R^5$ are independently selected from $C_{3-10}$cycloalkyl; wherein each cycloalkyl is independently optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, $R^4$ and $R^5$ are independently selected from $C_{3-10}$cycloalkyl; wherein each cycloalkyl is independently optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, and —$NR^{13}SO_2NR^9R^{10}$. In some embodiments, $R^4$ and $R^5$ are independently selected from $C_{3-10}$cycloalkyl; wherein each cycloalkyl is independently optionally substituted with 1 to 3 substituents independently selected from halo, —$NR^9R^{10}$, —$OR^{11}$, —$C(O)R^{11}$, —$C(O)OR^{11}$, and —$C(O)NR^9R^{10}$.

In some embodiments, $R^4$ and $R^5$ are taken together, along with the nitrogen atom to which they are attached, to form a 3- to 10-membered heterocycloalkyl optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, $R^4$ and $R^5$ are taken together, along with the nitrogen atom to which they are attached, to form a 3- to 10-membered heterocycloalkyl optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, and $C_{1-6}$haloalkyl. In some embodiments, $R^4$ and $R^5$ are taken together, along with the nitrogen atom to which they are attached, to form a 3- to 10-membered heterocycloalkyl optionally substituted with 1 to 3 substituents independently selected from halo, —$NR^9R^{10}$, —$OR^{11}$, —$C(O)R^1$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, and —$NR^{13}SO_2NR^9R^{10}$. In some embodiments, $R^4$ and $R^5$ are taken together, along with the nitrogen atom to which they are attached, to form a 3- to 10-membered heterocycloalkyl optionally substituted with 1 to 3 substituents independently selected from halo, —$NR^9R^{10}$, —$OR^{11}$, —$C(O)R^{11}$, —$C(O)OR^{11}$, and —$C(O)NR^9R^{10}$.

In some embodiments, each $R^6$ is independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, each $R^6$ is independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$ $C_{1-6}$alkyl, $C_{1-6}$heteroalkyl, and $C_{1-6}$haloalkyl. In some embodiments, each $R^6$ is independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, and —$NR^{13}SO_2NR^9R^{10}$. In some embodiments, each $R^6$ is independently selected from halo, —$NR^9R^{10}$, —$OR^{11}$, —$C(O)R^{11}$, —$C(O)OR^{11}$, and —$C(O)NR^9R^{10}$.

In some embodiments, two $R^6$'s attached to the same carbon atom are taken together to form oxo, thio, or $C_{3-10}$cycloalkyl, and any remaining $R^6$'s are independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, two R$^6$'s attached to the same carbon atom are taken together to form oxo, thio, or C$_{3-10}$cycloalkyl, and any remaining R$^6$'s are independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, and C$_{1-6}$haloalkyl. In some embodiments, two R$^6$'s attached to the same carbon atom are taken together to form oxo, thio, or C$_{3-10}$cycloalkyl, and any remaining R$^6$'s are independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, two R$^6$'s attached to the same carbon atom are taken together to form oxo, thio, or C$_{3-10}$cycloalkyl, and any remaining R$^6$'s are independently selected from halo, —NR$^9$R$^{10}$, —OR$^{11}$, —C(O)R$^{11}$, —C(O)OR$^{11}$, and —C(O)NR$^9$R$^{10}$.

In some embodiments, each R$^7$ is independently selected from H, halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, each R$^7$ is independently selected from H, halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^3$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, and C$_{1-6}$haloalkyl. In some embodiments, each R$^7$ is independently selected from H, halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, each R$^7$ is independently selected from H, halo, —NR$^9$R$^{10}$, —OR$^{11}$, —C(O)R$^{11}$, —C(O)OR$^{11}$, and —C(O)NR$^9$R$^{10}$.

In some embodiments, each R$^8$ is independently selected from H, halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, each R$^8$ is independently selected from H, halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, and C$_{1-6}$haloalkyl. In some embodiments, each R$^8$ is independently selected from H, halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, each R$^8$ is independently selected from H, halo, —NR$^9$R$^{10}$, —OR$^{11}$, —C(O)R$^{11}$, —C(O)OR$^{11}$, and —C(O)NR$^9$R$^{10}$.

In some embodiments, two R$^8$'s can be taken together to form a C$_{3-10}$cycloalkyl optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, two R$^8$'s can be taken together to form a C$_{3-10}$cycloalkyl optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, and C$_{1-6}$haloalkyl. In some embodiments, two R$^8$'s can be taken together to form a C$_{3-10}$cycloalkyl optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, two R$^8$'s can be taken together to form a C$_{3-10}$cycloalkyl optionally substituted with 1 to 3 substituents independently selected from halo, —NR$^9$R$^{10}$, —OR$^{11}$, —C(O)R$^{11}$, —C(O)OR$^{11}$, and —C(O)NR$^9$R$^{10}$.

In some embodiments, R$^9$ and R$^{10}$ are independently selected at each occurrence from H, C$_{1-6}$alkyl, C$_{1-6}$heteroalkyl, C$_{1-6}$haloalkyl, and C$_{3-10}$cycloalkyl. In some embodiments, R$^9$ and R$^{10}$ are independently selected at each occurrence from H, C$_{1-6}$alkyl, C$_{1-6}$heteroalkyl, and C$_{1-6}$haloalkyl. In some embodiments, R$^9$ and R$^{10}$ are independently selected at each occurrence from H and C$_{1-6}$alkyl.

In some embodiments, each R$^{11}$ is independently selected from H, C$_{1-6}$alkyl, C$_{1-6}$heteroalkyl, C$_{1-6}$haloalkyl, C$_{3-10}$cycloalkyl, C$_{6-10}$aryl, and 5- to 10-membered heteroaryl. In some embodiments, each R$^{11}$ is independently selected from H, C$_{1-6}$alkyl, C$_{1-6}$heteroalkyl, and C$_{1-6}$haloalkyl. In some embodiments, each R$^{11}$ is independently selected from H and C$_{1-6}$alkyl.

In some embodiments, each R$^{12}$ is independently selected from C$_{1-6}$alkyl, C$_{1-6}$heteroalkyl, C$_{1-6}$haloalkyl, C$_{3-10}$cycloalkyl, C$_{6-10}$aryl, and 5- to 10-membered heteroaryl. In some embodiments, each R$^{12}$ is independently selected from C$_{1-6}$alkyl, C$_{1-6}$heteroalkyl, and C$_{1-6}$haloalkyl. In some embodiments, each R$^{12}$ is independently selected from C$_{1-6}$alkyl.

In some embodiments, each R$^{13}$ is independently selected from H, C$_{1-6}$alkyl, C$_{1-6}$haloalkyl, and C$_{3-10}$cycloalkyl. In some embodiments, each R$^{13}$ is independently selected from H, C$_{1-6}$alkyl, and C$_{1-6}$haloalkyl. In some embodiments, each R$^{13}$ is independently selected from H and C$_{1-6}$alkyl.

In some embodiments, m is 1 or 2. In some embodiments, m is 1. In some embodiments, m is 2.

In some embodiments, n is 0, 1, 2, 3, or 4. In some embodiments, n is 0. In some embodiments, n is 1. In some embodiments, n is 2. In some embodiments, n is 3. In some embodiments, n is 4.

In some embodiments, the compound is a compound of Formula IIIa:

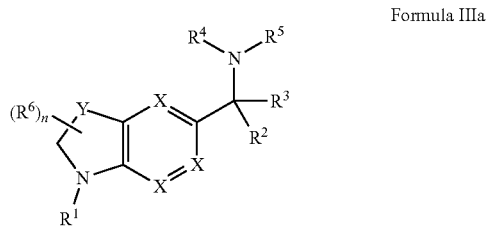

Formula IIIa or a pharmaceutically acceptable salt thereof.

In some embodiments, the compound is a compound of Formula IIIb:

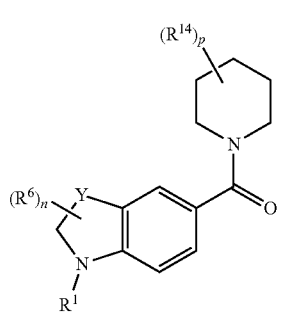

Formula IIIb or a pharmaceutically acceptable salt thereof, wherein:
each $R^{14}$ is independently selected from halo, $-NR^9R^{10}$, $-OR^{11}$, $-C(O)R^1$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; and
p is 0, 1, 2, or 3.

In some embodiments, each $R^{14}$ is independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each $R^{14}$ is independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, and $C_{1-6}$haloalkyl. In some embodiments, each $R^{14}$ is independently selected from halo, $-NR^9R^{10}$, $-OR^{11}$, $-C(O)R^1$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, and $-NR^{13}SO_2NR^9R^{10}$. In some embodiments, each $R^{14}$ is independently selected from halo, $-NR^9R^{10}$, $-OR^{11}$, $-C(O)R^{11}$, $-C(O)OR^{11}$, and $-C(O)NR^9R^{10}$. In some embodiments, each $R^{14}$ is independently halo. In some embodiments, each $R^{14}$ is independently fluoro.

In some embodiments, p is 0, 1, 2, or 3. In some embodiments, p is 0. In some embodiments, p is 1. In some embodiments, p is 2. In some embodiments, p is 3.

In some embodiments, the compound is a compound of Formula IIIc:

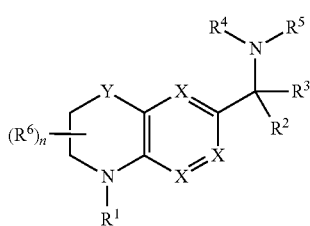

Formula IIIc or a pharmaceutically acceptable salt thereof.

In some embodiments, the compound is a compound of Formula IIId:

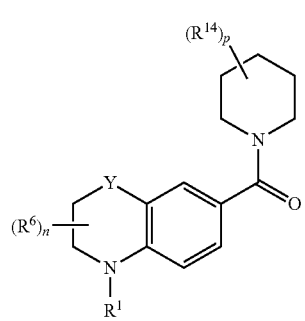

Formula IIId or a pharmaceutically acceptable salt thereof, wherein:
each $R^{14}$ is independently selected from halo, $-NR^9R^{10}$, $-OR^{11}$, $-C(O)R^1$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; and
p is 0, 1, 2, or 3.

In some embodiments, each $R^{14}$ is independently selected from halo, $-NR^9R^{10}$, $-OR^{11}$, $-C(O)R^{11}$, $-C(O)OR^1$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each $R^{14}$ is independently selected from halo, $-NR^9R^{10}$, $-OR^{11}$, $-C(O)R^{11}$, $-C(O)OR^{11}$, $-C(O)NR^9R^{10}$, $-SOR^{12}$, $-SO_2R^{12}$, $-SO_2NR^9R^{10}$, $-NR^{13}C(O)R^{11}$, $-NR^{13}C(O)NR^9R^{10}$, $-NR^{13}SO_2R^{11}$, $-NR^{13}SO_2NR^9R^{10}$, $C_{1-6}$alkyl, $C_{1-6}$heteroalkyl, and $C_{1-6}$haloalkyl. In some embodiments, each $R^{14}$ is independently selected from halo, $-NR^9R^{10}$, $-OR^{11}$, $-C(O)R^1$, $-C(O)OR^1$, $-C(O)NR^9R^{10}$, $-SOR^{12}$, $-SO_2R^{12}$, $-SO_2NR^9R^{10}$, $-NR^{13}C(O)R^1$, $-NR^{13}C(O)NR^9R^{10}$, $-NR^{13}SO_2R^{11}$, and $-NR^{13}SO_2NR^9R^{10}$. In some embodiments, each $R^{14}$ is independently selected from halo, $-NR^9R^{10}$, $-OR^{11}$, $-C(O)R^{11}$, $-C(O)OR^{11}$, and $-C(O)NR^9R^{10}$. In some embodiments, each $R^{14}$ is independently halo. In some embodiments, each $R^{14}$ is independently fluoro.

In some embodiments, p is 0, 1, 2, or 3. In some embodiments, p is 0. In some embodiments, p is 1. In some embodiments, p is 2. In some embodiments, p is 3.

Compounds

In one aspect, provided herein is a compound of Formula IIk:

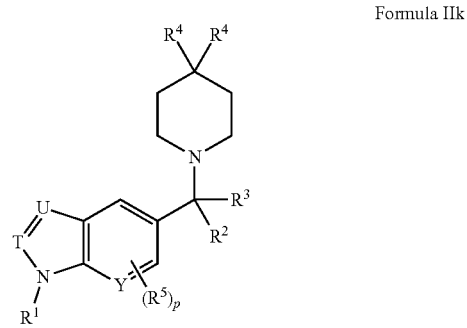

Formula IIk or a pharmaceutically acceptable salt thereof, wherein:

T, U, and Y are independently selected from N and $CR^6$, provided that when U is N, at least one of T and Y is N;

$R^1$ is selected from $C_{6-10}$aryl and 5- to 10-membered heteroaryl; wherein the aryl or heteroaryl is optionally substituted with 1 to 3 substituents independently selected from halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, $C_{1-6}$haloalkyl, $C_{3-6}$cycloalkyl, and 5- to 10-membered heteroaryl;

$R^2$ is H and $R^3$ is $-CF_3$; or $R^2$ and $R^3$ are taken together to form oxo;

each $R^4$ is independently selected from H and halo;

$R^5$ is selected from halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;

$R^6$ is selected from H, halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;

$R^7$ and $R^8$ are independently selected at each occurrence from H, $C_{1-6}$alkyl, $C_{1-6}$heteroalkyl, $C_{1-6}$haloalkyl, and $C_{3-6}$cycloalkyl;

each $R^9$ is independently selected from H, $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;

each $R^{10}$ is independently selected from $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;

each $R^{11}$ is independently selected from H, $C_{1-6}$alkyl, $C_{1-6}$haloalkyl, and $C_{3-6}$cycloalkyl; and p is 0, 1, or 2.

In some embodiments, T, U, and Y are independently selected from N and $CR^6$, provided that when U is N, at least one of T and Y is N. In some embodiments, one of T, U, and Y is N and the rest are $CR^6$. In some embodiments, two of T, U, and Y are N and the rest are $CR^6$. In some embodiments, one of T, U, and Y is $CR^6$ and the rest are N. In some embodiments, two of T, U, and Y are $CR^6$ and the rest are N. In some embodiments, T, U, and Y are N. In some embodiments, T, U, and Y are $CR^6$.

In some embodiments, $R^1$ is selected from $C_{6-10}$aryl and 5- to 10-membered heteroaryl; wherein the aryl or heteroaryl is optionally substituted with 1 to 3 substituents independently selected from halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, and $C_{1-6}$haloalkyl. In some embodiments, $R^1$ is selected from $C_{6-10}$aryl and 5- to 10-membered heteroaryl; wherein the aryl or heteroaryl is optionally substituted with 1 to 3 substituents independently selected from halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, and $-NR^{11}SO_2NR^7R^8$. In some embodiments, $R^1$ is selected from $C_{6-10}$aryl and 5- to 10-membered heteroaryl; wherein the aryl or heteroaryl is optionally substituted with 1 to 3 substituents independently selected from halo, $-NR^7R^8$, $-OR^9$, $-C(O)R^9$, $-C(O)OR^9$, and $-C(O)NR^7R^8$.

In some embodiments, $R^2$ is H and $R^3$ is $-CF_3$. In some embodiments, $R^2$ and $R^3$ are taken together to form oxo.

In some embodiments, each $R^4$ is independently selected from H and halo. In some embodiments, each $R^4$ is independently selected from H and fluoro. In some embodiments, each $R^4$ is H. In some embodiments, each $R^4$ is fluoro. In some embodiments, one $R^4$ is H and one $R^4$ is fluoro.

In some embodiments, $R^5$ is selected from halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl. In some embodiments, $R^5$ is selected from halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, and $C_{1-6}$haloalkyl. In some embodiments, $R^5$ is selected from halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, and $-NR^{11}SO_2NR^7R^8$. In some embodiments, $R^5$ is selected from halo, $-NR^7R^8$, $-OR^9$, $-C(O)R^9$, $-C(O)OR^9$, and $-C(O)NR^7R^8$.

In some embodiments, $R^6$ is selected from H, halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl. In some embodiments, $R^6$ is selected from H, halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, $-NR^{11}SO_2NR^7R^8$, $C_{1-6}$alkyl, $C_{1-6}$heteroalkyl, and $C_{1-6}$haloalkyl. In some embodiments, $R^6$ is selected from H, halo, $-NR^7R^8$, $-OR^9$, $-C(O)R^9$, $-C(O)OR^9$, $-C(O)NR^7R^8$, $-SOR^{10}$, $-SO_2R^{10}$, $-SO_2NR^7R^8$, $-NR^{11}C(O)R^9$, $-NR^{11}C(O)NR^7R^8$, $-NR^{11}SO_2R^9$, and $-NR^{11}SO_2NR^7R^8$. In some embodiments, $R^6$ is selected from H, halo, $-NR^7R^8$, $-OR^9$, $-C(O)R^9$, $-C(O)OR^9$, and $-C(O)NR^7R^8$.

In some embodiments, $R^7$ and $R^8$ are independently selected at each occurrence from H, $C_{1-6}$alkyl, $C_{1-6}$heteroalkyl, $C_{1-6}$haloalkyl, and $C_{3-6}$cycloalkyl. In some embodiments, $R^7$ and $R^8$ are independently selected at each occurrence from H, $C_{1-6}$alkyl, $C_{1-6}$heteroalkyl, and $C_{1-6}$haloalkyl. In some embodiments, $R^7$ and $R^8$ are independently selected at each occurrence from H and $C_{1-6}$alkyl.

In some embodiments, each $R^9$ is independently selected from H, $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl. In some embodiments, each $R^9$ is independently selected from H, $C_{1-6}$alkyl, $C_{1-6}$heteroalkyl, and $C_{1-6}$haloalkyl. In some embodiments, each $R^9$ is independently selected from H and $C_{1-6}$alkyl.

In some embodiments, each $R^{10}$ is independently selected from $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl. In some embodiments, each $R^{10}$ is independently selected from $C_{1-6}$alkyl, $C_{1-6}$heteroalkyl, and $C_{1-6}$haloalkyl. In some embodiments, each $R^{10}$ is independently selected from $C_{1-6}$alkyl.

In some embodiments, each $R^{11}$ is independently selected from H, $C_{1-6}$alkyl, $C_{1-6}$haloalkyl, and $C_{3-6}$cycloalkyl. In some embodiments, each $R^{11}$ is independently selected from H, $C_{1-6}$alkyl, and $C_{1-6}$haloalkyl. In some embodiments, each $R^{11}$ is independently selected from H and $C_{1-6}$alkyl.

In some embodiments, p is 0, 1, or 2. In some embodiments, p is 0. In some embodiments, p is 1. In some embodiments, p is 2.

In another aspect, provided herein is a compound of Formula IIm:

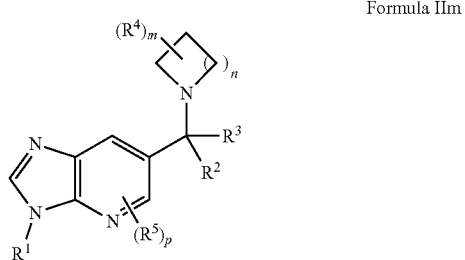

Formula IIm or a pharmaceutically acceptable salt thereof, wherein:

$R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, and 5- to 10-membered heteroaryl;

$R^2$ is H and $R^3$ is —$CF_3$; or $R^2$ and $R^3$ are taken together to form oxo;

each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; or two $R^4$'s are taken together with the carbon atoms to which they are attached and any intervening atoms to form a $C_{3-10}$cycloalkyl, and any remaining $R^4$'s are independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

$R^5$ is selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl;

$R^6$ and $R^7$ are independently selected at each occurrence from H, $C_{1-6}$ alkyl, $C_{1-6}$ heteroalkyl, $C_{1-6}$haloalkyl, and $C_{3-10}$cycloalkyl;

each $R^8$ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^9$ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each $R^{10}$ is independently selected from H, $C_{1-6}$alkyl, $C_{1-6}$haloalkyl, and $C_{3-10}$cycloalkyl;

n is 1, 2, 3, or 4;

m is 0, 1, 2, 3, 4, 5, 6, 7, 8, 9, or 10; and p is 0, 1, 2, or 3.

In some embodiments, $R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$ haloalkyl, $C_{3-10}$cycloalkyl, and 5- to 10-membered heteroaryl. In some embodiments, $R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, and $C_{1-6}$haloalkyl. In some embodiments, $R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, $R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, and —$C(O)NR^6R^7$.

In some embodiments, $R^2$ is H and $R^3$ is —$CF_3$. In some embodiments, $R^2$ and $R^3$ are taken together to form oxo.

In some embodiments, each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$heteroalkyl, and $C_{1-6}$haloalkyl. In some embodiments, each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, and —$NR^{10}SO_2NR^6R^7$. In some embodiments, each $R^4$ is independently selected from halo, —$NR^6R^7$, —$OR^8$, —$C(O)R^8$, —$C(O)OR^8$, and —$C(O)NR^6R^7$. In some embodiments, each $R^4$ is independently selected from halo. In some embodiments, each $R^4$ is fluoro.

In some embodiments, two $R^4$'s are taken together with the carbon atoms to which they are attached and any intervening atoms to form a $C_{3-10}$cycloalkyl, and any remaining $R^4$'s are independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$ heteroalkyl, $C_{1-6}$ haloalkyl, $C_{3-10}$cycloalkyl, $C_{6-10}$aryl, and 5- to 10-membered heteroaryl. In some embodiments, two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, and $C_{1-6}$ haloalkyl. In some embodiments, two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, and —NR¹⁰SO₂NR⁶R⁷. In some embodiments, two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, and —C(O)NR⁶R⁷.

In some embodiments, R⁵ is selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, R⁵ is selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, and $C_{1-6}$haloalkyl. In some embodiments, R⁵ is selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, and —NR¹⁰SO₂NR⁶R⁷. In some embodiments, R⁵ is selected from halo, —NR⁶R⁷, —OR⁸, —C(O)R⁸, —C(O)OR⁸, and —C(O)NR⁶R⁷.

In some embodiments, R⁶ and R⁷ are independently selected at each occurrence from H, $C_{1-6}$alkyl, $C_{1-6}$heteroalkyl, $C_{1-6}$ haloalkyl, and $C_{3-10}$cycloalkyl. In some embodiments, R⁶ and R⁷ are independently selected at each occurrence from H, $C_{1-6}$alkyl, $C_{1-6}$heteroalkyl, $C_{1-6}$haloalkyl. In some embodiments, R⁶ and R⁷ are independently selected at each occurrence from H and $C_{1-6}$alkyl.

In some embodiments, each R⁸ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each R⁸ is independently selected from H, $C_{1-6}$alkyl, $C_{1-6}$heteroalkyl, and $C_{1-6}$haloalkyl. In some embodiments, each R⁸ is independently selected from H and $C_{1-6}$alkyl.

In some embodiments, each R⁹ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each R⁹ is independently selected from $C_{1-6}$alkyl, $C_{1-6}$heteroalkyl, $C_{1-6}$haloalkyl. In some embodiments, each R⁹ is independently selected from $C_{1-6}$alkyl.

In some embodiments, each R¹⁰ is independently selected from H, $C_{1-6}$alkyl, $C_{1-6}$haloalkyl, and $C_{3-10}$cycloalkyl. In some embodiments, each R¹⁰ is independently selected from H, $C_{1-6}$alkyl, and $C_{1-6}$haloalkyl. In some embodiments, each R¹⁰ is independently selected from H and $C_{1-6}$alkyl.

In some embodiments, n is 1, 2, 3, or 4. In some embodiments, n is 1. In some embodiments, n is 2. In some embodiments, n is 3. In some embodiments, n is 4.

In some embodiments, m is 0, 1, 2, 3, 4, 5, 6, 7, 8, 9, or 10. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, p is 0, 1, 2, or 3. In some embodiments, p is 0. In some embodiments, p is 1. In some embodiments, p is 2. In some embodiments, p is 3.

In another aspect, provided herein is a compound of Formula IIq:

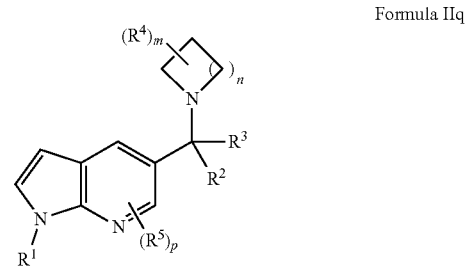

Formula IIq or a pharmaceutically acceptable salt thereof, wherein:
R¹ is selected from $C_{6-10}$aryl and 5- to 10-membered heteroaryl; wherein said aryl or heteroaryl is optionally substituted with 1 to 3 substituents independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$haloalkyl, $C_{3-10}$cycloalkyl, and 5- to 10-membered heteroaryl;
R² is H and R³ is —CF₃; or
R² and R³ are taken together to form oxo;
each R⁴ is independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl; or
two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$ haloalkyl, $C_{3-10}$cycloalkyl, $C_{6-10}$aryl, and 5- to 10-membered heteroaryl;
R⁵ is selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$ haloalkyl, $C_{3-10}$cycloalkyl, 3- to 10-membered heterocycloalkyl, $C_{6-10}$aryl, and 5- to 10-membered heteroaryl;

R⁶ and R⁷ are independently selected at each occurrence from H, $C_{1-6}$alkyl, $C_{1-6}$heteroalkyl, $C_{1-6}$haloalkyl, and $C_{3-10}$cycloalkyl;

each R⁸ is independently selected from H, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each R⁹ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl;

each R¹⁰ is independently selected from H, $C_{1-6}$alkyl, $C_{1-6}$haloalkyl, and $C_{3-10}$cycloalkyl;

n is 1, 2, 3, or 4;

m is 0, 1, 2, 3, 4, 5, 6, 7, 8, 9, or 10; and p is 0, 1, 2, or 3.

In some embodiments, R¹ is selected from $C_{6-10}$aryl and 5- to 10-membered heteroaryl; wherein said aryl or heteroaryl is optionally substituted with 1 to 3 substituents independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$ haloalkyl, $C_{3-10}$cycloalkyl, and 5- to 10-membered heteroaryl. In some embodiments, R¹ is selected from $C_{6-10}$aryl and 5- to 10-membered heteroaryl; wherein said aryl or heteroaryl is optionally substituted with 1 to 3 substituents independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁸, —NR¹⁰SO₂R⁸, —NR¹⁰SO₂NR⁶R⁷, $C_{1-6}$alkyl, $C_{1-6}$heteroalkyl, and $C_{1-6}$haloalkyl. In some embodiments, R¹ is selected from $C_{6-10}$aryl and 5- to 10-membered heteroaryl; wherein said aryl or heteroaryl is optionally substituted with 1 to 3 substituents independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, and —NR¹⁰SO₂NR⁶R⁷. In some embodiments, R¹ is selected from $C_{6-10}$aryl and 5- to 10-membered heteroaryl; wherein said aryl or heteroaryl is optionally substituted with 1 to 3 substituents independently selected from halo, —NR⁶R⁷, —OR⁸, —C(O)R⁸, —C(O)OR⁸, and —C(O)NR⁶R⁷.

In some embodiments, R² is H and R³ is —CF₃. In some embodiments, R² and R³ are taken together to form oxo.

In some embodiments, each R⁴ is independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each R⁴ is independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, and $C_{1-6}$haloalkyl. In some embodiments, each R⁴ is independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, and —NR¹⁰SO₂NR⁶R⁷. In some embodiments, each R⁴ is independently selected from halo, —NR⁶R⁷, —OR⁸, —C(O)R⁸, —C(O)OR⁸, and —C(O)NR⁶R⁷. In some embodiments, each R⁴ is independently selected from halo. In some embodiments, each R⁴ is fluoro.

In some embodiments, two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$ heteroalkyl, $C_{1-6}$ haloalkyl, $C_{3-10}$cycloalkyl, $C_{6-10}$aryl, and 5- to 10-membered heteroaryl. In some embodiments, two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, and $C_{1-6}$ haloalkyl. In some embodiments, two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, and —NR¹⁰SO₂NR⁶R⁷. In some embodiments, two R⁴'s are taken together with the carbon atoms to which they are attached and any intervening atoms to form a $C_{3-10}$cycloalkyl, and any remaining R⁴'s are independently selected from halo, —NR⁶R⁷, —OR⁸, —C(O)R⁸, —C(O)OR⁸, and —C(O)NR⁶R⁷.

In some embodiments, R⁵ is selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, $C_{1-6}$haloalkyl, $C_{3-10}$cycloalkyl, 3- to 10-membered heterocycloalkyl, $C_{6-10}$aryl, and 5- to 10-membered heteroaryl. In some embodiments, R⁵ is selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, —NR¹⁰SO₂NR⁶R⁷, $C_{1-6}$alkyl, $C_{1-6}$heteroalkyl, and $C_{1-6}$ haloalkyl. In some embodiments, R⁵ is selected from halo, —NR⁶R⁷, —OR⁸, —C(O)R⁸, —C(O)OR⁸, —C(O)NR⁶R⁷, —SOR⁹, —SO₂R⁹, —SO₂NR⁶R⁷, —NR¹⁰C(O)R⁸, —NR¹⁰C(O)NR⁶R⁷, —NR¹⁰SO₂R⁸, and —NR¹⁰SO₂NR⁶R⁷. In some embodiments, R⁵ is selected from halo, —NR⁶R⁷, —OR⁸, —C(O)R⁸, —C(O)OR⁸, and —C(O)NR⁶R⁷.

In some embodiments, R⁶ and R⁷ are independently selected at each occurrence from H, $C_{1-6}$alkyl, $C_{1-6}$heteroalkyl, $C_{1-6}$ haloalkyl, and $C_{3-10}$cycloalkyl. In some embodiments, R⁶ and R⁷ are independently selected at each occurrence from H, $C_{1-6}$alkyl, $C_{1-6}$heteroalkyl, $C_{1-6}$haloalkyl. In some embodiments, R⁶ and R⁷ are independently selected at each occurrence from H and $C_{1-6}$alkyl.

In some embodiments, each R⁸ is independently selected from H, $C_{1-6}$alkyl, $C_{1-6}$heteroalkyl, $C_{1-6}$ haloalkyl, $C_{3-10}$cycloalkyl, $C_{6-10}$aryl, and 5- to 10-membered heteroaryl. In some embodiments, each R⁸ is independently selected from H, $C_{1-6}$alkyl, $C_{1-6}$heteroalkyl, and $C_{1-6}$haloalkyl. In some embodiments, each R⁸ is independently selected from H and $C_{1-6}$alkyl.

In some embodiments, each R⁹ is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each R⁹ is independently selected from $C_{1-6}$alkyl, $C_{1-6}$heteroalkyl, $C_{1-6}$haloalkyl. In some embodiments, each R⁹ is independently selected from $C_{1-6}$alkyl.

In some embodiments, each R¹⁰ is independently selected from H, $C_{1-6}$alkyl, $C_{1-6}$haloalkyl, and $C_{3-10}$cycloalkyl. In some embodiments, each R¹⁰ is independently selected from H, $C_{1-6}$alkyl, and $C_{1-6}$haloalkyl. In some embodiments, each $R^{10}$ is independently selected from H and $C_{1-6}$alkyl.

In some embodiments, n is 1, 2, 3, or 4. In some embodiments, n is 1. In some embodiments, n is 2. In some embodiments, n is 3. In some embodiments, n is 4.

In some embodiments, m is 0, 1, 2, 3, 4, 5, 6, 7, 8, 9, or 10. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, p is 0, 1, 2, or 3. In some embodiments, p is 0. In some embodiments, p is 1. In some embodiments, p is 2. In some embodiments, p is 3.

In another aspect, provided herein is a compound of Formula IIIc:

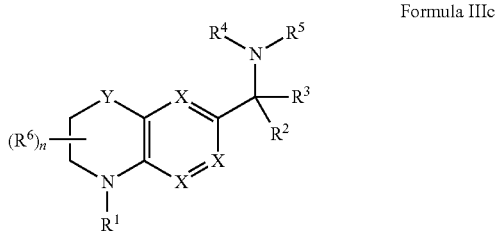

Formula IIIc or a pharmaceutically acceptable salt thereof, wherein:
each X is independently selected from N and $CR^7$;
Y is selected from O, S, $SO_2$, and $C(R^8)_2$;
$R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-6}$cycloalkyl, and 5- to 10-membered heteroaryl;
$R^2$ is H and $R^3$ is —$CF_3$; or
$R^2$ and $R^3$ are taken together to form oxo;
$R^4$ and $R^5$ are independently selected from $C_{1-6}$alkyl, $C_{1-6}$heteroalkyl, $C_{1-6}$haloalkyl, and $C_{3-6}$ cycloalkyl; wherein each alkyl, heteroalkyl, haloalkyl, and cycloalkyl is independently optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^1$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl; or
$R^4$ and $R^5$ are taken together, along with the nitrogen atom to which they are attached, to form a 3- to 10-membered heterocycloalkyl optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^2$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;
each $R^6$ is independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl; or two $R^6$'s attached to the same carbon atom are taken together to form oxo, and any remaining $R^6$'s are independently selected from halo, —$NR^9R^{10}$, —$OR^{11}$, —$C(O)R^1$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;
each $R^7$ and $R^8$ is independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$haloalkyl, $C_{3-6}$cycloalkyl, 3- to 10-membered heterocycloalkyl, $C_{6-10}$aryl, and 5- to 10-membered heteroaryl;
$R^9$ and $R^{10}$ are independently selected at each occurrence from H, $C_{1-6}$alkyl, $C_{1-6}$heteroalkyl, $C_{1-6}$haloalkyl, and $C_{3-6}$cycloalkyl;
each $R^{11}$ is independently selected from H, $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;
each $R^{12}$ is independently selected from $C_{1-6}$alkyl, $C_{1-6}$heteroalkyl, $C_{1-6}$haloalkyl, $C_{3-6}$cycloalkyl, $C_{6-10}$aryl, and 5- to 10-membered heteroaryl;
each $R^{13}$ is independently selected from H, $C_{1-6}$alkyl, $C_{1-6}$haloalkyl, and $C_{3-6}$cycloalkyl; and
n is 0, 1, 2, 3, or 4.

In some embodiments, each X is independently selected from N and $CR^7$. In some embodiments, at least one X is N and the rest are $CR^7$. In some embodiments, at least two X are N and the rest are $CR^7$. In some embodiments, each X is N. In some embodiments, each X is $CR^7$.

In some embodiments, Y is selected from O, S, $SO_2$, and $C(R^8)_2$. In some embodiments, Y is O. In some embodiments, Y is S. In some embodiments, Y is $SO_2$. In some embodiments, Y is $C(R^8)_2$.

In some embodiments, $R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^1$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, $C_{1-6}$ haloalkyl, $C_{3-6}$cycloalkyl, and 5- to 10-membered heteroaryl. In some embodiments, $R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, —$NR^{13}SO_2NR^9R^{10}$, $C_{1-6}$alkyl, $C_{1-6}$heteroalkyl, and $C_{1-6}$haloalkyl. In some embodiments, $R^1$ is selected from $C_{6-10}$aryl and 5- to 10-membered heteroaryl; wherein the aryl or heteroaryl is optionally substituted with 1 to 3 substituents independently selected from halo, —$NR^9R^{10}$, —$OR^{11}$, —$C(O)R^{11}$, —$C(O)OR^{11}$, —$C(O)NR^9R^{10}$, —$SOR^{12}$, —$SO_2R^{12}$, —$SO_2NR^9R^{10}$, —$NR^{13}C(O)R^{11}$, —$NR^{13}C(O)NR^9R^{10}$, —$NR^{13}SO_2R^{11}$, and —$NR^{13}SO_2NR^9R^{10}$. In some embodiments, $R^1$ is selected from $C_{6-10}$aryl and 5- to 10-membered heteroaryl; wherein the aryl or heteroaryl is optionally substituted with 1 to 3 substituents independently selected from halo, —NR$^9$R$^{10}$, —OR$^{11}$, —C(O)R$^{11}$, —C(O)OR$^{11}$, and —C(O)NR$^9$R$^{10}$.

In some embodiments, R$^2$ is H and R$^3$ is —CF$_3$. In some embodiments, R$^2$ and R$^3$ are taken together to form oxo.

In some embodiments, R$^4$ and R$^5$ are independently selected from C$_{1-6}$alkyl, C$_{1-6}$heteroalkyl, C$_{1-6}$ haloalkyl, and C$_{3-10}$cycloalkyl; wherein each alkyl, heteroalkyl, haloalkyl, and cycloalkyl is independently optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, R$^4$ and R$^5$ are independently selected from C$_{3-10}$cycloalkyl; wherein each cycloalkyl is independently optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$ haloalkyl, C$_{3-10}$cycloalkyl, 3- to 10-membered heterocycloalkyl, C$_{6-10}$aryl, and 5- to 10-membered heteroaryl. In some embodiments, R$^4$ and R$^5$ are independently selected from C$_{3-10}$cycloalkyl; wherein each cycloalkyl is independently optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, and C$_{1-6}$haloalkyl. In some embodiments, R$^4$ and R$^5$ are independently selected from C$_{3-10}$cycloalkyl; wherein each cycloalkyl is independently optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, R$^4$ and R$^5$ are independently selected from C$_{3-10}$cycloalkyl; wherein each cycloalkyl is independently optionally substituted with 1 to 3 substituents independently selected from halo, —NR$^9$R$^{10}$, —OR$^{11}$, —C(O)R$^{11}$, —C(O)OR$^{11}$, and —C(O)NR$^9$R$^{10}$.

In some embodiments, R$^4$ and R$^5$ are taken together, along with the nitrogen atom to which they are attached, to form a 3- to 10-membered heterocycloalkyl optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, C$_{6-10}$aryl, and 5- to 10-membered heteroaryl. In some embodiments, R$^4$ and R$^5$ are taken together, along with the nitrogen atom to which they are attached, to form a 3- to 10-membered heterocycloalkyl optionally substituted with 1 to 3 substituents independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$ —NR$^{13}$SO$_2$NR$^9$R$^{10}$C$_{1-6}$alkyl, C$_{1-6}$heteroalkyl, and C$_{1-6}$haloalkyl. In some embodiments, R$^4$ and R$^5$ are taken together, along with the nitrogen atom to which they are attached, to form a 3- to 10-membered heterocycloalkyl optionally substituted with 1 to 3 substituents independently selected from halo, —NR$^9$R$^{10}$, —OR$^{11}$, —C(O)R$^1$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, R$^4$ and R$^5$ are taken together, along with the nitrogen atom to which they are attached, to form a 3- to 10-membered heterocycloalkyl optionally substituted with 1 to 3 substituents independently selected from halo, —NR$^9$R$^{10}$, —OR$^{11}$, —C(O)R$^{11}$, —C(O)OR$^{11}$, and —C(O)NR$^9$R$^{10}$.

In some embodiments, each R$^6$ is independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, each R$^6$ is independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^3$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$C$_{1-6}$alkyl, C$_{1-6}$heteroalkyl, and C$_{1-6}$haloalkyl. In some embodiments, each R$^6$ is independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, each R$^6$ is independently selected from halo, —NR$^9$R$^{10}$, —OR$^{11}$, —C(O)R$^{11}$, —C(O)OR$^{11}$, and —C(O)NR$^9$R$^{10}$.

In some embodiments, two R$^6$'s attached to the same carbon atom are taken together to form oxo, and any remaining R$^6$'s are independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-10}$cycloalkyl, 3- to 10-membered heterocycloalkyl, C$_{6-10}$aryl, and 5- to 10-membered heteroaryl. In some embodiments, two R$^6$'s attached to the same carbon atom are taken together to form oxo, and any remaining R$^6$'s are independently selected from halo, —NR$^9$R$^{10}$, —OR$^{11}$, —C(O)R$^1$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, and C$_{1-6}$haloalkyl. In some embodiments, two R$^6$'s attached to the same carbon atom are taken together to form oxo, and any remaining R$^6$'s are independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, and —NR$^{13}$SO$_2$NR$^9$R$^{10}$. In some embodiments, two R$^6$'s attached to the same carbon atom are taken together to form oxo, and any remaining R$^6$'s are independently selected from halo, —NR$^9$R$^{10}$, —OR$^{11}$, —C(O)R$^{11}$, —C(O)OR$^{11}$, and —C(O)NR$^9$R$^{10}$.

In some embodiments, each R$^7$ and R$^8$ is independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^{11}$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, C$_{1-6}$haloalkyl, C$_{3-6}$ cycloalkyl, 3- to 10-membered heterocycloalkyl, C$_{6-10}$aryl, and 5- to 10-membered heteroaryl. In some embodiments, each R$^7$ and R$^8$ is independently selected from halo, —NR$^9$R$^{10}$, —OR$^{11}$, —C(O)R$^{11}$, —C(O)OR$^{11}$, —C(O)NR$^9$R$^{10}$, —SOR$^{12}$, —SO$_2$R$^{12}$, —SO$_2$NR$^9$R$^{10}$, —NR$^{13}$C(O)R$^1$, —NR$^{13}$C(O)NR$^9$R$^{10}$, —NR$^{13}$SO$_2$R$^{11}$, —NR$^{13}$SO$_2$NR$^9$R$^{10}$, C$_{1-6}$alkyl, C$_{1-6}$heteroalkyl, and C$_{1-6}$haloalkyl. In some embodiments, each R$^7$ and R[8] is independently selected from halo, —NR[9]R[10], —OR[11], —C(O)R[11], —C(O)OR[11], —C(O)NR[9]R[10], —SOR[12], —SO$_2$R[12], —SO$_2$NR[9]R[10], —NR[13]C(O)R[11], —NR[13]C(O)NR[9]R[10], —NR[13]SO$_2$R[11], and —NR[13]SO$_2$NR[9]R[10]. In some embodiments, each R[7] and R[8] is independently selected from halo, —NR[9]R[10], —OR[11], —C(O)R[11], —C(O)OR[11], and —C(O)NR[9]R[10].

In some embodiments, R[9] and R[10] are independently selected at each occurrence from H, $C_{1-6}$alkyl, $C_{1-6}$heteroalkyl, $C_{1-6}$ haloalkyl, and $C_{3-10}$cycloalkyl. In some embodiments, R[9] and R[10] are independently selected at each occurrence from H, $C_{1-6}$alkyl, $C_{1-6}$heteroalkyl, and $C_{1-6}$haloalkyl. In some embodiments, R[9] and R[10] are independently selected at each occurrence from H and $C_{1-6}$alkyl.

In some embodiments, each R[11] is independently selected from H, $C_{1-6}$alkyl, $C_{1-6}$heteroalkyl, $C_{1-6}$ haloalkyl, $C_{3-10}$cycloalkyl, $C_{6-10}$aryl, and 5- to 10-membered heteroaryl. In some embodiments, each R[11] is independently selected from H, $C_{1-6}$alkyl, $C_{1-6}$heteroalkyl, and $C_{1-6}$haloalkyl. In some embodiments, each R[11] is independently selected from H and $C_{1-6}$alkyl.

In some embodiments, each R[12] is independently selected from $C_{1-6}$alkyl, $C_{1-6}$heteroalkyl, $C_{1-6}$haloalkyl, $C_{3-10}$cycloalkyl, $C_{6-10}$aryl, and 5- to 10-membered heteroaryl. In some embodiments, each R[12] is independently selected from $C_{1-6}$alkyl, $C_{1-6}$heteroalkyl, and $C_{1-6}$haloalkyl. In some embodiments, each R[12] is independently selected from $C_{1-6}$alkyl.

In some embodiments, each R[13] is independently selected from H, $C_{1-6}$alkyl, $C_{1-6}$haloalkyl, and $C_{3-10}$cycloalkyl. In some embodiments, each R[13] is independently selected from H, $C_{1-6}$alkyl, and $C_{1-6}$haloalkyl. In some embodiments, each R[13] is independently selected from H and $C_{1-6}$alkyl.

In some embodiments, n is 0, 1, 2, 3, or 4. In some embodiments, n is 0. In some embodiments, n is 1. In some embodiments, n is 2. In some embodiments, n is 3. In some embodiments, n is 4.

In another aspect, provided herein is a composition comprising a compound selected from the group consisting of:

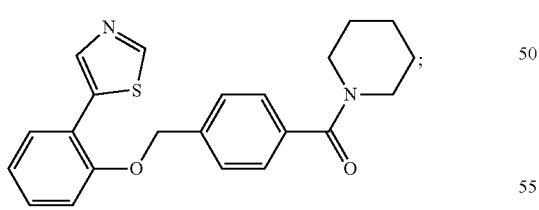

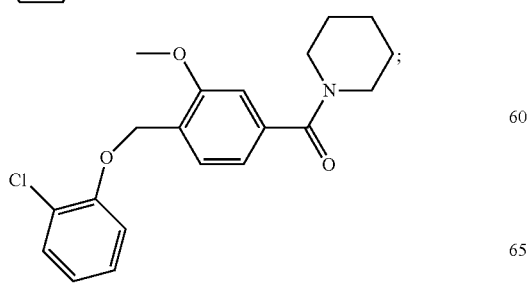

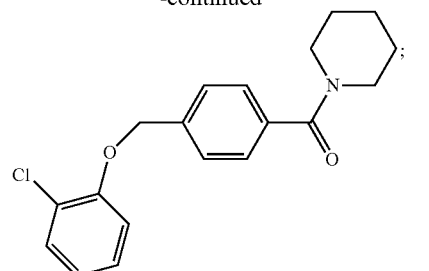

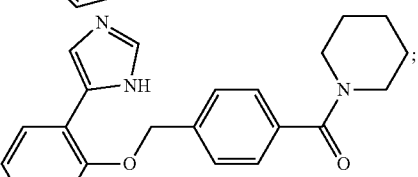

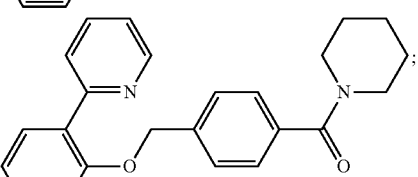

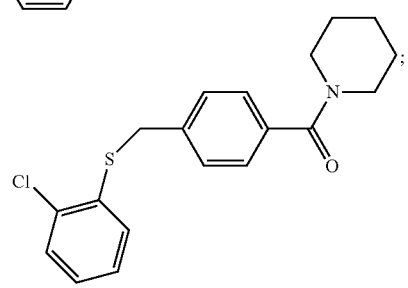

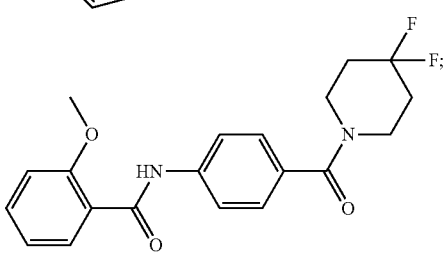

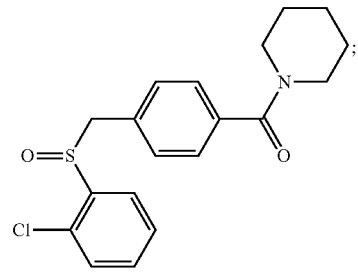

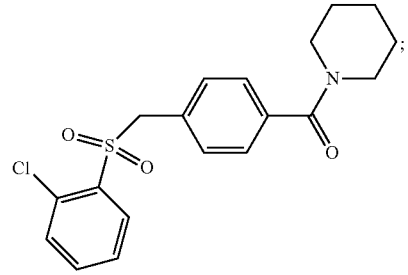

131
-continued
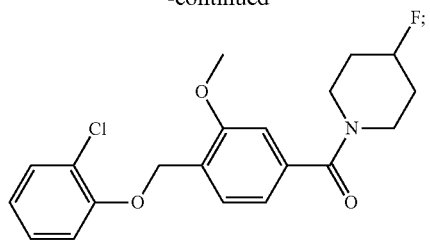
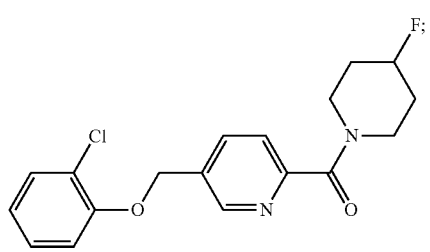
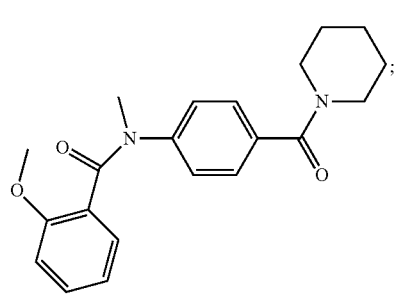
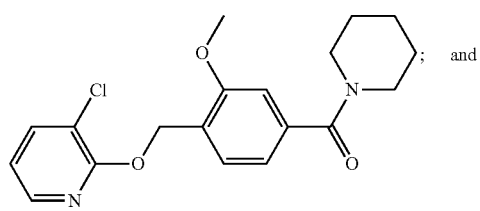 ; and
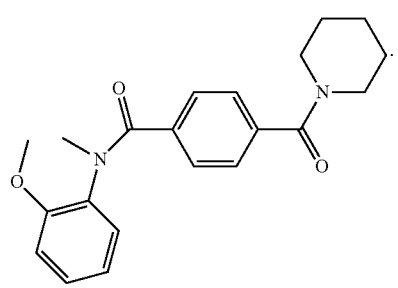
In another aspect, provided herein is a composition comprising a compound selected from the group consisting of:
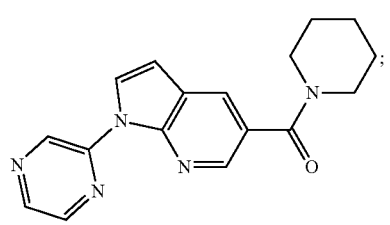
132
-continued
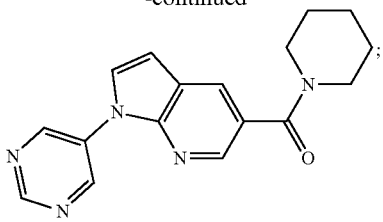
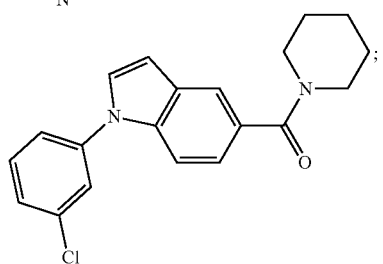
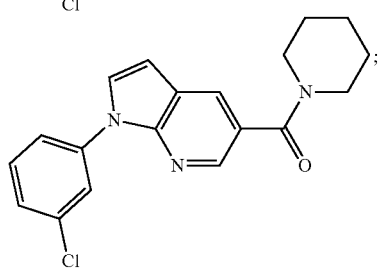
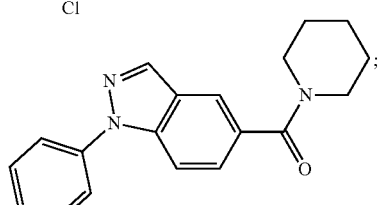
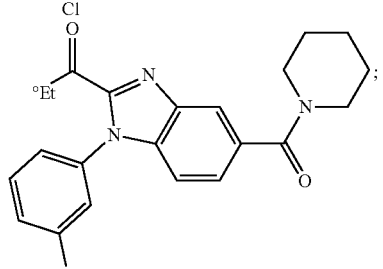
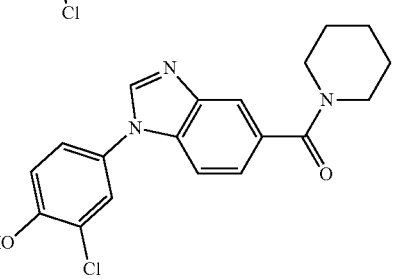
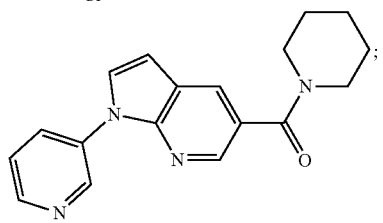

133
-continued
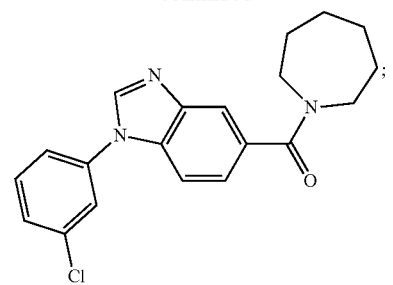
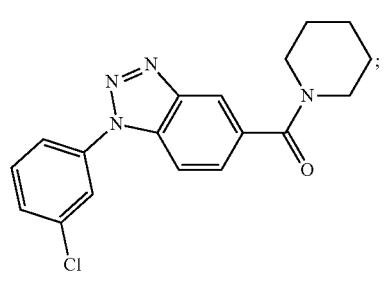
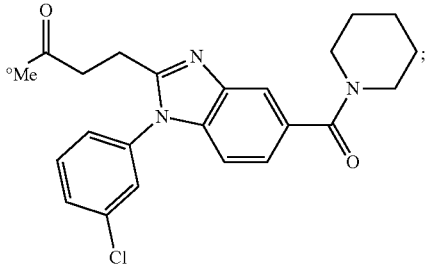
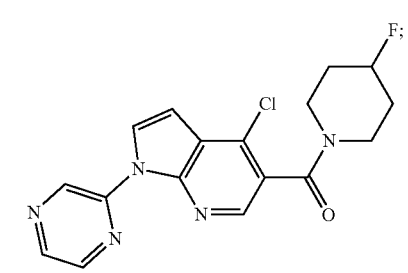
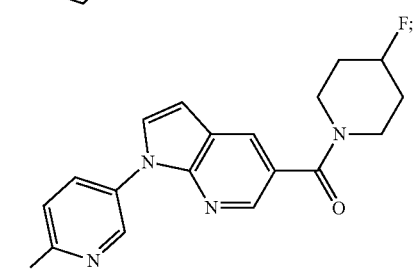
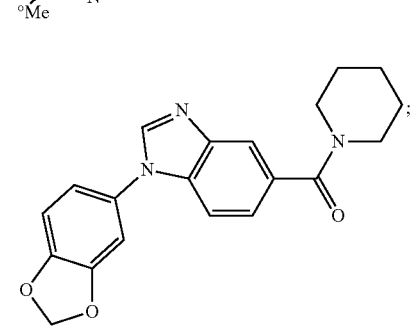
134
-continued
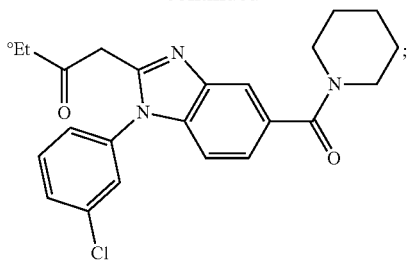
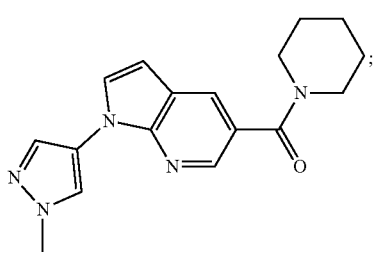
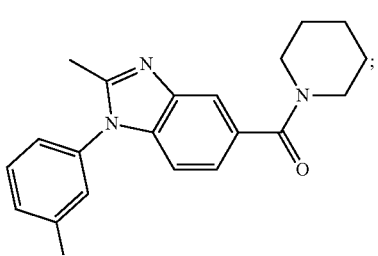
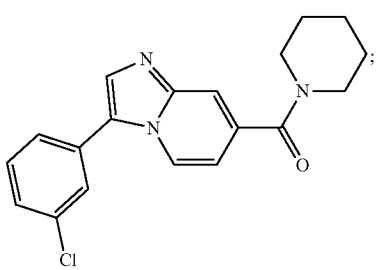
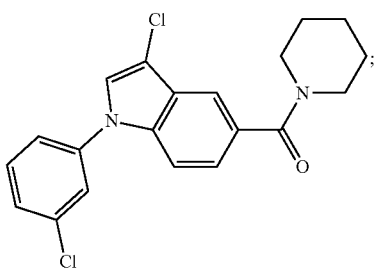
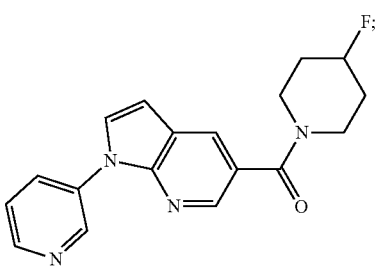

135
-continued
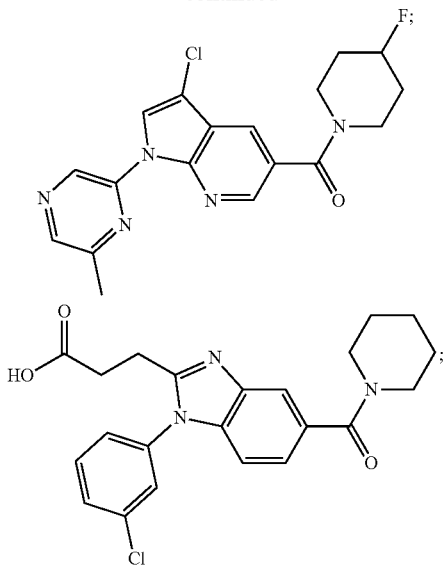
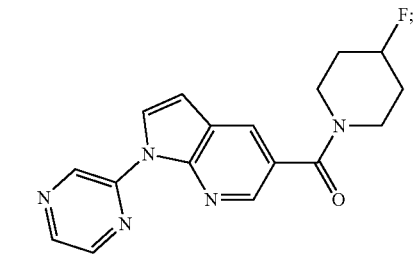
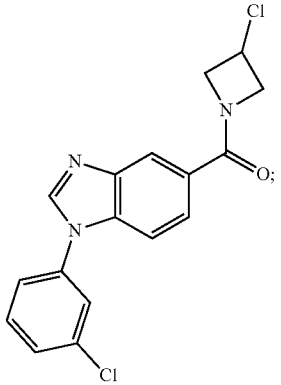
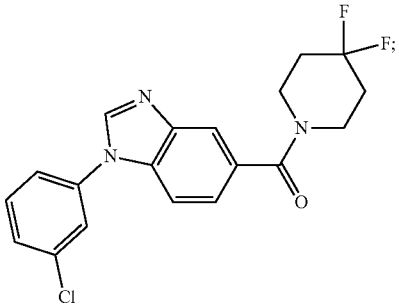
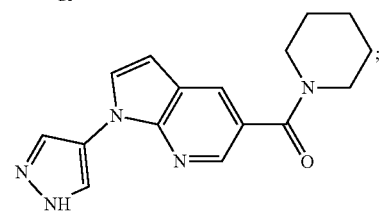
136
-continued
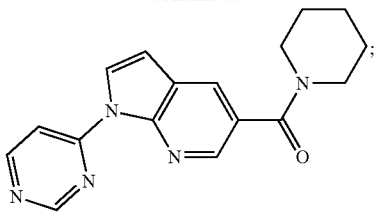
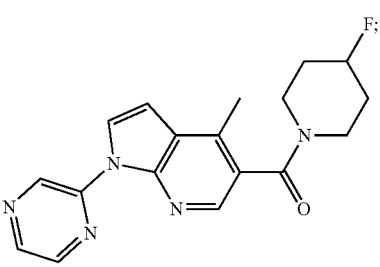
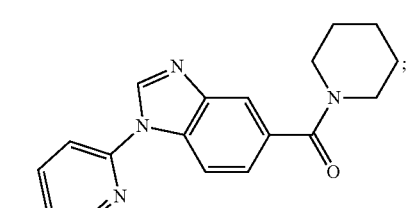
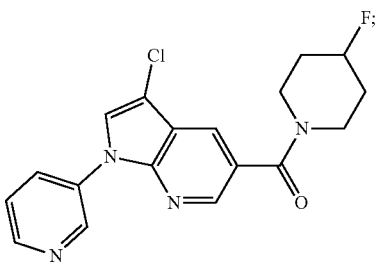
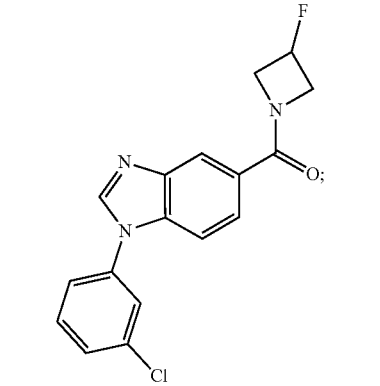
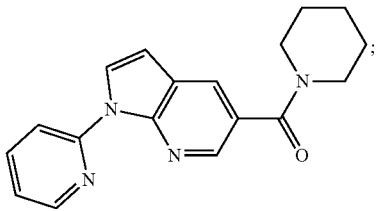

137
-continued
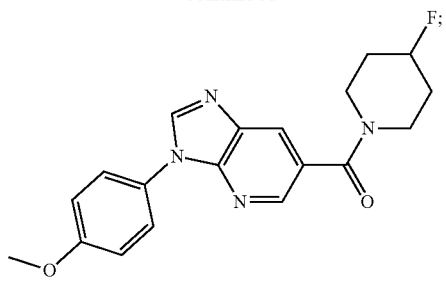
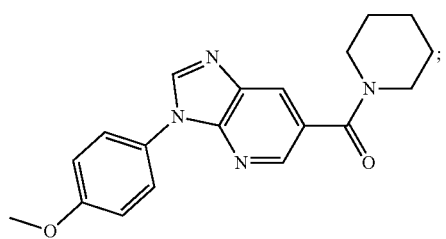
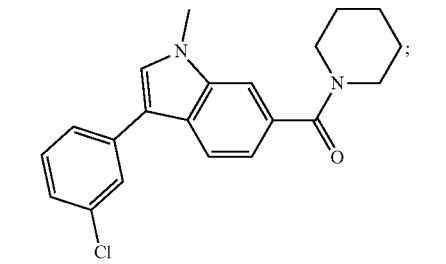
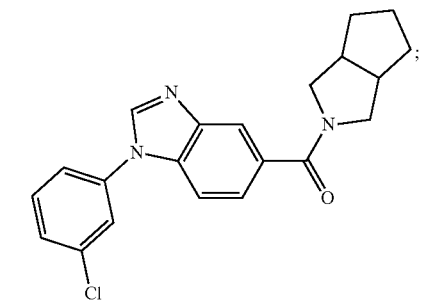
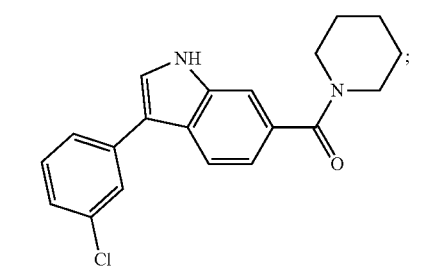
138
-continued
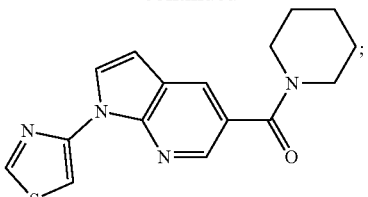
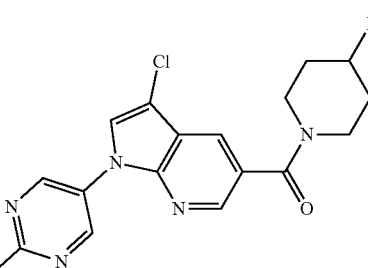
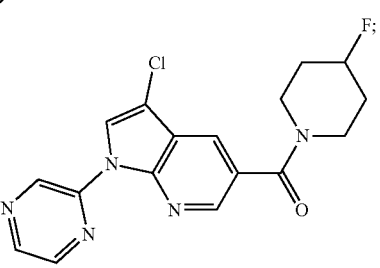
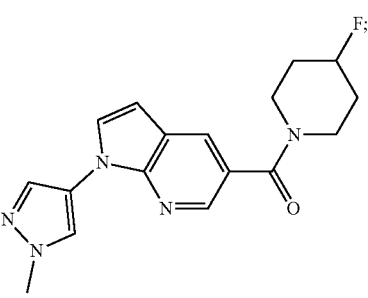
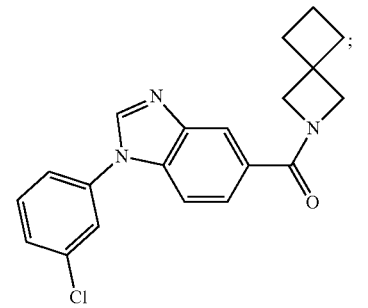
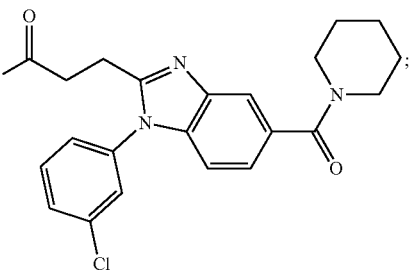

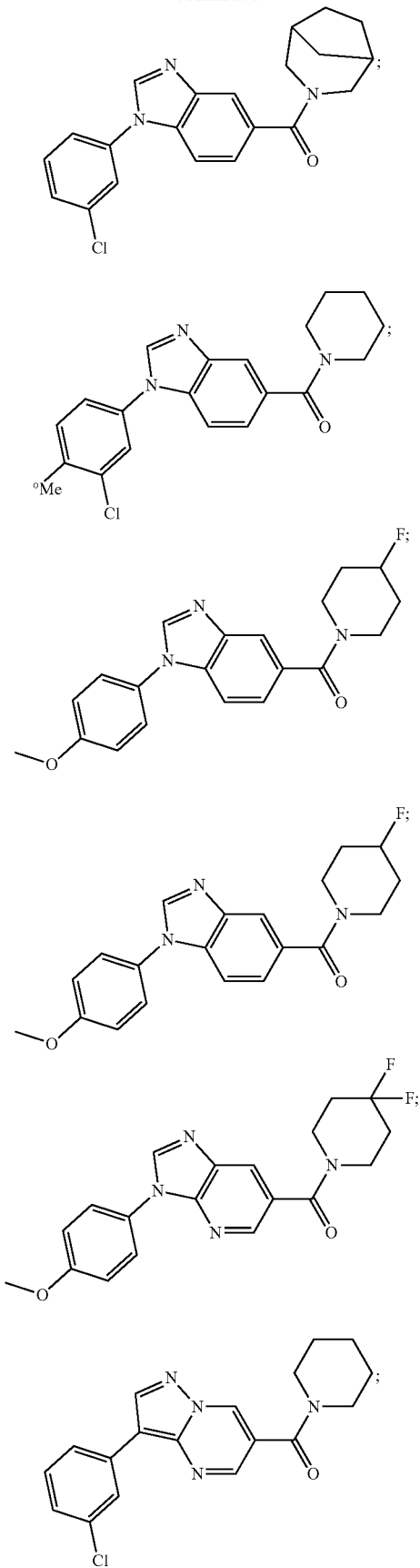
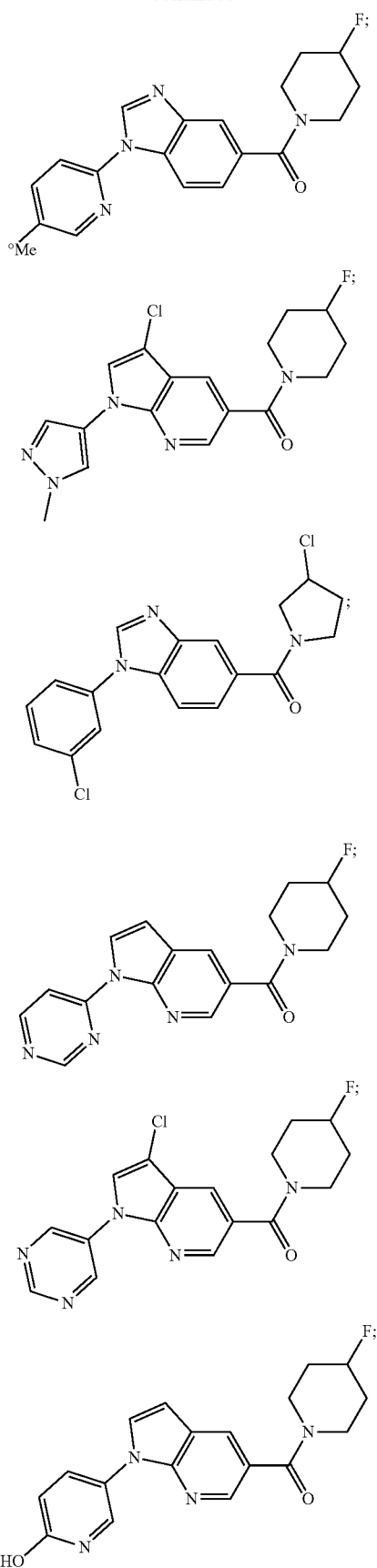

141
-continued
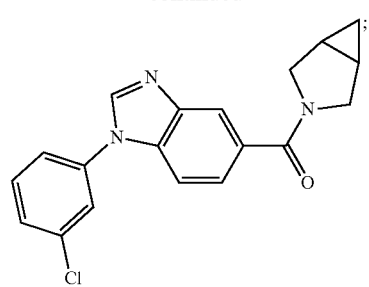
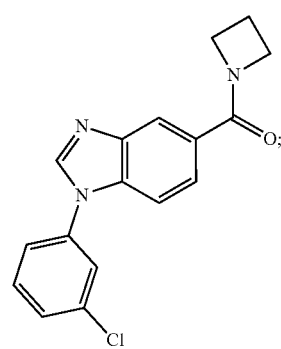
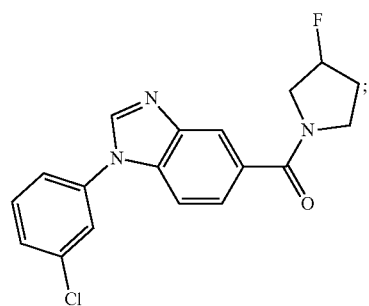
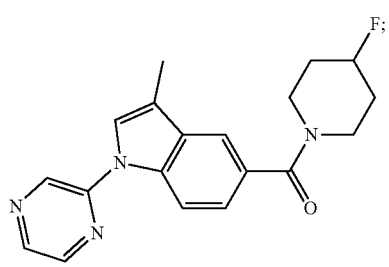
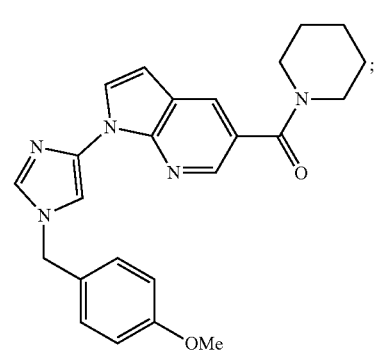
142
-continued
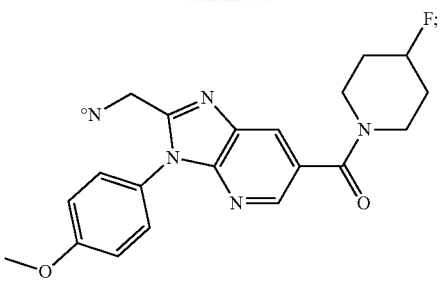
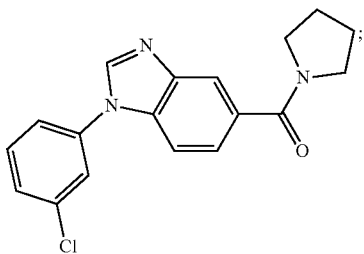
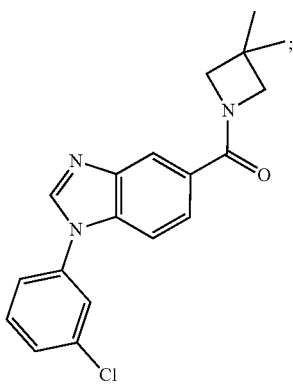
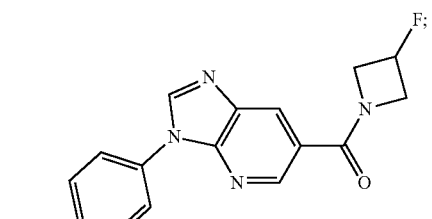
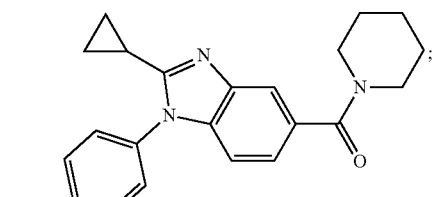
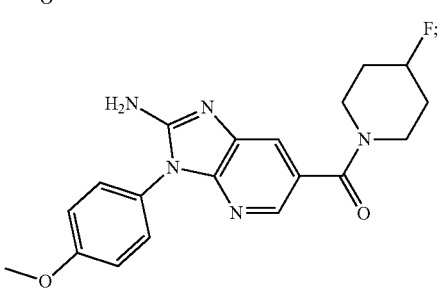

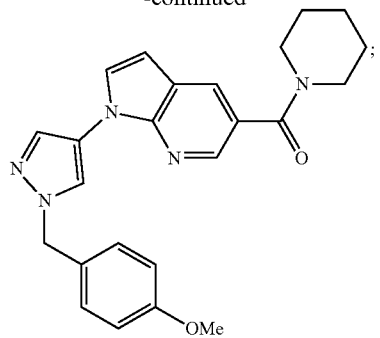
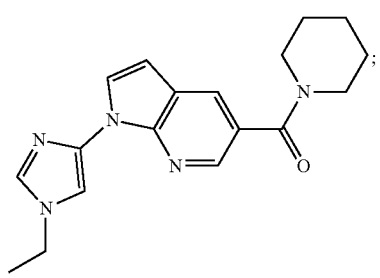
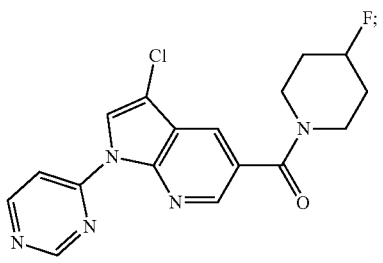
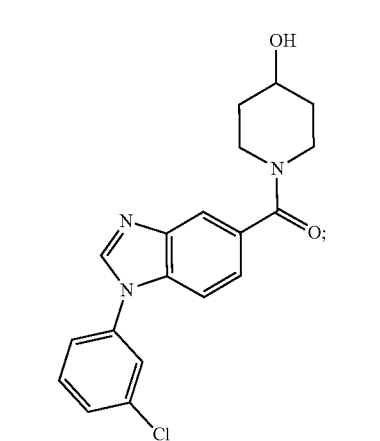
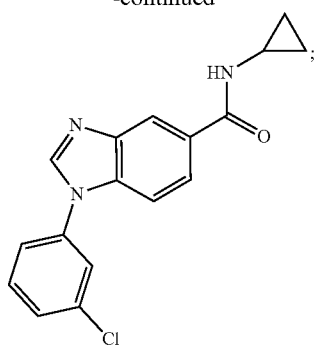
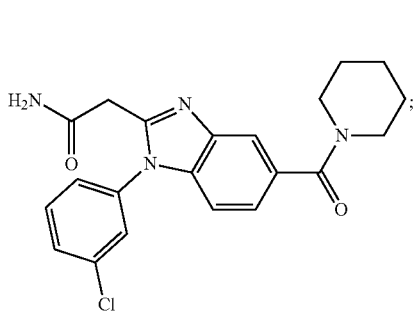
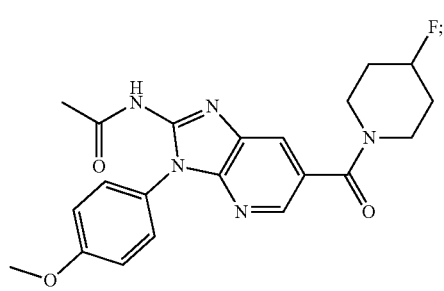
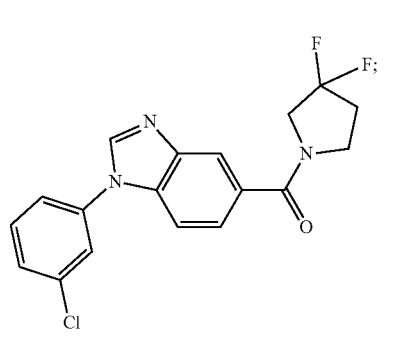
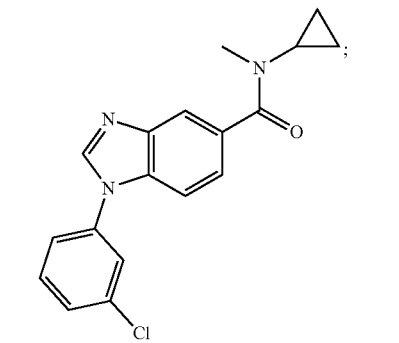

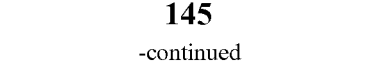
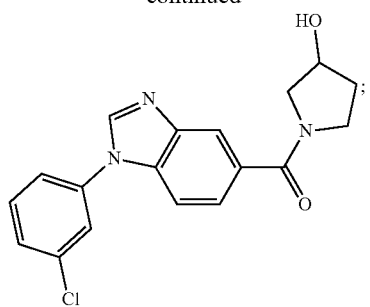
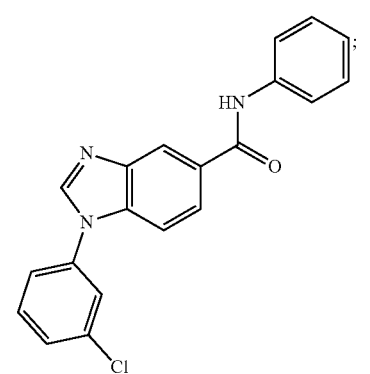
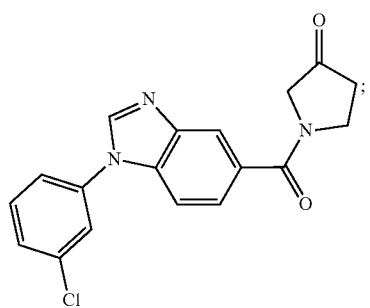
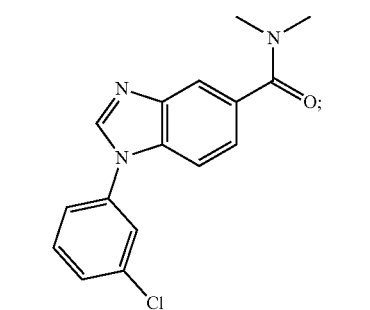
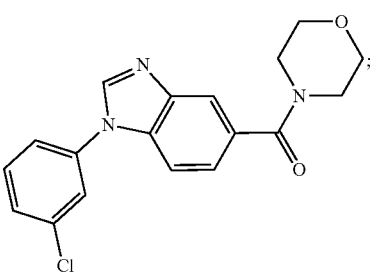
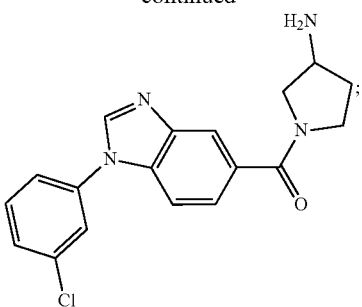
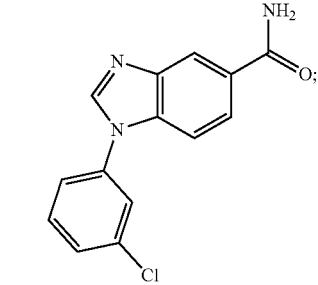
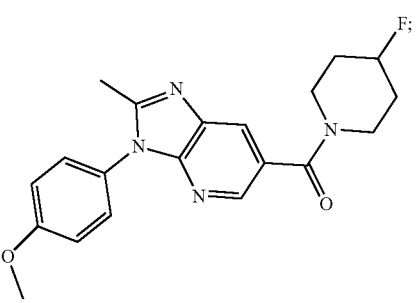
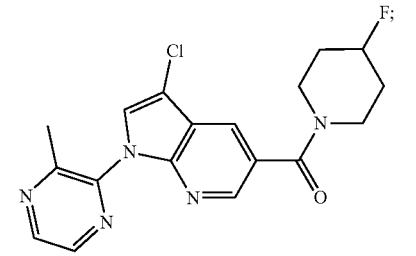
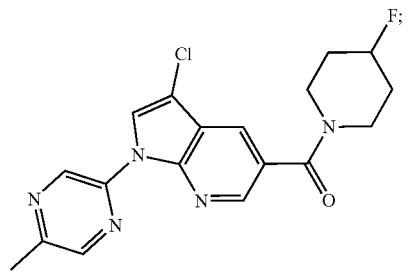
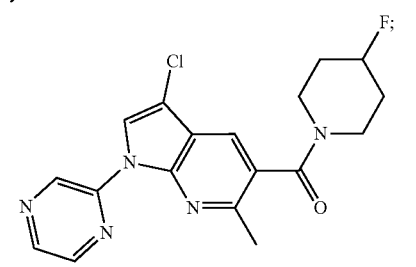

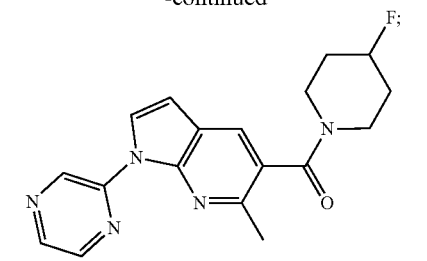
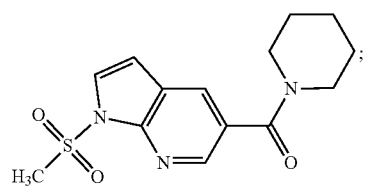
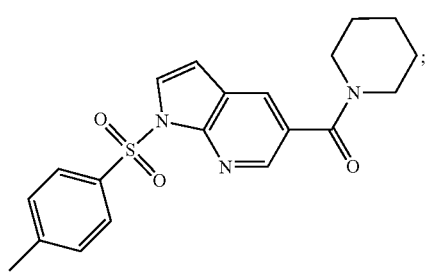
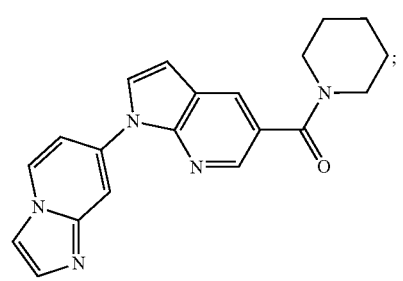
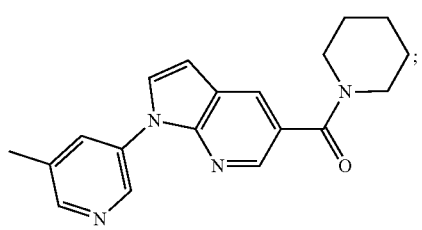
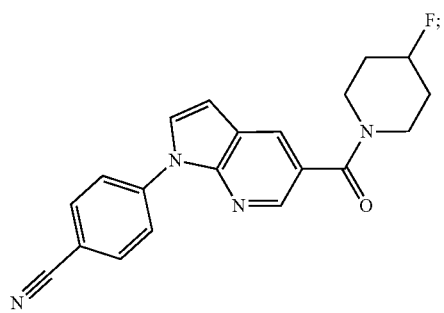
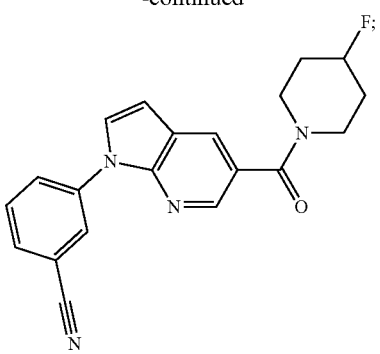
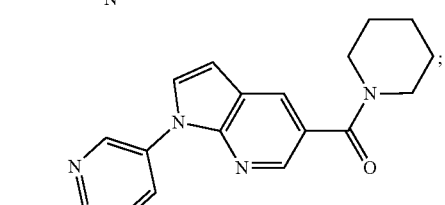
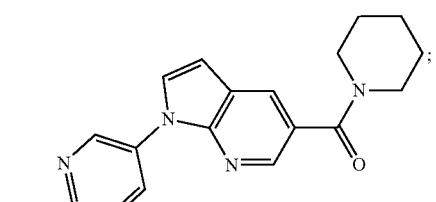
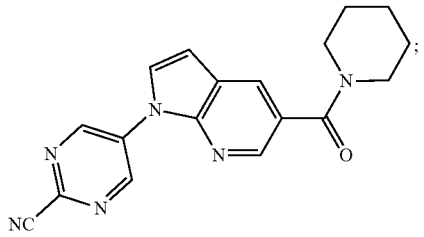
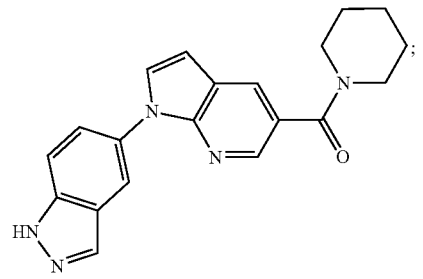
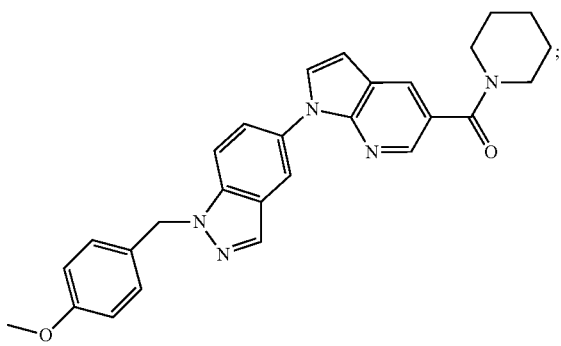

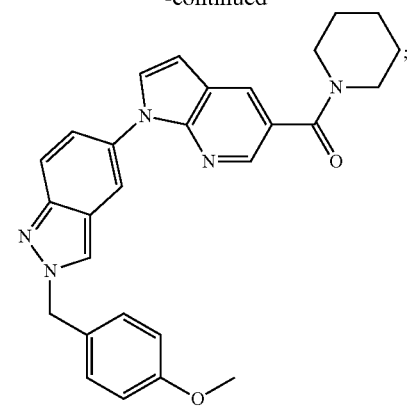
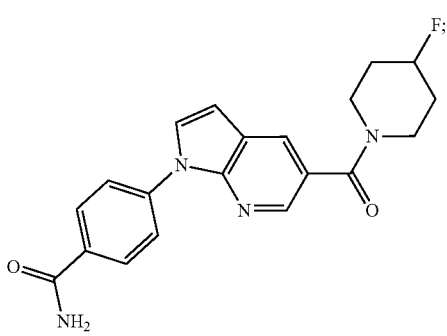
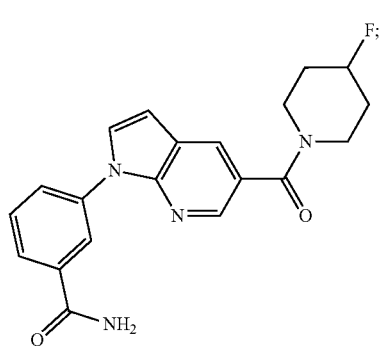
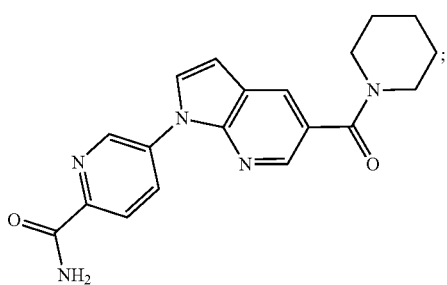
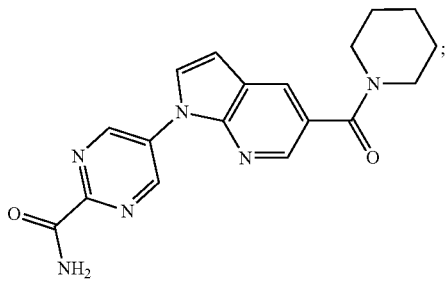
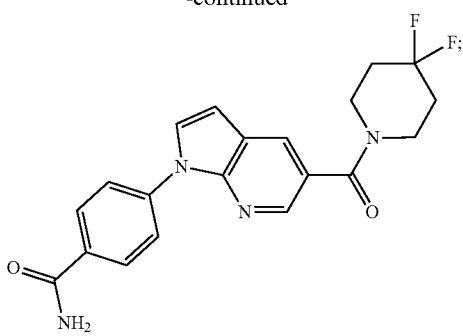
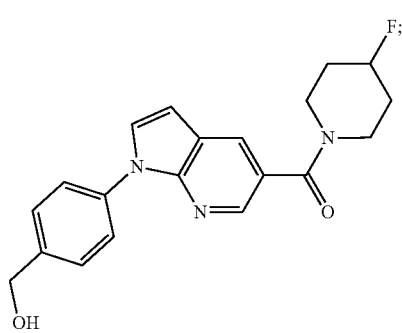
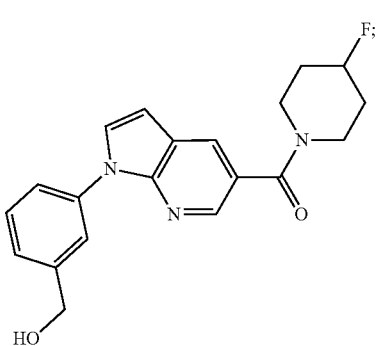
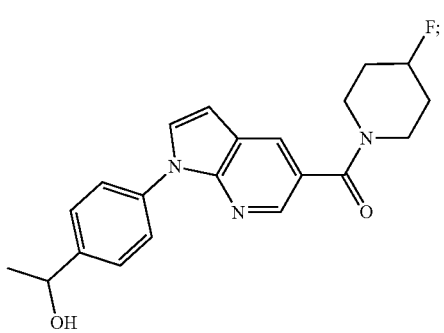
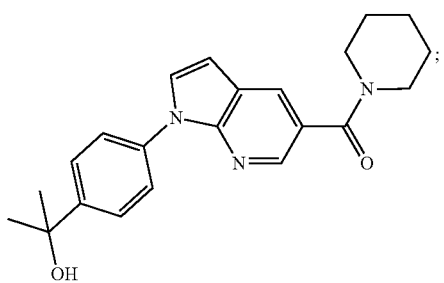

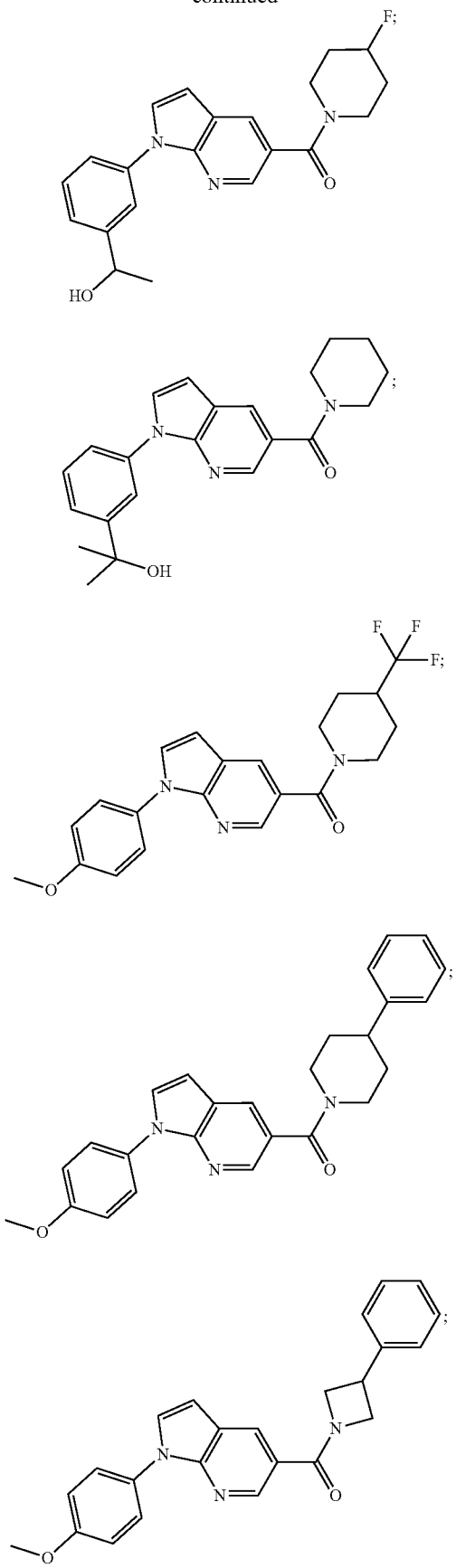

153
-continued
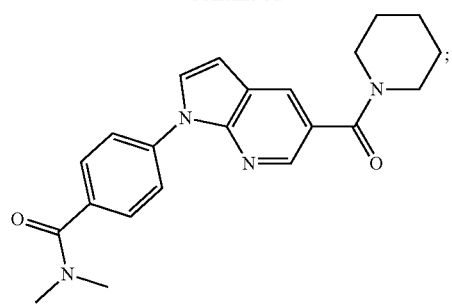
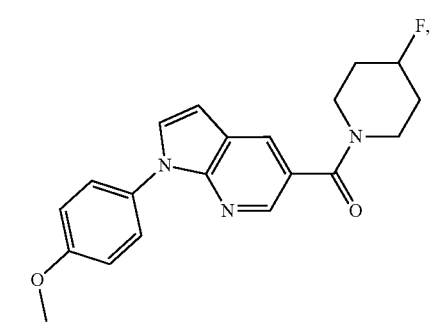
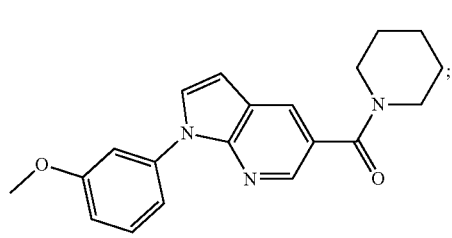
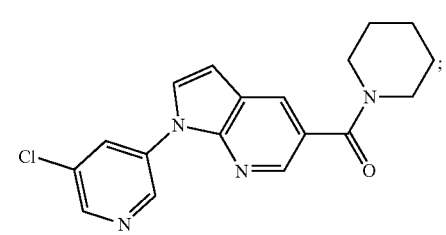
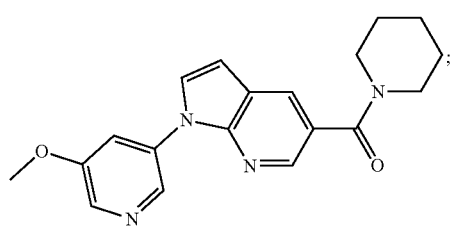
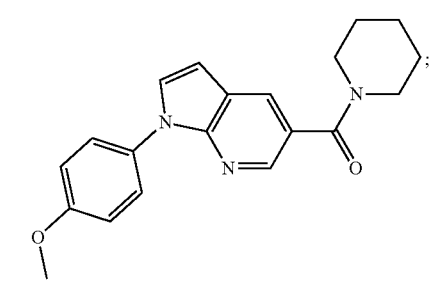
154
-continued
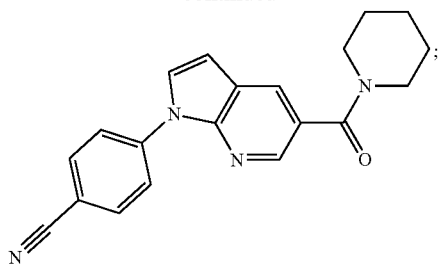
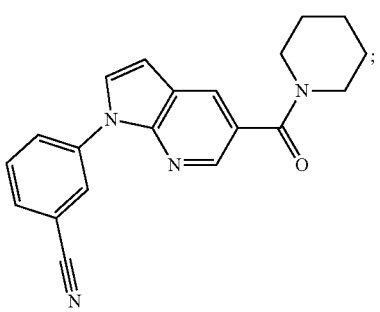
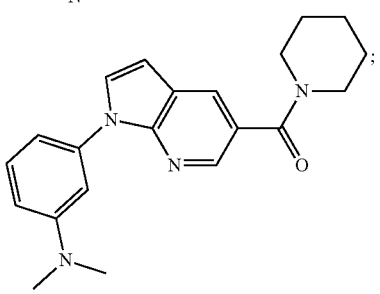
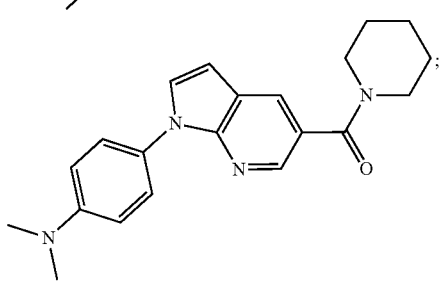
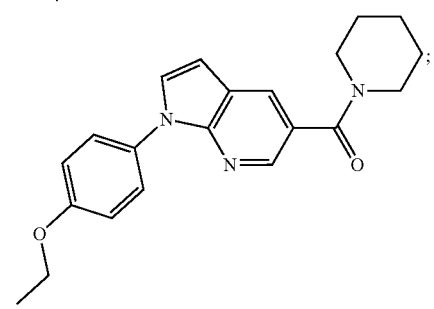
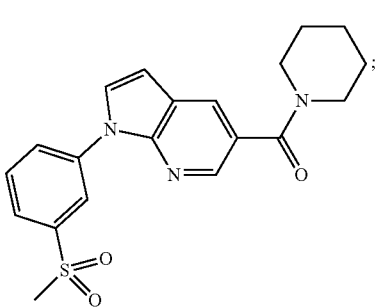

155
-continued
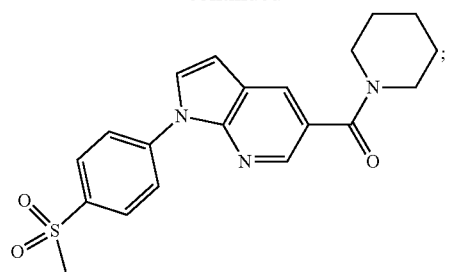
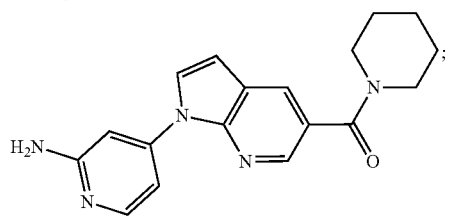
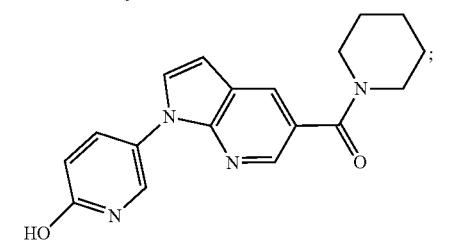
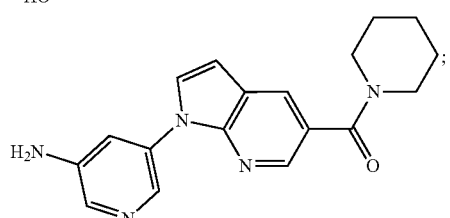
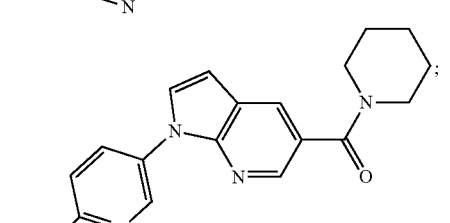
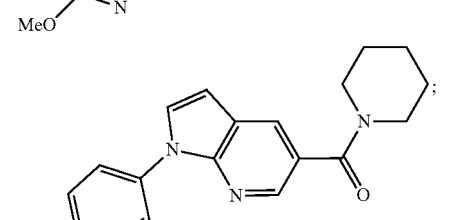
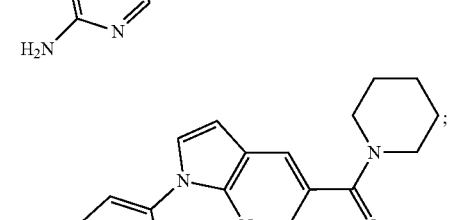
156
-continued
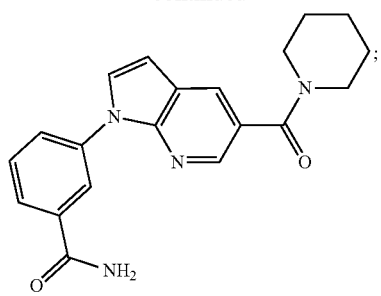
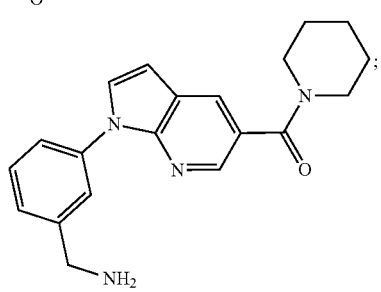
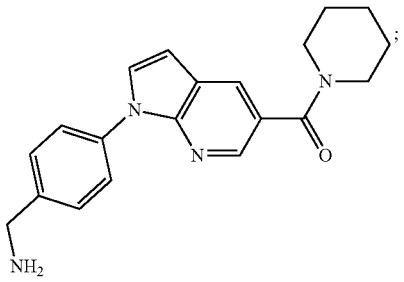
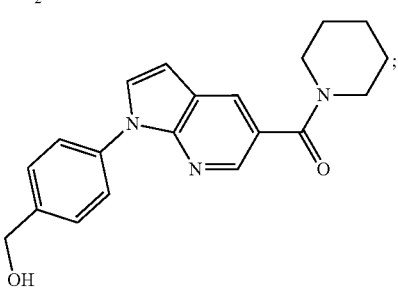
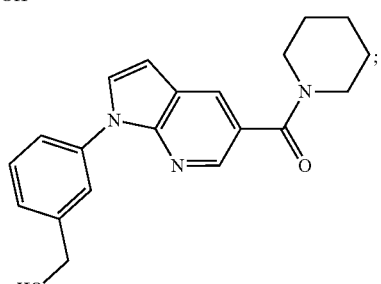
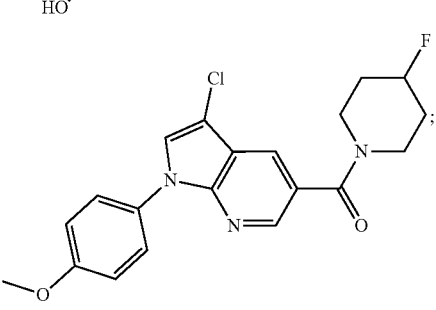

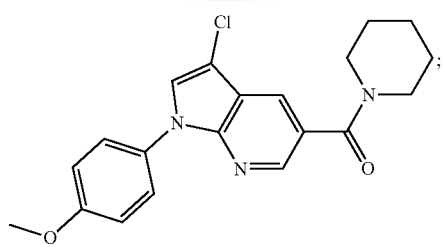
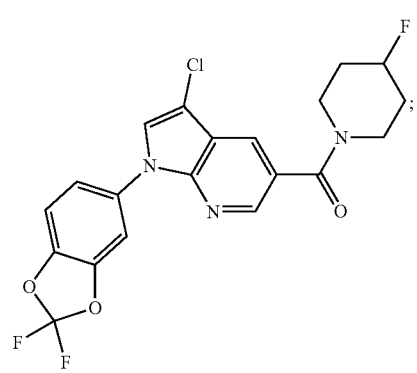
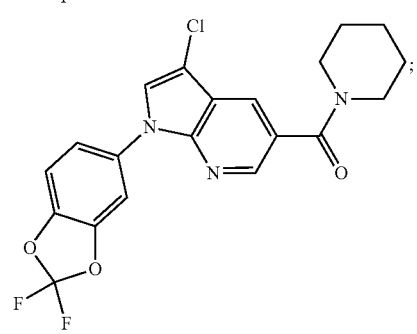
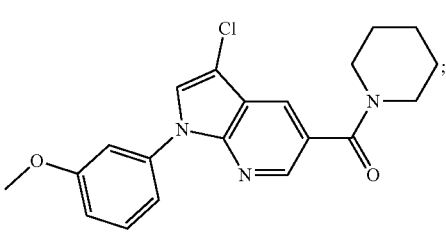
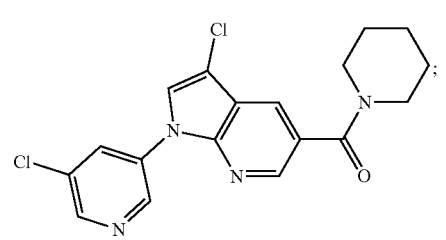
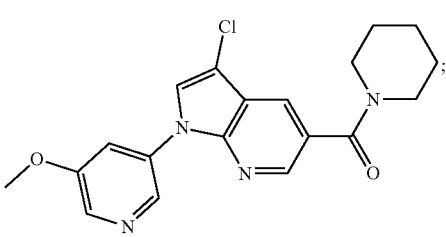
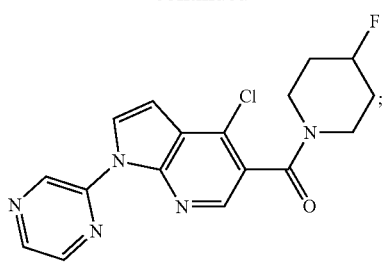
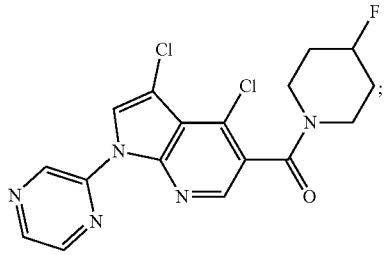
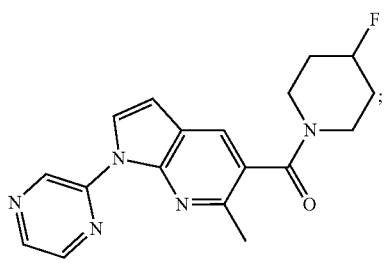
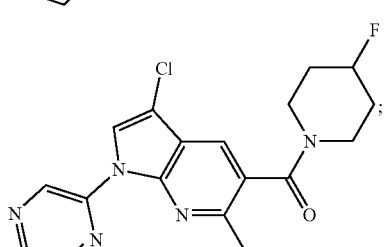
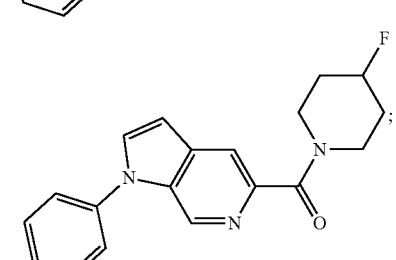
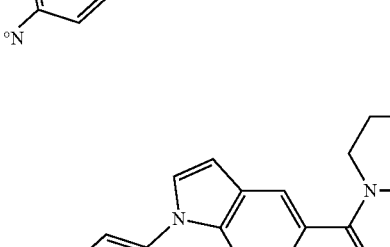
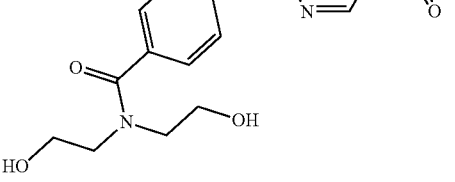

159
-continued
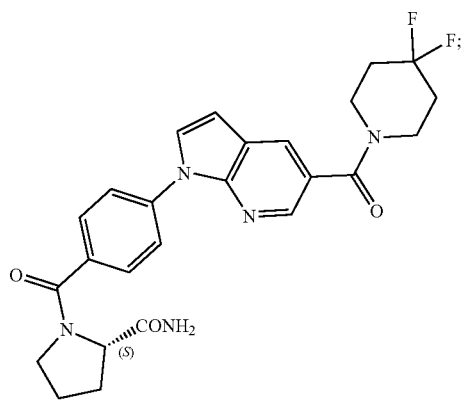
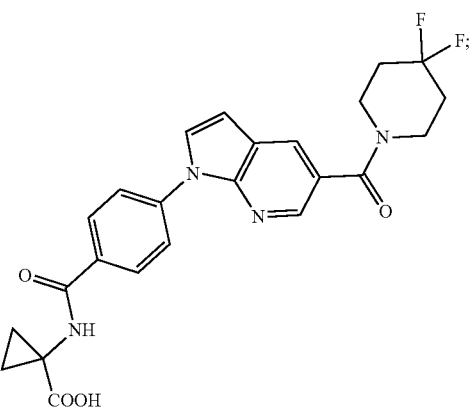
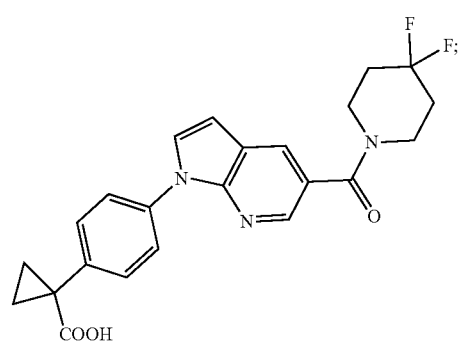
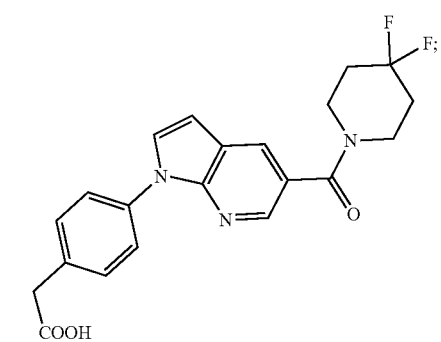
160
-continued
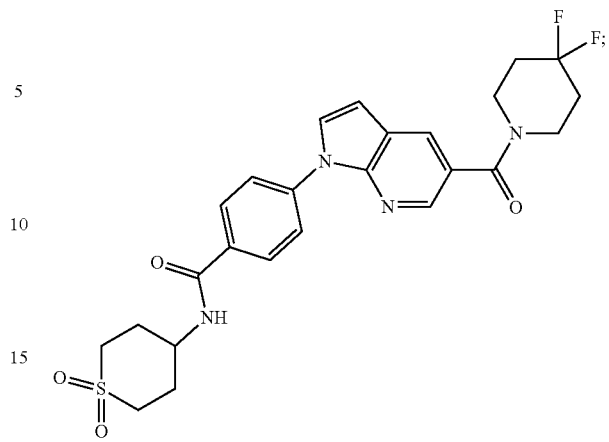
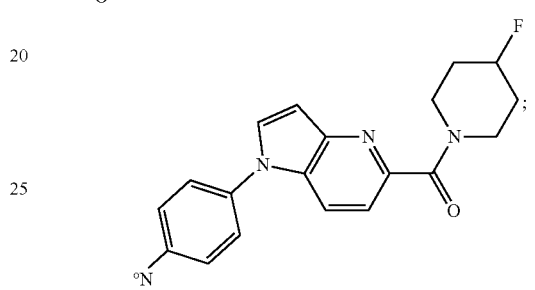
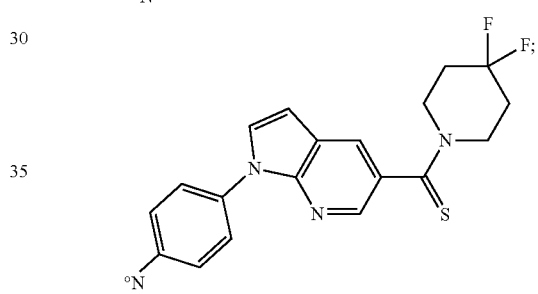
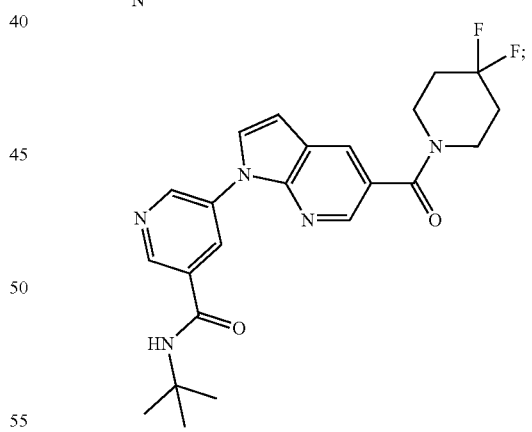
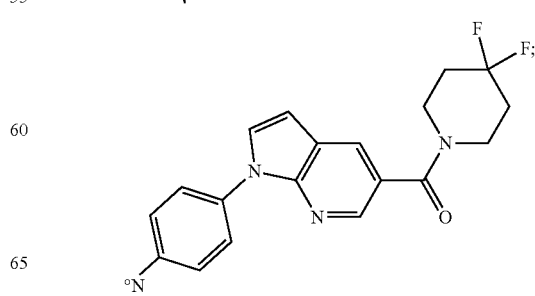

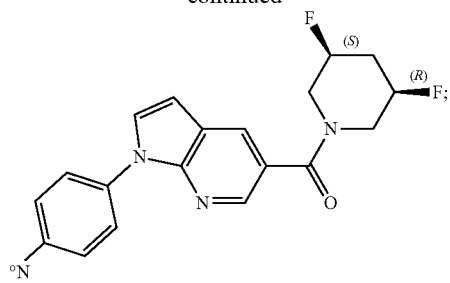
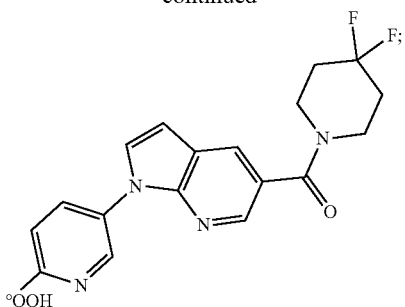
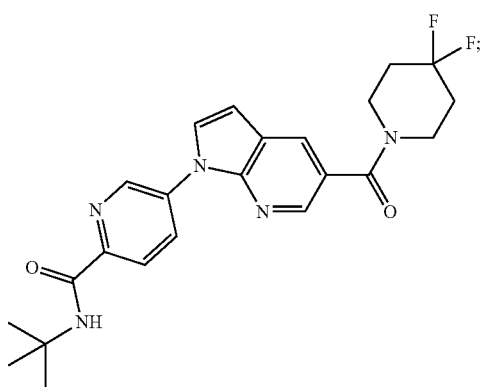
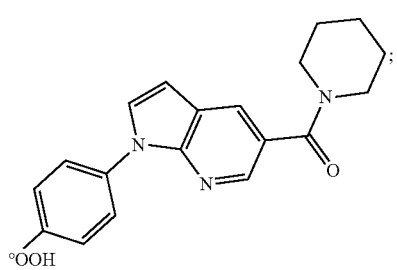
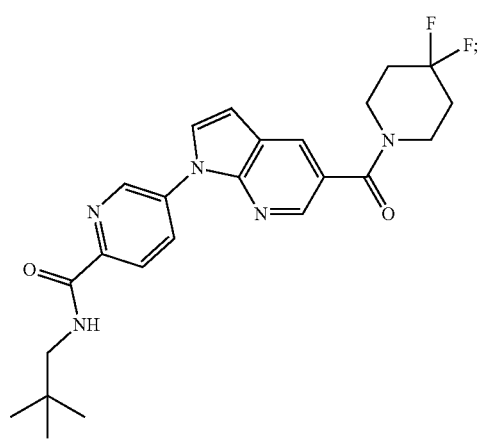
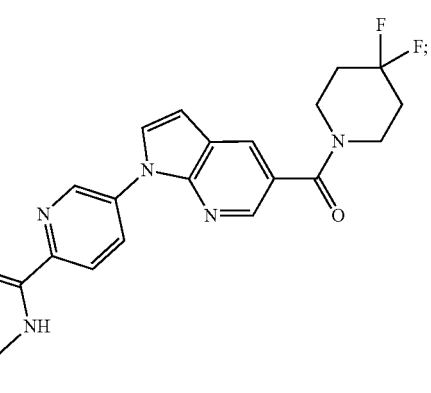
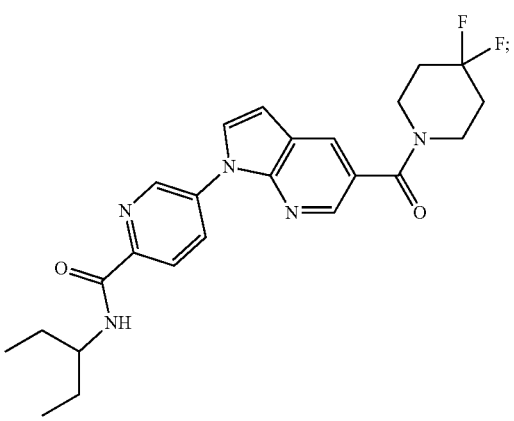
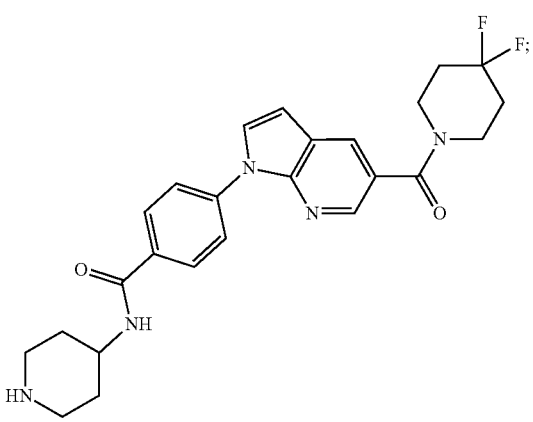

163
-continued
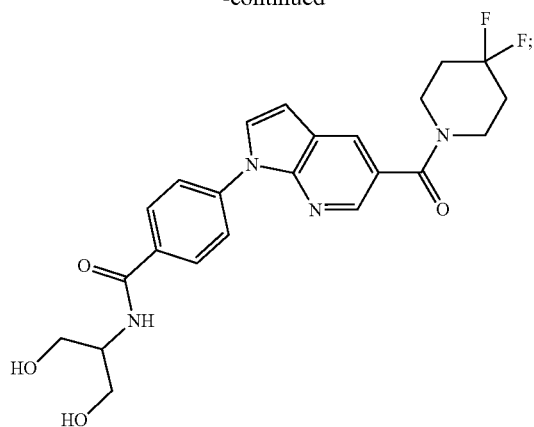
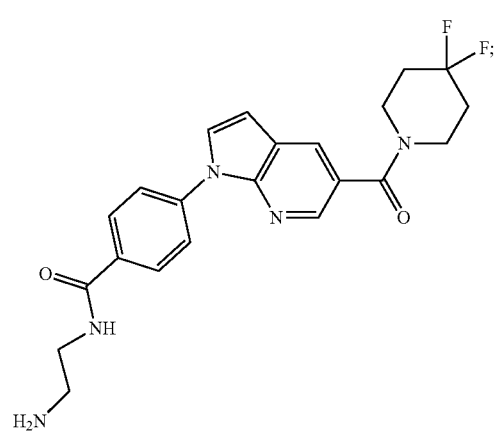
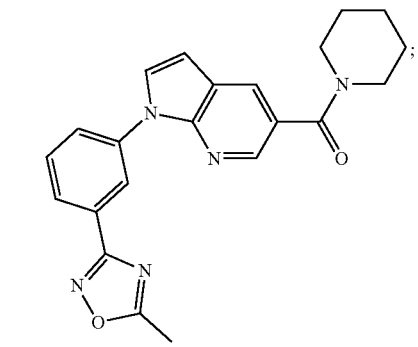
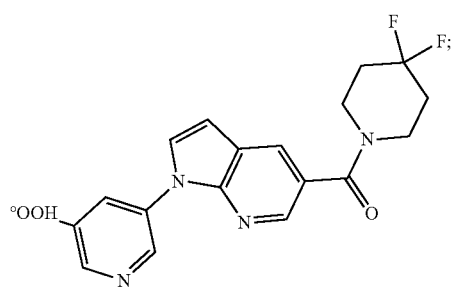
164
-continued
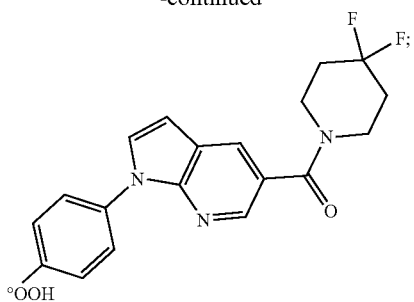
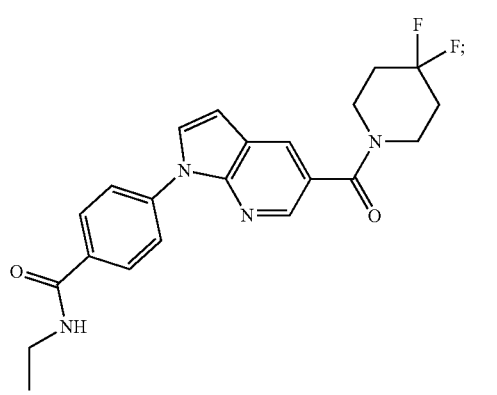
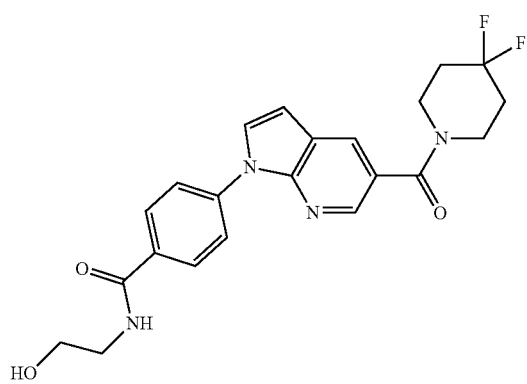
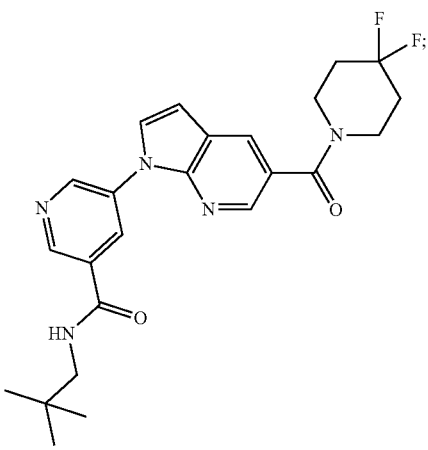

165
-continued
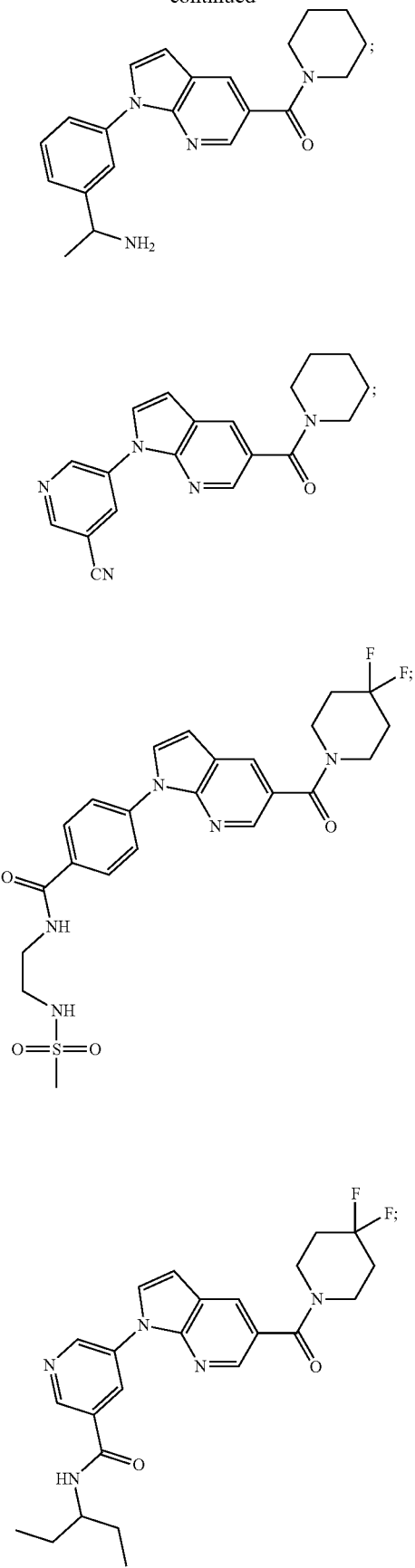
166
-continued
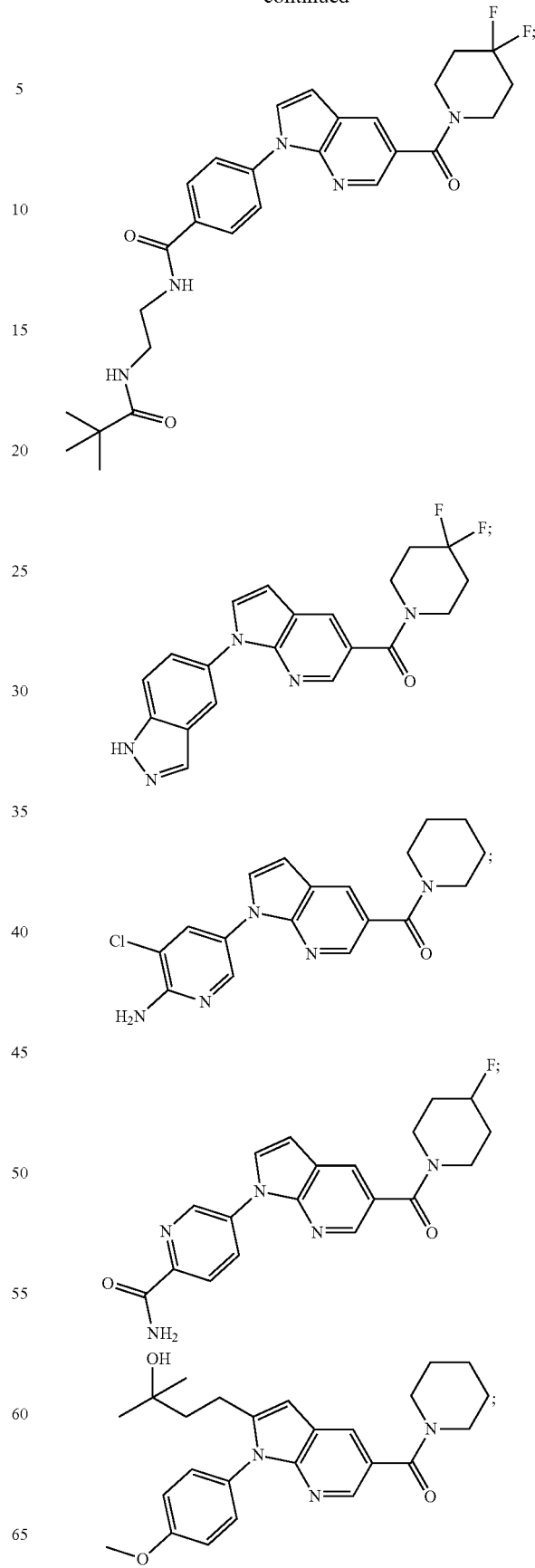

167
-continued
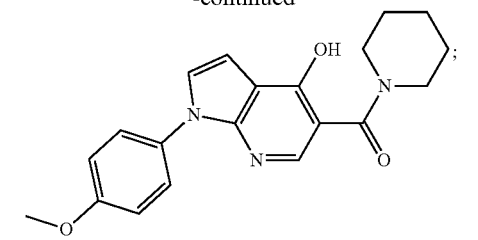
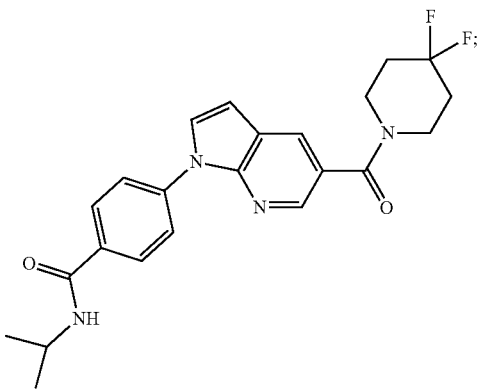
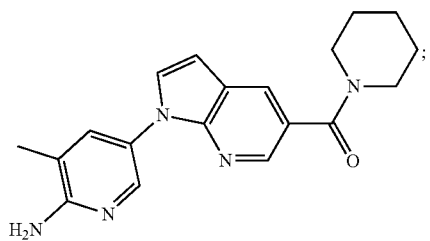
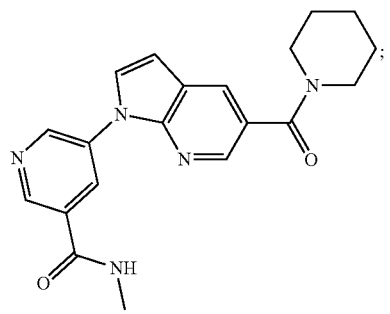
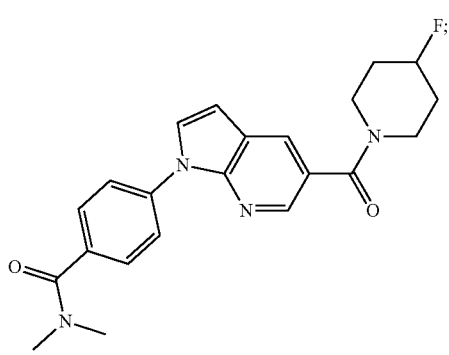
168
-continued
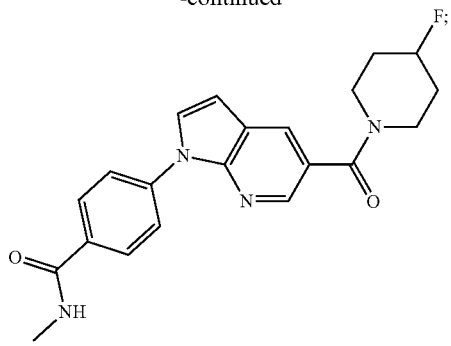
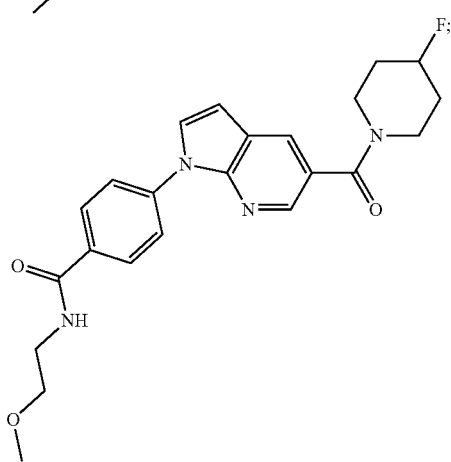
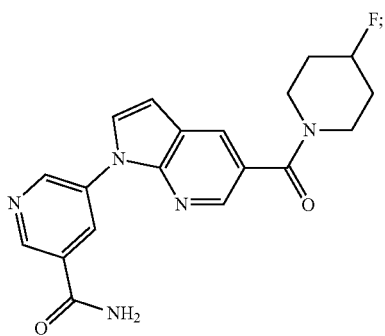
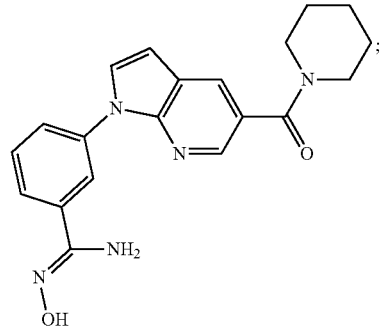
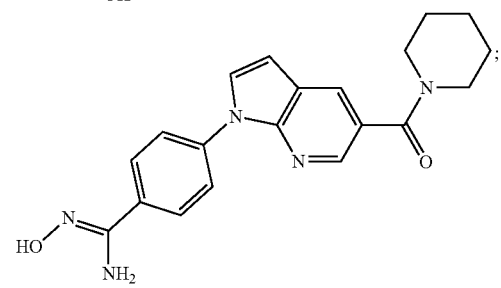

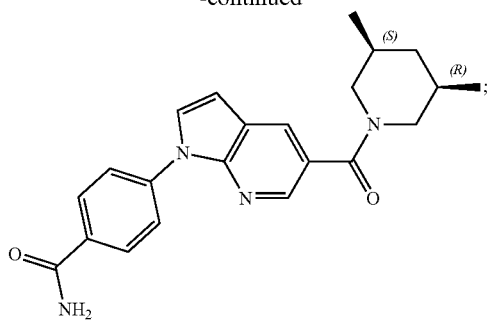
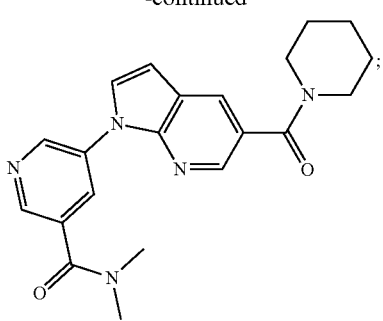
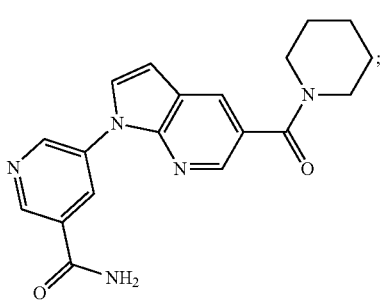
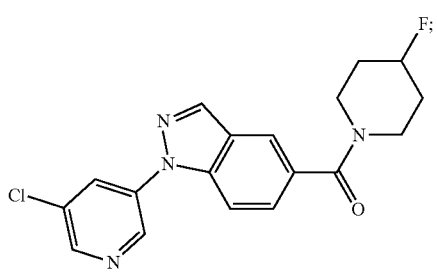
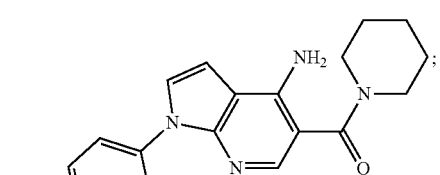
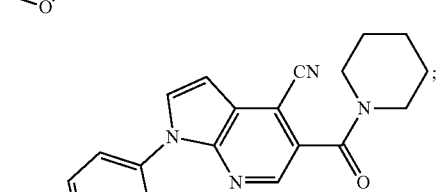
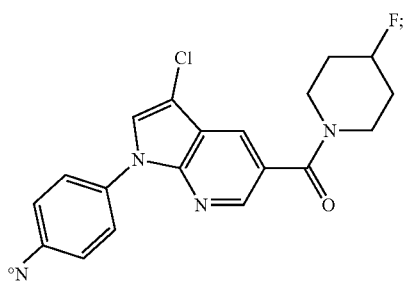

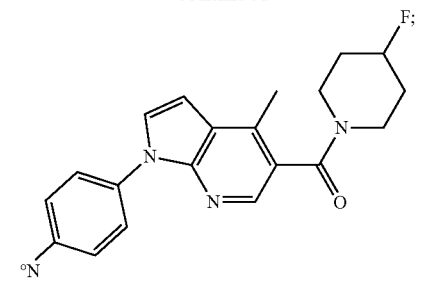
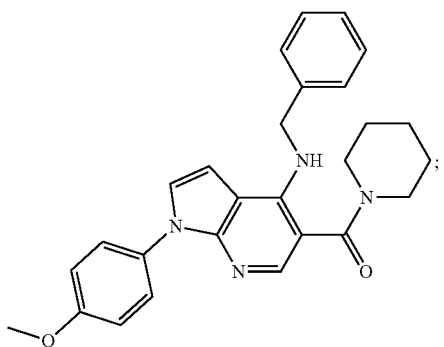
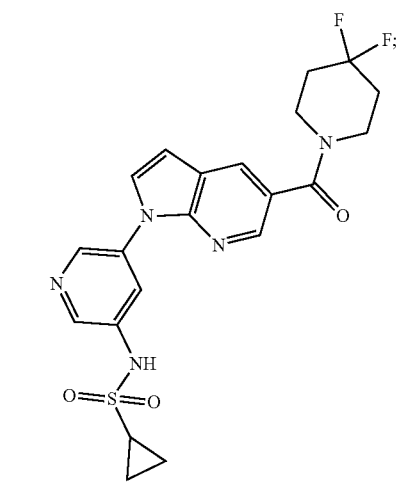
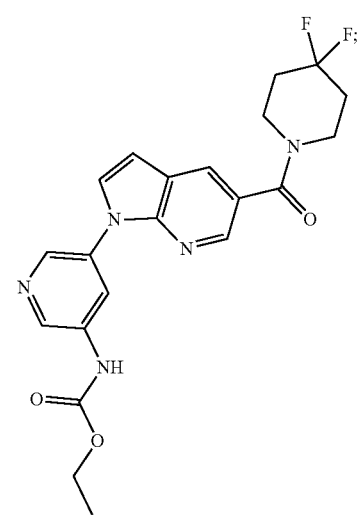
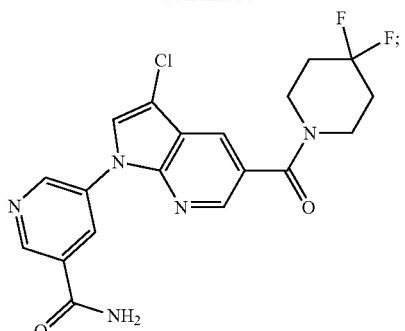
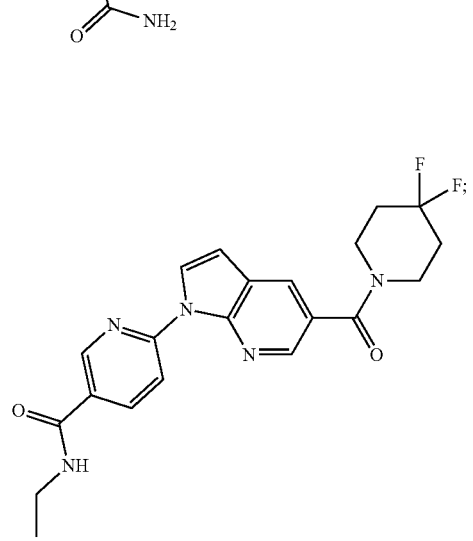
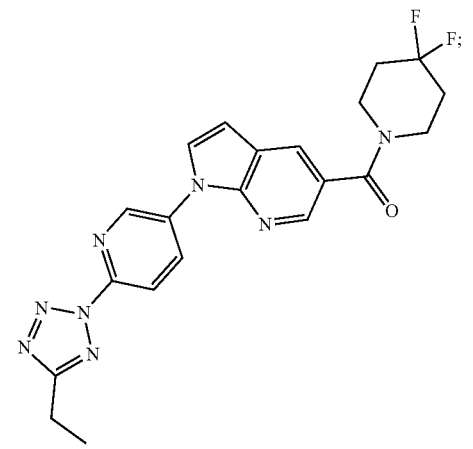
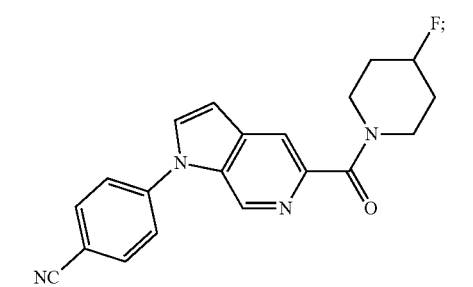

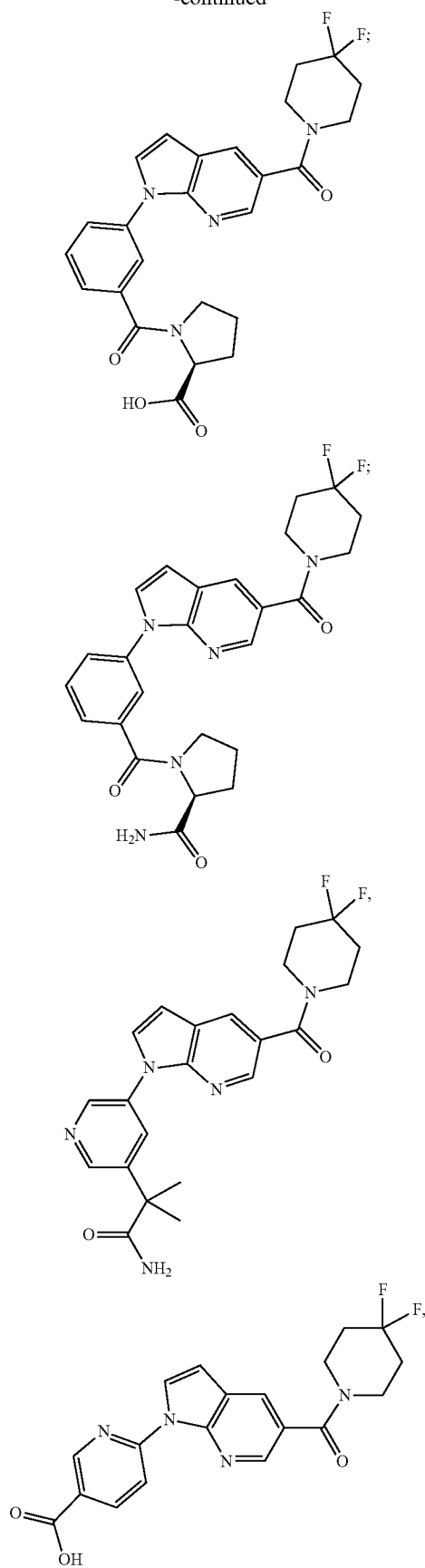
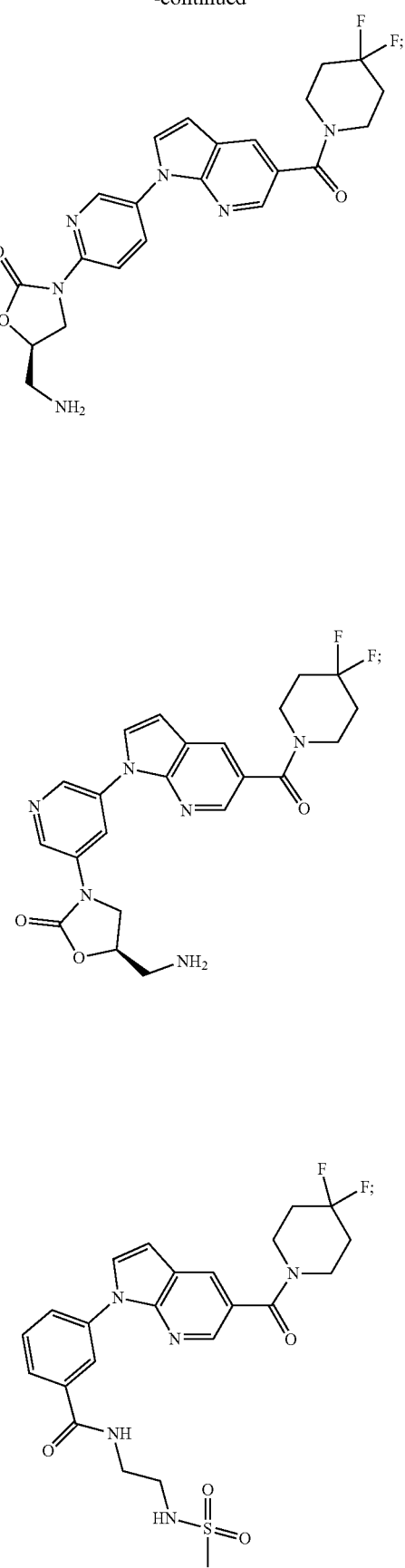

175
-continued
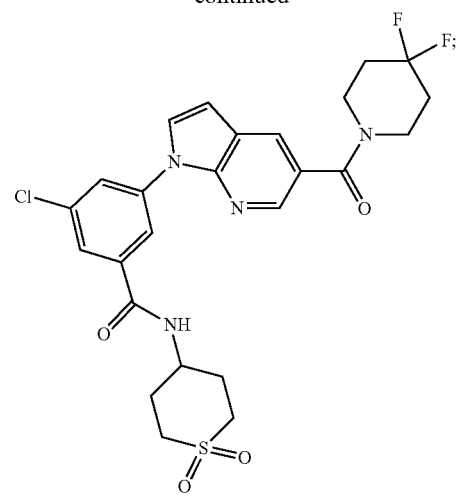
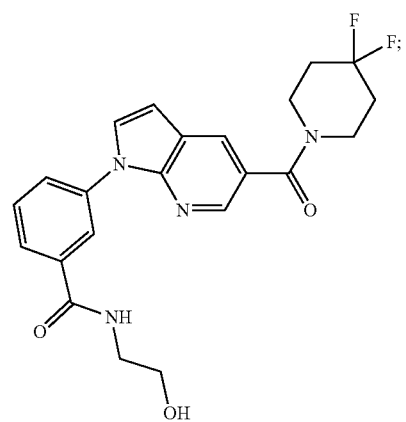
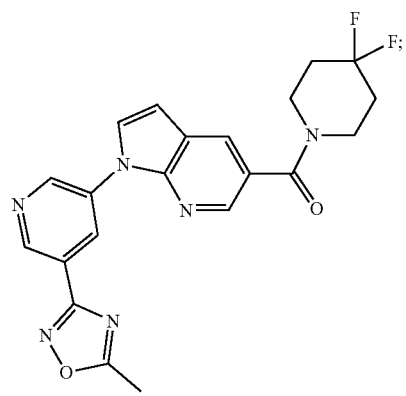
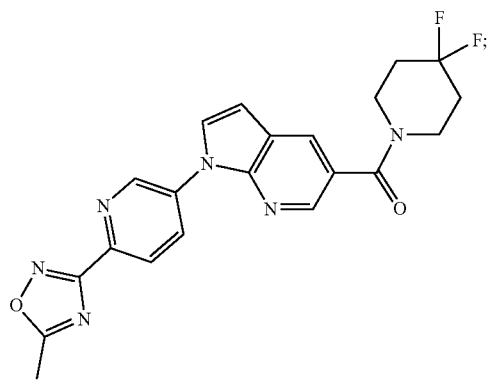
176
-continued
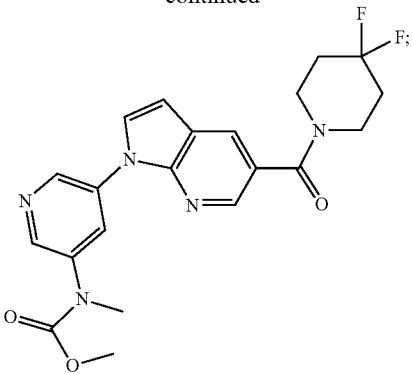
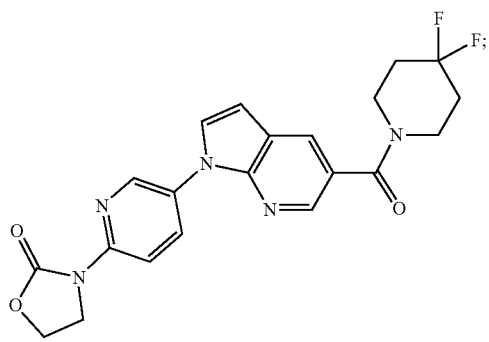
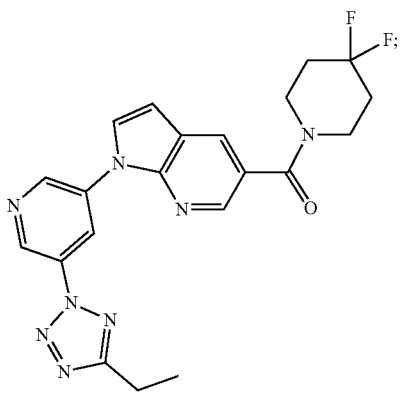
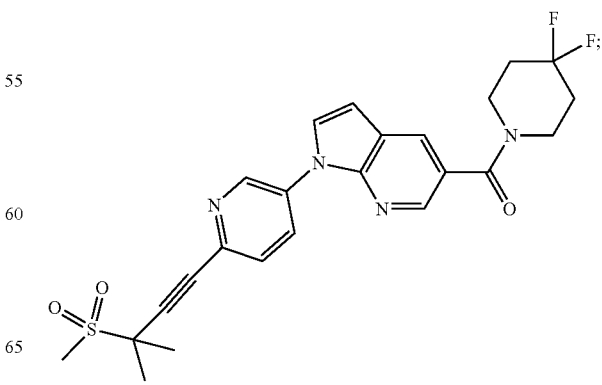

177
-continued
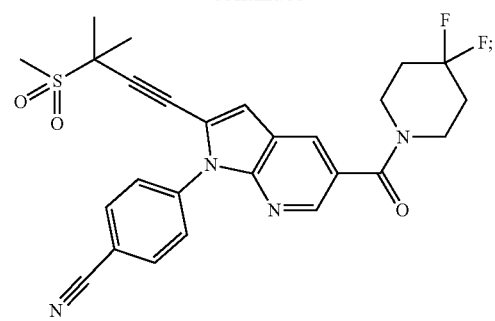
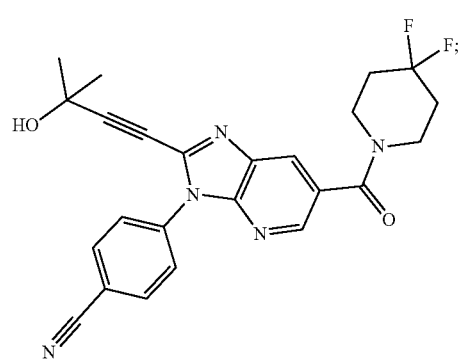
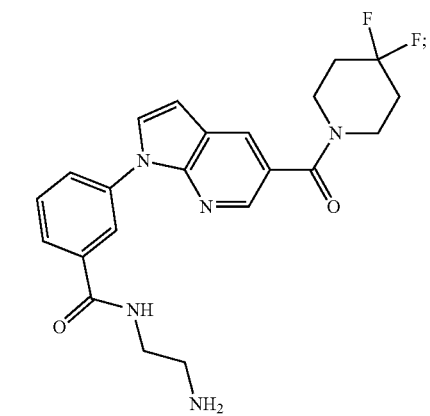
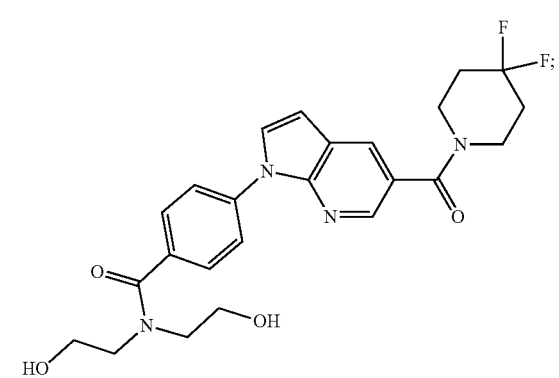
178
-continued
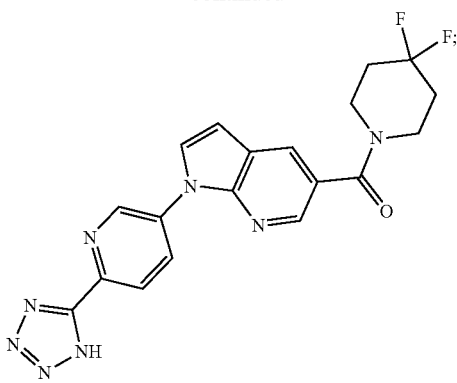
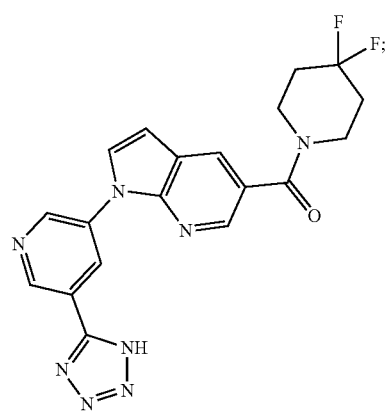
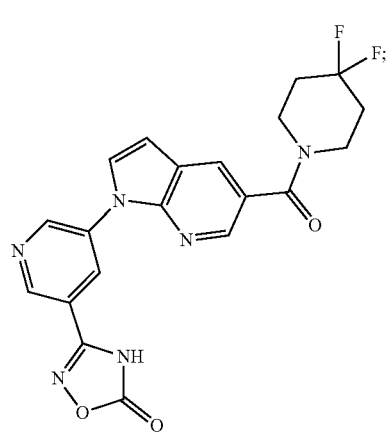
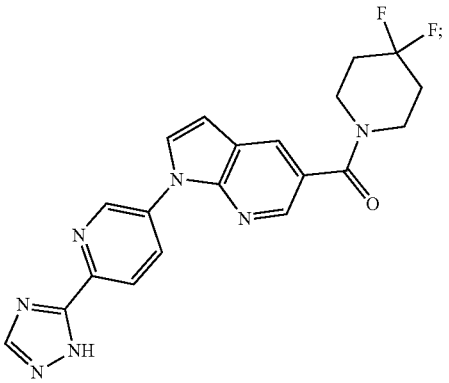

179
-continued
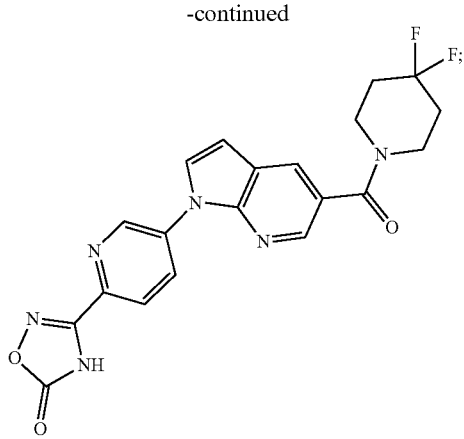
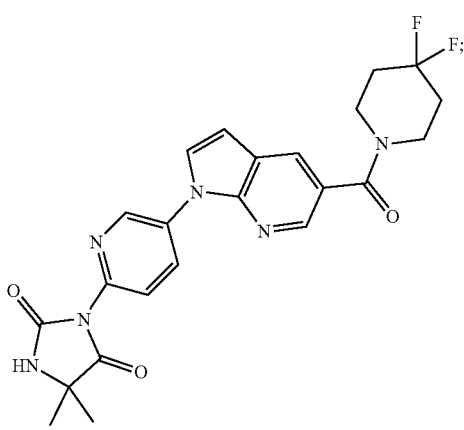
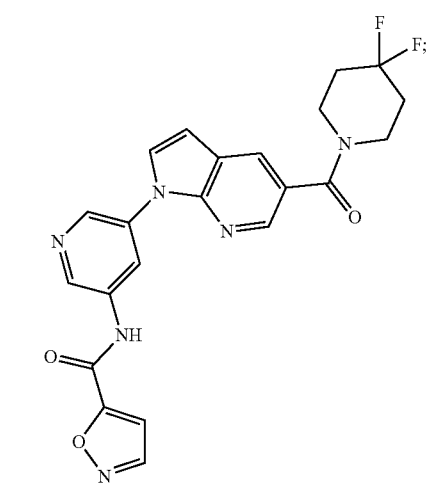
180
-continued
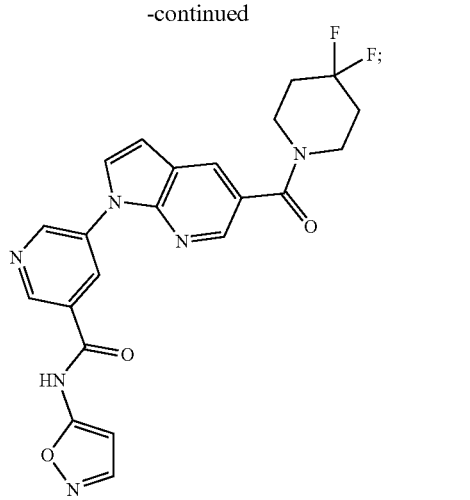
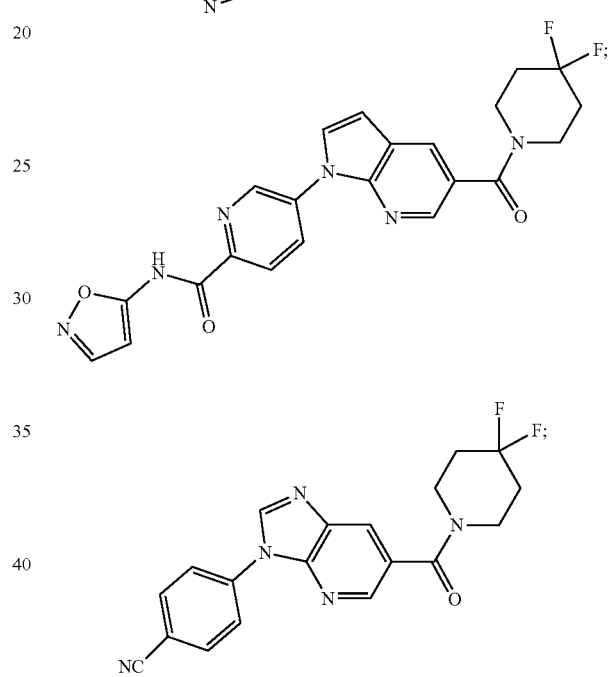
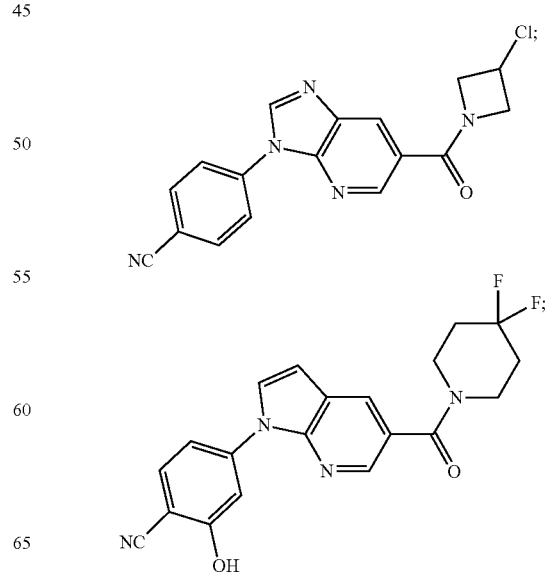

181
-continued
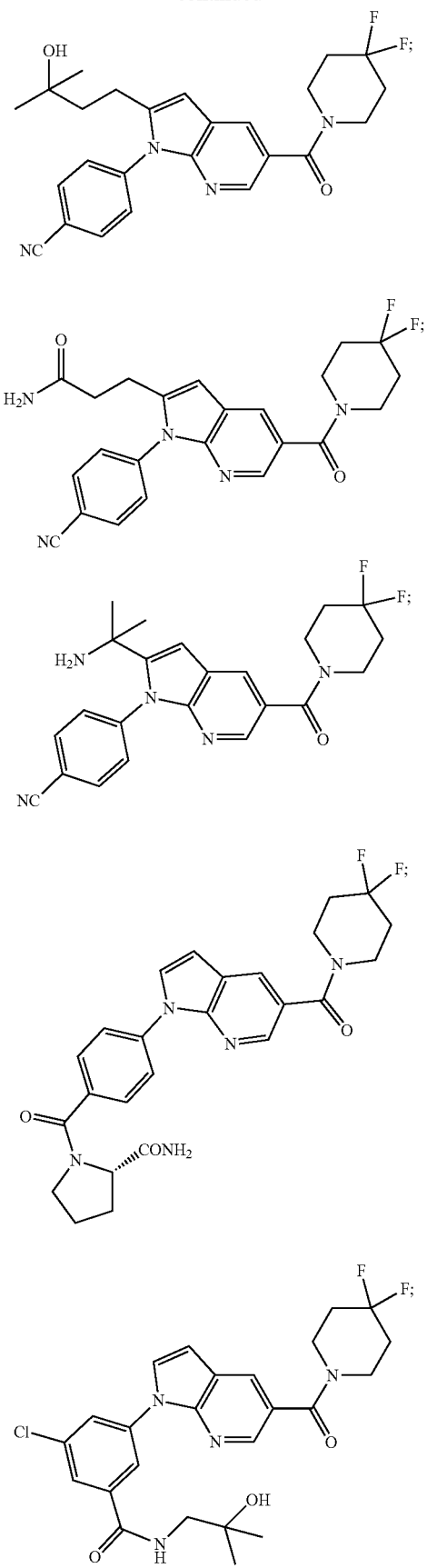
182
-continued
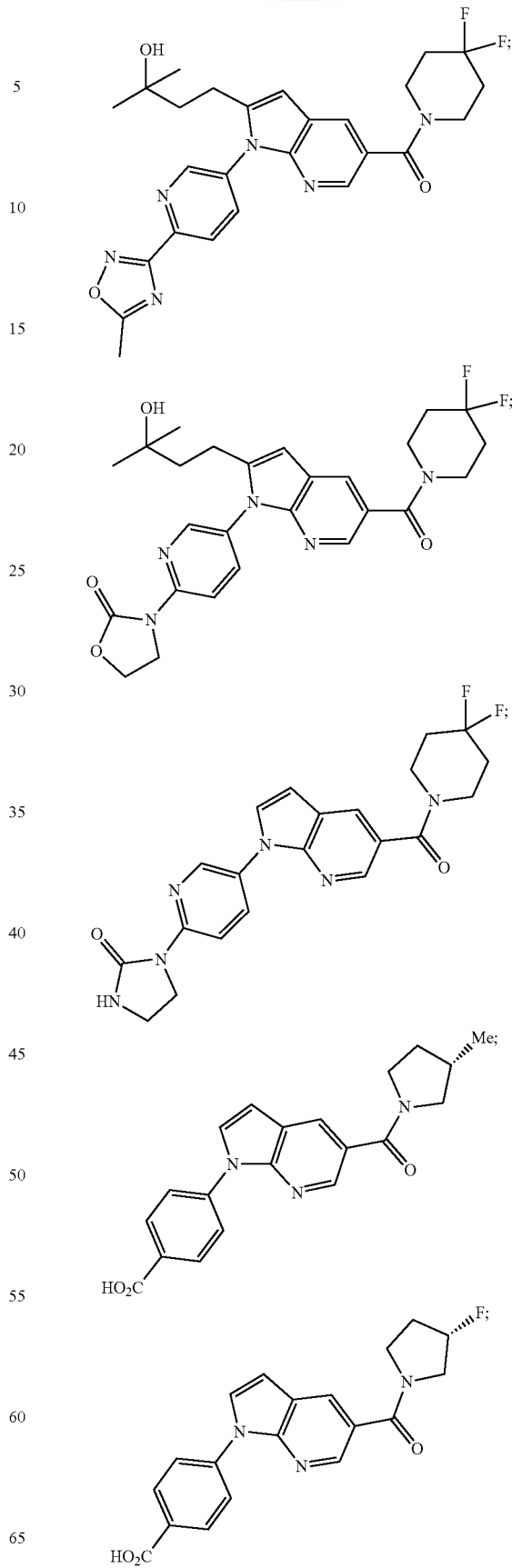

-continued
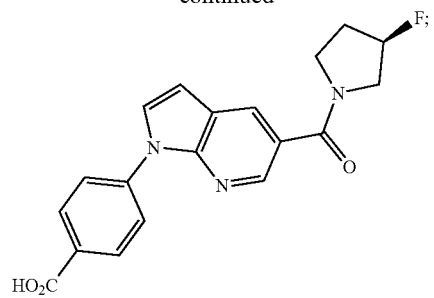
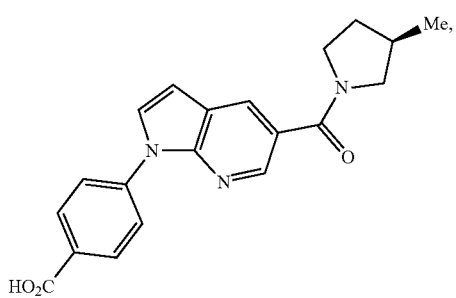
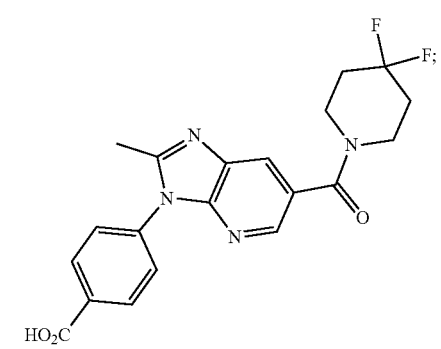
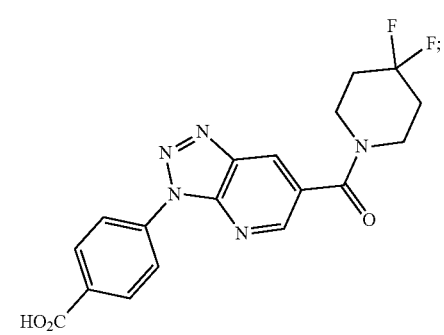
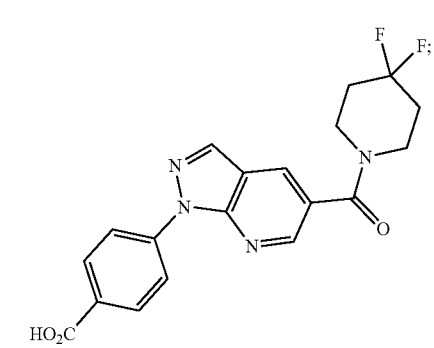
-continued
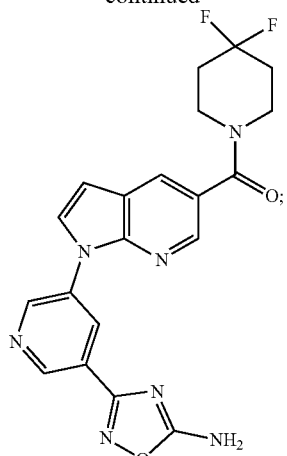
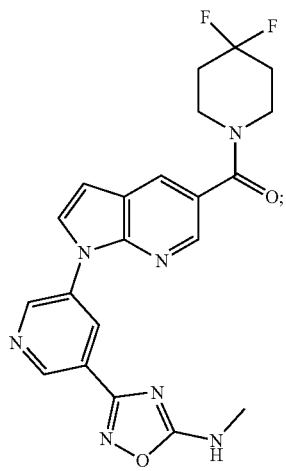
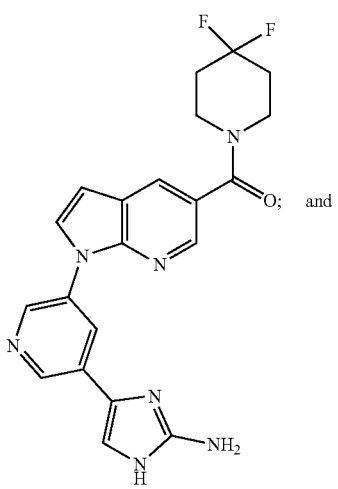

185
-continued
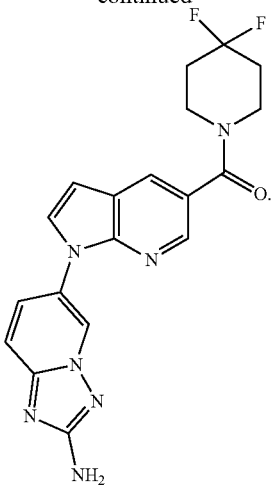
In another aspect, provided herein is a composition comprising a compound selected from the group consisting of:
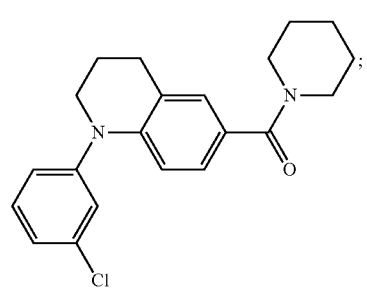
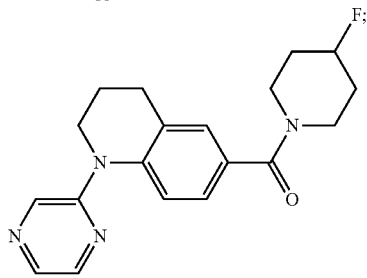
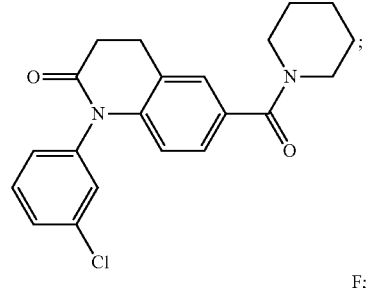
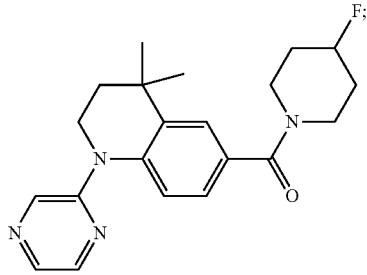
186
-continued
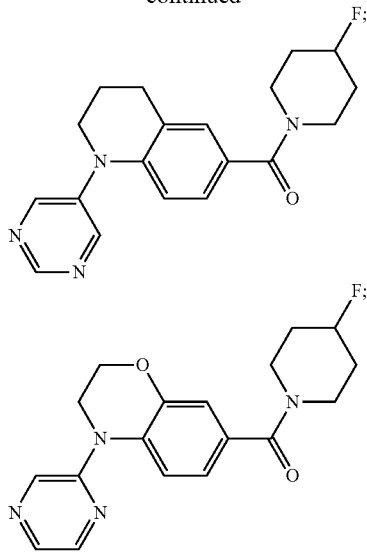
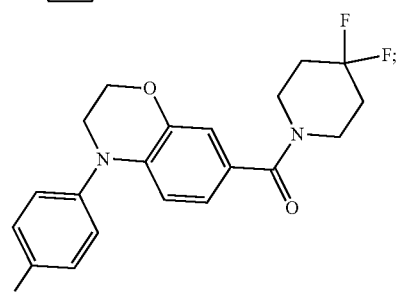
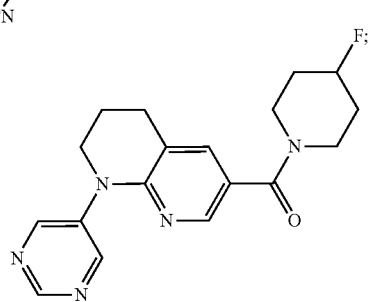
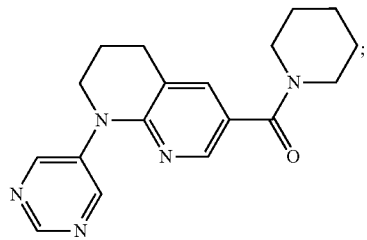
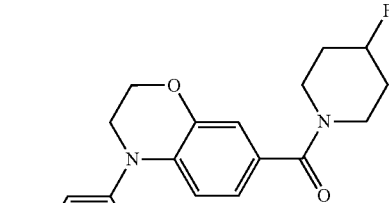
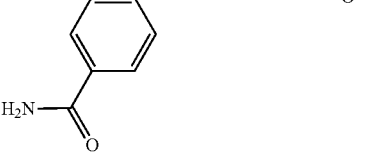

187
-continued
188
-continued
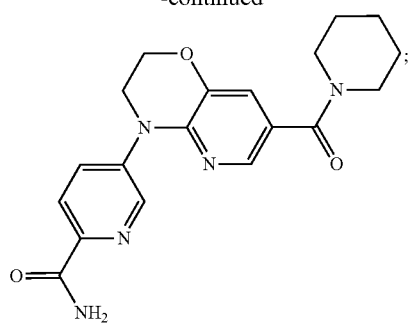
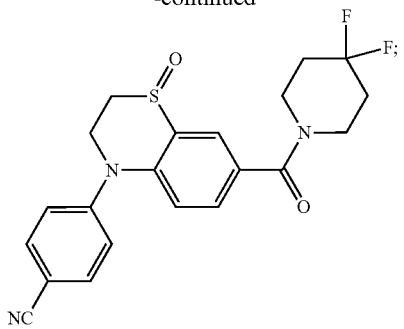

-continued
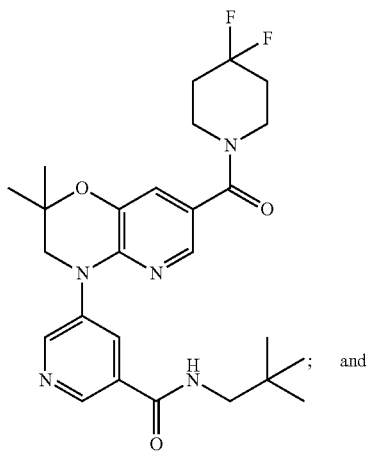; and
-continued
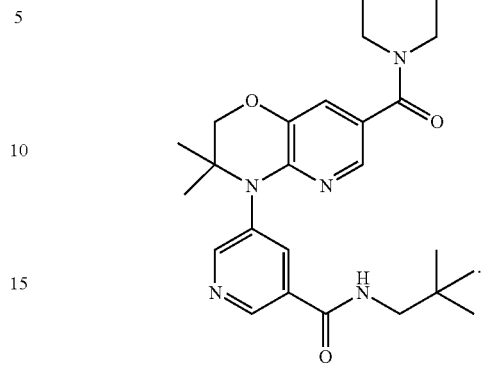
In some cases, the solubility and hPGDH IC50 of the inhibitors are characterized as shown in Tables 1 and 2.
TABLE 1
Characteristics of PGDH Inhibitors with a 6-5 ring core.
| Structure | hPGDH: IC50 (uM) | Solubility at pH 7.4 (μM) |
| --- | --- | --- |
| 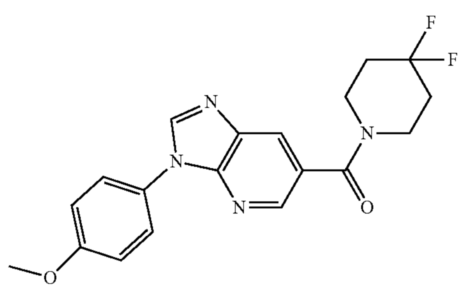 [SMILES: COc1ccc(-n2cnc3cc(C(=O)N4CCC(F)(F)CC4)cnc32)cc1] | 0.0574 | 140 |
| 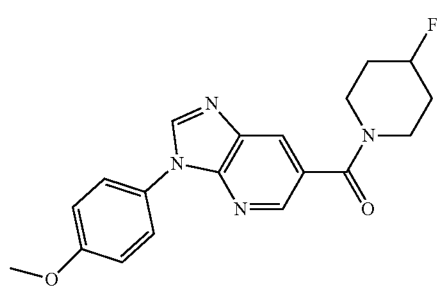 [SMILES: COc1ccc(-n2cnc3cc(C(=O)N4CCC(F)CC4)cnc32)cc1] | 0.0195 | 140 |
| 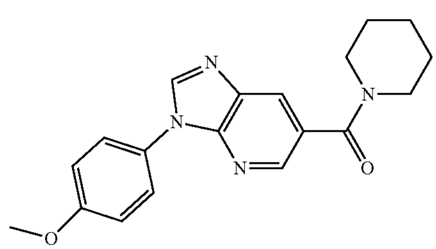 [SMILES: COc1ccc(-n2cnc3cc(C(=O)N4CCCCC4)cnc32)cc1] | 0.0201 | 160 |

TABLE 1-continued

Characteristics of PGDH Inhibitors with a 6-5 ring core.

| Structure | hPGDH: IC50 (uM) | Solubility at pH 7.4 (µM) |
|---|---|---|
| 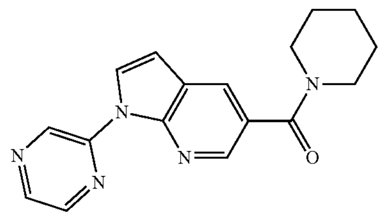 [SMILES: O=C(c1cnc2c(ccn2-c2cnccn2)c1)N1CCCCC1] | 0.0006 | |
| 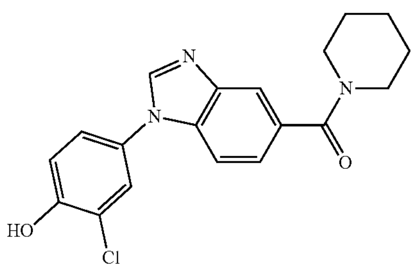 [SMILES: O=C(c1ccc2c(c1)ncn2-c1ccc(O)c(Cl)c1)N1CCCCC1] | 0.0025 | |
| 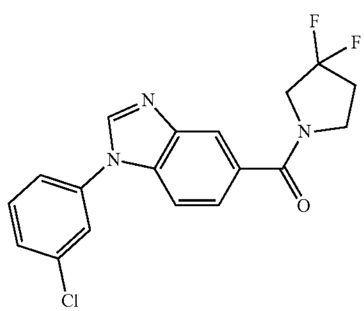 [SMILES: O=C(c1ccc2c(c1)ncn2-c1cccc(Cl)c1)N1CCC(F)(F)C1] | 1.2593 | |
| 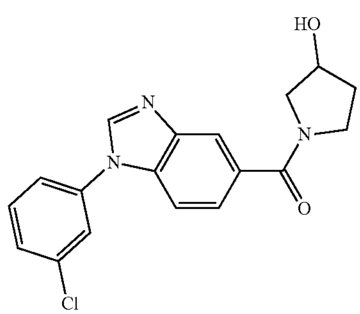 | 2.8696 | |
| 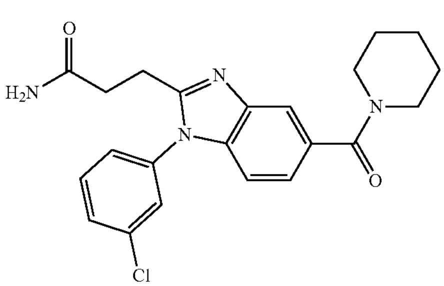 [SMILES: NC(=O)CCc1nc2cc(C(=O)N3CCCCC3)ccc2n1-c1cccc(Cl)c1] | 0.0449 | |

TABLE 1-continued

Characteristics of PGDH Inhibitors with a 6-5 ring core.

| Structure | hPGDH: IC50 (uM) | Solubility at pH 7.4 (µM) |
|---|---|---|
| 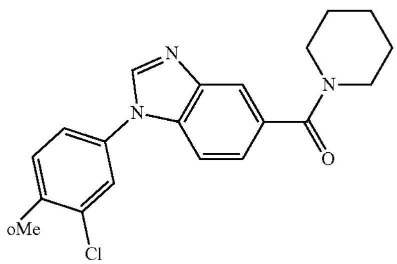 | 0.0471 | |
| 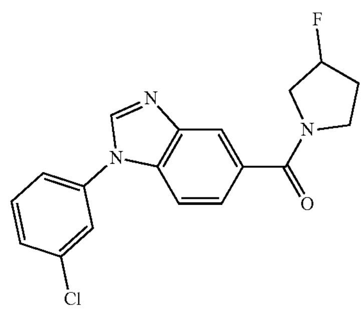 [SMILES: O=C(c1ccc2c(c1)ncn2-c1cccc(Cl)c1)N1CCC(F)C1] | 0.1579 | |
| 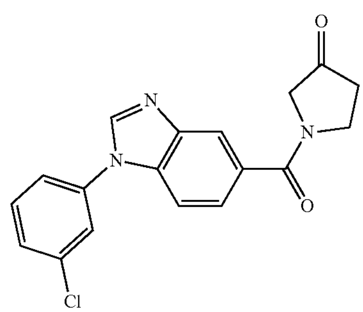 [SMILES: O=C1CCN(C(=O)c2ccc3c(c2)ncn3-c2cccc(Cl)c2)C1] | 4.5407 | |
| 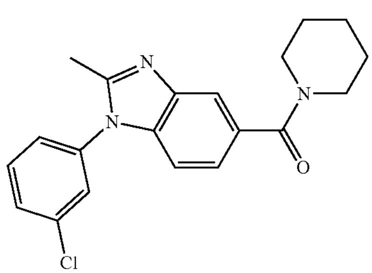 [SMILES: Cc1nc2cc(C(=O)N3CCCCC3)ccc2n1-c1cccc(Cl)c1] | 0.0056 | |
| 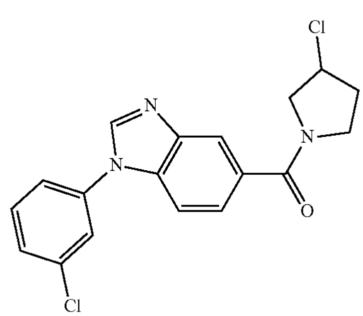 [SMILES: O=C(c1ccc2c(c1)ncn2-c1cccc(Cl)c1)N1CCC(Cl)C1] | 0.0647 | |

TABLE 1-continued

Characteristics of PGDH Inhibitors with a 6-5 ring core.

| Structure | hPGDH: IC50 (uM) | Solubility at pH 7.4 (μM) |
|---|---|---|
| 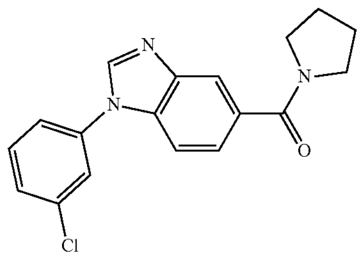 [SMILES: O=C(c1ccc2c(c1)ncn2-c1cccc(Cl)c1)N1CCCC1] | 0.2736 | |
| 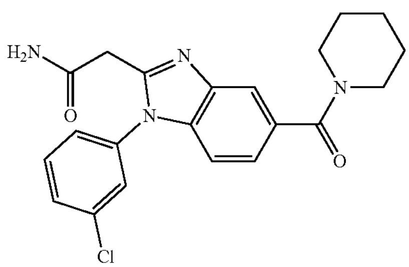 [SMILES: NC(=O)Cc1nc2cc(C(=O)N3CCCCC3)ccc2n1-c1cccc(Cl)c1] | 0.5757 | |
| 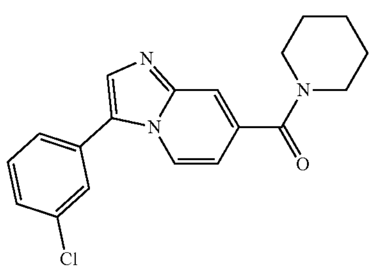 [SMILES: O=C(c1ccn2c(-c3cccc(Cl)c3)cnc2c1)N1CCCCC1] | 0.0057 | |
| 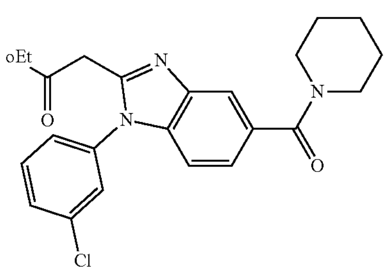 | 0.0052 | |
| 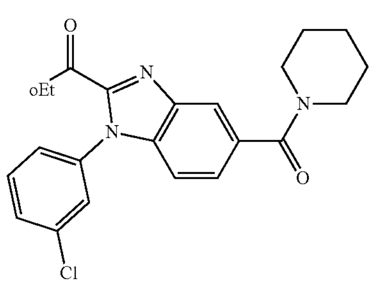 | 0.0018 | 34 |

TABLE 1-continued

Characteristics of PGDH Inhibitors with a 6-5 ring core.

| Structure | hPGDH: IC50 (uM) | Solubility at pH 7.4 (μM) |
|---|---|---|
| 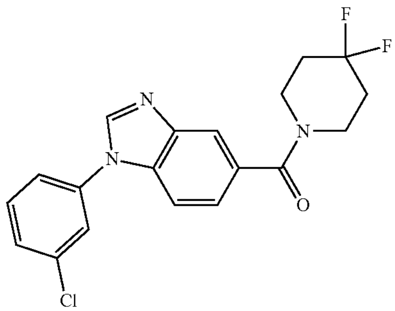 [SMILES: O=C(c1ccc2c(c1)ncn2-c1cccc(Cl)c1)N1CCC(F)(F)CC1] | 0.0122 | |
| 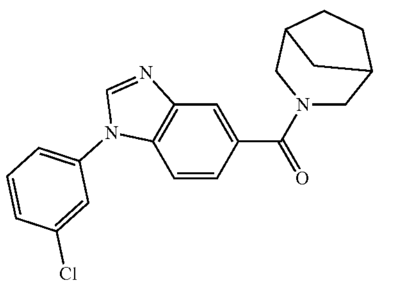 [SMILES: O=C(c1ccc2c(c1)ncn2-c1cccc(Cl)c1)N1CC2CCC(C2)C1] | 0.0466 | |
| 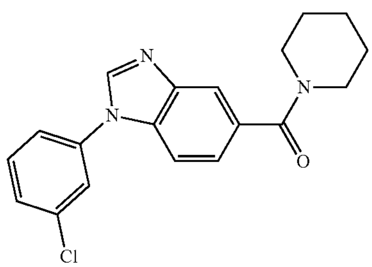 [SMILES: O=C(c1ccc2c(c1)ncn2-c1cccc(Cl)c1)N1CCCCC1] | 0.0027 | 120 |
| 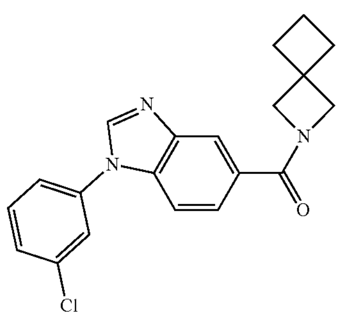 [SMILES: O=C(c1ccc2c(c1)ncn2-c1cccc(Cl)c1)N1CC2(CCC2)C1] | 0.0439 | 16 |
| 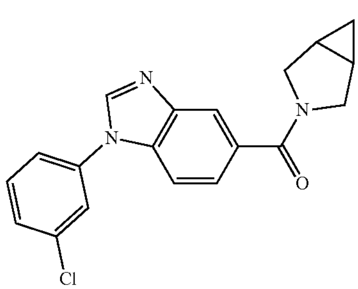 [SMILES: O=C(c1ccc2c(c1)ncn2-c1cccc(Cl)c1)N1CC2CC2C1] | 0.1164 | |

TABLE 1-continued

Characteristics of PGDH Inhibitors with a 6-5 ring core.

| Structure | hPGDH: IC50 (uM) | Solubility at pH 7.4 (μM) |
|---|---|---|
| 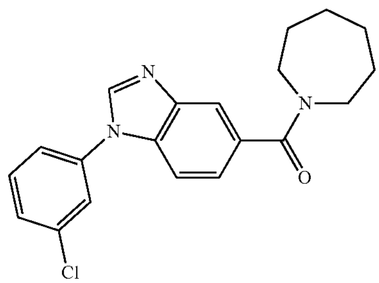 [SMILES: O=C(c1ccc2c(c1)ncn2-c1cccc(Cl)c1)N1CCCCCC1] | 0.0032 | |
| 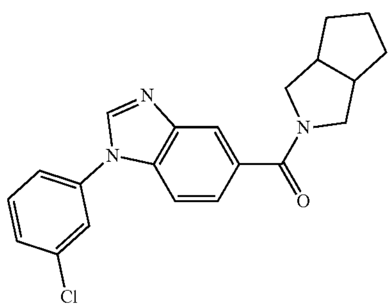 [SMILES: O=C(c1ccc2c(c1)ncn2-c1cccc(Cl)c1)N1CC2CCCC2C1] | 0.0249 | 33 |
| 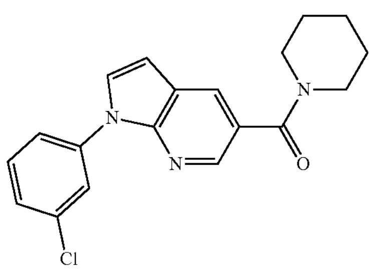 | 0.0015 | 21 |
| 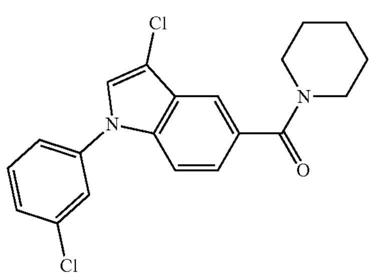 [SMILES: O=C(c1ccc2c(c1)c(Cl)cn2-c1cccc(Cl)c1)N1CCCCC1] | 0.0106 | |
| 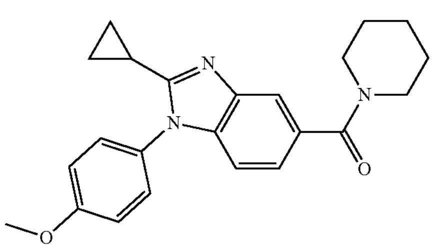 [SMILES: COc1ccc(-n2c(C3CC3)nc3cc(C(=O)N4CCCCC4)ccc32)cc1] | 0.1968 | 45 |

TABLE 1-continued

Characteristics of PGDH Inhibitors with a 6-5 ring core.

| Structure | hPGDH: IC50 (uM) | Solubility at pH 7.4 (µM) |
|---|---|---|
| 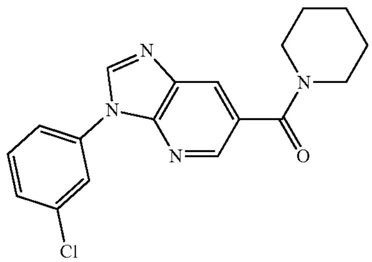 [SMILES: O=C(c1cnc2c(c1)ncn2-c1cccc(Cl)c1)N1CCCCC1] | 0.0128 | 150 |
| 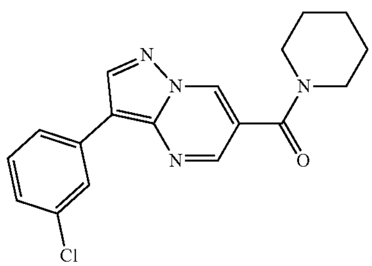 [SMILES: O=C(c1cnc2c(-c3cccc(Cl)c3)cnn2c1)N1CCCCC1] | 0.0493 | <5.0 |
| 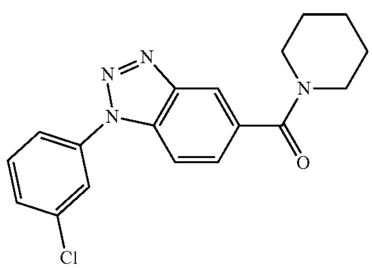 | 0.0031 | 68 |
| 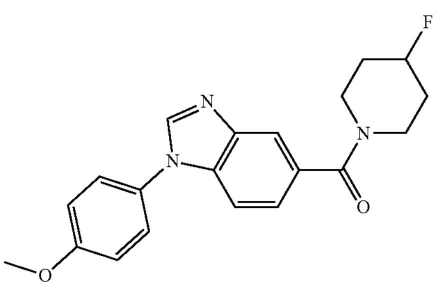 [SMILES: COc1ccc(-n2cnc3cc(C(=O)N4CCC(F)CC4)ccc32)cc1] | 0.0437 | 160 |
| 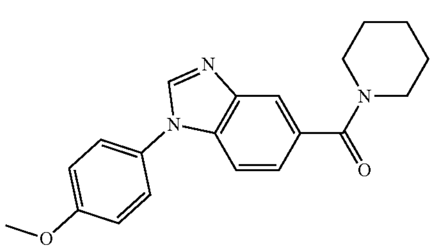 [SMILES: COc1ccc(-n2cnc3cc(C(=O)N4CCCCC4)ccc32)cc1] | 0.0064 | 150 |

TABLE 1-continued
Characteristics of PGDH Inhibitors with a 6-5 ring core.
| Structure | hPGDH: IC50 (uM) | Solubility at pH 7.4 (μM) |
|---|---|---|
| 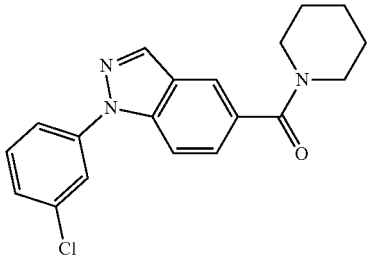 [SMILES: O=C(c1ccc2c(cnn2-c2cccc(Cl)c2)c1)N1CCCCC1] | 0.0058 | 6.9 |
| 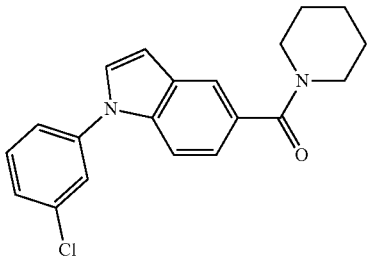 [SMILES: O=C(c1ccc2c(ccn2-c2cccc(Cl)c2)c1)N1CCCCC1] | 0.0005 | <5.0 |
TABLE 2
Characteristics of PGDH Inhibitors with a phenyl core.
| Structure | hPGDH: IC50 (uM) | Solubility at pH 7.4 (μM) |
|---|---|---|
| 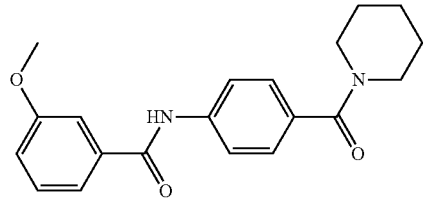 [SMILES: COc1cccc(C(=O)Nc2ccc(C(=O)N3CCCCC3)cc2)c1] | 0.135 | |
| 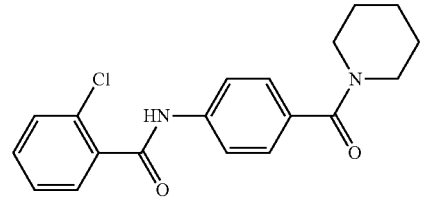 [SMILES: O=C(Nc1ccc(C(=O)N2CCCCC2)cc1)c1ccccc1Cl] | 0.2772 | |
| 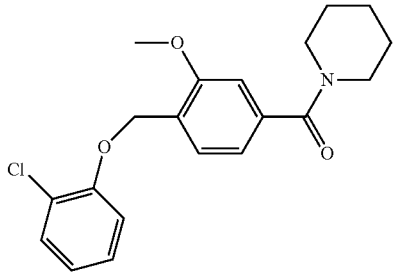 [SMILES: COc1cc(C(=O)N2CCCCC2)ccc1COc1ccccc1Cl] | 0.0085 | |

TABLE 2-continued

Characteristics of PGDH Inhibitors with a phenyl core.

| Structure | hPGDH: IC50 (uM) | Solubility at pH 7.4 (μM) |
|---|---|---|
| [structure] | 2.2838 | 160 |
| [structure] | 0.0186 | 38 |
| [structure] | 0.0271 | 29 |
| [structure] | 0.5933 | 88 |
| [structure] | 0.0031 | 6.3 |

Provided in Table 3 are analytical data for some of the inhibitors described herein.

TABLE 3

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-015 | 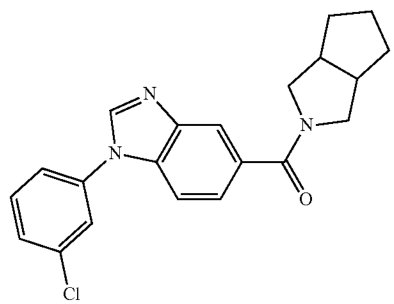 [SMILES: O=C(c1ccc2c(c1)ncn2-c1cccc(Cl)c1)N1CC2CCCC2C1] | 10.5%/ 98.06% | 365.13 for C21H20ClN3O/ 366.0 (M + 1) | δ 8.69 (s, 1H), 7.86-7.89 (m, 2H), 7.65-7.73 (m, 3H), 7.58-7.61 (m, 1H), 7.48 (dd, J = 1.5, 8.4 Hz, 1H), 3.69 (br s, 2H), 3.37 (br d, J = 8.8 Hz, 1H), 3.26 (br s, 1H), 2.61-2.68 (m, 2H), 1.65-1.79 (m, 3H), 1.48-1.60 (m, 2H), 1.29-1.41 (m, 1H). |
| MF-PGDH-016 | 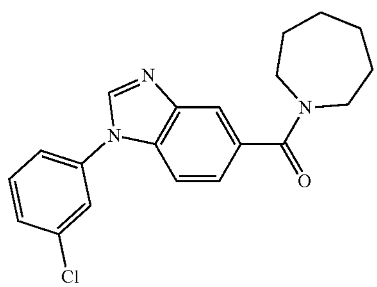 [SMILES: O=C(c1ccc2c(c1)ncn2-c1cccc(Cl)c1)N1CCCCCC1] | 8.6%/ 98.08% | 353.13 for C20H20ClN3O/ 354.0 (M + 1) | δ 8.69 (s, 1H), 7.87 (t, J = 1.8 Hz, 1H), 7.65-7.75 (m, 4H), 7.57-7.61 (m, 1H), 7.32-7.36 (m, 1H), 3.59 (br t, J = 5.3 Hz, 2H), 3.37 (br s, 2H), 1.75 (br s, 2H), 1.52-1.62 (m, 6H). |
| MF-PGDH-017 | 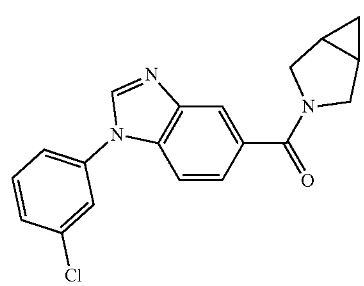 [SMILES: O=C(c1ccc2c(c1)ncn2-c1cccc(Cl)c1)N1CC2CC2C1] | 9.8%/ 98.72% | 337.10 for C19H16ClN3O/ 338.0 (M + 1) | δ 8.69-8.69 (m, 1H), 7.86-7.87 (m, 2H), 7.65-7.73 (m, 3H), 7.58-7.61 (m, 1H), 7.44 (dd, J = 1.5, 8.4 Hz, 1H), 3.97-4.02 (m, 1H), 3.72 (br d, J = 8.3 Hz, 1H), 3.36-3.42 (m, 2H), 1.56 (br d, J = 1.3 Hz, 2H), 0.62-0.68 (m, 1H), 0.12 (q, J = 4.1 Hz, 1H). |
| MF-PGDH-018 | 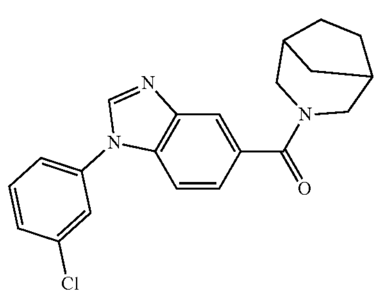 [SMILES: O=C(c1ccc2c(c1)ncn2-c1cccc(Cl)c1)N1CC2CCC(C2)C1] | 13.7%/ 97.46% | 365.13 for C21H20ClN3O/ 366.0 (M + 1) | δ 8.68 (s, 1H), 7.86 (t, J = 2.0 Hz, 1H), 7.70-7.73 (m, 2H), 7.64-7.69 (m, 2H), 7.57-7.61 (m, 1H), 7.33 (dd, J = 1.4, 8.4 Hz, 1H), 4.29-4.43 (m, 1H), 3.32-3.42 (m, 1H), 3.17-3.28 (m, 1H), 2.76-3.00 (m, 1H), 2.04-2.33 (m, 2H), 1.49-1.67 (m, 5H), 1.31-1.45 (m, 1H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-019 | 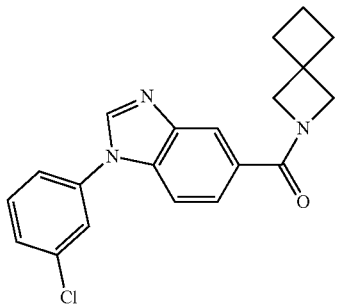 [SMILES: O=C(c1ccc2c(c1)ncn2-c1cccc(Cl)c1)N1CC2(CCC2)C1] | 16.6%/ 92.94% | 351.11 for C20H18ClN3O/ 352.0 (M + 1) | δ 8.72 (s, 1H), 8.03 (s, 1H), 7.88 (t, J = 1.9 Hz, 1H), 7.60-7.74 (m, 5H), 4.35 (br s, 2H), 4.07 (br s, 2H), 2.19 (t, J = 7.6 Hz, 4H), 1.76-1.83 (m, 2H). |
| MF-PGDH-023 | 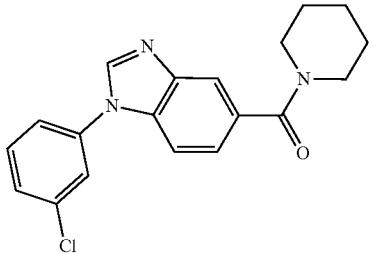 [SMILES: O=C(c1ccc2c(c1)ncn2-c1cccc(Cl)c1)N1CCCCC1] | 4.8%/ 98.86% | 339.11 for C19H18ClN3O/ 340.00 (M + 1) | δ 8.70 (s, 1H), 7.88 (s, 1H), 7.75 (m, 1H), 7.63-7.73 (m, 3H), 7.57-7.61 (m, 1H), 7.35-7.39 (m, 1H), 3.35-3.70 (br s, 4H), 1.45-1.70 (m, 6H). |
| MF-PGDH-025 | 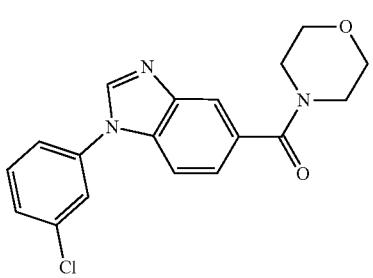 [SMILES: O=C(c1ccc2c(c1)ncn2-c1cccc(Cl)c1)N1CCOCC1] | 4.6%/ 99.70% | 341.09 for C18H16ClN3O2/ 342.0 (M + 1) | δ 8.70 (s, 1H), 7.86 (t, J = 1.9 Hz, 1H), 7.83 (d, J = 1.0 Hz, 1H), 7.65-7.73 (m, 3H), 7.58-7.61 (m, 1H), 7.41 (dd, J = 1.5, 8.4 Hz, 1H), 3.62 (br s, 5H), 3.55 (br d, J = 9.9 Hz, 3H). |
| MF-PGDH-026 | 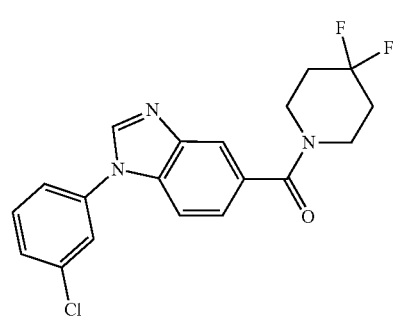 [SMILES: O=C(c1ccc2c(c1)ncn2-c1cccc(Cl)c1)N1CCC(F)(F)CC1] | 8.8%/ 98.37% | 375.09 for $C_{23}H_{28}ClFN_4O_3$/ 376.0 (M + 1) | δ 8.70 (s, 1H), 7.86-7.89 (m, 2H), 7.65-7.74 (m, 3H), 7.58-7.61 (m, 1H), 7.43-7.46 (m, 1H), 3.52-3.73 (m, 4H), 2.07 (br d, J = 5.1 Hz, 4H). |
| MF-PGDH-046 | 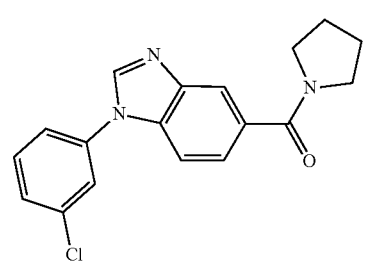 [SMILES: O=C(c1ccc2c(c1)ncn2-c1cccc(Cl)c1)N1CCCC1] | 23.3%/ 99.32% | 325.10 for C18H16ClN3O/ 326.2 (M + 1) | δ 8.69 (s, 1H), 7.93 (d, J = 0.9 Hz, 1H), 7.87 (t, J = 1.9 Hz, 1H), 7.65-7.73 (m, 3H), 7.58-7.61 (m, 1H), 7.51-7.54 (m, 1H), 3.44-3.53 (m, 4H), 1.78-1.93 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-047 | 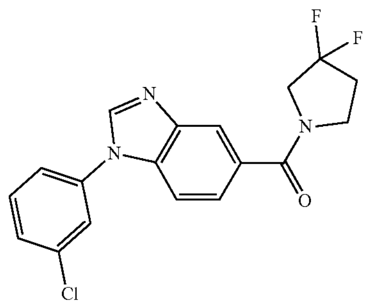 [SMILES: O=C(c1ccc2c(c1)ncn2-c1cccc(Cl)c1)N1CCC(F)(F)C1] | 23.46%/ 99.75% | 361.08 for C18H14ClF2N3O/ 362.2 (M + 1) | δ 8.72 (s, 1H), 7.99 (d, J = 0.98 Hz, 1H), 7.87 (t, J = 1.9 Hz, 1H), 7.65-7.74 (m, 3H), 7.54-7.62 (m, 2H), 3.90-4.00 (m, 2H), 3.76 (t, J = 7.4 Hz, 2H), 2.39-2.47 (m, 2H). |
| MF-PGDH-048 | 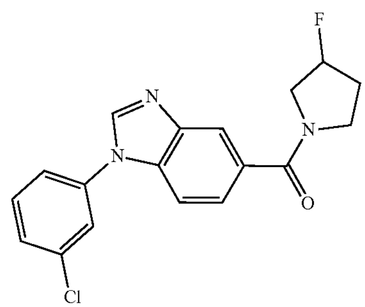 [SMILES: O=C(c1ccc2c(c1)ncn2-c1cccc(Cl)c1)N1CCC(F)C1] | 23.2%/ 99.56% | 343.09 for C18H15ClFN3O/ 344.2 (M + 1) | δ 8.71 (s, 1H), 7.96 (br d, J = 7.58 Hz, 1H), 7.87 (t, J = 1.9 Hz, 1H), 7.64-7.74 (m, 3H), 7.51-7.62 (m, 2H), 5.22-5.48 (m, 1H), 3.51-3.97 (m, 4H), 2.03-2.26 (m, 2H). |
| MF-PGDH-049 | 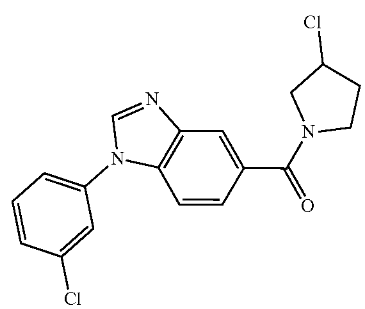 [SMILES: O=C(c1ccc2c(c1)ncn2-c1cccc(Cl)c1)N1CCC(Cl)C1] | 57%/ 99.51% | 359.06 for C18H15Cl2N3O/ 360.1 (M + 1) | δ 8.71 (s, 1H), 7.95 (br d, J = 13.6 Hz, 1H), 7.87 (t, J = 1.9 Hz, 1H), 7.65-7.74 (m, 3H), 7.58-7.62 (m, 1H), 7.51-7.57 (m, 1H), 4.72-4.87 (m, 1H), 3.91-4.09 (m, 1H), 3.74-3.81 (m, 1H), 3.52-3.67 (m, 2H), 2.37-2.45 (m, 1H), 2.08-2.20 (m, 1H). |
| MF-PGDH-050 | 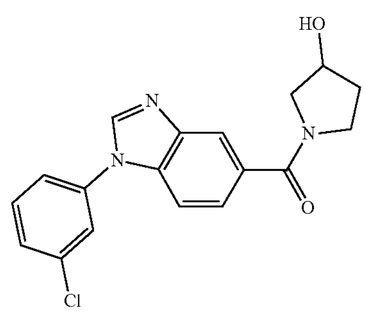 [SMILES: O=C(c1ccc2c(c1)ncn2-c1cccc(Cl)c1)N1CCC(O)C1] | 64%/ 99.53% | 341.09 for C18H16ClN3O2/ 342.2 (M + 1) | δ 8.70 (s, 1H), 7.86-7.92 (m, 2H), 7.66-7.73 (m, 3H), 7.58-7.61 (m, 1H), 7.51-7.54 (m, 1H), 4.91-5.03 (m, 1H), 4.22-4.37 (m, 1H), 3.41-3.67 (m, 4H), 1.78-1.99 (m, 2H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-PGDH-052 | 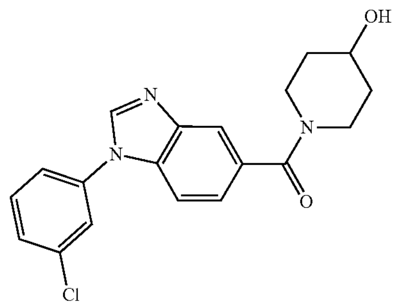 [SMILES: O=C(c1ccc2c(c1)ncn2-c1cccc(Cl)c1)N1CCC(O)CC1] | 11.34%/ 99.89% | 355.11 for C19H18ClN3O2/ 356.2 (M + 1) | δ 8.69 (s, 1H), 7.87 (t, J = 1.9 Hz, 1H), 7.77 (d, J = 1.0 Hz, 1H), 7.64-7.73 (m, 3H), 7.58-7.61 (m, 1H), 7.37 (dd, J = 1.5, 8.31 Hz, 1H), 4.77 (d, J = 4.0 Hz, 1H), 3.87-4.1 (m, 1H), 3.75 (dt, J = 4.2, 8.16 Hz, 1H), 3.21 (br s, 2H), 1.70-1.83 (m, 2H), 1.32-1.44 (m, 2H). |
| MF-PGDH-063 | 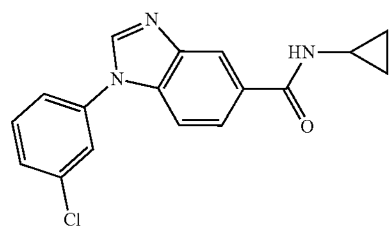 [SMILES: O=C(NC1CC1)c1ccc2c(c1)ncn2-c1cccc(Cl)c1] | 11.09%/ 99.48% | 311.08 for C17H14ClN3O/ 312.0 (M + 1) | δ 8.70 (s, 1H), 8.50 (br d, J = 4.0 Hz, 1H), 8.30 (d, J = 0.9 Hz, 1H), 7.85-7.89 (m, 2H), 7.64-7.74 (m, 3H), 7.57-7.62 (m, 1H), 2.85-2.93 (m, 1H), 0.58-0.73 (m, 4H). |
| MF-PGDH-065 | 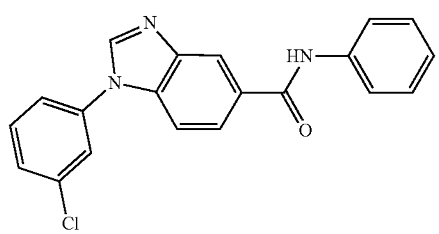 [SMILES: O=C(Nc1ccccc1)c1ccc2c(c1)ncn2-c1cccc(Cl)c1] | 20.22%/ 99.07% | 347.08 for C20H14ClN3O/ 348.1 (M + 1) | δ 10.31 (s, 1H), 8.76 (s, 1H), 8.51 (d, J = 1.3 Hz, 1H), 7.98-8.02 (m, 1H), 7.89-7.91 (m, 1H), 7.84 (d, J = 7.6 Hz, 2H), 7.73-7.78 (m, 2H), 7.67-7.71 (m, 1H), 7.60-7.63 (m, 1H), 7.34-7.39 (m, 2H), 7.08-7.12 (m, 1H). |
| MF-PGDH-103 | 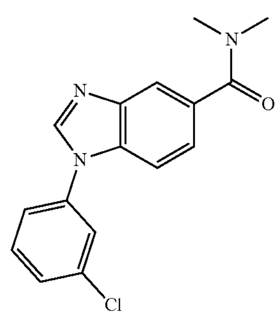 [SMILES: CN(C)C(=O)c1ccc2c(c1)ncn2-c1cccc(Cl)c1] | 7.58%/ 99.74% | 299.08 for C16H14ClN3O/ 300.2 (M + 1) | δ 8.69 (s, 1H), 7.87 (t, J = 1.9 Hz, 1H), 7.82 (d, J = 0.9 Hz, 1H), 7.65-7.73 (m, 3H), 7.58-7.61 (m, 1H), 7.40 (dd, J = 1.5, 8.4 Hz, 1H), 3.00 (br s, 6H). |
| MF-PGDH-104 | 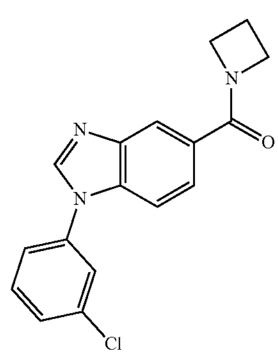 [SMILES: O=C(c1ccc2c(c1)ncn2-c1cccc(Cl)c1)N1CCC1] | 23.91%/ 98.08% | 311.08 for C17H14ClN3O/ 312.2 (M + 1) | δ 8.71 (s, 1H), 8.00 (d, J = 0.8 Hz, 1H), 7.87 (t, J = 1.9 Hz, 1H), 7.58-7.73 (m, 5H), 4.36 (br t, J = 6.7 Hz, 2H), 4.08 (br t, J = 6.8 Hz, 2H), 2.24-2.31 (m, 2H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-PGDH-105 | 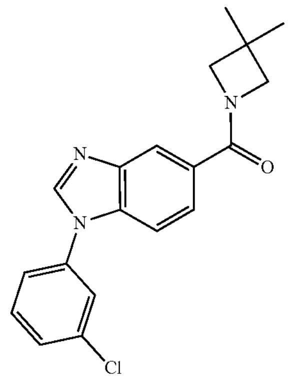 [SMILES: CC1(C)CN(C(=O)c2ccc3c(c2)ncn3-c2cccc(Cl)c2)C1] | 11.5%/ 99.69% | 339.11 for C19H18ClN3O/ 340.0 (M + 1) | δ 8.71 (s, 1H), 8.02 (s, 1H), 7.87 (t, J = 1.8 Hz, 1H), 7.63-7.73 (m, 4H), 7.58-7.61 (m, 1H), 4.05 (s, 2H), 3.76 (s, 2H), 1.26 (s, 6H). |
| MF-PGDH-106 | 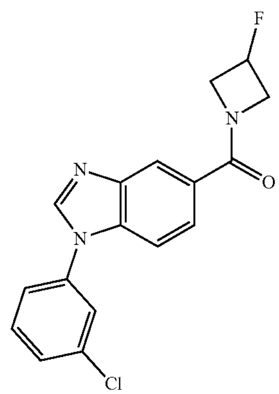 | 57%/ 97.93% | 329.07 for C17H13ClFN3O/ 330.1 (M + 1) | δ 8.73 (s, 1H), 8.05 (s, 1H), 7.87 (t, J = 1.8 Hz, 1H), 7.59-7.73 (m, 5H), 5.36-5.56 (m, 1H), 4.33-4.74 (m, 3H), 4.03-4.23 (m, 1H). |
| MF-PGDH-107 | 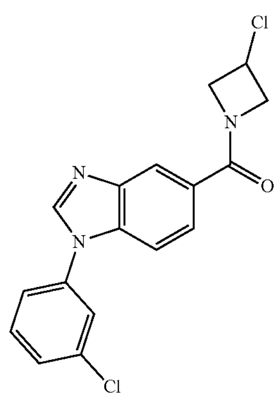 [SMILES: O=C(c1ccc2c(c1)ncn2-c1cccc(Cl)c1)N1CC(Cl)C1] | 9.8%/ 99.89% | 345.04 for C17H13Cl2N3O/ 345.9 (M + 1) | δ 8.73 (s, 1H), 8.03 (s, 1H), 7.87-7.88 (m, 1H), 7.64-7.74 (m, 4H), 7.59-7.62 (m, 1H), 4.88 (dd, J = 4.0, 6.5 Hz, 2H), 4.61-4.69 (m, 1H), 4.43-4.52 (m, 1H), 4.06-4.18 (m, 1H). |
| MF-PGDH-051 | 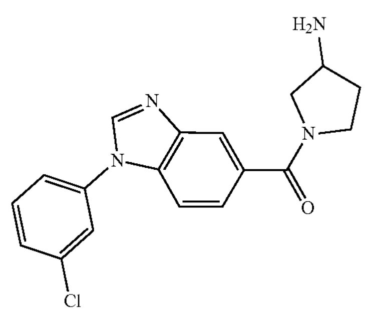 [SMILES: NC1CCN(C(=O)c2ccc3c(c2)ncn3-c2cccc(Cl)c2)C1] | 57%/ 98.33% | 340.11 for C18H17ClN4O/ 341.2 (M + 1) | δ 8.70 (s, 1H), 7.85-7.96 (m, 2H), 7.65-7.73 (m, 3H), 7.49-7.61 (m, 2H), 3.58-3.70 (m, 3H), 3.40-3.55 (m, 3H), 3.15-3.27 (m, 1H), 1.97-2.07 (m, 1H), 1.66-1.75 (m, 1H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-PGDH-064 | 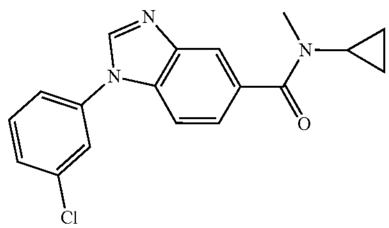 [SMILES: CN(C(=O)c1ccc2c(c1)ncn2-c1cccc(Cl)c1)C1CC1] | 6.84%/ 99.68% | 325.10 for C18H16ClN3O/ 326.2 (M + 1) | δ 8.68 (s, 1H), 7.94 (s, 1H), 7.88 (t, J = 2.0 Hz, 1H), 7.71-7.74 (m, 1H), 7.64-7.69 (m, 2H), 7.57-7.61 (m, 1H), 7.49-7.52 (m, 1H), 3.00 (s, 4H), 0.40-0.56 (m, 4H). |
| MF-PGDH-090 | 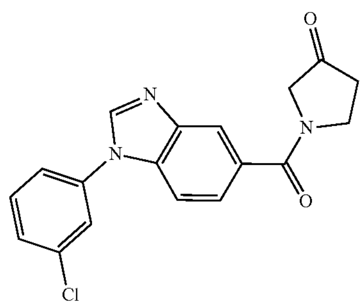 [SMILES: O=C1CCN(C(=O)c2ccc3c(c2)ncn3-c2cccc(Cl)c2)C1] | 3.85%/ 91.38% | 339.08 for C18H14ClN3O2/ 340.2 (M + 1) | CDCl$_3$ δ 8.19-8.19 (m, 1H), 8.04 (s, 1H), 7.58-7.61 (m, 2H), 7.55 (dd, J = 2.7, 4.9 Hz, 2H), 7.49-7.52 (m, 1H), 7.42-7.45 (m, 1H), 4.05-4.16 (br s, 2H), 3.76-3.79 (m, 1H), 3.62-3.65 (m, 1H), 2.67 (br t, J = 7.8 Hz, 2H). |
| MF-PGDH-102 | 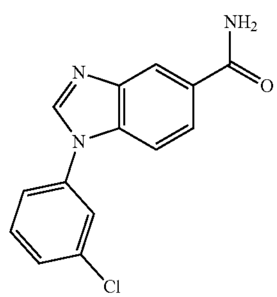 [SMILES: NC(=O)c1ccc2c(c1)ncn2-c1cccc(Cl)c1] | 69.51%/ 99.99% | 271.05 for C14H10ClN3O/ 272.1 (M + 1) | δ 8.70 (s, 1H), 8.36 (s, 1H), 8.05 (br s, 1H), 7.91-7.93 (m, 1H), 7.87 (s, 1H), 7.68-7.73 (m, 3H), 7.66-7.67 (m, 1H), 7.59 (br d, J = 7.7 Hz, 1H). |
| MF-PGDH-027 | 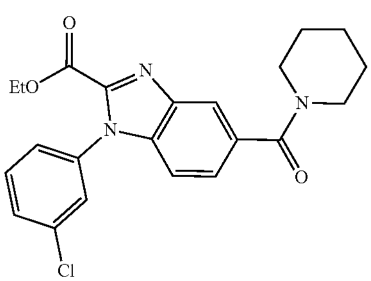 [SMILES: CCOC(=O)c1nc2cc(C(=O)N3CCCCC3)ccc2n1-c1cccc(Cl)c1] | 7.55%/ 99.90% | 411.13 for C22H22ClN3O3/ 412.0 (M + 1) | δ 7.88-7.89 (m, 1H), 7.79 (t, J = 1.77 Hz, 1H), 7.60-7.69 (m, 2H), 7.54-7.58 (m, 1H), 7.42 (dd, J = 1.47, 8.56 Hz, 1H), 7.24 (dd, J = 0.61, 8.44 Hz, 1H), 4.25 (q, J = 7.09 Hz, 2H), 3.48-3.68 (m, 2H), 3.33-3.47 (m, 2H), 1.45-1.67 (m, 6H), 1.18 (t, J = 7.09 Hz, 4H). |
| MF-PGDH-030 | 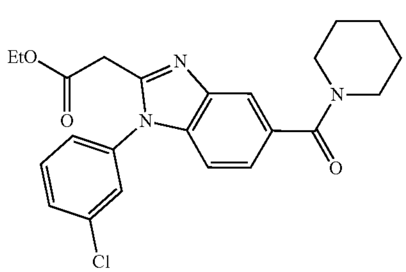 [SMILES: CCOC(=O)Cc1nc2cc(C(=O)N3CCCCC3)ccc2n1-c1cccc(Cl)c1] | 13.7%/ 94.95% | 425.15 for 23H24ClN3O3/ 426.0 (M + 1) | δ 7.72-7.74 (m, 1H), 7.66-7.69 (m, 3H), 7.53-7.56 (m, 1H), 7.21-7.29 (m, 2H), 4.05 (s, 2H), 3.93-3.99 (m, 2H), 3.37-3.68 (m, 4H), 1.60-1.64 (m, 2H), 1.45-1.58 (m, 4H), 1.05 (t, J = 7.09 Hz, 3H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-091 | 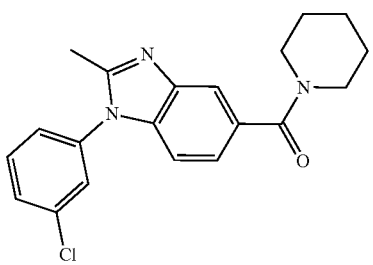 [SMILES: Cc1nc2cc(C(=O)N3CCCCC3)ccc2n1-c1cccc(Cl)c1] | 2.9%/ 98.92% | 353.13 for C20H20ClN3O/ 354.2 (M + 1) | δ 7.78-7.79 (m, 1H), 7.65-7.70 (m, 2H), 7.56-7.62 (m, 2H), 7.17-7.23 (m, 2H), 3.41-3.65 (m, 4H), 2.46 (s, 3H), 1.59-1.64 (m, 2H), 1.46-1.57 (m, 4H). |
| MF-PGDH-033 | 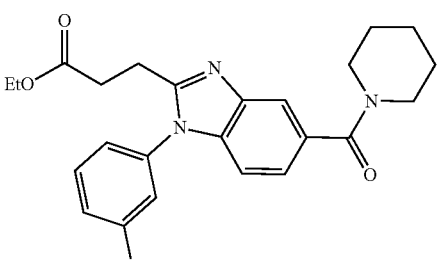 | 7.1%/ 97.95% | 425.15 for C24H26ClN3O3/ 426.0 (M + 1) | δ 7.77-7.79 (m, 1H), 7.67-7.73 (m, 2H), 7.63-7.66 (m, 1H), 7.56-7.61 (m, 1H), 7.16-7.24 (m, 2H), 3.57 (s, 3H), 3.38-3.51 (m, 2H), 2.89-3.01 (m, 4H), 1.46-1.66 (m, 6H). |
| MF-PGDH-034 | 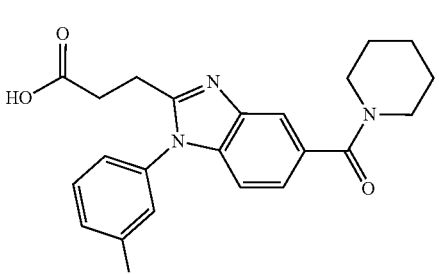 | 3.6%/ 95.15% | 411.13 for C22H22ClN3O3/ 426.0 (M + 1) | δ 7.77-7.78 (m, 1H), 7.68-7.71 (m, 2H), 7.63-7.64 (m, 1H), 7.56-7.60 (m, 1H), 7.16-7.25 (m, 2H), 6.97-7.15 (m, 2H), 3.39-3.56 (m, 3H), 2.92-2.96 (m, 2H), 2.80-2.85 (m, 2H), 1.62 (br d, J = 3.55 Hz, 2H), 1.51 (br s, 4H). |
| MF-PGDH-035 | 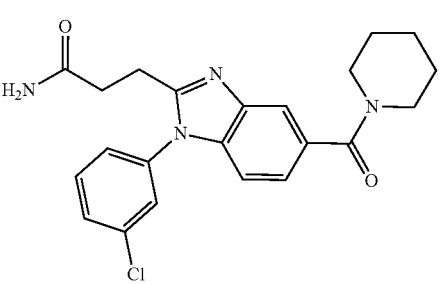 [SMILES: NC(=O)CCc1nc2cc(C(=O)N3CCCCC3)ccc2n1-c1cccc(Cl)c1] | 17.3%/ 97.93% | 410.15 for C22H23ClN4O2/ 411.3 (M + 1) | δ 7.79-7.80 (m, 1H), 7.67-7.70 (m, 2H), 7.57-7.63 (m, 2H), 7.40 (br s, 1H), 7.15-7.23 (m, 2H), 6.80 (br s, 1H), 3.34-3.61 (m, 4H), 2.89-2.94 (m, 2H), 2.66-2.70 (m, 2H), 1.47-1.65 (m, 6H). |
| MF-PGDH-008 | 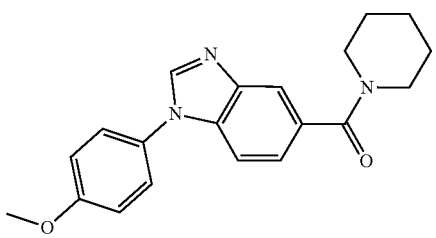 [SMILES: COc1ccc(-n2cnc3cc(C(=O)N4CCCCC4)ccc32)cc1] | 13.5%/ 96.97% | 335.16 for C20H21N3O2/ 336.1 (M + 1) | δ 8.55 (s, 1H), 7.74 (s, 1H), 7.60 (d, J = 8.9 Hz, 2H), 7.54 (d, J = 8.3 Hz, 1H), 7.32 (dd, J = 8.3, 1.5 Hz, 1H), 7.18 (d, J = 9.0 Hz, 2H), 3.85 (s, 3H), 3.52-3.40 (m, 4H), 1.62-1.51 (m, 6H). |

TABLE 3-continued

Analytical data for select inhibitors

| Target No | Structure | Yield/Purity | Mass Spec. Calculated/Mass Spec. Found (m/z) | $^1$H NMR (DMSO-$d_6$*, 400 MHz) (*unless otherwise indicated) |
|---|---|---|---|---|
| MF-PGDH-009 | 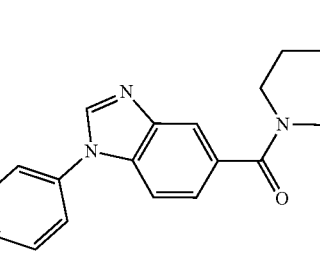 | 18.2%/99.52% | 353.15 for C20H20FN3O2/354.0 (M + 1) | δ 8.56 (s, 1H), 7.80 (d, J = 0.98 Hz, 1H), 7.54-7.63 (m, 3H), 7.36 (dd, J = 1.47, 8.4 Hz, 1H), 7.16-7.20 (m, 2H), 4.83-5.01 (m, 1H), 3.85 (s, 3H), 3.43-3.70 (m, 4H), 1.84-2.00 (m, 2H), 1.74 (br d, J = 2.9 Hz, 2H). |
| MF-PGDH-021 | 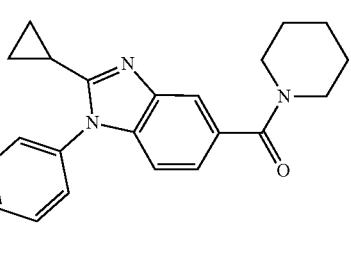 | 14.6%/99.43% | 375.19 for C23H25N3O2/376.0 (M + 1) | δ 7.50-7.54 (m, 3H), 7.14-7.22 (m, 3H), 7.07-7.10 (m, 1H), 3.87 (s, 3H), 3.35-3.55 (m, 3H), 1.78-1.86 (m, 1H), 1.45-1.65 (m, 6H), 1.21-1.28 (m, 1H), 1.10-1.14 (m, 2H), 0.98-1.03 (m, 2H). |
| MF-PGDH-022 | 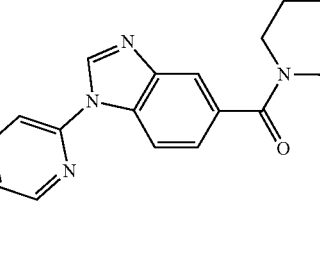 | 51%/99.72% | 336.16 for C19H20N4O2/337.1 (M + 1) | δ 8.92 (s, 1H), 8.36 (d, J = 2.93 Hz, 1H), 8.17 (d, J = 8.44 Hz, 1H), 7.91 (d, J = 8.93 Hz, 1H), 7.75-7.70 (m, 2H), 7.37 (dd, J = 1.53, 8.38 Hz, 1H), 3.92 (s, 3H), 3.56-3.37 (m, 4H), 1.63-1.53 (m, 6H). |
| MF-PGDH-024 | 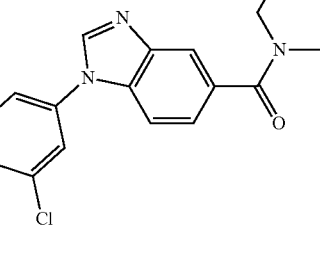 | 45.3%/99.10% | 369.12 for C20H20ClN3O2/370.2 (M + 1) | δ 8.68 (s, 1H), 7.76 (s, 1H), 7.73 (d, J = 8.3 Hz, 1H), 7.68 (d, J = 8.4 Hz, 1H), 7.49 (d, J = 2.4 Hz, 1H), 7.35 (dd, J = 8.3, 1.5 Hz, 1H), 7.32-7.29 (dd, J = 8.4, 2.3 Hz, 1H), 3.97 (s, 3H), 3.50-3.46 (m, 4H), 1.63-1.53 (m, 6 H) |
| MF-PGDH-062 | 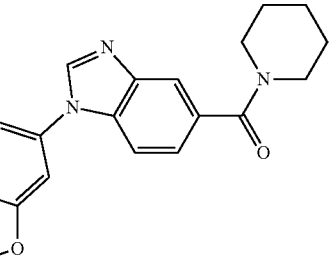 | 23.6%/97.72% | 349.14 for C20H19N3O3/350.0 (M + 1) | δ 8.54 (s, 1H), 7.73 (s, 1H), 7.57 (d, J = 8.3 Hz, 1H), 7.35-7.31 (m, 2H), 7.18-7.06 (m, 2H), 6.17 (s, 2H), 3.53-3.41 (m, 4H), 1.63-1.52 (m, 6 H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-141 | 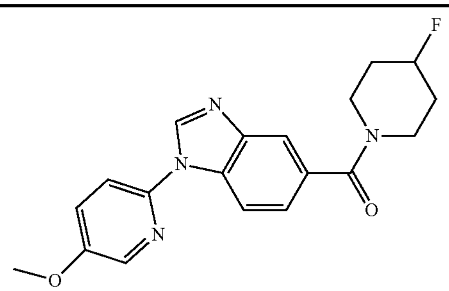 | 14.5%/ 99.11% | 325.13 for C19H19FN4O2/ 326.1 (M + 1) | δ 9.12 (s, 1H), 9.03 (d, J = 5.8 Hz, 1H), 8.94 (d, J = 5.77 Hz, 1H), 8.54-8.52 (m, 2H), 8.24 (d, J = 1.92 Hz, 1H), 6.94 (d, J = 3.84 Hz, 1H), 5.02-4.97 (m, 1H), 3.93 (s, 3H), 3.60 (m, 4H), 1.99-1.75 (m, 6H). |
| MF-PGDH-061 | 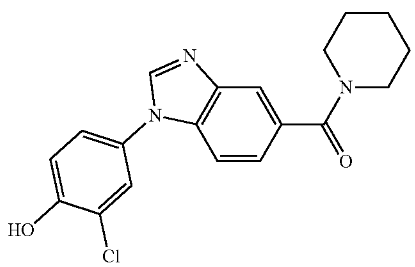 [SMILES: O=C(c1ccc2c(c1)ncn2-c1ccc(O)c(Cl)c1)N1CCCCC1] | 34.8%/ 98.88% | 355.11 for C19H18ClN3O2/ 356.2 (M + 1) | δ 10.83 (br s, 1H), 8.62 (s, 1H), 7.75 (d, J = 0.9 Hz, 1H), 7.64 (dd, J = 0.5, 8.3 Hz, 1H), 7.59 (d, J = 8.4 Hz, 1H), 7.36 (dd, J = 8.4, 1.5 Hz, 1H), 7.23 (d, J = 2.6 Hz, 1H), 7.14 (dd, J = 8.4, 2.4 Hz, 1H), 3.54-3.42 (m, 4H), 3.32 (s, 3H) 1.63-1.53 (m, 6 H). |
| MF-PGDH-014 | 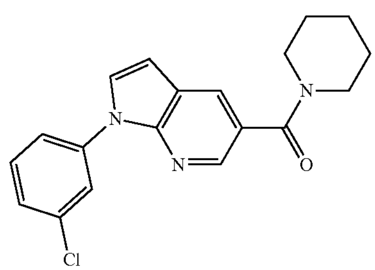 | 21.4%/ 99.15% | 339.11 for C19H18ClN3O/ 340.0 (M + 1) | δ 8.39 (s, 1H), 8.18-8.07 (m, 3H), 7.94-7.87 (m, 1H), 7.62-7.55 (m, 1H), 7.46-7.38 (m, 1H), 6.82 (s, 1H), 3.67-3.38 (m, 4H), 1.68-1.43 (m, 6H) |
| MF-PGDH-067 | 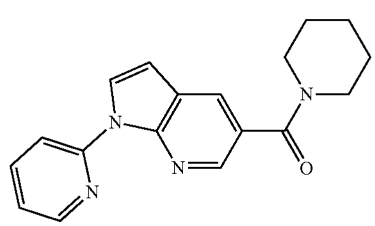 [SMILES: O=C(c1cnc2c(ccn2-c2ccccn2)c1)N1CCCCC1] | 21.0%/ 99.65% | 306.15 for C18H18N4O/ 307.3 (M + 1) | δ 8.85 (d, J = 8.3 Hz, 1H), 8.55 (dd, J = 1.0, 4.8 Hz, 1H), 8.47 (d, J = 3.8 Hz, 1H), 8.43 (d, J = 2.0 Hz, 1H), 8.16 (d, J = 2.1 Hz, 1H), 8.06 (ddd, J = 2.0, 7.4, 8.3 Hz, 1H), 7.36 (ddd, J = 0.8, 4.9, 7.3 Hz, 1H), 6.84 (d, J = 3.9 Hz, 1H), 3.73-3.37 (m, 4H), 1.71-1.42 (m, 6H) |
| MF-PGDH-068 | 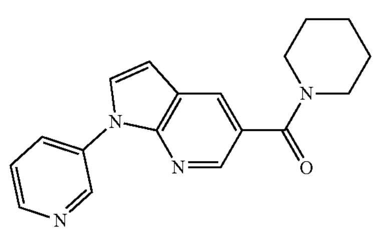 [SMILES: O=C(c1cnc2c(ccn2-c2cccnc2)c1)N1CCCCC1] | 37.5%/ 99.00% | 306.15 for C18H18N4O/ 307.2 (M + 1) | δ 9.14 (d, J = 2.4 Hz, 1H), 8.58 (dd, J = 1.6, 4.8 Hz, 1H), 8.38 (dd, J = 1.6, 2.8 Hz, 1H), 8.36 (t, J = 2.0 Hz, 1H), 8.15-8.13 (m, 2H), 7.63-7.60 (m, 1H), 6.85 (d, J = 3.6 Hz, 1H), 3.59-3.42 (m, 4H), 1.68-1.43 (m, 6H) |
| MF-PGDH-069 | 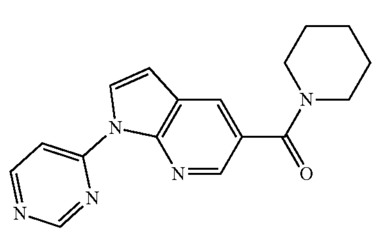 | 2.3%/ 97.98% | 307.14 for C17H17N5O/ 308.2 (M + 1) | δ 9.12 (d, J = 1.0 Hz, 1H), 9.03 (dd, J = 1.3, 5.7 Hz, 1H), 8.94 (d, J = 5.7 Hz, 1H), 8.53 (d, J = 4.0 Hz, 1H), 8.48 (d, J = 2.0 Hz, 1H), 8.19 (d, J = 2.0 Hz, 1H), 6.93 (d, J = 4.0 Hz, 1H), 3.72-3.35 (m, 4H), 1.71-1.40 (m, 6H) |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-PGDH-070 | 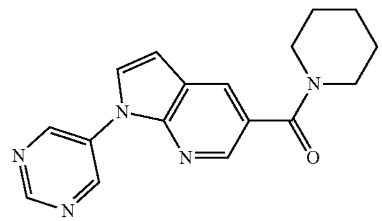 [SMILES: O=C(c1cnc2c(ccn2-c2cncnc2)c1)N1CCCCC1] | 15.2%/ 99.91% | 307.14 for C17H17N5O/ 308.2 (M + 1) | δ 9.47 (s, 2H), 9.18 (s, 1H), 8.40 (d, J = 2.0 Hz, 1H), 8.23 (d, J = 3.7 Hz, 1H), 8.18 (d, J = 2.1 Hz, 1H), 6.91 (d, J = 3.8 Hz, 1H), 3.79-3.37 (m, 4H), 1.74-1.40 (m, 6H) |
| MF-PGDH-071 | 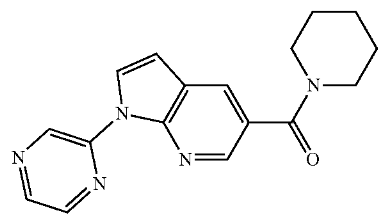 [SMILES: O=C(c1cnc2c(ccn2-c2cnccn2)c1)N1CCCCC1] | 19.3%/ 99.50% | 307.14 for C17H17N5O/ 308.2 (M + 1) | δ 10.10 (d, J = 1.3 Hz, 1H), 8.69-8.58 (m, 2H), 8.48 (d, J = 2.1 Hz, 1H), 8.40 (d, J = 3.8 Hz, 1H), 8.19 (d, J = 2.0 Hz, 1H), 6.93 (d, J = 3.8 Hz, 1H), 3.75-3.39 (m, 4H), 1.75-1.43 (m, 6H) |
| MF-PGDH-073 | 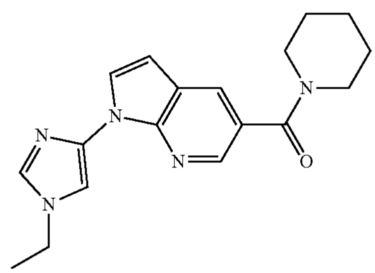 [SMILES: CCn1cnc(-n2ccc3cc(C(=O)N4CCCCC4)cnc32)c1] | 31.5%/ 95.38% | 323.17 for C18H21N5O/ 324.1 (M + 1) | δ 8.37 (br s, 1H), 8.10 (br s, 2H), 7.93-7.59 (m, 2H), 6.73 (br s, 1H), 4.11 (q, J = 7.1 Hz, 2H), 3.74-3.35 (m, 4H), 1.71-1.48 (m, 6H), 1.42 (t, J = 7.2 Hz, 3H) |
| MF-PGDH-074 | 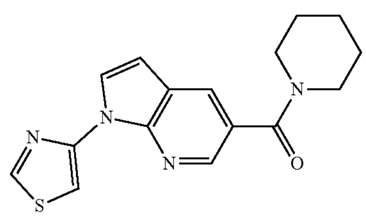 [SMILES: O=C(c1cnc2c(ccn2-c2cscn2)c1)N1CCCCC1] | 30.4%/ 99.72% | 312.10 for C16H16N4OS/ 313.0 (M + 1) | δ 9.22 (d, J = 1.8 Hz, 1H), 8.44 (d, J = 1.1 Hz, 1H), 8.36 (d, J = 1.8 Hz, 1H), 8.29 (d, J = 3.7 Hz, 1H), 8.16 (d, J = 1.5 Hz, 1H), 6.81 (d, J = 3.7 Hz, 1H), 3.76-3.36 (m, 4H), 1.78-1.36 (m, 6H) |
| MF-PGDH-075 | 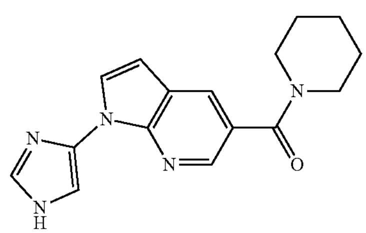 [SMILES: O=C(c1cnc2c(ccn2-c2c[nH]cn2)c1)N1CCCCC1] | 26.8%/ 99.41% | 295.14 for C16H17N5O/ 296.0 (M + 1) | δ 13.34-12.77 (m, 1H), 8.42 (s, 1H), 8.37 (d, J = 2.0 Hz, 1H), 8.14 (s, 1H), 8.11 (d, J = 2.0 Hz, 1H), 7.98 (d, J = 3.4 Hz, 1H), 6.76 (d, J = 3.5 Hz, 1H), 3.69-3.41 (m, 4H), 1.73-1.46 (m, 6H) |
| MF-PGDH-076 | 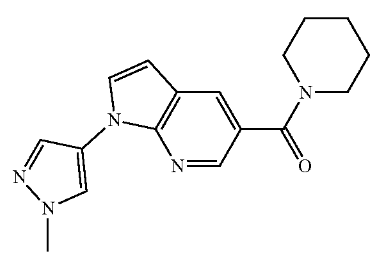 [SMILES: Cn1cc(-n2ccc3cc(C(=O)N4CCCCC4)cnc32)cn1] | 34.5%/ 98.55% | 309.16 for C17H19N5O/ 310.1 (M + 1) | δ 8.43 (s, 1H), 8.35 (d, J = 2.1 Hz, 1H), 8.09 (d, J = 2.1 Hz, 1H), 8.03 (d, J = 0.6 Hz, 1H), 7.96 (d, J = 3.5 Hz, 1H), 6.74 (d, J = 3.5 Hz, 1H), 3.93 (s, 3H), 3.69-3.37 (m, 4H), 1.77-1.39 (m, 6H) |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-123 | 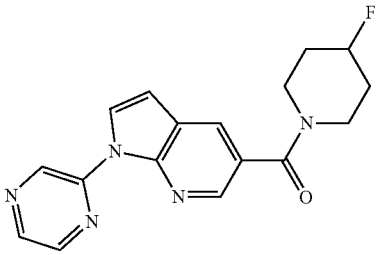 [SMILES: O=C(c1cnc2c(ccn2-c2cnccn2)c1)N1CCC(F)CC1] | 30.9%/ 99.52% | 325.13 for C17H16FN5O/ 326.1 (M + 1) | δ 10.11 (d, J = 1.3 Hz, 1H), 8.68-8.61 (m, 2H), 8.54 (d, J = 2.0 Hz, 1H), 8.43 (d, J = 3.9 Hz, 1H), 8.26 (d, J = 2.1 Hz, 1H), 6.95 (d, J = 3.8 Hz, 1H), 5.08-4.84 (m, 1H), 3.85-3.54 (m, 4H), 2.07-1.73 (m, 4H) |
| MF-DH-128 | 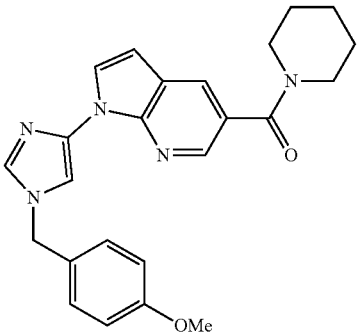 [SMILES: COc1ccc(Cn2cnc(-n3ccc4cc(C(=O)N5CCCCC5)cnc43)c2)cc1] | 48.2%/ 99.68% | 415.20 for C24H25N5O2/ 416.1 (M + 1) | δ 8.36 (br s, 1H), 8.17-8.04 (m, 2H), 7.83 (br d, J = 16.0 Hz, 2H), 7.35 (d, J = 8.6 Hz, 2H), 6.96 (d, J = 8.7 Hz, 2H), 6.74 (br s, 1H), 5.25 (s, 2H), 3.75 (s, 3H), 3.66-3.37 (m, 4H), 1.79-1.43 (m, 6H) |
| MF-DH-129 | 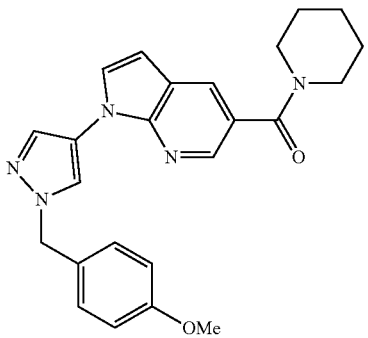 [SMILES: COc1ccc(Cn2cc(-n3ccc4cc(C(=O)N5CCCCC5)cnc43)cn2)cc1] | 45.8%/ 99.17% | 415.20 for C24H25N5O2/ 416.1 (M + 1) | δ 8.52 (d, J = 0.6 Hz, 1H), 8.34 (d, J = 2.0 Hz, 1H), 8.08 (dd, J = 1.4, 3.2 Hz, 2H), 7.98 (d, J = 3.7 Hz, 1H), 7.29 (d, J = 8.7 Hz, 2H), 6.92 (d, J = 8.7 Hz, 2H), 6.74 (d, J = 3.7 Hz, 1H), 5.33 (s, 2H), 3.73 (s, 3H), 3.66-3.35 (m, 4H), 1.72-1.43 (m, 6H) |
| MF-DH-131 | 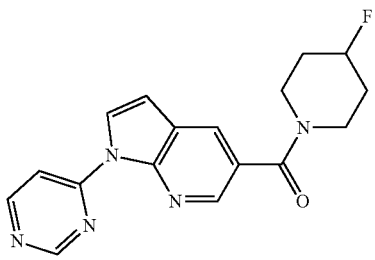 [SMILES: O=C(c1cnc2c(ccn2-c2ccncn2)c1)N1CCC(F)CC1] | 48.2%/ 99.11% | 325.13 for C17H16FN5O/ 326.1 (M + 1) | δ 9.12 (s, 1H), 9.03 (d, J = 5.8 Hz, 1H), 8.94 (d, J = 5.8 Hz, 1H), 8.59-8.49 (m, 2H), 8.24 (d, J = 1.9 Hz, 1H), 6.94 (d, J = 3.8 Hz, 1H), 5.05-4.81 (m, 1H), 3.83-3.36 (m, 4H), 2.04-1.64 (m, 4H) |
| MF-132 | 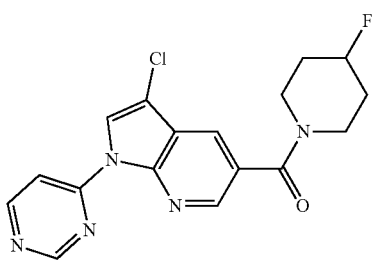 [SMILES: O=C(c1cnc2c(c1)c(Cl)cn2-c1ccncn1)N1CCC(F)CC1] | 11.2%/ 98.86% | 359.09 for C17H15ClFN5O/ 360.0 (M + 1) | δ 9.14 (s, 1H), 8.96 (s, 2H), 8.69 (s, 1H), 8.62 (d, J = 1.8 Hz, 1H), 8.21 (d, J = 1.8 Hz, 1H), 5.13-4.80 (m, 1H), 3.88-3.43 (m, 4H), 2.05-1.65 (m, 4H) |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-133 | 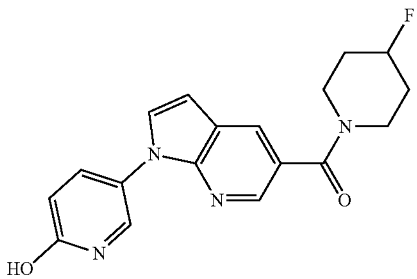 | 2.02%/ 92.41% | 340.13 for C18H17FN4O2/ 341.0 (M + 1) | CDCl$_3$ δ 8.42 (s, 1H), 8.21 (br s, 1H), 8.11 (br d, J = 1.2 Hz, 2H), 7.46 (d, J = 3.5 Hz, 1H), 6.96 (br d, J = 9.4 Hz, 1H), 6.75 (d, J = 3.5 Hz, 1H), 5.72-5.37 (m, 1H), 5.06-4.83 (m, 1H), 4.15-3.41 (m, 4H), 2.20-1.72 (m, 4H) |
| MF-134 | 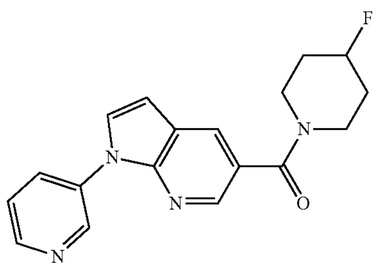 [SMILES: O=C(c1cnc2c(ccn2-c2cccnc2)c1)N1CCC(F)CC1] | 19.7%/ 99.09% | 324.14 for C18H17FN4O/ 325.0 (M + 1) | δ 9.15 (br s, 1H), 8.59 (br d, J = 3.7 Hz, 1H), 8.46-8.34 (m, 2H), 8.20 (d, J = 2.0 Hz, 1H), 8.15 (d, J = 3.7 Hz, 1H), 7.62 (dd, J = 4.7, 8.3 Hz, 1H), 6.86 (d, J = 3.8 Hz, 1H), 5.11-4.80 (m, 1H), 3.79-3.39 (m, 4H), 2.09-1.64 (m, 4H) |
| MF-135 | 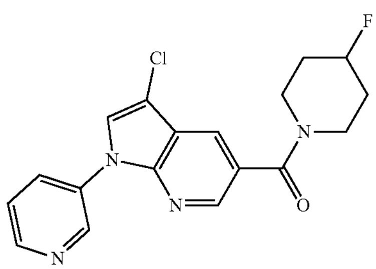 [SMILES: O=C(c1cnc2c(c1)c(Cl)cn2-c1cccnc1)N1CCC(F)CC1] | 5.4%/ 98.86% | 358.10 for C18H16ClFN4O/ 359.0 (M + 1) | δ 9.12 (d, J = 2.4 Hz, 1H), 8.61 (dd, J = 1.3, 4.8 Hz, 1H), 8.49 (d, J = 1.8 Hz, 1H), 8.43 (s, 1H), 8.38-8.29 (m, 1H), 8.16 (d, J = 2.0 Hz, 1H), 7.63 (dd, J = 4.8, 8.3 Hz, 1H), 5.15-4.76 (m, 1H), 3.88-3.41 (m, 4H), 2.09-1.62 (m, 4H) |
| MF-139 | 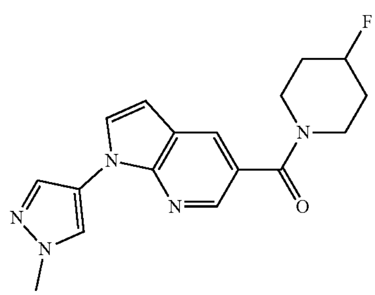 [SMILES: Cn1cc(-n2ccc3cc(C(=O)N4CCC(F)CC4)cnc32)cn1] | 12.2%/ 99.18% | 327.15 for C17H18FN5O/ 328.2 (M + 1) | δ 8.43 (s, 1H), 8.39 (d, J = 2.0 Hz, 1H), 8.14 (d, J = 2.1 Hz, 1H), 8.03 (d, J = 0.7 Hz, 1H), 7.97 (d, J = 3.7 Hz, 1H), 6.75 (d, J = 3.5 Hz, 1H), 5.08-4.76 (m, 1H), 3.93 (s, 3H), 3.73-3.43 (m, 4H), 2.03-1.67 (m, 4H) |
| MF-140 | 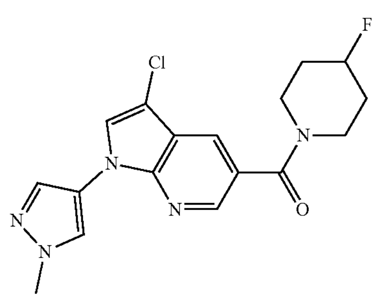 [SMILES: Cn1cc(-n2cc(Cl)c3cc(C(=O)N4CCC(F)CC4)cnc32)cn1] | 2.6%/ 99.84% | 361.11 for C17H17ClFN5O/ 362.0 (M + 1) | δ 8.48 (d, J = 1.8 Hz, 1H), 8.41 (s, 1H), 8.26 (s, 1H), 8.10 (d, J = 2.0 Hz, 1H), 8.01 (s, 1H), 5.07-4.76 (m, 1H), 3.93 (s, 3H), 3.79-3.38 (m, 4H), 2.10-1.66 (m, 4H) |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-145 | 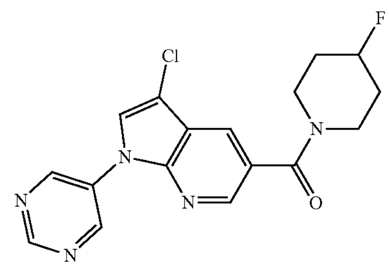 [SMILES: O=C(c1cnc2c(c1)c(Cl)cn2-c1cncnc1)N1CCC(F)CC1] | 36.5%/ 98.03% | 359.09 for C17H15ClFN5O/ 360.0 (M + 1) | δ 9.43 (s, 2H), 9.21 (s, 1H), 8.58-8.44 (m, 2H), 8.19 (d, J = 2.0 Hz, 1H), 5.15-4.74 (m, 1H), 3.85-3.39 (m, 4H), 2.10-1.59 (m, 4H) |
| MF-157 | 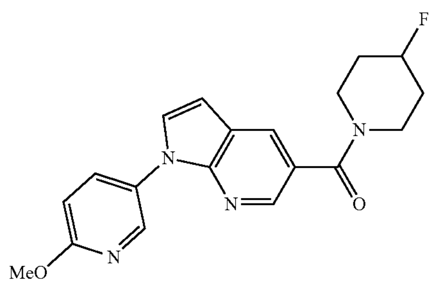 [SMILES: COc1ccc(-n2ccc3cc(C(=O)N4CCC(F)CC4)cnc32)cn1] | 7.4%/ 99.53% | 354.15 for C19H19FN4O2/ 355.1 (M + 1) | δ 8.60 (d, J = 2.6 Hz, 1H), 8.36 (d, J = 2.0 Hz, 1H), 8.27-8.13 (m, 2H), 8.00 (d, J = 3.7 Hz, 1H), 7.03 (d, J = 8.8 Hz, 1H), 6.81 (d, J = 3.7 Hz, 1H), 5.10-4.77 (m, 1H), 3.93 (s, 3H), 3.78-3.44 (m, 4H), 2.05-1.68 (m, 4H) |
| MF-PGDH-020 | 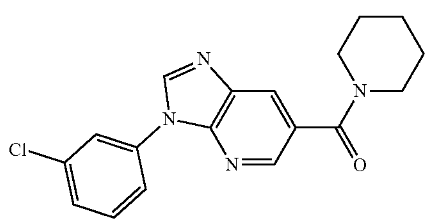 [SMILES: O=C(c1cnc2c(c1)ncn2-c1cccc(Cl)c1)N1CCCCC1] | 13.7%/ 99.94% | 340.11 for C18H17ClN4O/ 341.0 (M + 1) | δ 9.11 (s, 1H), 8.51 (d, 1H), 8.30 (d, 1H), 8.20-8.22 (m, 1H), 8.01-8.03 (m, 1H), 7.70-7.72 (m, 1H), 7.57-7.59 (m, 1H), 3.54-3.67 (m, 2H), 3.34-3.42 (m, 2H), 1.48-1.68 (m, 6H). |
| MF-PGDH-077 | 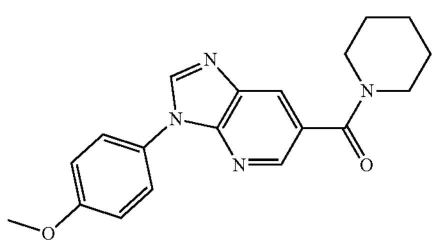 | 14.8%/ 99.66% | 336.16 for C19H20N4O2/ 337.2 (M + 1) | δ 8.89 (s, 1H), 8.43 (d, J = 1.83 Hz, 1H), 8.20 (d, J = 1.96 Hz, 1H), 7.78-7.82 (m, 2H), 7.15-7.19 (m, 2H), 3.84 (s, 3H), 3.54-3.68 (m, 2H), 3.34-3.45 (m, 2H), 1.49-1.67 (m, 6H). |
| MF-PGDH-078 | 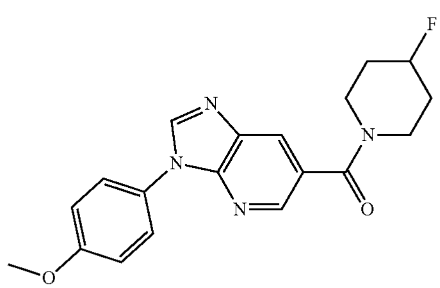 | 15%/ 99.73% | 354.15 for C19H19FN4O2/ 355.2 (M + 1) | δ 8.90 (s, 1H), 8.47-8.48 (d, J = 1.83 Hz, 1H), 8.25-8.26 (d, J = 1.96 Hz, 1H), 7.79-7.81 (m, 2H), 7.13-7.15 (m, 2H), 4.82-5.01 (m, 1H), 3.84-3.85 (s, 3H), 3.52-3.80 (m, 4H), 1.83-2.01 (m, 2H), 1.71-1.82 (m, 2H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-079 | 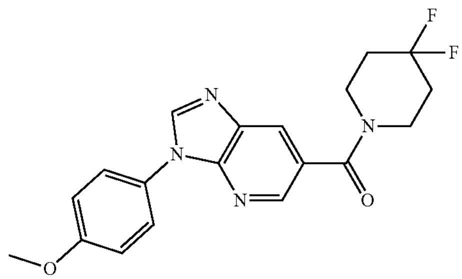 [SMILES: COc1ccc(-n2cnc3cc(C(=O)N4CCC(F)(F)CC4)cnc32)cc1] | 5.5%/ 98.59% | 372.14 for C19H18F2N4O2/ 373.2 (M + 1) | δ 8.90 (s, 1H), 8.50-8.51 (d, J = 1.83 Hz, 1H), 8.30-8.31 (d, J = 1.96 Hz, 1H), 7.79-7.81 (m, 2H), 7.16-7.18 (m, 2H), 3.84-3.85 (s, 3H), 3.55-3.70 (m, 4H), 2.03-2.12 (m, 4H). |
| MF-DH-138 | 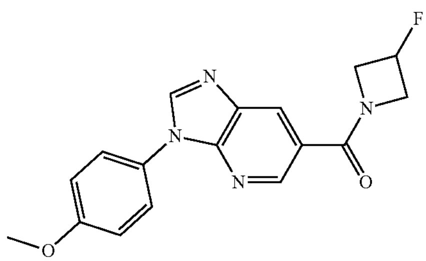 [SMILES: COc1ccc(-n2cnc3cc(C(=O)N4CC(F)C4)cnc32)cc1] | 13.1%/ 99.72% | 326.12 for C17H15FN4O2/ 327.0 (M + 1) | δ 8.92 (s, 1H), 8.70 (d, J = 1.92 Hz, 1H), 8.42 (d, J = 1.92 Hz, 1H), 7.78-7.81 (m, 2H), 7.17 (d, J = 8.97 Hz, 2H), 5.38-5.55 (m, 1H), 4.41-4.71 (m, 3H), 4.09-4.19 (m, 1H), 3.84 (s, 3H). |
| MF-DH-115 | 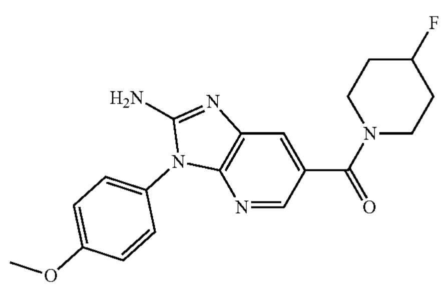 [SMILES: COc1ccc(-n2c(N)nc3cc(C(=O)N4CCC(F)CC4)cnc32)cc1] | 3.96%/ 98.04% | 369.16 for C19H20FN5O2/ 370.1 (M + 1) | δ 7.78 (d, J = 1.83 Hz, 1H), 7.41 (d, J = 1.83 Hz, 1H), 7.31-7.34 (m, 2H), 7.06 (d, J = 8.93 Hz, 2H), 6.64 (s, 2H), 4.75-4.94 (m, 1H), 3.77 (s, 3H), 3.51 (br d, J = 0.86 Hz, 4H), 1.79-1.88 (m, 2H), 1.67 (br d, J = 2.20 Hz, 2H). |
| MF-DH-116 | 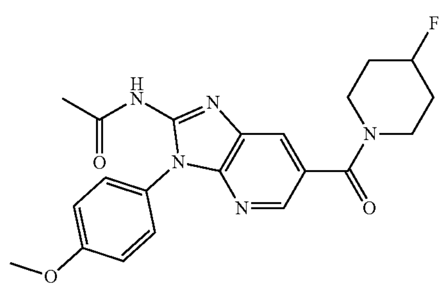 [SMILES: COc1ccc(-n2c(NC(C)=O)nc3cc(C(=O)N4CCC(F)CC4)cnc32)cc1] | 2.12%/ 99.12% | 411.17 for C21H22FN5O3/ 410.1 (M − 1) | δ 10.49-10.64 (m, 1H), 8.21-8.23 (m, 1H), 8.00 (br s, 1H), 7.32-7.34 (m, 2H), 7.02-7.05 (m, 2H), 4.77-4.94 (m, 1H), 3.77 (s, 3H), 3.48-3.62 (m, 4H), 1.82-1.94 (m, 7H). |
| MF-PGDH-036 | 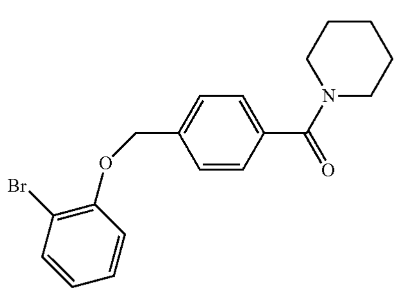 | 2.05%/ 99.77% | 373.07 for C19H20BrNO2/ 375.9 (M + 3) | δ 7.60 (dd, J = 1.53, 7.89 Hz, 1H), 7.53 (d, J = 8.07 Hz, 2H), 7.36-7.42 (m, 2H), 7.32-7.35 (m, 1H), 7.21 (dd, J = 1.22, 8.31 Hz, 1H), 6.91 (dt, J = 1.28, 7.61 Hz, 1H), 5.25 (s, 2H), 3.57 (br s, 2H), 3.27 (br s, 2H), 1.39-1.65 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-PGDH-037 | 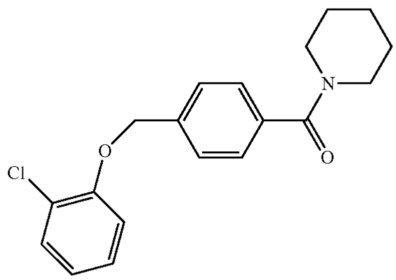 [SMILES: O=C(c1ccc(COc2ccccc2Cl)cc1)N1CCCCC1] | 2.1%/ 99% | 329.12 for C19H20ClNO2/ 330.1 (M + 1) | δ 7.52 (d, J = 8.1 Hz, 2H), 7.47-7.38 (m, 3H), 7.33-7.22 (m, 2H), 6.97 (dt, J = 1.5, 7.6 Hz, 1H), 5.25 (s, 2H), 3.57 (br s, 2H), 3.22-3.30 (m, 2H), 1.65-1.41 (m, 6H). |
| MF-PGDH-038 | 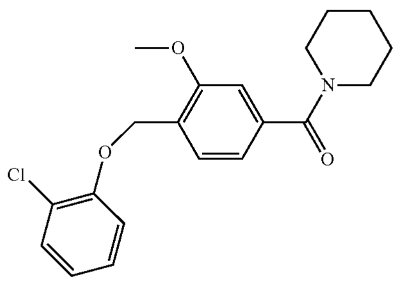 [SMILES: COc1cc(C(=O)N2CCCCC2)ccc1COc1ccccc1Cl] | 2.1%/ 99.95% | 359.13 for C20H22ClNO3/ 360.0 (M + 1) | δ 7.40-7.53 (m, 2H), 7.29 (dd, J = 1.53, 7.40 Hz, 1H), 7.18-7.26 (m, 1H), 7.03 (d, J = 1.10 Hz, 1H), 6.95-7.00 (m, 2H), 5.17 (s, 2H), 3.86 (s, 3H), 3.48-3.66 (m, 2H), 3.19-3.30 (m, 2H), 1.39-1.66 (m, 6H). |
| MF-PGDH-039 | 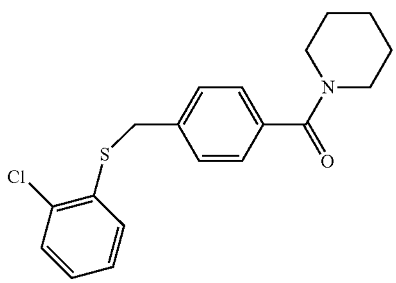 [SMILES: O=C(c1ccc(CSc2ccccc2Cl)cc1)N1CCCCC1] | 1.4%/ 98.03% | 345.10 for C19H20ClNOS/ 346.0 (M + 1) | δ 7.69-7.78 (m, 3H), 7.46-7.50 (m, 1H), 7.22-7.28 (m, 4H), 4.89 (s, 2H), 3.48-3.58 (m, 2H), 3.08-3.17 (m, 2H), 1.39-1.62 (m, 6H). |
| MF-PGDH-040 | 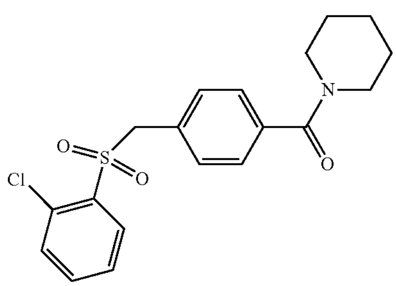 [SMILES: O=C(c1ccc(CS(=O)(=O)c2ccccc2Cl)cc1)N1CCCCC1] | 9.6%/ 99.83% | 377.09 for C19H20ClNO3/ 378.0 (M + 1) | δ 7.69-7.78 (m, 3H), 7.45-7.51 (m, 1H), 7.25 (d, J = 1.34 Hz, 4H), 4.89 (s, 2H), 3.54 (brs, 2H), 3.12 (brs, 2H), 1.56-1.63 (m, 2H), 1.34-1.55 (m, 4H). |
| MF-PGDH-045 | 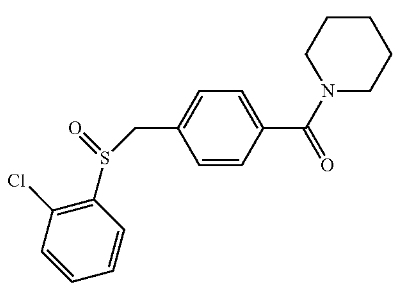 [SMILES: O=C(c1ccc(CS(=O)c2ccccc2Cl)cc1)N1CCCCC1] | 68%/ 99.84% | 361.09 for C19H20ClNO2S/ 362.0 (M + 1) | δ 7.51-7.60 (m, 2H), 7.40-7.45 (m, 1H), 7.29-7.33 (m, 1H), 7.19-7.22 (m, 2H), 7.02-7.05 (m, 2H), 4.39-4.45 (m, 1H), 4.17-4.21 (m, 1H), 3.47-3.61 (m, 2H), 3.12-3.20 (m, 2H), 1.57-1.65 (m, 2H), 1.38-1.56 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-038 | 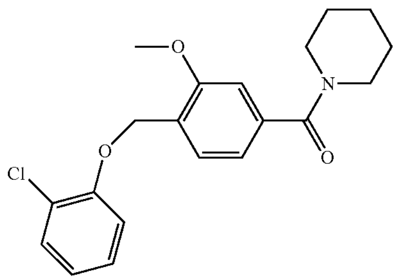 [SMILES: COc1cc(C(=O)N2CCCCC2)ccc1COc1ccccc1Cl] | 30.37%/ 99.95% | 359.13 for C20H22ClNO3/ 360.0 (M + 1) | δ 7.40-7.53 (m, 2H), 7.29 (dd, J = 1.53, 7.40 Hz, 1H), 7.18-7.26 (m, 1H), 7.03 (d, J = 1.10 Hz, 1H), 6.95-7.00 (m, 2H), 5.17 (s, 2H), 3.86 (s, 3H), 3.48-3.66 (m, 2H), 3.19-3.30 (m, 2H), 1.39-1.66 (m, 6H). |
| MF-DH-118 | 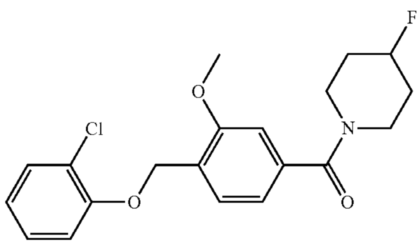 [SMILES: COc1cc(C(=O)N2CCC(F)CC2)ccc1COc1ccccc1Cl] | 14.6%/ 99.53% | 377.12 for C20H21ClFNO3/ 378.0 (M + 1) | δ 7.43-7.51 (m, 2H), 7.31 (dt, J = 1.59, 7.83 Hz, 1H), 7.18-7.26 (m, 1H), 7.08 (d, J = 1.10 Hz, 1H), 6.95-7.03 (m, 2H), 5.17 (s, 2H), 4.82-5.01 (m, 1H), 3.86 (s, 4H), 3.34-3.76 (m, 4H), 1.62-2.02 (m, 4H). |
| MF-DH-121 | 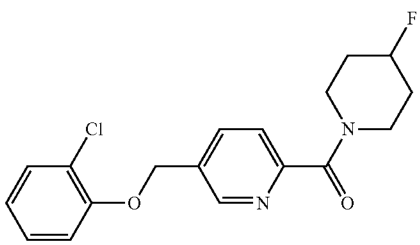 [SMILES: O=C(c1ccc(COc2ccccc2Cl)cn1)N1CCC(F)CC1] | 61.4%/ 99.67% | 348.10 for C18H18ClFN2O2/ 349.0 (M + 1) | δ 8.67-8.71 (m, 1H), 8.01 (dd, J = 2.02, 8.01 Hz, 1H), 7.64 (d, J = 7.95 Hz, 1H), 7.46 (dd, J = 1.47, 7.82 Hz, 1H), 7.26-7.36 (m, 2H), 7.00 (dt, J = 1.59, 7.52 Hz, 1H), 5.31 (s, 2H), 4.83-5.02 (m, 1H), 3.70 (br t, J = 5.50 Hz, 2H), 3.43-3.55 (m, 1H), 3.33-3.40 (m, 1H), 1.64-2.03 (m, 4H). |
| MF-PGDH-095 | 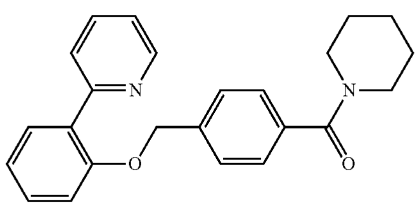 [SMILES: O=C(c1ccc(COc2ccccc2-c2ccccn2)cc1)N1CCCCC1] | 12.4%/ 99.23% | 372.18 for C24H24N2O2/ 373.1 (M + 1) | δ 8.65-8.68 (m, 1H), 7.88-7.92 (m, 1H), 7.77-7.82 (m, 1H), 7.71-7.74 (m, 1H), 7.47 (d, J = 8.19 Hz, 2H), 7.30-7.42 (m, 4H), 7.21-7.25 (m, 1H), 7.06-7.11 (m, 1H), 5.24 (s, 2H), 3.52-3.62 (m, 2H), 3.20-3.30 (m, 2H), 1.58-1.64 (m, 2H), 1.41-1.56 (m, 4H). |
| MF-PGDH-096 | 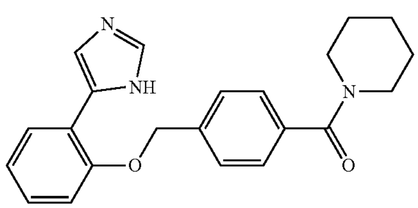 [SMILES: O=C(c1ccc(COc2ccccc2-c2cnc[nH]2)cc1)N1CCCCC1] | 2.05%/ 99.19% | 378.14 for C22H23N3O2/ 379.0 (M + 1) | δ 11.63-12.41 (m, 1H), 8.04 (br d, J = 7.09 Hz, 1H), 7.71 (s, 1H), 7.56 (d, J = 8.07 Hz, 2H), 7.36-7.48 (m, 3H), 7.11-7.20 (m, 2H), 6.99 (t, J = 7.21 Hz, 1H), 5.28 (s, 2H), 3.57 (br d, J = 2.32 Hz, 2H), 3.43-3.52 (m, 2H), 1.43-1.65 (m, 6H). |
| MF-PGDH-097 | 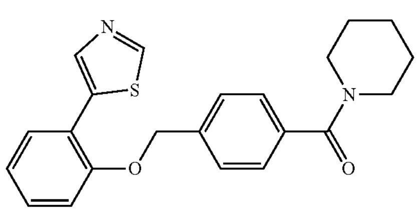 [SMILES: O=C(c1ccc(COc2ccccc2-c2cncs2)cc1)N1CCCCC1] | 30.9%/ 99.72% | 326.12 for C22H22N2O2S/ 327.0 (M + 1) | δ 9.06 (s, 1H), 8.38 (s, 1H), 7.80 (br d, J = 7.34 Hz, 1H), 7.53-7.57 (m, 2H), 7.34-7.42 (m, 3H), 7.26-7.29 (m, 1H), 7.07 (t, J = 7.34 Hz, 1H), 5.32 (s, 2H), 3.53-3.62 (m, 2H), 3.20-3.34 (m, 2H), 1.43-1.65 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-041 | 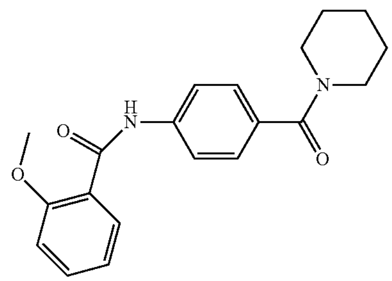 | 3.53%/ 98.91% | 338.16 for C20H22N2O3/ 339.1 (M + 1) | δ 10.28 (s, 1H), 7.79 (d, J = 8.56 Hz, 2H), 7.61 (dd, J = 1.71, 7.58 Hz, 1H), 7.51 (ddd, J = 1.83, 7.40, 8.38 Hz, 1H), 7.35 (d, J = 8.56 Hz, 2H), 7.18 (d, J = 8.19 Hz, 1H), 7.07 (dt, J = 0.86, 7.46 Hz, 1H), 3.89 (s, 3H), 3.48-3.63 (m, 2H), 3.37-3.47 (m, 2H), 1.61 (br d, J = 4.16 Hz, 2H), 1.51 (br s, 4H). |
| MF-PGDH-042 | 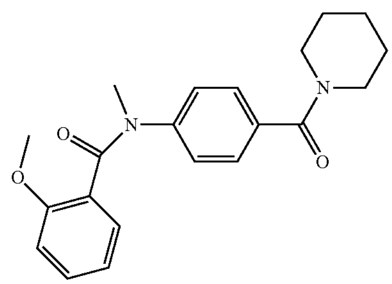 [SMILES: COc1ccccc1C(=O)N(C)c1ccc(C(=O)N2CCCCC2)cc1] | 16.71%/ 99.67% | 352.18 for C21H24N2O3/ 353.1 (M + 1) | δ 7.04-7.27 (m, 6H), 6.67-6.89 (m, 2H), 3.42-3.59 (m, 5H), 3.31 (br s, 3H), 2.99-3.12 (m, 2H), 1.31-1.57 (m, 6H). |
| MF-PGDH-087 | 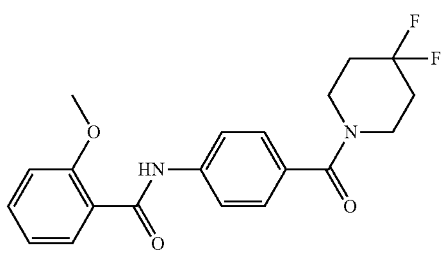 [SMILES: COc1ccccc1C(=O)Nc1ccc(C(=O)N2CCC(F)(F)CC2)cc1] | 4.77%/ 92.51% | 374.14 for C20H20F2N2O3/ 375.0 (M + 1) | δ 10.30 (s, 1H), 7.81 (d, J = 8.56 Hz, 2H), 7.61 (dd, J = 1.71, 7.58 Hz, 1H), 7.48-7.54 (m, 1H), 7.44 (d, J = 8.56 Hz, 2H), 7.19 (d, J = 8.19 Hz, 1H), 7.07 (s, 1H), 3.89 (s, 3H), 3.47-3.68 (m, 4H), 1.98-2.10 (m, 4H). |
| MF-PGDH-088 | 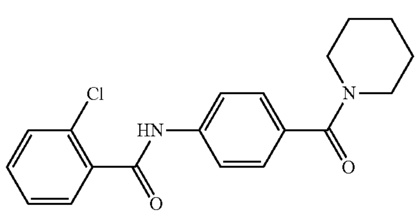 [SMILES: O=C(Nc1ccc(C(=O)N2CCCCC2)cc1)c1ccccc1Cl] | 66.1%/ 98.39% | 342.11 for C19H19ClN2O2/ 343.2 (M + 1) | δ 10.67 (s, 1H), 7.77 (d, J = 8.56 Hz, 2H), 7.44-7.61 (m, 4H), 7.37 (d, J = 8.56 Hz, 2H), 3.36-3.68 (m, 4H), 1.57-1.66 (m, 2H), 1.42-1.56 (m, 4H). |
| MF-PGDH-089 | 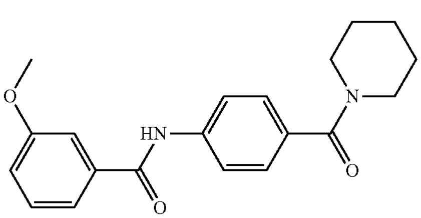 [SMILES: COc1cccc(C(=O)Nc2ccc(C(=O)N3CCCCC3)cc2)c1] | 2.49%/ 93.52% | 338.16 for C20H22N2O3/ 339.2 (M + 1) | δ 10.36 (s, 1H), 7.80-7.86 (m, 2H), 7.52-7.56 (m, 1H), 7.43-7.49 (m, 2H), 7.35-7.39 (m, 2H), 7.15-7.19 (m, 1H), 3.84-3.85 (s, 3H), 3.34-3.64 (m, 4H), 1.46-1.65 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-043 | 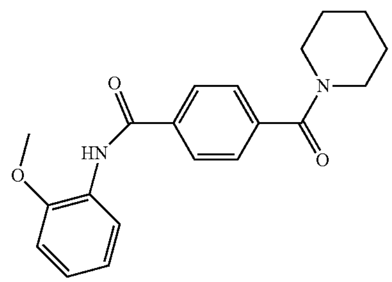 [SMILES: COc1ccccc1NC(=O)c1ccc(C(=O)N2CCCCC2)cc1] | 90%/ 94.19% | 338.16 for C20H22N2O3/ 339.1 (M + 1) | δ 9.53 (s, 1H), 7.98-8.01 (m, 2H), 7.71-7.76 (m, 1H), 7.48-7.51 (m, 2H), 7.19-7.21 (m, 1H), 7.09-7.12 (m, 1H), 6.92-7.01 (m, 1H), 3.82 (s, 3H), 3.60 (br s, 2H), 3.21 (br s, 2H), 1.41-1.72 (m, 6H). |
| MF-PGDH-044 | 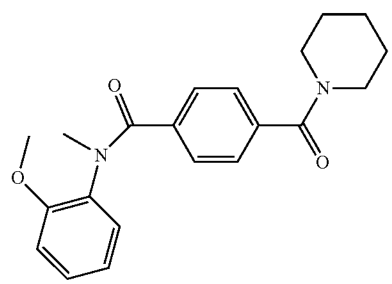 [SMILES: COc1ccccc1N(C)C(=O)c1ccc(C(=O)N2CCCCC2)cc1] | 23.69%/ 99.96% | 352.18 for C21H24N2O3/ 353.1 (M + 1) | δ 7.08-7.31 (m, 6H), 6.93 (br d, J = 8.19 Hz, 1H), 6.84 (br t, J = 7.46 Hz, 1H), 3.68 (s, 3H), 3.50 (br s, 2H), 3.22 (s, 3H), 3.00-3.13 (m, 2H), 1.53-1.61 (m, 2H), 1.24-1.52 (m, 4H). |
| MF-PGDH-004 | 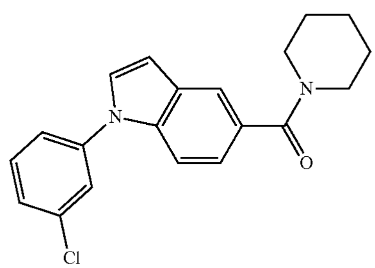 | 2.7%/ 99.50% | 338.12 for C20H19ClN2O/ 339.0 (M + 1) | δ 7.79 (d, J = 3.4 Hz, 1H), 7.73-7.68 (m, 2H), 7.64-7.58 (m, 3H), 7.50-7.47 (m, 1H), 7.26-7.22 (m, 1H), 6.79 (dd, J = 0.6, 3.3 Hz, 1H), 3.48 (br s, 4H), 1.62 (br d, J = 4.4 Hz, 2H), 1.52 (br s, 4H). |
| MF-PGDH-005 | 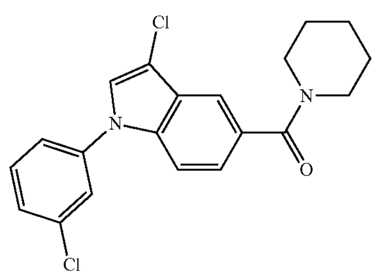 [SMILES: O=C(c1ccc2c(c1)c(Cl)cn2-c1cccc(Cl)c1)N1CCCCC1] | 3.5%/ 99.35% | 372.08 for C20H18Cl2N2O/ 372.9 (M + 1) | δ 8.08 (s, 1H), 7.76-7.75 (m, 1H), 7.66-7.61 (m, 3H), 7.59 (d, J = 1.5 Hz, 1H), 7.50-7.53 (m, 1H), 7.31-7.35 (m, 1H), 3.34-3.65 (m, 4H), 1.62 (br d, J = 3.9 Hz, 2H), 1.44-1.58 (m, 4H). |
| MF-PGDH-053 | 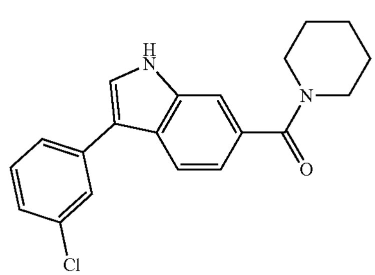 [SMILES: O=C(c1ccc2c(-c3cccc(Cl)c3)c[nH]c2c1)N1CCCCC1] | 2%/ 98.66% | 338.12 for C20H19ClN2O/ 339.2 (M + 1) | $^1$H NMR (400 MHz, DMSO-$d_6$): δ 11.65 (br s, 1H), 7.93-7.88 (m, 2H), 7.72-7.68 (m, 2H), 7.51-7.42 (m, 2H), 7.29-7.26 (m, 1H), 7.13-7.09 (m, 1H), 3.62-3.40 (m, 4H), 1.68-1.43 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-054 | 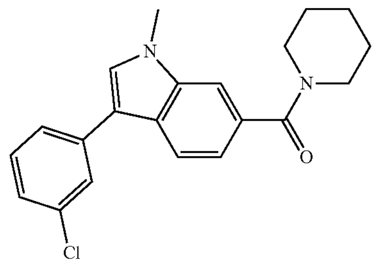 [SMILES: Cn1cc(-c2cccc(Cl)c2)c2ccc(C(=O)N3CCCCC3)cc21] | 81.4%/ 99.81% | 352.13 for C21H21ClN2O/ 353.2 (M + 1) | δ 7.93-7.88 (m, 2H), 7.70-7.65 (m, 2H), 7.57 (d, J = 0.7 Hz, 1H), 7.46 (t, J = 7.9 Hz, 1H), 7.29 (ddd, J = 0.9, 2.1, 8.0 Hz, 1H), 7.16 (dd, J = 1.3, 8.19 Hz, 1H), 3.87 (s, 3H), 3.66-3.40 (m, 4H), 1.67-1.48 (m, 6H). |
| MF-PGDH-057 | 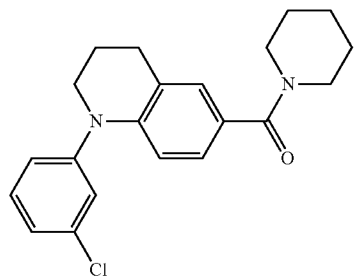 [SMILES: O=C(c1ccc2c(c1)CCCN2c1cccc(Cl)c1)N1CCCCC1] | 7.0%/ 95.07% | 354.15 for C21H23ClN2O/ 355.2 (M + 1) | δ 7.42-7.37 (m, 1H), 7.30 (t, J = 2.0 Hz, 1H), 7.23 (ddd, J = 0.9, 2.1, 8.1 Hz, 1H), 7.17 (ddd, J = 0.9, 2.0, 8.1 Hz, 1H), 7.10 (d, J = 1.8 Hz, 1H), 6.97 (dd, J = 2.0, 8.4 Hz, 1H), 6.64 (d, J = 8.4 Hz, 1H), 3.63-3.58 (m, 2H), 3.44 (br s, 4H), 2.81-2.77 (m, 2H), 1.99-1.92 (m, 2H), 1.64-1.56 (m, 2H), 1.48 (br d, J = 3.7 Hz, 4H). |
| MF-PGDH-058 | 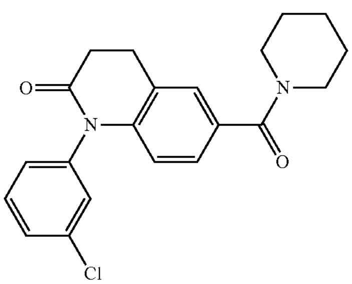 [SMILES: O=C(c1ccc2c(c1)CCC(=O)N2c1cccc(Cl)c1)N1CCCCC1] | 8.2%/ 98.34% | 368.13 for C21H21ClN2O2/ 369.0 (M + 1) | δ 7.60-7.52 (m, 2H), 7.46 (t, J = 1.7 Hz, 1H), 7.33-7.26 (m, 2H), 7.12-7.08 (m, 1H), 6.25 (d, J = 8.3 Hz, 1H), 3.69-3.35 (m, 4H), 3.07 (br t, J = 7.3 Hz, 2H), 2.76-2.71 (m, 2H), 1.64-1.56 (m, 2H), 1.55-1.42 (m, 4H). |
| MF-PGDH-006 | 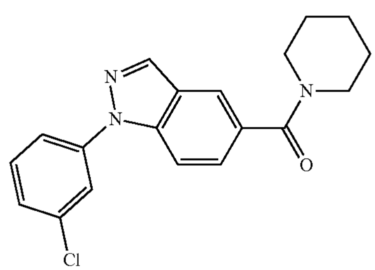 | 4.41%/ 99.75% | 339.11 for C19H18ClN3O/ 340.0 (M + 1) | δ 8.49 (s, 1H), 7.96-7.89 (m, 2H), 7.94-7.88 (m, 1H), 7.85-7.81 (m, 1H), 7.64-7.61 (m, 1H), 7.55-7.51 (m, 2H), 3.69-3.31 (m, 4H), 1.71-1.42 (m, 6H). |
| MF-PGDH-007 | 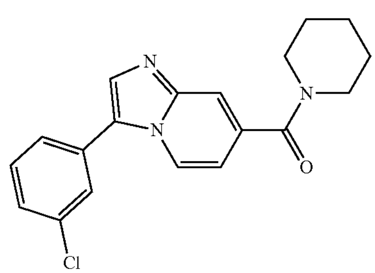 [SMILES: O=C(c1ccn2c(-c3cccc(Cl)c3)cnc2c1)N1CCCCC1] | 15.7%/ 98.0% | 339.11 for C19H18ClN3O/ 340.0 (M + 1) | δ 8.64-8.61 (m, 1H), 7.92 (s, 1H), 7.79 (s, 1H), 7.68-7.62 (m, 2H), 7.59-7.54 (m, 1H), 7.52-7.49 (m, 1H), 6.99-6.95 (m, 1H), 3.69-3.35 (m, 4H), 1.69-1.45 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-PGDH-011 | 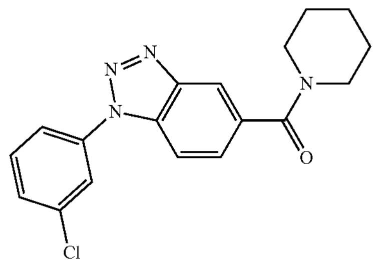 [SMILES: O=C(c1ccc2c(c1)nnn2-c1cccc(Cl)c1)N1CCCCC1] | 45.29%/ 97.16% | 340.11 for C18H17ClN4O/ 341.0 (M + 1) | δ 8.21 (s, 1H), 8.03-8.00 (m, 2H), 7.92-7.89 (m, 1H), 7.76-7.65 (m, 3H), 3.73-3.52 (m, 2H), 1.70-1.21 (m, 8H). |
| MF-PGDH-012 | 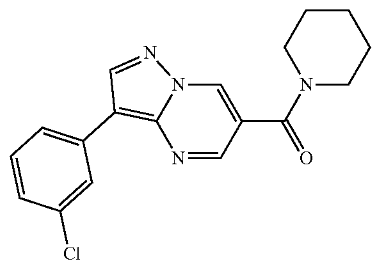 [SMILES: O=C(c1cnc2c(-c3cccc(Cl)c3)cnn2c1)N1CCCCC1] | 9.9%/ 98.76% | 340.11 for C18H17ClN4O/ 341.0 (M + 1) | δ 9.33 (d, J = 2.1 Hz, 1H), 8.94 (s, 1H), 8.73 (d, J = 2.1 Hz, 1H), 8.28 (t, J = 1.8 Hz, 1H), 8.14-8.10 (m, 1H), 7.49 (t, J = 7.9 Hz, 1H), 7.34-7.30 (m, 1H), 3.66-3.43 (m, 4H), 1.67-1.54 (m, 6H). |
| MF-DH-150 | 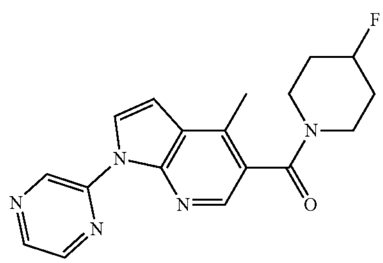 [SMILES: Cc1c(C(=O)N2CCC(F)CC2)cnc2c1ccn2-c1cnccn1] | 35.7%/ 99.98% | 339.15 for C18H18FN5O/ 340.1 (M + 1) | δ 10.10 (d, J = 1.2 Hz, 1H), 8.58-8.64 (m, 2H), 8.36 (d, J = 3.9 Hz, 1H), 8.30 (s, 1H), 7.02 (d, J = 3.9 Hz, 1H), 4.82-5.02 (m, 1H), 3.64-3.90 (m, 2H), 3.34-3.41 (m, 1H), 3.11-3.26 (m, 1H), 2.50 (s, 3H), 1.60-2.08 (m, 4H). |
| MF-DH-151 | 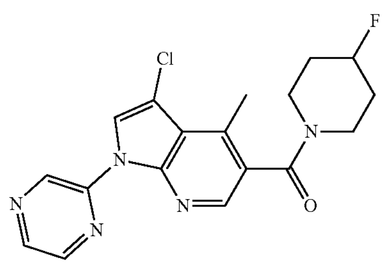 [SMILES: Cc1c(C(=O)N2CCC(F)CC2)cnc2c1c(Cl)cn2-c1cnccn1] | 6.1%/ 99.45% | 373.11 for C18H17ClFN5O/ 374.0 (M + 1) | δ 9.98 (s, 1H), 8.63 (s, 2H), 8.46 (s, 1H), 8.36 (s, 1H), 4.82-5.04 (m, 1H), 3.84 (br s, 1H), 3.65-3.76 (m, 1H), 3.14-3.23 (m, 1H), 2.70 (s, 3H), 1.70-2.03 (m, 4H). |
| MF-DH-161 | 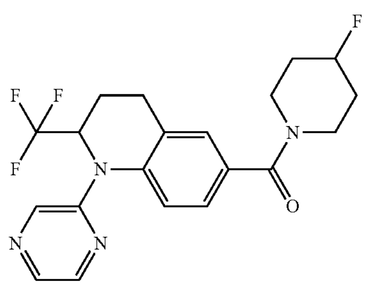 [SMILES: O=C(c1ccc2c(c1)CCC(C(F)(F)F)N2c1cnccn1)N1CCC(F)CC1] | 17.0%/ 99.13% | 408.16 for C20H20F4N4O/ 409.1 (M + 1) | δ 8.39-8.43 (m, 1H), 8.30-8.33 (m, 1H), 8.16 (d, J = 2.45 Hz, 1H), 7.35-7.41 (m, 2H), 7.29 (s, 1H), 5.52-5.60 (m, 1H), 4.82-5.01 (m, 1H), 3.36-3.71 (m, 4H), 2.74-2.83 (m, 1H), 2.61-2.69 (m, 1H), 1.67-2.04 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-164 | 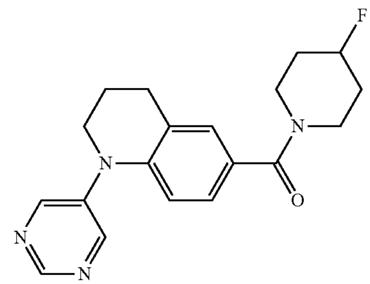 [SMILES: O=C(c1ccc2c(c1)CCCN2c1cncnc1)N1CCC(F)CC1] | 18.6%/ 92.70% | 340.17 for C19H21FN4O/ 341.1 (M + 1) | δ 8.89 (s, 1H), 8.77 (s, 2H), 7.17 (s, 1H), 7.03 (br d, J = 8.3 Hz, 1H), 6.72-6.75 (m, 1H), 4.80-4.96 (m, 1H), 3.66 (t, J = 5.8 Hz, 2H), 3.45-3.60 (m, 4H), 2.81 (t, J = 6.4 Hz, 2H), 1.86-2.00 (m, 4H), 1.65-1.72 (m, 2H). |
| MF-DH-162 | 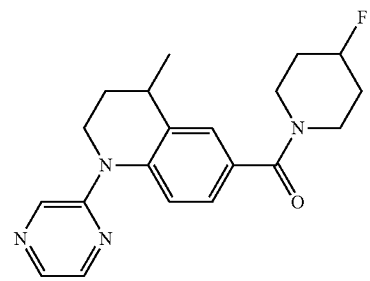 [SMILES: CC1CCN(c2cnccn2)c2ccc(C(=O)N3CCC(F)CC3)cc21] | 7.5%/ 99.77% | 354.19 for C20H23FN4O/ 355.1 (M + 1) | δ 8.55 (s, 1H), 8.24-8.32 (m, 1H), 8.08 (d, J = 2.6 Hz, 1H), 7.37 (d, J = 8.3 Hz, 1H), 7.28-7.35 (m, 1H), 7.17 (dd, J = 1.7, 8.3 Hz, 1H), 4.82-5.01 (m, 1H), 3.83 (t, J = 6.2 Hz, 2H), 3.38-3.67 (m, 4H), 2.86-2.97 (m, 1H), 2.04-2.13 (m, 1H), 1.81-2.01 (m, 2H), 1.58-1.79 (m, 3H), 1.29 (d, J = 7.0 Hz, 3H). |
| MF-DH-160 | 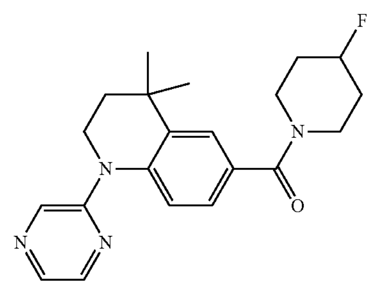 [SMILES: CC1(C)CCN(c2cnccn2)c2ccc(C(=O)N3CCC(F)CC3)cc21] | 16.7%/ 98.63% | 368.20 for C21H25FN4O/ 369.1 (M + 1) | δ 8.53-8.58 (s, 1H), 8.27-8.30 (s, 1H), 8.08-8.1.1 (m, 1H), 7.42 (s, 1H), 7.32-7.39 (m, 1H), 7.11-7.17 (m, 1H), 4.82-5.00 (m, 1H), 3.82-3.91 (m, 2H), 3.41-3.71 (m, 4H), 1.81-1.98 (m, 2H), 1.68-1.81 (m, 4H), 1.29 (s, 6H) |
| MF-DH-167 | 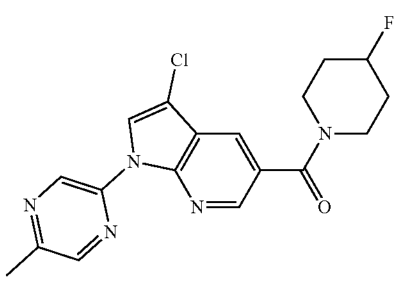 [SMILES: Cc1cnc(-n2cc(Cl)c3cc(C(=O)N4CCC(F)CC4)cnc32)cn1] | 16.5%/ 99.68% | 373.11 for C18H17ClFN5O/ 374.0 (M + 1) | δ 9.82 (s, 1H), 8.56-8.63 (m, 1H), 8.50-8.56 (m, 2H), 8.18 (d, J = 1.83 Hz, 1H), 4.85-5.04 (m, 1H), 3.40-3.88 (m, 4H), 2.58 (s, 3H), 1.69-2.05 (m, 4H). |
| MF-DH-168 | 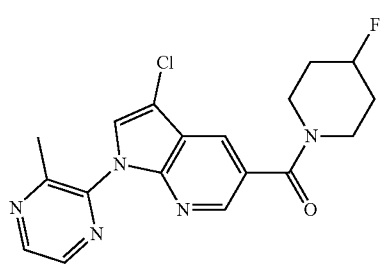 [SMILES: Cc1nccnc1-n1cc(Cl)c2cc(C(=O)N3CCC(F)CC3)cnc21] | 9.5%/ 98.46% | 373.11 for C18H17ClFN5O/ 374.0 (M + 1) | δ 8.76 (d, J = 2.4 Hz, 1H), 8.59 (d, J = 2.1 Hz, 1H), 8.42 (d, J = 1.6 Hz, 1H), 8.15-8.23 (m, 2H), 4.83-5.02 (m, 1H), 3.38-3.79 (m, 4H), 2.43 (s, 3H), 1.85-2.02 (m, 2H), 1.69-1.83 (m, 2H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-159 | 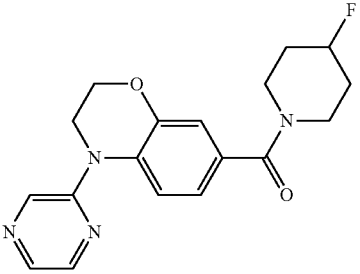 [SMILES: O=C(c1ccc2c(c1)OCCN2c1cnccn1)N1CCC(F)CC1] | 5.48%/ 99.36% | 342.15 for C18H19FN4O2/ 343.1 (M + 1) | $^1$H NMR (400 MHz, DMSO-$d_6$): δ 8.64 (s, 1H), 8.31 (br s, 1H), 8.14 (d, J = 2.4 Hz, 1H), 7.55 (d, J = 8.3 Hz, 1H), 6.86-7.00 (m, 2H), 4.81-5.01 (m, 1H), 4.23-4.38 (m, 2H), 4.02 (br d, J = 4.2 Hz, 2H), 3.39-3.67 (m, 4H), 1.82-1.99 (m, 2H), 1.65-1.79 (m, 2H). |
| MF-DH-207 | 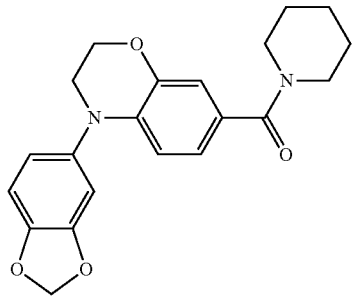 [SMILES: O=C(c1ccc2c(c1)OCCN2c1ccc2c(c1)OCO2)N1CCCCC1] | 30.3%/ 99.84% | 366.16 for C21H22N2O4/ 367.2 (M + 1) | $^1$H NMR (400 MHz, DMSO-$d_6$): δ 6.89-7.00 (m, 2H), 6.69-6.82 (m, 3H), 6.53 (d, J = 8.2 Hz, 1H), 6.05 (s, 2H), 4.24-4.33 (m, 2H), 3.57-3.69 (m, 2H), 3.42 (br s, 4H), 1.59 (br d, J = 4.4 Hz, 2H), 1.40-1.53 (m, 4H). |
| MF-DH-209 | 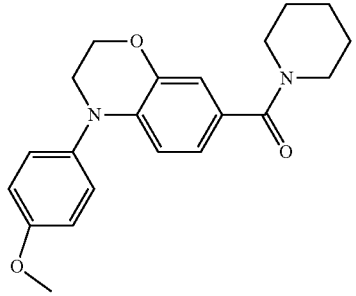 [SMILES: COc1ccc(N2CCOc3cc(C(=O)N4CCCCC4)ccc32)cc1] | 2.2%/ 93.69% | 352.18 for C21H24N2O3/ 353.2 (M + 1) | $^1$H NMR (400 MHz, DMSO-$d_6$): δ 7.24 (br d, J = 8.8 Hz, 2H), 7.00 (br d, J = 8.8 Hz, 2H), 6.78 (d, J = 1.5 Hz, 1H), 6.71 (br d, J = 8.4 Hz, 1H), 6.49 (s, 1H), 4.30 (br s, 2H), 3.77 (s, 3H), 3.60-3.72 (m, 2H), 3.43 (br s, 4H), 1.59 (br d, J = 3.7 Hz, 2H), 1.47 (br s, 4H). |
| MF-DH-203 | 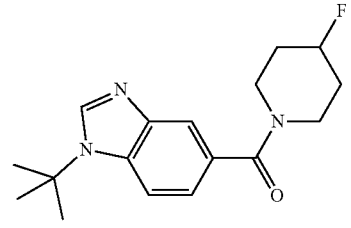 [SMILES: CC(C)(C)n1cnc2cc(C(=O)N3CCC(F)CC3)ccc21] | 20.36%/ 99.43% | 303.17 for C17H22FN3O/ 304.1 (M + 1) | δ 8.33 (s, 1H), 7.87 (d, J = 8.4 Hz, 1H), 7.69 (s, 1H), 7.28 (brd, J = 8.4 Hz, 1H), 4.82-5.01 (m, 1H), 3.37-3.68 (m, 4H), 1.82-1.99 (m, 2H), 1.67-1.77 (m, 11H). |
| MF-DH-165 | 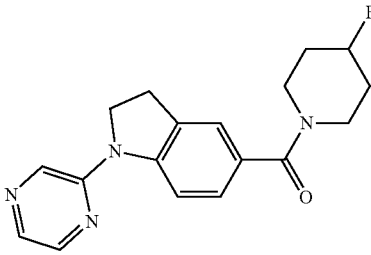 | 7.2%/ 97.23% | 326.15 for C18H19FN4O/ 327.1 (M + 1) | δ 8.26-8.37 (m, 3H), 8.11 (d, J = 2.6 Hz, 1H), 7.31 (s, 1H), 7.23-7.30 (m, 1H), 4.82-5.00 (m, 1H), 4.18 (t, J = 8.7 Hz, 2H), 3.41-3.66 (m, 4H), 3.22-3.28 (m, 2H), 1.81-1.99 (m, 2H), 1.64-1.78 (m, 2H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-311 | 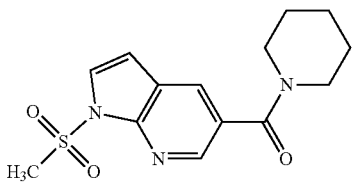 [SMILES: CS(=O)(=O)n1ccc2cc(C(=O)N3CCCCC3)cnc21] | 61.3%/ 99.78% | 307.10 for C14H17N3O3S/ 308.1 (M + 1) | δ 8.49-8.42 (m, 1H), 8.17 (d, J = 1.7 Hz, 1H), 7.81 (d, J = 3.9 Hz, 1H), 6.84 (d, J = 3.9 Hz, 1H), 3.74 (s, 3H), 3.69-3.47 (m, 2H), 1.67-1.45 (m, 6H). |
| MF-DH-312 | 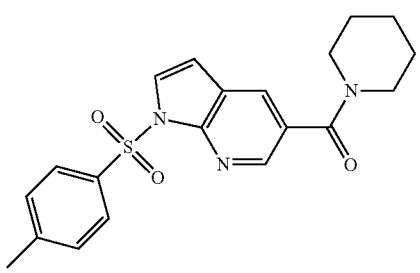 [SMILES: Cc1ccc(S(=O)(=O)n2ccc3cc(C(=O)N4CCCCC4)cnc32)cc1] | 46.4%/ 99.99% | 383.13 for C20H21N3O3S/ 384.1 (M + 1) | δ 8.39-8.35 (m, 1H), 8.08 (d, J = 1.8 Hz, 1H), 8.04-7.95 (m, 3H), 7.43 (br d, J = 8.1 Hz, 2H), 6.86 (d, J = 4.0 Hz, 1H), 3.69-3.49 (m, 2H), 3.44-3.32 (m, 2H), 2.34 (s, 3H), 1.65-1.42 (m, 6H). |
| MF-DH-318 | 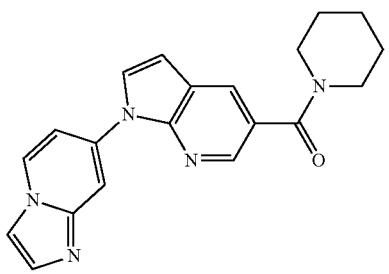 [SMILES: O=C(c1cnc2c(ccn2-c2ccn3ccnc3c2)c1)N1CCCCC1] | 34.1%/ 97.63% | 345.16 for C20H19N5O/ 346.2 (M + 1) | δ 9.19 (s, 1H), 8.36 (d, J = 1.9 Hz, 1H), 8.15 (d, J = 1.9 Hz, 1H), 8.09 (s, 1H), 8.06-7.98 (m, 1H), 7.77-7.66 (m, 3H), 6.85-6.82 (m, 1H), 3.78-3.36 (m, 4H), 1.69-1.48 (m, 6H). |
| MF-DH-320 | 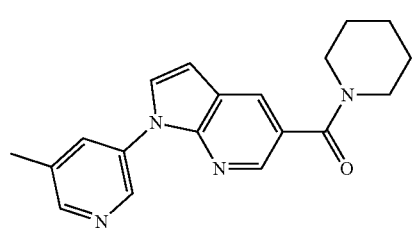 [SMILES: Cc1cncc(-n2ccc3cc(C(=O)N4CCCCC4)cnc32)c1] | 3.5%/ 99.12% | 320.16 for C19H20N4O/ 321.2 (M + 1) | δ 8.95 (s, 1H), 8.44-8.35 (m, 2H), 8.21-8.08 (m, 3H), 6.84 (d, J = 3.7 Hz, 1H), 3.64-3.37 (m, 4H), 2.42 (s, 3H), 1.68-1.50 (m, 6H). |
| MF-DH-342 | 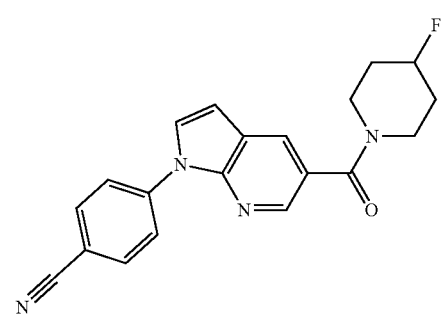 [SMILES: N#Cc1ccc(-n2ccc3cc(C(=O)N4CCC(F)CC4)cnc32)cc1] | 43.6%/ 99.48% | 348.14 for C20H17FN4O/ 349.0 (M + 1) | δ 8.43 (d, J = 2.0 Hz, 1H), 8.34-8.25 (m, 2H), 8.23-8.18 (m, 2H), 8.08-8.02 (m, 2H), 6.89 (d, J = 3.8 Hz, 1H), 5.02-4.84 (m, 1H), 3.84-3.39 (m, 4H), 2.05-1.69 (m, 4H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-344 | 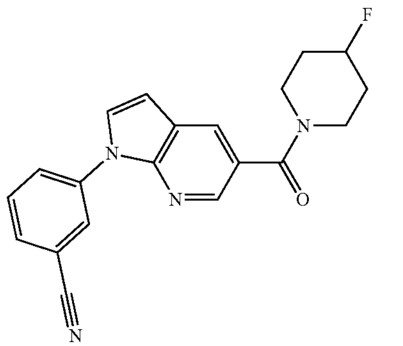 [SMILES: N#Cc1cccc(-n2ccc3cc(C(=O)N4CCC(F)CC4)cnc32)c1] | 39.6%/ 99.64% | 348.14 for C20H17FN4O/ 349.2 (M + 1) | δ 8.50-8.47 (m, 1H), 8.44-8.42 (m, 1H), 8.39-8.35 (m, 1H), 8.22-8.16 (m, 2H), 7.85-7.76 (m, 2H), 6.86 (d, J = 3.8 Hz, 1H), 5.03-4.84 (m, 1H), 3.77-3.36 (m, 4H), 2.02-1.70 (m, 4H). |
| MF-DH-366 | 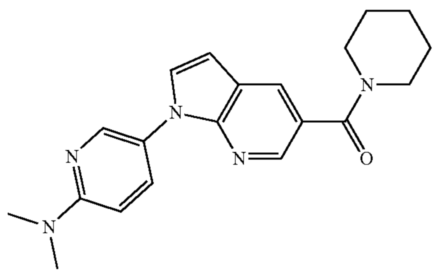 [SMILES: CN(C)c1ccc(-n2ccc3cc(C(=O)N4CCCCC4)cnc32)cn1] | 63.9%/ 99.68% | 349.19 for C20H23N5O/ 350.2 (M + 1) | δ 8.43 (d, J = 2.4 Hz, 1H), 8.29 (d, J = 2.0 Hz, 1H), 8.10 (d, J = 2.0 Hz, 1H), 7.92-7.86 (m, 2H), 6.82-6.73 (m, 2H), 3.69-3.34 (m, 4H), 3.09 (s, 6H), 1.67-1.49 (m, 6H). |
| MF-DH-389 | 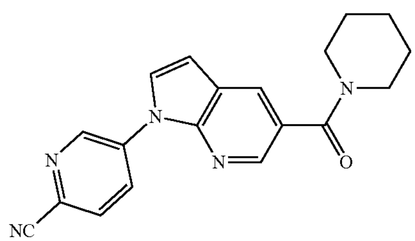 | 51.0%/ 99.81% | 331.14 for C19H17N5O/ 332.2 (M + 1) | δ 9.44-9.36 (m, 1H), 8.70 (dd, J = 8.5, 2.1 Hz, 1H), 8.32 (s, 1H), 8.24-8.12 (m, 2H), 8.12-8.04 (m, 1H), 6.84 (d, J = 3.7 Hz, 1H), 3.59-3.25 (m, 4H), 1.58-1.38 (m, 6H). |
| MF-DH-397 | 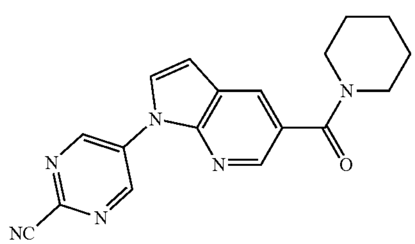 | 5.46%/ 99.77% | 332.14 for C18H16N6O/ 333.2 (M + 1) | δ 9.82 (s, 2H), 8.45 (d, J = 1.9 Hz, 1H), 8.36 (d, J = 3.9 Hz, 1H), 8.21 (d, J = 1.9 Hz, 1H), 7.00 (d, J = 3.9 Hz, 1H), 3.74-3.33 (m, 4H), 1.68-1.46 (m, 6H). |
| MF-DH-319 | 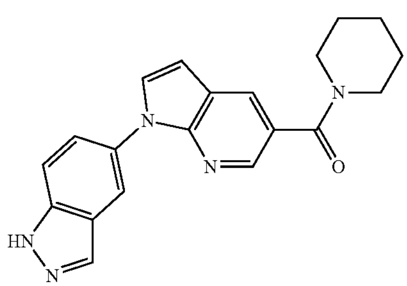 [SMILES: O=C(c1cnc2c(ccn2-c2ccc3[nH]ncc3c2)c1)N1CCCCC1] | 30.5%/ 99.93% | 345.16 for C20H19N5O/ 346.1 (M + 1) | δ 13.25 (br s, 1H), 8.35 (s, 1H), 8.23-8.01 (m, 3H), 7.99-7.97 (m, 1H), 7.82-7.69 (m, 2H), 6.81 (s, 1H), 3.72-3.42 (m, 4H), 1.71-1.42 (m, 6H). |

TABLE 3-continued

Analytical data for select inhibitors

| Target No | Structure | Yield/ Purity | Mass Spec. Calculated/ Mass Spec. Found (m/z) | $^{1}$H NMR (DMSO-$d_6$*, 400 MHz) (*unless otherwise indicated) |
|---|---|---|---|---|
| MF-DH-337 | 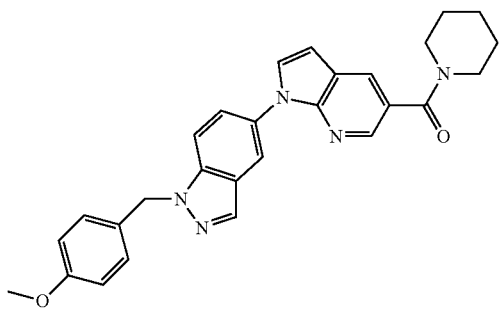 [SMILES: COc1ccc(Cn2ncc3cc(-n4ccc5cc(C(=O)N6CCCCC6)cnc54)ccc32)cc1] | 33.3%/ 98.99% | 465.22 for C28H27N5O2/ 466.1 (M + 1) | δ 8.31 (d, J = 1.9 Hz, 1H), 8.21-8.19 (m, 1H), 8.19-8.09 (m, 2H), 8.00 (d, J = 3.5 Hz, 1H), 7.87 (d, J = 9.0 Hz, 1H), 7.83-7.74 (m, 1H), 7.27-7.22 (m, 2H), 6.91-6.86 (m, 2H), 6.80-6.77 (m, 1H), 5.65 (s, 2H), 3.70 (s, 3H), 3.64-3.34 (m, 4H), 1.68-1.45 (m, 6H). |
| MF-DH-340 | 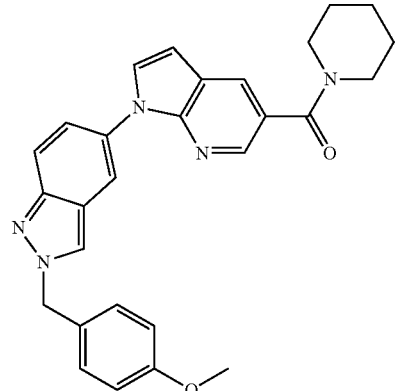 | 34.1%/ 99.35% | 465.22 for C28H27N5O2/ 466.2 (M + 1) | δ 8.55 (s, 1H), 8.32 (s, 1H), 8.10 (br d, J = 14.5 Hz, 2H), 8.06-7.93 (m, 1H), 7.76 (br d, J = 9.2 Hz, 1H), 7.72-7.63 (m, 1H), 7.33 (br d, J = 8.4 Hz, 2H), 6.93 (br d, J = 8.4 Hz, 2H), 6.88-6.73 (m, 1H), 5.61 (s, 2H), 3.73 (s, 3H), 3.66-3.37 (m, 4H), 1.69-1.47 (m, 6H). |
| MF-DH-343 | 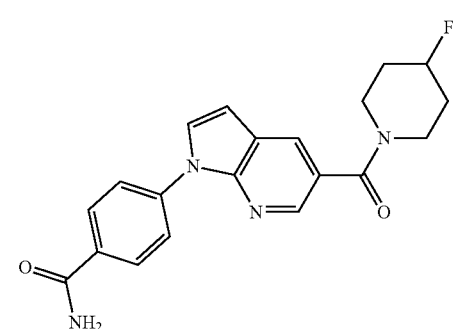 | 27.5%/ 98.89% | 366.15 for C20H19FN4O2/ 367.1 (M + 1) | δ 8.42 (d, J = 2.0 Hz, 1H), 8.22-8.11 (m, 2H), 8.06 (s, 5H), 7.43-7.40 (m, 1H), 6.86-6.83 (m, 1H), 5.03-4.84 (m, 1H), 3.75-3.36 (m, 4H), 2.03-1.85 (m, 2H), 1.84-1.69 (m, 2H). |
| MF-DH-345 | 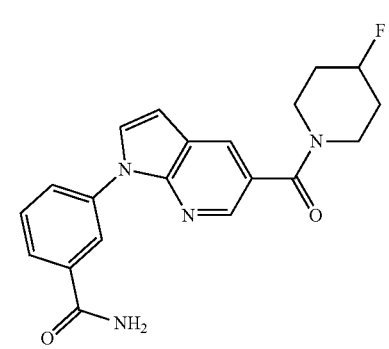 [SMILES: NC(=O)c1cccc(-n2ccc3cc(C(=O)N4CCC(F)CC4)cnc32)c1] | 21.4%/ 99.38% | 366.15 for C20H19FN4O2/ 367.1 (M + 1) | δ 8.40 (d, J = 2.0 Hz, 1H), 8.31 (t, J = 1.8 Hz, 1H), 8.19 (d, J = 2.0 Hz, 1H), 8.16-8.03 (m, 3H), 7.86 (s, 1H), 7.69-7.61 (m, 1H), 7.53-7.48 (m, 1H), 6.84 (d, J = 3.6 Hz, 1H), 5.03-4.84 (m, 1H), 3.77-3.37 (m, 4H), 2.03-1.87 (m, 2H), 1.84-1.69 (m, 2H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-365 | 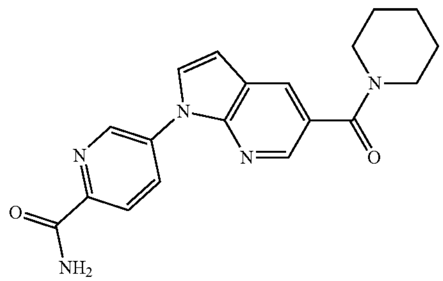 | 20.5%/ 96.50% | 349.15 for C19H19N5O2/ 350.2 (M + 1) | δ 9.27 (brs, 1H), 8.62 (brd, J = 7.1 Hz, 1H), 8.40 (br s, 1H), 8.29-8.10 (m, 4H), 7.69 (br s, 1H), 6.90 (br d, J = 3.1 Hz, 1H), 3.73-3.40 (m, 4H), 1.68-1.50 (m, 6H). |
| MF-DH-384 | 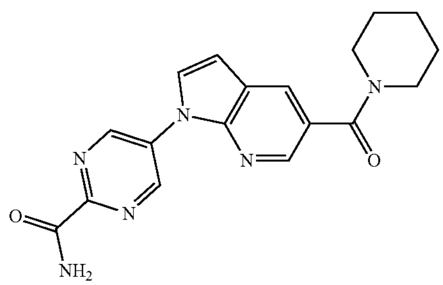 [SMILES: NC(=O)c1ccc(-n2ccc3cc(C(=O)N4CCCCC4)cnc32)cn1] | 43.6%/ 99.72% | 350.15 for C18H18N6O2/ 351.2 (M + 1) | δ 9.63 (s, 2H), 8.43 (d, J = 1.7 Hz, 1H), 8.31 (d, J = 3.8 Hz, 1H), 8.28-8.23 (m, 1H), 8.23-8.17 (m, 1H), 7.84 (br s, 1H), 6.95 (d, J = 3.8 Hz, 1H), 3.70-3.35 (m, 4H), 1.70-1.49 (m, 6H). |
| MF-DH-394 | 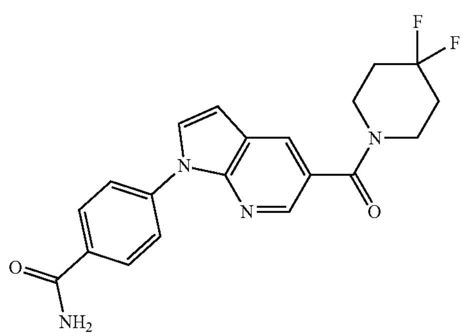 [SMILES: NC(=O)c1ccc(-n2ccc3cc(C(=O)N4CCC(F)(F)CC4)cnc32)cc1] | 40.3%/ 96.60% | 384.14 for C20H18F2N4O2/ 385.2 (M + 1) | δ 8.45 (d, J = 2.0 Hz, 1H), 8.23 (d, J = 1.8 Hz, 1H), 8.15 (d, J = 3.8 Hz, 1H), 8.06 (s, 5H), 7.43 (br s, 1H), 6.85 (d, J = 3.8 Hz, 1H), 3.78-3.52 (m, 4H), 2.08 (br s, 4H). |
| MF-DH-347 | 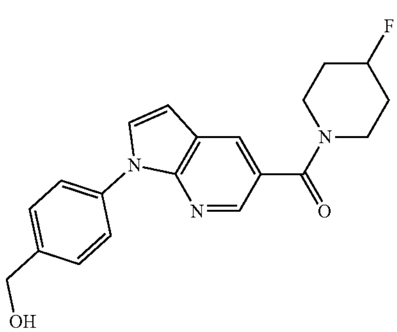 [SMILES: O=C(c1cnc2c(ccn2-c2ccc(CO)cc2)c1)N1CCC(F)CC1] | 14.2%/ 99.30% | 353.15 for C20H20FN3O2/ 354.2 (M + 1) | δ 8.37 (d, J = 2.0 Hz, 1H), 8.16 (d, J = 2.0 Hz, 1H), 8.01 (d, J = 3.6 Hz, 1H), 7.86-7.80 (m, 2H), 7.49 (d, J = 8.6 Hz, 2H), 6.79 (d, J = 3.6 Hz, 1H), 5.27 (t, J = 5.8 Hz, 1H), 5.02-4.83 (m, 1H), 4.57 (d, J = 5.8 Hz, 2H), 3.78-3.43 (m, 4H), 2.03-1.70 (m, 4H). |

TABLE 3-continued

Analytical data for select inhibitors

| Target No | Structure | Yield/ Purity | Mass Spec. Calculated/ Mass Spec. Found (m/z) | ¹H NMR (DMSO-d₆*, 400 MHz) (*unless otherwise indicated) |
|---|---|---|---|---|
| MF-DH-348 | 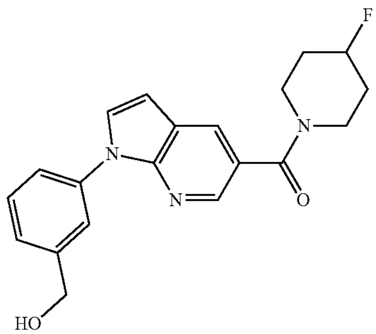 [SMILES: O=C(c1cnc2c(ccn2-c2cccc(CO)c2)c1)N1CCC(F)CC1] | 28.0%/ 97.73% | 353.15 for C20H20FN3O2/ 354.2 (M + 1) | δ 8.38 (d, J = 2.0 Hz, 1H), 8.17 (d, J = 2.0 Hz, 1H), 8.00 (d, J = 3.6 Hz, 1H), 7.81 (s, 1H), 7.78-7.68 (m, 1H), 7.51 (t, J = 7.8 Hz, 1H), 7.33 (d, J = 7.8 Hz, 1H), 6.80 (d, J = 3.8 Hz, 1H), 5.43-5.13 (m, 1H), 5.03-4.85 (m, 1H), 4.61 (s, 2H), 3.71-3.38 (m, 4H), 2.04-1.85 (m, 2H), 1.84-1.67 (m, 2H). |
| MF-DH-370 | 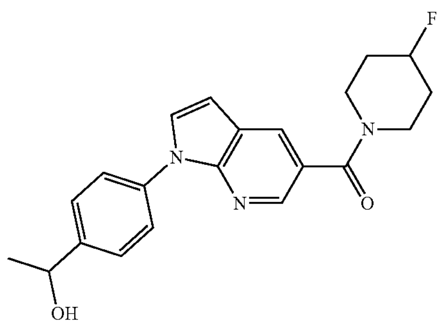 | 63.0%/ 99.30% | 353.15 for C20H20FN3O2/ 354.2 (M + 1) | δ 8.37 (d, J = 2.0 Hz, 1H), 8.16 (d, J = 2.0 Hz, 1H), 8.01 (d, J = 3.6 Hz, 1H), 7.86-7.80 (m, 2H), 7.49 (d, J = 8.6 Hz, 2H), 6.79 (d, J = 3.6 Hz, 1H), 5.27 (t, J = 5.8 Hz, 1H), 5.02-4.83 (m, 1H), 4.57 (d, J = 5.8 Hz, 2H), 3.78-3.43 (m, 4H), 2.03-1.70 (m, 4H). |
| MF-DH-371 | 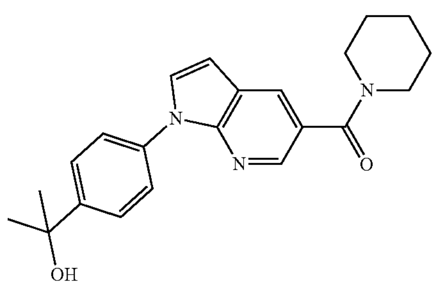 [SMILES: CC(C)(O)c1ccc(-n2ccc3cc(C(=O)N4CCCCC4)cnc32)cc1] | 34.6%/ 95.05% | 363.19 for C22H25N3O2/ 364.2 (M + 1) | δ 8.32 (d, J = 2.0 Hz, 1H), 8.11 (d, J = 2.0 Hz, 1H), 7.99 (d, J = 3.6 Hz, 1H), 7.81-7.72 (m, 2H), 7.68-7.58 (m, 2H), 6.78 (d, J = 3.6 Hz, 1H), 5.10 (s, 1H), 3.64-3.33 (m, 4H), 1.68-1.51 (m, 6H), 1.49 (s, 6H). |
| MF-DH-374 | 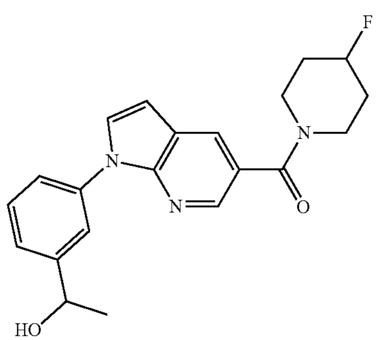 | 56.3%/ 97.83% | 353.15 for C20H20FN3O2/ 354.2 (M + 1) | δ 8.38 (d, J = 2.0 Hz, 1H), 8.17 (d, J = 2.0 Hz, 1H), 8.00 (d, J = 3.6 Hz, 1H), 7.81 (s, 1H), 7.78-7.68 (m, 1H), 7.51 (t, J = 7.8 Hz, 1H), 7.33 (d, J = 7.8 Hz, 1H), 6.80 (d, J = 3.8 Hz, 1H), 5.43-5.13 (m, 1H), 5.03-4.85 (m, 1H), 4.61 (s, 2H), 3.71-3.38 (m, 4H), 2.04-1.85 (m, 2H), 1.84-1.67 (m, 2H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-375 | 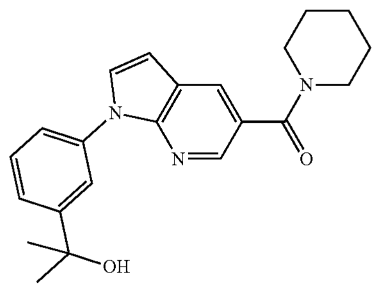 [SMILES: CC(C)(O)c1cccc(-n2ccc3cc(C(=O)N4CCCCC4)cnc32)c1] | 38.65%/ 96.62% | 363.19 for C22H25N3O2/ 364.1 (M + 1) | δ 8.32 (d, J = 2.0 Hz, 1H), 8.12 (d, J = 2.0 Hz, 1H), 7.98 (d, J = 3.8 Hz, 1H), 7.90-7.84 (m, 1H), 7.76-7.65 (m, 1H), 7.52-7.43 (m, 2H), 6.79 (d, J = 3.6 Hz, 1H), 5.13 (s, 1H), 3.66-3.35 (m, 4H), 1.67-1.51 (m, 6H), 1.49 (s, 6H). |
| MF-DH-324 | 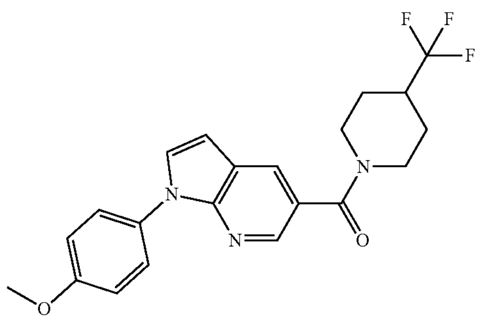 [SMILES: COc1ccc(-n2ccc3cc(C(=O)N4CCC(C(F)(F)F)CC4)cnc32)cc1] | 14.6%/ 99.78% | 403.15 for C21H20F3N3O2/ 404.1 (M + 1) | δ 8.34 (d, J = 2.0 Hz, 1H), 8.16 (d, J = 2.1 Hz, 1H), 7.93 (d, J = 3.6 Hz, 1H), 7.76-7.71 (m, 2H), 7.14-7.09 (m, 2H), 6.76 (d, J = 3.6 Hz, 1H), 4.65-4.27 (m, 1H), 3.83 (s, 3H), 3.14-2.78 (m, 2H), 2.71-2.55 (m, 2H), 1.93-1.77 (m, 2H), 1.53-1.41 (m, 2H). |
| MF-DH-325 | 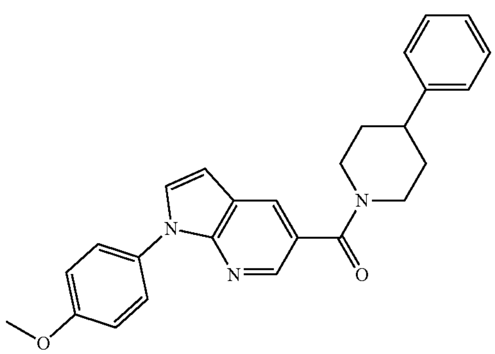 [SMILES: COc1ccc(-n2ccc3cc(C(=O)N4CCC(c5ccccc5)CC4)cnc32)cc1] | 32.0%/ 99.14% | 411.19 for C26H25N3O2/ 412.1 (M + 1) | δ 8.38 (d, J = 2.0 Hz, 1H), 8.18 (d, J = 2.0 Hz, 1H), 7.93 (d, J = 3.6 Hz, 1H), 7.78-7.71 (m, 2H), 7.34-7.27 (m, 4H), 7.27-7.17 (m, 1H), 7.16-7.08 (m, 2H), 6.77-6.76 (m, 1H), 4.82-4.38 (m, 1H), 3.83 (s, 3H), 3.20-2.89 (m, 2H), 2.88-2.58 (m, 2H), 1.92-1.62 (m, 4H). |
| MF-DH-326 | 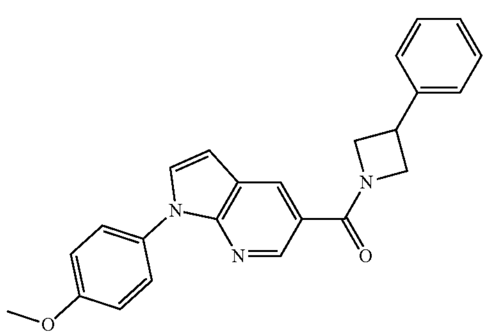 [SMILES: COc1ccc(-n2ccc3cc(C(=O)N4CC(c5ccccc5)C4)cnc32)cc1] | 24.5%/ 98.96% | 383.16 for C24H21N3O2/ 384.1 (M + 1) | δ 8.62 (d, J = 2.0 Hz, 1H), 8.41 (d, J = 2.0 Hz, 1H), 7.94 (d, J = 3.6 Hz, 1H), 7.77-7.70 (m, 2H), 7.45-7.35 (m, 4H), 7.35-7.23 (m, 1H), 7.16-7.08 (m, 2H), 6.79 (d, J = 3.8 Hz, 1H), 4.82-4.39 (m, 3H), 4.13-3.91 (m, 2H), 3.83 (s, 3H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-327 | 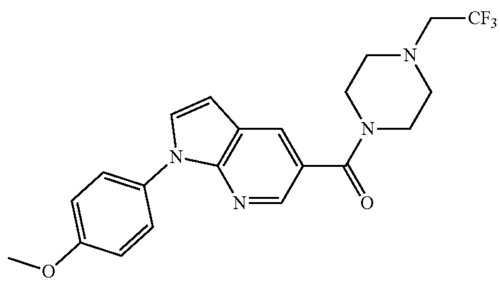 [SMILES: COc1ccc(-n2ccc3cc(C(=O)N4CCN(CC(F)(F)F)CC4)cnc32)cc1] | 21.2%/ 99.33% | 418.16 for C21H21F3N4O2/ 419.2 (M + 1) | δ 8.33 (d, J = 2.0 Hz, 1H), 8.13 (d, J = 2.0 Hz, 1H), 7.94 (d, J = 3.6 Hz, 1H), 7.78-7.69 (m, 2H), 7.16-7.08 (m, 2H), 6.76 (d, J = 3.6 Hz, 1H), 3.83 (s, 3H), 3.66-3.39 (m, 4H), 3.26-3.22 (m, 2H), 2.71-2.62 (m, 4H). |
| MF-DH-328 | 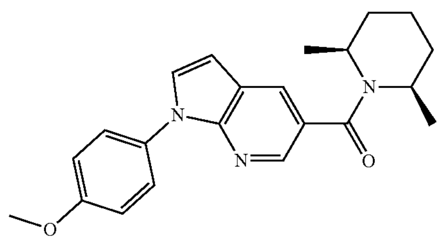 | 11.2%/ 91.01% | 363.19 for C22H25N3O2/ 364.1 (M + 1) | δ 8.26 (d, J = 2.0 Hz, 1H), 8.07 (d, J = 2.0 Hz, 1H), 7.92 (d, J = 3.6 Hz, 1H), 7.79-7.68 (m, 2H), 7.17-7.06 (m, 2H), 6.74 (d, J = 3.6 Hz, 1H), 4.66-4.17 (m, 2H), 3.83 (s, 3H), 1.91-1.77 (m, 1H), 1.71-1.61 (m, 2H), 1.58-1.32 (m, 3H), 1.27-1.09 (m, 7H). |
| MF-DH-329 (Cis) | 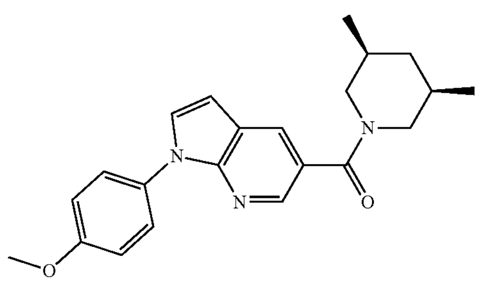 | 54.6%/ 98.52% | 363.19 for C22H25N3O2/ 364.1 (M + 1) | δ 8.31 (d, J = 2.0 Hz, 1H), 8.10 (d, J = 2.0 Hz, 1H), 7.93 (d, J = 3.6 Hz, 1H), 7.78-7.70 (m, 2H), 7.16-7.07 (m, 2H), 6.76 (d, J = 3.6 Hz, 1H), 4.56-4.34 (m, 1H), 3.83 (s, 3H), 3.73-3.51 (m, 1H), 2.77-2.57 (m, 1H), 2.38-2.16 (m, 1H), 1.80 (br d, J = 12.8 Hz, 1H), 1.68-1.56 (m, 2H), 0.95-0.66 (m, 7H). |
| MF-DH-367 | 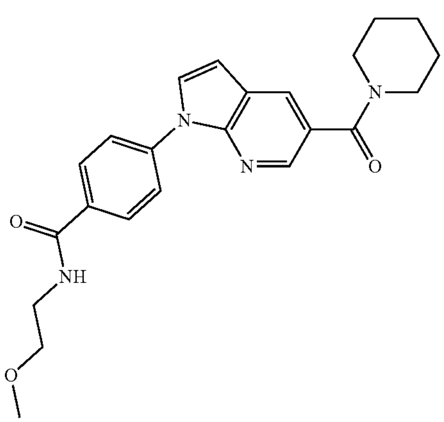 [SMILES: COCCNC(=O)c1ccc(-n2ccc3cc(C(=O)N4CCCCC4)cnc32)cc1] | 7.34%/ 98.31% | 406.20 for C23H26N4O3/ 407.3 (M + 1) | δ 8.58 (br s, 1H), 8.35 (d, J = 1.7 Hz, 1H), 8.15-7.99 (m, 6H), 6.82 (d, J = 3.7 Hz, 1H), 3.61-3.38 (m, 8H), 3.27 (s, 3H), 1.66-1.46 (m, 6H). |

TABLE 3-continued

Analytical data for select inhibitors

| Target No | Structure | Yield/Purity | Mass Spec. Calculated/Mass Spec. Found (m/z) | $^1$H NMR (DMSO-d$_6$*, 400 MHz) (*unless otherwise indicated) |
|---|---|---|---|---|
| MF-DH-368 | 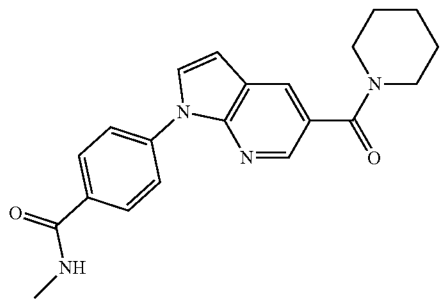 [SMILES: CNC(=O)c1ccc(-n2ccc3cc(C(=O)N4CCCCC4)cnc32)cc1] | 24.2%/99.85% | 362.17 for C21H22N4O2/363.2 (M + 1) | δ 8.51 (br d, J = 4.5 Hz, 1H), 8.37 (d, J = 2.0 Hz, 1H), 8.15-7.99 (m, 6H), 6.84 (d, J = 3.7 Hz, 1H), 3.71-3.35 (m, 4H), 2.82 (d, J = 4.4 Hz, 3H), 1.66-1.54 (m, 4H). |
| MF-DH-369 | 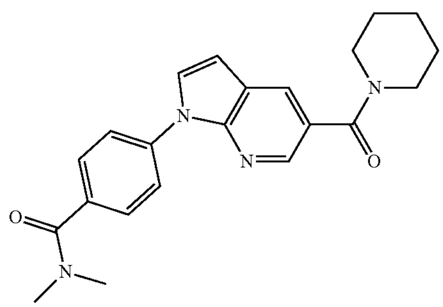 [SMILES: CN(C)C(=O)c1ccc(-n2ccc3cc(C(=O)N4CCCCC4)cnc32)cc1] | 18.5%/98.31% | 376.19 for C22H24N4O2/377.2 (M + 1) | δ 8.36 (d, J = 2.0 Hz, 1H), 8.18-8.06 (m, 2H), 8.06-7.97 (m, 2H), 7.60 (d, J = 8.6 Hz, 2H), 6.83 (d, J = 3.8 Hz, 1H), 3.68-3.35 (m, 4H), 3.04-2.96 (m, 6H), 1.67-1.49 (m, 6H). |
| MF-DH-285 | 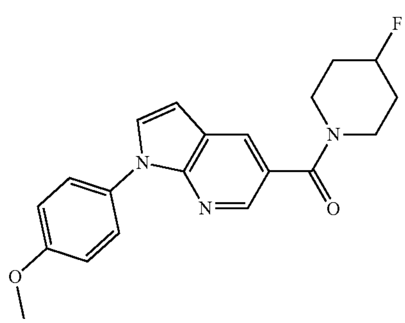 [SMILES: COc1ccc(-n2ccc3cc(C(=O)N4CCC(F)CC4)cnc32)cc1] | 43.4%/99.84% | 353.15 for C20H20FN3O2/354.2 (M + 1) | δ 8.36-8.34 (m, 1H), 8.16-8.14 (m, 1H), 7.95-7.92 (m, 1H), 7.76-7.72 (m, 2H), 7.13-7.10 (m, 2H), 6.77-6.75 (m, 1H), 5.01-4.86 (m, 1H), 3.83 (s, 3H), 3.73-3.52 (m, 3H), 3.38-3.33 (m, 1H), 2.01-1.73 (m, 4H). |
| MF-DH-294 | 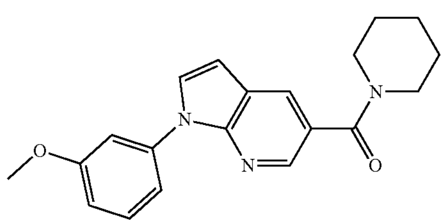 [SMILES: COc1cccc(-n2ccc3cc(C(=O)N4CCCCC4)cnc32)c1] | 34.13%/98.52% | 335.16 for C20H21N3O2/336.2 (M + 1) | δ 8.34 (d, J = 1.7 Hz, 1H), 8.12 (d, J = 1.7 Hz, 1H), 8.05 (d, J = 3.7 Hz, 1H), 7.52-7.44 (m, 3H), 6.98-6.94 (m, 1H), 6.80-6.78 (m, 1H), 3.84 (s, 3H), 3.66-3.37 (m, 4H), 1.66-1.51 (m, 6H). |
| MF-DH-295 | 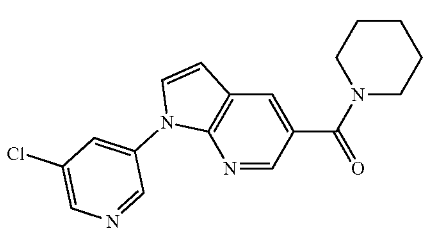 [SMILES: O=C(c1cnc2c(ccn2-c2cncc(Cl)c2)c1)N1CCCCC1] | 40.2%/99.52% | 340.11 for C18H17ClN4O/341.1 (M + 1) | δ 9.23-9.21 (m, 1H), 8.68-8.62 (m, 2H), 8.41-8.39 (m, 1H), 8.23-8.15 (m, 2H), 6.90-6.87 (m, 1H), 3.68-3.40 (m, 4H), 1.65-1.52 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-296 | 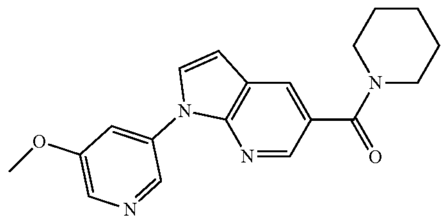 [SMILES: COc1cncc(-n2ccc3cc(C(=O)N4CCCCC4)cnc32)c1] | 52.7%/ 97.61% | 336.16 for C19H20N4O2/ 337.2 (M + 1) | δ 8.81 (s, 1H), 8.39-8.30 (m, 2H), 8.19-8.12 (m, 2H), 7.99 (br s, 1H), 6.85 (d, J = 3.7 Hz, 1H), 3.93 (s, 3H), 3.68-3.35 (m, 4H), 1.68-1.47 (m, 6H). |
| MF-DH-297 | 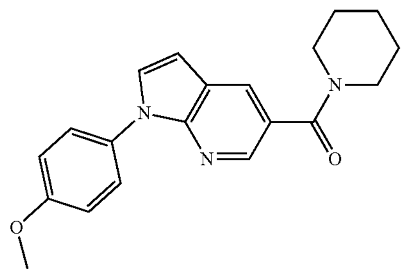 [SMILES: COc1ccc(-n2ccc3cc(C(=O)N4CCCCC4)cnc32)cc1] | 45.8%/ 99.26% | 335.16 for C20H21N3O2/ 336.1 (M + 1) | δ 8.31 (d, J = 1.6 Hz, 1H), 8.10 (d, J = 1.7 Hz, 1H), 7.93 (d, J = 3.5 Hz, 1H), 7.74 (br d, J = 8.8 Hz, 2H), 7.11 (br d, J = 8.9 Hz, 2H), 6.75 (d, J = 3.5 Hz, 1H), 3.83 (s, 3H), 3.65-3.35 (m, 4H), 1.68-1.48 (m, 6H). |
| MF-DH-298 | 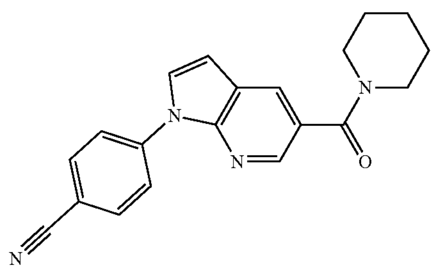 [SMILES: N#Cc1ccc(-n2ccc3cc(C(=O)N4CCCCC4)cnc32)cc1] | 31.4%/ 99.99% | 330.15 for C20H18N4O/ 331.1 (M + 1) | δ 8.42-8.36 (m, 1H), 8.33-8.25 (m, J = 8.7 Hz, 2H), 8.23-8.13 (m, 2H), 8.04 (br d, J = 8.6 Hz, 2H), 6.88 (d, J = 3.7 Hz, 1H), 3.70-3.34 (m, 4H), 1.67-1.47 (m, 6H). |
| MF-DH-300 | 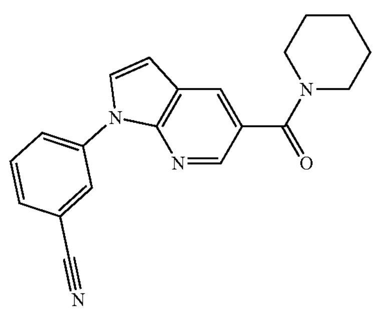 [SMILES: N#Cc1cccc(-n2ccc3cc(C(=O)N4CCCCC4)cnc32)c1] | 61.4%/ 99.46% | 330.15 for C20H18N4O/ 331.1 (M + 1) | δ 8.48 (s, 1H), 8.42-8.33 (m, 2H), 8.19-8.12 (m, 2H), 7.86-7.74 (m, 2H), 6.85 (d, J = 3.8 Hz, 1H), 3.67-3.35 (m, 4H), 1.68-1.48 (m, 6H). |
| MF-DH-302 | 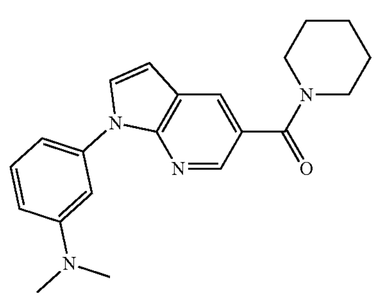 [SMILES: CN(C)c1cccc(-n2ccc3cc(C(=O)N4CCCCC4)cnc32)c1] | 57.5%/ 99.57% | 348.45 for C21H24N4O/ 349.2 (M + 1) | δ 8.32 (d, J = 2.0 Hz, 1H), 8.10 (d, J = 2.0 Hz, 1H), 7.98 (d, J = 3.6 Hz, 1H), 7.36-7.29 (m, 1H), 7.16-7.08 (m, 2H), 6.78-6.71 (m, 2H), 3.66-3.34 (m, 4H), 2.97 (s, 6H), 1.67-1.49 (m, 6H). |

TABLE 3-continued

Analytical data for select inhibitors

| Target No | Structure | Yield/ Purity | Mass Spec. Calculated/ Mass Spec. Found (m/z) | ¹H NMR (DMSO-$d_6$*, 400 MHz) (*unless otherwise indicated) |
|---|---|---|---|---|
| MF-DH-305 | 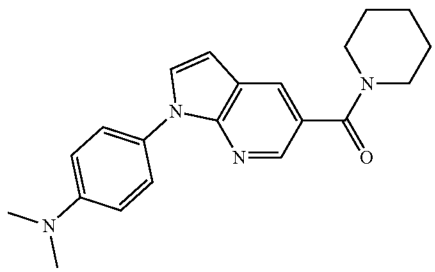 [SMILES: CN(C)c1ccc(-n2ccc3cc(C(=O)N4CCCCC4)cnc32)cc1] | 18.4%/ 99.14% | 348.20 for C21H24N4O/ 349.2 (M + 1) | δ 8.33-8.24 (m, 1H), 8.13-8.03 (m, 1H), 7.85 (d, J = 3.4 Hz, 1H), 7.58 (br d, J = 8.9 Hz, 2H), 6.87 (br d, J = 8.8 Hz, 2H), 6.72 (d, J = 3.5 Hz, 1H), 3.65-3.37 (m, 4H), 2.96 (s, 6H), 1.67-1.47 (m, 6H). |
| MF-DH-306 | 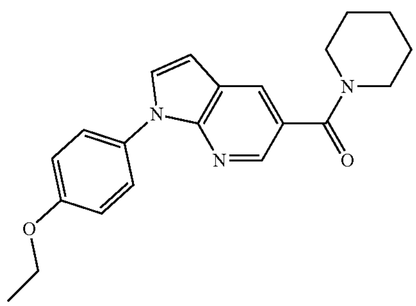 [SMILES: CCOc1ccc(-n2ccc3cc(C(=O)N4CCCCC4)cnc32)cc1] | 14.2%/ 99.73% | 349.18 for C21H23N3O2/ 350.2 (M + 1) | δ 8.31 (d, J = 2.0 Hz, 1H), 8.10 (d, J = 2.0 Hz, 1H), 7.93 (d, J = 3.6 Hz, 1H), 7.72 (d, J = 9.0 Hz, 2H), 7.10 (d, J = 9.0 Hz, 2H), 6.75 (d, J = 3.6 Hz, 1H), 4.10 (d, J = 7.0 Hz, 2H), 3.63-3.36 (m, 4H), 1.68-1.48 (m, 6H), 1.39-1.34 (m, 3H). |
| MF-DH-309 | 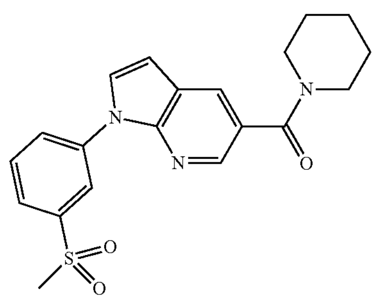 [SMILES: CS(=O)(=O)c1cccc(-n2ccc3cc(C(=O)N4CCCCC4)cnc32)c1] | 68.3%/ 99.16% | 383.13 for C20H21N3O3S/ 384.2 (M + 1) | δ 8.50 (t, J = 1.8 Hz, 1H), 8.40-8.30 (m, 2H), 8.21-8.14 (m, 2H), 7.94-7.83 (m, 2H), 6.87 (d, J = 3.8 Hz, 2H), 3.70-3.34 (m, 4H), 3.32 (s, 3H), 1.67-1.46 (m, 6H). |
| MF-DH-310 | 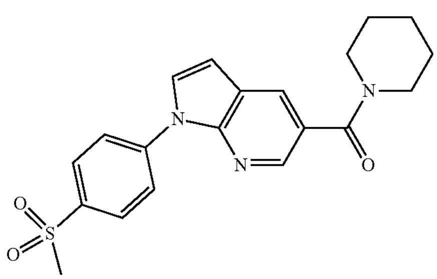 [SMILES: CS(=O)(=O)c1ccc(-n2ccc3cc(C(=O)N4CCCCC4)cnc32)cc1] | 57.3%/ 99.25% | 383.13 for C20H21N3O3S/ 384.1 (M + 1) | δ 8.39 (d, J = 2.0 Hz, 1H), 8.33-8.27 (m, 2H), 8.21-8.08 (m, 4H), 6.88 (d, J = 3.9 Hz, 1H), 3.71-3.34 (m, 4H), 3.28 (s, 3H), 1.68-1.49 (m, 6H). |
| MF-DH-317 | 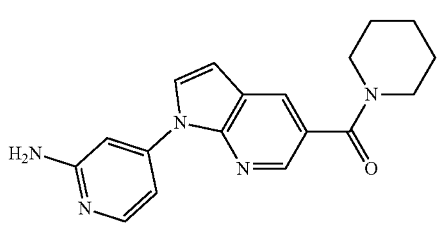 [SMILES: Nc1cc(-n2ccc3cc(C(=O)N4CCCCC4)cnc32)ccn1] | 17.5%/ 96.14% | 321.16 for C18H19N5O/ 322.2 (M + 1) | δ 8.37 (d, J = 2.0 Hz, 1H), 8.12 (d, J = 2.0 Hz, 1H), 8.09-7.98 (m, 2H), 7.27 (d, J = 1.8 Hz, 1H), 7.10 (dd, J = 5.8, 2.0 Hz, 1H), 6.82 (d, J = 3.9 Hz, 1H), 6.15 (s, 2H), 3.67-3.34 (m, 4H), 1.68-1.50 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-321 | 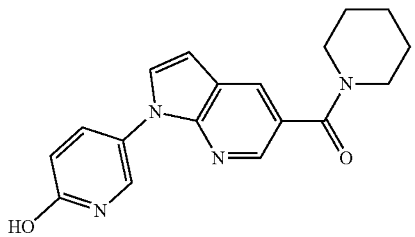 [SMILES: O=C(c1cnc2c(ccn2-c2ccc(O)nc2)c1)N1CCCCC1] | 11.5%/ 93.50% | 322.14 for C18H18N4O2/ 323.1 (M + 1) | δ 11.97-11.85 (m, 1H), 8.30 (d, J = 1.9 Hz, 1H), 8.09 (d, J = 1.9 Hz, 1H), 7.85 (br d, J = 3.6 Hz, 3H), 6.73 (d, J = 3.5 Hz, 1H), 6.53-6.49 (m, 1H), 3.71-3.36 (m, 4H), 1.67-1.44 (m, 6H). |
| MF-DH-322 | 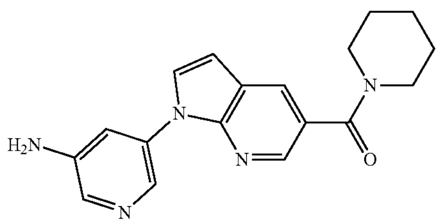 [SMILES: Nc1cncc(-n2ccc3cc(C(=O)N4CCCCC4)cnc32)c1] | 21.4%/ 99.58% | 321.16 for C18H19N5O/ 322.2 (M + 1) | δ 8.33 (d, J = 2.0 Hz, 1H), 8.21-8.07 (m, 2H), 8.01-7.90 (m, 2H), 7.50 (t, J = 2.3 Hz, 1H), 6.79 (d, J = 3.6 Hz, 2H), 5.63 (s, 2H), 3.66-3.34 (m, 4H), 1.68-1.47 (m, 6H). |
| MF-DH-323 | 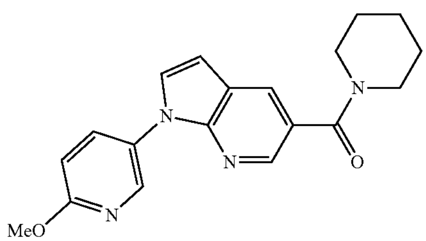 [SMILES: COc1ccc(-n2ccc3cc(C(=O)N4CCCCC4)cnc32)cn1] | 69.0%/ 99.53% | 336.16 for C19H20N4O2/ 337.2 (M + 1) | δ 8.60 (d, J = 2.4 Hz, 1H), 8.32 (d, J = 2.0 Hz, 1H), 8.20 (dd, J = 8.9, 2.8 Hz, 1H), 8.13 (d, J = 2.0 Hz, 1H), 7.99 (d, J = 3.6 Hz, 1H), 7.03 (d, J = 8.9 Hz, 1H), 6.80 (d, J = 3.6 Hz, 1H), 3.93 (s, 3H), 3.71-3.35 (m, 4H), 1.67-1.49 (m, 6H). |
| MF-DH-336 | 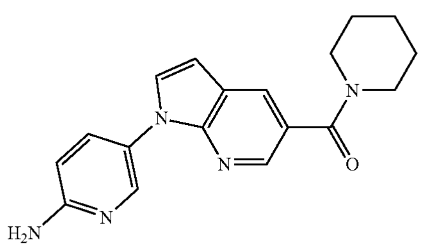 [SMILES: Nc1ccc(-n2ccc3cc(C(=O)N4CCCCC4)cnc32)cn1] | 35.5%/ 98.03% | 321.16 for C18H19N5O/ 322.2 (M + 1) | δ 8.36-8.17 (m, 2H), 8.08 (br s, 1H), 7.87-7.79 (m, 1H), 7.79-7.69 (m, 1H), 6.78-6.67 (m, 1H), 6.59 (br d, J = 8.7 Hz, 1H), 6.15 (br s, 2H), 3.75-3.35 (m, 4H), 1.71-1.40 (m, 6H). |
| MF-DH-299 | 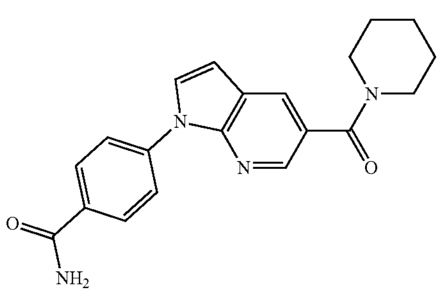 [SMILES: NC(=O)c1ccc(-n2ccc3cc(C(=O)N4CCCCC4)cnc32)cc1] | 42.2%/ 99.76% | 348.16 for C20H20N4O2/ 349.2 (M + 1) | δ 8.37 (d, J = 2.0 Hz, 1H), 8.18-8.10 (m, 2H), 8.06 (s, 5H), 7.42 (br s, 1H), 6.84 (d, J = 3.8 Hz, 1H), 3.70-3.33 (m, 4H), 1.68-1.47 (m, 6H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-301 | 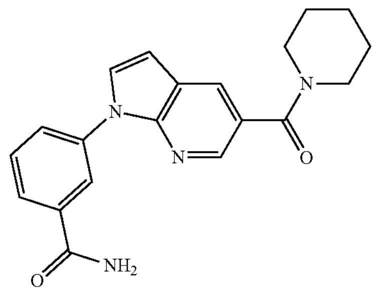 [SMILES: NC(=O)c1cccc(-n2ccc3cc(C(=O)N4CCCCC4)cnc32)c1] | 47.4%/ 99.94% | 348.16 for C20H20N4O2/ 349.1 (M + 1) | δ 8.39-8.28 (m, 2H), 8.18-8.03 (m, 4H), 7.87 (d, J = 7.8 Hz, 1H), 7.65 (t, J = 7.9 Hz, 1H), 7.50 (br s, 1H), 6.83 (d, J = 3.8 Hz, 1H), 3.68-3.34 (m, 4H), 1.67-1.48 (m, 6H). |
| MF-DH-303 | 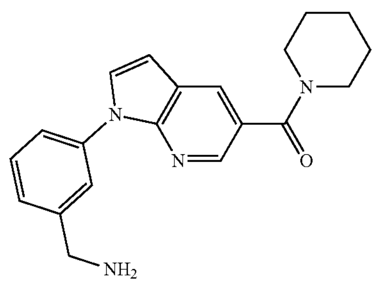 [SMILES: NCc1cccc(-n2ccc3cc(C(=O)N4CCCCC4)cnc32)c1] | 8.4%/ 98.61% | 334.18 for C20H22N4O/ 335.2 (M + 1) | δ 8.33 (s, 1H), 8.13-8.11 (m, 1H), 8.00-7.98 (m, 1H), 7.79 (s, 1H), 7.73 (br d, J = 7.5 Hz, 1H), 7.50-7.46 (m, 1H), 7.36-7.32 (m, 1H), 6.80-6.78 (m, 1H), 3.81 (s, 2H), 3.66-3.38 (m, 4H), 1.66-1.52 (m, 6H). |
| MF-DH-304 | 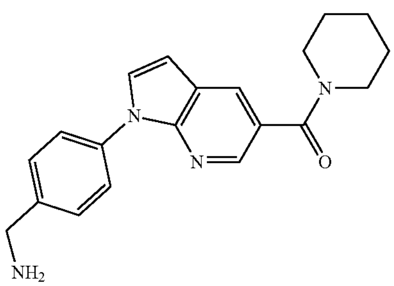 [SMILES: NCc1ccc(-n2ccc3cc(C(=O)N4CCCCC4)cnc32)cc1] | 9.6%/ 95.06% | 334.18 for C20H22N4O/ 335.1 (M + 1) | δ 8.33-8.32 (m, 1H), 8.12-8.11 (m, 1H), 8.01-7.99 (m, 1H), 7.82 (br d, J = 8.7 Hz, 2H), 7.54-7.50 (m, 2H), 6.79-6.77 (m, 1H), 3.83-3.82 (m, 2H), 3.61-3.42 (m, 4H), 1.65-1.53 (m, 6H). |
| MF-DH-307 | 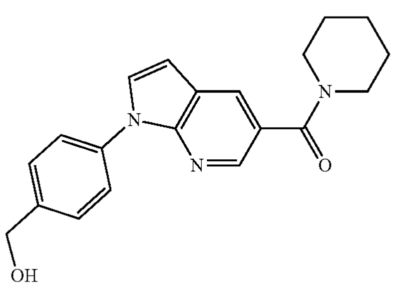 [SMILES: O=C(c1cnc2c(ccn2-c2ccc(CO)cc2)c1)N1CCCCC1] | 36.6%/ 99.38% | 335.16 for C20H21N3O2/ 336.2 (M + 1) | δ 8.33 (d, J = 2.0 Hz, 1H), 8.12 (d, J = 2.0 Hz, 1H), 8.01 (d, J = 3.8 Hz, 1H), 7.83 (d, J = 8.5 Hz, 2H), 7.49 (d, J = 8.5 Hz, 2H), 6.78 (d, J = 3.6 Hz, 1H), 5.27 (t, J = 5.7 Hz, 1H), 4.57 (d, J = 5.8 Hz, 2H), 3.68-3.33 (m, 4H), 1.67-1.48 (m, 6H). |
| MF-DH-308 | 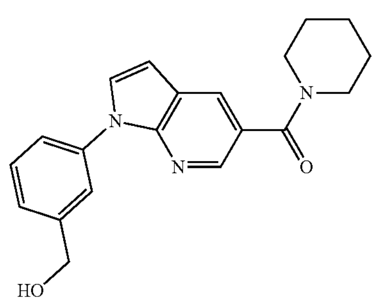 [SMILES: O=C(c1cnc2c(ccn2-c2cccc(CO)c2)c1)N1CCCCC1] | 70.4%/ 97.68% | 335.16 for C20H21N3O2/ 336.2 (M + 1) | δ 8.34 (d, J = 1.8 Hz, 1H), 8.12 (d, J = 1.8 Hz, 1H), 7.99 (d, J = 3.6 Hz, 1H), 7.81 (s, 1H), 7.78-7.68 (m, 1H), 7.51 (t, J = 7.8 Hz, 1H), 7.43-7.22 (m, 1H), 6.79 (d, J = 3.5 Hz, 1H), 5.32 (t, J = 5.8 Hz, 1H), 4.61 (d, J = 5.8 Hz, 2H), 3.75-3.35 (m, 4H), 1.75-1.35 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-191 | 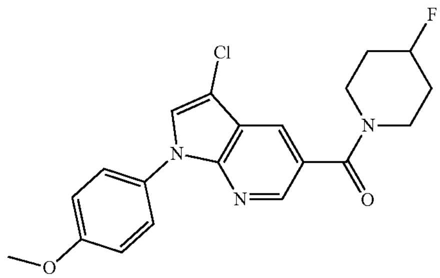 [SMILES: COc1ccc(-n2cc(Cl)c3cc(C(=O)N4CCC(F)CC4)cnc32)cc1] | 67.5%/ 95.24% | 387.11 for C20H19ClFN3O2/ 388.0 (M + 1) | δ 8.43 (d, J = 1.71 Hz, 1H), 8.22 (s, 1H), 8.10 (d, J = 1.83 Hz, 1H), 7.72 (br d, J = 8.93 Hz, 2H), 7.12 (br d, J = 8.93 Hz, 2H), 5.03-4.83 (m, 1H), 3.83 (s, 3H), 3.75-3.38 (m, 4H), 2.02-1.69 (m, 4H). |
| MF-DH-239 | 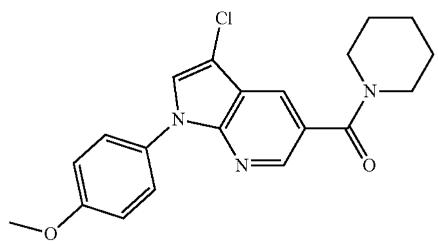 [SMILES: COc1ccc(-n2cc(Cl)c3cc(C(=O)N4CCCCC4)cnc32)cc1] | 11.5%/ 99.59% | 369.12 for C17H22FN3O/ 370.1 (M + 1) | δ 8.41-8.01 (m, 3H), 7.72 (d, J = 8.7 Hz, 2H), 7.12 (d, J = 8.7 Hz, 2H), 3.83 (s, 3H), 3.71-3.33 (m, 4H), 1.68-1.46 (m, 6H). |
| MF-DH-250 | 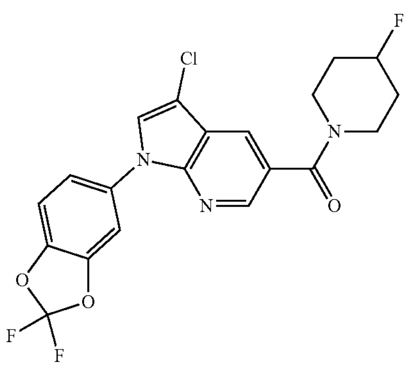 [SMILES: O=C(c1cnc2c(c1)c(Cl)cn2-c1ccc2c(c1)OC(F)(F)O2)N1CCC(F)CC1] | 27.0%/ 98.63% | 437.08 for C20H15ClF3N3O3/ 438.0 (M + 1) | δ 8.47 (d, J = 1.8 Hz, 1H), 8.31 (s, 1H), 8.14 (d, J = 2.0 Hz, 1H), 8.00 (d, J = 2.1 Hz, 1H), 7.74-7.70 (m, 1H), 7.64-7.61 (m, 1H), 5.02-4.84 (m, 1H), 3.88-3.39 (m, 4H), 2.02-1.69 (m, 4H). |
| MF-DH-251 | 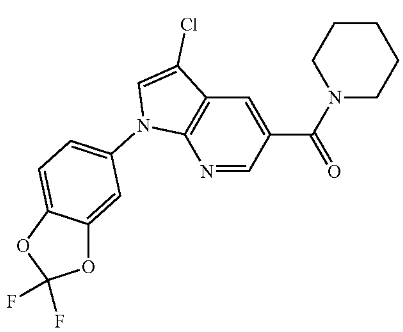 [SMILES: O=C(c1cnc2c(c1)c(Cl)cn2-c1ccc2c(c1)OC(F)(F)O2)N1CCCCC1] | 31.6%/ 99.67% | 419.08 for C20H16ClF2N3O3/ 420.1 (M + 1) | δ 8.43 (d, J = 1.8 Hz, 1H), 8.30 (s, 1H), 8.07 (d, J = 1.8 Hz, 1H), 8.00 (d, J = 2.2 Hz, 1H), 7.72 (dd, J = 8.7, 2.1 Hz, 1H), 7.62 (d, J = 8.7 Hz, 1H), 3.69-3.33 (m, 4H), 1.68-1.46 (m, 6H). |
| MF-DH-273 | 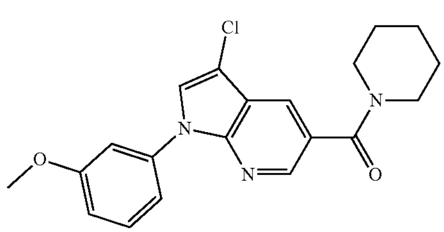 [SMILES: COc1cccc(-n2cc(Cl)c3cc(C(=O)N4CCCCC4)cnc32)c1] | 42.8%/ 99.80% | 369.12 for C20H20ClN3O2/ 370.1 (M + 1) | δ 8.43 (s, 1H), 8.34 (s, 1H), 8.08-8.03 (m, 1H), 7.52-7.43 (m, 3H), 7.02-6.95 (m, 1H), 3.84 (s, 3H), 3.68-3.33 (m, 4H), 1.68-1.45 (m, 6H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-274 | 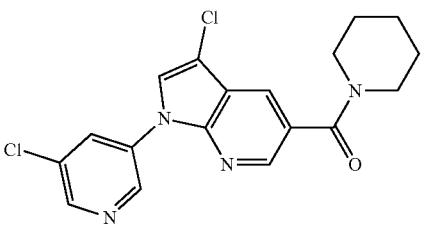 [SMILES: O=C(c1cnc2c(c1)c(Cl)cn2-c1cncc(Cl)c1)N1CCCCC1] | 57.2%/ 99.89% | 374.07 for C18H16Cl2N4O/ 375.0 (M + 1) | δ 9.18 (d, J = 2.1 Hz, 1H), 8.68-8.61 (m, 2H), 8.49 (s, 2H), 8.11 (d, J = 1.7 Hz, 1H), 3.71-3.33 (m, 4H), 1.68-1.48 (m, 6H). |
| MF-DH-275 | 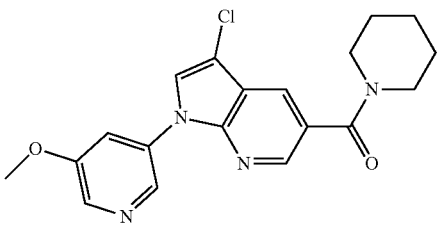 [SMILES: COc1cncc(-n2cc(Cl)c3cc(C(=O)N4CCCCC4)cnc32)c1] | 43.3%/ 99.42% | 370.12 for C19H19ClN4O2/ 371.1 (M + 1) | δ 8.80-8.79 (m, 1H), 8.47-8.43 (m, 2H), 8.35-8.33 (m, 1H), 8.10-8.08 (m, 1H), 7.97-7.95 (m, 1H), 3.93 (s, 3H), 3.68-3.57 (m, 1H), 3.33-3.33 (s, 3H), 1.67-1.51 (m, 6H). |
| MF-DH-146 | 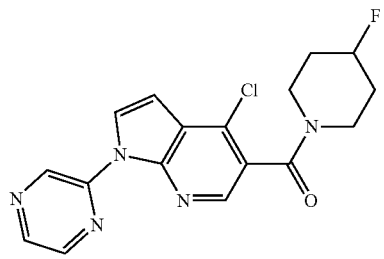 [SMILES: O=C(c1cnc2c(ccn2-c2cnccn2)c1Cl)N1CCC(F)CC1] | 11.23%/ 99.67% | 359.09 for C17H15ClFN5O/ 360.3 (M + 1) | δ 10.00 (s, 1H), 8.66 (s, 2H), 8.50-8.44 (m, 2H), 6.98 (d, J = 3.8 Hz, 1H), 5.04-4.84 (m, 1H), 3.86-3.69 (m, 2H), 3.45-3.36 (m, 1H), 3.27-3.19 (m, 1H), 2.06-1.81 (m, 3H), 1.76-1.63 (m, 1H). |
| MF-DH-147 | 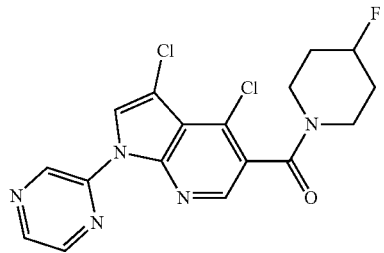 | 7.5%/ 94.04% | 393.06 for C17H14Cl2FN5O/ 394.0 (M + 1) | 67 9.90 (s, 1H), 8.68 (s, 2H), 8.61 (s, 1H), 8.50 (d, J = 1.6 Hz, 1H), 5.04-4.86 (m, 1H), 3.87-3.73 (m, 2H), 3.43-3.36 (m, 1H), 3.24-3.18 (m, 1H), 2.04-1.84 (m, 3H), 1.75-1.66 (m, 1H). |
| MF-DH-148 | 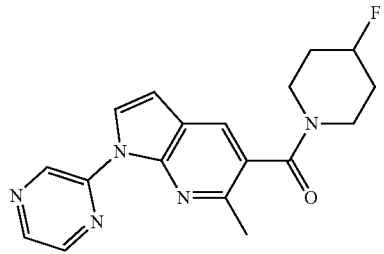 [SMILES: Cc1nc2c(ccn2-c2cnccn2)cc1C(=O)N1CCC(F)CC1] | 22.4%/ 99.72% | 339.15 for C18H18FN5O/ 340.1 (M + 1) | δ 10.18 (s, 1H), 8.62-8.59 (m, 2H), 8.31 (d, J = 3.8 Hz, 1H), 8.02 (s, 1H), 6.84 (d, J = 3.8 Hz, 1H), 5.02-4.84 (m, 1H), 3.90-3.65 (m, 2H), 3.41-3.34 (m, 1H), 3.21-3.14 (m, 1H), 2.57-2.56 (m, 3H), 2.05-1.76 (m, 4H). |
| MF-DH-149 | 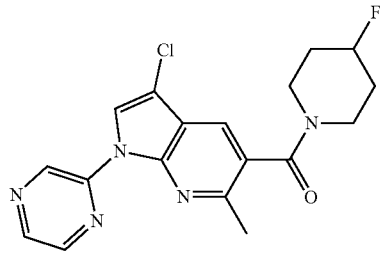 [SMILES: Cc1nc2c(cc1C(=O)N1CCC(F)CC1)c(Cl)cn2-c1cnccn1] | 11.2%/ 99.40% | 373.11 for C18H17ClFN5O/ 374.0 (M + 1) | δ 10.10 (s, 1H), 8.63 (s, 2H), 8.47-8.45 (m, 1H), 8.05-8.03 (m, 1H), 5.02-4.84 (m, 1H), 3.89-3.66 (m, 2H), 3.37-3.34 (m, 1H), 3.21-3.15 (m, 1H), 2.59 (s, 3H), 2.02-1.68 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-PGDH-020 | 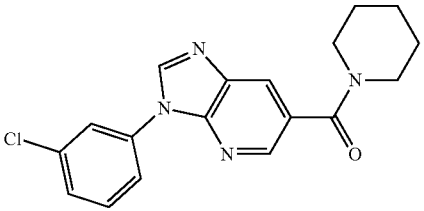 [SMILES: O=C(c1cnc2c(c1)ncn2-c1cccc(Cl)c1)N1CCCCC1] | 13.7%/ 99.94% | 340.11 for C18H17ClN4O/ 341.0 (M + 1) | δ 9.11 (s, 1H), 8.51 (d, 1H), 8.30 (d, 1H), 8.20-8.22 (m, 1H), 8.01-8.03 (m, 1H), 7.70-7.72 (m, 1H), 7.57-7.59 (m, 1H), 3.54-3.67 (m, 2H), 3.34-3.42 (m, 2H), 1.48-1.68 (m, 6H). |
| MF-PGDH-077 | 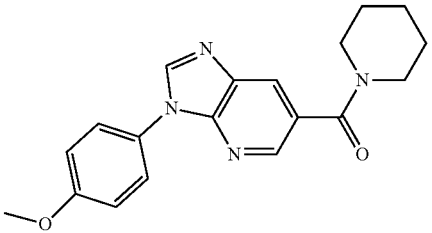 [SMILES: COc1ccc(-n2cnc3cc(C(=O)N4CCCCC4)cnc32)cc1] | 14.8%/ 99.66% | 336.16 for C19H20N4O2/ 337.2 (M + 1) | δ 8.89 (s, 1H), 8.43 (d, J = 1.83 Hz, 1H), 8.20 (d, J = 1.96 Hz, 1H), 7.78-7.82 (m, 2H), 7.15-7.19 (m, 2H), 3.84 (s, 3H), 3.54-3.68 (m, 2H), 3.34-3.45 (m, 2H), 1.49-1.67 (m, 6H). |
| MF-PGDH-078 | 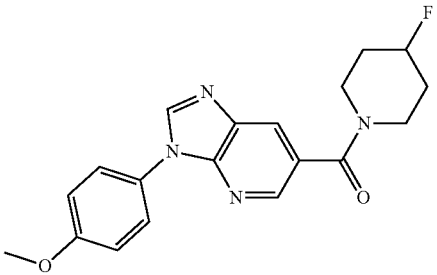 | 15%/ 99.73% | 354.15 for C19H19FN4O2/ 355.2 (M + 1) | δ 8.90 (s, 1H), 8.47-8.48 (d, J = 1.83 Hz, 1H), 8.25-8.26 (d, J = 1.96 Hz, 1H), 7.79-7.81 (m, 2H), 7.13-7.15 (m, 2H), 4.82-5.01 (m, 1H), 3.84-3.85 (s, 3H), 3.52-3.80 (m, 4H), 1.83-2.01 (m, 2H), 1.71-1.82 (m, 2H). |
| MF-PGDH-079 | 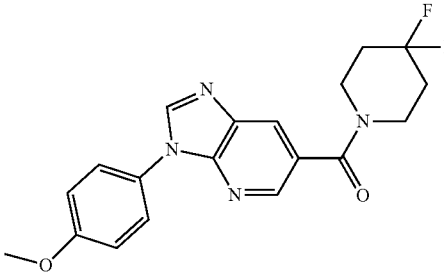 | 5.5%/ 98.59% | 372.14 for C19H18F2N4O2/ 373.2 (M + 1) | δ 8.90 (s, 1H), 8.50-8.51 (d, J = 1.83 Hz, 1H), 8.30-8.31 (d, J = 1.96 Hz, 1H), 7.79-7.81 (m, 2H), 7.16-7.18 (m, 2H), 3.84-3.85 (s, 3H), 3.55-3.70 (m, 4H), 2.03-2.12 (m, 4H). |
| MF-DH-201 | 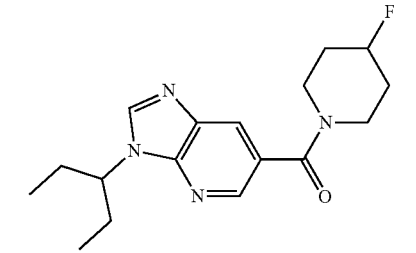 [SMILES: CCC(CC)n1cnc2cc(C(=O)N3CCC(F)CC3)cnc21] | 18%/ 99.77% | 318.19 for C17H23FN4O/ 319.3 (M + 1) | δ 8.65-8.63 (m, 1H), 8.41 (d, J = 1.8 Hz, 1H), 8.14 (d, J = 1.8 Hz, 1H), 5.02-4.83 (m, 1H), 4.51-4.42 (m, 1H), 3.76-3.45 (m, 4H), 2.11-1.92 (m, 6H), 1.83-1.71 (m, 2H), 0.73-0.68 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-214 | 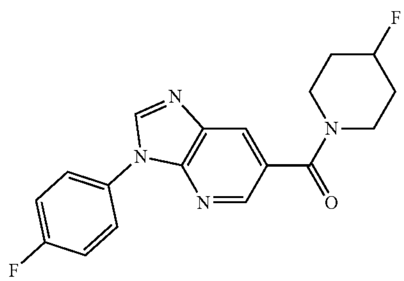 [SMILES: O=C(c1cnc2c(c1)ncn2-c1ccc(F)cc1)N1CCC(F)CC1] | 18.7%/ 97.08% | 342.13 for C18H16F2N4O/ 343.1 (M + 1) | δ 8.97-8.96 (m, 1H), 8.50-8.48 (m, 1H), 8.29-8.27 (m, 1H), 8.01-7.96 (m, 2H), 7.51-7.46 (m, 2H), 5.03-4.84 (m, 1H), 3.76-3.48 (m, 4H), 2.02-1.76 (m, 4H). |
| MF-DH-215 | 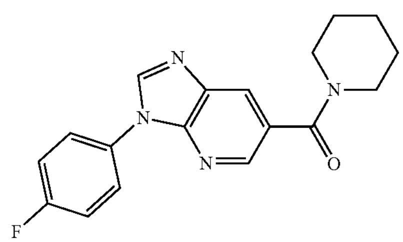 [SMILES: O=C(c1cnc2c(c1)ncn2-c1ccc(F)cc1)N1CCCCC1] | 19%/ 98.20% | 324.14 for C18H17FN4O/ 325.1 (M + 1) | δ 8.97-8.95 (m, 1H), 8.46-8.44 (m, 1H), 8.24-8.21 (m, 1H), 8.01-7.95 (m, 2H), 7.51-7.46 (m, 2H), 3.69-3.38 (m, 4H), 1.67-1.50 (m, 6H). |
| MF-DH-216 | 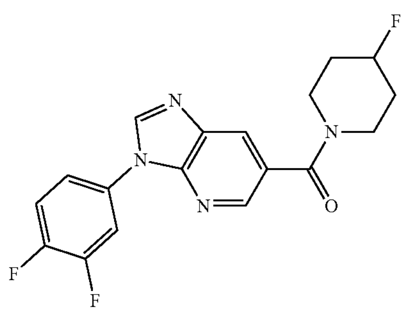 [SMILES: O=C(c1cnc2c(c1)ncn2-c1ccc(F)c(F)c1)N1CCC(F)CC1] | 19.15%/ 99.63% | 360.12 for C18H15F3N4O/ 361.2 (M + 1) | δ 9.03-9.00 (m, 1H), 8.52 (d, J = 1.7 Hz, 1H), 8.30-8.28 (m, 1H), 8.22-8.16 (m, 1H), 7.92-7.87 (m, 1H), 7.77-7.69 (m, 1H), 5.02-4.84 (m, 1H), 3.76-3.43 (m, 4H), 2.02-1.76 (m, 4H). |
| MF-DH-217 | 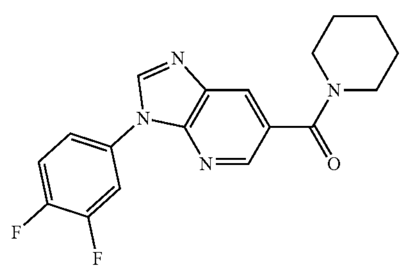 [SMILES: O=C(c1cnc2c(c1)ncn2-c1ccc(F)c(F)c1)N1CCCCC1] | 20.74%/ 98.35% | 342.13 for C18H16F2N4O/ 343.1 (M + 1) | δ 9.02-9.00 (m, 1H), 8.48 (d, J = 1.7 Hz, 1H), 8.24 (d, J = 1.8 Hz, 2H), 7.93-7.87 (m, 1H), 7.78-7.69 (m, 1H), 3.72-3.52 (m, 2H), 3.49-3.33 (m, 2H), 1.67-1.52 (m, 6H). |
| MF-DH-218 | 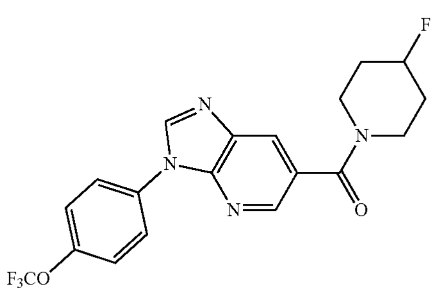 [SMILES: O=C(c1cnc2c(c1)ncn2-c1ccc(OC(F)(F)F)cc1)N1CCC(F)CC1] | 12%/ 87.77% | 408.12 for C19H16F4N4O2/ 409.2 (M + 1) | δ 9.04-9.02 (m, 1H), 8.52-8.50 (m, 1H), 8.31-8.29 (m, 1H), 8.13-8.10 (m, 2H), 7.68-7.64 (m, 2H), 5.04-4.84 (m, 1H), 3.80-3.54 (m, 4H), 2.00-1.76 (m, 4H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-219 | 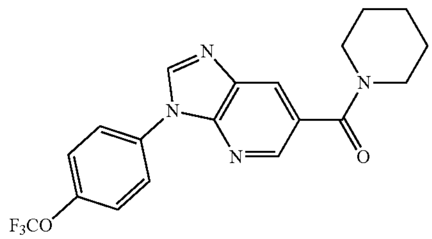 [SMILES: O=C(c1cnc2c(c1)ncn2-c1ccc(OC(F)(F)F)cc1)N1CCCCC1] | 18%/ 97.93% | 390.13 for C19H17F3N4O2/ 391.1 (M + 1) | δ 9.04-9.00 (m, 1H), 8.48-8.45 (m, 1H), 8.24 (d, J = 1.7 Hz, 1H), 8.11 (br d, J = 8.9 Hz, 2H), 7.65 (brd, J = 8.3 Hz, 2H), 3.75-3.40 (m, 4H), 1.67-1.51 (m, 6H). |
| MF-DH-222 | 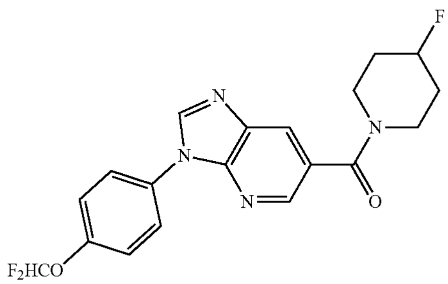 [SMILES: O=C(c1cnc2c(c1)ncn2-c1ccc(OC(F)F)cc1)N1CCC(F)CC1] | 14.2%/ 99.99% | 390.13 for C19H17F3N4O2/ 391.1 (M + 1) | δ 8.99-8.98 (m, 1H), 8.50 (d, J = 1.8 Hz, 1H), 8.28 (d, J = 1.8 Hz, 1H), 8.02-7.98 (m, 2H), 7.54-7.34 (m, 3H), 5.03-4.84 (m, 1H), 3.79-3.47 (m, 4H), 2.04-1.76 (m, 4H). |
| MF-DH-223 | 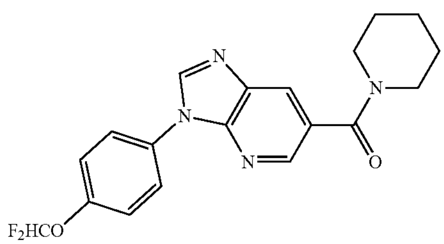 [SMILES: O=C(c1cnc2c(c1)ncn2-c1ccc(OC(F)F)cc1)N1CCCCC1] | 16.6%/ 99.68% | 372.14 for C19H17F3N4O2/ 373.1 (M + 1) | δ 8.99-8.95 (m, 1H), 8.47-8.44 (m, 1H), 8.22 (d, J = 1.7 Hz, 1H), 8.02-7.99 (m, 1H), 7.54-7.32 (m, 3H), 3.74-3.33 (m, 4H), 1.67-1.49 (m, 6H). |
| MF-DH-224 | 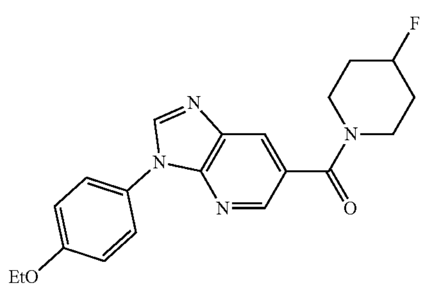 [SMILES: CCOc1ccc(-n2cnc3cc(C(=O)N4CCC(F)CC4)cnc32)cc1] | 28.5%/ 99.38% | 366.13 for C20H16F2N4O/ 367.2 (M + 1) | δ 8.91-8.87 (m, 1H), 8.50-8.44 (m, 1H), 8.25 (d, J = 1.7 Hz, 1H), 7.79 (br d, J = 8.8 Hz, 2H), 7.15 (br d, J = 8.9 Hz, 2H), 5.03-4.84 (m, 1H), 4.16-4.08 (m, 2H), 3.80-3.40 (m, 4H), 2.03-1.89 (m, 2H), 1.83-1.70 (m, 2H), 1.37 (br t, J = 6.9 Hz, 3H). |
| MF-DH-225 | 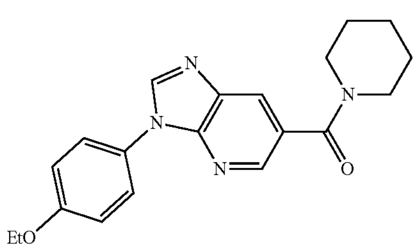 [SMILES: CCOc1ccc(-n2cnc3cc(C(=O)N4CCCCC4)cnc32)cc1] | 24.2%/ 97.80% | 350.17 for C20H22N4O2/ 351.2 (M + 1) | δ 8.90-8.85 (m, 1H), 8.43 (d, J = 1.7 Hz, 1H), 8.19 (d, J = 1.7 Hz, 1H), 7.79 (d, J = 8.9 Hz, 2H), 7.15 (d, J = 8.9 Hz, 2H), 4.12 (q, J = 6.9 Hz, 2H), 3.70-3.54 (m, 2H), 3.49-3.34 (m, 2H), 1.67-1.49 (m, 6H), 1.37 (t, J = 7.0 Hz, 3H). |

TABLE 3-continued

Analytical data for select inhibitors

| Target No | Structure | Yield/ Purity | Mass Spec. Calculated/ Mass Spec. Found (m/z) | ¹H NMR (DMSO-d₆*, 400 MHz) (*unless otherwise indicated) |
|---|---|---|---|---|
| MF-DH-226 | 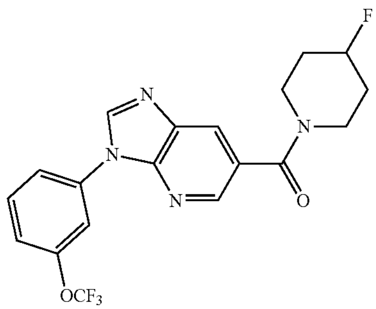 | 15.07%/ 97.09% | 408.12 for C19H16F4N4O2/ 409.1 (M + 1) | δ 9.10-9.07 (m, 1H), 8.55-8.52 (m, 1H), 8.32-8.29 (m, 1H), 8.15-8.12 (m, 1H), 8.09 (br d, J = 7.7 Hz, 1H), 7.80-7.74 (m, 1H), 7.53-7.48 (m, 1H), 5.03-4.84 (m, 1H), 3.81-3.40 (m, 4H), 2.03-1.73 (m, 4H). |
| MF-DH-227 | 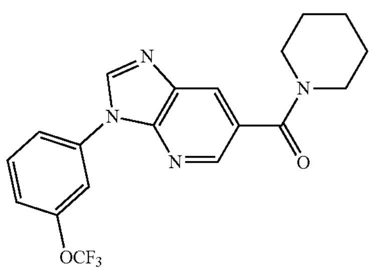 | 11.61%/ 98.05% | 390.13 for C19H17F3N4O2/ 391.1 (M + 1) | δ 9.09-9.07 (m, 1H), 8.50-8.48 (m, 1H), 8.26-8.23 (m, 1H), 8.15-8.12 (m, 1H), 8.10-8.06 (m, 1H), 7.80-7.74 (m, 1H), 7.53-7.47 (m, 1H), 3.78-3.50 (m, 4H), 1.69-1.53 (m, 6H). |
| MF-DH-228 | 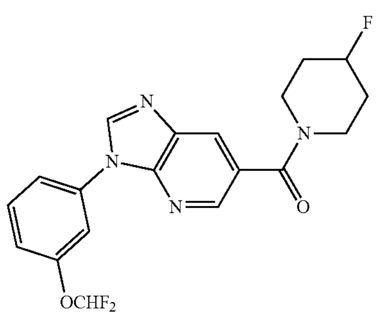 [SMILES: O=C(c1cnc2c(c1)ncn2-c1cccc(OC(F)(F)F)c1)N1CCC(F)CC1] | 29.1%/ 98.28% | 390.13 for C19H17F3N4O2/ 391.1 (M + 1) | δ 9.07-9.04 (m, 1H), 8.53-8.51 (m, 1H), 8.30-8.28 (m, 1H), 7.93-7.88 (m, 2H), 7.71-7.65 (m, 1H), 7.56-7.18 (m, 2H), 5.03-4.84 (m, 1H), 3.80-3.39 (m, 4H), 2.03-1.72 (m, 4H). |
| MF-DH-229 | 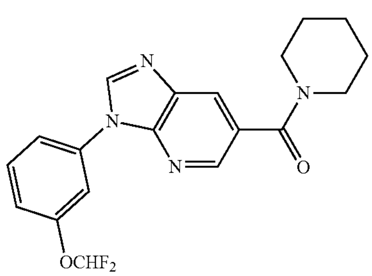 [SMILES: O=C(c1cnc2c(c1)ncn2-c1cccc(OC(F)F)c1)N1CCCCC1] | 5.3%/ 95.11% | 372.14 for C19H18F2N4O2/ 373.1 (M + 1) | δ 9.06-9.03 (m, 1H), 8.48 (d, J = 1.7 Hz, 1H), 8.23 (d, J = 1.7 Hz, 1H), 7.93-7.87 (m, 2H), 7.68 (s, 1H), 7.57-7.17 (m, 2H), 3.70-3.35 (m, 4H), 1.67-1.51 (m, 6H). |
| MF-DH-236 | 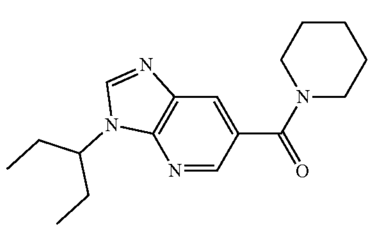 [SMILES: CCC(CC)n1cnc2cc(C(=O)N3CCCCC3)cnc21] | 47.3%/ 99.81% | 300.20 for C17H24N4O/ 301.2 (M + 1) | δ 8.65-8.62 (m, 1H), 8.37 (d, J = 1.8 Hz, 1H), 8.08 (d, J = 1.7 Hz, 1H), 4.52-4.42 (m, 1H), 3.72-3.35 (m, 4H), 2.13-1.91 (m, 4H), 1.66-1.49 (m, 6H), 0.73-0.67 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-238 | 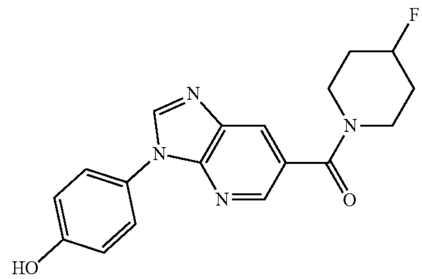 | 15%/ 99.77% | 340.13 for C18H17FN4O2/ 341.2 (M + 1) | δ 9.83-9.81 (m, 1H), 8.82 (s, 1H), 8.46 (d, J = 1.7 Hz, 1H), 8.24 (d, J = 1.7 Hz, 1H), 7.64 (d, J = 8.8 Hz, 2H), 6.97 (d, J = 8.8 Hz, 2H), 5.03-4.84 (m, 1H), 3.80-3.40 (m, 4H), 2.01-1.75 (m, 4H). |
| MF-DH-442 | 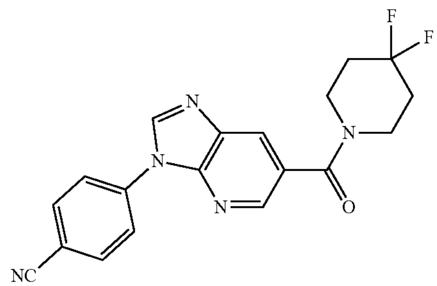 | 28.77%/ 97.51% | 367.12 for C19H15F2N5O/ 368.2 (M + 1) | δ 9.17 (s, 1H), 8.58 (d, J = 1.7 Hz, 1H), 8.38-8.36 (m, 1H), 8.36-8.28 (m, J = 8.8 Hz, 2H), 8.13 (d, J = 8.7 Hz, 2H), 3.84-3.44 (m, 4H), 2.16-2.01 (m, 4H). |
| MF-DH-443 | 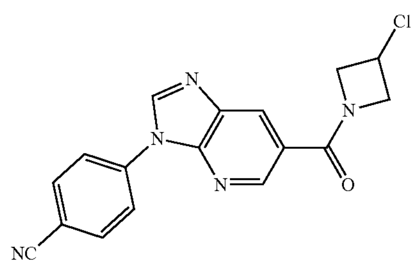 [SMILES: N#Cc1ccc(-n2cnc3cc(C(=O)N4CC(Cl)C4)cnc32)cc1] | 31.25%/ 98.35% | 337.07 for C17H12ClN5O/ 338.1 (M + 1) | δ 9.18 (s, 1H), 8.75 (d, J = 1.8 Hz, 1H), 8.46 (d, J = 1.8 Hz, 1H), 8.31 (d, J = 8.8 Hz, 2H), 8.13 (d, J = 8.7 Hz, 2H), 4.89 (br s, 2H), 4.73-4.51 (m, 2H), 4.16 (br s, 1H). |
| MF-DH-464 | 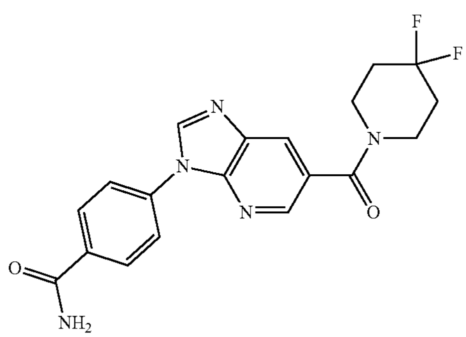 [SMILES: NC(=O)c1ccc(-n2cnc3cc(C(=O)N4CCC(F)(F)CC4)cnc32)cc1] | 67.3%/ 99.47% | 385.14 for C19H17F2N5O2/ 386.2 (M + 1) | δ 9.10 (s, 1H), 8.56 (d, J = 1.8 Hz, 1H), 8.35 (d, J = 1.8 Hz, 1H), 8.11 (s, 5H), 7.49 (br s, 1H), 3.86-3.42 (m, 4H), 2.17-2.00 (m, 4H). |
| MF-DH-176 | 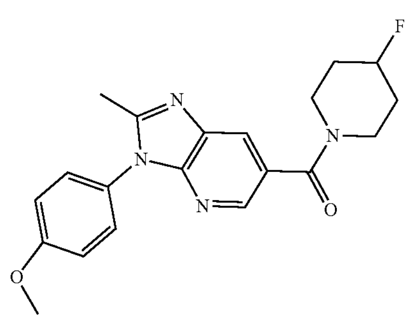 [SMILES: COc1ccc(-n2c(C)nc3cc(C(=O)N4CCC(F)CC4)cnc32)cc1] | 9.37%/ 99.23% | 368.16 for C20H21FN4O2/ 369.1 (M + 1) | δ 8.29-8.26 (m, 1H), 8.08-8.06 (m, 1H), 7.50-7.45 (m, 2H), 7.17-7.13 (m, 2H), 5.00-4.85 (m, 1H), 3.87-3.84 (m, 3H), 3.80-3.36 (m, 4H), 2.46 (s, 3H), 2.01-1.71 (m, 4H). |

TABLE 3-continued

Analytical data for select inhibitors

| Target No | Structure | Yield/ Purity | Mass Spec. Calculated/ Mass Spec. Found (m/z) | ¹H NMR (DMSO-$d_6$*, 400 MHz) (*unless otherwise indicated) |
|---|---|---|---|---|
| MF-DH-205 | 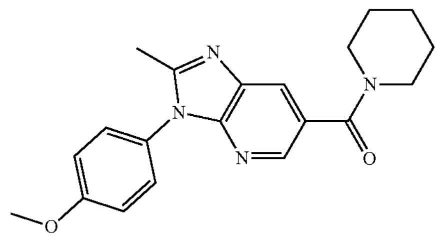 [SMILES: COc1ccc(-n2c(C)nc3cc(C(=O)N4CCCCC4)cnc32)cc1] | 20.79%/ 99.72% | 350.17 for C20H22N4O2/ 351.1 (M + 1) | δ 8.25-8.22 (m, 1H), 8.01 (s, 1H), 7.48 (br d, J = 8.7 Hz, 2H), 7.15 (br d, J = 8.8 Hz, 2H), 3.86 (s, 3H), 3.69-3.51 (m, 2H), 3.43-3.34 (m, 2H), 2.46 (br s, 3H), 1.67-1.49 (m, 6H). |
| MF-DH-117 | 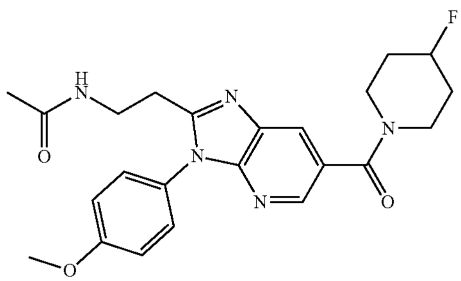 [SMILES: COc1ccc(-n2c(CCNC(C)=O)nc3cc(C(=O)N4CCC(F)CC4)cnc32)cc1] | 28.6%/ 97.00% | 439.20 for C23H26FN5O3/ 440.1 (M + 1) | δ 8.30-8.27 (m, 1H), 8.12 (d, J = 1.7 Hz, 1H), 7.96-7.91 (m, 1H), 7.46 (br d, J = 8.8 Hz, 2H), 7.15 (br d, J = 8.9 Hz, 2H), 5.03-4.84 (m, 1H), 3.89-3.84 (m, 3H), 3.76-3.44 (m, 6H), 2.89 (br t, J = 7.0 Hz, 2H), 2.02-1.85 (m, 2H), 1.80-1.70 (m, 5H). |
| MF-DH-130 | 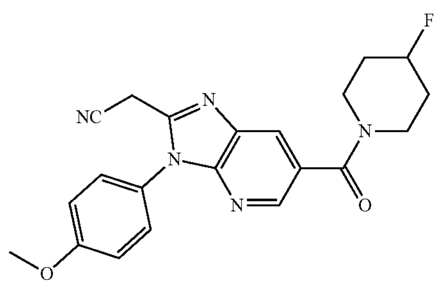 [SMILES: COc1ccc(-n2c(CC#N)nc3cc(C(=O)N4CCC(F)CC4)cnc32)cc1] | 40%/ 98.58% | 393.16 for C20H22N4O2/ 391.8 (M − 1) | δ 8.37-8.35 (m, 1H), 8.24 (d, J = 1.8 Hz, 1H), 7.51 (d, J = 8.9 Hz, 2H), 7.18-7.15 (m, 2H), 5.02-4.84 (m, 1H), 4.41 (s, 2H), 3.87-3.85 (m, 3H), 3.78-3.51 (m, 4H), 1.99-1.76 (m, 4H). |
| MF-DH-184 | 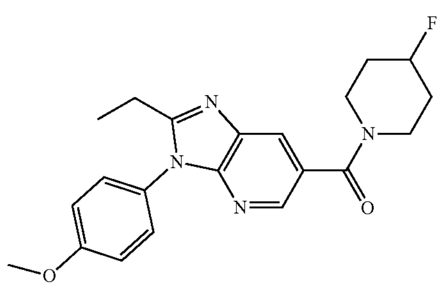 [SMILES: CCc1nc2cc(C(=O)N3CCC(F)CC3)cnc2n1-c1ccc(OC)cc1] | 27%/ 97.46% | 382.18 for C21H23N3O2/ 383.1 (M + 1) | δ 8.29-8.26 (m, 1H), 8.10 (d, J = 1.7 Hz, 1H), 7.47 (d, J = 8.8 Hz, 2H), 7.15 (d, J = 8.8 Hz, 2H), 5.02-4.83 (m, 1H), 3.86 (s, 3H), 3.74-3.47 (m, 4H), 2.81-2.74 (m, 2H), 2.01-1.75 (m, 4H), 1.28-1.25 (m, 3H). |
| MF-DH-185 | 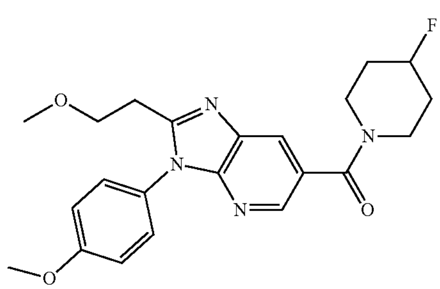 [SMILES: COCCc1nc2cc(C(=O)N3CCC(F)CC3)cnc2n1-c1ccc(OC)cc1] | 1.96%/ 91.31% | 412.19 for C22H25FN4O3/ 413.1 (M + 1) | δ 8.32-8.29 (m, 1H), 8.13-8.10 (m, 1H), 7.49-7.44 (m, 2H), 7.18-7.14 (m, 2H), 5.03-4.84 (m, 1H), 3.87-3.85 (m, 3H), 3.73-3.71 (m, 4H), 3.21-3.18 (m, 3H), 3.04-2.99 (m, 2H), 2.01-1.72 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-195 | 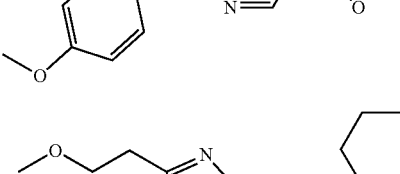 | 26%/ 99.27% | 450.17 for C22H22F4N4O2/ 451.1 (M + 1) | δ 8.34-8.30 (m, 1H), 8.15 (s, 1H), 7.50 (br d, J = 8.6 Hz, 2H), 7.17 (br d, J = 8.7 Hz, 2H), 5.02-4.83 (m, 1H), 3.88-3.85 (m, 3H), 3.74-3.47 (m, 4H), 3.06-3.00 (m, 2H), 2.93-2.79 (m, 2H), 2.02-1.76 (m, 4H). |
| MF-DH-267 | 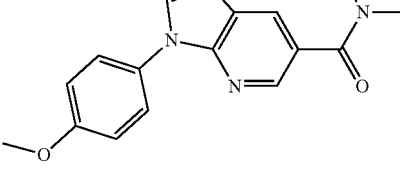 | 10%/ 93.70% | 394.20 for C22H26N4O3/ 395.2 (M + 1) | δ 8.26-8.23 (m, 1H), 8.05 (d, J = 1.7 Hz, 1H), 7.46 (d, J = 8.8 Hz, 2H), 7.16 (d, J = 8.8 Hz, 2H), 3.86 (s, 3H), 3.76-3.71 (m, 2H), 3.66-3.44 (m, 3H), 3.19 (s, 3H), 3.04-2.98 (m, 2H), 1.66-1.46 (m, 7H). |
| MF-DH-268 | 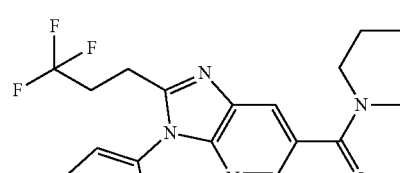 | 22%/ 98.27% | 432.18 for C22H23F3N4O2/ 433.1 (M + 1) | δ 8.28 (s, 1H), 8.09 (s, 1H), 7.56-7.46 (m, 2H), 7.21-7.11 (m, 2H), 3.86 (s, 3H), 3.72-3.59 (m, 2H), 3.46-3.44 (m, 2H), 3.09-2.98 (m, 2H), 2.94-2.88 (m, 2H), 1.66-1.46 (m, 6H). |
| MF-DH-337 | 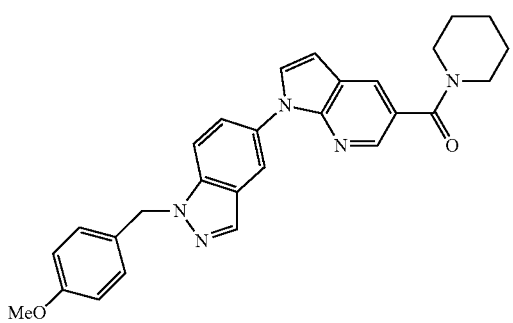 [SMILES: COc1ccc(Cn2ncc3cc(-n4ccc5cc(C(=O)N6CCCCC6)cnc54)ccc32)cc1] | 32.7%/ 98.99% | 465.22 for C28H27N5O2/ 466.1 (M + 1) | δ 8.31 (d, J = 1.9 Hz, 1H), 8.21-8.19 (m, 1H), 8.19-8.09 (m, 2H), 8.00 (d, J = 3.5 Hz, 1H), 7.87 (d, J = 9.0 Hz, 1H), 7.83-7.74 (m, 1H), 7.27-7.22 (m, 2H), 6.91-6.86 (m, 2H), 6.80-6.77 (m, 1H), 5.65 (s, 2H), 3.70 (s, 3H), 3.64-3.34 (m, 4H), 1.68-1.45 (m, 6H). |
| MF-DH-340 | 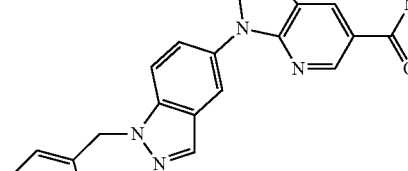 | 34.2%/ 99.35% | 465.22 for C28H27N5O2/ 466.2 (M + 1) | δ 8.55 (s, 1H), 8.32 (s, 1H), 8.10 (br d, J = 14.5 Hz, 2H), 8.06-7.93 (m, 1H), 7.76 (br d, J = 9.2 Hz, 1H), 7.72-7.63 (m, 1H), 7.33 (br d, J = 8.4 Hz, 2H), 6.93 (br d, J = 8.4 Hz, 2H), 6.88-6.73 (m, 1H), 5.61 (s, 2H), 3.73 (s, 3H), 3.66-3.37 (m, 4H), 1.69-1.47 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-351 | 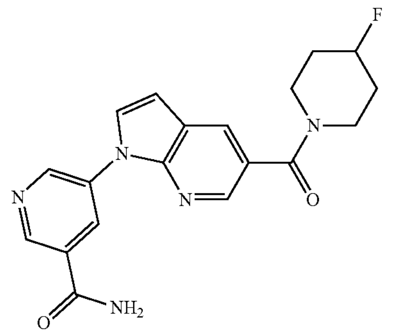 [SMILES: NC(=O)c1cncc(-n2ccc3cc(C(=O)N4CCC(F)CC4)cnc32)c1] | 21.4%/ 99.26% | 367.14 for C19H18FN5O2/ 368.2 (M + 1) | δ 9.33-9.31 (m, 1H), 9.01 (d, J = 1.6 Hz, 1H), 8.76-8.73 (m, 1H), 8.43 (d, J = 2.0 Hz, 1H), 8.28 (br s, 1H), 8.23-8.19 (m, 2H), 7.76 (br s, 1H), 6.91-6.88 (m, 1H), 5.03-4.84 (m, 1H), 3.76-3.56 (m, 4H), 1.99-1.75 (m, 4H). |
| MF-DH-355 | 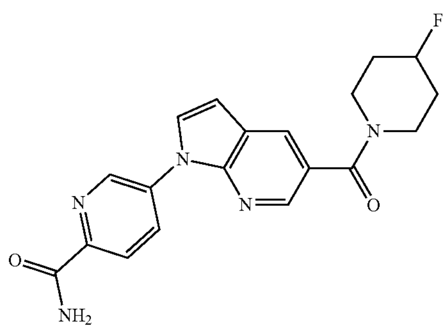 [SMILES: NC(=O)c1ccc(-n2ccc3cc(C(=O)N4CCC(F)CC4)cnc32)cn1] | 38.7%/ 90.57% | 367.14 for C19H18FN5O2/ 368.2 (M + 1) | δ 9.27 (d, J = 2.4 Hz, 1H), 8.64-8.59 (m, 1H), 8.44 (d, J = 2.0 Hz, 1H), 8.32-8.20 (m, 3H), 8.20-8.05 (m, 1H), 7.70 (br s, 1H), 6.91 (d, J = 3.8 Hz, 1H), 5.03-4.84 (m, 1H), 3.79-3.46 (m, 4H), 2.03-1.74 (m, 4H). |
| MF-DH-361 | 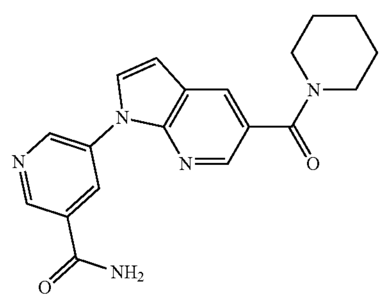 [SMILES: NC(=O)c1cncc(-n2ccc3cc(C(=O)N4CCCCC4)cnc32)c1] | 53.1%/ 99.56% | 349.15 for C19H19N5O2/ 350.2 (M + 1) | δ 9.32 (d, J = 2.4 Hz, 1H), 9.00 (d, J = 1.7 Hz, 1H), 8.74 (t, J = 2.2 Hz, 1H), 8.39 (d, J = 2.0 Hz, 1H), 8.27 (br s, 1H), 8.22-8.15 (m, 2H), 7.78-7.73 (m, 1H), 6.89 (d, J = 3.8 Hz, 1H), 3.71-3.37 (m, 4H), 1.68-1.50 (m, 6H). |
| MF-DH-362 | 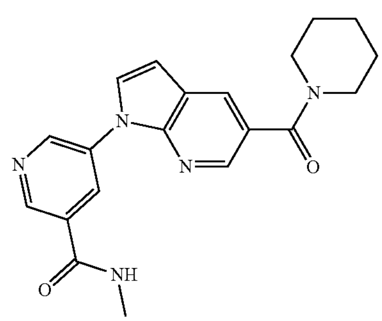 [SMILES: CNC(=O)c1cncc(-n2ccc3cc(C(=O)N4CCCCC4)cnc32)c1] | 46.6%/ 95.07% | 363.17 for C20H21N5O2/ 364.2 (M + 1) | δ 9.32-9.29 (m, 1H), 8.96 (d, J = 1.9 Hz, 1H), 8.75 (br d, J = 4.6 Hz, 1H), 8.72 (t, J = 2.2 Hz, 1H), 8.40-8.38 (m, 1H), 8.20-8.15 (m, 2H), 6.90-6.87 (m, 1H), 3.70-3.44 (m, 4H), 2.87-2.83 (m, 3H), 1.67-1.61 (m, 2H), 1.60-1.48 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-363 | 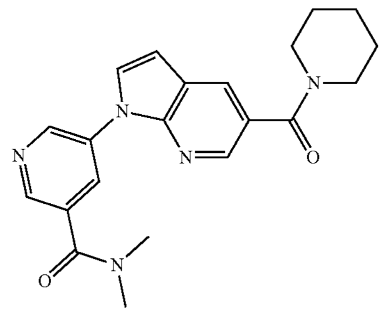 [SMILES: CN(C)C(=O)c1cncc(-n2ccc3cc(C(=O)N4CCCCC4)cnc32)c1] | 34.2%/ 98.79% | 377.19 for C21H23N5O2/ 378.2 (M + 1) | δ 9.33-9.18 (m, 1H), 8.60 (s, 1H), 8.48 (br s, 1H), 8.43-8.34 (m, 1H), 8.26-8.12 (m, 2H), 6.87 (br d, J = 3.4 Hz, 1H), 3.76-3.37 (m, 4H), 3.09-2.97 (m, 6H), 1.67-1.44 (m, 6H). |
| MF-DH-364 | 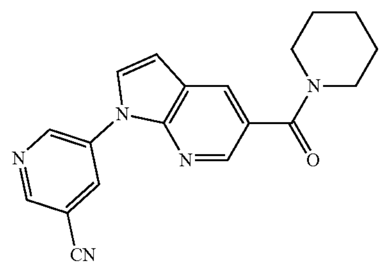 [SMILES: N#Cc1cncc(-n2ccc3cc(C(=O)N4CCCCC4)cnc32)c1] | 32.7%/ 97.33% | 331.14 for C19H17N5O/ 332.2 (M + 1) | δ 9.58-9.55 (m, 1H), 9.01-8.95 (m, 2H), 8.43-8.39 (m, 1H), 8.25-8.14 (m, 2H), 6.93-6.89 (m, 1H), 3.68-3.34 (m, 4H), 1.68-1.50 (m, 6H). |
| MF-DH-365 | 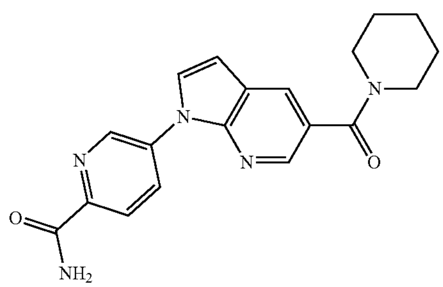 | 51.5%/ 96.50% | 349.15 for C19H19N5O2/ 350.2 (M + 1) | δ 9.27 (br s, 1H), 8.62 (br d, J = 7.1 Hz, 1H), 8.40 (br s, 1H), 8.29-8.10 (m, 4H), 7.69 (br s, 1H), 6.90 (br d, J = 3.1 Hz, 1H), 3.73-3.40 (m, 4H), 1.68-1.50 (m, 6H). |
| MF-DH-366 | 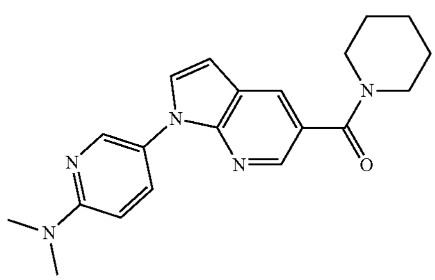 [SMILES: CN(C)c1ccc(-n2ccc3cc(C(=O)N4CCCCC4)cnc32)cn1] | 44.7%/ 99.68% | 349.19 for C20H23N5O/ 350.2 (M + 1) | δ 8.43 (d, J = 2.4 Hz, 1H), 8.29 (d, J = 2.0 Hz, 1H), 8.10 (d, J = 2.0 Hz, 1H), 7.92-7.86 (m, 2H), 6.82-6.73 (m, 2H), 3.69-3.34 (m, 4H), 3.09 (s, 6H), 1.67-1.49 (m, 6H). |
| MF-DH-376 | 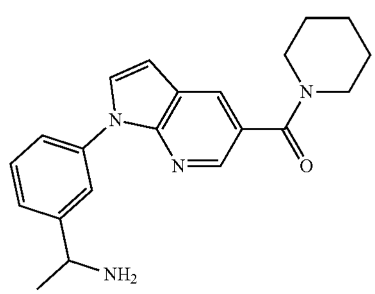 [SMILES: CC(N)c1cccc(-n2ccc3cc(C(=O)N4CCCCC4)cnc32)c1] | 12.5%/ 99.64% | 348.20 for C21H24N4O/ 349.2 (M + 1) | δ 8.34-8.32 (m, 1H), 8.12 (d, J = 2.0 Hz, 1H), 8.00 (d, J = 3.7 Hz, 1H), 7.82-7.72 (m, 2H), 7.48 (t, J = 7.8 Hz, 1H), 7.39 (d, J = 7.7 Hz, 1H), 6.79 (d, J = 3.7 Hz, 1H), 4.13-4.06 (m, 1H), 3.79-3.33 (m, 6H), 1.68-1.51 (m, 6H), 1.36-1.30 (m, 3H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-380 | 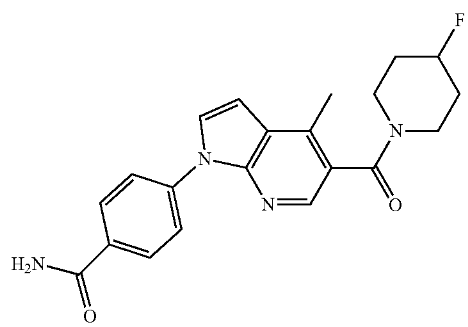 [SMILES: Cc1c(C(=O)N2CCC(F)CC2)cnc2c1ccn2-c1ccc(C(N)=O)cc1] | 38.2%/ 99.26% | 380.16 for C21H21FN4O2/ 381.2 (M + 1) | δ 8.19 (s, 1H), 8.13-7.99 (m, 6H), 7.41 (br s, 1H), 6.94-6.91 (m, 1H), 5.01-4.82 (m, 1H), 3.88-3.65 (m, 2H), 3.41-3.33 (m, 1H), 3.22-3.13 (m, 1H), 2.52 (br s, 3H), 2.06-1.57 (m, 4H). |
| MF-DH-382 | 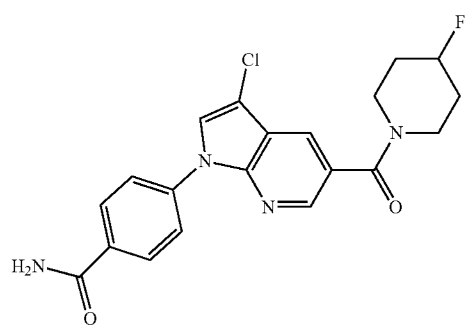 [SMILES: NC(=O)c1ccc(-n2cc(Cl)c3cc(C(=O)N4CCC(F)CC4)cnc32)cc1] | 70.1%/ 99.58% | 400.11 for C20H18ClFN4O2/ 401.2 (M + 1) | δ 8.51-8.42 (m, 2H), 8.13 (s, 1H), 8.10-8.01 (m, 5H), 7.42 (s, 1H), 5.01-4.80 (m, 1H), 3.81-3.40 (m, 4H), 2.03-1.72 (m, 4H). |
| MF-DH-383 | 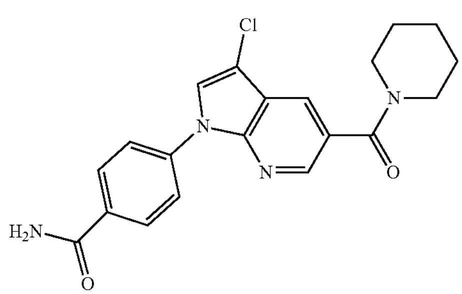 [SMILES: NC(=O)c1ccc(-n2cc(Cl)c3cc(C(=O)N4CCCCC4)cnc32)cc1] | 39.5%/ 97.76% | 382.12 for C20H19ClN4O2/ 383.1 (M + 1) | δ 8.47-8.45 (m, 1H), 8.43-8.41 (m, 1H), 8.09-8.03 (m, 6H), 7.46-7.42 (m, 1H), 3.72-3.40 (m, 4H), 1.67-1.52 (m, 6H). |
| MF-DH-385 | 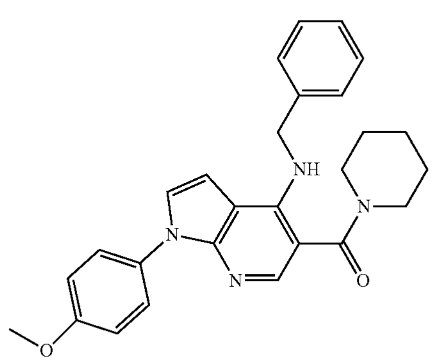 [SMILES: COc1ccc(-n2ccc3c(NCc4ccccc4)c(C(=O)N4CCCCC4)cnc32)cc1] | 50.6%/ 99.68% | 440.22 for C27H28N4O2/ 441.3 (M + 1) | δ 7.77 (br s, 1H), 7.65 (d, J = 8.9 Hz, 2H), 7.45 (d, J = 3.8 Hz, 1H), 7.37-7.30 (m, 4H), 7.30-7.17 (m, 1H), 7.11-7.00 (m, 3H), 6.72 (d, J = 3.7 Hz, 1H), 4.76 (d, J = 6.5 Hz, 2H), 3.80 (s, 3H), 3.38 (br s, 4H), 1.60-1.42 (m, 6H). |

TABLE 3-continued

Analytical data for select inhibitors

| Target No | Structure | Yield/Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-387 | 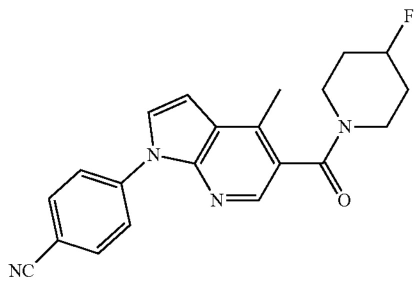 [SMILES: Cc1c(C(=O)N2CCC(F)CC2)cnc2c1ccn2-c1ccc(C#N)cc1] | 38.4%/ 99.79% | 362.15 for C21H19FN4O/ 363.2 (M + 1) | δ 8.29 (d, J = 8.8 Hz, 2H), 8.23-8.15 (m, 2H), 8.03 (d, J = 8.7 Hz, 2H), 6.98 (d, J = 3.9 Hz, 1H), 5.02-4.82 (m, 1H), 3.88-3.64 (m, 2H), 3.40-3.33 (m, 1H), 3.22-3.12 (m, 1H), 2.56-2.51 (m, 3H), 2.06-1.58 (m, 4H). |
| MF-DH-388 | 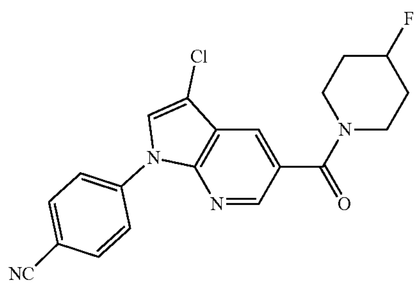 [SMILES: N#Cc1ccc(-n2cc(Cl)c3cc(C(=O)N4CCC(F)CC4)cnc32)cc1] | 16.66%/ 99.83% | 382.10 for C20H16ClFN4O/ 383.2 (M + 1) | δ 8.50-8.46 (m, 2H), 8.24-8.20 (m, 2H), 8.14-8.12 (m, 1H), 8.05-8.01 (m, 2H), 4.99-4.80 (m, 1H), 3.89-3.43 (m, 4H), 1.99-1.65 (m, 4H). |
| MF-DH-392 | 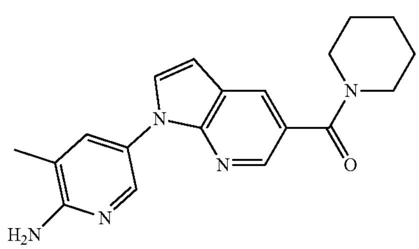 [SMILES: Cc1cc(-n2ccc3cc(C(=O)N4CCCCC4)cnc32)cnc1N] | 6.84%/ 95.06% | 335.17 for C19H21N5O/ 336.2 (M + 1) | δ 8.30-8.27 (m, 1H), 8.08 (d, J = 1.9 Hz, 2H), 7.82 (d, J = 3.5 Hz, 1H), 7.64 (d, J = 1.9 Hz, 1H), 6.73-6.71 (m, 1H), 5.94 (s, 2H), 3.60-3.43 (m, 4H), 2.13 (s, 3H), 1.65-1.52 (m, 6H). |
| MF-DH-393 | 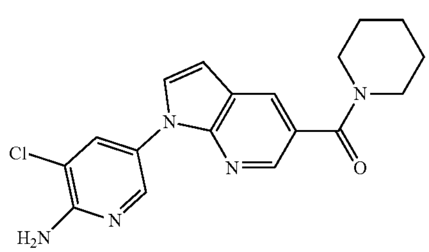 [SMILES: Nc1ncc(-n2ccc3cc(C(=O)N4CCCCC4)cnc32)cc1Cl] | 16.5%/ 98.32% | 355.12 for C18H18ClN5O/ 356.2 (M + 1) | δ 8.33-8.30 (m, 2H), 8.10 (d, J = 2.1 Hz, 2H), 7.93-7.91 (m, 1H), 6.76-6.74 (m, 1H), 6.52 (s, 2H), 3.55-3.39 (m, 4H), 1.67-1.53 (m, 6H). |
| MF-DH-395 (Cis-relative) | 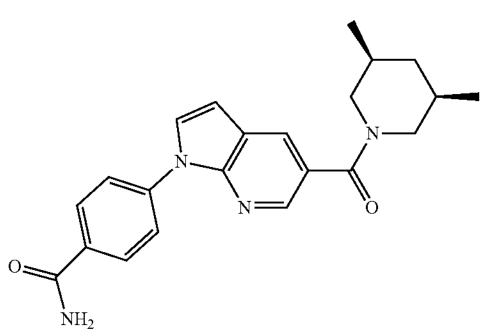 [SMILES: C[C@@H]1C[C@H](C)CN(C(=O)c2cnc3c(ccn3-c3ccc(C(N)=O)cc3)c2)C1] | 13.7%/ 99.97% | 376.19 for C22H24N4O2/ 377.2 (M + 1) | δ 8.33 (d, J = 1.9 Hz, 1H), 8.14-8.10 (m, 2H), 8.10-8.02 (m, 5H), 7.44-7.38 (m, 1H), 6.82 (d, J = 3.8 Hz, 1H), 4.48-4.27 (m, 2H), 1.92-1.78 (m, 1H), 1.72-1.61 (m, 2H), 1.59-1.44 (m, 3H), 1.29-1.17 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-396 | 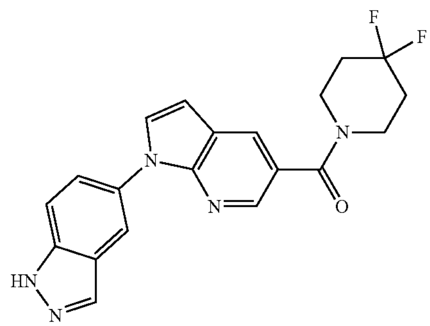 [SMILES: O=C(c1cnc2c(ccn2-c2ccc3[nH]ncc3c2)c1)N1CCC(F)(F)CC1] | 68.1%/ 99.29% | 381.14 for C20H17F2N5O/ 382.2 (M + 1) | δ 13.26 (br s, 1H), 8.41-8.40 (m, 1H), 8.22 (d, J = 2.1 Hz, 1H), 8.20-8.18 (m, 1H), 8.16-8.14 (m, 1H), 8.04-8.02 (m, 1H), 7.80-7.77 (m, 1H), 7.73-7.70 (m, 1H), 6.80 (d, J = 3.6 Hz, 1H), 3.72-3.59 (m, 4H), 2.12-2.04 (m, 4H). |
| MF-DH-397 | 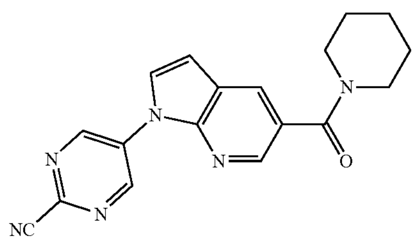 [SMILES: N#Cc1ncc(-n2ccc3cc(C(=O)N4CCCCC4)cnc32)cn1] | 68.9%/ 99.77% | 332.14 for C18H16N6O/ 333.2 (M + 1) | δ 9.82 (s, 2H), 8.45 (d, J = 1.9 Hz, 1H), 8.36 (d, J = 3.9 Hz, 1H), 8.21 (d, J = 1.9 Hz, 1H), 7.00 (d, J = 3.9 Hz, 1H), 3.74-3.33 (m, 4H), 1.68-1.46 (m, 6H). |
| MF-DH-399 | 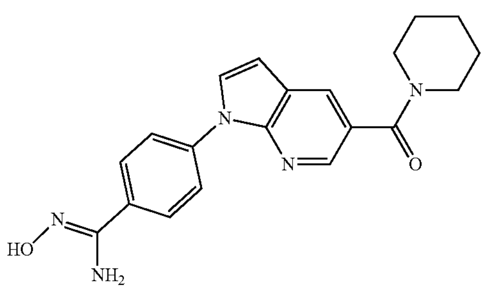 [SMILES: N/C(=N\O)c1ccc(-n2ccc3cc(C(=O)N4CCCCC4)cnc32)cc1] | 36.05%/ 95.01% | 363.17 for C20H21N5O2/ 364.2 (M + 1) | δ 9.70 (s, 1H), 8.36 (d, J = 1.8 Hz, 1H), 8.13 (d, J = 1.8 Hz, 1H), 8.12-8.04 (m, 1H), 7.99-7.90 (m, J = 8.7 Hz, 2H), 7.89-7.82 (m, 2H), 6.81 (d, J = 3.7 Hz, 1H), 5.89 (s, 2H), 3.68-3.37 (m, 4H), 1.68-1.50 (m, 6H). |
| MF-DH-400 | 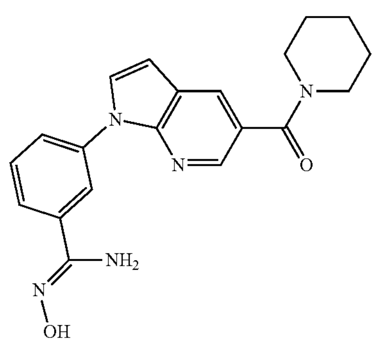 [SMILES: N/C(=N\O)c1cccc(-n2ccc3cc(C(=O)N4CCCCC4)cnc32)c1] | 19.2%/ 92.70% | 363.17 for C20H21N5O2/ 364.2 (M + 1) | δ 9.75 (s, 1H), 8.34 (d, J = 2.0 Hz, 1H), 8.14-8.06 (m, 3H), 7.96-7.84 (m, 1H), 7.68 (d, J = 8.0 Hz, 1H), 7.60-7.52 (m, 1H), 6.81 (d, J = 3.8 Hz, 1H), 5.93 (s, 2H), 3.75-3.40 (m, 4H), 1.69-1.51 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-402 | 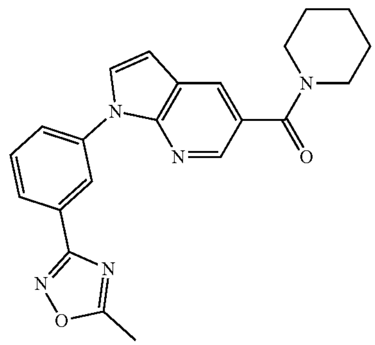 [SMILES: Cc1nc(-c2cccc(-n3ccc4cc(C(=O)N5CCCCC5)cnc43)c2)no1] | 31.2%/ 99.68% | 387.17 for C22H21N5O2/ 388.3 (M + 1) | δ 8.22-8.18 (m, 1H), 8.00-7.99 (m, 1H), 7.85-7.79 (m, 2H), 7.48-7.43 (m, 1H), 7.26-7.23 (m, 1H), 7.11-7.04 (m, 2H), 3.90 (s, 3H), 3.87-3.62 (m, 2H), 3.37 (br s, 2H), 1.71 (br s, 6H). |
| MF-DH-403 | 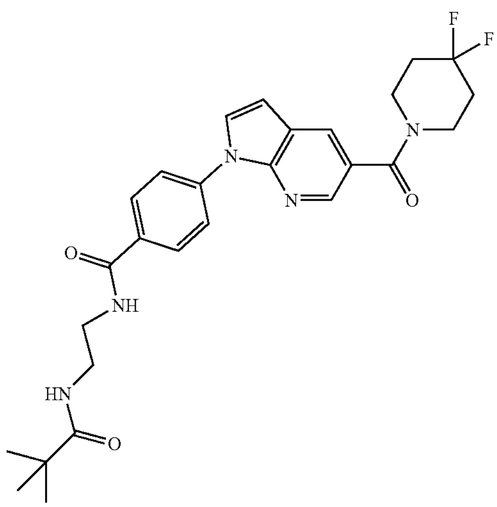 [SMILES: CC(C)(C)C(=O)NCCNC(=O)c1ccc(-n2ccc3cc(C(=O)N4CCC(F)(F)CC4)cnc32)cc1] | 45.4%/ 98.95% | 511.24 for C27H31F2N5O3/ 512.3 (M + 1) | δ 8.62-8.55 (m, 1H), 8.55-8.44 (m, 1H), 8.23 (d, J = 2.0 Hz, 1H), 8.16 (d, J = 3.6 Hz, 1H), 8.11-7.98 (m, 4H), 7.62 (s, 1H), 6.85 (d, J = 3.8 Hz, 1H), 3.79-3.51 (m, 4H), 3.40-3.36 (m, 2H), 3.29-3.23 (m, 2H), 2.14-2.02 (m, 4H), 1.09 (s, 9H). |
| MF-DH-404 | 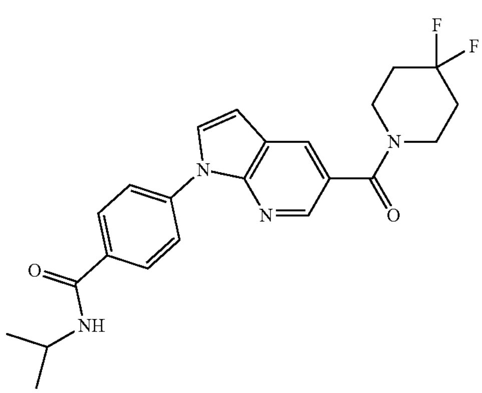 [SMILES: CC(C)NC(=O)c1ccc(-n2ccc3cc(C(=O)N4CCC(F)(F)CC4)cnc32)cc1] | 18.1%/ 99.02% | 426.19 for C23H24F2N4O2/ 427.2 (M + 1) | δ 8.45 (d, J = 2.0 Hz, 1H), 8.30-8.27 (m, 1H), 8.24-8.22 (m, 1H), 8.22-8.11 (m, 1H), 8.10-7.99 (m, 4H), 6.85 (d, J = 3.8 Hz, 1H), 4.18-4.08 (m, 1H), 3.76-3.50 (m, 4H), 2.15-2.01 (m, 4H), 1.21-1.18 (m, 6H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-405 | 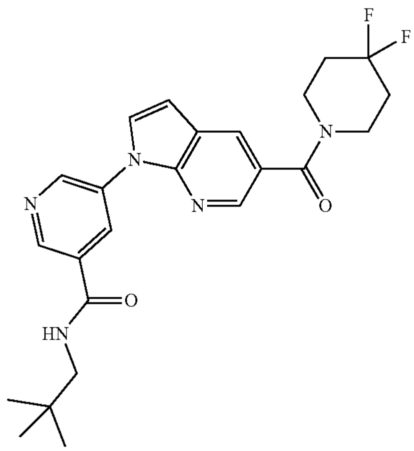 [SMILES: CC(C)(C)CNC(=O)c1cncc(-n2ccc3cc(C(=O)N4CCC(F)(F)CC4)cnc32)c1] | 35.32%/ 99.98% | 455.21 for C24H27F2N5O2/ 456.3 (M + 1) | δ 9.32-9.30 (m, 1H), 8.99 (d, J = 1.9 Hz, 1H), 8.72 (t, J = 2.3 Hz, 1H), 8.68-8.60 (m, 1H), 8.47 (d, J = 2.0 Hz, 1H), 8.26 (d, J = 2.0 Hz, 1H), 8.23-8.21 (m, 1H), 6.91-6.89 (m, 1H), 3.75-3.56 (m, 4H), 3.19-3.15 (m, 2H), 2.16-2.02 (m, 4H), 0.94 (s, 9H). |
| MF-DH-406 | 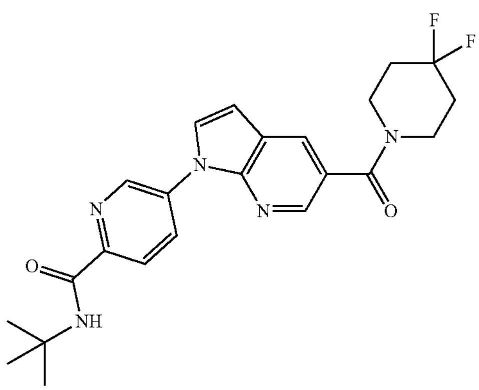 [SMILES: CC(C)(C)NC(=O)c1ccc(-n2ccc3cc(C(=O)N4CCC(F)(F)CC4)cnc32)cn1] | 38.9%/ 93.87% | 441.20 for C23H25F2N5O2/ 442.2 (M + 1) | δ 9.28-9.26 (m, 1H), 8.65-8.61 (m, 1H), 8.48-8.46 (m, 1H), 8.27-8.19 (m, 3H), 8.05 (s, 1H), 6.93-6.91 (m, 1H), 3.81-3.53 (m, 4H), 2.16-2.01 (m, 4H), 1.44 (s, 9H). |
| MF-DH-407 | 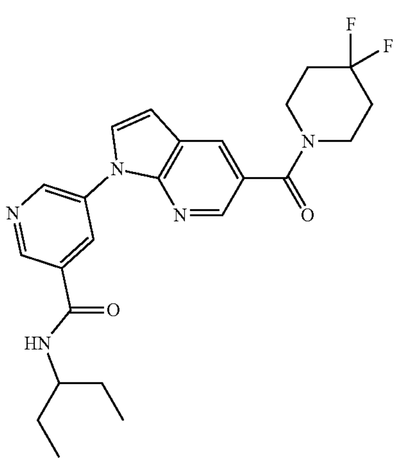 [SMILES: CCC(CC)NC(=O)c1cncc(-n2ccc3cc(C(=O)N4CCC(F)(F)CC4)cnc32)c1] | 29.2%/ 97.29% | 455.21 for C24H27F2N5O2/ 456.3 (M + 1) | δ 9.32-9.29 (m, 1H), 9.00 (d, J = 1.5 Hz, 1H), 8.71 (s, 1H), 8.47 (d, J = 1.8 Hz, 1H), 8.39-8.19 (m, 3H), 6.90 (d, J = 3.7 Hz, 1H), 3.89-3.79 (m, 1H), 3.76-3.52 (m, 4H), 2.17-2.01 (m, 4H), 1.65-1.47 (m, 4H), 0.92-0.87 (m, 6H). |

TABLE 3-continued

Analytical data for select inhibitors

| Target No | Structure | Yield/ Purity | Mass Spec. Calculated/ Mass Spec. Found (m/z) | ¹H NMR (DMSO-$d_6$*, 400 MHz) (*unless otherwise indicated) |
|---|---|---|---|---|
| MF-DH-409 | 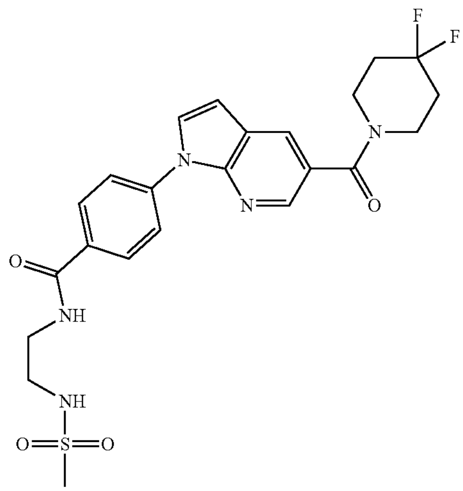 [SMILES: CS(=O)(=O)NCCNC(=O)c1ccc(-n2ccc3cc(C(=O)N4CCC(F)(F)CC4)cnc32)cc1] | 18.3%/ 95.45% | 505.16 for C23H25F2N5O4S/ 506.2 (M + 1) | δ 8.64-8.58 (m, 1H), 8.47-8.44 (m, 1H), 8.23 (d, J = 2.0 Hz, 1H), 8.17-8.14 (m, 1H), 8.12-8.02 (m, 4H), 7.20-7.15 (m, 1H), 6.87-6.84 (m, 1H), 3.78-3.52 (m, 4H), 3.45-3.38 (m, 2H), 3.19-3.12 (m, 2H), 2.92 (s, 3H), 2.14-2.02 (m, 4H). |
| MF-DH-411 | 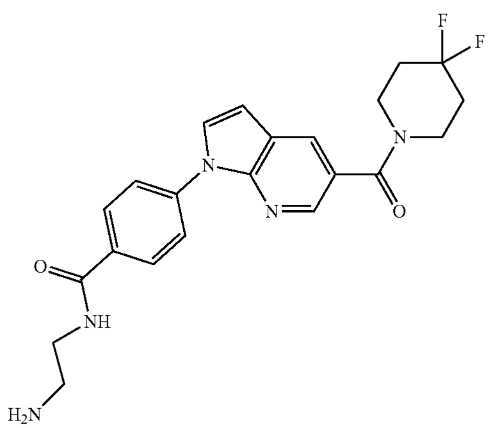 [SMILES: NCCNC(=O)c1ccc(-n2ccc3cc(C(=O)N4CCC(F)(F)CC4)cnc32)cc1] | 49.6%/ 98.58% | 427.18 for C22H23F2N5O2/ 428.2 (M + 1) | ¹H NMR (CD$_3$OD): δ 8.46-8.43 (m, 1H), 8.21 (d, J = 1.9 Hz, 1H), 8.11-7.99 (m, 4H), 7.93 (d, J = 3.8 Hz, 1H), 6.85 (d, J = 3.8 Hz, 1H), 3.93-3.68 (m, 4H), 3.65-3.59 (m, 2H), 3.11-3.04 (m, 2H), 2.17-2.02 (m, 4H). |
| MF-DH-412 | 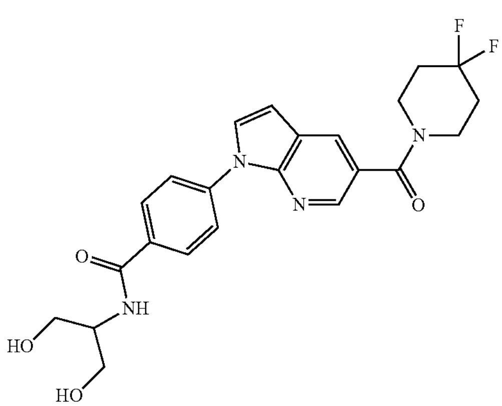 [SMILES: O=C(NC(CO)CO)c1ccc(-n2ccc3cc(C(=O)N4CCC(F)(F)CC4)cnc32)cc1] | 25.3%/ 99.18% | 458.18 for C23H24F2N4O4/ 459.2 (M + 1) | δ 8.46 (d, J = 2.1 Hz, 1H), 8.23 (d, J = 2.0 Hz, 1H), 8.15 (d, J = 3.7 Hz, 1H), 8.10-8.03 (m, 5H), 6.86 (d, J = 3.8 Hz, 1H), 4.68 (t, J = 5.7 Hz, 2H), 4.03-3.96 (m, 1H), 3.83-3.58 (m, 4H), 3.58-3.52 (m, 4H), 2.08 (br s, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-413 | 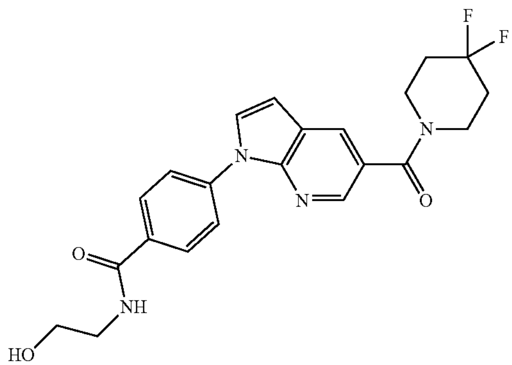 [SMILES: O=C(NCCO)c1ccc(-n2ccc3cc(C(=O)N4CCC(F)(F)CC4)cnc32)cc1] | 18.1%/ 95.26% | 428.17 for C22H22F2N4O3/ 429.2 (M + 1) | δ 8.56-8.50 (m, 1H), 8.47-8.44 (m, 1H), 8.25-8.21 (m, 1H), 8.17-8.13 (m, 1H), 8.10-8.02 (m, 4H), 6.87-6.83 (m, 1H), 4.78-4.73 (m, 1H), 3.71-3.52 (m, 6H), 3.40-3.37 (m, 2H), 2.15-2.03 (m, 4H). |
| MF-DH-417 (Cis-relative) | 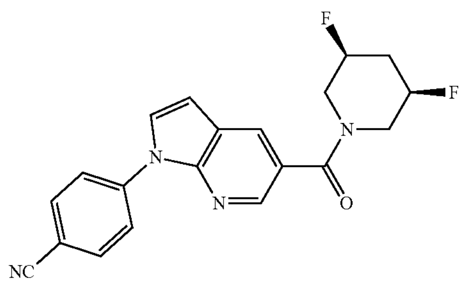 [SMILES: N#Cc1ccc(-n2ccc3cc(C(=O)N4C[C@H](F)C[C@H](F)C4)cnc32)cc1] | 54.34%/ 99.38% | 366.13 for C20H16F2N4O/ 367.2 (M + 1) | δ 8.43-8.38 (m, 1H), 8.30 (br d, J = 8.4 Hz, 2H), 8.25-8.19 (m, 1H), 8.19-8.12 (m, 1H), 8.05 (br d, J = 8.4 Hz, 2H), 6.91 (br d, J = 3.4 Hz, 1H), 5.08-4.63 (m, 3H), 4.13-3.84 (m, 1H), 2.70-2.66 (m, 1H), 2.36-2.22 (m, 2H), 2.18-1.98 (m, 1H). |
| MF-DH-418 | 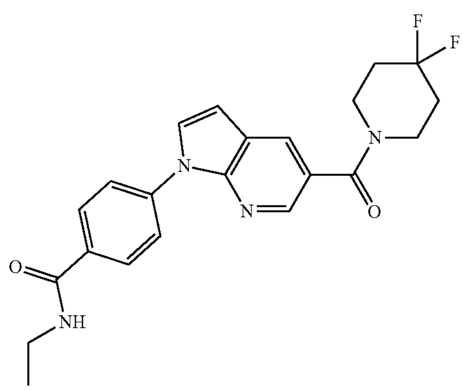 [SMILES: CCNC(=O)c1ccc(-n2ccc3cc(C(=O)N4CCC(F)(F)CC4)cnc32)cc1] | 48.5%/ 97.93% | 412.17 for C22H22F2N4O2/ 413.2 (M + 1) | δ 8.56-8.51 (m, 1H), 8.45 (d, J = 2.0 Hz, 1H), 8.23 (d, J = 2.1 Hz, 1H), 8.14 (d, J = 3.8 Hz, 1H), 8.10-7.99 (m, 4H), 6.85 (d, J = 3.8 Hz, 1H), 3.80-3.52 (m, 4H), 3.36-3.32 (m, 2H), 2.14-2.00 (m, 4H), 1.18-1.13 (m, 3H). |
| MF-DH-419 | 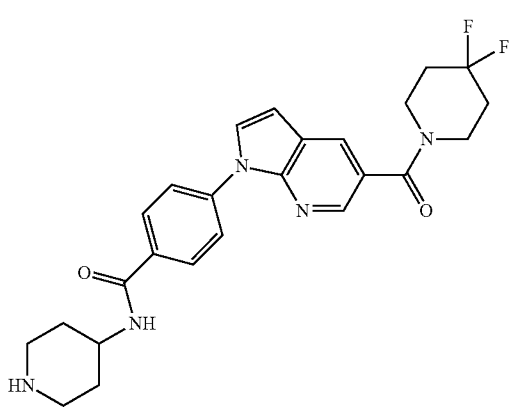 [SMILES: O=C(NC1CCNCC1)c1ccc(-n2ccc3cc(C(=O)N4CCC(F)(F)CC4)cnc32)cc1] | 19.7%/ 99.55% | 467.21 for C25H27F2N5O2/ 468.3 (M + 1) | δ 8.47-8.43 (m, 1H), 8.37 (br d, J = 7.7 Hz, 1H), 8.25-8.21 (m, 1H), 8.17-8.12 (m, 1H), 8.09-8.01 (m, 4H), 6.87-6.83 (m, 1H), 3.99-3.87 (m, 1H), 3.82-3.53 (m, 4H), 3.44-3.38 (m, 1H), 3.09 (br d, J = 12.1 Hz, 2H), 2.67 (br d, J = 5.3 Hz, 2H), 2.14-2.03 (m, 4H), 1.88-1.80 (m, 2H), 1.58-1.49 (m, 2H). |

TABLE 3-continued

Analytical data for select inhibitors

| Target No | Structure | Yield/ Purity | Mass Spec. Calculated/ Mass Spec. Found (m/z) | ¹H NMR (DMSO-d$_6$*, 400 MHz) (*unless otherwise indicated) |
|---|---|---|---|---|
| MF-DH-420 | 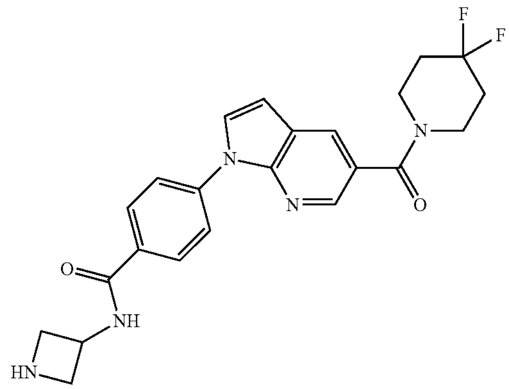 [SMILES: O=C(NC1CNC1)c1ccc(-n2ccc3cc(C(=O)N4CCC(F)(F)CC4)cnc32)cc1] | 8.5%/ 98.08% | 439.18 for C23H23F2N5O2/ 440.0 (M + 1) | δ 8.93-8.86 (m, 1H), 8.45 (d, J = 2.0 Hz, 1H), 8.23 (d, J = 2.0 Hz, 1H), 8.15 (s, 1H), 8.06 (d, J = 4.0 Hz, 4H), 6.86 (d, J = 3.8 Hz, 1H), 4.78-4.68 (m, 1H), 3.82-3.44 (m, 8H), 2.15-2.01 (m, 4H). |
| MF-DH-421 | 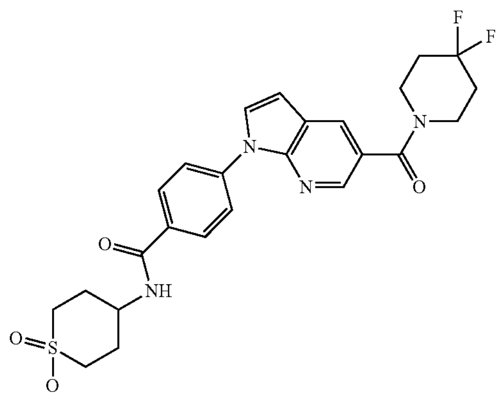 | 13.7%/ 97.62% | 516.16 for C25H26F2N4O4S/ 516.9 | δ 8.51-8.47 (m, 1H), 8.46-8.44 (m, 1H), 8.25-8.22 (m, 1H), 8.16-8.13 (m, 1H), 8.10-8.03 (m, 4H), 6.88-6.84 (m, 1H), 4.28-4.20 (m, 1H), 3.84-3.37 (m, 6H), 3.20-3.09 (m, 2H), 2.20-2.04 (m, 8H). |
| MF-DH-422 | 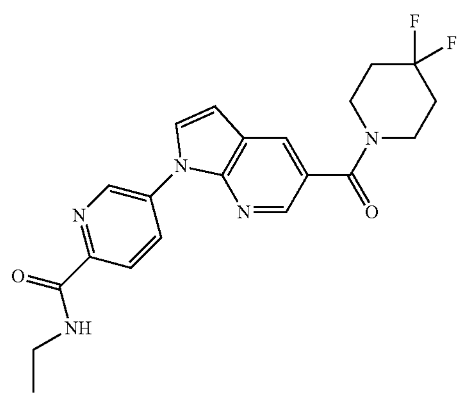 [SMILES: CCNC(=O)c1ccc(-n2ccc3cc(C(=O)N4CCC(F)(F)CC4)cnc32)cn1] | 46.72%/ 93.38% | 413.17 for C21H21F2N5O2/ 414.2 (M + 1) | δ 9.28-9.26 (m, 1H), 8.85-8.80 (m, 1H), 8.64-8.59 (m, 1H), 8.49-8.45 (m, 1H), 8.28-8.19 (m, 3H), 6.93-6.90 (m, 1H), 3.80-3.52 (m, 4H), 3.41-3.34 (m, 2H), 2.15-2.01 (m, 4H), 1.19-1.13 (m, 3H). |
| MF-DH-426 | 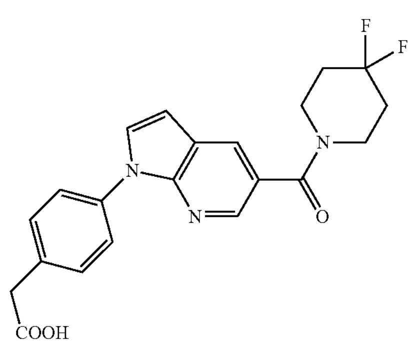 [SMILES: O=C(O)Cc1ccc(-n2ccc3cc(C(=O)N4CCC(F)(F)CC4)cnc32)cc1] | 56.5%/ 90.34% | 399.14 for C21H19F2N3O3/ 400.0 (M + 1) | δ 12.48-12.15 (m, 1H), 8.42-8.39 (m, 1H), 8.21 (d, J = 2.0 Hz, 1H), 8.02 (d, J = 3.7 Hz, 1H), 7.82 (d, J = 8.6 Hz, 2H), 7.45 (d, J = 8.4 Hz, 2H), 6.80 (d, J = 3.7 Hz, 1H), 3.78-3.51 (m, 6H), 2.15-1.98 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-427 | 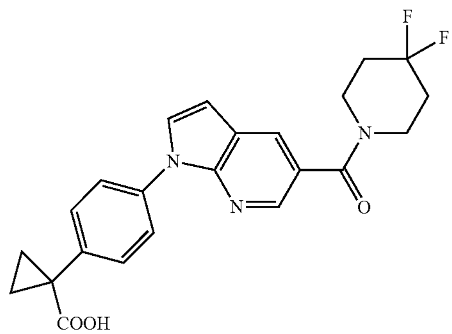 [SMILES: O=C(c1cnc2c(ccn2-c2ccc(C3(C(=O)O)CC3)cc2)c1)N1CCC(F)(F)CC1] | 31.3%/ 98.54% | 425.16 for C23H21F2N3O3/ 426.0 (M + 1) | δ 12.55-12.22 (m, 1H), 8.40 (d, J = 2.1 Hz, 1H), 8.21 (d, J = 2.0 Hz, 1H), 8.02 (d, J = 3.7 Hz, 1H), 7.79 (d, J = 8.4 Hz, 2H), 7.51 (d, J = 8.6 Hz, 2H), 6.80 (d, J = 3.5 Hz, 1H), 3.73-3.54 (m, 4H), 2.14-2.01 (m, 4H), 1.50 (br d, J = 2.9 Hz, 2H), 1.26-1.17 (m, 2H). |
| MF-DH-428 | 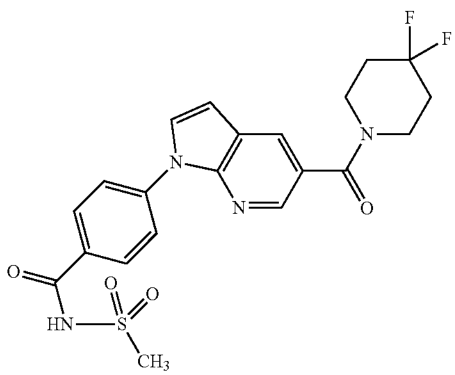 [SMILES: CS(=O)(=O)NC(=O)c1ccc(-n2ccc3cc(C(=O)N4CCC(F)(F)CC4)cnc32)cc1] | 21.3%/ 98.9% | 462.12 for C21H20F2N4O4S/ 463.2 (M + 1) | δ 12.27-12.14 (m, 1H), 8.48 (d, J = 2.0 Hz, 1H), 8.26-8.19 (m, 4H), 8.17-8.12 (m, 2H), 6.88 (d, J = 3.8 Hz, 1H), 3.80-3.53 (m, 4H), 3.42-3.40 (m, 3H), 2.08 (br s, 4H). |
| MF-DH-429 | 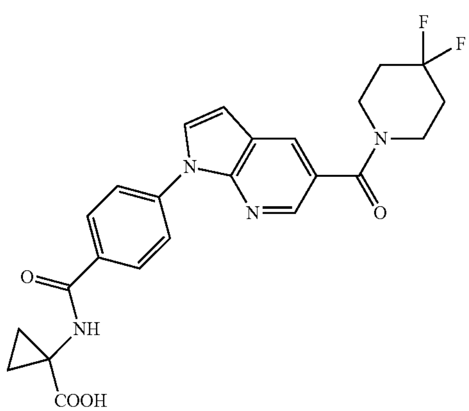 [SMILES: O=C(NC1(C(=O)O)CC1)c1ccc(-n2ccc3cc(C(=O)N4CCC(F)(F)CC4)cnc32)cc1] | 27.6%/ 98.97% | 468.16 for C24H22F2N4O4/ 469.0 (M + 1) | δ 12.43-12.28 (m, 1H), 9.07-8.99 (m, 1H), 8.48-8.43 (m, 1H), 8.24-8.21 (m, 1H), 8.18-8.13 (m, 1H), 8.12-8.07 (m, 2H), 8.06-8.01 (m, 2H), 6.88-6.82 (m, 1H), 3.75-3.53 (m, 4H), 2.15-1.99 (m, 4H), 1.46-1.40 (m, 2H), 1.17-1.10 (m, 2H). |
| MF-DH-430 | 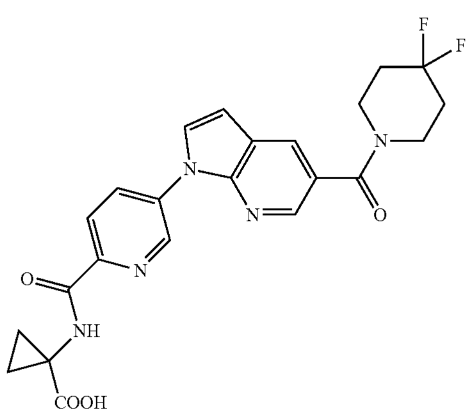 [SMILES: O=C(NC1(C(=O)O)CC1)c1ccc(-n2ccc3cc(C(=O)N4CCC(F)(F)CC4)cnc32)cn1] | 30.1%/ 98.97% | 468.16 for C24H22F2N4O4/ 469.0 (M + 1) | δ 12.43-12.28 (m, 1H), 9.07-8.99 (m, 1H), 8.48-8.43 (m, 1H), 8.24-8.21 (m, 1H), 8.18-8.13 (m, 1H), 8.12-8.07 (m, 2H), 8.06-8.01 (m, 2H), 6.88-6.82 (m, 1H), 3.75-3.53 (m, 4H), 2.15-1.99 (m, 4H), 1.46-1.40 (m, 2H), 1.17-1.10 (m, 2H). |

TABLE 3-continued

Analytical data for select inhibitors

| Target No | Structure | Yield/ Purity | Mass Spec. Calculated/ Mass Spec. Found (m/z) | $^{1}$H NMR (DMSO-d$_{6}$*, 400 MHz) (*unless otherwise indicated) |
|---|---|---|---|---|
| MF-DH-431 | 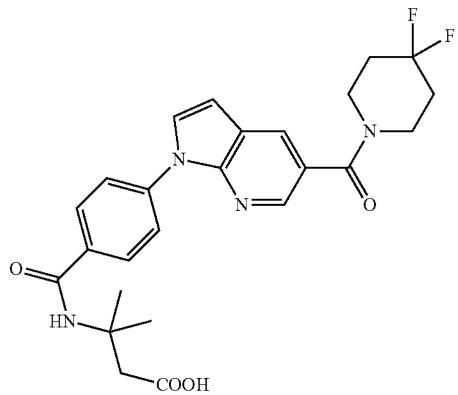 [SMILES: CC(C)(CC(=O)O)NC(=O)c1ccc(-n2ccc3cc(C(=O)N4CCC(F)(F)CC4)cnc32)cc1] | 4.9%/ 95.80% | 484.19 for C25H26F2N4O4/ 455.2 (M + 1) | δ 12.12-11.99 (m, 1H), 8.46-8.44 (m, 1H), 8.24-8.22 (m, 1H), 8.15-8.12 (m, 1H), 8.06-8.02 (m, 2H), 7.98-7.91 (m, 3H), 6.85 (d, J = 3.7 Hz, 1H), 3.77-3.54 (m, 4H), 2.84-2.80 (m, 2H), 2.15-2.03 (m, 4H), 1.49-1.45 (m, 6H). |
| MF-DH-432 | 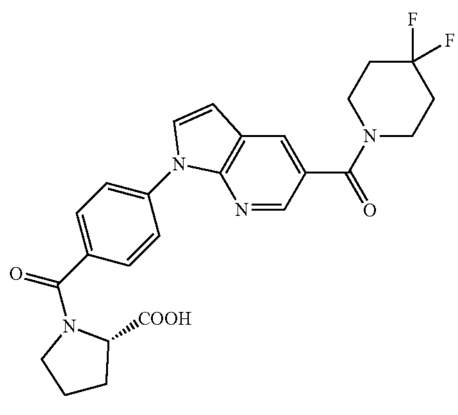 [SMILES: O=C(O)[C@@H]1CCCN1C(=O)c1ccc(-n2ccc3cc(C(=O)N4CCC(F)(F)CC4)cnc32)cc1] | 6.8%/ 99.48% | 482.18 for C25H24F2N4O4/ 483.2 (M + 1) | δ = 8.45 (d, J = 2.0 Hz, 1H), 8.23 (d, J = 2.0 Hz, 1H), 8.13 (d, J = 3.8 Hz, 1H), 8.05 (d, J = 8.6 Hz, 2H), 7.73 (d, J = 8.6 Hz, 2H), 6.85 (d, J = 3.5 Hz, 1H), 4.50-4.42 (m, 1H), 3.75-3.57 (m, 6H), 2.36-2.26 (m, 1H), 2.15-2.00 (m, 4H), 1.97-1.80 (m, 3H). |
| MF-DH-433 | 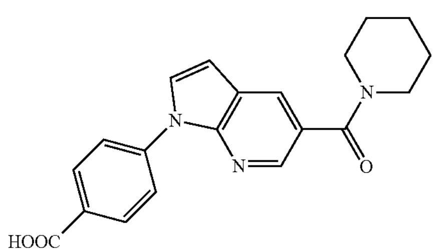 [SMILES: O=C(O)c1ccc(-n2ccc3cc(C(=O)N4CCCCC4)cnc32)cc1] | 78.1%/ 99.82% | 349.14 for C20H19N3O3/ 350.1 (M + 1) | δ 13.08-12.95 (m, 1H), 8.38 (d, J = 2.0 Hz, 1H), 8.18-8.09 (m, 6H), 6.86 (d, J = 3.8 Hz, 1H), 3.76-3.40 (m, 4H), 1.69-1.50 (m, 6H) |
| MF-DH-434 | 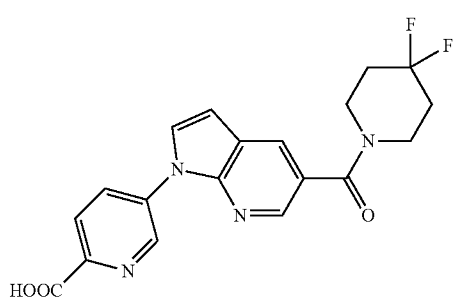 [SMILES: O=C(O)c1ccc(-n2ccc3cc(C(=O)N4CCC(F)(F)CC4)cnc32)cn1] | 53.2%/ 94.01% | 386.12 for C19H16F2N4O3/ 387.1 (M + 1) | δ 13.73-12.61 (m, 1H), 9.36-9.34 (m, 1H), 8.66 (dd, J = 8.5, 2.5 Hz, 1H), 8.49 (d, J = 1.9 Hz, 1H), 8.30-8.22 (m, 3H), 6.93 (d, J = 3.8 Hz, 1H), 3.76-3.50 (m, 4H), 2.15-2.01 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-437 | 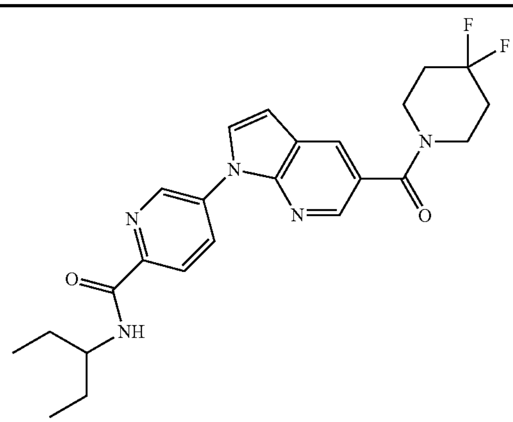 | 61.3%/ 94.05% | 455.21 for C24H27F2N5O2/ 456.2 (M + 1) | δ 9.28-9.25 (m, 1H), 8.63-8.59 (m, 1H), 8.48-8.46 (m, 1H), 8.37-8.31 (m, 1H), 8.28-8.20 (m, 3H), 6.93-6.89 (m, 1H), 3.87-3.78 (m, 1H), 3.75-3.48 (m, 4H), 2.16-2.02 (m, 4H), 1.65-1.55 (m, 4H), 0.87 (t, J = 7.4 Hz, 6H). |
| MF-DH-438 | 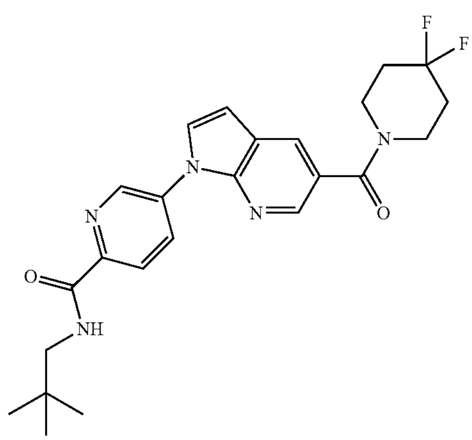 [SMILES: CC(C)(C)CNC(=O)c1ccc(-n2ccc3cc(C(=O)N4CCC(F)(F)CC4)cnc32)cn1] | 42.7%/ 95.24% | 455.21 for C24H27F2N5O2/ 456.2 (M + 1) | δ 9.31-9.27 (m, 1H), 8.66-8.55 (m, 2H), 8.47 (d, J = 1.9 Hz, 1H), 8.28-8.21 (m, 3H), 6.93-6.91 (m, 1H), 3.81-3.44 (m, 4H), 3.19 (d, J = 6.6 Hz, 2H), 2.15-2.01 (m, 4H), 0.93 (s, 9H). |
| MF-DH-439 | 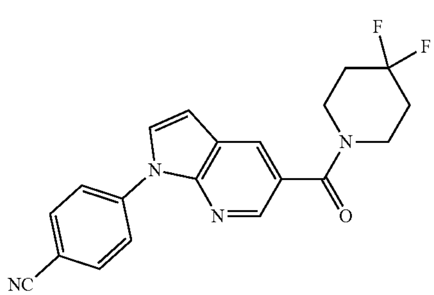 [SMILES: N#Cc1ccc(-n2ccc3cc(C(=O)N4CCC(F)(F)CC4)cnc32)cc1] | 41.6%/ 95.51% | 366.13 for C20H16F2N4O/ 367.1 (M + 1) | δ 8.48-8.46 (m, 1H), 8.32-8.27 (m, 2H), 8.26-8.21 (m, 2H), 8.07-8.03 (m, 2H), 6.91-6.88 (m, 1H), 3.77-3.48 (m, 4H), 2.15-2.02 (m, 4H). |
| MF-DH-440 | 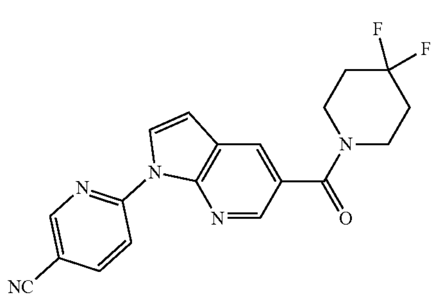 [SMILES: N#Cc1ccc(-n2ccc3cc(C(=O)N4CCC(F)(F)CC4)cnc32)nc1] | 37.5%/ 98.38% | 367.12 for C19H15F2N5O/ 368.1 (M + 1) | δ 9.17 (d, J = 8.8 Hz, 1H), 9.01 (d, J = 1.6 Hz, 1H), 8.57-8.50 (m, 3H), 8.28 (d, J = 2.0 Hz, 1H), 6.94 (d, J = 3.9 Hz, 1H), 3.81-3.38 (m, 4H), 2.15-2.02 (m, 4H |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-441 | 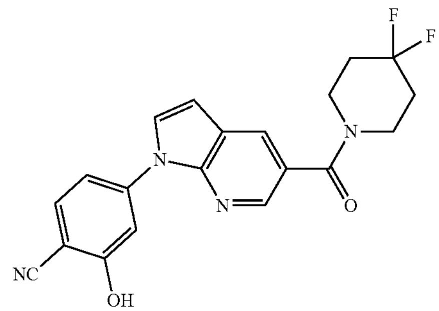 [SMILES: N#Cc1ccc(-n2ccc3cc(C(=O)N4CCC(F)(F)CC4)cnc32)cc1O] | 32.4%/ 96.34% | 382.12 for C20H16F2N4O2/ 383.1 (M + 1) | δ 9.44-9.41 (m, 1H), 9.27-9.23 (m, 1H), 9.15-9.10 (m, 1H), 8.58-8.55 (m, 1H), 8.35-8.32 (m, 2H), 7.01-6.98 (m, 1H), 3.79-3.67 (m, 4H), 2.22-2.12 (m, 4H). |
| MF-DH-442 | 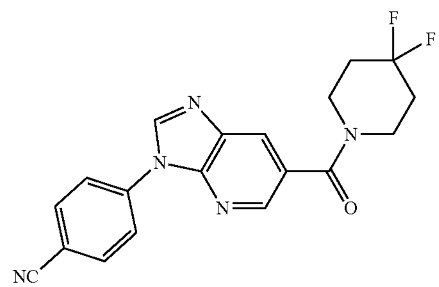 [SMILES: N#Cc1ccc(-n2cnc3cc(C(=O)N4CCC(F)(F)CC4)cnc32)cc1] | 28.7%/ 97.51% | 367.12 for C19H15F2N5O/ 368.2 (M + 1) | δ 9.17 (s, 1H), 8.58 (d, J = 1.7 Hz, 1H), 8.38-8.36 (m, 1H), 8.36-8.28 (m, J = 8.8 Hz, 2H), 8.13 (d, J = 8.7 Hz, 2H), 3.84-3.44 (m, 4H), 2.16-2.01 (m, 4H). |
| MF-DH-443 | 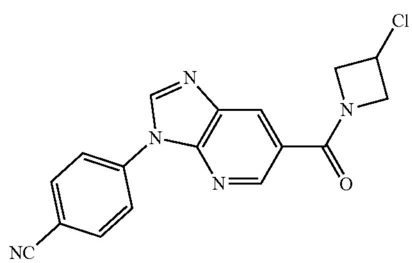 [SMILES: N#Cc1ccc(-n2cnc3cc(C(=O)N4CC(Cl)C4)cnc32)cc1] | 31.2%/ 98.35% | 337.07 for C17H12ClN5O/ 338.1 (M + 1) | δ 9.18 (s, 1H), 8.75 (d, J = 1.8 Hz, 1H), 8.46 (d, J = 1.8 Hz, 1H), 8.31 (d, J = 8.8 Hz, 2H), 8.13 (d, J = 8.7 Hz, 2H), 4.89 (br s, 2H), 4.73-4.51 (m, 2H), 4.16 (br s, 1H). |
| MF-DH-444 | 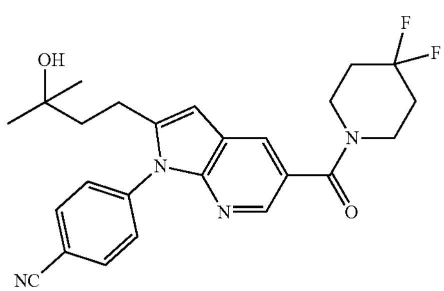 [SMILES: CC(C)(O)CCc1cc2cc(C(=O)N3CCC(F)(F)CC3)cnc2n1-c1ccc(C#N)cc1] | 7.2%/ 99.93% | 452.2 for C21H19F2N3O2/ 453.2 (M + 1) | δ 8.24-8.20 (m, 1H), 8.11-8.04 (m, 3H), 7.75 (d, J = 8.5 Hz, 2H), 6.60-6.56 (m, 1H), 4.24-4.21 (m, 1H), 3.73-3.52 (m, 4H), 2.79-2.71 (m, 2H), 2.13-2.00 (m, 4H), 1.68-1.58 (m, 2H), 1.04-1.01 (m, 6H). |
| MF-DH-446 | 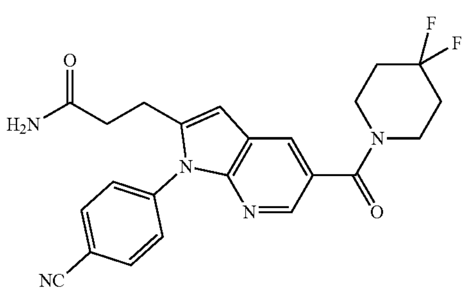 [SMILES: N#Cc1ccc(-n2c(CCC(N)=O)cc3cc(C(=O)N4CCC(F)(F)CC4)cnc32)cc1] | 3.5%/ 91.47% | 437.17 for C23H21F2N5O2/ 438.2 (M + 1) | δ 8.24-8.22 (m, 1H), 8.11-8.07 (m, 3H), 7.78-7.73 (m, 2H), 7.39-7.35 (m, 1H), 6.85-6.81 (m, 1H), 6.58-6.56 (m, 1H), 3.73-3.54 (m, 4H), 2.92-2.89 (m, 2H), 2.69-2.66 (m, 2H), 2.11-2.00 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-448 | 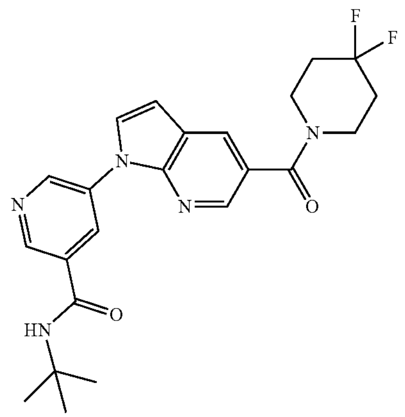 [SMILES: CC(C)(C)NC(=O)c1cncc(-n2ccc3cc(C(=O)N4CCC(F)(F)CC4)cnc32)c1] | 35.1%/ 97.53% | 441.20 for C23H25F2N5O2/ 442.2 (M + 1) | δ 9.30-9.27 (m, 1H), 8.96-8.92 (m, 1H), 8.65 (s, 1H), 8.50-8.44 (m, 1H), 8.28-8.20 (m, 2H), 8.15-8.10 (m, 1H), 6.92-6.87 (m, 1H), 3.77-3.58 (m, 4H), 2.16-2.02 (m, 4H), 1.45-1.40 (s, 9H). |
| MF-DH-449 | 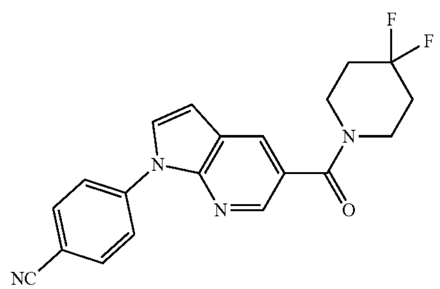 [SMILES: N#Cc1ccc(-n2ccc3cc(C(=O)N4CCC(F)(F)CC4)cnc32)cc1] | 12.8%/ 94.14% | 382.11 for C20H16F2N4S/ 383.1 (M + 1) | δ 8.41-8.38 (m, 1H), 8.31-8.26 (m, 2H), 8.22-8.19 (m, 1H), 8.16-8.13 (m, 1H), 8.08-8.02 (m, 2H), 6.89-6.86 (m, 1H), 4.49-4.43 (m, 2H), 3.76-3.70 (m, 2H), 2.31-2.21 (m, 2H), 2.18-2.08 (m, 2H). |
| MF-DH-450 | 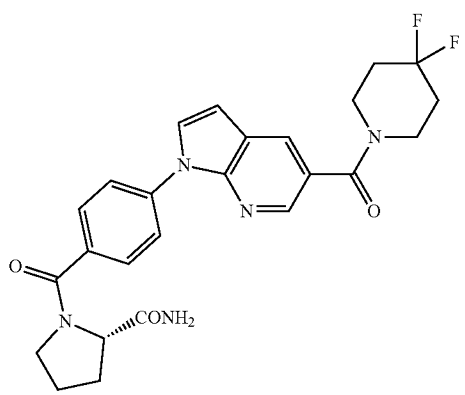 [SMILES: NC(=O)[C@@H]1CCCN1C(=O)c1ccc(-n2ccc3cc(C(=O)N4CCC(F)(F)CC4)cnc32)cc1] | 31.3%/ 92.56% | 481.19 for C25H25F2N5O3/ 482.0 (M + 1) | δ 8.46-8.43 (m, 1H), 8.25-8.21 (m, 1H), 8.16-8.10 (m, 1H), 8.06-7.99 (m, 2H), 7.81-7.74 (m, 2H), 7.59-7.40 (m, 1H), 7.00-6.94 (m, 1H), 6.87-6.82 (m, 1H), 4.43-4.27 (m, 1H), 3.75-3.45 (m, 6H), 2.25-2.03 (m, 5H), 1.97-1.77 (m, 3H). |
| MF-DH-451 | 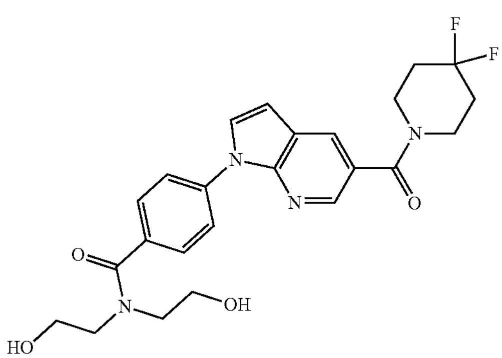 [SMILES: O=C(c1ccc(-n2ccc3cc(C(=O)N4CCC(F)(F)CC4)cnc32)cc1)N(CCO)CCO] | 32.78%/ 95.52% | 472.19 for C24H26F2N4O4/ 473.0 (M + 1) | δ 8.48-8.42 (m, 1H), 8.27-8.20 (m, 1H), 8.13-8.09 (m, 1H), 8.01-7.96 (m, 2H), 7.62-7.58 (m, 2H), 6.86-6.82 (m, 1H), 3.60-3.36 (m, 14H), 2.15-2.01 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-452 | 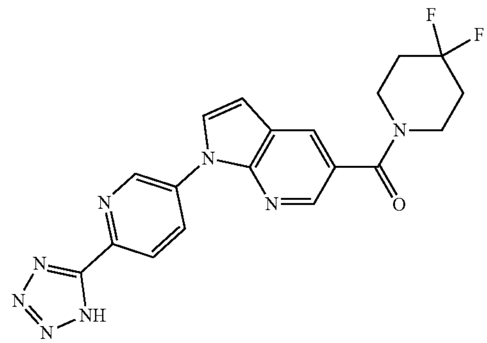 [SMILES: O=C(c1cnc2c(ccn2-c2ccc(-c3nnn[nH]3)nc2)c1)N1CCC(F)(F)CC1] | 45.3%/ 94.26% | 410.14 for C19H16F2N8O/ 411.1 (M + 1) | δ 9.41-8.99 (m, 1H), 8.62-8.57 (m, 1H), 8.41-8.32 (m, 2H), 8.27-8.24 (m, 1H), 8.18-8.12 (m, 1H), 6.94-6.88 (m, 1H), 3.81-3.50 (m, 4H), 2.13-2.03 (m, 4H). |
| MF-DH-453 | 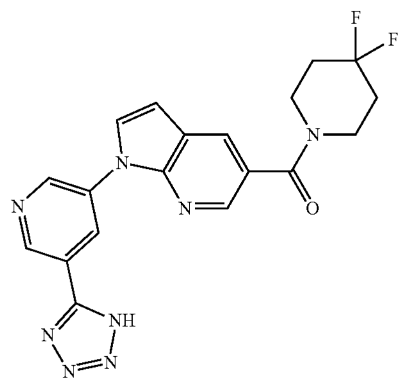 [SMILES: O=C(c1cnc2c(ccn2-c2cncc(-c3nnn[nH]3)c2)c1)N1CCC(F)(F)CC1] | 32.6%/ 98.39% | 410.14 for C19H16F2N8O/ 409.2 (M − 1) | δ 9.44-9.41 (m, 1H), 9.25 (d, J = 1.3 Hz, 1H), 9.14-9.12 (m, 1H), 8.58-8.55 (m, 1H), 8.36-8.32 (m, 2H), 7.01-6.98 (m, 1H), 3.80-3.68 (m, 4H), 2.21-2.12 (m, 4H). |
| MF-DH-454 | 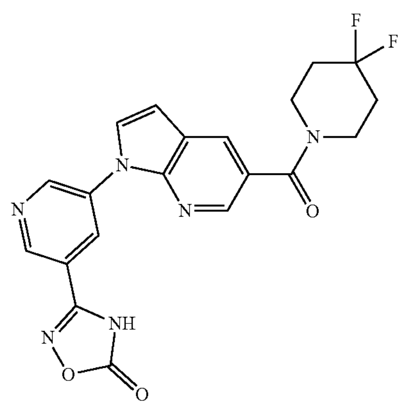 [SMILES: O=C(c1cnc2c(ccn2-c2cncc(-c3noc(=O)[nH]3)c2)c1)N1CCC(F)(F)CC1] | 13.3%/ 94.20% | 426.13 for C20H16F2N6O3/ 425.2 (M − 1) | δ 9.33-9.29 (m, 1H), 8.96-8.92 (m, 1H), 8.82-8.78 (m, 1H), 8.50-8.46 (m, 1H), 8.28-8.21 (m, 2H), 6.92-6.89 (m, 1H), 3.75-3.57 (m, 4H), 2.15-2.05 (m, 4H). |
| MF-DH-455 | 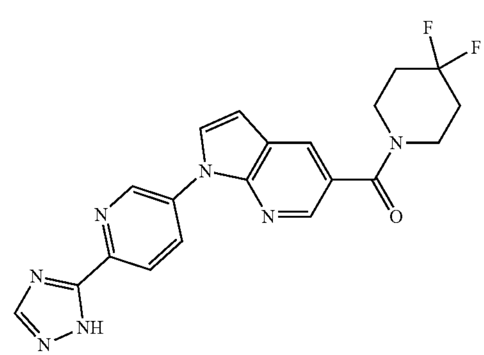 [SMILES: O=C(c1cnc2c(ccn2-c2ccc(-c3ncn[nH]3)nc2)c1)N1CCC(F)(F)CC1] | 5.8%/ 91.76% | 409.15 for C20H17F2N7O/ 410.2 (M + 1) | δ 9.32-9.28 (m, 1H), 8.65-8.59 (m, 1H), 8.52-8.47 (m, 1H), 8.32-8.25 (m, 4H), 6.95-6.90 (m, 1H), 3.84-3.51 (m, 4H), 2.17-2.06 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-456 | 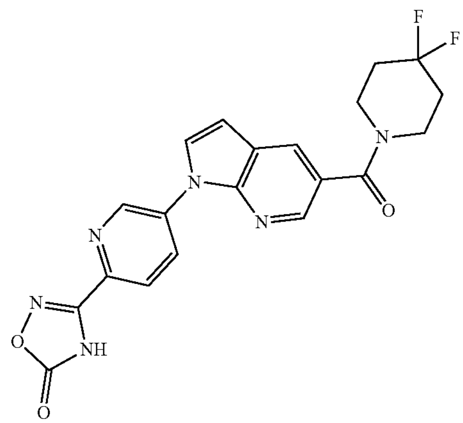 [SMILES: O=C(c1cnc2c(ccn2-c2ccc(-c3noc(=O)[nH]3)nc2)c1)N1CCC(F)(F)CC1] | 37.7%/ 92.01% | 426.13 for C20H16F2N6O3/ 427.12 (M + 1) | δ 13.29-13.14 (m, 1H), 9.42 (d, J = 2.1 Hz, 1H), 8.78-8.71 (m, 1H), 8.49 (d, J = 1.7 Hz, 1H), 8.33-8.24 (m, 2H), 8.24-8.17 (m, 1H), 6.94 (d, J = 3.7 Hz, 1H), 3.82-3.55 (m, 4H), 2.08 (br d, J = 3.5 Hz, 4H). |
| MF-DH-457 | 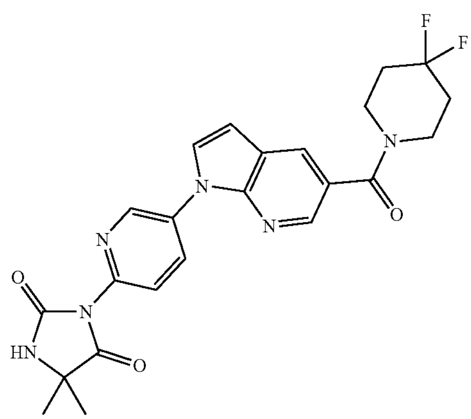 [SMILES: CC1(C)NC(=O)N(c2ccc(-n3ccc4cc(C(=O)N5CCC(F)(F)CC5)cnc43)cn2)C1=O] | 19.1%/ 97.36% | 468.17 for C23H22F2N6O3/ 469.3 (M + 1) | δ 8.97-8.92 (m, 1H), 8.72-8.69 (m, 1H), 8.61-8.57 (m, 1H), 8.54-8.47 (m, 2H), 8.29-8.24 (m, 1H), 8.15-8.10 (m, 1H), 6.90-6.86 (m, 1H), 3.79-3.54 (m, 4H), 2.15-2.04 (m, 4H), 1.45 (s, 6H). |
| MF-DH-458 | 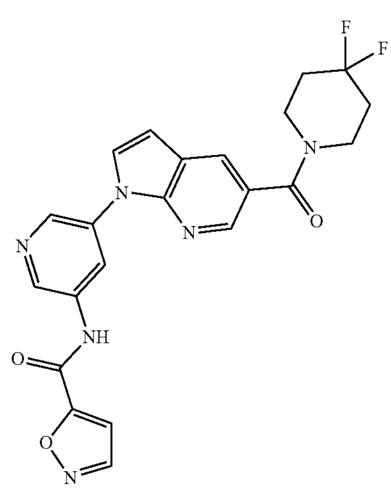 [SMILES: O=C(Nc1cncc(-n2ccc3cc(C(=O)N4CCC(F)(F)CC4)cnc32)c1)c1ccno1] | 23.8%/ 99.36% | 452.14 for C22H18F2N6O3/ 453.2 (M + 1) | δ 11.25-11.22 (m, 1H), 8.98 (d, J = 2.2 Hz, 1H), 8.92-8.89 (m, 1H), 8.87-8.84 (m, 2H), 8.47-8.45 (m, 1H), 8.27-8.24 (m, 1H), 8.15-8.12 (m, 1H), 7.35-7.32 (m, 1H), 6.90-6.87 (m, 1H), 3.74-3.45 (m, 4H), 2.14-2.02 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-459 | 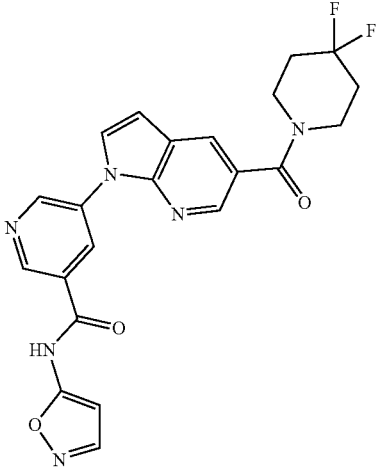 [SMILES: O=C(Nc1ccno1)c1cncc(-n2ccc3cc(C(=O)N4CCC(F)(F)CC4)cnc32)c1] | 39.3%/ 99.82% | 452.14 for C22H18F2N6O3/ 451.2 (M − 1) | δ 12.42-12.37 (m, 1H), 9.47 (d, J = 2.4 Hz, 1H), 9.14-9.12 (m, 1H), 8.93 (t, J = 2.1 Hz, 1H), 8.56 (d, J = 1.8 Hz, 1H), 8.49 (d, J = 1.8 Hz, 1H), 8.29-8.24 (m, 2H), 6.93 (d, J = 3.7 Hz, 1H), 6.50 (d, J = 1.8 Hz, 1H), 3.81-3.48 (m, 4H), 2.12-2.02 (m, 4H). |
| MF-DH-460 | 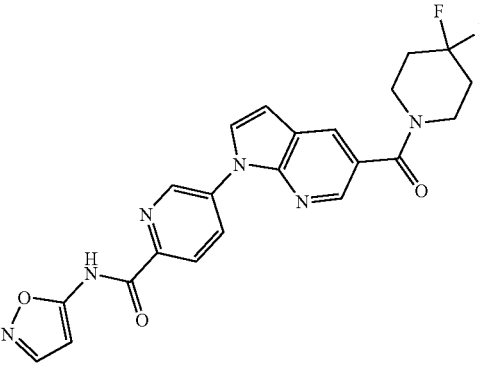 | 8.5%/ 95.03% | 452.14 for C22H18F2N6O3/ 453.2 (M + 1) | δ 12.23-12.19 (m, 1H), 9.45-9.42 (m, 1H), 8.77-8.72 (m, 1H), 8.55-8.53 (m, 1H), 8.51-8.49 (m, 1H), 8.38-8.34 (m, 1H), 8.33-8.31 (m, 1H), 8.29-8.27 (m, 1H), 6.96-6.94 (m, 1H), 6.50-6.47 (m, 1H), 3.79-3.56 (m, 4H), 2.16-2.04 (m, 4H). |
| MF-DH-462 | 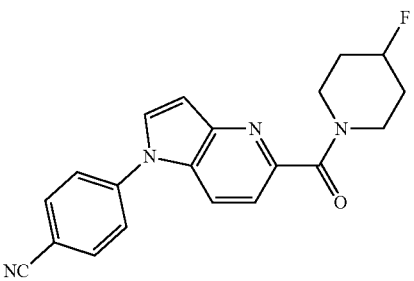 [SMILES: N#Cc1ccc(-n2ccc3nc(C(=O)N4CCC(F)CC4)ccc32)cc1] | 38.5%/ 99.52% | 348.14 for C20H17FN4O/ 349.1 (M + 1) | δ 8.24-8.15 (m, 2H), 8.10-8.06 (m, 2H), 7.93-7.88 (m, 2H), 7.49-7.46 (m, 1H), 6.97-6.94 (m, 1H), 5.03-4.85 (m, 1H), 3.79-3.44 (m, 4H), 2.06-1.67 (m, 4H). |
| MF-DH-463 | 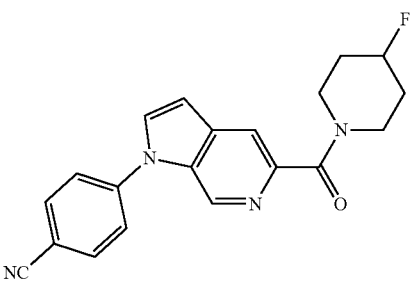 [SMILES: N#Cc1ccc(-n2ccc3cc(C(=O)N4CCC(F)CC4)ncc32)cc1] | 42.1%/ 99.89% | 348.14 for C20H17FN4O/ 349.0 (M + 1) | δ 8.98 (s, 1H), 8.15-8.05 (m, 3H), 8.01-7.92 (m, 3H), 6.95 (d, J = 3.1 Hz, 1H), 5.03-4.84 (m, 1H), 3.78-3.43 (m, 4H), 2.01-1.66 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-464 | 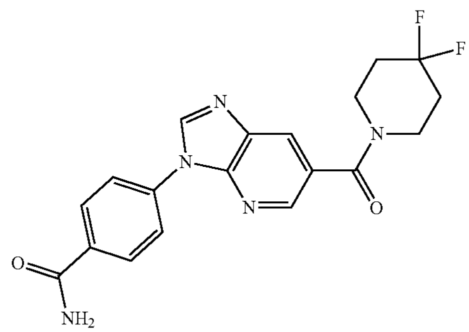 [SMILES: NC(=O)c1ccc(-n2cnc3cc(C(=O)N4CCC(F)(F)CC4)cnc32)cc1] | 46.5%/ 99.47% | 385.14 for C19H17F2N5O2/ 386.2 (M + 1) | δ 9.10 (s, 1H), 8.56 (d, J = 1.8 Hz, 1H), 8.35 (d, J = 1.8 Hz, 1H), 8.11 (s, 5H), 7.49 (br s, 1H), 3.84-3.42 (m, 4H), 2.16-2.03 (m, 4H). |
| MF-DH-465 | 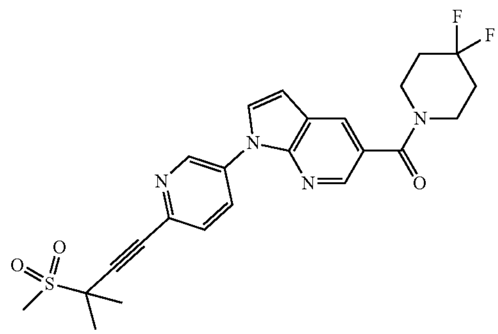 [SMILES: CC(C)(C#Cc1ccc(-n2ccc3cc(C(=O)N4CCC(F)(F)CC4)cnc32)cn1)S(C)(=O)=O] | 61.3%/ 99.17% | 486.15 for C24H24F2N4O3S/ 487.2 (M + 1) | δ 8.98 (d, J = 8.6 Hz, 1H), 8.66 (d, J = 1.8 Hz, 1H), 8.56-8.47 (m, 2H), 8.26 (d, J = 1.9 Hz, 1H), 8.19 (s, 1H), 6.89 (d, J = 3.9 Hz, 1H), 3.87-3.61 (m, 4H), 3.22-3.19 (m, 3H), 2.15-2.02 (m, 4H), 1.69 (s, 6H). |
| MF-DH-467 | 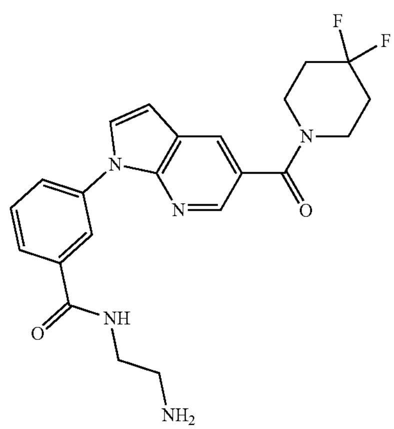 [SMILES: NCCNC(=O)c1cccc(-n2ccc3cc(C(=O)N4CCC(F)(F)CC4)cnc32)c1] | 16.8%/ 99.17% | 427.18 for C22H23F2N5O2/ 428.2 (M + 1) | δ 8.56-8.50 (m, 1H), 8.44 (d, J = 2.0 Hz, 1H), 8.31-8.23 (m, 2H), 8.14-8.07 (m, 2H), 7.85 (br d, J = 7.8 Hz, 1H), 7.65 (t, J = 7.9 Hz, 1H), 6.84 (d, J = 3.7 Hz, 1H), 3.86-3.44 (m, 6H), 2.73-2.67 (m, 2H), 2.13-2.05 (m, 4H). |
| MF-DH-468 | 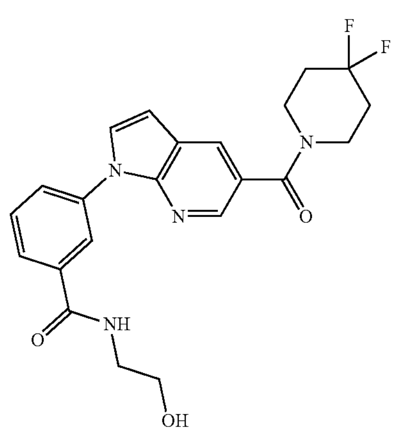 [SMILES: O=C(NCCO)c1cccc(-n2ccc3cc(C(=O)N4CCC(F)(F)CC4)cnc32)c1] | 53.2%/ 99.80% | 428.17 for C22H22F2N4O3/ 429.2 (M + 1) | d, J = 2.0 Hz, 1H), 8.29 (t, J = 1.8 Hz, 1H), 8.23 (d, J = 2.0 Hz, 1H), 8.13-8.07 (m, 2H), 7.86 (d, J = 7.9 Hz, 1H), 7.66 (t, J = 7.9 Hz, 1H), 6.85 (d, J = 3.8 Hz, 1H), 3.65-3.59 (m, 3H), 3.59-3.51 (m, 4H), 3.39-3.34 (m, 2H), 2.14-2.02 (m, 4H). |

TABLE 3-continued

Analytical data for select inhibitors

| Target No | Structure | Yield/Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-469 | 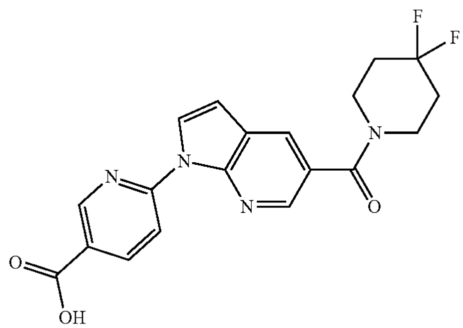 [SMILES: O=C(O)c1ccc(-n2ccc3cc(C(=O)N4CCC(F)(F)CC4)cnc32)nc1] | 41.5%/ 96.50% | 386.12 for C19H16F2N4O3/ 387.2 (M + 1) | δ 13.62-13.07 (m, 1H), 9.09-9.00 (m, 2H), 8.58-8.50 (m, 3H), 8.29-8.25 (m, 1H), 6.91 (d, J = 4.0 Hz, 1H), 3.82-3.49 (m, 4H), 2.16-2.01 (m, 4H). |
| MF-DH-470 | 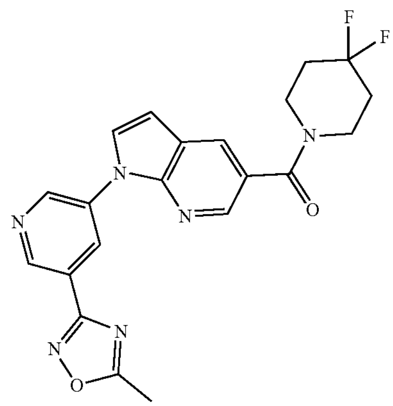 [SMILES: Cc1nc(-c2cncc(-n3ccc4cc(C(=O)N5CCC(F)(F)CC5)cnc43)c2)no1] | 24.3%/ 99.63% | 424.41 for C21H18F2N6O2/ 425.2 (M + 1) | δ 9.35 (d, J = 2.6 Hz, 1H), 9.13 (d, J = 1.8 Hz, 1H), 9.05-9.02 (m, 1H), 8.49 (d, J = 1.9 Hz, 1H), 8.32-8.26 (m, 2H), 6.91 (d, J = 3.8 Hz, 1H), 3.76-3.48 (m, 4H), 2.74 (s, 3H), 2.14-2.01 (m, 4H). |
| MF-DH-471 | 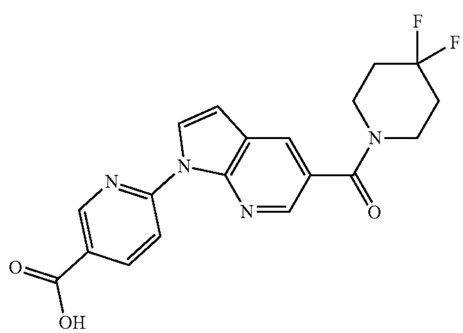 [SMILES: O=C(O)c1ccc(-n2ccc3cc(C(=O)N4CCC(F)(F)CC4)cnc32)nc1] | 46.3%/ 99.45% | 424.15 for C19H16F2N4O3/ 425.2 (M + 1) | δ 9.39 (d, J = 2.4 Hz, 1H), 8.70 (dd, J = 2.6, 8.6 Hz, 1H), 8.49 (d, J = 2.0 Hz, 1H), 8.32-8.23 (m, 3H), 6.93 (d, J = 3.8 Hz, 1H), 3.65 (br d, J = 4.9 Hz, 4H), 2.72 (s, 3H), 2.16-2.00 (m, 4H). |
| MF-DH-472 | 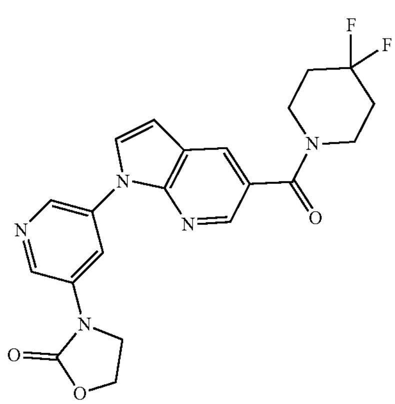 [SMILES: O=C(c1cnc2c(ccn2-c2cncc(N3CCOC3=O)c2)c1)N1CCC(F)(F)CC1] | 52.8%/ 98.32% | 428.1 for C21H19F2N5O3/ 427.15 (M − 1) | δ 8.90 (d, J = 2.2 Hz, 1H), 8.79 (d, J = 2.3 Hz, 1H), 8.61 (t, J = 2.3 Hz, 1H), 8.44 (d, J = 2.0 Hz, 1H), 8.25 (d, J = 2.0 Hz, 1H), 8.14 (d, J = 3.7 Hz, 1H), 6.88 (d, J = 3.7 Hz, 1H), 4.54 (t, J = 7.9 Hz, 2H), 4.25-4.15 (m, 2H), 3.78-3.48 (m, 4H), 2.15-2.01 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-477 | 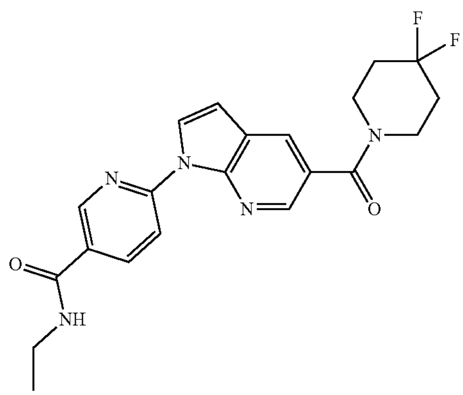 [SMILES: CCNC(=O)c1ccc(-n2ccc3cc(C(=O)N4CCC(F)(F)CC4)cnc32)nc1] | 12.4%/ 99.8% | 413.17 for C21H19F2N5O3/ 414.2 (M + 1) | δ 9.01-8.95 (m, 2H), 8.71-8.66 (m, 1H), 8.57-8.51 (m, 2H), 8.46-8.42 (m, 1H), 8.28-8.25 (m, 1H), 6.89 (d, J = 3.9 Hz, 1H), 3.78-3.50 (m, 4H), 3.38-3.33 (m, 2H), 2.15-2.03 (m, 4H), 1.17 (t, J = 7.2 Hz, 3H). |
| MF-DH-478 | 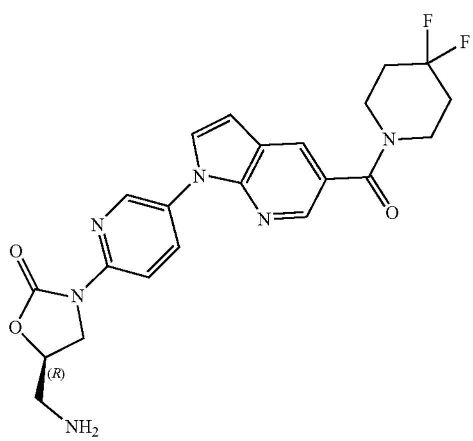 | 33.6%/ 99.73% | 456.17 for C22H22F2N6O3/ 457.2 (M + 1) | δ 8.85 (d, J = 9.0 Hz, 1H), 8.71 (d, J = 2.5 Hz, 1H), 8.51 (d, J = 1.8 Hz, 1H), 8.44 (d, J = 3.8 Hz, 1H), 8.31-8.21 (m, 2H), 8.21-8.11 (m, 3H), 6.86 (d, J = 3.9 Hz, 1H), 5.04-4.94 (m, 1H), 4.35-4.28 (m, 1H), 3.97-3.93 (m, 1H), 3.83-3.69 (m, 4H), 3.34-3.27 (m, 2H), 2.15-2.02 (m, 4H). |
| MF-DH-479 | 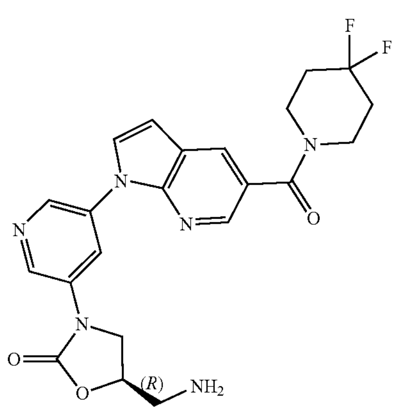 | 25.6.5%/ 94.32% | 456.17 for C22H22F2N6O3/ 457.2 (M + 1) | δ 8.93-8.89 (m, 1H), 8.77-8.73 (m, 1H), 8.68-8.65 (m, 1H), 8.45-8.41 (m, 1H), 8.28-8.25 (m, 1H), 8.14 (br d, J = 3.7 Hz, 4H), 6.90 (d, J = 3.8 Hz, 1H), 5.06-4.97 (m, 1H), 4.38-4.35 (m, 1H), 4.00-3.96 (m, 1H), 3.80-3.59 (m, 4H), 3.34-3.28 (m, 2H), 2.14-2.02 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-480 | 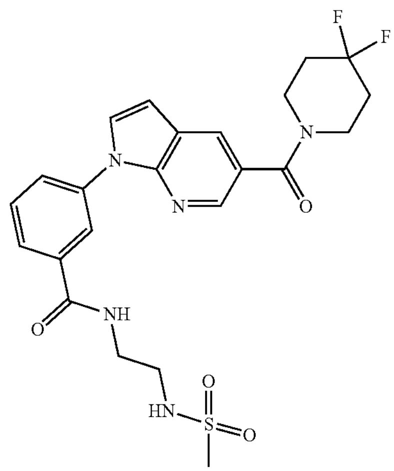 [SMILES: CS(=O)(=O)NCCNC(=O)c1cccc(-n2ccc3cc(C(=O)N4CCC(F)(F)CC4)cnc32)c1] | 48.3%/ 97.43% | 505.16 for C21H19F2N5O3/ 506.2 (M + 1) | δ 8.71-8.68 (m, 1H), 8.43 (s, 1H), 8.31 (s, 1H), 8.25 (s, 1H), 8.12-8.08 (m, 2H), 7.81-7.76 (m, 1H), 8.74-7.68 (m, 1H), 7.19-7.13 (m, 1H), 6.85 (s, 1H), 3.76-3.49 (m, 4H), 3.51-3.48 (m, 2H), 3.18-3.12 (m, 2H), 2.91 (s, 3H), 2.18-2.01 (m, 4H). |
| MF-DH-481 | 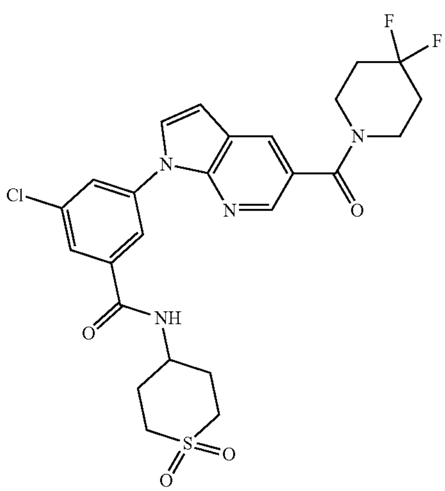 [SMILES: O=C(NC1CCS(=O)(=O)CC1)c1cc(Cl)cc(-n2ccc3cc(C(=O)N4CCC(F)(F)CC4)cnc32)c1] | 35.0%/ 98.45% | 550.13 for C25H25ClF2N4O4S/ 551.2 (M + 1) | δ 8.62 (br d, J = 7.6 Hz, 1H), 8.47 (s, 1H), 8.32 (s, 2H), 8.25 (s, 1H), 8.22-8.14 (m, 1H), 7.91 (s, 1H), 6.87 (d, J = 3.5 Hz, 1H), 4.29-4.19 (m, 1H), 3.75-3.50 (m, 4H), 3.35 (brs, 1H), 3.30-3.26 (m, 1H), 3.19-3.11 (m, 2H), 2.21-2.03 (m, 8H). |
| MF-DH-482 | 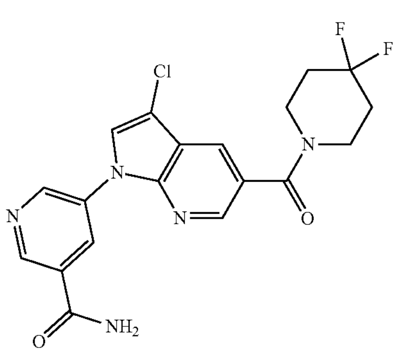 [SMILES: NC(=O)c1cncc(-n2cc(Cl)c3cc(C(=O)N4CCC(F)(F)CC4)cnc32)c1] | 61.4%/ 99.74% | 419.1 for C19H16ClF2N5O2/ 420.1 (M + 1) | δ 9.36-9.21 (m, 1H), 9.03 (s, 1H), 8.74 (br s, 1H), 8.58-8.46 (m, 2H), 8.32-8.20 (m, 2H), 7.77 (br s, 1H), 3.86-3.44 (m, 4H), 2.09 (br s, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-484 | 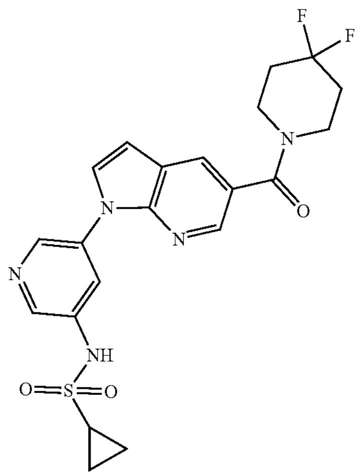 [SMILES: O=C(c1cnc2c(ccn2-c2cncc(NS(=O)(=O)C3CC3)c2)c1)N1CCC(F)(F)CC1] | 34.7%/ 99.58% | 461.13 for C21H21F2N5O3S/ 462.2 (M + 1) | δ 10.31 (s, 1H), 8.83 (s, 1H), 8.44 (br s, 2H), 8.33 (s, 1H), 8.25 (s, 1H), 8.14 (d, J = 3.8 Hz, 1H), 6.88 (d, J = 3.7 Hz, 1H), 3.77-3.46 (m, 4H), 2.88-2.78 (m, 1H), 2.13-2.01 (m, 4H), 1.06-0.99 (m, 4H). |
| MF-DH-485 | 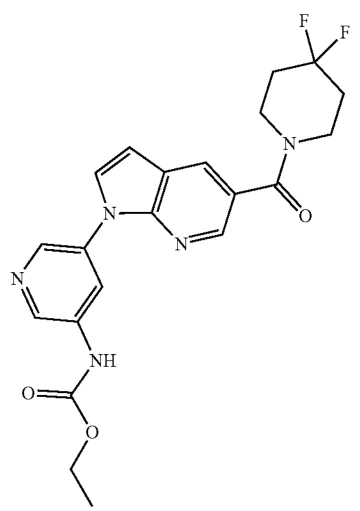 [SMILES: CCOC(=O)Nc1cncc(-n2ccc3cc(C(=O)N4CCC(F)(F)CC4)cnc32)c1] | 64.6%/ 99.52% | 429.16 for C21H19F2N5O3/ 430.2 (M + 1) | δ 10.14-10.10 (m, 1H), 8.70 (d, J = 2.3 Hz, 1H), 8.62 (d, J = 2.2 Hz, 1H), 8.53 (s, 1H), 8.43 (d, J = 2.0 Hz, 1H), 8.24 (d, J = 2.0 Hz, 1H), 8.07 (d, J = 3.7 Hz, 1H), 6.86 (d, J = 3.7 Hz, 1H), 4.18 (d, J = 7.1 Hz, 2H), 3.76-3.49 (m, 4H), 2.15-2.02 (m, 4H), 1.27 (t, J = 7.1 Hz, 3H). |
| MF-DH-486 | 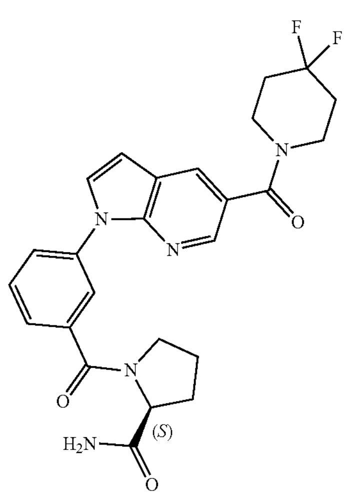 | 23.4%/ 99.55% | 481.19 for C25H25F2N5O3/ 482.3 (M + 1) | δ 8.44 (d, J = 1.8 Hz, 1H), 8.23 (d, J = 1.8 Hz, 1H), 8.15-7.97 (m, 3H), 7.68-7.54 (m, 2H), 7.44-7.31 (m, 1H), 6.99-6.96 (m, 1H), 6.85-6.81 (m, 1H), 4.42-4.24 (m, 1H), 3.74-3.46 (m, 6H), 2.24-2.02 (m, 5H), 1.93-1.76 (m, 3H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-487 | 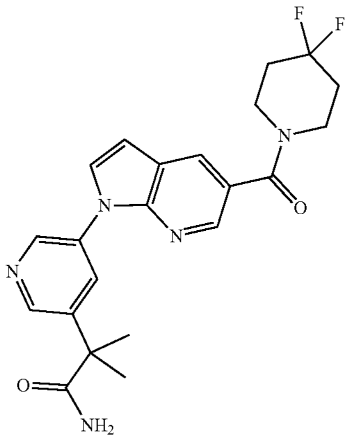 [SMILES: CC(C)(C(N)=O)c1cncc(-n2ccc3cc(C(=O)N4CCC(F)(F)CC4)cnc32)c1] | 41.8%/ 99.22% | 427.18 for C22H23F2N5O2/ 428.2 (M + 1) | δ 9.04-8.99 (m, 1H), 8.58-8.53 (m, 1H), 8.47-8.40 (m, 1H), 8.27-8.20 (m, 2H), 8.16-8.12 (m, 1H), 7.17-7.03 (m, 2H), 6.89-6.85 (m, 1H), 3.79-3.54 (m, 4H), 2.13-2.04 (m, 4H), 1.58-1.55 (m, 6H). |
| MF-DH-489 | 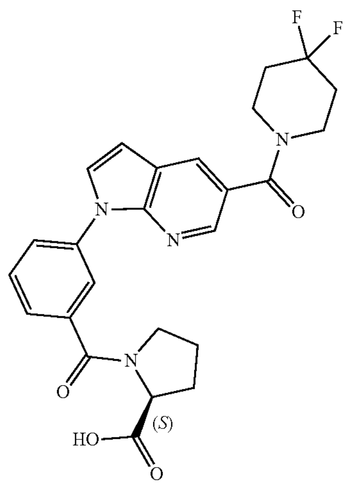 | 17.5%/ 96.47% | 482.18 for C25H24F2N4O4/ 483.2 (M + 1) | δ 12.77-12.14 (m, 1H), 8.44 (d, J = 2.0 Hz, 1H), 8.23 (d, J = 1.8 Hz, 1H), 8.14-8.06 (m, 2H), 7.99 (br d, J = 8.3 Hz, 1H), 7.69-7.62 (m, 1H), 7.54-7.48 (m, 1H), 6.83 (d, J = 3.7 Hz, 1H), 4.47-4.40 (m, 1H), 3.77-3.51 (m, 6H), 2.14-2.01 (m, 4H), 1.98-1.83 (m, 3H). |
| MF-DH-495 | 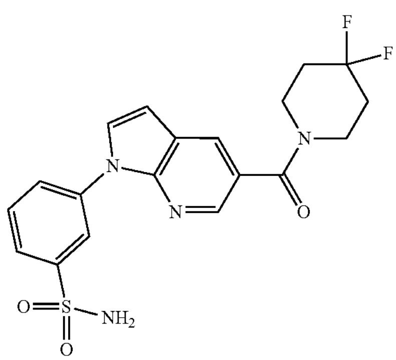 [SMILES: NS(=O)(=O)c1cccc(-n2ccc3cc(C(=O)N4CCC(F)(F)CC4)cnc32)c1] | 8.1%/ 95.00% | 420.11 for C18H18F2N4O2/ 421.1 (M + 1) | δ 8.46-8.41 (m, 2H), 8.25 (d, J = 2.1 Hz, 1H), 8.14-8.08 (m, 2H), 7.84-7.75 (m, 2H), 7.50 (s, 2H), 6.87 (d, J = 3.6 Hz, 1H), 3.77-3.53 (m, 4H), 2.15-1.99 (m, 4H). |

TABLE 3-continued

Analytical data for select inhibitors

| Target No | Structure | Yield/ Purity | Mass Spec. Calculated/ Mass Spec. Found (m/z) | ¹H NMR (DMSO-d₆*, 400 MHz) (*unless otherwise indicated) |
|---|---|---|---|---|
| MF-DH-496 | 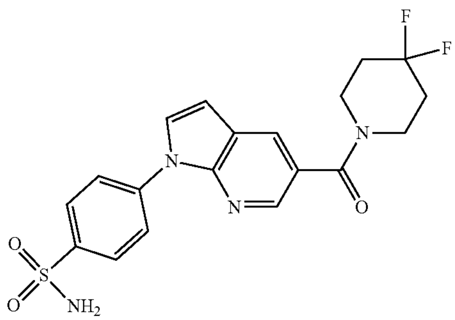 [SMILES: NS(=O)(=O)c1ccc(-n2ccc3cc(C(=O)N4CCC(F)(F)CC4)cnc32)cc1] | 12.2%/ 99.75% | 420.11 for C18H18F2N4O2/ 421.1 (M + 1) | δ 8.46 (d, J = 2.0 Hz, 1H), 8.24 (d, J = 2.0 Hz, 1H), 8.21-8.15 (m, 3H), 7.99 (d, J = 8.8 Hz, 2H), 7.44 (s, 2H), 6.88 (d, J = 3.7 Hz, 1H), 3.76-3.49 (m, 4H), 2.15-2.02 (m, 4H). |
| MF-DH-497 | 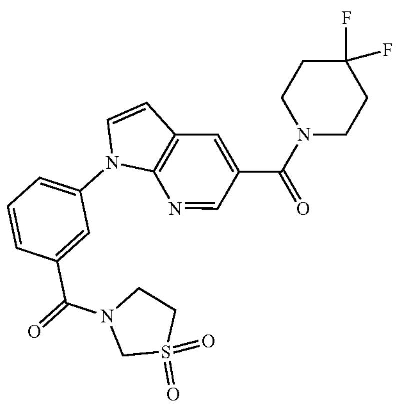 [SMILES: O=C(c1cnc2c(ccn2-c2cccc(C(=O)N3CCS(=O)(=O)C3)c2)c1)N1CCC(F)(F)CC1] | 21.0%/ 99.02% | 488.13 for C23H22F2N4O4S/ 489.1 (M + 1) | δ 8.46 (d, J = 2.0 Hz, 1H), 8.25 (d, J = 2.0 Hz, 1H), 8.16 (br d, J = 3.7 Hz, 3H), 7.74-7.68 (m, 1H), 7.58-7.53 (m, 1H), 6.86 (d, J = 3.7 Hz, 1H), 4.77 (s, 2H), 4.16-4.09 (m, 2H), 3.77-3.57 (m, 4H), 3.52 (t, J = 7.2 Hz, 2H), 2.14-2.04 (m, 4H). |
| MF-DH-498 | 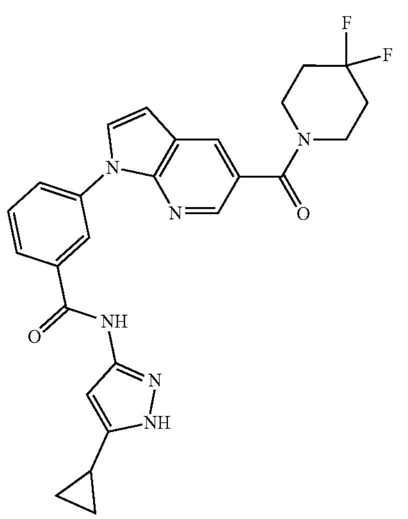 [SMILES: O=C(Nc1cc(C2CC2)[nH]n1)c1cccc(-n2ccc3cc(C(=O)N4CCC(F)(F)CC4)cnc32)c1] | 44.0%/ 99.46% | 490.19 for C26H24F2N6O2/ 491.2 (M + 1) | δ 8.49-8.42 (m, 2H), 8.24 (d, J = 2.1 Hz, 1H), 8.11 (br d, J = 3.4 Hz, 2H), 7.96-7.91 (m, 1H), 7.72-7.67 (m, 1H), 6.85 (d, J = 3.7 Hz, 1H), 6.70 (s, 2H), 3.74-3.49 (m, 4H), 2.14-2.01 (m, 4H), 1.77-1.69 (m, 1H), 0.88-0.81 (m, 2H), 0.68-0.62 (m, 2H). |

TABLE 3-continued

Analytical data for select inhibitors

| Target No | Structure | Yield/ Purity | Mass Spec. Calculated/ Mass Spec. Found (m/z) | ¹H NMR (DMSO-d₆*, 400 MHz) (*unless otherwise indicated) |
|---|---|---|---|---|
| MF-DH-499 | 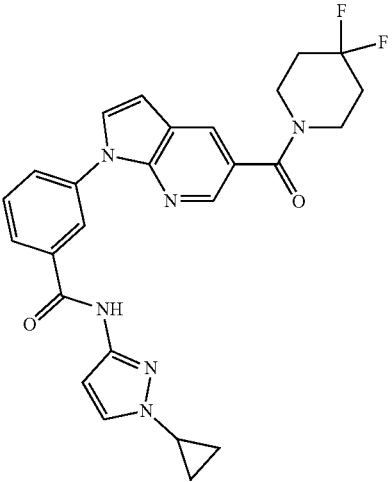 [SMILES: O=C(Nc1ccn(C2CC2)n1)c1cccc(-n2ccc3cc(C(=O)N4CCC(F)(F)CC4)cnc32)c1] | 53.7%/ 99.19% | 490.19 for C26H24F2N6O2/ 491.2 (M + 1) | δ 11.07-10.99 (m, 1H), 8.48-8.41 (m, 2H), 8.28-8.16 (m, 3H), 8.00-7.94 (m, 1H), 7.74-7.65 (m, 2H), 6.89-6.83 (m, 1H), 6.67-6.58 (m, 1H), 3.77-3.59 (m, 5H), 2.16-2.04 (m, 4H), 1.07-1.00 (m, 2H), 0.97-0.92 (m, 2H). |
| MF-DH-500 | 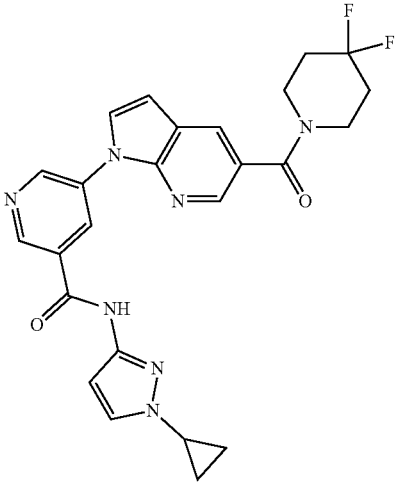 [SMILES: O=C(Nc1ccn(C2CC2)n1)c1cncc(-n2ccc3cc(C(=O)N4CCC(F)(F)CC4)cnc32)c1] | 46.0%/ 99.61% | 491.19 for C25H23F2N7O2/ 492.2 (M + 1) | δ 11.26 (s, 1H), 9.41 (d, J = 2.3 Hz, 1H), 9.09 (d, J = 1.6 Hz, 1H), 8.90-8.86 (m, 1H), 8.49 (d, J = 1.8 Hz, 1H), 8.29-8.24 (m, 2H), 7.75 (d, J = 2.2 Hz, 1H), 6.92 (d, J = 3.7 Hz, 1H), 6.66 (d, J = 2.2 Hz, 1H), 3.68 (br dd, J = 7.3, 3.5 Hz, 5H), 2.08 (br s, 4H), 1.03 (br d, J = 3.8 Hz, 2H), 0.99-0.93 (m, 2H). |
| MF-DH-501 | 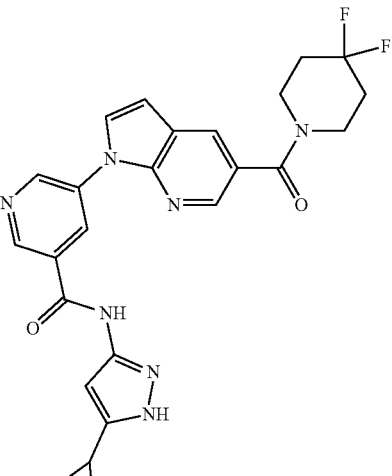 | 23.9%/ 92.56% | 491.19 for C24H29F2N5O3/ 492.2 (M + 1) | δ 9.32 (d, J = 2.6 Hz, 1H), 9.06 (d, J = 1.7 Hz, 1H), 8.94 (t, J = 2.1 Hz, 1H), 8.47 (d, J = 1.8 Hz, 1H), 8.29-8.25 (m, 1H), 8.24-8.20 (m, 1H), 6.91 (d, J = 3.7 Hz, 1H), 6.76 (s, 2H), 5.18 (s, 1H), 3.81-3.49 (m, 4H), 2.13-2.03 (m, 4H), 1.80-1.71 (m, 1H), 0.88-0.83 (m, 2H), 0.70-0.66 (m, 2H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-502 | 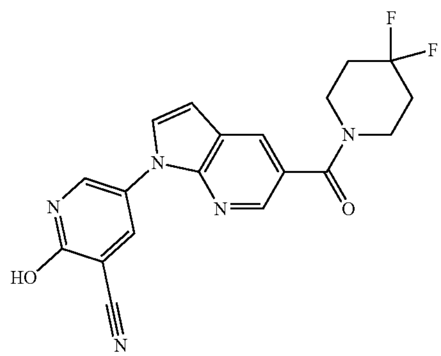 [SMILES: N#Cc1cc(-n2ccc3cc(C(=O)N4CCC(F)(F)CC4)cnc32)cnc1O] | 3.5%/ 96.91% | 483.12 for C19H15F2N5O2/ 383.95 (M + 1) | δ 13.13-12.91 (m, 1H), 8.64 (s, 1H), 8.41 (d, J = 1.6 Hz, 2H), 8.21 (d, J = 1.7 Hz, 1H), 7.93 (br s, 1H), 6.77 (d, J = 3.5 Hz, 1H), 3.84-3.51 (m, 4H), 2.12-2.00 (m, 4H). |
| MF-DH-507 | 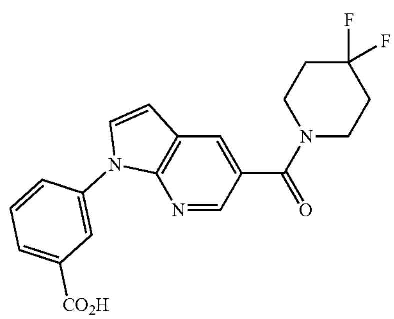 [SMILES: O=C(O)c1cccc(-n2ccc3cc(C(=O)N4CCC(F)(F)CC4)cnc32)c1] | 62.5%/ 97.07% | 385.12 for C20H17F2N3O3/ 386.1 (M + 1) | δ 13.39-12.96 (m, 1H), 8.50-8.48 (m, 1H), 8.48-8.43 (m, 1H), 8.23 (d, J = 2.0 Hz, 1H), 8.14-8.12 (m, 1H), 7.97-7.91 (m, 1H), 7.70 (t, J = 7.9 Hz, 1H), 6.84 (d, J = 3.7 Hz, 1H), 3.76-3.51 (m, 4H), 2.13-2.02 (m, 4H). |
| MF-DH-508 | 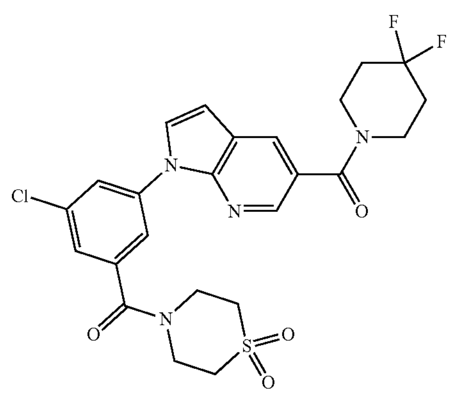 [SMILES: O=C(c1cnc2c(ccn2-c2cc(Cl)cc(C(=O)N3CCS(=O)(=O)CC3)c2)c1)N1CCC(F)(F)CC1] | 21.8%/ 99.24% | 536.11 for C24H23ClF2N4O4S/ 537.2 (M + 1) | δ 8.48 (d, J = 2.0 Hz, 1H), 8.24 (d, J = 1.9 Hz, 2H), 8.19-8.10 (m, 2H), 7.60-7.56 (m, 1H), 6.87 (d, J = 3.8 Hz, 1H), 4.11-3.94 (m, 2H), 3.86-3.46 (m, 6H), 3.39-3.31 (m, 4H), 2.14-2.02 (m, 4H). |
| MF-DH-509 | 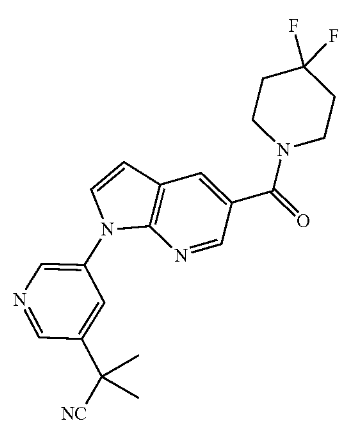 [SMILES: CC(C)(C#N)c1cncc(-n2ccc3cc(C(=O)N4CCC(F)(F)CC4)cnc32)c1] | 44.5%/ 98.82% | 409.17 for C22H21F2N5O/ 409.95 (M + 1) | δ 9.20 (d, J = 2.2 Hz, 1H), 8.77 (d, J = 2.1 Hz, 1H), 8.48-8.44 (m, 2H), 8.27-8.24 (m, 1H), 8.22-8.19 (m, 1H), 6.89 (d, J = 3.7 Hz, 1H), 3.79-3.49 (m, 4H), 2.15-2.02 (m, 4H), 1.82 (s, 6H). |

TABLE 3-continued

Analytical data for select inhibitors

| Target No | Structure | Yield/Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-514 | 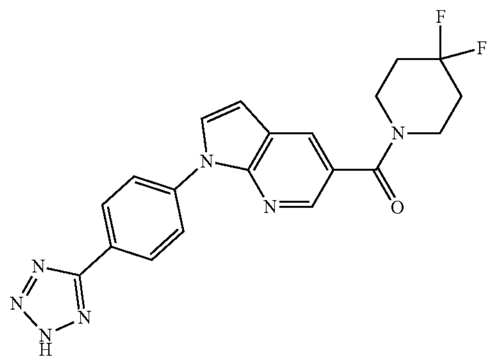 [SMILES: O=C(c1cnc2c(ccn2-c2ccc(-c3nn[nH]n3)cc2)c1)N1CCC(F)(F)CC1] | 23.5%/ 99.40% | 409.15 for C20H17F2N7O/ 410.1 (M + 1) | δ 8.47 (d, J = 2.0 Hz, 1H), 8.28-8.19 (m, 5H), 6.88 (d, J = 3.8 Hz, 1H), 3.79-3.53 (m, 4H), 2.15-2.02 (m, 4H). |
| MF-DH-515 | 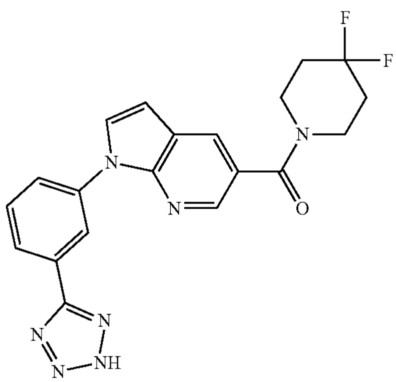 [SMILES: O=C(c1cnc2c(ccn2-c2cccc(-c3nn[nH]n3)c2)c1)N1CCC(F)(F)CC1] | 3.5%/ 99.37% | 409.15 for C20H17F2N7O/ 410.1 (M + 1) | δ 8.51 (t, J = 1.6 Hz, 1H), 8.45 (d, J = 2.0 Hz, 1H), 8.24 (d, J = 2.0 Hz, 1H), 8.10 (d, J = 3.6 Hz, 1H), 8.01 (d, J = 7.8 Hz, 1H), 7.92-7.85 (m, 1H), 7.67 (t, J = 7.9 Hz, 1H), 7.15-7.00 (m, 1H), 6.85 (d, J = 3.6 Hz, 1H), 3.74-3.57 (m, 4H), 2.14-2.02 (m, 4H). |
| MF-DH-516 | 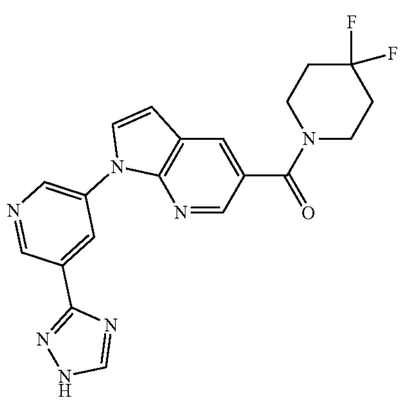 [SMILES: O=C(c1cnc2c(ccn2-c2cncc(-c3nc[nH]n3)c2)c1)N1CCC(F)(F)CC1] | 8.1%/ 91.09% | 409.15 for C20H17F2N7O/ 410.1 (M + 1) | δ 9.19-9.13 (m, 2H), 8.99-8.95 (m, 1H), 8.64-8.60 (m, 1H), 8.50-8.46 (m, 1H), 8.27-8.24 (m, 2H), 6.91-6.88 (m, 1H), 5.77-5.74 (m, 1H), 3.70-3.59 (m, 4H), 2.13-2.05 (m, 4H). |
| MF-DH-521 | 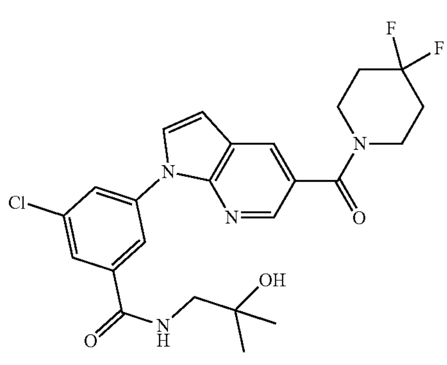 [SMILES: CC(C)(O)CNC(=O)c1cc(Cl)cc(-n2ccc3cc(C(=O)N4CCC(F)(F)CC4)cnc32)c1] | 4.8%/ 98.07% | 490.16 for C20H17F2N7O/ 491.1 (M + 1) | δ 8.57-8.51 (m, 1H), 8.48 (d, J = 2.0 Hz, 1H), 8.33 (br d, J = 5.9 Hz, 2H), 8.20 (d, J = 3.8 Hz, 1H), 7.92-7.89 (m, 1H), 7.73-7.67 (m, 1H), 6.89-6.86 (m, 1H), 4.54 (s, 1H), 3.76-3.54 (m, 4H), 3.29-3.25 (m, 2H), 2.16-2.03 (m, 4H), 1.15-1.11 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-527 | 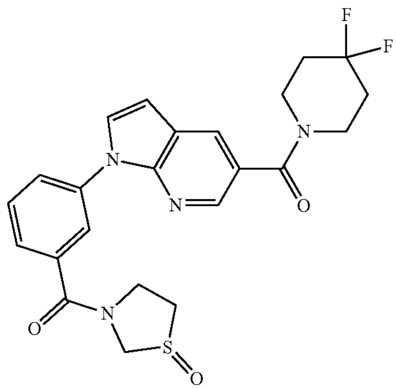 [SMILES: O=C(c1cnc2c(ccn2-c2cccc(C(=O)N3CCS(=O)C3)c2)c1)N1CCC(F)(F)CC1] | 11.0%/ 99.12% | 472.14 for C23H22F2N4O3S/ 491.1 (M + 1) | δ 8.47 (d, J = 2.0 Hz, 1H), 8.25 (d, J = 2.1 Hz, 1H), 8.19-8.12 (m, 2H), 8.10-8.05 (m, 1H), 7.72-7.67 (m, 1H), 7.59-7.51 (m, 1H), 6.86 (d, J = 3.7 Hz, 1H), 4.93-4.64 (m, 1H), 4.60-4.54 (m, 1H), 4.48-3.93 (m, 4H), 3.89-3.76 (m, 4H), 2.16-2.02 (m, 4H). |
| MF-DH-124 | 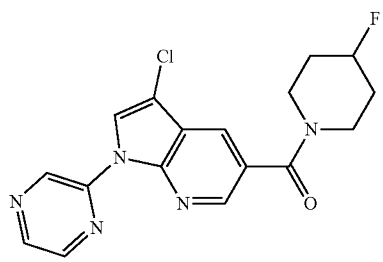 [SMILES: O=C(c1cnc2c(c1)c(Cl)cn2-c1cnccn1)N1CCC(F)CC1] | 8.5%/ 99.91% | 359.09 for C17H15ClFN5O/ 360.0 (M + 1) | δ 10.02 (d, J = 0.9 Hz, 1H), 8.67-8.64 (m, 2H), 8.62-8.60 (m, 1H), 8.59-8.57 (m, 1H), 8.20 (d, J = 2.0 Hz, 1H), 5.04-4.85 (m, 1H), 3.84-3.44 (m, 4H), 2.06-1.74 (m, 4H). |
| MF-DH-166 | 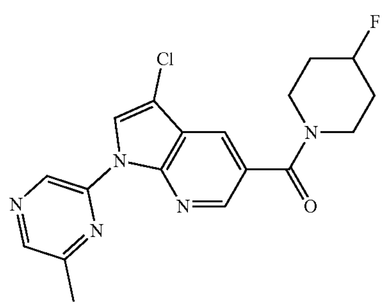 [SMILES: Cc1cncc(-n2cc(Cl)c3cc(C(=O)N4CCC(F)CC4)cnc32)n1] | 49.1%/ 95.19% | 373.11 for C18H17ClFN5O/ 374.0 (M + 1) | δ 9.80 (s, 1H), 8.60 (d, J = 1.8 Hz, 1H), 8.57-8.51 (m, 2H), 8.19 (d, J = 2.0 Hz, 1H), 5.05-4.84 (m, 1H), 3.82-3.38 (m, 4H), 2.58 (s, 3H), 2.04-1.71 (m, 4H). |
| MF-DH-169 | 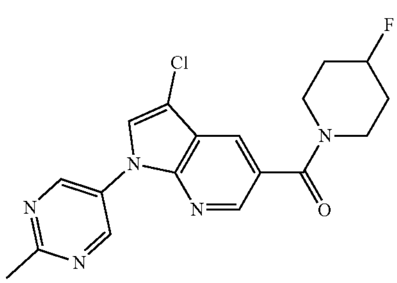 [SMILES: Cc1ncc(-n2cc(Cl)c3cc(C(=O)N4CCC(F)CC4)cnc32)cn1] | 51.1%/ 99.91% | 373.11 for C18H17ClFN5O/ 374.0 (M + 1) | δ 9.26 (s, 2H), 8.51-8.49 (m, 1H), 8.46 (s, 1H), 8.17 (d, J = 2.0 Hz, 1H), 5.02-4.84 (m, 1H), 3.80-3.41 (m, 4H), 2.71 (s, 3H), 2.04-1.72 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-175 | 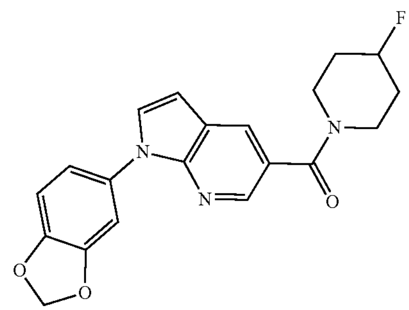 [SMILES: O=C(c1cnc2c(ccn2-c2ccc3c(c2)OCO3)c1)N1CCC(F)CC1] | 15.1%/ 99.0% | 367.13 for C20H18FN3O3/ 368.1 (M + 1) | δ 8.37-8.35 (m, 1H), 8.15 (s, 1H), 7.93 (d, J = 3.3 Hz, 1H), 7.46 (s, 1H), 7.28 (br d, J = 8.8 Hz, 1H), 7.08 (d, J = 8.2 Hz, 1H), 6.75 (d, J = 3.3 Hz, 1H), 6.12 (s, 2H), 5.00-4.86 (m, 1H), 3.78-3.38 (m, 4H), 2.00-1.72 (m, 4H). |
| MF-DH-178 | 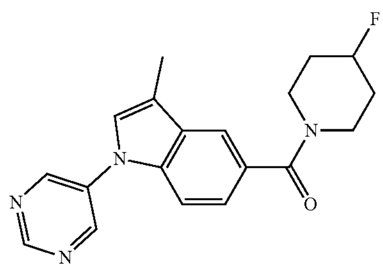 [SMILES: Cc1cn(-c2cncnc2)c2ccc(C(=O)N3CCC(F)CC3)cc12] | 16.1%/ 95.85% | 338.15 for C19H19FN4O/ 339.1 (M + 1) | δ 9.18 (s, 1H), 9.14 (s, 2H), 7.71-7.63 (m, 3H), 7.30-7.26 (m, 1H), 5.01-4.81 (m, 1H), 3.71-3.35 (m, 4H), 2.33 (d, J = 0.98 Hz, 3H), 1.99-1.81 (m, 2H), 1.79-1.65 (m, 2H). |
| MF-DH-180 | 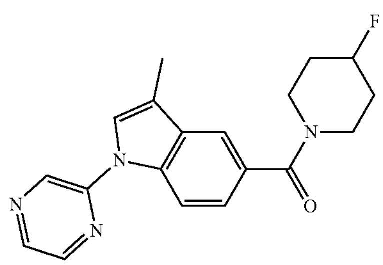 [SMILES: Cc1cn(-c2cnccn2)c2ccc(C(=O)N3CCC(F)CC3)cc12] | 9.1%/ 99.31% | 338.15 for C19H19FN4O/ 339.1 (M + 1) | δ 9.14 (d, J = 1.22 Hz, 1H), 8.59 (dd, J = 2.51, 1.53 Hz, 1H), 8.52-8.47 (m, 2H), 8.10-8.07 (m, 1H), 7.68 (d, J = 1.10 Hz, 1H), 7.36 (dd, J = 8.62, 1.53 Hz, 1H), 5.02, 4.83 (m, 1H), 3.76, 3.38 (m, 4H), 2.35 (d, J = 0.73 Hz, 3H), 2.01-1.66 (m, 4H). |
| MF-DH-181 | 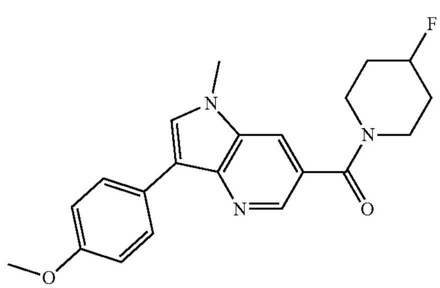 [SMILES: COc1ccc(-c2cn(C)c3cc(C(=O)N4CCC(F)CC4)cnc23)cc1] | 6.1%/ 99.94% | 367.17 for C21H22FN3O2/ 368.2 (M + 1) | δ 8.48 (d, J = 1.8 Hz, 1H), 8.19-8.10 (m, 3H), 8.03 (d, J = 1.7 Hz, 1H), 7.00 (d, J = 8.8 Hz, 2H), 5.03-4.84 (m, 1H), 3.89 (s, 3H), 3.80-3.76 (m, 3H), 3.72-3.43 (m, 4H), 2.03-1.71 (m, 4H). |
| MF-DH-186 | 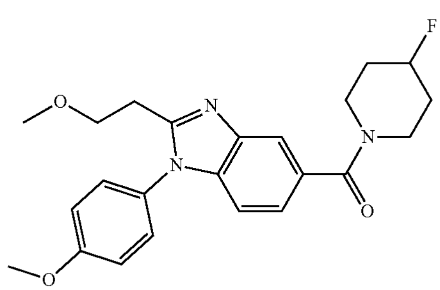 | 10.6%/ 99.77% | 411.20 for C23H26FN3O3/ 412.1 (M + 1) | δ 7.81 (s, 1H), 7.54 (d, J = 8.8 Hz, 2H), 7.51-7.33 (m, 1H), 7.23 (dd, J = 8.7, 2.8 Hz, 3H), 5.01-4.85 (m, 1H), 3.88 (s, 3H), 3.73-3.67 (m, 2H), 3.67-3.31 (m, 4H), 3.20 (s, 3H), 3.17-3.02 (m, 2H), 2.00-1.66 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-187 | 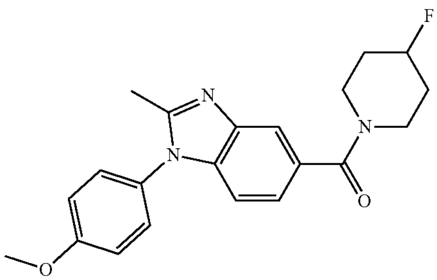 [SMILES: COc1ccc(-n2c(C)nc3cc(C(=O)N4CCC(F)CC4)ccc32)cc1] | 61.9%/ 99.32% | 367.17 for C21H22FN3O2/ 368.1 (M + 1) | δ 7.81 (s, 1H), 7.54 (d, J = 8.8 Hz, 2H), 7.41-7.19 (m, 4H), 5.00-4.85 (m, 1H), 3.88 (s, 3H), 3.75-3.58 (m, 4H), 3.20 (s, 3H), 1.99-1.68 (m, 4H). |
| MF-DH-189 | 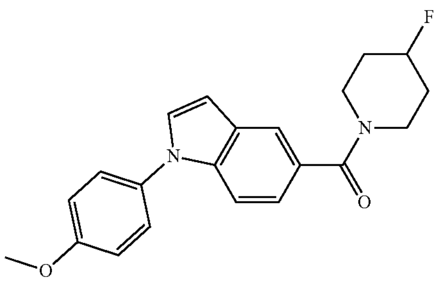 | 12.6%/ 99.27% | 352.16 for C21H21FN2O2/ 353.1 (M + 1) | δ 7.73 (s, 1H), 7.65 (d, J = 3.2 Hz, 1H), 7.55-7.43 (m, 3H), 7.28-7.18 (m, 1H), 7.14 (d, J = 8.9 Hz, 2H), 6.73 (d, J = 3.2 Hz, 1H), 5.00-4.83 (m, 1H), 3.84 (s, 3H), 3.70-3.36 (m, 4H), 1.99-1.65 (m, 4H). |
| MF-DH-190 | 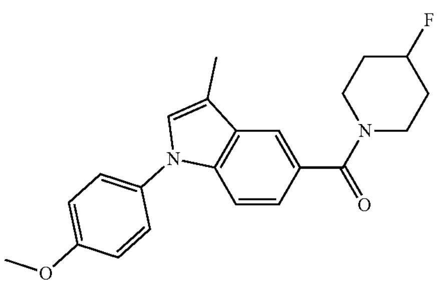 [SMILES: COc1ccc(-n2cc(C)c3cc(C(=O)N4CCC(F)CC4)ccc32)cc1] | 28.2%/ 99.47% | 366.17 for C22H23FN2O2/ 367.2 (M + 1) | δ 7.66 (s, 1H), 7.49-7.41 (m, 4H), 7.22 (br d, J = 8.4 Hz, 1H), 7.12 (br d, J = 8.9 Hz, 2H), 5.01-4.83 (m, 1H), 3.83 (s, 3H), 3.70-3.46 (m, 4H), 2.33 (s, 3H), 1.99-1.69 (m, 4H). |
| MF-DH-193 | 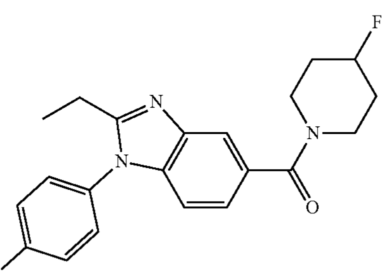 | 35.1%/ 95.66% | 381.19 for C22H24FN3O2/ 382.1 (M + 1) | δ 7.68 (s, 1H), 7.47 (d, J = 8.80 Hz, 2H), 7.23 (dd, J = 8.19, 1.10 Hz, 1H), 7.21-7.14 (m, 2H), 7.14-7.04 (m, 1H), 5.01-4.82 (m, 1H), 3.86 (s, 3H), 3.70-3.36 (m, 4H), 2.72 (q, J = 7.54 Hz, 2H), 2.01-1.82 (m, 2H), 1.73 (br s, 2H), 1.24 (t, J = 7.46 Hz, 3H). |
| MF-DH-199 | 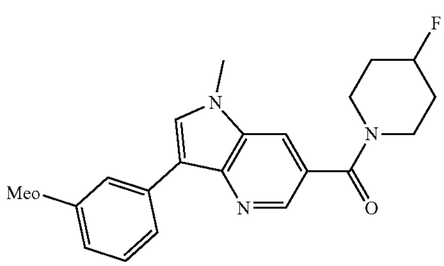 | 17.1%/ 91.40% | 367.17 for C21H22FN3O2/ 368.1 (M + 1) | δ 8.51 (d, J = 1.34 Hz, 1H), 8.31 (s, 1H), 8.05 (d, J = 1.47 Hz, 1H), 7.87-7.78 (m, 2H), 7.32 (t, J = 7.95 Hz, 1H), 6.79 (dd, J = 8.13, 2.14 Hz, 1H), 5.04-4.85 (m, 1H), 3.90 (s, 3H), 3.81 (s, 3H), 3.75-3.44 (m, 4H), 2.03-1.70 (m, 4H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-200 | 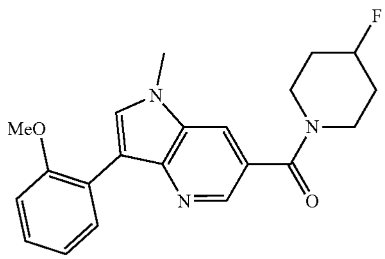 [SMILES: COc1ccccc1-c1cn(C)c2cc(C(=O)N3CCC(F)CC3)cnc12] | 27.1%/ 99.91% | 367.17 for C21H22FN3O2/ 368.1 (M + 1) | δ 8.57 (s, 1H), 8.52-8.40 (m, 1H), 8.37 (s, 1H), 8.34-8.25 (m, 1H), 7.28 (br d, J = 7.34 Hz, 1H), 7.13 (d, J = 8.19 Hz, 1H), 7.06 (t, J = 7.40 Hz, 1H), 5.04-4.87 (m, 1H), 3.97 (s, 3H), 3.88 (s, 3H), 3.79-3.51 (m, 4H), 2.04-1.72 (m, 4H). |
| MF-DH-204 | 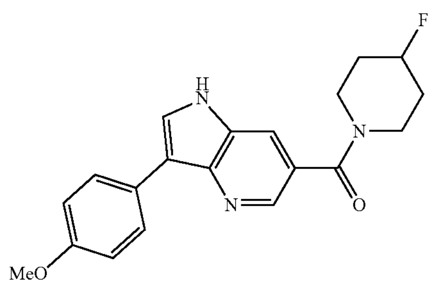 [SMILES: COc1ccc(-c2c[nH]c3cc(C(=O)N4CCC(F)CC4)cnc23)cc1] | 17.1%/ 97.52% | 353.15 for C20H20FN3O2/ 354.1 (M + 1) | δ 11.89 (br s, 1H), 8.51 (d, J = 1.47 Hz, 1H), 8.23 (d, J = 2.69 Hz, 1H), 8.09 (br d, J = 8.68 Hz, 2H), 8.06-7.96 (m, 1H), 7.01 (d, J = 8.80 Hz, 2H), 4.99-4.88 (m, 1H), 3.79 (s, 3H), 3.73-3.51 (m, 4H), 2.02-1.87 (m, 2H), 1.77 (br d, J = 2.08 Hz, 2H). |
| MF-DH-206 | 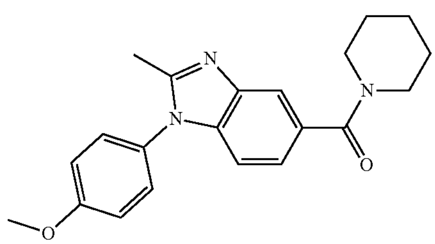 [SMILES: COc1ccc(-n2c(C)nc3cc(C(=O)N4CCCCC4)ccc32)cc1] | 16.1%/ 99.65% | 349.18 for C21H23N3O2/ 350.2 (M + 1) | δ 7.59 (s, 1H), 7.54-7.42 (m, 2H), 7.21-7.15 (m, 3H), 7.12-7.06 (m, 1H), 3.86 (s, 3H), 3.72-3.32 (m, 4H), 2.41 (s, 3H), 1.70-1.42 (m, 6H). |
| MF-DH-237 | 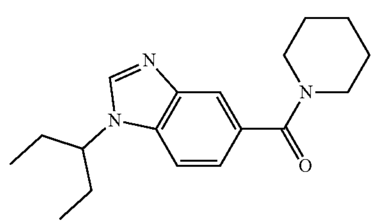 [SMILES: CCC(CC)n1cnc2cc(C(=O)N3CCCCC3)ccc21] | 3.3%/ 99.58% | 299.20 for C18H25N3O/ 300.3 (M + 1) | δ 9.29 (s, 1H), 7.99 (d, J = 8.4 Hz, 1H), 7.80 (s, 1H), 7.47 (dd, J = 8.4, 1.2 Hz, 1H), 4.55 (br t, J = 7.2 Hz, 1H), 3.70-3.21 (m, 4H), 2.04-1.95 (m, 4H), 1.66-1.37 (m, 6H), 0.79-0.70 (m, 6H). |
| MF-DH-242 | 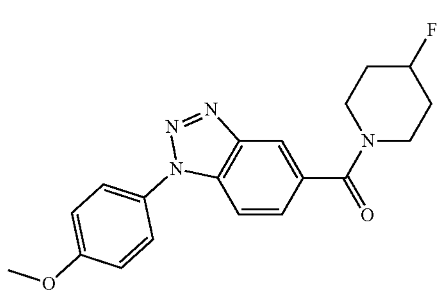 [SMILES: COc1ccc(-n2nnc3cc(C(=O)N4CCC(F)CC4)ccc32)cc1] | 52.1%/ 99.77% | 354.15 for C18H19FN4O2/ 355.1 (M + 1) | δ 8.23 (s, 1H), 7.87 (d, J = 8.6 Hz, 1H), 7.79 (d, J = 8.9 Hz, 2H), 7.66 (dd, J = 8.6, 1.2 Hz, 1H), 7.24 (d, J = 8.9 Hz, 2H), 5.03-4.85 (m, 1H), 3.88 (s, 3H), 3.80-3.35 (m, 4H), 2.02-1.68 (m, 4H). |

TABLE 3-continued

Analytical data for select inhibitors

| Target No | Structure | Yield/ Purity | Mass Spec. Calculated/ Mass Spec. Found (m/z) | ¹H NMR (DMSO-d₆*, 400 MHz) (*unless otherwise indicated) |
|---|---|---|---|---|
| MF-DH-243 | 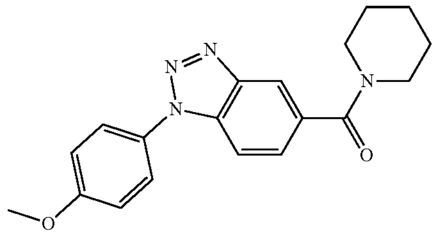 [SMILES: COc1ccc(-n2nnc3cc(C(=O)N4CCCCC4)ccc32)cc1] | 24.1%/ 99.17% | 336.16 for C19H21FN4O/ 337.2 (M + 1) | δ 8.17 (s, 1H), 7.86 (d, J = 8.6 Hz, 1H), 7.79 (d, J = 8.9 Hz, 2H), 7.62 (dd, J = 8.6, 1.2 Hz, 1H), 7.24 (d, J = 8.9 Hz, 2H), 3.88 (s, 3H), 3.75-3.34 (m, 4H), 1.70-1.44 (m, 6H). |
| MF-DH-245 | 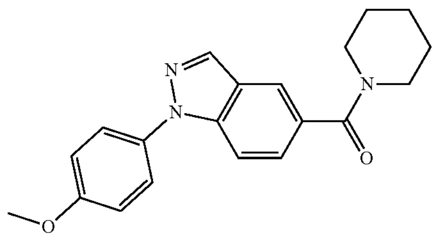 [SMILES: COc1ccc(-n2ncc3cc(C(=O)N4CCCCC4)ccc32)cc1] | 48.2%/ 98.74% | 335.16 for C20H21N3O2/ 336.2 (M + 1) | δ 8.39 (s, 1H), 7.91 (s, 1H), 7.75-7.63 (m, 3H), 7.46 (dd, J = 8.7, 1.3 Hz, 1H), 7.15 (d, J = 8.9 Hz, 2H), 3.85 (s, 3H), 3.66-3.34 (m, 4H), 1.67-1.48 (m, 6H). |
| MF-DH-246 | 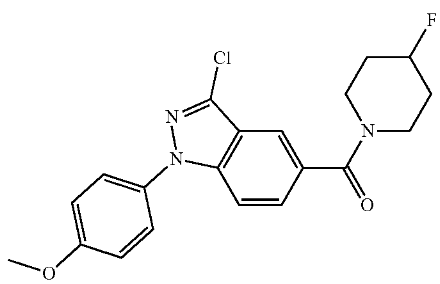 [SMILES: COc1ccc(-n2nc(Cl)c3cc(C(=O)N4CCC(F)CC4)ccc32)cc1] | 38.8%/ 97.11% | 387.11 for C20H19ClFN3O2/ 388.1 (M + 1) | δ 7.84 (s, 1H), 7.76 (d, J = 8.8 Hz, 1H), 7.68-7.63 (m, 2H), 7.63-7.57 (m, 1H), 7.16 (br d, J = 8.9 Hz, 2H), 5.03-4.84 (m, 1H), 3.85 (s, 3H), 3.72-3.34 (m, 4H), 2.02-1.66 (m, 4H). |
| MF-DH-247 | 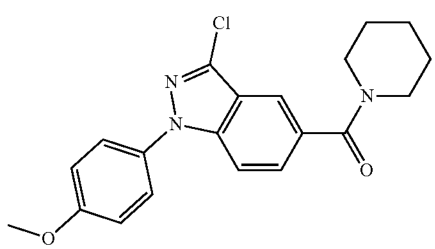 [SMILES: COc1ccc(-n2nc(Cl)c3cc(C(=O)N4CCCCC4)ccc32)cc1] | 58.4%/ 95.80% | 369.12 for C20H20ClN3O2/ 370.1 (M + 1) | δ 781-7.79 (m, 2H), 7.71-7.62 (m, 2H), 7.58-7.53 (m, 1H), 7.18-7.12 (m, 2H), 3.82 (s, 3H), 3.73-3.34 (m, 4H), 1.71-1.42 (m, 6H). |
| MF-DH-249 | 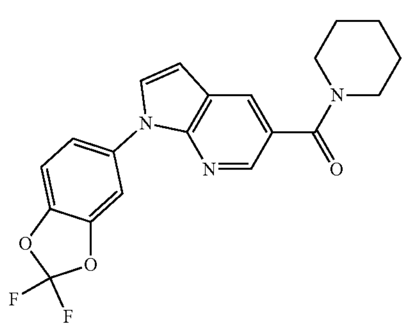 [SMILES: O=C(c1cnc2c(ccn2-c2ccc3c(c2)OC(F)(F)O3)c1)N1CCCCC1] | 10.1%/ 98.21% | 385.12 for C20H17F2N3O3/ 386.2 (M + 1) | δ 8.35 (s, 1H), 8.13 (s, 1H), 8.05-7.98 (m, 2H), 7.78-7.76 (m, 1H), 7.62-7.58 (m, 1H), 6.81 (s, 1H), 3.70-3.35 (m, 4H), 1.68-1.48 (m, 6H). |

TABLE 3-continued

Analytical data for select inhibitors

| Target No | Structure | Yield/ Purity | Mass Spec. Calculated/ Mass Spec. Found (m/z) | ¹H NMR (DMSO-d₆*, 400 MHz) (*unless otherwise indicated) |
|---|---|---|---|---|
| MF-DH-271 | 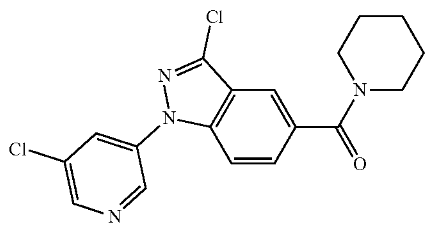 | 26.7%/ 95.09% | 374.07 for C18H16Cl2N4O/ 375.0 (M + 1) | δ 9.03 (d, J = 1.8 Hz, 1H), 8.75-8.71 (m, 1H), 8.42 (s, 1H), 8.05 (d, J = 8.8 Hz, 1H), 7.83 (s, 1H), 7.64 (br d, J = 8.7 Hz, 1H), 3.71-3.34 (m, 4H), 1.68-1.49 (m, 6H). |
| MF-DH-272 | 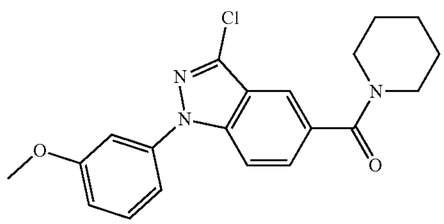 [SMILES: COc1cccc(-n2nc(Cl)c3cc(C(=O)N4CCCCC4)ccc32)c1] | 51.1%/ 98.82% | 369.12 for C20H20ClN3O2/ 370.2 (M + 1) | δ 7.92 (d, J = 8.8 Hz, 1H), 7.79 (s, 1H), 7.62-7.49 (m, 2H), 7.36-7.26 (m, 2H), 7.04 (dd, J = 8.3, 2.3 Hz, 1H), 3.86 (s, 3H), 3.74-3.33 (m, 4H), 1.69-1.45 (m, 6H). |
| MF-DH-284 | 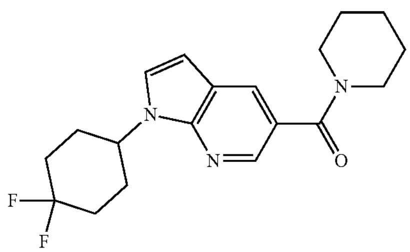 [SMILES: O=C(c1cnc2c(ccn2C2CCC(F)(F)CC2)c1)N1CCCCC1] | 6.6%/ 97.83% | 347.18 for C19H23F2N3O/ 348.2 (M + 1) | δ 8.29-8.27 (m, 1H), 8.00 (d, J = 1.9 Hz, 1H), 7.78-7.76 (m, 1H), 6.57-6.55 (m, 1H), 4.99-4.89 (m, 1H), 3.65-3.42 (m, 4H), 2.16 (br d, J = 19.6 Hz, 6H), 2.06-1.99 (m, 2H), 1.64-1.51 (m, 6H). |
| MF-DH-287 | 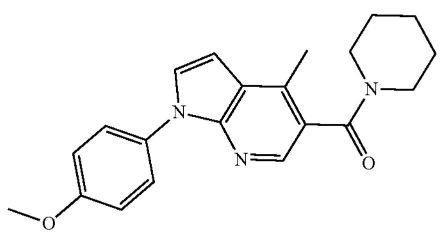 [SMILES: COc1ccc(-n2ccc3c(C)c(C(=O)N4CCCCC4)cnc32)cc1] | 60.4%/ 99.06% | 349.18 for C21H23N3O2/ 350.2 (M + 1) | δ 8.07 (s, 1H), 7.87 (d, J = 3.7 Hz, 1H), 7.73 (d, J = 8.9 Hz, 2H), 7.10 (d, J = 8.9 Hz, 2H), 6.81 (d, J = 3.7 Hz, 1H), 3.82 (s, 3H), 3.75-3.59 (m, 2H), 3.16 (br s, 2H), 2.47 (s, 3H), 1.60 (br s, 4H), 1.53-1.32 (m, 2H). |
| MF-DH-288 | 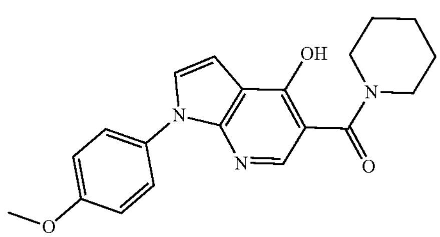 [SMILES: COc1ccc(-n2ccc3c(O)c(C(=O)N4CCCCC4)cnc32)cc1] | 15.1%/ 96.48% | 351.16 for C20H21N3O3/ 352.2 (M + 1) | δ 11.16-10.98 (m, 1H), 7.98-7.92 (m, 1H), 7.73-7.63 (m, 3H), 7.11-7.05 (m, 2H), 6.91-6.86 (m, 1H), 3.82 (s, 3H), 3.43 (br s, 4H), 1.64-1.51 (m, 6H). |
| MF-DH-289 | 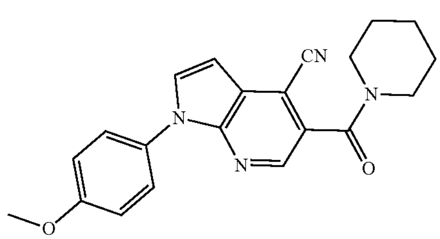 [SMILES: COc1ccc(-n2ccc3c(C#N)c(C(=O)N4CCCCC4)cnc32)cc1] | 37.1%/ 99.94% | 360.16 for C21H20N4O2/ 361.1 (M + 1) | δ 8.46 (s, 1H), 8.25 (d, J = 3.7 Hz, 1H), 7.70 (d, J = 8.9 Hz, 2H), 7.14 (d, J = 9.0 Hz, 2H), 6.94 (d, J = 3.7 Hz, 1H), 3.84 (s, 3H), 3.82-3.58 (m, 2H), 3.29-3.22 (m, 2H), 1.68-1.44 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-290 | 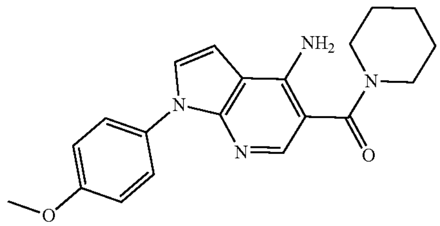 [SMILES: COc1ccc(-n2ccc3c(N)c(C(=O)N4CCCCC4)cnc32)cc1] | 39.9%/ 94.39% | 350.17 for C20H22N4O2/ 351.2 (M + 1) | δ 7.82-7.80 (m, 1H), 7.69 (d, J = 8.9 Hz, 2H), 7.50-7.48 (m, 1H), 7.06 (d, J = 9.0 Hz, 2H), 6.89-6.86 (m, 1H), 6.47-6.43 (m, 2H), 3.81 (s, 3H), 3.51-3.44 (m, 4H), 1.63-1.51 (m, 6H). |
| MF-DH-292 | 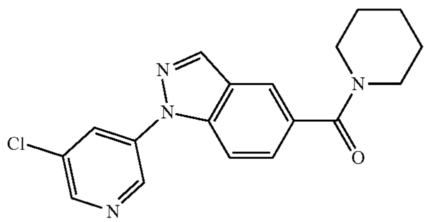 [SMILES: O=C(c1ccc2c(cnn2-c2cncc(Cl)c2)c1)N1CCCCC1] | 19.3%/ 99.93% | 340.11 for C18H17ClN4O/ 341.1 (M + 1) | δ 9.06 (d, J = 2.1 Hz, 1H), 8.69 (d, J = 2.0 Hz, 1H), 8.56 (s, 1H), 8.41 (br d, J = 2.1 Hz, 1H), 8.05-7.94 (m, 2H), 7.55 (br d, J = 8.7 Hz, 1H), 3.70-3.35 (m, 4H), 1.68-1.48 (m, 6H). |
| MF-DH-330 | 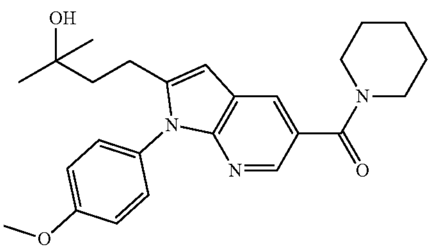 [SMILES: COc1ccc(-n2c(CCC(C)(C)O)cc3cc(C(=O)N4CCCCC4)cnc32)cc1] | 46.6%/ 99.04% | 421.24 for C25H31N3O3/ 422.3 (M + 1) | 1δ 8.12-8.08 (m, 1H), 7.93 (d, J = 1.9 Hz, 1H), 7.35 (d, J = 8.9 Hz, 2H), 7.11 (d, J = 8.9 Hz, 2H), 6.46 (s, 1H), 4.22 (s, 1H), 3.85 (s, 3H), 3.68-3.46 (m, 4H), 2.69-2.65 (m, 2H), 1.69-1.51 (m, 8H), 1.04 (s, 6H). |
| MF-DH-389 | 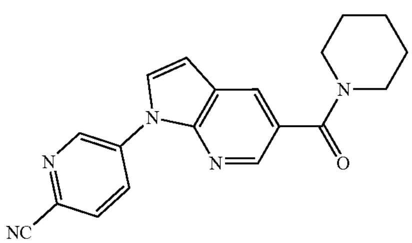 | 3.5%/ 99.81% | 331.14 for C19H17N5O/ 332.2 (M + 1) | δ 9.44-9.36 (m, 1H), 8.70 (dd, J = 8.5, 2.1 Hz, 1H), 8.32 (s, 1H), 8.24-8.12 (m, 2H), 8.12-8.04 (m, 1H), 6.84 (d, J = 3.7 Hz, 1H), 3.59-3.25 (m, 4H), 1.58-1.38 (m, 6H). |
| MF-DH-346 | 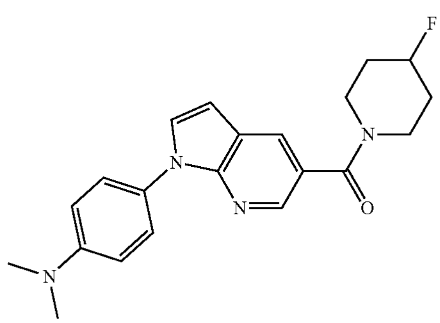 [SMILES: CN(C)c1ccc(-n2ccc3cc(C(=O)N4CCC(F)CC4)cnc32)cc1] | 34.2%/ 99.29% | 366.19 for C21H23FN4O/ 367.1 (M + 1) | δ 8.31 (s, 1H), 8.13 (s, 1H), 7.87-7.83 (m, 1H), 7.58-7.53 (m, 2H), 6.91-6.85 (m, 2H), 6.72 (s, 1H), 5.03-4.82 (m, 1H), 3.78-3.37 (m, 4H), 2.98 (s, 6H), 2.03-1.65 (m, 4H). |
| MF-DH-241 | 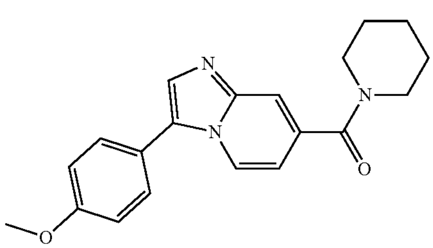 [SMILES: COc1ccc(-c2cnc3cc(C(=O)N4CCCCC4)ccn23)cc1] | 24.2%/ 89.16% | 335.16 for C20H21N3O2/ 336.2 (M + 1) | δ 8.48-8.46 (m, 1H), 7.78-7.76 (m, 1H), 7.66-7.56 (m, 3H), 7.14-7.01 (m, 2H), 6.94-6.92 (m, 1H), 3.84 (s, 3H), 3.68-3.35 (m, 4H), 1.67-1.42 (m, 6H). |

TABLE 3-continued

Analytical data for select inhibitors

| Target No | Structure | Yield/ Purity | Mass Spec. Calculated/ Mass Spec. Found (m/z) | $^1$H NMR (DMSO-d$_6$*, 400 MHz) (*unless otherwise indicated) |
|---|---|---|---|---|
| MF-DH-424 | 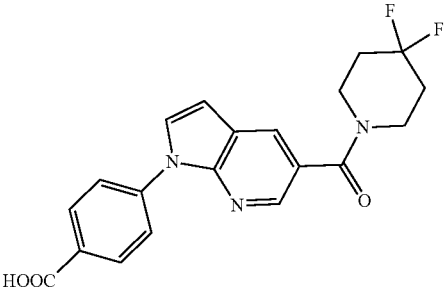 [SMILES: O=C(O)c1ccc(-n2ccc3cc(C(=O)N4CCC(F)(F)CC4)cnc32)cc1] | 47.3%/ 94.90% | 385.12 for C20H17F2N3O3/ 386.2 (M + 1) | δ 13.42-12.82 (m, 1H), 8.48-8.46 (m, 1H), 8.26-8.20 (m, 1H), 8.18-8.06 (m, 5H), 6.86-6.84 (m, 1H), 3.80-3.52 (m, 4H), 2.18-2.01 (m, 4H). |
| MF-DH-425 | 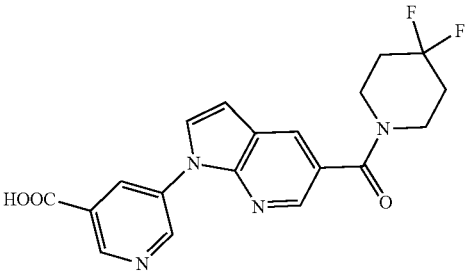 [SMILES: O=C(O)c1cncc(-n2ccc3cc(C(=O)N4CCC(F)(F)CC4)cnc32)c1] | 42.0%/ 98.59% | 386.12 for C19H16F2N4O3/ 387.2 (M + 1) | δ 13.82-13.42 (m, 1H), 9.34-9.32 (m, 1H), 9.04 (s, 1H), 8.88-8.86 (m, 1H), 8.48 (s, 1H), 8.28-8.22 (m, 2H), 6.90-6.88 (m, 1H), 3.82-3.52 (m, 4H), 2.18-2.01 (m, 4H). |
| MF-DH-476 | 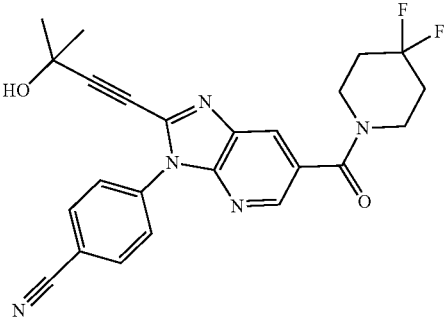 [SMILES: CC(C)(O)C#Cc1nc2cc(C(=O)N3CCC(F)(F)CC3)cnc2n1-c1ccc(C#N)cc1] | 34.0%/ 88.98% | 449.17 for C24H21F2N5O2/ 450.2 (M + 1) | δ 8.52 (d, J = 1.8 Hz, 1H), 8.32 (d, J = 1.8 Hz, 1H), 8.18-8.12 (m, 2H), 7.97 (d, J = 8.7 Hz, 2H), 5.74 (s, 1H), 3.83-3.44 (m, 4H), 2.14-2.03 (m, 4H), 1.39 (s, 6H). |
| MF-DH-517 | 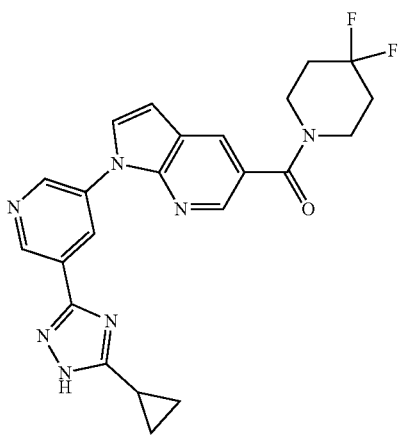 [SMILES: O=C(c1cnc2c(ccn2-c2cncc(-c3n[nH]c(C4CC4)n3)c2)c1)N1CCC(F)(F)CC1] | 8.0%/ 96.91% | 449.18 for C23H21F2N7O/ 450.1 (M + 1) | δ 13.97-13.91 (m, 1H), 9.13-9.09 (m, 2H), 8.84-8.82 (m, 1H), 8.49-8.46 (m, 1H), 8.27-8.22 (m, 2H), 6.91-6.87 (m, 1H), 3.78-3.53 (m, 4H), 2.18-2.05 (m, 5H), 1.13-0.98 (m, 4H). |

TABLE 3-continued
Analytical data for select inhibitors
| Target No | Structure | Yield/Purity | Mass Spec. Calculated/Mass Spec. Found (m/z) | $^1$H NMR (DMSO-d$_6$*, 400 MHz) (*unless otherwise indicated) |
|---|---|---|---|---|
| MF-DH-518 | 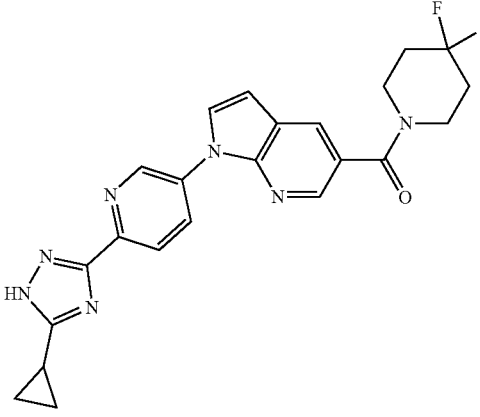 | 12.0%/96.52% | 449.18 for C13H21F2N7O/450.1 (M + 1) | δ 14.15 (s, 1H), 9.41-9.13 (m, 1H), 8.66-8.41 (m, 2H), 8.31-8.17 (m, 3H), 6.99-6.87 (m, 1H), 3.78-3.54 (m, 4H), 2.18-2.02 (m, 5H), 1.05-0.79 (m, 4H). |
| MF-DH-519 | 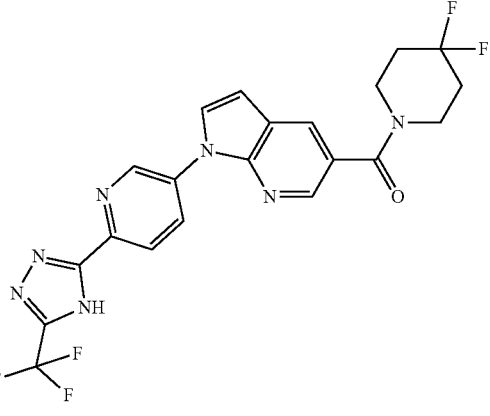 | 8.0%/91.47% | 477.13 for C21H16F5N7O/478.1 (M + 1) | δ 15.75-15.70 (m, 1H), 9.40-9.38 (m, 1H), 8.76-8.70 (m, 1H), .51-8.49 (m, 1H), 8.36-8.30 (m, 2H), 8.29-8.27 (m, 1H), 6.96-6.91 (m, 1H), 3.83-3.57 (m, 4H), 2.16-2.05 (m, 4H). |
| MF-DH-520 | 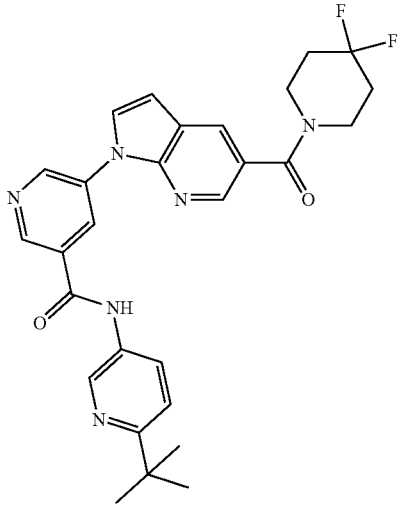 [SMILES: CC(C)(C)c1ccc(NC(=O)c2cncc(-n3ccc4cc(C(=O)N5CCC(F)(F)CC5)cnc43)c2)cn1] | 13.4%/98.9% | 518.22 for C28H28F2N6O2/519.2 (M + 1) | δ 10.70-10.67 (m, 1H), 9.41-9.39 (m, 1H), 9.13-9.11 (m, 1H), 8.89-8.83 (m, 2H), 8.50-8.48 (m, 1H), 8.29-8.26 (m, 2H), 8.15-8.11 (m, 1H), 7.49-7.45 (m, 1H), 6.94-6.92 (m, 1H), 3.78-3.54 (m, 4H), 2.15-2.02 (m, 4H), 1.33-1.32 (m, 9H). |

TABLE 3-continued

Analytical data for select inhibitors

| Target No | Structure | Yield/ Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-538 | 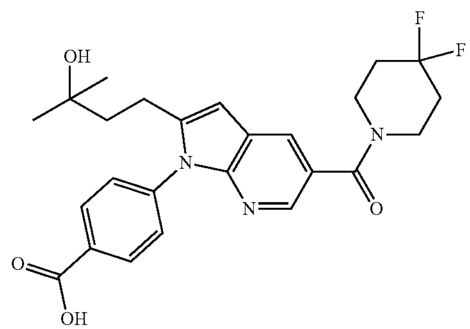 [SMILES: CC(C)(O)CCc1cc2cc(C(=O)N3CCC(F)(F)CC3)cnc2n1-c1ccc(C(=O)O)cc1] | 43.0%/ 94.34% | 471.20 for C25H27F2N3O4/ 472.2 (M + 1) | δ 12.46-12.12 (m, 1H), 8.21 (d, J = 2.0 Hz, 1H), 8.14 (d, J = 8.4 Hz, 2H), 8.07 (d, J = 2.0 Hz, 1H), 7.62 (d, J = 8.6 Hz, 2H), 6.56 (s, 1H), 4.22 (s, 1H), 3.75-3.46 (m, 4H), 2.69-2.62 (m, 2H), 2.13-1.99 (m, 4H), 1.67-1.60 (m, 2H), 1.01 (s, 6H). |
| MF-DH-542 | 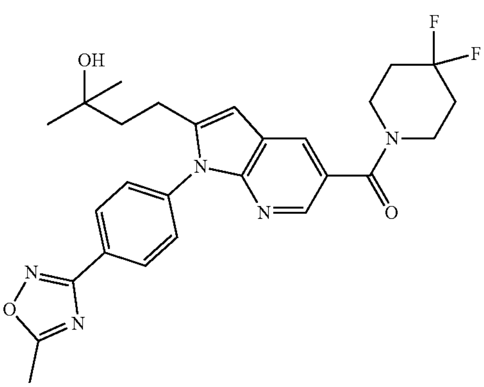 [SMILES: Cc1nc(-c2ccc(-n3c(CCC(C)(C)O)cc4cc(C(=O)N5CCC(F)(F)CC5)cnc43)cc2)no1] | 35.0%/ 90.64% | 509.22 for C17H29F2N5O3/ 510.2 (M + 1) | δ 8.24-8.17 (m, 3H), 8.07 (d, J = 2.0 Hz, 1H), 7.69 (d, J = 8.7 Hz, 2H), 6.57 (s, 1H), 4.22 (s, 1H), 3.72-3.46 (m, 4H), 2.79-2.65 (m, 5H), 2.12-1.98 (m, 4H), 1.68-1.62 (m, 2H), 1.03-0.99 (m, 6H). |
| MF-DH-544 | 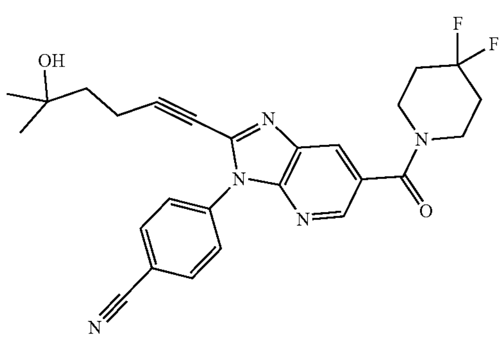 [SMILES: CC(C)(O)CCC#Cc1nc2cc(C(=O)N3CCC(F)(F)CC3)cnc2n1-c1ccc(C#N)cc1] | 13.0%/ 99.40% | 477.20 for C26H25F2N5O2/ 478.2 (M + 1) | δ 8.22-8.20 (m, 1H), 8.14-8.09 (m, 2H), 8.05-8.03 (m, 1H), 7.77-7.72 (m, 2H), 3.81-3.52 (m, 2.05 (m, 4H), 1.59-1.54 (m, 2H), 1.34 (s, 6H). |
| MF-DH-562 | 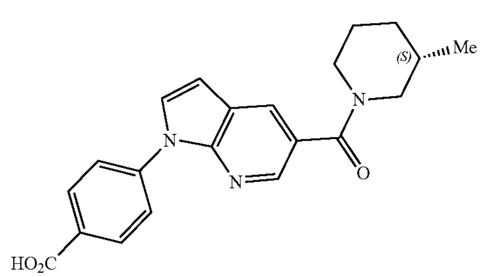 | 49.3%/ 97.41% | 363.16 for C21H21N3O3/ 364.2 (M + 1) | δ 13.18-12.81 (m, 1H), 8.38 (d, J = 2.0 Hz, 1H), 8.19-8.09 (m, 6H), 6.86 (d, J = 3.8 Hz, 1H), 4.42-4.20 (m, 1H), 3.70-3.51 (m, 1H), 3.09-2.69 (m, 2H), 1.84-1.76 (m, 1H), 1.70-1.40 (m, 3H), 1.36-1.01 (m, 2H), 0.98-0.64 (m, 3H). |

TABLE 3-continued

Analytical data for select inhibitors

| Target No | Structure | Yield/Purity | Mass Spec. Calculated/ Mass Spec. Found (m/z) | $^1$H NMR (DMSO-$d_6$*, 400 MHz) (*unless otherwise indicated) |
|---|---|---|---|---|
| MF-DH-574 (absolute stereochemistry not determined) | | 43.6%/ 99.22% | 334.12 for C19H15FN4O/ 335.1 (M + 1) | δ 8.58 (brs, 1H), 8.38-8.25 (m, 3H), 8.25-8.18 (m, 1H), 8.05 (d, J = 8.8 Hz, 2H), 6.89 (d, J = 3.8 Hz, 1H), 5.50-5.23 (m, 1H), 4.06-3.58 (m, 4H), 2.27-2.02 (m, 2H). |
| MF-DH-575 (absolute stereochemistry not determined) | | 43.6%/ 98.76% | 334.12 for C19H15FN4O/ 335.1 (M + 1) | δ 8.58 (brs, 1H), 8.37-8.28 (m, 3H), 8.28-8.16 (m, 1H), 8.05 (d, J = 8.9 Hz, 2H), 6.89 (d, J = 3.8 Hz, 1H), 5.49-5.23 (m, 1H), 4.04-3.58 (m, 4H), 2.29-2.02 (m, 2H). |

Methods of Use

In one aspect, provided herein are methods for treating various disorders in a subject in need thereof, comprising administering to said subject a compound described herein. In some embodiments, the inhibitors of hydroxyprostaglandin dehydrogenase provided herein may be used for the prevention or treatment of a disease or a disorder that is associated with hydroxyprostaglandin dehydrogenase (such as 15-PGDH) and/or decreased levels of prostaglandins. In some embodiments, the inhibitors of hydroxyprostaglandin dehydrogenase provided herein may be used for the prevention or treatment of a disease or a disorder in which it is desirable to increase prostaglandin levels in the subject having said disease or disorder.

In some embodiments, the methods for treating the disorders comprises administering to said subject a 15-PGDH inhibitor. In some embodiments, a compound described herein is the 15-PGDH inhibitor. In some embodiments, a compound having Formula I, Formula II, or Formula III is the 15-PGDH inhibitor. In some embodiments, the methods comprise administering a therapeutically effective amount of a compound described herein. In some embodiments, the methods comprise administering a therapeutically effective amount of a compound having Formula I, Formula II, or Formula III In some embodiments, the compound described herein is a 15-PGDH inhibitor. In some embodiments, the compound having Formula I, Formula II, or Formula III is a 15-PGDH inhibitor. In some embodiments, the administration takes place in vitro. In other embodiments, the administration takes place in vivo.

As used herein, a therapeutically effective amount of a 15-PGDH inhibitor refers to an amount sufficient to effect the intended application, including but not limited to, disease treatment, as defined herein. Also contemplated in the subject methods is the use of a sub-therapeutic amount of a 15-PGDH inhibitor for treating an intended disease condition.

The amount of the 15-PGDH inhibitor administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring inhibition of biological effects of 15-PGDH can comprise performing an assay on a biological sample, such as a sample from a subject. Any of a variety of samples may be selected, depending on the assay. Examples of samples include, but are not limited to, blood samples (e.g. blood plasma or serum), exhaled breath condensate samples, bronchoalveolar lavage fluid, sputum samples, urine samples, and tissue samples.

A subject being treated with a 15-PGDH inhibitor may be monitored to determine the effectiveness of treatment, and the treatment regimen may be adjusted based on the subject's physiological response to treatment. For example, if inhibition of a biological effect of 15-PGDH is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with a 15-PGDH inhibitor is discontinued if inhibition of the biological effect is above or below a threshold, such as in a lack of response or an adverse reaction. The biological effect may be a change in any of a variety of physiological indicators.

In general, a 15-PGDH inhibitor is a compound that inhibits one or more biological effects of 15-PGDH. Such biological effects may be inhibited by about or more than about 10%, 20%, 30%, 40%, 50%, 60%, 70%, 80%, 90%, 95%, or more.

In some other embodiments, the subject methods are useful for treating a disease condition associated with 15-PGDH. Any disease condition that results directly or indirectly from an abnormal activity or expression level of 15-PGDH can be an intended disease condition.

In one aspect, provided herein is a method of promoting and/or stimulation skin pigmentation, comprising administering one or more of the compositions described herein to a subject in need thereof. Inhibitors of 15-PGDH are known to promote skin pigmentation (Markowitz et. al., WO 2015/065716). The hydroxyprostaglandin dehydrogenase inhibitors described herein can be used for promoting and/or inducing and/or stimulating pigmentation of the skin and/or skin appendages, and/or as an agent for preventing and/or limiting depigmentation and/or whitening of the skin and/or skin appendages, in particular as an agent for preventing and/or limiting canities. In some embodiments, the 15-PGDH inhibitors provided herein can be applied to skin of a subject, e.g., in a topical application, to promote and/or stimulate pigmentation of the skin and/or hair growth, inhibit hair loss, and/or treat skin damage or inflammation, such as skin damage caused by physical or chemical irritants and/or UV-exposure.

In another aspect, provided herein is a method of inhibiting hair loss, comprising administering one or more of the compositions described herein to a subject in need thereof. It is known that prostaglandins play an important role in hair growth. Prostaglandins such as prostaglandin A1, F2a and E2 are stored in hair follicles or adjacent skin environments and have been shown to be essential in maintaining and increasing hair density (Colombe L et. al, 2007, Exp. Dermatol, 16(9), 762-9). It has been reported that 15-PGDH, which is involved in the degradation of prostaglandins is present in the hair follicle dermal papillae, inactivates prostaglandins, especially, PGF2a and PGE2, to cause scalp damage and alopecia (Michelet J F et. al., 2008, Exp. Dermatol, 17(10), 821-8). Thus, the hydroxyprostaglandin dehydrogenase inhibitors described herein that have a suppressive or inhibitory activity against 15-PGDH can improve scalp damage, prevent alopecia and promote hair growth and be used in a pharmaceutical composition for the prevention of alopecia and the promotion of hair growth.

In another aspect, provided herein is a method of preventing and/or treating skin inflammation and/or damage, comprising administering one or more of the compositions described herein to a subject in need thereof.

In another aspect, provided herein is a method of preventing and/or treating vascular insufficiency, comprising administering one or more of the compositions described herein to a subject in need thereof. Prostaglandins including prostaglandin homologues produced in the body have been known to maintain the proper action of the blood vessel wall, especially to contribute to vasodilation for blood flow, preventing platelet aggregation and modulating the proliferation of smooth muscle that surrounds blood vessel walls (Yan. Cheng et. al., 2006, J. Clin., Invest). In addition, the inhibition of prostaglandins production or the loss of their activity causes the degeneration of the endothelium in the blood vessel walls, platelet aggregation and the dysfunction of cellular mechanism in the smooth muscle. Among others, the production of prostaglandins in blood vessels was shown to be decreased in hypertension patients, including pulmonary artery hypertension. the 15-PGDH inhibitors described herein can be used in a pharmaceutical composition for the prevention or the treatment of cardiovascular disease and/or diseases of vascular insufficiency, such as Raynaud's disease, Buerger's disease, diabetic neuropathy, and pulmonary artery hypertension.

In another aspect, provided herein is a method of preventing, treating, minimizing and/or reversing congestive heart failure, cardiomyopathy, comprising administering one or more of the compositions described herein to a subject in need thereof. In another aspect, provided herein is a method of reducing cardiac ejection fraction, comprising administering one or more of the compositions described herein to a subject in need thereof. It has been shown that administration of a 15-PGDH inhibitor can be used to treat, prevent, minimize, and/or reverse congestive heart failure, cardiomyopathy, and/or reduction of cardiac ejection fraction (Markowitz et. al., WO2018/187810). As such, the hydroxyprostaglandin dehydrogenase inhibitors described herein can be administered to a subject in need to treat, prevent, minimize and/or reverse congestive heart failure, cardiomyopathy, and/or reduction of cardiac ejection fraction.

In another aspect, provided herein is a method of preventing and/or treating a gastrointestinal disease, comprising administering one or more of the compositions described herein to a subject in need thereof. Prostaglandins are essential for maintaining the mechanism for protecting and defending gastric mucus membrane (Wallace J L., 2008, Physiol Rev., 88(4), 1547-65, S. J. Konturek et al., 2005, Journal of Physiology and Pharmacology, 56(5)). The inhibitors of hydroxyprostaglandin dehydrogenase described herein show a suppressive or inhibitory activity against 15-PGDH, which degrades prostaglandins that protect gastric mucus membranes. As such, the hydroxyprostaglandin dehydrogenase inhibitors can be effective for the prevention or the treatment of gastrointestinal diseases, inter alia, gastritis and gastric ulcer. In addition, the hydroxyprostaglandin dehydrogenase inhibitors provided herein may be used to prevent and/or treat other forms of intestinal injury including toxicity from radiation and/or chemotherapy, and chemotherapy-induced mucositis.

Additionally, it has been shown that administration of 15-PGDH inhibitors, alone or in combination with corticosteroids and/or TNF inhibitors can treat intestinal, gastrointestinal, or bowel disorders such as oral ulcers, gum disease, gastritis, colitis, ulcerative colitis, gastric ulcers, inflammatory bowel disease, and Crohn's disease (Markowitz et. al., WO 2018/102552). As such, the hydroxyprostaglandin dehydrogenase inhibitors provided herein can be used to treat and/or prevent treat intestinal, gastrointestinal, or bowel disorders such as oral ulcers, gum disease, gastritis, colitis, ulcerative colitis, gastric ulcers, inflammatory bowel disease, and Crohn's disease.

In another aspect, provided herein is a method of preventing and/or treating renal dysfunction, comprising administering one or more of the compositions described herein to a subject in need thereof. In the kidney, prostaglandins modulate renal blood flow and may serve to regulate urine formation by both renovascular and tubular effects. In clinical studies, inhibitors of prostaglandin have been used to improve creatinine clearance in patients with chronic renal disease, to prevent graft rejection and cyclosporine toxicity in renal transplant patients, to reduce the urinary albumin excretion rate and N-acetyl-beta-D-glucosaminidase levels in patients with diabetic nephropathy (Porter, Am., 1989, J. Cardiol., 64: 22E-26E). Furthermore, it has been reported that prostaglandins serve as vasodilators in the kidney, and, thus, the inhibition of prostaglandin production in the kidney results in renal dysfunction (Hao. C M, 2008, Annu Rev Physiol, 70, 357.about.77). The hydroxyprostaglandin dehydrogenase inhibitors described herein have a suppressive or inhibitory activity against 15-PGDH that degrades prostaglandins and can be used for the prevention and/or treatment of renal diseases that are associated with renal dysfunction.

In another aspect, provided herein is a method of stimulation bone resorption and bone formation, comprising administering one or more of the compositions described herein to a subject in need thereof. Prostaglandins have been shown to stimulate bone resorption and bone formation to increase the volume and the strength of the bone (H. Kawaguchi et. al., Clinical Orthop. Rel. Res., 313, 1995; J. Keller et al., Eur. Jr. Exp. Musculoskeletal Res., 1, 1992, 8692). Furthermore, inhibition of 15-PGDH increases callus size and mineralization after bone fracture (Collier et. al., ORS 2017 Annual Meeting Paper No. 0190). Considering that 15-PGDH inhibits the activities of prostaglandins as mentioned in the above, the inhibition of 15-PGDH activity may lead to the promotion of bone resorption and bone formation that are inhibited by 15-PGDH. Thus, the inhibitors of hydroxyprostaglandin dehydrogenase described herein can be effective for the promotion of bone resorption and bone formation by inhibiting 15-PGDH activity. The hydroxyprostaglandin dehydrogenase inhibitors provided herein can also be used to increase bone density, treat osteoporosis, promote healing of fractures, promote healing after bone surgery or joint replacement, and/or to promote healing of bone to bone implants, bone to artificial implants, dental implants, and bone grafts.

In another aspect, provided herein is a method of stimulating tissue regeneration by stimulating, comprising administering one or more of the compositions described herein to a subject in need thereof. Prostaglandin PGE2 supports expansion of several types of tissue stem cells. Inhibition of 15-hydroxyprostaglandin dehydrogenase (15-PGDH), a prostaglandin-degrading enzyme, potentiates tissue regeneration in multiple organs. Studies show that inhibition of 15-PGDH increases prostaglandin PGE2 levels in bone marrow and other tissues; accelerates hematopoietic recovery following a bone marrow transplant; promotes tissue regeneration of colon and liver injury (Zhang, Y. et. al. Science 2015, 348 (6240)). The hydroxyprostaglandin dehydrogenase inhibitors provided herein can be used for tissue regeneration by supporting the expansion of tissue stem cells.

In another aspect, provided herein is a method of modulating cervical ripening, comprising administering one or more of the compositions described herein to a subject in need thereof. Prostaglandin E2 (PGE2) is a known cervical ripening agent that mediates EP2-receptor-signaling pathways in human cervical stromal cells; targets its own synthesis by increasing COX-2 and PTGES expression; and decreases its metabolism by loss of its degradative enzyme 15-PGDH (Word et. Al., WO2019010482) Downregulation of 15-PGDH was also found to be crucial for PGE2-induced cervical ripening and preterm birth. Modulation of 15-PDGH activity can be used to modulate cervical ripening; and induce or prevent preterm labor. The hydroxyprostaglandin dehydrogenase inhibitors provided herein can be used to induce cervical ripening and labor, alone or in combination with another labor inducing agent.

In another aspect, provided herein is a method of promoting neuroprotection and/or stimulating neuronal regeneration, comprising administering one or more of the compositions described herein to a subject in need thereof. Prostaglandins, via their specific G protein coupled receptors, have a variety of physiological functions in the central nervous system. The major prostaglandin, prostaglandin E2 (PGE2) can activate receptor types EP1, 2, 3, and 4. Activation of EP2 and EP4 receptors can regulate adenylate cyclase and the generation of 3,5'-cyclic adenosine monophosphate (cAMP), whereas the activation of EP1 and EP3 receptors can regulate Ca2+ signaling. Studies show that the EP1 and EP2 receptors are expressed in neurons and microglia as well as neurons of the cerebral cortex, striatum, and hippocampus. In addition, activation of the EP2 receptor by PGE2 is involved in long-term synaptic plasticity and cognitive function (Chemtob et al. Semin Perinatol. 1994 February; 18(1):23-9; Yang et al., J Neurochem. 2009 January; 108(1):295-304). Studies also show that following activation, different PGE2 receptors can contribute or protect against N-methyl-D-aspartate (NMDA) neurotoxicity and ischemic stroke (Ahmad et al., Exp Transl Stroke Med. 2010 Jul. 8; 2(1):12). Other studies show that activation of the EP2 receptors protected neurons from amyloid P-peptide neurotoxicity in vitro (Echeverria et al., Eur J Neurosci. 2005 November; 22(9):2199-206). Several studies suggest that the mechanism by which PGE2 affords neuroprotection is through EP2 or EP4 receptors, as they both increases cAMP, followed by a protein kinase A (PKA)-dependent pathway (Echeverria et al. Eur J Neurosci. 2005 November; 22(9):2199-206; McCullough et al., J Neurosci. 2004 Jan. 7; 24(1):257-68). Stimulation of these receptors with PGE2 by administration of a compound that inhibits, reduces, and/or antagonizes 15-PGDH activity, such as the hydroxyprostaglandin dehydrogenase inhibitors that can inhibit 15-PGDH described herein, can promote neuroprotection in a subject from axonal degeneration, neuronal cell death, and/or glia cell damage after injury, augment neuronal signaling underlying learning and memory, stimulate neuronal regeneration after injury, and/or treat diseases, disorders, and/or conditions of the nervous system.

In another aspect, provided herein is a method of treating and/or preventing a neurological disorder, a neuropsychiatric disorder, a neural injury, a neural toxicity disorder, a neuropathic pain, or a neural degenerative disorder, comprising administering one or more of the compositions described herein to a subject in need thereof. In some embodiments, the disease, disorder, and/or condition of the nervous system, which can be treated with hydroxyprostaglandin dehydrogenase inhibitors provided herein, can include at least one of a neurological disorder, a neuropsychiatric disorder, a neural injury, a neural toxicity disorder, a neuropathic pain, or a neural degenerative disorder. For example, the neurological disorder can include at least one of traumatic or toxic injuries to peripheral or cranial nerves, spinal cord or brain, such as traumatic brain injury, stroke, cerebral aneurism, and spinal cord injury. The neurological disorder can also include at least one of Alzheimer's disease, dementias related to Alzheimer's disease, Parkinson's, Lewy diffuse body diseases, senile dementia, Huntington's disease, Gilles de Ia Tourette's syndrome, multiple sclerosis, amyotrophic lateral sclerosis, hereditary motor and sensory neuropathy, diabetic neuropathy, progressive supranuclear palsy, epilepsy, or Jakob-Creutzfieldt disease.

In some embodiments, the neural injury can be caused by or associated with at least one of epilepsy, cerebrovascular diseases, autoimmune diseases, sleep disorders, autonomic disorders, urinary bladder disorders, abnormal metabolic states, disorders of the muscular system, infectious and parasitic diseases, neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, or conditions originating in the perinatal period.

In certain embodiments, the hydroxyprostaglandin dehydrogenase inhibitors can be administered to a subject or neurons of the subject to promote the survival, growth, development and/or function of the neurons, particularly, the central nervous system (CNS), brain, cerebral, and hippocampal neurons. In certain embodiments, the hydroxyprostaglandin dehydrogenase inhibitors can be used stimulate hippocampal neurogenesis, for the treatment of neuropsychiatric and neurodegenerative diseases, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuroactive drugs, such as alcohol, opiates, methamphetamine, phencyclidine, and cocaine.

In another aspect, provided herein is a method of treating and/or preventing fibrotic or adhesion disease, disorder or condition, comprising administering one or more of the compositions described herein to a subject in need thereof. It has been shown that inhibitors of short-chain dehydrogenase activity, such as 15-PGDH inhibitors, can be administered to a subject in need thereof to decrease fibrotic symptoms, such as collagen deposition, collagen accumulation, collagen fiber formation, inflammatory cytokine expression, and inflammatory cell infiltration, and treat and/or prevent various fibrotic diseases, disorders, and conditions characterized, in whole or in part, by the excess production of fibrous material, including excess production of fibrotic material within the extracellular matrix, or the replacement of normal tissue elements by abnormal, non-functional, and/or excessive accumulation of matrix-associated components (Markowitz et. al., WO2016/144958).

Fibrotic diseases, disorders and conditions characterized, in whole or in part, by excess production of fibrotic material can include systemic sclerosis, multifocal fibrosclerosis, nephrogenic systemic fibrosis, scleroderma (including morphea, generalized morphea, or linear scleroderma), sclerodermatous graft-vs-host-disease, kidney fibrosis (including glomerular sclerosis, renal tubulointerstitial fibrosis, progressive renal disease or diabetic nephropathy), cardiac fibrosis (e.g., myocardial fibrosis), pulmonary fibrosis (e.g. pulmonary fibrosis, glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fasciitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, myelodysplastic syndrome, myeloproliferative syndrome, collagenous colitis, acute fibrosis, organ specific fibrosis, and the like. The hydroxyprostaglandin dehydrogenase inhibitors provided herein can be used to treat or prevent a fibrotic disease, disorder or condition.

The hydroxyprostaglandin dehydrogenase inhibitors provided herein can be used to treat or prevent kidney fibrosis, including kidney fibrosis resulting from dialysis following kidney failure, catheter placement, a nephropathy, glomerulosclerosis, glomerulonephritis, chronic renal insufficiency, acute kidney injury, end stage renal disease or renal failure, or combinations thereof.

The hydroxyprostaglandin dehydrogenase inhibitors provided herein can be used to treat or prevent liver fibrosis, including liver fibrosis resulting from a chronic liver disease, viral induced hepatic cirrhosis, hepatitis B virus infection, hepatitis C virus infection, hepatitis D virus infection, schistosomiasis, primary biliary cirrhosis, alcoholic liver disease or non-alcoholic steatohepatitis (NASH), NASH associated cirrhosis obesity, diabetes, protein malnutrition, coronary artery disease, auto-immune hepatitis, cystic fibrosis, alpha-1-antitrypsin deficiency, primary biliary cirrhosis, drug reaction and exposure to toxins, or combinations thereof.

The hydroxyprostaglandin dehydrogenase inhibitors provided herein can be used to treat or prevent heart fibrosis such as cardiac fibrosis, endomyocardial fibrosis, idiopathic pulmonary fibrosis, and kidney fibrosis.

The hydroxyprostaglandin dehydrogenase inhibitors provided herein can be used to treat or prevent systemic sclerosis.

The hydroxyprostaglandin dehydrogenase inhibitors provided herein can be used to treat or prevent fibrotic diseases, disorders or conditions caused by post-surgical adhesion formation.

The hydroxyprostaglandin dehydrogenase inhibitors provided herein can be used to reduce in intensity, severity, or frequency, and/or delay onset of one or more symptoms or features of a fibrotic disease, disorder or condition, or other related diseases, disorders or conditions.

The hydroxyprostaglandin dehydrogenase inhibitors provided herein can be used to decrease or reduce collagen secretion, or collagen deposition, or collagen fiber accumulation, in a tissue or organ, such as the lung, the liver, the intestines, the colon, the skin or the heart, or a combination thereof.

Studies have shown that 15-PGDH inhibition ameliorates inflammatory pathology and fibrosis in pulmonary fibrosis (Smith et. al., bioRxiv 2019.12.16.878215; Barnthaler et. al., J. Allergy Clin. Immunol. 2019, 145 (3), 818-833). In some embodiments, the hydroxyprostaglandin dehydrogenase inhibitors described herein can be used to treat or prevent lung fibrosis, including pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension, and combinations thereof.

In another aspect, provided herein is a method of reducing and/or preventing scar formation, comprising administering one or more of the compositions described herein to a subject in need thereof. The hydroxyprostaglandin dehydrogenase inhibitors provided herein can used for reducing or preventing scar formation in a subject. The hydroxyprostaglandin dehydrogenase inhibitors provided herein can be used to reduce or prevent scar formation on skin or scleroderma.

In another aspect, provided herein is a method of treating and/or preventing muscle disorder, muscle injury and/or muscle atrophy, comprising administering one or more of the compositions described herein to a subject in need thereof. Studies have shown that inhibition of PGE2 degrading enzymes such as 15-PGDH, enable muscle regeneration and muscle repair after injury (Ho et al., PNAS 2017; Dong et al., Stem cell research and therapy 2020). The inhibitors of hydroxyprostaglandin dehydrogenase provided herein can be used to treat muscle disorder, muscle injury and/or muscle atrophy in a subject. In some cases, said subject suffering from a muscle disorder, muscle injury and/or muscle atrophy may have Duchenne muscular dystrophy (DMD), Becker muscular dystrophy, Fukuyama congenital muscular dystrophy (FCMD), limb girdle muscular dystrophy, congenital muscular dystrophy, facioscapulohumeral muscular dystrophy (FHMD), amyotrophic lateral sclerosis (ALS), distal muscular dystrophy (DD), an inherited myopathy, myotonic muscular dystrophy (MDD), oculopharyngeal muscular dystrophy, distal muscular dystrophy, Emery-Dreifuss muscular dystrophy, myotonia congenita, mitochondrial myopathy (DD), myotubular myopathy (MM), myasthenia gravis (MG), periodic paralysis, polymyositis, rhabdomyolysis, dermatomyositis, cancer cachexia, AIDS cachexia, stress induced urinary incontinence, urethral sphincter deficiency, sarcopenia, or a combination thereof.

In some embodiments, the inhibitors of hydroxyprostaglandin dehydrogenase provided herein can be used to treat sarcopenia. In another embodiment, the inhibitors of hydroxyprostaglandin dehydrogenase provided herein can be used to treat diaphragmatic atrophy or limb muscle atrophy due to the use of a mechanical ventilator. In some embodiments, the inhibitors of hydroxyprostaglandin dehydrogenase provided herein can be used to treat genetic disorders or neuromuscular disorders such as Spinal Muscular Atrophy (SMA). In some embodiments, the inhibitors of hydroxyprostaglandin dehydrogenase provided herein can be used to treat ptosis, rotator cuff muscle atrophy, immobilization related muscle atrophy, surgical procedure related muscle atrophy, sarcopenia, or a combination thereof.

Pharmaceutical Compositions

The inhibitors of hydroxyprostaglandin dehydrogenase can be formulated into pharmaceutical compositions to treat diseases and disorders described herein. In some embodiments, a pharmaceutical composition may comprise a therapeutically effective amount of one or more inhibitors of hydroxyprostaglandin dehydrogenase provided herein.

The pharmaceutical composition described herein may be administered in such oral dosage forms as tablets, capsules (each of which includes sustained release or timed release formulations), pills, powders, micronized compositions, granules, elixirs, tinctures, suspensions, ointments, vapors, liposomal particles, nanoparticles, syrups and emulsions. In some embodiments, the pharmaceutical composition may also be administered in intravenous (bolus or infusion), subcutaneous injection, suppository, intraperitoneal, topical (e.g., dermal epidermal, transdermal), ophthalmically such as ocular eyedrop, intranasally, subcutaneous, inhalation, intramuscular or transdermal (e.g., patch) form, all using forms well known to those of ordinary skill in the pharmaceutical arts.

In some embodiments, a compound provided herein can be administered as part of a therapeutic regimen that comprises administering one or more second agents (e.g. 1, 2, 3, 4, 5, or more second agents), either simultaneously or sequentially with the compound provided herein. When administered sequentially, the compound provided herein may be administered before or after the one or more second agents. When administered simultaneously, the compound provided herein and the one or more second agents may be administered by the same route (e.g. injections to the same location; tablets taken orally at the same time), by a different route (e.g. a tablet taken orally while receiving an intravenous infusion), or as part of the same combination (e.g. a solution comprising a compound provided herein and one or more second agents).

A combination treatment according to the disclosure may be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. The exact dosage will depend upon the agent selected, the route of administration, the form in which the compound is administered, the subject to be treated, the body weight of the subject to be treated, and the preference and experience of the attending physician.

EXAMPLES

Example 1: Synthesis and Characterization of Compounds

In another aspect, methods of making the inhibitors described herein are provided herein. In some cases, the inhibitors are isolated or extracted from one or more plants. In some cases, the inhibitors derived from the one or more plants may be further modified. In some cases, the inhibitors are further purified after isolation from the one or more plants.

Exemplary synthesis schemes for the inhibitors with phenyl core as described herein include:

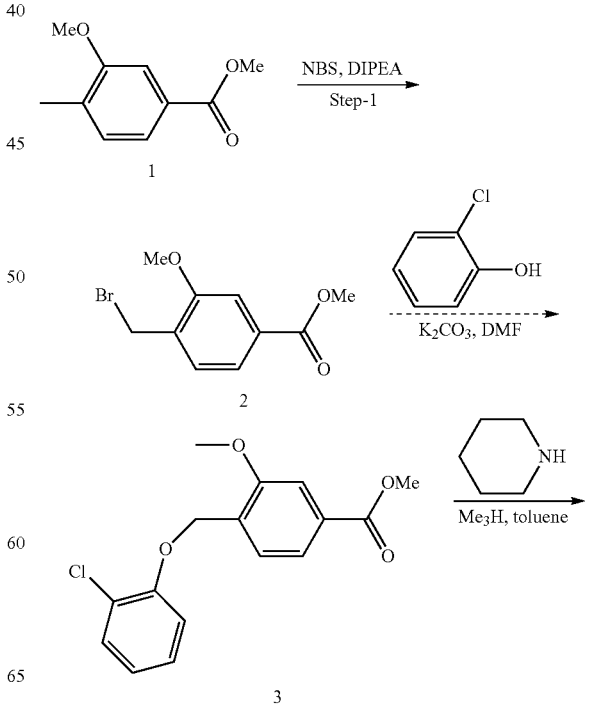

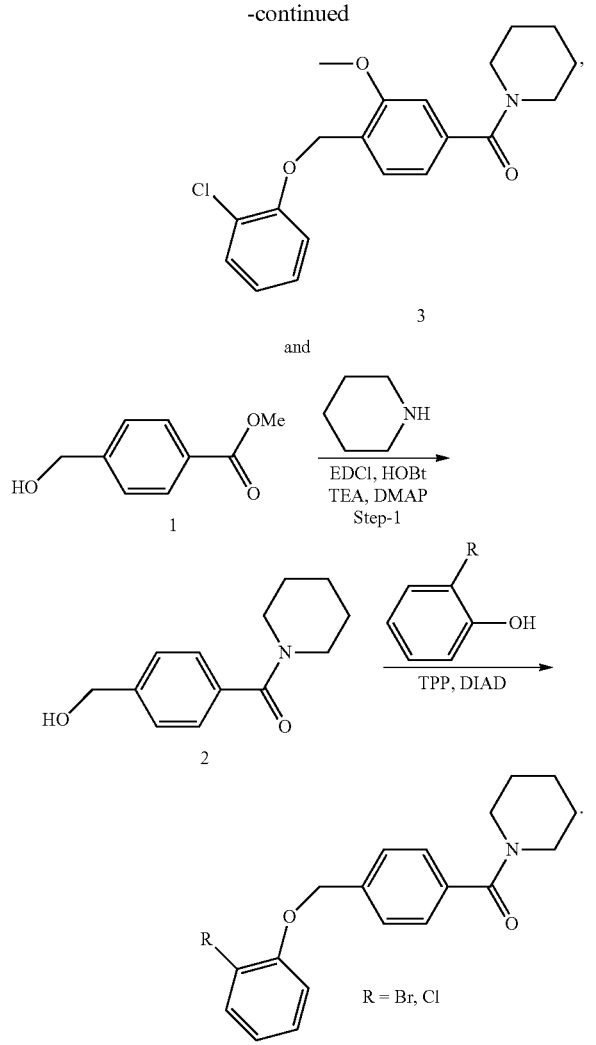
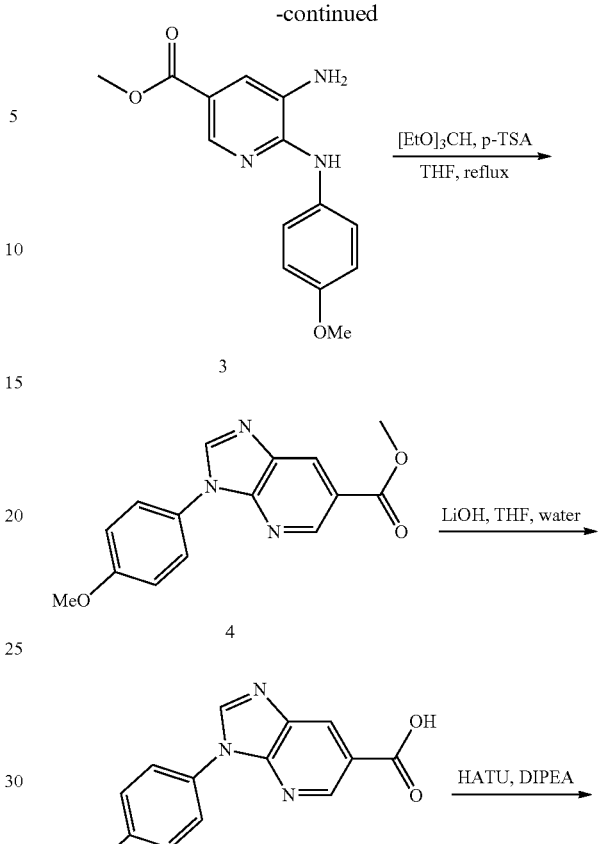
Exemplary synthesis schemes for the inhibitors with 6-5 ring cores as described herein include:

383
-continued
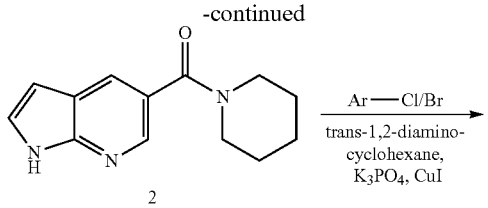
Ar—Cl/Br
trans-1,2-diamino-
cyclohexane,
K₃PO₄, CuI
Other analogs to be made:
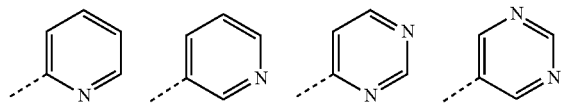
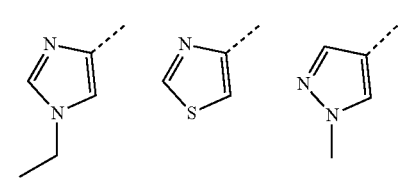
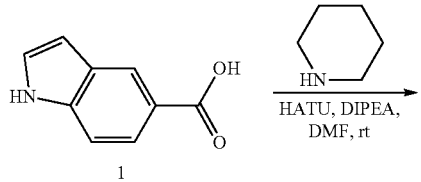
HN⟩ piperidine
HATU, DIPEA,
DMF, rt
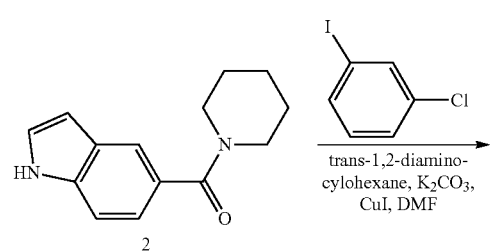
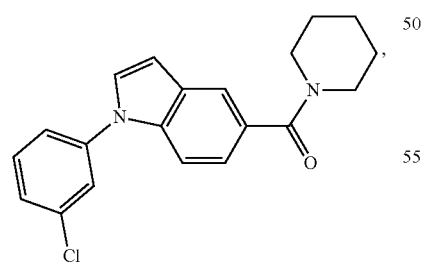
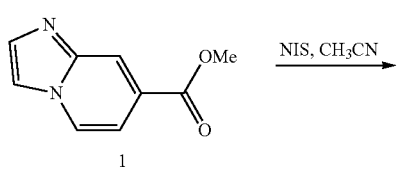
NIS, CH₃CN
384
-continued
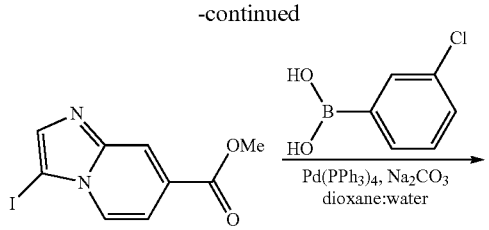
Pd(PPh₃)₄, Na₂CO₃
dioxane:water
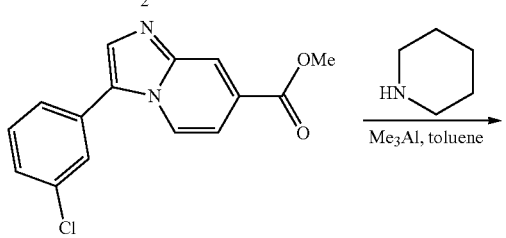
HN⟩
Me₃Al, toluene
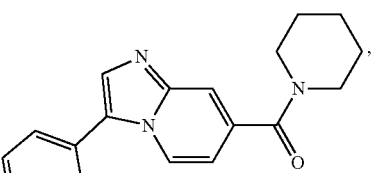
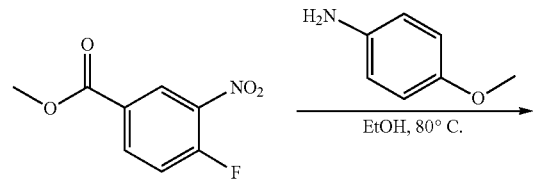
H₂N-C₆H₄-OMe
EtOH, 80° C.
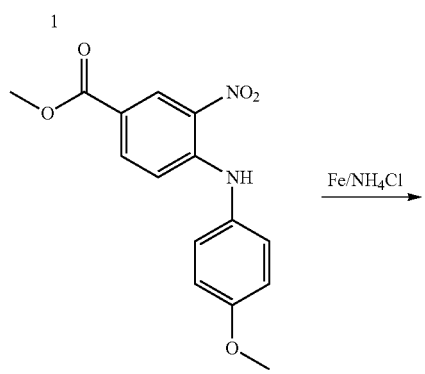
Fe/NH₄Cl
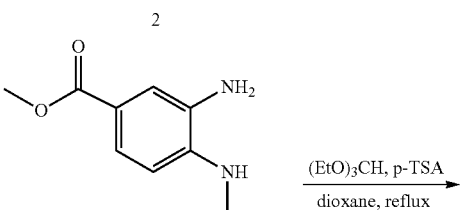
(EtO)₃CH, p-TSA
dioxane, reflux
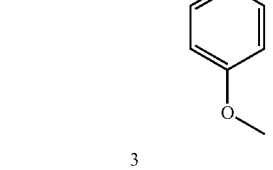

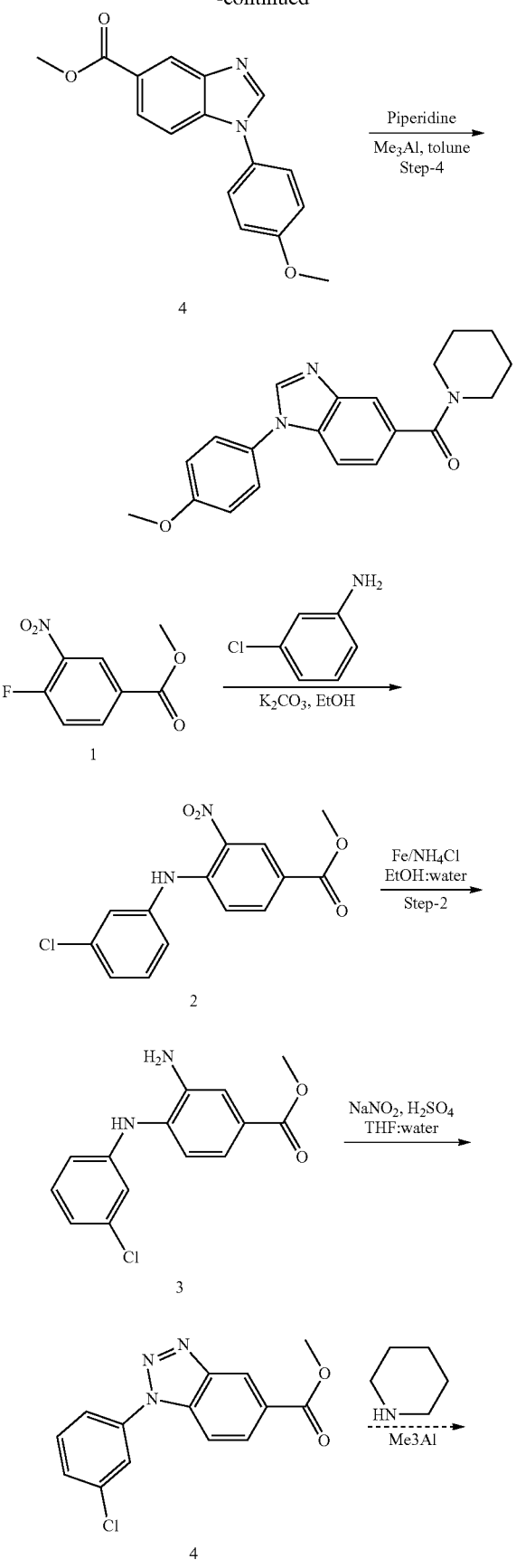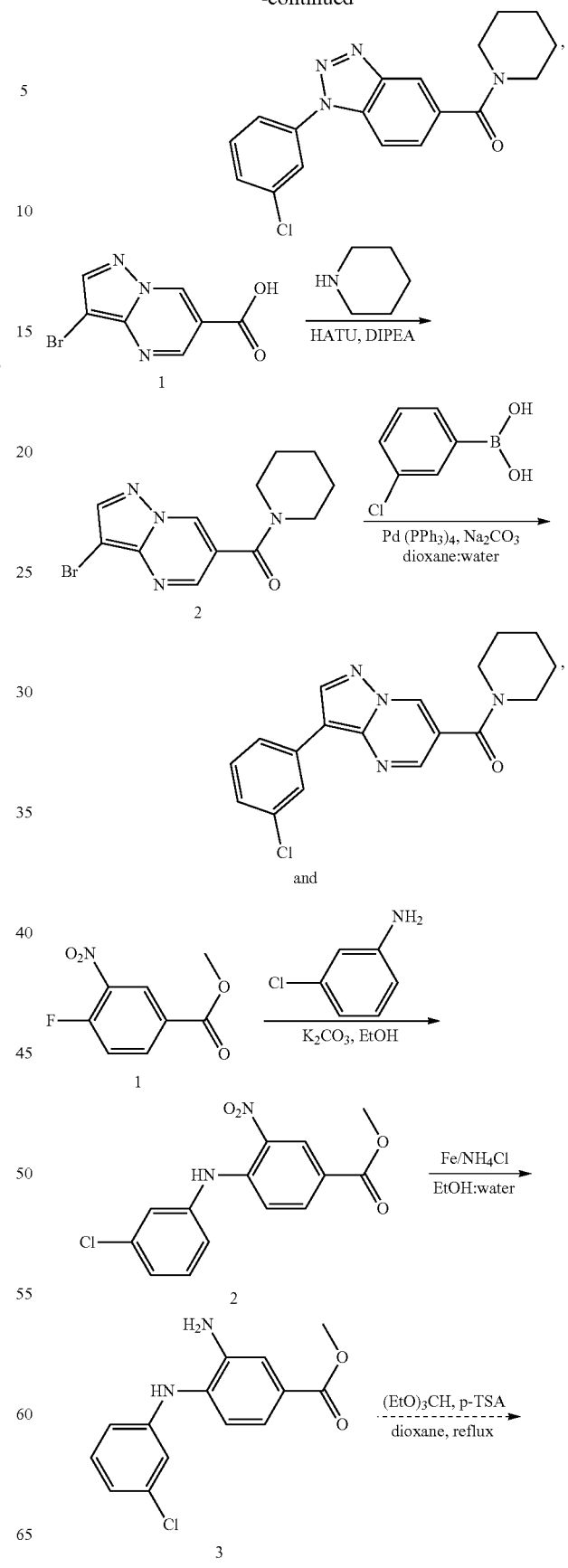

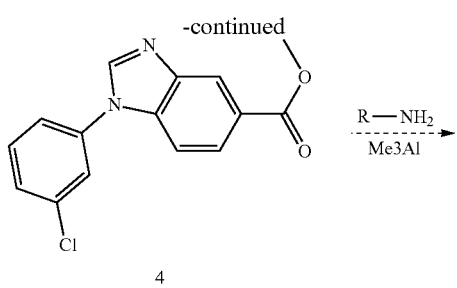

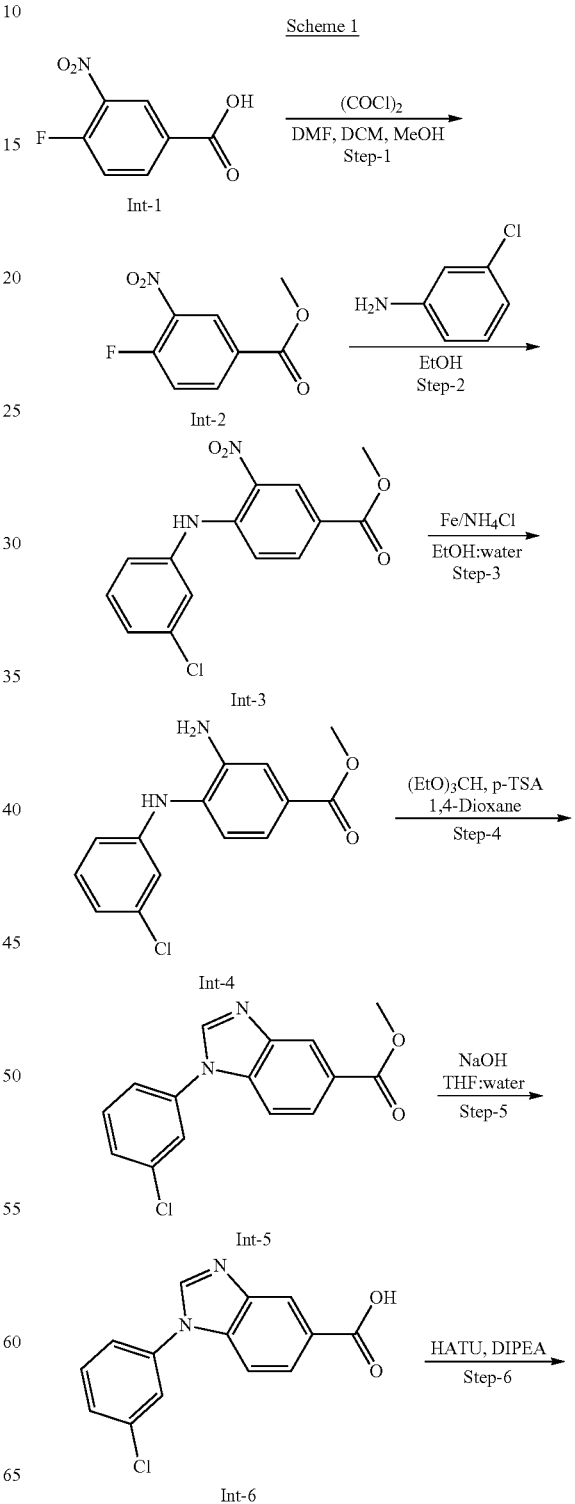

Synthesis of Benzimidazole-5-Carboxyamide Analogs with Amide Variation

Provided below is an exemplary scheme to synthesize benzimidazole-5-carboxyamide analogs with amide variation that are inhibitors of hydroxyprostaglandin dehydrogenase.

In some cases, synthesis schemes may be entire synthesis schemes for producing the inhibitors provided herein. In other cases, synthesis schemes may be partial schemes for producing inhibitors provided herein.

Described herein are exemplary synthesis schemes that can be used to synthesize the inhibitors described herein. The following abbreviations are used:

| Abbreviation | Description |
|---|---|
| AIBN | azobisisobutyronitrile |
| DCM | dichloromethane |
| DIAD | diisopropyl azodicarboxylate |
| DIPEA | N,N'-diisopropylethylamine |
| DMAP | 4-dimethylaminopyridine |
| DMF | dimethylformamide |
| EDCI | 1-ethyl-3-(3-dimethylaminopropyl)carbodiimide |
| HATU | 1-[Bis(dimethylamino)methylene]-1H-1,2,3-triazolo[4,5-b]pyridinium 3-oxide hexafluorophosphate |
| HOBt | hydroxybenzotriazole |
| m-CPBA | Meta-chloroperoxybenzoic acid |
| NBS | N-bromosuccinimide |
| NCS | N-chlorosuccinimide |
| NIS | N-iodosuccinimide |
| p-TSA | para-toluenesulfonic acid |
| TEA | triethylamine |
| TFA | trifluoroacetic acid |
| THF | tetrahydrofuran |
| TPP | triphenylphosphine |
| mmol | Milli molar |
| vol | Volume |
| g | Gram |
| kg | Kilogram |
| L | Litre |
| mL | Milli litre |
| ° C. | Degree Celsius |
| TLC | Thin Layer Chromatography |
| HPLC | High-performance liquid chromatography |
| LCMS | Liquid chromatography - mass spectrometry |
| min | Minutes |
| h | Hour |
| eq | Equivalents |
| RT | Room temperature |
| Rf | Retention factor |
| RP | Reversed phase |
| NMR | Nuclear magnetic resonance |
| Ppm | Parts per million |

-continued

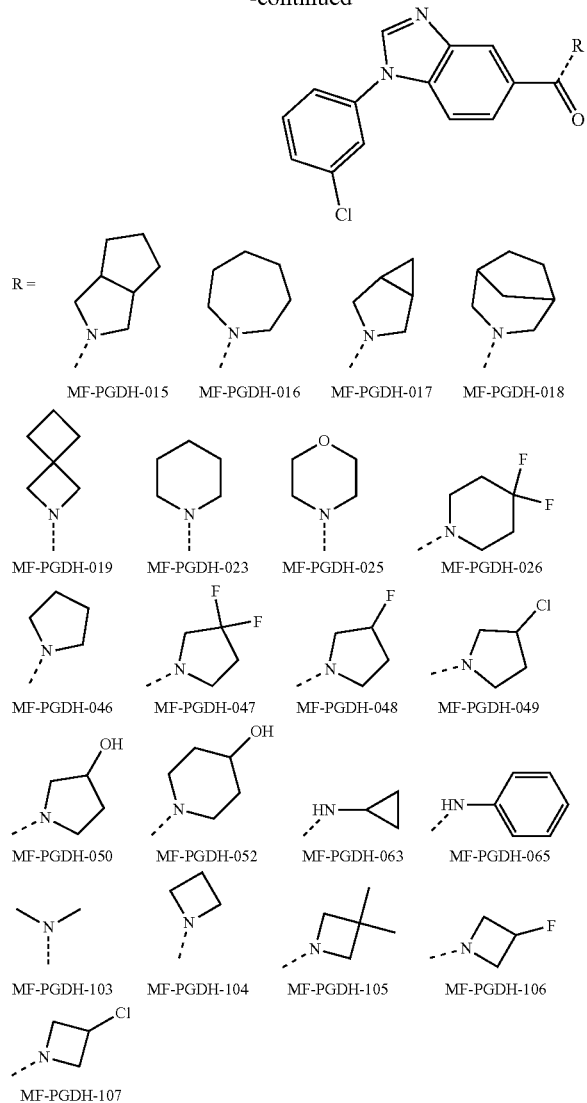

Step-1: Synthesis of methyl 4-fluoro-3-nitrobenzoate (Int-2): To a stirred solution of methyl 4-fluoro-3-nitrobenzoic acid (10 g, 54.02 mmol) in DCM (100 mL) were added oxalylchloride (9.42 mL, 108.04 mmol, 2 eq) and followed by the DMF (1 mL) at 0° C. The RM was stirred at 0° C. for 1 h. The reaction was monitored by TLC, after completion of the reaction, quenched with methanol (20 mL), and stirred at room temperature for 1 h. Then solvent was evaporated under reduced pressure and diluted with ethyl acetate (100 mL), washed with sat.NaHCO$_3$ solution (50 mL), and brine solution (50 mL), the organic phases are dried over sodium sulfate, filtered and concentrated under reduced pressure to obtain methyl 4-fluoro-3-nitrobenzoate (10.4 g, 96.7%) as an off white solid. LCMS: 75.82%, m/z=199.8 [M+H]$^+$; $^1$H NMR (CDCl$_3$, 400 MHz): δ 8.75 (dd, J=2.20, 7.21 Hz, 1H), 8.32 (ddd, J=2.2, 4.3, 8.7 Hz, 1H), 7.39 (dd, J=8.7, 10.2 Hz, 1H), 3.97-3.99 (m, 3H).

Step-2: Synthesis of methyl 4-((3-chlorophenyl)amino)-3-nitrobenzoate (Int-3), (general procedure for SNAr reactions #1): In sealed bomb; To a stirred solution of methyl 4-fluoro-3-nitrobenzoate (10 g, 50.21 mmol, 1 eq) in EtOH (100 mL), 3-chloroaniline (7.68 g, 60.25 mmol, 1.2 eq) was added at room temperature. Steel bomb cap was tightly closed and then resultant reaction mixture was heated to 100° C. for 16 h. The reaction was monitored by LCMS/TLC, after completion of the reaction cooled to room temperature, volatiles were evaporated, quenched with sat.NH$_4$Cl (100 mL), extracted with EtOAc (3×50 mL), combined organic extracts were washed with brine (50 mL); dried over sodium sulfate, filtered and concentrated in vacuo to get crude, trituration with diethyl ether (100 mL) to obtained methyl 4-((3-chlorophenyl)amino)-3-nitrobenzoate (8.2 g, 53.24%) as a yellow solid. LCMS: 95.95%, m/z=307.1 [M+H]$^+$; $^1$H NMR (CDCl$_3$, 400 MHz): δ 9.73 (br s, 1H), 8.92 (d, J=2.1 Hz, 1H), 8.01 (dd, J=1.8, 8.9 Hz, 1H), 7.36-7.41 (m, 1H), 7.26-7.31 (m, 2H), 7.19 (d, J=8.9 Hz, 2H), 3.92 (s, 3H).

Step-3: Synthesis of methyl 3-amino-4-((3-chlorophenyl)amino)benzoate (Int-4), (general procedure for aryl nitro reduction using Fe): To a stirred solution of methyl 4-((3-chlorophenyl)amino)-3-nitrobenzoate (8.2 g, 26.79 mmol, 1 eq) in EtOH/water (1:1, 160 mL), iron powder (10.47 g, 187.55 mmol, 7 eq) and NH$_4$Cl (10.03 g, 187.55 mmol, 7 eq) were added at room temperature. The resultant reaction mixture was heated to 100° C. for 16 h. The reaction was monitored by LCMS/TLC and after completion, the reaction mixture was filtered through celite bed and washed with EtOAc (2×100 mL). Volatiles were evaporated, quenched with sat. NaHCO$_3$ (100 mL), extracted with EtOAc (3×50 mL) and combined organic extracts were washed with brine (100 mL), dried over sodium sulfate, filtered and concentrated in vacuo to obtain the crude. The crude was purified through silica gel column chromatography using 50% EtOAc/heptane to obtained methyl 3-amino-4-((3-chlorophenyl) amino) benzoate (7.1 g, 96.07%) as a gummy liquid. LCMS: 67.71%, m/z=277.1 [M+H]$^+$; $^1$H NMR (CDCl$_3$, 400 MHz): δ 7.45-7.50 (m, 2H), 7.14-7.19 (m, 2H), 6.86-6.91 (m, 2H), 6.77 (td, J=1.2, 8.8 Hz, 1H), 5.55 (br s, 1H), 3.88 (s, 3H).

Step-4: Synthesis of methyl 1-(3-chlorophenyl)-1H-benzo[d]imidazole-5-carboxylate (Int-5): To a stirred solution of methyl 3-amino-4-((3-chlorophenyl)amino)benzoate (7.1 g, 25.72 mmol, 1 eq) and triethyl orthoformate (19.06 g, 128.62 mmol, 5 eq) in 1,4-Dioxane (80 mL) PTSA (884 mg, 5.144 mmol, 0.2 eq) was added at room temperature. The resulting reaction mixture was heated to 100° C. for 16 h until SM was consumed as indicated by crude LCMS/TLC. The reaction mixture was filtered through celite bed, washed with EtOAc (2×100 mL). Volatiles were evaporated, washed with sat. NaHCO$_3$ (100 mL) and extracted with EtOAc (3×100 mL). The combined organic extracts were washed with brine (200 mL); dried over sodium sulfate, filtered and concentrated in vacuo to obtain the crude. The crude was purified through silica gel column chromatography using 40% EtOAc/heptane to obtained methyl 1-(3-chlorophenyl)-1H-benzo[d]imidazole-5-carboxylate (5.8 g, 78.6%) as a pale brown solid. LCMS: 89.6%, m/z=287.2 [M+H]$^+$; $^1$H NMR (CDCl$_3$, 400 MHz): δ 8.60 (d, J=1.0 Hz, 1H), 8.18 (s, 1H), 8.08 (dd, J=1.5, 8.6 Hz, 1H), 7.53-7.58 (m, 3H), 7.42-7.51 (m, 2H), 3.97 (s, 3H).

Step-5: Synthesis of 1-(3-chlorophenyl)-1H-benzo[d]imidazole-5-carboxylic acid (Int-6), general procedure for ester hydrolysis using NaOH: To a stirred solution of methyl 1-(3-chlorophenyl)-1H-benzo[d]imidazole-5-carboxylate) (5.8 g, 20.23 mmol, 1 eq) in THF/water (8:2, 60 mL) or MeOH/water (8:2, 60 mL), NaOH (1.21 g, 30.34 mmol, 1.5 eq) was added room temperature and then continued stirring at room temperature for 16 h. The reaction was monitored by crude LCMS/TLC; after consumption of the starting material, volatiles were evaporated, neutralized with 1N HCl up to pH=7. The solids were filtered, washed with Et$_2$O (200 mL) and dried in vacuo to obtain 1-(3-chlorophenyl)-1H-benzo[d]imidazole-5-carboxylic acid (4.5 g, 81.66%) as a pale brown solid. LCMS: 99.58%, m/z=273.1 [M+H]$^+$; $^1$H NMR (DMSO-d$_6$, 500 MHz): δ 12.44-13.20 (m, 1H), 8.73

(s, 1H), 8.32 (s, 1H), 7.96 (br d, J=8.6 Hz, 1H), 7.88 (s, 1H), 7.65-7.73 (m, 3H), 7.58-7.61 (m, 1H).

Step 6: General procedure for amide coupling using HATU: To a stirred solution of Int-6 (1 eq) in DMF (10 v) under inert atmosphere were added HATU (1.5 eq), Amine (1.2 eq) was added at 0° C. To this stirred solution N,N'-diisopropylethylamine (3 eq) was added at 0° C. and then continued for stirring at room temperature for 16 h. The reaction was monitored by crude LCMS/TLC; after consumption of the starting material, the reaction mixture was quenched with ice water (10 mL) and extracted with EtOAc (2×15 mL). The combined organic extracts were washed with ice water (2×10 mL) and brine (10 mL); dried over sodium sulfate, filtered and concentrated in vacuo to obtain the crude. The crude was purified through silica gel column chromatography using 40% EtOAc/heptane, followed by prep-HPLC to obtain the products shown in Scheme 1.

Synthesis of (3-aminopyrrolidin-1-yl) (1-(3-chlorophenyl)-1H-benzo[d]imidazol-5-yl) methanone Provided below is an exemplary scheme to synthesize (3-aminopyrrolidin-1-yl) (1-(3-chlorophenyl)-1H-benzo[d]imidazol-5-yl) methanone that are inhibitors of hydroxyprostaglandin dehydrogenase.

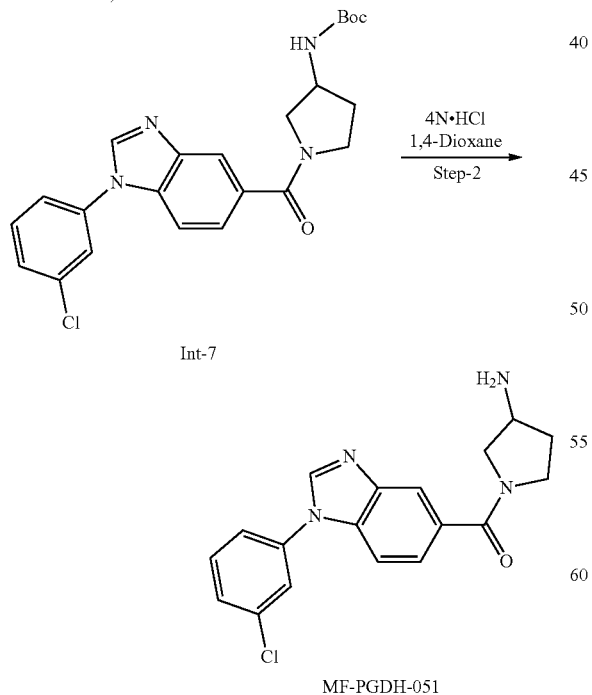

MF-PGDH-051

Step-1: Synthesis of tert-butyl (1-(1-(3-chlorophenyl)-1H-benzo[d]imidazole-5-carbonyl)pyrrolidin-3-yl)carbamate (Int-7): Int-6 (400 mg, 1.47 mmol) was reacted with 3-Boc amino pyrrolidine (326 mg, 1.76 mmol, 1.2 eq) using the general procedure for amide coupling using HATU described above to afford tert-butyl (1-(1-(3-chlorophenyl)-1H-benzo[d]imidazole-5-carbonyl)pyrrolidin-3-yl)carbamate (280 mg, 43%) as a pale yellow liquid. LCMS: 81.8%, m/z=441.2 [M+H]+; 1H NMR (DMSO-d6, 400 MHz): δ 8.76 (s, 1H), 7.85-7.98 (m, 2H), 7.49-7.74 (m, 4H), 7.20-7.29 (m, 1H), 3.87-4.12 (m, 1H), 3.59-3.68 (m, 2H), 3.08-3.35 (m, 2H), 2.81-2.89 (m, 1H), 2.65-2.73 (m, 1H), 1.94-2.09 (m, 1H), 1.69-1.89 (m, 1H), 1.30-1.40 (m, 9H).

Step-2: Synthesis of (3-aminopyrrolidin-1-yl)(1-(3-chlorophenyl)-1H-benzo[d]imidazol-5-yl)methanone (MF-PGDH-051): To a stirred solution of Int-7 (280 mg, 0.63 mmol, 1 eq) in DCM (5 mL), cooled to 0° C. and added 4N HCl in 1,4-Dioxane (5 mL), allowed to warm to room temperature then continued stirring at room temperature for 16 h. The reaction was monitored by LCMS/TLC; after consumption of the starting material, the reaction mixture was concentrated and dissolved in water and washed with EtOAc (20 mL), then the aq. layer was basified with sat. NaHCO3 solution and extracted with EtOAc (3×20 mL). The combined organic extracts were dried over sodium sulfate, filtered and concentrated in vacuo to afford (3-aminopyrrolidin-1-yl) (1-(3-chlorophenyl)-1H-benzo[d]imidazol-5-yl) methanone (120 mg, 57% yield) as an off-white solid. LCMS: m/z=341.2 [M+H]+.

Synthesis of 1-(3-chlorophenyl)-N-cyclopropyl-N-methyl-1H-benzo[d]imidazole-5-carboxamide (MF-PGDH-064)

Provided below is an exemplary scheme to synthesize 1-(3-chlorophenyl)-N-cyclopropyl-N-methyl-1H-benzo[d]imidazole-5-carboxamide that are inhibitors of hydroxyprostaglandin dehydrogenase.

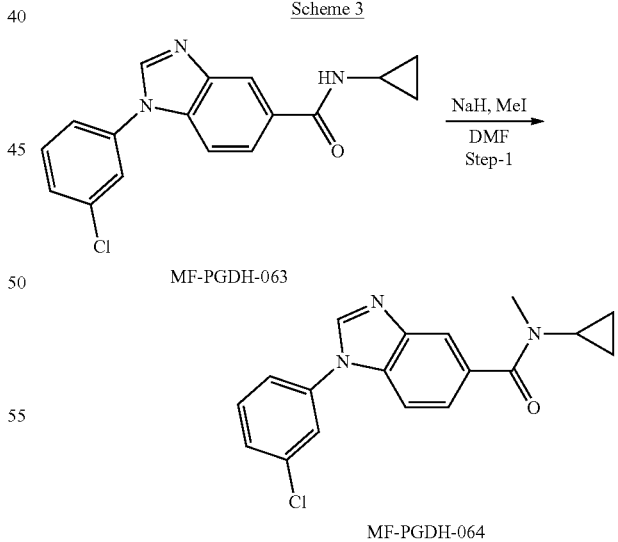

Step-1: Synthesis of 1-(3-chlorophenyl)-N-cyclopropyl-N-methyl-1H-benzo[d]imidazole-5-carboxamide (MF-PGDH-064): A stirred solution of 1-(3-chlorophenyl)-N-cyclopropyl-1H-benzo[d]imidazole-5-carboxamide (200 mg, 0.641 mmol, 1 eq) in DMF (3 mL) was cooled to 0° C. and NaH (60% in mineral oil) (24 mg, 0.96 mmol, 1.5 eq)

added. After stirring at 0° C. for 20 min, methyl iodide (136.05 mg, 0.961 mmol, 1.5 eq) was added at 0° C. and allowed to warm to room temperature stirred for 6 h. The reaction was monitored by LCMS/TLC; after consumption of the starting material the reaction mixture was quenched with sat. ammonium chloride solution (20 mL) and extracted with EtOAc (2×20 mL). The combined organic extracts were washed with brine (10 mL), dried over sodium sulfate, filtered and concentrated in vacuo to obtain the crude. The crude was purified through silica gel column chromatography using 40% EtOAc/heptane, followed by prep-HPLC purification to obtain 1-(3-chlorophenyl)-N-cyclopropyl-N-methyl-1H-benzo[d]imidazole-5-carboxamide (14.31 mg, 6.84% yield) as a brown liquid. LCMS: m/z=326.1 [M+H]$^+$.

Synthesis of 1-(1-(3-chlorophenyl)-1H-benzo[d]imidazole-5-carbonyl) pyrrolidin-3-one (MF-PGDH-090)

Provided below is an exemplary scheme to synthesize 1-(1-(3-chlorophenyl)-1H-benzo[d]imidazole-5-carbonyl) pyrrolidin-3-one that are inhibitors of hydroxyprostaglandin dehydrogenase.

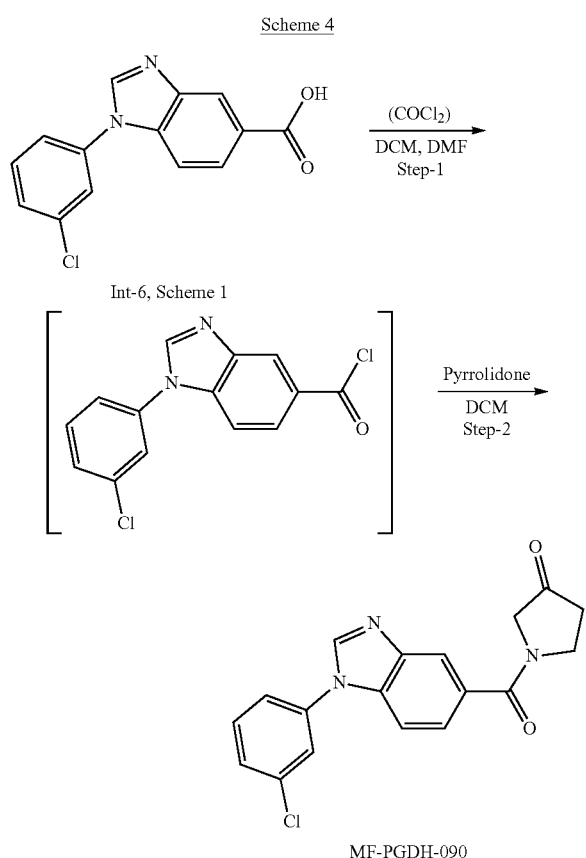

Step-1 and 2: Synthesis of 1-(1-(3-chlorophenyl)-1H-benzo[d]imidazole-5-carbonyl)pyrrolidin-3-one (MF-PGDH-090): To a stirred solution of Int-6 (100 mg, 0.367 mmol, 1 eq) in DCM (2 mL), cool to 0° C. and added Oxalyl chloride (92.73 mg, 0.735 mmol, 2.0 eq), DMF (0.1 mL), then stirred at 0° C. for 30 min. The reaction was monitored by TLC; after completion of the starting material the reaction mixture was concentrated and followed to the next step. Crude was dissolved in DCM (2 mL), cooled to 0° C., added pyrrolidone (53.60 mg, 121.5 mmol, 1.2 eq), warmed to room temperature then continued stirring at room temperature for 16 h. The reaction was monitored by crude LCMS/TLC; after consumption of the starting material the reaction mixture was concentrated in vacuo to obtain the crude. The crude was purified through prep-HPLC purification to obtain 1-(1-(3-chlorophenyl)-1H-benzo[d]imidazole-5-carbonyl) pyrrolidin-3-one (MF-PGDH-090, 4.8 mg, 3.85% yield) as a brown liquid.

Synthesis of 1-(3-chlorophenyl)-1H-benzo[d]imidazole-5-carboxamide (MF-PGDH-102)

Provided below is an exemplary scheme to synthesize 1-(3-chlorophenyl)-1H-benzo[d]imidazole-5-carboxamide that are inhibitors of hydroxyprostaglandin dehydrogenase.

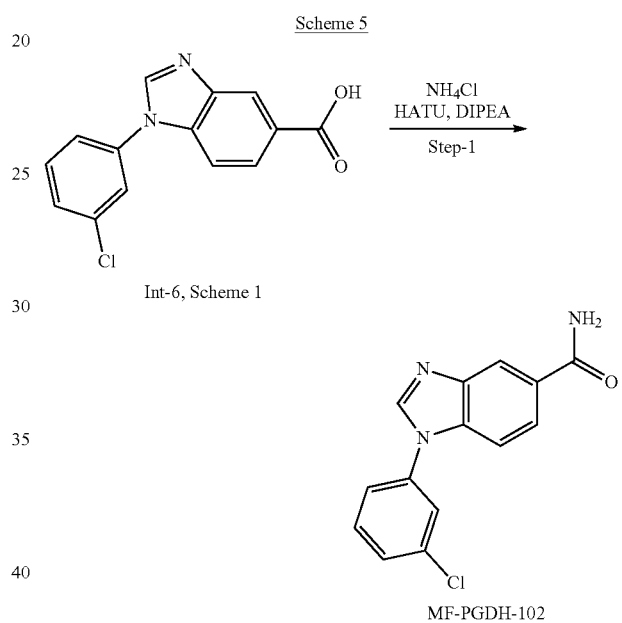

Step-1: Synthesis of 1-(3-chlorophenyl)-1H-benzo[d]imidazole-5-carboxamide (MF-PGDH-102): To a stirred solution of Int-6 (200 mg, 0.733 mmol, 1 eq) in DMF (5 mL) under inert atmosphere were added HATU (416 mg, 1.093 mmol, 1.5 eq), NH$_4$Cl (196.33 mg, 3.669 mmol, 5.0 eq) was added at 0° C. To this stirred solution N,N'-diisopropylethylamine (282 mg, 2.177 mmol, 3.0 eq) was added at 0° C. and then continued for stirring at room temperature for 16 h. The reaction was monitored by crude LCMS/TLC; after completion of the starting material the reaction mixture was quenched with ice water (10 mL), extracted with EtOAc (2×15 mL). The combined organic extracts were washed with ice water (2×10 mL) and brine (10 mL); dried over sodium sulfate, filtered and concentrated in vacuo to obtained 1-(3-chlorophenyl)-1H-benzo[d]imidazole-5-carboxamide (138.52 mg, 69.51%) as an off-white solid. LCMS: m/z=272.1 [M+H]$^+$.

Synthesis of Benzimidazoles Analogs with 2-Substituents

Provided below is an exemplary scheme to synthesize benzimidazoles analogs with 2-substituents that are inhibitors of hydroxyprostaglandin dehydrogenase.

Scheme 6
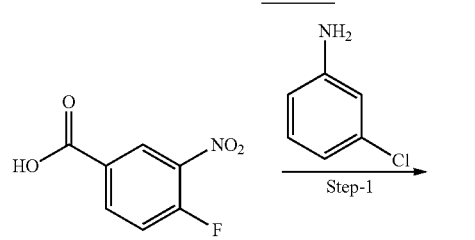
Step-1
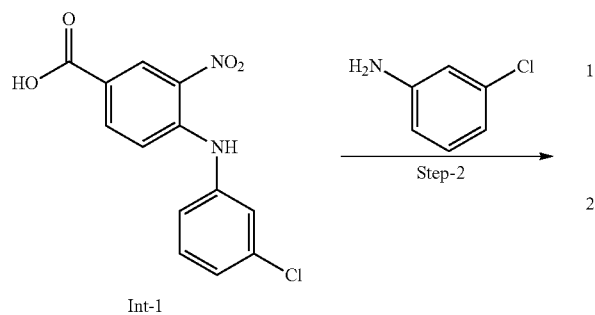
Step-2
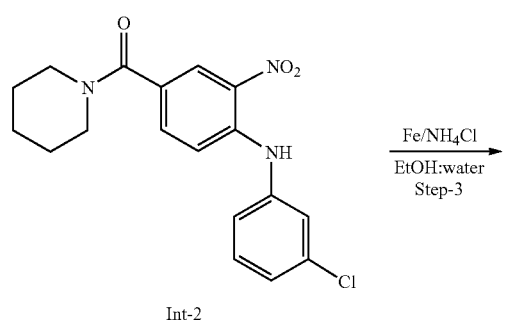
Fe/NH₄Cl
EtOH:water
Step-3
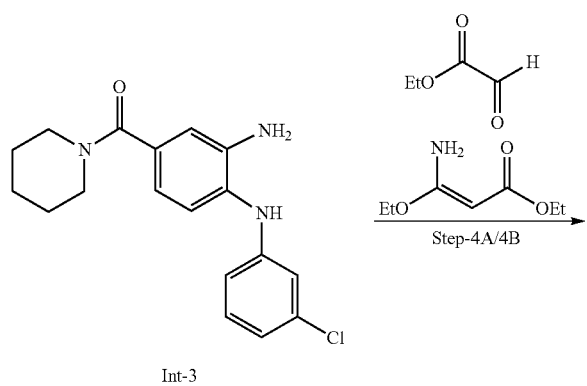
Step-4A/4B
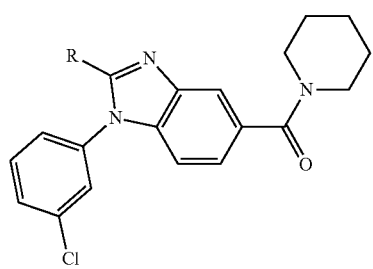
R = CO₂Et, MF-PGDH-27
R = CH₂CO₂Et, MF-PGDH-30
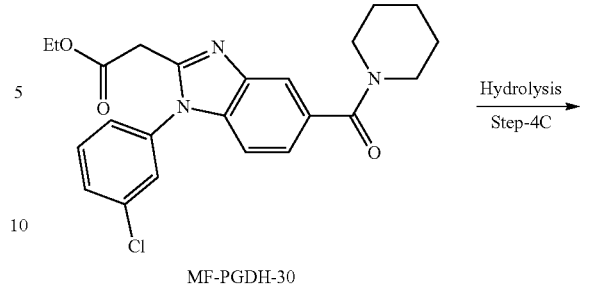
MF-PGDH-30
Hydrolysis
Step-4C
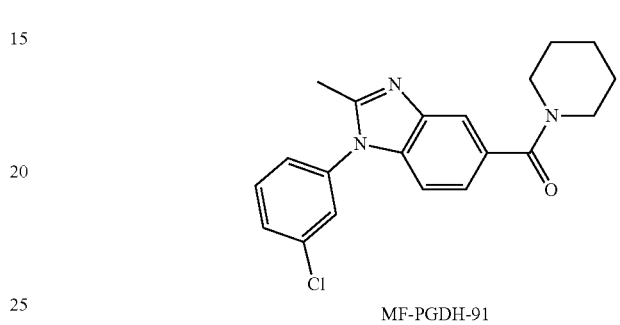
MF-PGDH-91
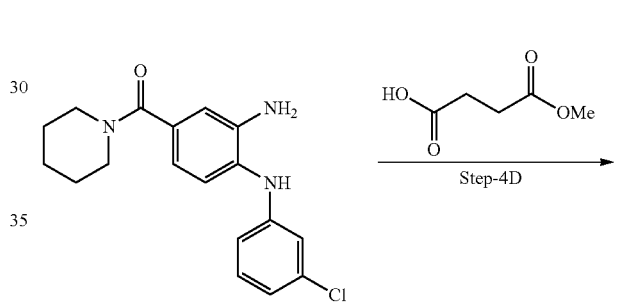
Step-4D
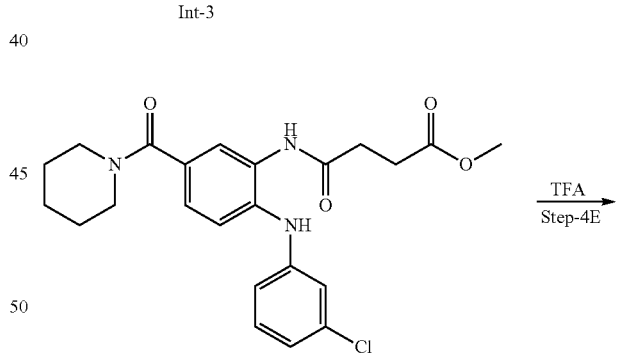
Int-4
TFA
Step-4E
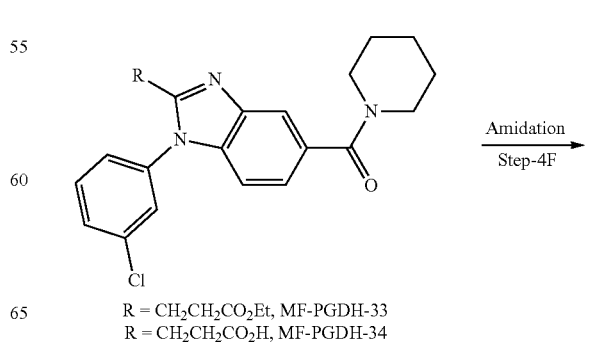
R = CH₂CH₂CO₂Et, MF-PGDH-33
R = CH₂CH₂CO₂H, MF-PGDH-34
Amidation
Step-4F

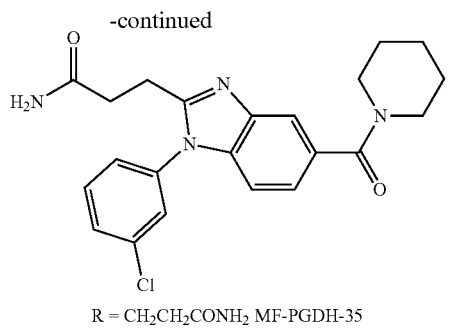

R = CH₂CH₂CONH₂ MF-PGDH-35

Step-1: Synthesis of 4-((3-chlorophenyl)amino)-3-nitrobenzoic acid (Int-1): In sealed bomb; To a stirred solution of 4-fluoro-3-nitrobenzoic acid (5 g, 27.02 mmol, 1 eq) in ethanol (100 mL) at room temperature, were added meta chloro aniline (4.18 g, 32.96 mmol, 1.22 eq) followed by the potassium carbonate (1.86 g, 13.51 mmol, 0.5 eq) and then heated to 80° C. for 16 h. The reaction was monitored by TLC, after completion of the reaction, cooled to room temperature and filtered; the solid was washed with ethanol and dried to obtain 4-((3-chlorophenyl)amino)-3-nitrobenzoic acid (5.2 g, 65.8% yield) as an off white solid. LCMS: m/z=293.0[M+H]⁺.

Step-2: Synthesis of (4-((3-chlorophenyl)amino)-3-nitrophenyl)(piperidin-1-yl)methanone (Int-2): To a stirred solution of Int-1 (4.5 g, 15.41 mmol, 1 eq) in DCM (45 mL) was added oxalyl chloride (5.83 g, 46.23 mmol, 3 eq) drop-wise at 0° C., and then continued stirring at 0° C. for 1 h, The reaction was monitored by TLC. After completion of the reaction it was cooled to room temperature and volatiles were evaporated. This was dissolved in DCM (45 mL) and to this stirred solution piperidine (1.57 g, 18.49 mmol, 1.2 eq) was added, stirred at room temperature for 5 h, concentrated in vacuo to obtain the crude. The crude was purified through silica gel column chromatography using 5% MeOH/DCM to obtain (4-((3-chlorophenyl) amino)-3-nitrophenyl)(piperidin-1-yl) methanone (5.7 g, 89% yield) as a yellow solid. LCMS: 87.89%, m/z=360.0[M+H]⁺.

Step-3: Synthesis of (3-amino-4-((3-chlorophenyl)amino) phenyl)(piperidin-1-yl)methanone (Int-3): To a stirred solution of Int-2 (7 g, 19.44 mmol, 1 eq) in EtOH:water (1:1, 120 mL), Iron powder (7.6 g, 136.11 mmol, 7 eq) and NH₄Cl (7.4 g, 136.11 mmol, 7 eq) were added at room temperature. The resultant reaction mixture was heated to 90° C. for 16 h. The reaction was monitored by TLC; after consumption of the starting material, the reaction mixture was filtered through celite bed and washed with EtOAc (2×50 mL). Volatiles were evaporated, quenched with water (100 mL), extracted with EtOAc (3×100 mL). The combined organic extracts were washed with brine (50 mL), dried over sodium sulfate, filtered and concentrated in vacuo to obtain the crude. The crude was triturated with diethyl ether (20 mL) to afford (3-amino-4-((3-chlorophenyl)amino) phenyl) (piperidin-1-yl)methanone (5 g, 77.60%) as a gummy liquid. LCMS: m/z=330.0 [M+H]f.

Step-4A: Synthesis of ethyl 1-(3-chlorophenyl)-5-(piperidine-1-carbonyl)-1H-benzo[d]imidazole-2-carboxylate (MF-PGDH-027): In a sealed tube; the stirred solution of Int-3 (200 mg, 0.606 mmol, 1 eq), ethyl glyoxalate (186.2 mg, 1.823 mmol, 3 eq) and PTSA (20 mg, 0.116 mmol, 0.2 eq) was added at room temperature. The resulting reaction mixture was heated to 70° C. for 16 h. The reaction was monitored by TLC; after completion of the starting material, cooled to room temperature and concentrated in vacuo to obtain the crude. The crude was purified through silica gel column chromatography using 50% EtOAc/heptane, followed by Prep-HPLC purification to obtain MF-PGDH-027 (18.82 mg, 7.55% yield) as an off-white solid.

Step-4B: Synthesis of ethyl 2-(1-(3-chlorophenyl)-5-(piperidine-1-carbonyl)-1H-benzo[d]imidazol-2-yl)acetate (MF-PGDH-030): To a stirred solution of Int-3 (200 mg, 0.606 mmol, 1 eq) in DMF (3 mL), ethyl (E)-3-amino-3-ethoxyacrylate (355 mg, 1.818 mmol, 3 eq) was added at room temperature. The resulting reaction mixture was heated to 100° C. for 16 h. The reaction was monitored by TLC; after completion of the starting material, cooled to room temperature and concentrated in vacuo to obtain the crude. The crude was purified through silica gel column chromatography using 50% EtOAc/heptane, followed by Prep-HPLC purification to obtain MF-PGDH-030 (35.4 mg, 13.7%) as an off-white solid.

Step-4C: Synthesis of MF-PGDH-091 (general procedure for ester hydrolysis using LiOH): To a stirred solution of MF-PGDH-30 (1 g, 2.35 mmol, 1 eq) in THF:water (1:1, 10 mL) at 0° C., LiOH.H₂O (235 mg, 4.7 mmol, 2 eq) was added at 0° C. The resultant reaction mixture was stirred at room temperature for 12 h. reaction was monitored by TLC; after completion of the starting material, cooled to room temperature and concentrated in vacuo to obtain the crude. The crude was purified through silica gel column chromatography using 50% EtOAc/heptane, followed by Prep-HPLC purification to afford MF-PGDH-091 (20.38 mg, 2.9%) as an off-white solid. LCMS: m/z=354.2 [M+H]⁺.

Step-4D: Synthesis of methyl 4-((2-((3-chlorophenyl)amino)-5-(piperidine-1-carbonyl) phenyl) amino)-4-oxobutanoate (Int-4): Int-3 (500 mg, 1.51 mmol, 1 eq) was subjected to the general procedure for amide coupling with HATU to afford methyl 4-((2-((3-chlorophenyl)amino)-5-(piperidine-1-carbonyl)phenyl)amino)-4-oxobutanoate (600 mg, 89.1%) as an off-white solid. LCMS: m/z=444.1 [M+H]⁺.

Step-4E: Synthesis of ethyl 3-(1-(3-chlorophenyl)-5-(piperidine-1-carbonyl)-1H-benzo[d]imidazol-2-yl)propanoate (MF-PGDH-033) and 3-(1-(3-chlorophenyl)-5-(piperidine-1-carbonyl)-1H-benzo[d]imidazol-2-yl)propanoic acid (MF-PGDH-034): To a stirred solution of Int-4 (1 g, 2.252 mmol, 1 eq) in DCE (20 mL), TFA (10 mL) was added under inert atmosphere at 0° C. Slowly warmed to room temperature and then heated to 80° C. for 16 h. The reaction was monitored by TLC; after completion of the starting material the reaction mixture was cooled to room temperature and diluted with ice water (20 mL). Neutralized with 10% NaHCO₃ solution and extracted with EtOAc (2×50 mL). The combined organic extracts were washed with ice water (2×10 mL) and brine (10 mL); dried over sodium sulfate, filtered and concentrated in vacuo to get crude. The crude was purified through Prep-HPLC purification to obtain MF-PGDH-033 (68.36 mg) and MF-PGDH-034 (33.41 mg) as off-white solids.

Step-4F: Synthesis of 3-(1-(3-chlorophenyl)-5-(piperidine-1-carbonyl)-1H-benzo[d]imidazol-2-yl)propanamide (MF-PGDH-035): To a stirred solution of MF-PGDH-034 (200 mg, 2.252 mmol, 1 eq) in steel bomb, aqueous ammonia (10 mL) in MeOH was added at 0° C. The resulting reaction mixture was slowly warmed to room temperature and then heated to 80° C. for 16 h. The reaction was monitored by TLC; after completion of the starting material the reaction mixture was cooled to room temperature and concentrated in vacuo to get crude. The crude was purified through Prep-HPLC purification to obtain MF-PGDH-035 (33.27 mg, 17.3% yield) as an off-white solid.

Synthesis of Benzimidazole-5-carboxyamide Analogs with Aryl/alkyl/Amide Variation Provided below is an exemplary scheme to synthesize Benzimidazole-5-carboxyamide analogs with Aryl/alkyl/ Amide variation that are inhibitors of hydroxyprostaglandin dehydrogenase.

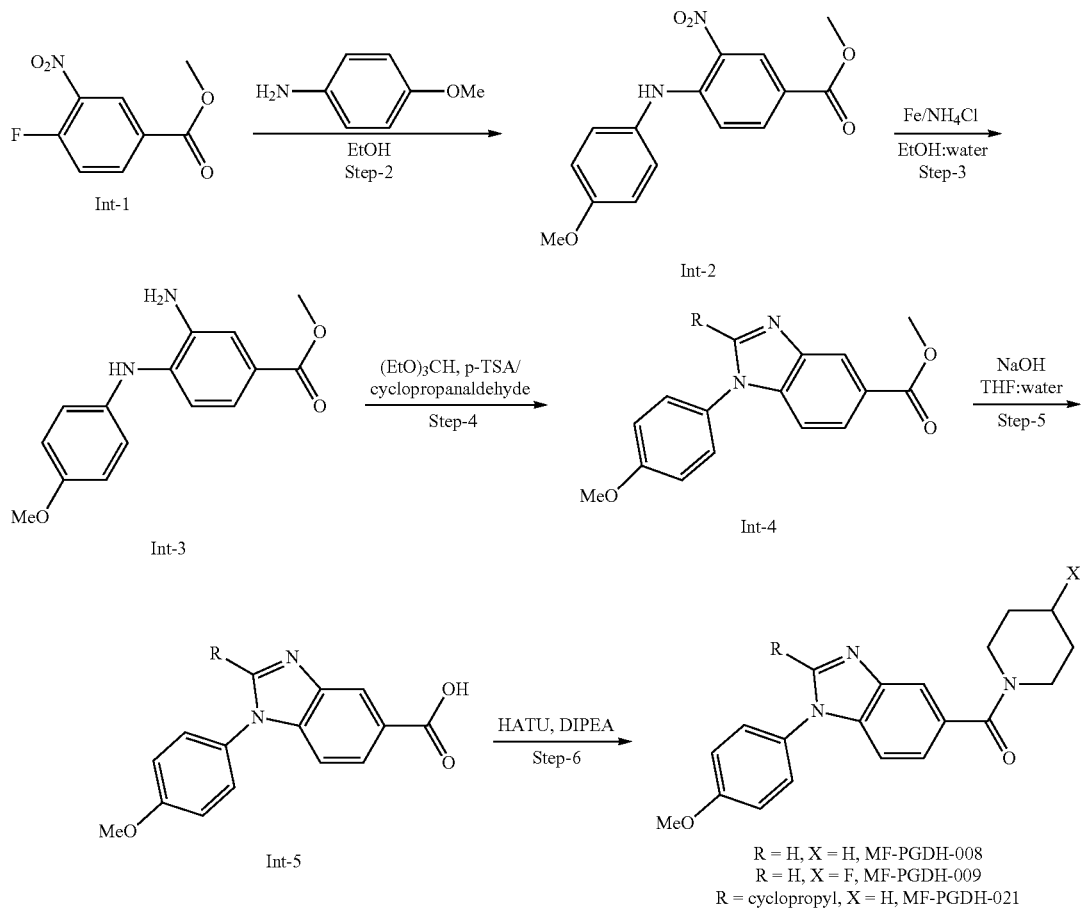

Scheme 7

R = H, X = H, MF-PGDH-008
R = H, X = F, MF-PGDH-009
R = cyclopropyl, X = H, MF-PGDH-021

The synthesis of Int-1 is described in 1a, Scheme 1 above.

Step-2: Synthesis of methyl 4-((4-methoxyphenyl) amino)-3-nitrobenzoate (Int-2): Methyl 4-fluoro-3-nitrobenzoate (10 g, 50.21 mmol, 1 eq) in EtOH (100 mL) was converted to Int-2 using the general procedure for SNAr reactions #1, with p-anisidine (7.68 g, 60.25 mmol, 1.2 eq) to afford methyl 4-((4-methoxyphenyl)amino)-3-nitrobenzoate (8.2 g, 53.24%) as a yellow solid. LCMS: 96.47%, m/z=303.1 [M+H]$^+$.

Step-3: Synthesis of methyl 3-amino-4-((4-methoxyphenyl)amino)benzoate (Int-3): Methyl-(4-methoxyphenyl) amino)-3-nitrobenzoate (8.09 g, 26.79 mmol) was converted to methyl 3-amino-4-((4-methoxyphenyl) amino) benzoate (7.1 g, 96.07%) using the general procedure for aryl nitro reduction using Fe to afford Int-3 as a gummy liquid. LCMS: 91.32%, m/z=273.2 [M+H]$^+$.

Step-4: Synthesis of methyl 1-(4-methoxyphenyl)-1H-benzo[d]imidazole-5-carboxylate/methyl 2-cyclopropyl-1-(4-methoxyphenyl)-1H-benzo[d]imidazole-5-carboxylate (Int-4a/4b): To a stirred solution of methyl 3-amino-4-((4-methoxyphenyl)amino)benzoate (7.02 g, 25.72 mmol, 1 eq) and triethyl orthoformate/cyclopropinaldehyde (128.62 mmol, 5 eq) in 1,4-Dioxane (80 mL)/DMF, PTSA (884 mg, 5.144 mmol, 0.2 eq)/Na$_2$S$_2$O$_3$ (1 eq) was added at room temperature. The resulting reaction mixture was heated to 90° C. for 16 h until consumption of SM by crude LCMS/ TLC. The reaction mixture was filtered through celite bed and washed with EtOAc (2×100 mL). Volatiles were evaporated, washed with sat. NaHCO$_3$ (100 mL) and extracted with EtOAc (3×100 mL). The combined organic extracts were washed with brine (200 mL), dried over sodium sulfate, filtered and concentrated in vacuo to obtain the crude. The crude was purified through silica gel column chromatography using 40% EtOAc/heptane to obtained methyl 1-(4-methoxyphenyl)-1H-benzo[d]imidazole-5-carboxylate, Int-4a (78.6% yield, m/z=283.3 [M+H]$^+$) and methyl 2-cyclopropyl-3-(4-methoxyphenyl)-3H-imidazo[4,5-b]pyridine-6-carboxylate (Int-4b) (53.40% yield, m/z=323.33[M+H]$^+$).

Step-5: Synthesis of 1-(4-methoxyphenyl)-1H-benzo[d] imidazole-5-carboxylic acid (Int-5a)/2-cyclopropyl-1-(4-methoxyphenyl)-1H-benzo[d]imidazole-5-carboxylic acid (Int-5b): Int-4a/4b (1 eq) was hydrolyzed using the general procedure for ester hydrolysis with NaOH to afford Int-5a (4.5 g, 81.66% yield, LCMS: m/z=269.2 [M+H]$^+$), and Int-5b (230 mg, 64.5% yield, LCMS: m/z=309.0 [M+H]$^+$) as a pale brown solid.

Step-6: Synthesis of MF-DH-008, MF-DH-009, and MF-DH-021: Int-5a/5b were subjected to the general procedure for amide coupling with HATU to afford MF-DH-008, MF-DH-009, and MF-DH-021.

Synthesis of Benzimidazole-5-Carboxyamide Analogs with Aryl/Amide Variation

Provided below is an exemplary scheme to synthesize benzimidazole-5-carboxyamide analogs with Aryl/alkyl/Amide variation that are inhibitors of hydroxyprostaglandin dehydrogenase.

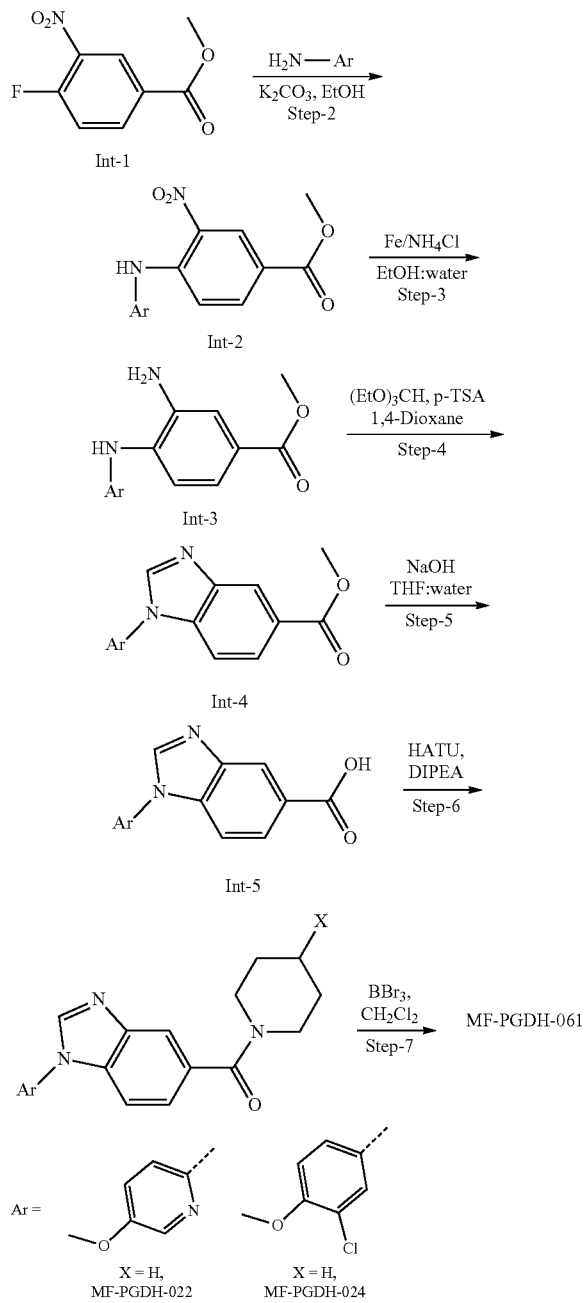

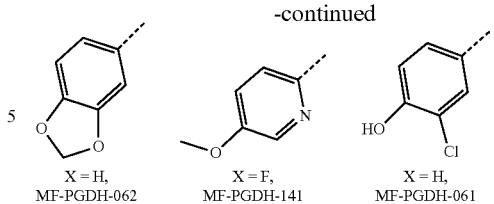

The synthesis of Int-1 is described in Scheme 1.

Step-2: Synthesis of Int-2; general procedure for SNAr reaction #2: To a stirred solution of methyl 4-fluoro-3-nitrobenzoate (2.5 g, 12.51 mmol, 1 eq) in EtOH (100 mL) in a sealed bomb, 5-methoxypyridin-2-amine/3-chloro-4-methoxyaniline (1.2 eq) and $K_2CO_3$ (1.726 g, 1 eq) were added at room temperature. The steel bomb was tightly sealed and the reaction mixture was heated to 100° C. for 16 h. The reaction was monitored by LCMS/TLC. Upon completion, the reaction mixture was cooled to room temperature and concentrated. The residue was quenched with sat.$NH_4Cl$ (100 mL) and extracted with EtOAc (3×50 mL), and the combined organic extracts were washed with brine (50 mL), dried over sodium sulfate, filtered, and concentrated in vacuo to afford the crude. The crude was triturated with diethyl ether (100 mL) to afford Int-2a (50.5% yield, LCMS: m/z=304.1[M+H]$^+$) for MF-PGDH-22 and MF-DH-141 as yellow solids.

Int-1 was converted to Int-2b (51.0% yield, m/z=337.2 [M+H]$^+$) for MF-PGDH-24 and MF-PGDH-61.

Int-1 was converted to Int-2c (59.0% yield, LCMS: m/z=317.1[M+H]$^+$) for MF-PGDH-62 using the general procedure for SNAr #1.

Step-3: Synthesis of Int-3a, Int-3b, and Int-3c was accomplished using the general procedure for aryl nitro reduction to afford Int-3a (82.3% yield, LCMS: m/z=274.1 [M+H]$^+$), Int-3b (79.2% yield, LCMS: m/z=307.1 [M+H]$^+$) and Int-3c (80.0% yield, LCMS: m/z=287.2 [M+H]$^+$) as gummy liquids.

Step-4: Synthesis of Int-4a, Int-4b, and Int-4c: To a stirred solution of Int-3a/Int-3b/Int-3c (1 eq) and triethyl orthoformate (19.06 g, 128.62 mmol, 5 eq) in 1,4-Dioxane (80 mL)/DMF, PTSA (884 mg, 0.2 eq) was added at room temperature. The resulting reaction mixture was heated to 90° C. for 16 h until consumption of SM by crude LCMS/TLC. The reaction mixture was filtered through celite bed, washed with EtOAc (2×50 mL). Volatiles were evaporated, washed with sat. $NaHCO_3$ (20 mL); extracted with EtOAc (3×30 mL), combined organic extracts were washed with brine (30 mL); dried over sodium sulfate, filtered and concentrated in vacuo to obtain the crude. The crude was purified through silica gel column chromatography using 40% EtOAc/heptane to obtain Int-4a (32.7% yield, LCMS: m/z=287.2 [M+H]$^+$), Int-4b (73.0% yield, LCMS: m/z=317.1 [M+H]$^+$), and Int-4c (83.0% yield, LCMS: m/z=297.0 [M+H]$^+$) as pale brown solids.

Step-5: Synthesis of Int-5a, Int-5b, and Int-5c: Using the general procedure for ester hydrolysis with NaOH, Int-4a, Int-4b, and Int-4c were converted to Int-5a (65.2% yield, LCMS: m/z=270.1 [M+H]$^+$), Int-5b (70.5% yield, LCMS: m/z=303.2 [M+H]$^+$) and Int-5c (81.4% yield, LCMS: m/z=282.1 [M+H]$^+$), all obtained as pale brown solids.

Step-6: Int-5 was coupled to the appropriate amines using the general procedure for amide couplings with HATU to afford MF-PGDH-022, MF-PGDH-024, MF-PGDH-062 and MF-DH-141.

Step-7: Synthesis of (1-(3-chloro-4-hydroxyphenyl)-1H-benzo[d]imidazol-5-yl)(piperidin-1-yl)methanone: To a stirred solution of (1-(3-chloro-4-methoxyphenyl)-1H-benzo[d]imidazol-5-yl)(piperidin-1-yl)methanone, MF-PGDH-024 (200 mg, 0.54 mmol, 1 eq) in $CH_2C_2$ (10 mL) under inert atmosphere; $BBr_3$ (1.62 mL, 1.62 mmol, 3.0 eq, 1M in $CH_2Cl_2$) was added at 0° C. and stirred at room temperature for 16 h. The reaction was monitored by crude LCMS/TLC; after consumption of the starting material, the reaction mixture was quenched with MeOH (10 mL), evaporated to dryness and then quenched with saturated $NaHCO_3$ solution (5 mL). It was extracted with EtOAc (2×15 mL), combined organic extracts were washed with brine (10 mL), dried over sodium sulfate, filtered and concentrated in vacuo to afford the crude which was purified by prep-HPLC to afford 1-(3-chloro-4-hydroxyphenyl)-1H-benzo[d]imidazol-5-yl)(piperidin-1-yl)methanone, MF-PGDH-061 (120 mg, 63%) as off white solid.

Synthesis of Pyrrolopyridine-5-Carboxyamide Analogs with Amide/Aryl/Hetero Aryl Variation Provided below is an exemplary scheme to synthesize pyrrolopyridine-5-carboxyamide analogs with amide/Aryl/Hetero Aryl variations that are inhibitors of hydroxyprostaglandin dehydrogenase.

Scheme 9

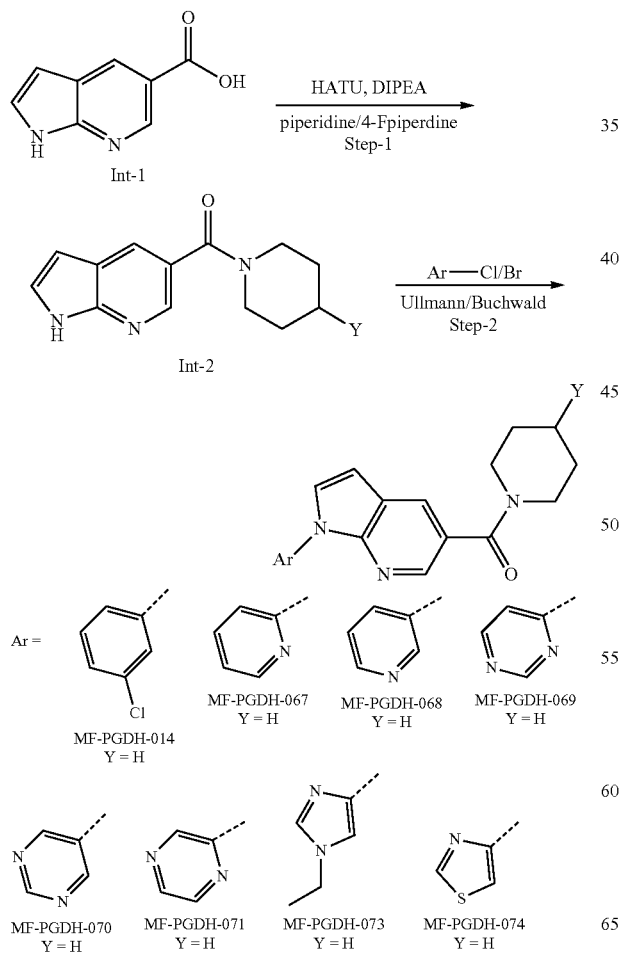

Scheme 10

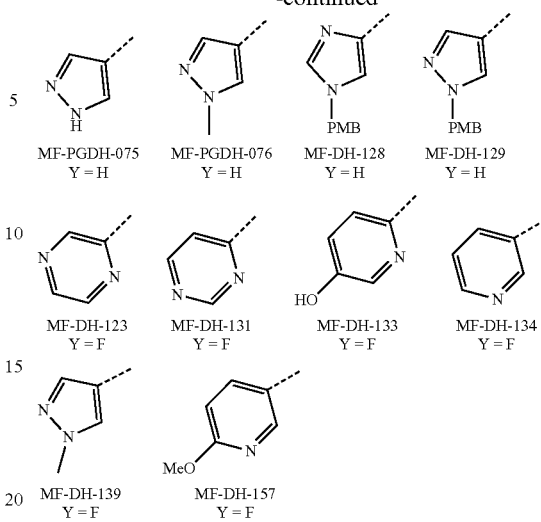

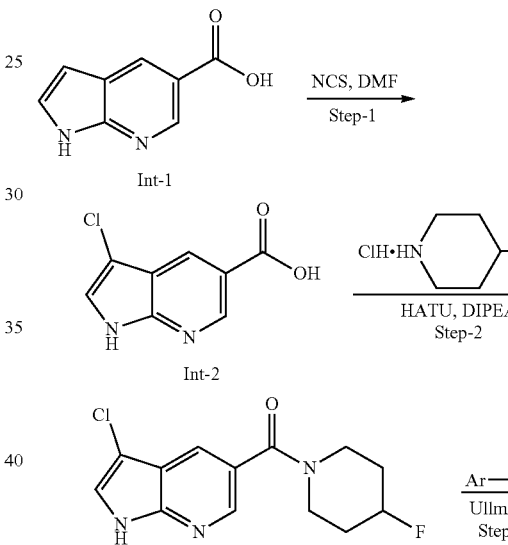

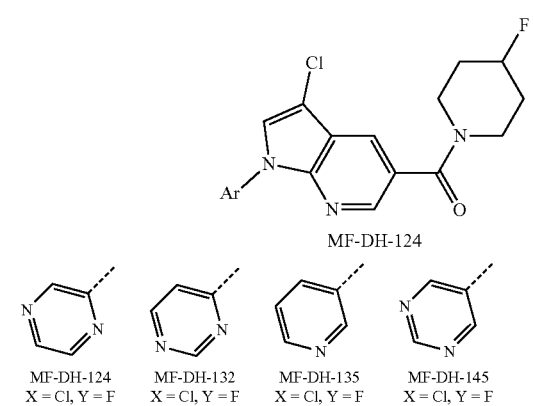

Step 1, Scheme 9: As shown in Scheme 9, Int-1 was subjected to amide coupling with the appropriate amine using HATU as described previously to afford Int-2.

Piperidin-1-yl (1H-pyrrolo[2,3-b]pyridin-5-yl)methanone: (950 mg, Yield: 79%); LCMS: m/z=230.2 [M+H]⁺; ¹H NMR (400 MHz, DMSO-d₆) δ=11.84 (s, 1H), 8.23 (s, 1H), 7.98 (s, 1H), 7.56 (d, J=1.83 Hz, 1H), 6.51 (d, J=1.89 Hz, 1H), 3.67-3.38 (m, 4H), 1.68-1.43 (m, 6H).

(4-fluoropiperidin-1-yl) (1H-pyrrolo[2,3-b]pyridin-5-yl)methanone: (2.17 g, Yield: 69%); LCMS: 88.5%, m/z=248.1 [M+H]⁺; ¹H NMR (400 MHz, DMSO-d₆) δ=11.83 (s, 1H), 8.25 (s, 1H), 8.01 (s, 1H), 7.65 (d, J=1.84 Hz, 1H), 6.78 (d, J=1.86 Hz, 1H), 3.76-3.35 (m, 4H), 1.98-1.54 (m, 4H).

(3-chloro-1H-pyrrolo[2,3-b]pyridin-5-yl)(4-fluoropiperidin-1-yl)methanone: (1.15 g, Yield: 69%); LCMS: 85.2%) m/z=282 [M+H]⁺; ¹H NMR (400 MHz, DMSO-d₆) δ=13.11 (br s, 1H), 12.35 (s, 1H), 8.84 (s, 1H), 8.46 (s, 1H), 7.80 (s, 1H), 5.03-4.80 (m, 1H), 3.82-3.33 (m, 4H), 2.04-1.64 (m, 4H).

Step-2, Scheme 9: General Buchwald procedure for synthesis of (MF-PGDH-071 and MF-DH-123, 124): In sealed tube, a stirring solution of piperidin-1-yl(1H-pyrrolo[2,3-b]pyridin-5-yl) methanone/(4-fluoropiperidin-1-yl)(1H-pyrrolo[2,3-b]pyridin-5-yl)methanone (Int-2) (0.65 mmol, 1 eq) in dioxane (15 mL) under inert atmosphere, Cs₂CO₃ (422 mg, 1.3 mmol, 2.0 eq) and the corresponding chloro/bromo arene (1.2 eq) were added at room temperature. Argon gas was purged for 15 min then Xantphos (75.14 mg, 0.13 mmol, 0.2 eq) and Pd₂(dba)₃ (59.47 mg, 0.065 mmol, 0.1 eq),) were added under argon atmosphere. Sealed tube cap was tightly closed and the resultant reaction mixture was heated to 100° C. for 16 h. The reaction was monitored by crude LCMS/TLC; after completion of the reaction, the reaction mixture was quenched with satd. NH₄Cl (10 mL), filtered through celite bed, washed with EtOAc (10 mL). The mixture was extracted with EtOAc (2×10 mL), combined organic extracts were washed with brine (10 mL), dried over sodium sulfate, filtered and concentrated in vacuo to obtain the crude. The crude was purified through silica gel column chromatography using 70% EtOAc/heptanes, followed by Prep-HPLC purification afforded MF-PGDH-071 and MF-DH-123, 124.

Step 1, Scheme 10: General procedure for chlorination using NCS. Synthesis of 3-chloro-1H-pyrrolo[2,3-b]pyridine-5-carboxylic acid (Int-2, Scheme 10): To a stirred solution of 1H-pyrrolo[2,3-b]pyridine-5-carboxylic acid (Int-1) (1 g, 6.17 mmol) in DMF (10 v) under inert atmosphere was added NCS (906 mg, 6.68 mmol) at 40° C. The resultant reaction mixture was heated to 60° C. for 4 h. The reaction was monitored by crude LCMS/TLC; after completion of the starting material the reaction mixture was quenched with ice water (20 mL), solids were filtered, washed with diethyl ether (3×10 mL). The crude product was azeotroped with toluene (2×10 mL) and then dried for 2 h to afford 3-chloro-1H-pyrrolo[2,3-b]pyridine-5-carboxylic acid (Int-2) as light brown solid (850 mg, Yield: 70%). LCMS: 88.2%) m/z=195.0 [M−H]⁻; ¹H NMR (500 MHz, DMSO-d₆) δ=13.18 (br s, 1H), 12.37 (s, 1H), 8.84 (s, 1H), 8.45 (s, 1H), 7.82 (s, 1H).

Step 2, Scheme 9 and Step 3, Scheme 10: General Ullmann coupling procedure: To a stirred solution of Int-2 (Scheme 9)/Int-3 (Scheme 10) (0.7 mmol, 1 eq) in Dioxane (100 mL), heteroaryl bromide (1.2 eq) 2.0 eq. K₃PO₄, 0.2 eq. CuI, 0.2 eq. trans-dimethylcyclohexane-1,2-diamine were added at room temperature. Reaction mixture was purged with argon gas for 15 min and then continued the reaction at 100° C. for 16 h. The reaction was monitored by TLC and after completion of the reaction, quenched with sat.NH₄Cl solution (10 mL), and stirred at room temperature for 1 h. The solvent was evaporated under reduced pressure and diluted with ethyl acetate (10 mL), washed with sat. NaHCO₃ solution (50 mL), and brine solution (50 mL) and the organic phase dried over sodium sulfate, filtered and concentrated under reduced pressure to afford crude product which was further purified by prep-HPLC to afford the final products MF-PGDH-014, MF-PGDH-067, MF-PGDH-069, MF-PGDH-070, MF-PGDH-073, MF-PGDH-074, MF-PGDH-075, MF-PGDH-076, MF-DH-128, MF-DH-129, MF-DH-131, MF-DH-132, MF-DH-133, MF-DH-134, MF-DH-135, MF-DH-139, MF-DH-140, MF-DH-145 and MF-DH-157.

Synthesis of Azabenzimidazole Analogs

Provided below is an exemplary scheme to synthesize Azabenzimidazole analogs that are inhibitors of hydroxyprostaglandin dehydrogenase.

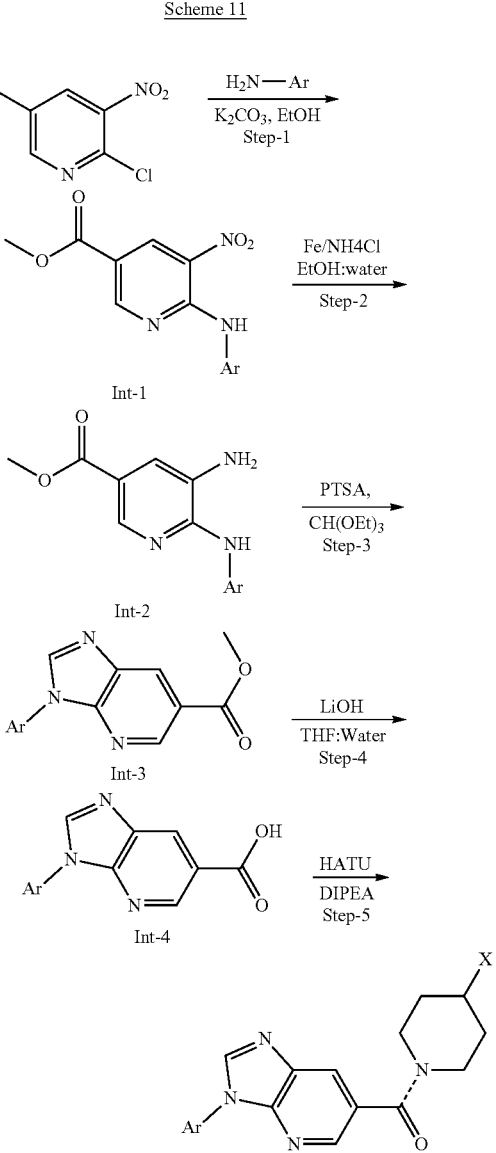

Scheme 11

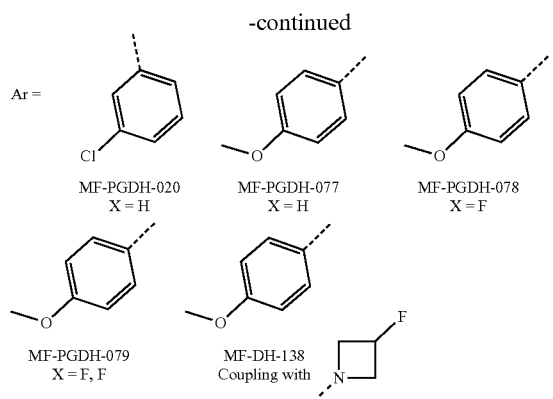

Step-1: Synthesis of Int-1: 6-Chloro-5-nitronicotinate (7 g, 32.31 mmol, 1 eq) and 3-Cl/4-methoxyaniline (1 eq) were subjected to SNAr #2 conditions to afford Int-1a (Ar=3-Cl phenyl, 95.2% yield, LCMS: m/z=308.2[M+H]⁺) as a yellow solid and Int-1b (Ar=4-OMe phenyl, 87.6% yield, LCMS: 96.0%, m/z=304.2[M+H]⁺) as a pale yellow solid.

Step-2: Synthesis of Int-2: Methyl-6-((4-methoxyphenyl)amino)-5-nitronicotinate/methyl-6-((3-chlorophenyl)amino)-5-nitronicotinate (Int-1) was subjected to the general procedure for aryl nitro reduction with Fe. The crude was purified through silica gel column chromatography using 60% EtOAc/heptane to obtain Int-2a (Ar=3-Cl phenyl, 97% yield, LCMS: m/z=278.2[M+H]⁺) as a yellow solid and Int-2b (Ar=4-OMe phenyl, 77% yield, LCMS: m/z=272.4 [M+H]⁺) as a pale yellow solid.

Step-3: Synthesis of Int-3 (general procedure for PTSA catalyzed ring closure to form imidazole): To a stirred solution of methyl-5-amino-6-((4-methoxyphenyl)amino) nicotinate/methyl-5-amino-6-((3-chlorophenyl) amino) nicotinate (Int-2) (1 g, 1 eq) and triethyl orthoformate (5 eq) in dioxane (20 mL), PTSA (0.2 eq) was added at room temperature. The resulting reaction mixture was heated to 100° C. for 16 h. The reaction was monitored by crude LCMS/TLC; after consumption of the starting material, reaction mixture was filtered through celite bed, washed with EtOAc (2×50 mL). Volatiles were evaporated, quenched with saturated NaHCO₃ solution (20 mL) and extracted with EtOAc (3×50 mL). The combined organic extracts were washed with brine (20 mL), dried over sodium sulfate, filtered and concentrated in vacuo to obtain the crude. The crude was purified through silica gel column chromatography using 50% EtOAc/heptane to obtain Int-3a (Ar=3-Cl phenyl, 83% yield, LCMS: m/z=288.2 [M+H]⁺) as a yellow solid and Int-3b (Ar=4-OMe phenyl, 71% yield, LCMS: m/z=284.2[M+H]⁺) as a pale yellow solid.

Step-4: Synthesis of Int-4, general procedure for ester hydrolysis with LiOH: To a stirred solution of methyl 3-(4-methoxyphenyl)-3H-imidazo[4,5-b]pyridine-6-carboxylate/methyl 3-(3-chlorophenyl)-3H-imidazo[4,5-b]pyridine-6-carboxylate (Int-3) (1 g, 1 eq) in THF/water (1:1, 20 mL) or MeOH/water (1:1, 20 mL), LiOH (2.5 eq) was added at room temperature and the resulting reaction mixture was stirred at room temperature for 16 h. The reaction was monitored by crude LCMS/TLC; upon completion, the reaction mixture was concentrated and neutralized with 1N HCl. The resulting solids were filtered, washed with Et₂O (50 mL), and dried in vacuo to obtain Int-4a (Ar=3-Cl phenyl, 65% yield, LCMS: m/z=274.2 [M+H]⁺) as an off-white solid and Int-4b (Ar=4-OMe phenyl, 90.5% yield, LCMS: m/z=270.1 [M+H]⁺) as an off-white solid.

Step-5: Synthesis of MF-PGDH-020, MF-PGDH-077, MF-PGDH-078, MF-PGDH-079 and MF-PGDH-138: Int-4 was subjected to amide coupling with the appropriate amine using HATU as described previously to afford the crude which was purified through silica gel column chromatography using 40% EtOAc: heptane/5% MeOH: CH2Cl2 followed by Prep-HPLC purification to obtain MF-PGDH-020, MF-PGDH-077, MF-PGDH-078, MF-PGDH-079 and MF-PGDH-138 as an off-white solid. The compounds in Scheme 11 above were synthesized by this procedure.

Synthesis of 2-Substituted Azabenzimidazole Analogs MF-DH-115 and MF-DH-116

Provided below is an exemplary scheme to synthesize 2-substituted azabenzimidazole analogs that are inhibitors of hydroxyprostaglandin dehydrogenase.

Scheme 12

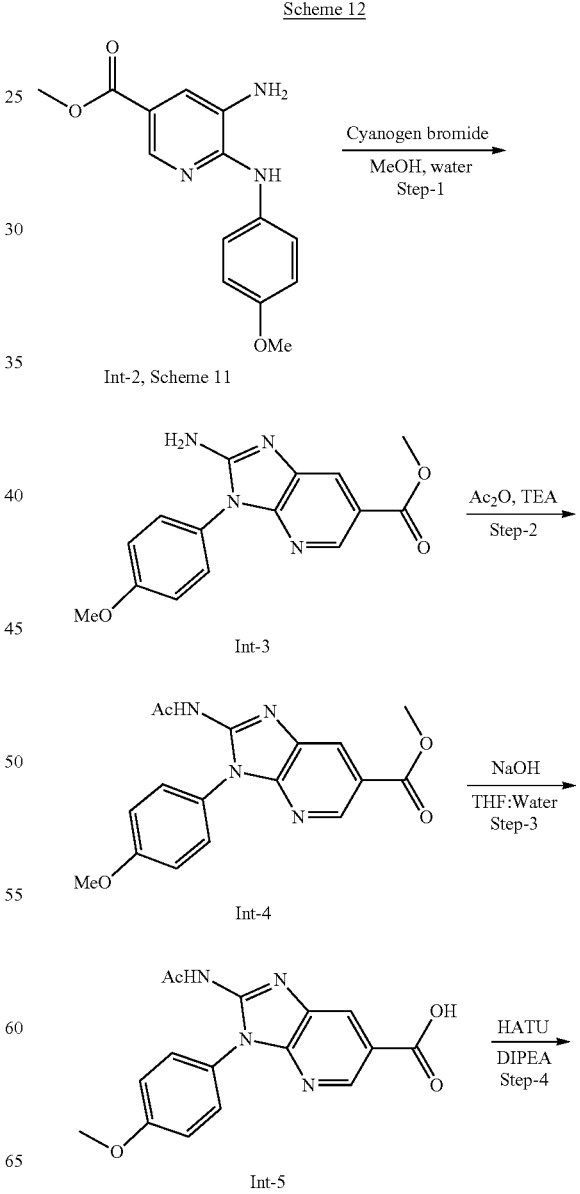

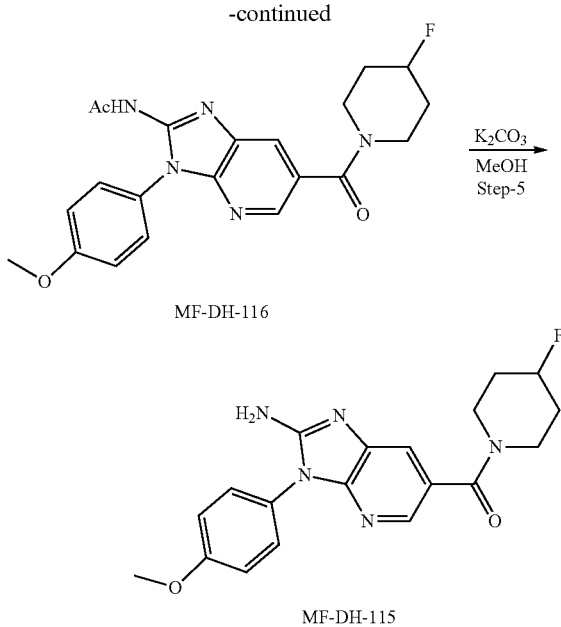

MF-DH-116

MF-DH-115

Step-1: Synthesis methyl 2-amino-3-(4-methoxyphenyl)-3H-imidazo[4,5-b]pyridine-6-carboxylate (Int-3): To a stirred solution of methyl 5-amino-6-((4-methoxyphenyl)amino)nicotinate (1 g, 3.54 mmol, 1 eq) in MeOH/water (1:1, 40 mL), cyanogen bromide (1.1 g, 10.63 mmol, 3 eq) was added at 0° C. The reaction mixture was slowly warmed to room temperature then heated to 80° C. for 16 h. The reaction was monitored by crude LCMS/TLC; after completion of the reaction it was cooled to room temperature and quenched with water (10 mL), extracted with EtOAc (3×50 mL), combined organic extracts were washed with brine (50 mL); dried over sodium sulfate, filtered and concentrated in vacuo to obtain methyl 2-amino-3-(4-methoxyphenyl)-3H-imidazo[4,5-b]pyridine-6-carboxylate (1.08 g, 99%) as a gummy liquid. LCMS: 80.63%, m/z=299.2[M+H]+.

Step-2: Synthesis methyl 2-acetamido-3-(4-methoxyphenyl)-3H-imidazo[4,5-b]pyridine-6-carboxylate (Int-4): To a stirred solution of Int-3 (800 mg, 2.68 mmol, 1 eq) in DCM (8 mL), triethylamine (829 mg, 8.05 mmol, 3 eq) was added at 0° C. It was stirred for 10 min at 0° C. and then acetic anhydride (821 mg, 8.05 mmol, 3 eq) was added. The reaction mixture was allowed to warm to room temperature then stirred for 16 h. The reaction was monitored by crude LCMS/TLC; after completion of the reaction it was quenched with ice water (10 mL), extracted with EtOAc (3×50 mL); combined organic extracts were washed with brine (50 mL), dried over sodium sulfate, filtered and concentrated in vacuo to afford the crude. The crude was purified through silica gel column chromatography using 20% EtOAc/heptane to afford methyl 2-acetamido-3-(4-methoxyphenyl)-3H-imidazo[4,5-b]pyridine-6-carboxylate (550 mg, 60.3%) as an off-white solid. LCMS: m/z=341.0 [M+H]+.

Step-3: Synthesis of 2-acetamido-3-(4-methoxyphenyl)-3H-imidazo[4,5-b]pyridine-6-carboxylic acid (Int-5): Int-4 (450 mg, 1.32 mmol, 1 eq) was subjected to the general procedure for ester hydrolysis with NaOH to afford 2-acetamido-3-(4-methoxyphenyl)-3H-imidazo[4,5-b]pyridine-6-carboxylic acid (400 mg, 96%) as a pale brown solid. LCMS: m/z=327.0[M+H]+.

Step-4: Synthesis of MF-DH-116: Int-5 (470 mg, 1.44 mmol, 1 eq) was subjected to amide coupling with 4-fluoro piperidine (241 mg, 1.73 mmol, 1.2 eq) using HATU as described previously. The crude was purified through silica gel column chromatography using 5% MeOH/DCM followed by Prep-HPLC purification to obtain MF-DH-116 (12.57 mg, 2.12%) as an off-white solid.

Step-5: Synthesis of MF-DH-115: To a stirred solution of MF-DH-116 (350 mg, 0.85 mmol, 1 eq) in methanol (5 mL) under inert atmosphere was added $K_2CO_3$ (235 mg, 1.70 mmol, 2.0 eq) at room temperature and then continued stirring at room temperature for 16 h. The reaction was monitored by crude LCMS/TLC; after consumption of the starting material, the reaction mixture was filtered and the filtrate was concentrated in vacuo to afford the crude. The crude was purified through silica gel column chromatography using 5% MeOH/DCM followed by Prep-HPLC purification to obtain MF-DH-115 (12.46 mg, 3.96%) as an off-white solid.

Synthesis of Benzamide Analogs

Provided below is an exemplary scheme to synthesize benzamide analogs that are inhibitors of hydroxyprostaglandin dehydrogenase.

Scheme 13

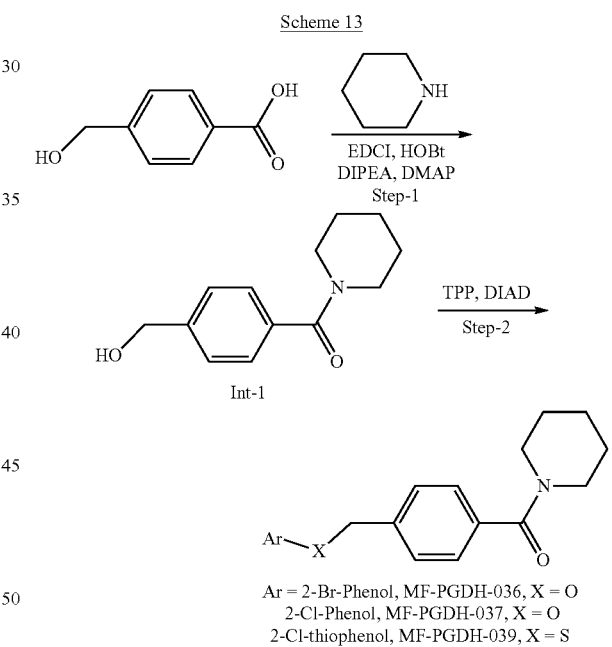

Ar = 2-Br-Phenol, MF-PGDH-036, X = O
2-Cl-Phenol, MF-PGDH-037, X = O
2-Cl-thiophenol, MF-PGDH-039, X = S Step-1: Synthesis of (4-(hydroxymethyl)phenyl)(piperidin-1-yl) methanone (Int-1): To a stirring solution of 4-(hydroxymethyl)benzoic acid (2 g, 13.15 mmol, 1 eq) and piperidine (1.12 g, 13.5 mol, 1 eq) in $CH_2Cl_2$ (20 mL) under inert atmosphere; EDCI (3.82 g, 19.72 mol, 1.2 eq), HOBt (2.13 g, 15.78 mol, 1.2 eq) were added at 0° C. To this stirred solution N,N'-diisopropylethylamine (373 mL, 2.14 mol, 3 eq) was added at 0° C. and then continued stirring at room temperature for 16 h. The reaction was monitored by crude LCMS/TLC; after consumption of starting materials, the reaction mixture was quenched with ice water (50 mL) and extracted with EtOAc (2×50 mL). The combined organic extracts were washed with ice water (2×20 mL) and brine (20 mL), dried over sodium sulfate, filtered and concentrated in vacuo to obtain the crude. The crude was purified through silica gel column chromatography using 40% EtOAc/heptane to afford Int-1 (1.6 g, 57.1%) as a pale-yellow solid. LCMS: m/z=220.1 [M+H]$^+$.

Step-2: Synthesis of MF-PGDH-036, MF-PGDH-037 and MF-PGDH-039: To a stirring solution of Int-1 (250 mg, 1.13 mmol, 1 eq) and 2-bromophenol/2-Clorophenol/2-chlorothiophenol (1.1 eq) in THE (10 mL) under inert atmosphere; TPP (446 mg, 1.7 mol, 1.5 eq) followed by DIAD (460 mg, 1.07 mmol, 1.5 eq) in THE (5 mL) were added sequentially and then continued stirring at room temperature for 16 h. The reaction was monitored by crude LCMS/TLC; after completion of the reaction, the reaction mixture was quenched with ice water (10 mL), extracted with EtOAc (2×10 mL). The combined organic extracts were washed with brine (10 mL), dried over sodium sulfate, filtered and concentrated in vacuo to obtain the crude. The crude was purified through silica gel column chromatography using 40% EtOAc/heptanes followed by Prep-HPLC purification to obtain MF-PGDH-036 (Yield: 2.05%), MF-PGDH-037 (Yield: 2.1%), and MF-PGDH-039 (Yield: 2.2%), as an off-white solid.

Synthesis of (4-(((2-chlorophenyl)sulfonyl)methyl) phenyl)(piperidin-1-yl)methanone (MF-PGDH-040)

Provided below is an exemplary scheme to synthesize (4-(((2-chlorophenyl)sulfonyl)methyl)phenyl)(piperidin-1-yl)methanone that is an inhibitor of hydroxyprostaglandin dehydrogenase.

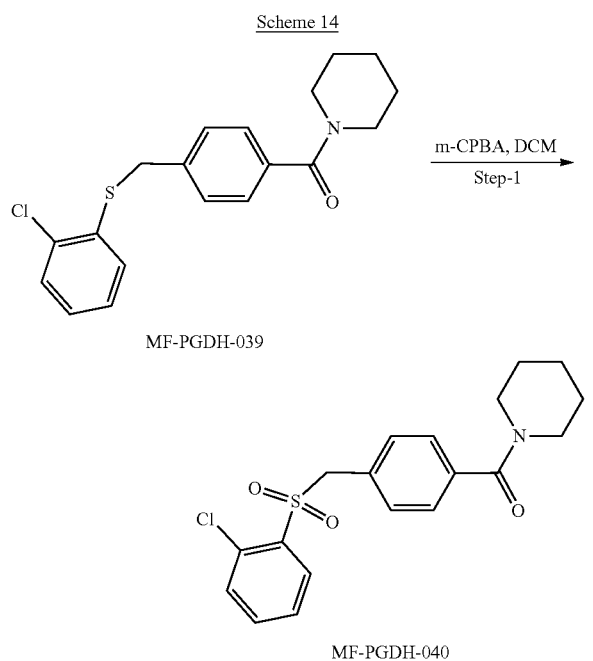

To a stirring solution of MF-PGDH-39 (from Scheme 13) (200 mg, 0.578 mmol, 1 eq) in CH$_2$C$_2$ (15 mL), m-CPBA (196.1 mg, 1.15 mmol, 2 eq) was added and then continued stirring at room temperature for 16 h. An additional aliquot of m-CPBA was added (1 equiv.). The reaction was monitored by crude LCMS/TLC; after consumption of the starting material, the reaction mixture was quenched with ice water (10 mL), extracted with CH$_2$C$_2$ (2×10 mL). The combined organic extracts were washed with brine (10 mL); dried over sodium sulfate, filtered and concentrated in vacuo to obtain the crude. The crude was purified through silica gel column chromatography using 40% EtOAc/heptane followed by Prep-HPLC purification to obtained (4-(((2-chlorophenyl)sulfonyl)methyl)phenyl)(piperidin-1-yl)methanone (MF-PGDH-040) (21.1 mg, 9.6%) as a brown liquid.

Synthesis of (4-(((2-chlorophenyl)sulfinyl)methyl) phenyl)(piperidin-1-yl)methanone (MF-PGDH-045)

Provided below is an exemplary scheme to synthesize (4-(((2-chlorophenyl)sulfinyl)methyl)phenyl)(piperidin-1-yl)methanone that is an inhibitor of hydroxyprostaglandin dehydrogenase.

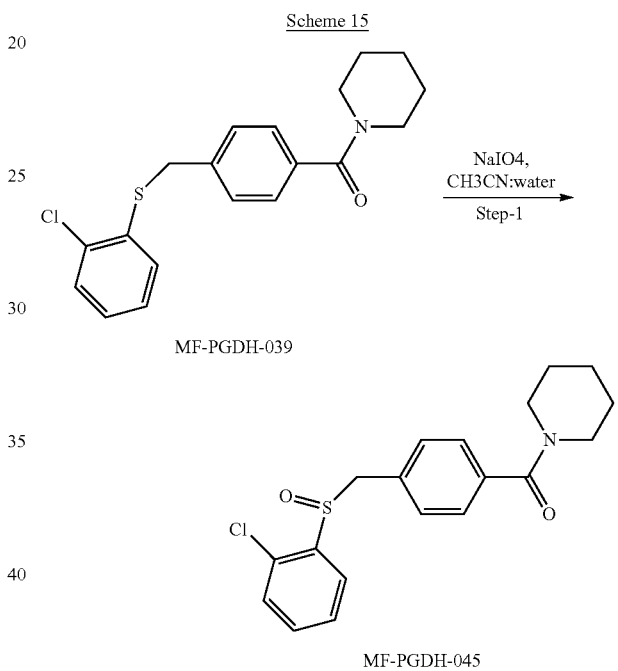

To a stirring solution of MF-PGDH-39 (50 mg, 0.144 mmol, 1 eq) in CH$_3$CN:water, NaIO4 (61.99 mg, 0.289 mmol, 2 eq) was added and then continued stirring at room temperature for 4 h. The reaction was monitored by crude LCMS/TLC; after consumption of starting material, the reaction mixture was quenched with ice water (10 mL) and extracted with EtOAc (2×10 mL). The combined organic extracts were washed with brine (10 mL), dried over sodium sulfate, filtered and concentrated in vacuo to obtain the crude. The crude was purified through silica gel column chromatography using 40% EtOAc/heptane followed by Prep-HPLC purification to afford 35.8 mg of MF-PGDH-045 as a brown liquid.

Synthesis of MF-PGDH-38, MF-PGDH-098, MF-DH-118, and MF-DH-121

Provided below is an exemplary scheme to synthesize inhibitors of hydroxyprostaglandin dehydrogenase labeled as MF-PGDH-38, MF-PGDH-098, MF-DH-118, and MF-DH-121 in Scheme 16 below.

Scheme 16 A

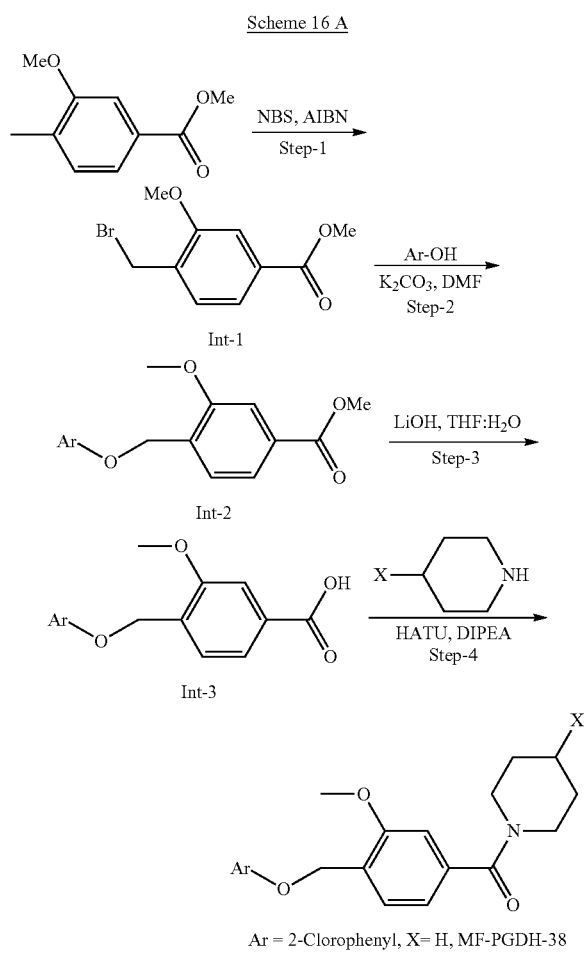

Int-3

Ar = 2-Clorophenyl, X= H, MF-PGDH-38
Ar = 2-Clorophenyl, X= F, MF-DH-118

Scheme 16B

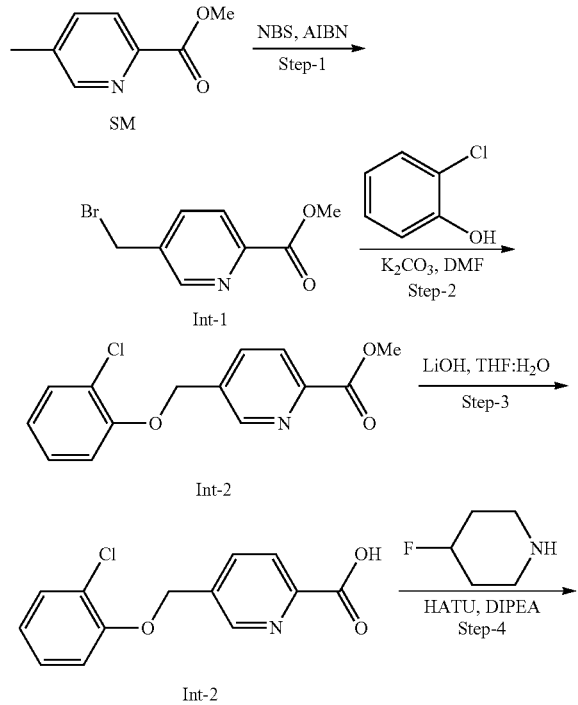

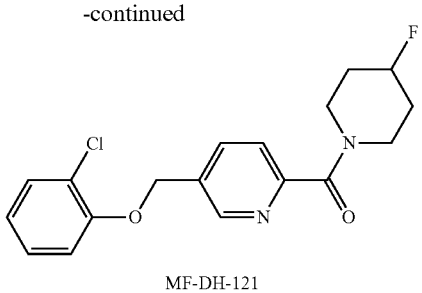

MF-DH-121

Scheme 16A Step-1: Synthesis of methyl 4-(bromomethyl)-3-methoxybenzoate (Int-1): To a stirring solution of methyl 3-methoxy-4-methylbenzoate/methyl 5-methylpicolinate (2.5 g, 13.87 mmol, 1 eq) in CHCl$_3$ (20 mL) under inert atmosphere, NBS (2.96 g, 16.66 mol, 1.2 eq) and AIBN (0.45 g, 2.74 mol, 0.2 eq) were added at room temperature and then the resultant reaction mixture was heated to reflux for 16 h. The reaction was monitored by crude LCMS/TLC; after consumption of the starting material, the reaction mixture was quenched with saturated Na$_2$S$_2$O$_3$ (10 mL) and extracted with EtOAc (2×20 mL). The combined organic extracts were washed with ice water (2×30 mL) and brine (20 mL), dried over sodium sulfate, filtered and concentrated in vacuo to afford the crude. The crude was purified through silica gel column chromatography using 30% EtOAc/heptane to obtain methyl 4-(bromomethyl)-3-methoxybenzoate (Int-1) (2.0 g, 55.7%) as off-white solid. MS: m/z=261.1 [M+2]$^+$.

Scheme 16A Step-2: Synthesis of Int-2: To a stirring solution of Int-1 (500 mg, 1.93 mmol, 1 eq), 2-chloro phenol (1 eq) in DMF (10 mL) under inert atmosphere, K$_2$CO$_3$ (1.5 eq) was added at room temperature and then heated to reflux for 16 h. The reaction was monitored by crude LCMS/TLC; after consumption of the starting material, the reaction mixture was quenched with ice water (10 mL), extracted with EtOAc (3×15 mL). The combined organic extracts were washed with ice water (2×10 mL) and brine (20 mL), dried over sodium sulfate, filtered and concentrated in vacuo to obtain the crude. The crude was purified through silica gel column chromatography using 15% EtOAc/heptane to obtain Int-2 (430 mg; Yield: 71.83%)) as off-white solid. LCMS: 91.35%: m/z=307.3 [M+H]$^+$.

Scheme 16A Step-3: Synthesis of Int-3: Int-2 was hydrolyzed using the general procedure for ester hydrolysis with LiOH to afford Int-3 (Yield: 58.7%) as a pale brown solid. LCMS: m/z=293.2 [M+H]$^+$.

Scheme 16A Step-4: Synthesis of MF-PGDH-038, MF-DH-118: Int-3 (200 mg, 1 eq) was coupled with piperidine/4-fluoro piperidine (1.2 eq) using HATU as the coupling agent as described previously to afford MF-PGDH-038, MF-DH-118 as off-white solids.

Scheme 16B Step-1: Synthesis of methyl 5-(bromomethyl)picolinate (Int-1): methyl 5-methylpicolinate was brominated using the general procedure for bromination described earlier using NBS to afford Int-1 (Yield: 52%) as off-white solid. LCMS: m/z=232.9 [M+2H]$^+$.

Scheme 16B Step-2: Synthesis of methyl 5-((2-chlorophenoxy)methyl)picolinate (Int-2): Int-1 was converted to Int-2 using the procedure for substitution reaction described earlier (Scheme 16A) with 2-chlorophenol to afford Int-2 (Yield: 66%) as pale yellow solid. LCMS: m/z=278.1 [M+H]$^+$.

Scheme 16B Step-3: Synthesis of 4-((2-chlorophenoxy)methyl)benzoic acid (Int-3): Int-2 was hydrolyzed using the general procedure for ester hydrolysis with LiOH to afford Int-3 (Yield: 84%) as off-white solid. LCMS: m/z=264.1 [M+H]⁺.

Scheme 16B Step-4: Synthesis of (5-((2-chlorophenoxy)methyl)pyridin-2-yl)(4-fluoropiperidin-1-yl)methanone (MF-DH-121): Int-3 was coupled with 4-fluoro piperidine using HATU as the coupling agent as described previously to afford MF-DH-121 (Yield: 61%) as off-white solids. LCMS: 99.96%, MS: m/z=349.0 [M+H]⁺.

Synthesis of MF-PGDH-095, MF-PGDH-096 and MF-PGDH-097

Provided below is an exemplary scheme to synthesize inhibitors of hydroxyprostaglandin dehydrogenase labeled as MF-PGDH-095, MF-PGDH-096 and MF-DH-097 in Scheme 17 below.

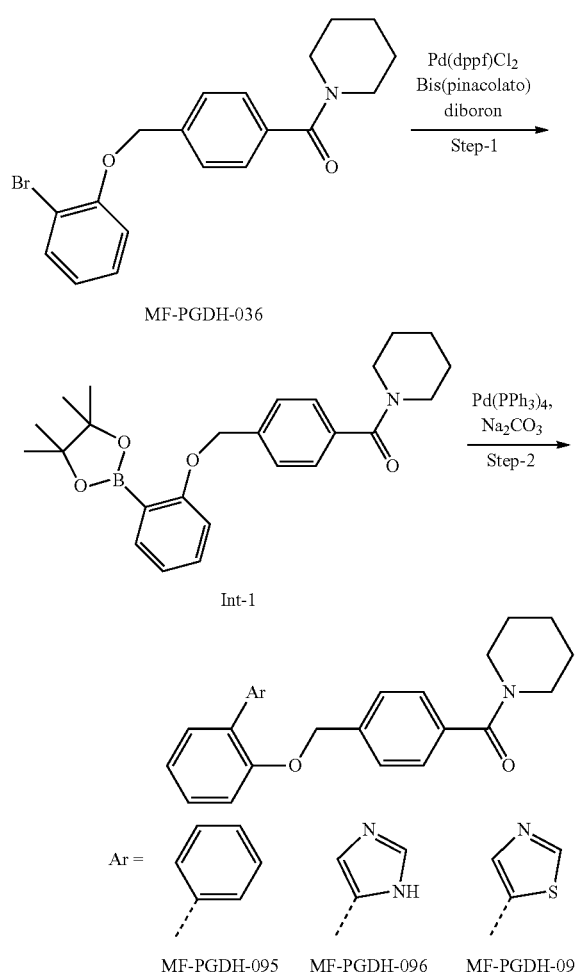

and evaporated to dryness. The residue was taken in ethyl acetate, washed with water, followed by brine, dried over anhydrous sodium sulfate and evaporated under reduced pressure. The crude product was purified by column chromatography to afford 2.82 g (51%) of Int-1; LCMS: m/z=422.2 [M+H]⁺, 340.2 [M+H]⁺.

Step-2: To a stirred solution of the aryl/heteroaryl bromide (2.1 mmol, 1 eq.) and Int-1 (2.52 mmol, 1.2 eq.) in 1,4-dioxane:water (3:1, 4.96 mL/mmol), $Na_2CO_3$ (6.5 mmol, 3 eq.) was added and purged with Argon for 15 min. To this solution, $Pd(PPh_3)_4$ (0.21 mmol, 0.1 eq.) was added and purged with Argon for another 10 min. The resulting reaction mixture was stirred at 90° C. for 16 h. The progress of the reaction was monitored by TLC. After completion of the reaction, the mixture was filtered through celite and evaporated to dryness. The residue was taken in ethyl acetate, washed with water, followed by brine, dried over anhydrous sodium sulfate and evaporated under reduced pressure. The crude product was purified by column chromatography followed by preparative HPLC to to obtain MF-PGDH-095, MF-PGDH-096, and MF-PGDH-097 as off-white solids.

Synthesis of MF-PGDH-041, MF-PGDH-042, MF-PGDH-087, MF-PGDH-088 and MF-PGDH-089

Provided below is an exemplary scheme to synthesize inhibitors of hydroxyprostaglandin dehydrogenase labeled as MF-PGDH-041, MF-PGDH-042 and MF-DH-087 in Scheme 18 below.

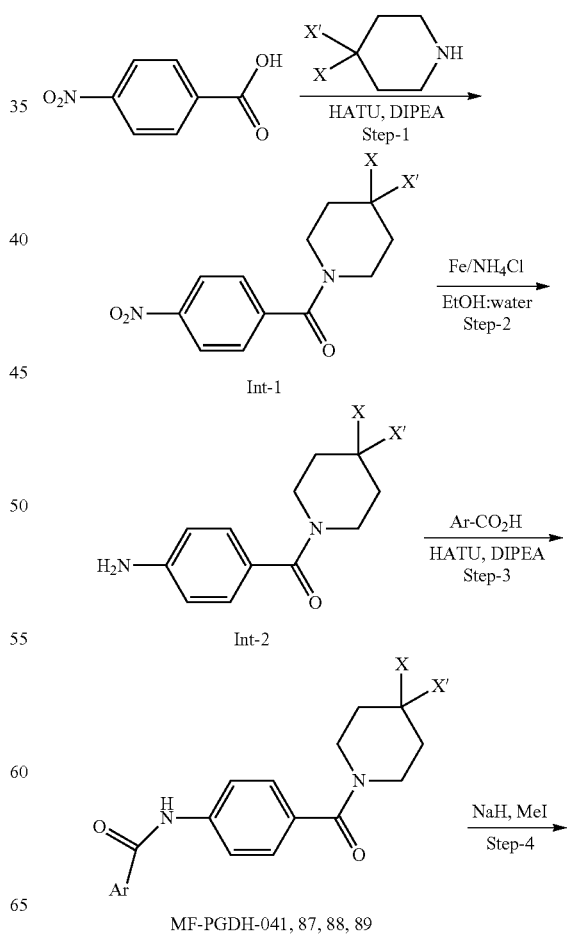

Step-1: To a stirred solution of bromo compound MF-PGDH-036 (5 g, 0.013 mol, 1 eq) and corresponding Bis(pinacolato)diboron (5.1 g, 0.02 mol, 1.5 eq.) in 1,4-dioxane (5 V, 50 mL/mmol), KOAc (3.82 g, 0.04 mmol, 3 eq.) was added and purged with Argon for 15 min. To this solution, $PdCl_2$ (dppf). DCM (1 g, 0.0013 mmol, 0.1 eq.) was added and purged with Argon for another 10 min. The resulting reaction mixture was stirred at 90° C. for 16 h. The progress of the reaction was monitored by TLC. After completion of the reaction, the reaction mixture was filtered through Celite -continued

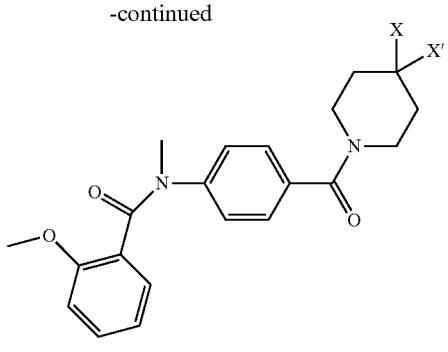

MF-PGDH-042

Ar = 2-methoxyphenyl, X, X' = H, MF-PGDH-041
Ar = 2-methoxyphenyl, X, X' = F, MF-PGDH-087
Ar = 2-Chlorophenyl, X, X' = H, MF-PGDH-088
Ar = 3-methoxyphenyl, X, X' = H, MF-PGDH-089

Step-1: Synthesis of Int-1: 4-nitrobenzoic acid (2 g, 1 eq) and piperidine/4,4-difluoropiperidine (1.5 eq) were coupled using HATU as described previously to afford Int-1a (X, X'=F, 85% yield, LCMS: m/z=271.1[M+H]$^+$) and Int-Tb (X, X'=H, 91% yield, LCMS: m/z=235.1 [M+H]$^+$).

Step-2: Synthesis of Int-2: Int-1 (1 eq) was converted to Int-2 using the general procedure for reduction of aryl nitro with Fe described above to afford Int-2a (X, X'=F, 51.7% yield, LCMS: m/z=240.1 [M+H]$^+$) and Int-2b: (X, X'=H, 53.5% yield, LCMS: m/z=205.2 [M+H]$^+$).

Step-3: Synthesis of Int-3: Int-2 (1 eq) and 2-methoxy phenyl/2-Chloro phenyl/3-methoxyphenyl carboxylic acid (0.7 eq) were coupled using HATU as described previously to afford MF-PGDH-041, MF-PGDH-087, MF-PGDH-088, and MF-PGDH-089 as off-white solids.

Step-4: Synthesis of MF-PGDH-042 (general procedure for N-methylation of amide): To a stirred solution of MF-PGDH-041 (140 mg, 0.414 mmol, 1 eq) in THF (5 mL), NaH (60% in mineral oil) (30 mg, 0.625 mmol, 1.5 eq) was added at 0° C. to room temperature for 1 h. To this stirred suspension, MeI ((88.18 mg, 0.625 mmol, 1.5 eq) was added and then resulting reaction mixture was stirred for 6 h. The reaction was monitored by crude LCMS/TLC; after consumption of the starting material, reaction mixture was quenched with saturated NH$_4$Cl (10 ml), extracted with EtOAc (2×50 mL). Combined organic extracts were washed with brine (20 mL); dried over sodium sulfate, filtered and concentrated in vacuo to obtain the crude. The crude was purified through silica gel column chromatography using 50% EtOAc/heptane followed by prep-HPLC purification to obtain MF-PGDH-042 (24.42 mg, 16.71%) as a pale brown solid.

Synthesis of MF-PGDH-043, and MF-PGDH-044

Provided below is an exemplary scheme to synthesize inhibitors of hydroxyprostaglandin dehydrogenase labeled as MF-PGDH-043 and MF-DH-044 in Scheme 19 below.

Scheme 19

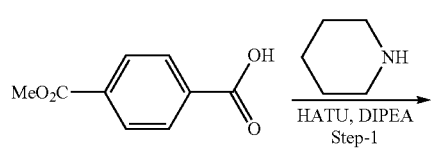

-continued

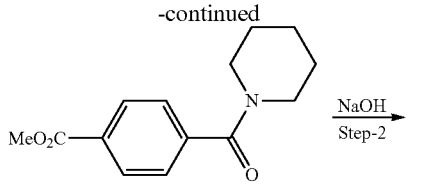

Int-1

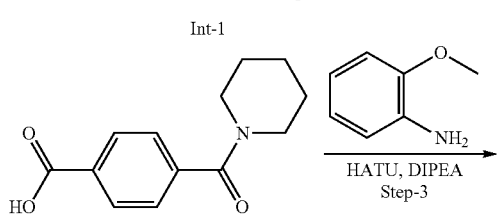

Int-2

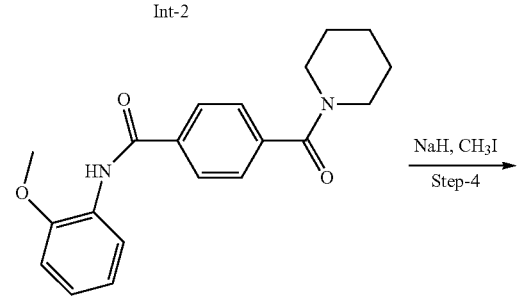

MF-PGDH-043

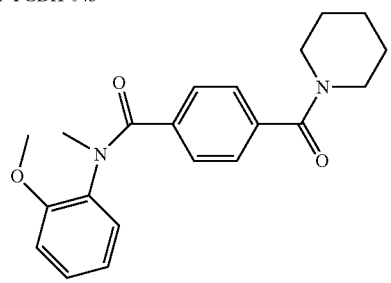

MF-PGDH-044

Step-1: Synthesis of methyl 4-(piperidine-1-carbonyl) benzoate (Int-1): 4-(methoxycarbonyl)benzoic acid (2 g, 11.09 mmol, 1 eq) and piperidine (1.3 mL, 13.31 mmol, 1.5 eq) in DMF (20 mL) were coupled using HATU as described previously to afford Int-1 (2.6 g, yield: 92%) as pale yellow solid. MS: m/z=248.1 [M+H]$^+$.

Step-2: Synthesis 4-(piperidine-1-carbonyl) benzoic acid (Int-2): Int-1 (2.8 g) was hydrolyzed using the general procedure for ester hydrolysis with NaOH to afford Int-2 (1.8 g, yield: 58%) as off-white solid. MS: m/z=234.0 [M+H]$^+$.

Step-3: Synthesis N-(2-methoxyphenyl)-4-(piperidine-1-carbonyl) benzamide (MF-PGDH-043): 4-(piperidine-1-carbonyl)benzoic acid (800 mg, 3.43 mmol, 1 eq) was coupled with 2-methoxy aniline (0.5 mL, 4.12 mol, 1.2 eq) using HATU (2 g, 5.14 mol, 1.5 eq), as described previously to afford MF-PGDH-043 (1 g, yield: 90%) as a pale yellow solid.

Step-4: N-(2-methoxyphenyl)-N-methyl-4-(piperidine-1-carbonyl) benzamide (MF-PGDH-044): MF-PGDH-043 (300 mg) was methylated with MeI using the general procedure for N-methylation of amide to afford MF-PGDH-044 (64.44 mg, 23.69%), as a pale brown solid.

Synthesis of Indoles MF-PGDH-004 and MF-PGDH-005

Provided below is an exemplary scheme to synthesize inhibitors of hydroxyprostaglandin dehydrogenase labeled as MF-PGDH-004 and MF-DH-005 in Scheme 20 below.

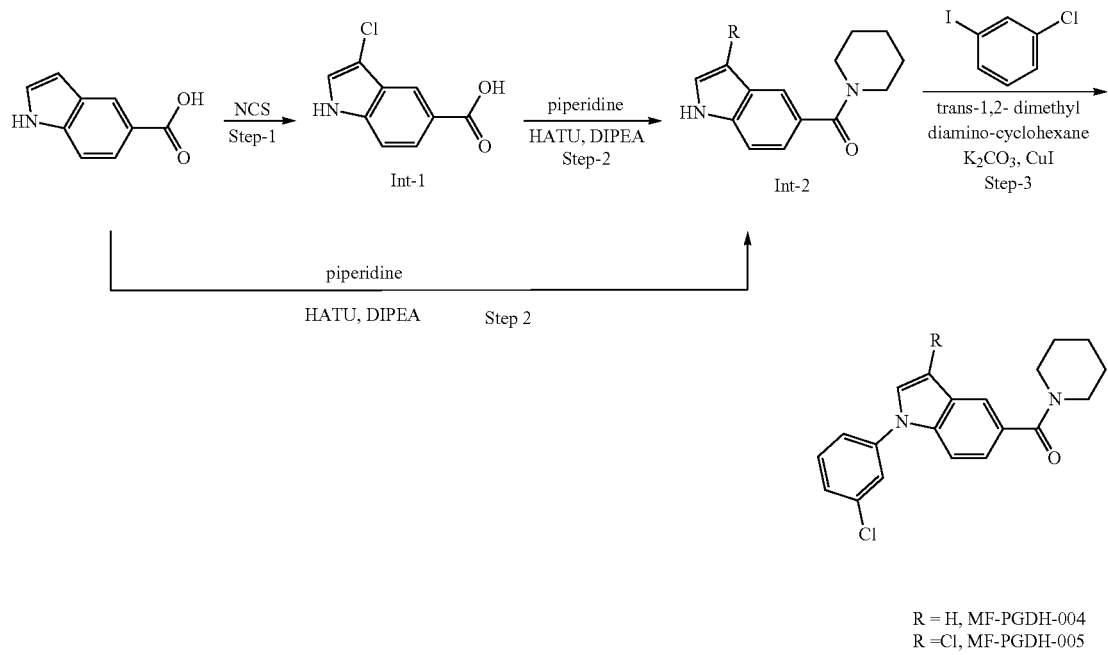

R = H, MF-PGDH-004
R = Cl, MF-PGDH-005

Step-1: Synthesis of Int-1: For R=Cl in Scheme 1 above, 1H-indole-5-carboxylic acid (2 g) was converted to Int-1 (2.3 g; Yield: 95%)) using the general procedure for chlorination with NCS. MS: m/z=196.01 [M+H]$^+$.

Step-2: Synthesis of Int-2: Int-1/1H-indole-5-carboxylic acid was coupled with piperidine using the general procedure of amide coupling with HATU to afford Int-2a (R=H, 71% yield, MS: m/z=229.1 [M+H]$^+$) and Int-2b (R=Cl, 68% yield, MS: m/z=263.6 [M+H]$^+$).

Step-3: Synthesis of MF-PGDH-004, and MF-PGDH-005: To a stirred solution of Int-2a/Int-2b (1 eq) in DMF (10 mL), 3-chloroiodobenzene (1.2 eq), K$_2$CO$_3$ (2 eq) were added at room temperature. The reaction mixture was purged with argon gas for 15 min. To this stirred solution CuI (0.2 eq), and trans-dimethyl cyclohexane-1,2-diamine (0.2 eq) was added and then continued stirring at 100° C. for 16 h. The reaction was monitored by TLC, after completion of starting material, quenched with sat.NH$_4$Cl solution (10 mL) filtered, washed with EtOAc. Extract with EtOAc, washed with ice water (2×30 mL) and brine solution (50 mL), the organic phase was dried over sodium sulfate, filtered and concentrated under reduced pressure to obtain the crude which was further purified by Prep-HPLC to afford MF-PGDH-004 and MF-PGDH-005 as off-white solids.

Synthesis of MF-PGDH-053, and MF-PGDH-054

Provided below is an exemplary scheme to synthesize inhibitors of hydroxyprostaglandin dehydrogenase labeled as MF-PGDH-053 and MF-DH-054 in Scheme 21 below.

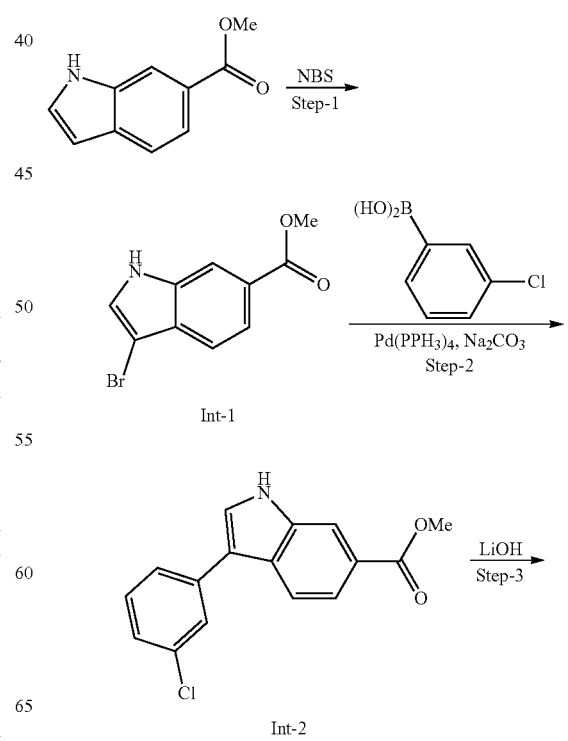

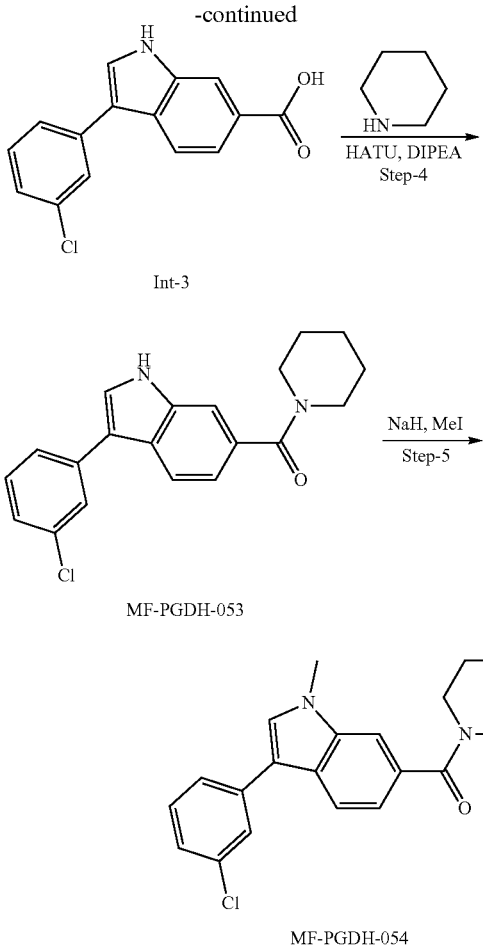

pressure. The crude product was purified by column chromatography using 40% EtOAc/heptane to obtain Int-2 (550 mg, 22%) as a brown solid. MS: m/z=287.1 [M+2]$^+$.

Step-3: Synthesis of 3-(3-chlorophenyl)-1H-indole-6-carboxylic acid (Int-3): Using the general procedure for ester hydrolysis with LiOH, methyl 3-(3-chlorophenyl)-1H-indole-6-carboxylate (550 mg) was converted to Int-3 (500 mg, 95.7%), as a pale brown solid. MS: m/z=270.1 [M−H]$^+$.

Step-4: Synthesis of (3-(3-chlorophenyl)-1H-indol-6-yl)(piperidin-1-yl)methanone, MF-PGDH-053: Using the general procedure for amide coupling with HATU, 3-(3-chlorophenyl)-1H-indole-6-carboxylic acid (500 mg) was converted to MF-PGDH-053 as an off-white solid.

Step-5: Synthesis of (3-(3-chlorophenyl)-1-methyl-1H-indol-6-yl)(piperidin-1-yl)methanone, MF-PGDH-054: To a stirred solution of MF-PGDH-053 (20 mg, 0.059 mmol, 1 eq) in THF (0.2 mL), NaH (60% in mineral oil) (3 mg, 0.11 mmol, 2 eq) was added at 0° C. to room temperature for 1 h. To this stirred suspension of MeI ((16 mg, 0.11 mmol, 2 eq) was added and then resulting reaction mixture was stirred for 2 h. The reaction was monitored by crude LCMS/TLC; after consumption of the starting material, the reaction mixture was quenched with saturated NH$_4$Cl (10 ml) and extracted with EtOAc (2×20 mL). Combined organic extracts were washed with brine (10 mL), dried over sodium sulfate, filtered and concentrated in vacuo to obtain the crude. The crude was purified through silica gel column chromatography using 50% EtOAc/heptane followed by prep-HPLC purification to obtain MF-PGDH-054 (16.94 mg, 81.4%), as an off white solid.

Synthesis of (1-(3-chlorophenyl)-1,2,3,4-tetrahydroquinolin-6-yl)(piperidin-1-yl)methanone, MF-PGDH-057

Step-1: Synthesis of methyl 3-bromo-1H-indole-6-carboxylate (Int-1): To a stirring solution of methyl 1H-indole-6-carboxylate (2 g, 11.42 mmol, 1 eq) in DMF (40 mL), NBS (3.04 g, 17.14 mmol, 1.5 eq) was added then stirred at room temperature for 2 h. The reaction was monitored by crude LCMS/TLC; after completion of the reaction, the mixture was quenched with ice water (10 mL) and extracted with EtOAc (2×50 mL). The combined organic extracts were washed with ice water (2×30 mL) and brine (20 mL), dried over sodium sulfate, filtered and concentrated in vacuo to obtain the crude. The crude was purified through silica gel column chromatography using 30% EtOAc/heptane to obtain Int-1 (1.51 g, 53%), as a pale brown solid. MS: m/z=256.1 [M+2]$^+$.

Step-2: Synthesis of methyl 3-(3-chlorophenyl)-1H-indole-6-carboxylate (Int-2), general procedure for Suzuki coupling: To a stirring solution of methyl 3-bromo-1H-indole-6-carboxylate (2.3 g, 9.05 mmol, 1 eq.), (3-chlorophenyl)boronic acid (2.11 g, 13.58 mmol, 1.5 eq.) in 1,4-dioxane:water (3:1, 20 mL), Na$_2$CO$_3$ (2.39 g, 22.63 mmol, 2.5 eq) was added and then the mixture was purged with Argon for 15 min. To this solution, Pd(PPh$_3$)$_4$ (1.04 g, 0.90 mmol, 0.1 eq) was added under argon. The resulting reaction mixture was stirred at 80° C. for 16 h. The progress of the reaction was monitored by TLC. After completion of the reaction, the reaction mixture was filtered through celite and evaporated to dryness. The residue was taken in ethyl acetate, washed with water, followed by brine, dried over anhydrous sodium sulfate and evaporated under reduced Provided below is an exemplary scheme to synthesize (1-(3-chlorophenyl)-1,2,3,4-tetrahydroquinolin-6-yl)(piperidin-1-yl)methanone, MF-PGDH-057 that is an inhibitor of hydroxyprostaglandin dehydrogenase.

Scheme 22

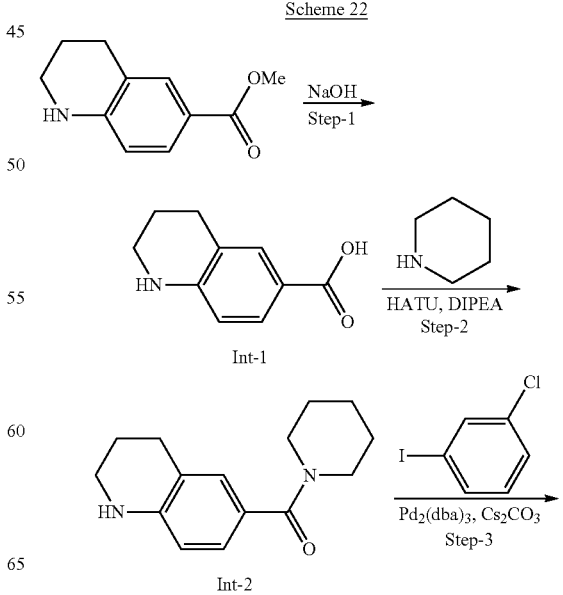

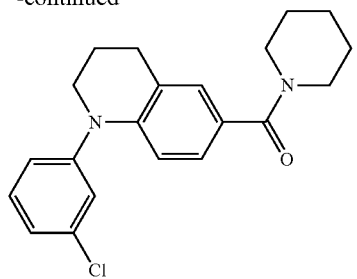

MF-PGDH-057

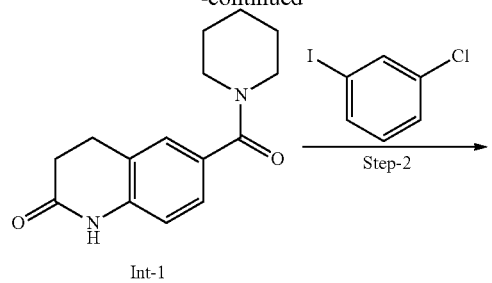

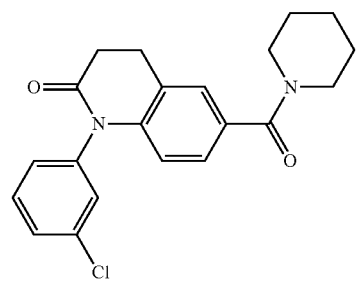

MF-PGDH-058

Step-1: Synthesis of 1,2,3,4-tetrahydroquinoline-6-carboxylic acid (Int-1): Using the general procedure for ester hydrolysis with NaOH, methyl 1,2,3,4-tetrahydroquinoline-6-carboxylate (1 g) was converted to Int-1 (800 mg, 86.9%), as a brown solid. MS: m/z=178.1 [M+H]$^+$.

Step-2: Synthesis of piperidin-1-yl(1,2,3,4-tetrahydroquinolin-6-yl)methanone (Int-2): Using the general procedure for amide coupling with HATU, 1,2,3,4-tetrahydroquinoline-6-carboxylic acid (800 mg) was converted to Int-2 (309 mg, 48%), as a brown solid. MS: m/z=245.2 [M+H]$^+$.

Step-3: Synthesis of (1-(3-chlorophenyl)-1,2,3,4-tetrahydroquinolin-6-yl)(piperidin-1-yl)methanone, MF-PGDH-057: To a stirring solution of piperidin-1-yl(1,2,3,4-tetrahydroquinolin-6-yl)methanone (200 mg, 0.819 mmol, 1 eq.), 1-chloro-3-iodobenzene (234 mg, 0.983 mmol, 1.2 eq.) in 1,4-dioxane (4 mL), Cs$_2$CO$_3$ (800 mg, 2.45 mmol, 3 eq) was added and then purged with argon for 15 min. To this solution, Pd$_2$(dba)$_3$ (37.5 mg, 0.0409 mmol, 0.1 eq) and xantphos (47.37 mg, 0.0819 mmol, 0.1 eq) was added and purged with Argon for another 10 min. The resulting reaction mixture was stirred at 90° C. for 16 h. The progress of the reaction was monitored by LCMS/TLC. After completion of the reaction, the mixture was filtered through celite and evaporated to dryness. The residue was taken in ethyl acetate, washed with water, followed by brine, dried over anhydrous sodium sulfate and evaporated under reduced pressure to obtain the crude. The crude was purified through prep-HPLC to afford MF-PGDH-057 (20.4 mg, 7.0%), as an off-white solid.

Synthesis of 1-(3-chlorophenyl)-6-(piperidine-1-carbonyl)-3,4-dihydroquinolin-2 (1H)-one, MF-PGDH-058

Provided below is an exemplary scheme to synthesize 1-(3-chlorophenyl)-6-(piperidine-1-carbonyl)-3,4-dihydroquinolin-2(1H)-one, MF-PGDH-058, that is an inhibitor of hydroxyprostaglandin dehydrogenase.

Scheme 23

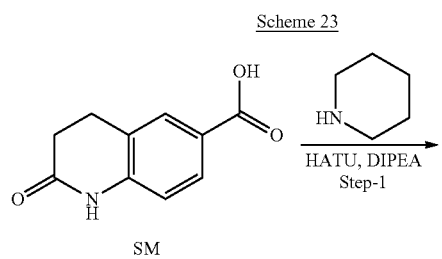

Step-1: Synthesis of 6-(piperidine-1-carbonyl)-3,4-dihydroquinolin-2(1H)-one (Int-1): Using the general procedure for amide coupling with HATU, 2-oxo-1,2,3,4-tetrahydroquinoline-6-carboxylic acid (1.5 g) was coupled with piperidine (806 mg, 9.46 mmol, 1.2 eq) to obtain Int-1 (1.7 g, 84.1%), as a brown solid. MS: m/z=259.1 [M+H]$^+$.

Step-2: Synthesis of 1-(3-chlorophenyl)-6-(piperidine-1-carbonyl)-3,4-dihydroquinolin-2(1H)-one, MF-PGDH-058: 6-(Piperidine-1-carbonyl)-3,4-dihydroquinolin-2(1H)-one (200 mg, 0.775 mmol, 1 eq.) and 1-chloro-3-iodobenzene (277 mg, 1.162 mmol, 1.5 eq.) were subjected to the general procedure for Ullmann coupling. The crude was purified through prep-HPLC to afford MF-PGDH-058 (23.5 mg, 8.2%), as an off-white solid.

Synthesis of (1-(3-chlorophenyl)-1H-indazol-5-yl)(piperidin-1-yl)methanone, MF-PGDH-006

Provided below is an exemplary scheme to synthesize (1-(3-chlorophenyl)-1H-indazol-5-yl)(piperidin-1-yl)methanone, MF-PGDH-006, that is an inhibitor of hydroxyprostaglandin dehydrogenase.

Scheme 24

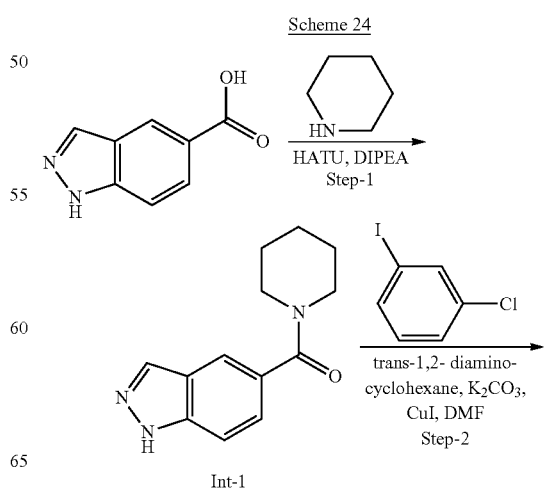

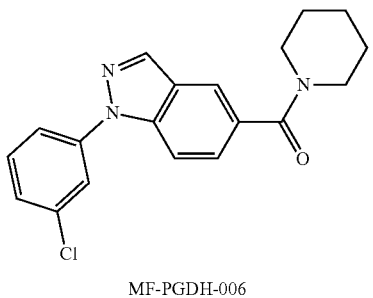

MF-PGDH-006

Step-1: Synthesis of (1H-indazol-5-yl)(piperidin-1-yl)methanone (Int-1): Using the general procedure for amide coupling with HATU, 1H-indazole-5-carboxylic acid (500 mg) was converted to Int-1 (610 mg, 86.28%), obtained as a brown solid. MS: m/z=230.1 [M+H]$^+$.

Step-2: Synthesis of MF-PGDH-006: To a stirring solution of (1H-indazol-5-yl)(piperidin-1-yl)methanone (610 mg, 2.66 mmol, 1 eq.) and 1-chloro-3-iodobenzene (623 mg, 2.66 mmol, 1 eq.) in DMF (5 mL), $K_2CO_3$ (734 mg, 5.32 mmol, 2 eq) was added and then purged with Argon for 15 min. To this solution, copper iodide (101 mg, 0.532 mmol, 0.2 eq) and trans-N,N'-dimethylcyclohexane-1,2-diamine (126 mg, 0.532 mmol, 0.2 eq) was added under argon and purged another 10 min. The resulting reaction mixture was heated at 90° C. for 16 h. The progress of the reaction was monitored by LCMS/TLC. After completion of the reaction, the reaction mixture was filtered through celite and evaporated to dryness. The residue was taken in ethyl acetate, washed with water, followed by brine, dried over anhydrous sodium sulfate and evaporated under reduced pressure to obtain the crude. The crude was purified through prep-HPLC to afford MF-PGDH-006 (40 mg, 4.41%), as a gummy liquid.

Synthesis of (3-(3-chlorophenyl)imidazo[1,2-a]pyridin-7-yl)(piperidin-1-yl)methanone, MF-PGDH-007

Provided below is an exemplary scheme to synthesize (3-(3-chlorophenyl)imidazo[1,2-a]pyridin-7-yl)(piperidin-1-yl)methanone, MF-PGDH-007, that is an inhibitor of hydroxyprostaglandin dehydrogenase.

Scheme 25

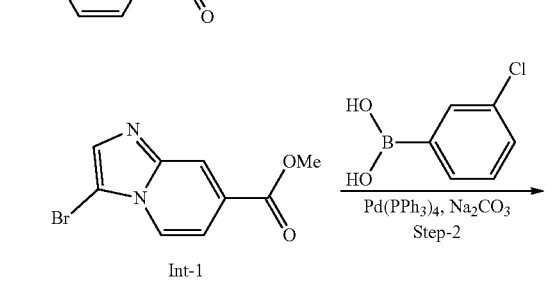

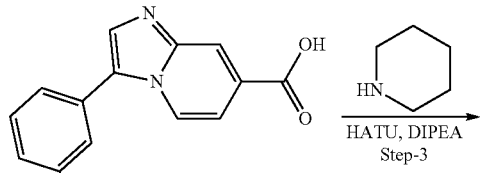

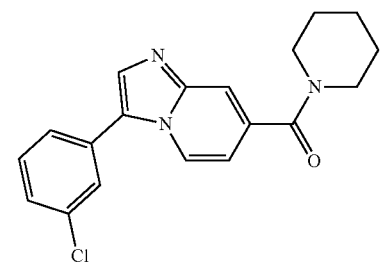

MF-PGDH-007

Step-1: Synthesis of methyl 3-bromoimidazo[1,2-a]pyridine-7-carboxylate (Int-1): To a stirring solution of methyl imidazo[1,2-a]pyridine-7-carboxylate (1 g, 5.68 mmol, 1 eq) in ethanol (10 mL), sodium acetate (931 mg, 11.36 mol, 2 eq), KBr (675 mg, 5.68 mmol, 1 eq), followed by bromine (897 mg, 11.36 mmol, 2 eq) were added at 0° C. and then the mixture was allowed to warm to room temperature for 1 h. The reaction was monitored by crude LCMS/TLC; after completion of the reaction, the mixture was quenched with saturated $Na_2S_2O_3$ (10 mL) and extracted with EtOAc (2×20 mL). The combined organic extracts were washed with ice water (2×30 mL) and brine (20 mL); dried over sodium sulfate, filtered and concentrated in vacuo to obtain Int-1 (900 mg, 62%) as a pale brown solid. MS: m/z=256.1 [M+H]$^+$.

Step-2: Synthesis of 3-(3-chlorophenyl)imidazo[1,2-a]pyridine-7-carboxylic acid (Int-2): Using the general procedure for Suzuki coupling, methyl 3-bromoimidazo[1,2-a]pyridine-7-carboxylate (600 mg, 2.38 mmol, 1 eq.) and (3-chlorophenyl)boronic acid (371 mg, 2.38 mmol, 1 eq.) were coupled to afford Int-2 (150 mg, 23%), as a brown solid. MS: m/z=273.1 [M+H]$^+$.

Step-3: Synthesis of (3-(3-chlorophenyl)imidazo[1,2-a]pyridin-7-yl)(piperidin-1-yl)methanone MF-PGDH-007: Using the general procedure for amide coupling with HATU, 3-(3-chlorophenyl)imidazo[1,2-a]pyridine-7-carboxylic acid (150 mg) was converted to MF-PGDH-007 (29.28 mg, 15.7%), as an off-white solid.

Synthesis of (1-(3-chlorophenyl)-1H-benzo[d][1,2,3]triazol-5-yl)(piperidin-1-yl)methanone, MF-PGDH-011

Provided below is an exemplary scheme to synthesize (1-(3-chlorophenyl)-1H-benzo[d][1,2,3]triazol-5-yl)(piperidin-1-yl)methanone, MF-PGDH-011, that is an inhibitor of hydroxyprostaglandin dehydrogenase.

Scheme 26

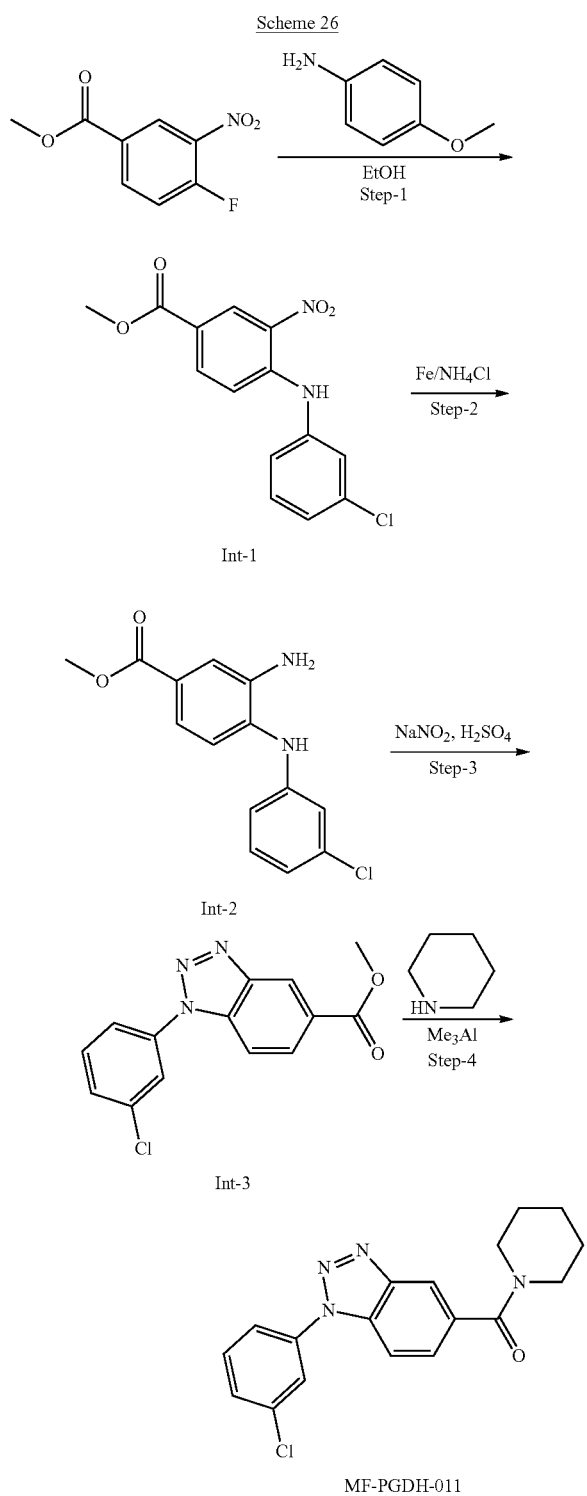

Step-1: Synthesis of methyl 4-((3-chlorophenyl)amino)-3-nitrobenzoate (Int-1): To a stirring solution of methyl 4-fluoro-3-nitrobenzoate (2.5 g, 13.50 mmol, 1 eq) in ethanol (25 mL), 4-methoxyaniline (1.72 g, 13.50 mol, 1 eq) was added at room temperature and then heated to 80° C. for 16 h. The reaction was monitored by crude LCMS/TLC; after completion of the reaction, the mixture was filtered to obtain Int-1 (2.10 g, 56.5%), as a pale brown solid. MS: m/z=307.1 [M+H]$^+$.

Step-2: Synthesis of methyl 3-amino-4-((3-chlorophenyl)amino) benzoate (Int-2): Using the general procedure for aryl nitro reduction using Fe, Int-1 (2 g) was converted to Int-2 (1.20 g, 66.6%) which was obtained as a gummy liquid. MS: m/z=277.2 [M+H]$^+$.

Step-3: Synthesis of methyl 1-(3-chlorophenyl)-1H-benzo[d][1,2,3]triazole-5-carboxylate (Int-3): To a stirred solution of methyl 3-amino-4-((3-chlorophenyl)amino)benzoate (700 mg, 2.545 mmol, 1 eq), NaNO$_2$ (175 mg, 2,545 mmol, 1 eq) in THF:water (1:1, 10 mL) under inert atmosphere, 6N H$_2$SO$_4$ (2 mL) was slowly added at 0° C. for 15 min and then gradually brought to room temperature and then heated to reflux for 12 h. The reaction was monitored by crude TLC; after completion of the reaction, the mixture was quenched with saturated NaHCO$_3$ (10 mL) and extracted with EtOAc (2×20 mL). The combined organic extracts were washed with ice water (2×30 mL) and brine (20 mL); dried over sodium sulfate, filtered and concentrated in vacuo to obtain the crude. The crude was purified through silica gel column chromatography using 30% EtOAc/heptane to afford Int-3 (300 mg, yield: 41.26%) as an off-white solid. MS: m/z=288.1 [M+H]$^+$.

Step-4: Synthesis of (1-(3-chlorophenyl)-1H-benzo[d][1,2,3]triazol-5-yl)(piperidin-1-yl)methanone, MF-PGDH-011: To a stirred solution of methyl 1-(3-chlorophenyl)-1H-benzo[d][1,2,3]triazole-5-carboxylate (300 mg, 1.045 mmol, 1 eq) in toluene (7 mL), piperidine (107 mg, 1.256 mmol, 1.2 eq) followed by trimethyl aluminum (1.5 mL, 5.22 mmol, 5 eq) was added slowly at 0° C. and then slowly heated to 50° C. for 16 h. The reaction was monitored by TLC; after completion of the reaction, the reaction mixture was quenched with water (5 mL) and extracted with EtOAc (2×30 mL). The combined organic extracts were washed with ice water (2×30 mL) and brine (20 mL), dried over sodium sulfate, filtered and concentrated in vacuo to obtain the crude. The crude was purified through prep-HPLC to afford MF-PGDH-011 (161.2 mg, 45.29%), as an off-white solid.

Synthesis of (3-(3-chlorophenyl)pyrazolo[1,5-a]pyrimidin-6-yl)(piperidin-1-yl)methanone
MF-PGDH-012

Provided below is an exemplary scheme to synthesize (3-(3-chlorophenyl)pyrazolo[1,5-a]pyrimidin-6-yl)(piperidin-1-yl)methanone, MF-PGDH-012, that is an inhibitor of hydroxyprostaglandin dehydrogenase.

Scheme 27

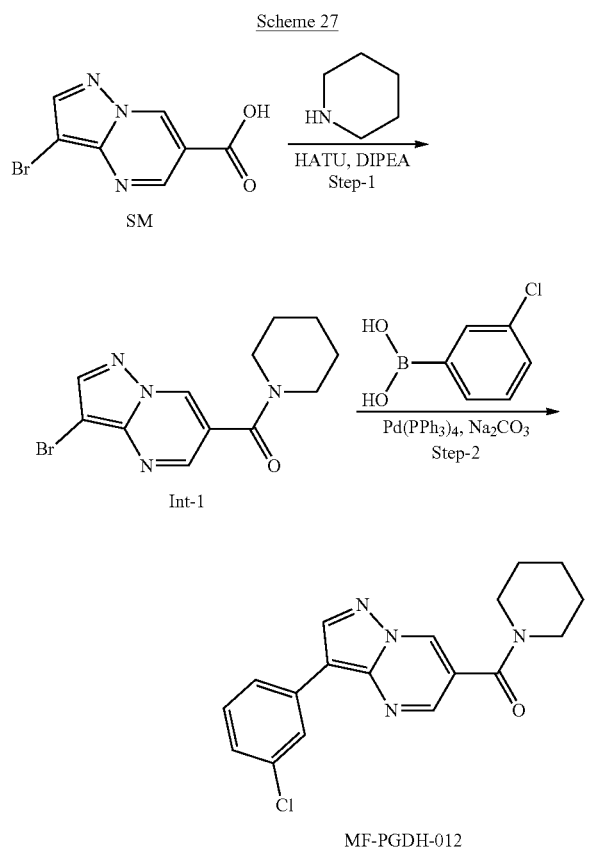

Step-1: Synthesis of (3-bromopyrazolo[1,5-a]pyrimidin-6-yl)(piperidin-1-yl)methanone (Int-1): Using the general procedure for amide coupling with HATU, 3-bromopyrazolo[1,5-a]pyrimidine-6-carboxylic acid (500 mg) was coupled with piperidine (212 mg, 2.49 mmol, 1.2 eq) to obtain Int-1 (309 mg, 48%), as a brown solid. MS: m/z=310.1 [M+2H]$^+$.

Step-2: Synthesis of (3-(3-chlorophenyl)pyrazolo[1,5-a]pyrimidin-6-yl)(piperidin-1-yl)methanone MF-PGDH-012: Using the general procedure for Suzuki coupling, (3-bromopyrazolo[1,5-a]pyrimidin-6-yl)(piperidin-1-yl)methanone (300 mg, 0.97 mmol, 1 eq.) and (3-chlorophenyl)boronic acid (227 mg, 1.455 mmol, 1.5 eq.) were coupled to afford MF-PGDH-012 (32.78 mg, 9.9%), as an off-white solid.

Synthesis of (4-fluoropiperidin-1-yl)(4-methyl-1-(pyrazin-2-yl)-1H-pyrrolo[2,3-b]pyridin-5-yl)methanone MF-DH-150 and (3-chloro-4-methyl-1-(pyrazin-2-yl)-1H-pyrrolo[2,3-b]pyridin-5-yl)(4-fluoropiperidin-1-yl)methanone MF-DH-151

Provided below is an exemplary scheme to synthesize (4-fluoropiperidin-1-yl)(4-methyl-1-(pyrazin-2-yl)-1H-pyrrolo[2,3-b]pyridin-5-yl)methanone, MF-DH-150, and (3-chloro-4-methyl-1-(pyrazin-2-yl)-1H-pyrrolo[2,3-b]pyridin-5-yl)(4-fluoropiperidin-1-yl)methanone, MF-DH-151, which are inhibitors of hydroxyprostaglandin dehydrogenase.

Scheme 28

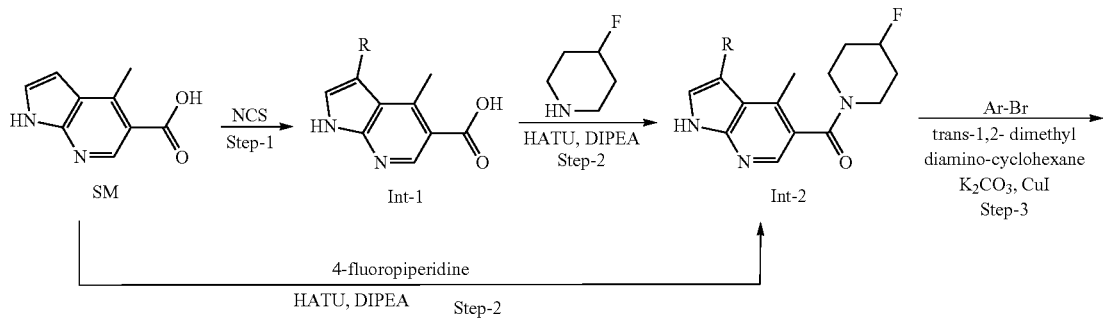

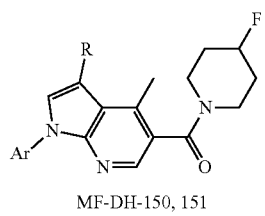

Ar = 2-pyrazenyl, R = H, MF-DH-150
Ar = 2-pyrazenyl, R = Cl, MF-DH-151

Step-1: Synthesis of Int-1: A solution of 1H-pyrrolo[2,3-b]pyridine-5-carboxylic acid (500 mg, 2.83 mmol, 1 eq) in DMF (15 mL), was converted to Int-1 (450 mg; Yield: 75.37%) as gummy liquid, using the general procedure for chlorination with NCS. MS: m/z=212.2 [M+H]$^+$.

Step-2: Synthesis of Int-2: Int-1 (300 mg, 1.43 mmol, 1 eq) was subjected to the general procedure for amide coupling using HATU to afford Int-2 (250 mg, 62%) as a brown liquid. MS: m/z=278.1 [M+H]$^+$.

Step-3: Synthesis of MF-DH-150, and MF-DH-151: Using the general procedure for Ullmann coupling, Int-2 (1 eq) and 2-bromopyrazine (1.2 eq) were converted to MF-DH-150 (35.7% yield) and MF-DH-151 (6.1% yield) which were isolated as off-white solids.

Synthesis of (4-fluoropiperidin-1-yl)(1-(pyrazin-2-yl)-2-(trifluoromethyl)-1,2,3,4-tetrahydroquinolin-6-yl)methanone MF-DH-161

Provided below is an exemplary scheme to synthesize (4-fluoropiperidin-1-yl)(1-(pyrazin-2-yl)-2-(trifluoromethyl)-1,2,3,4-tetrahydroquinolin-6-yl)methanone, MF-PGDH-012, that is an inhibitor of hydroxyprostaglandin dehydrogenase.

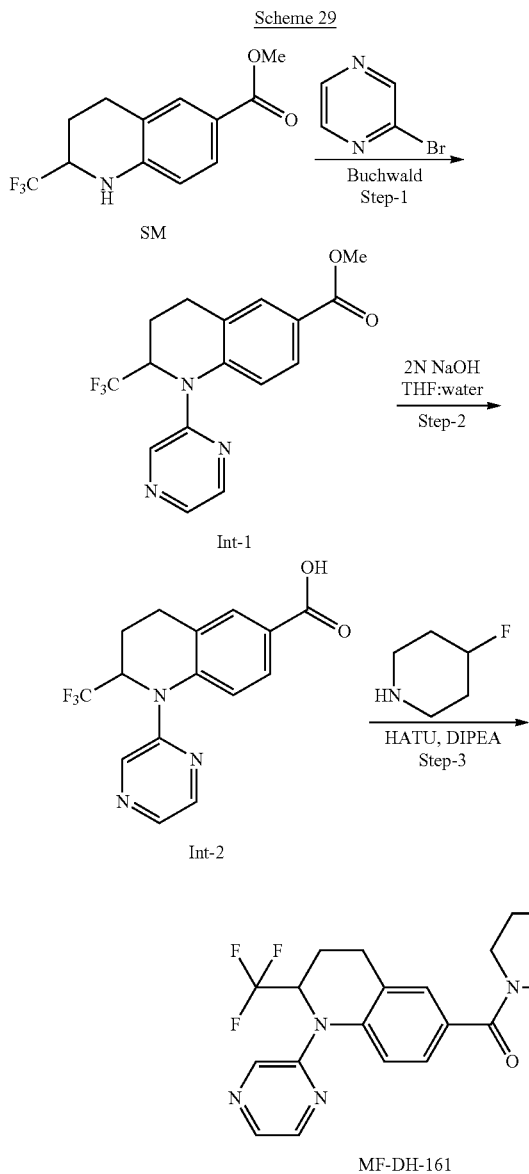

Step-1: Synthesis of methyl 1-(pyrazin-2-yl)-2-(trifluoromethyl)-1,2,3,4-tetrahydroquinoline-6-carboxylate (Int-1): In sealed tube; a stirring solution of methyl 2-(trifluoromethyl)-1,2,3,4-tetrahydroquinoline-6-carboxylate (SM) (300 mg, 1.16 mmol, 1 eq) in dioxane (15 mL) under inert atmosphere, Cs$_2$CO$_3$ (1.130 g, 3.47 mmol, 3.0 eq) and 2-bromopyrazine (220 mg, 1.38 mmol, 1.2 eq) were added at room temperature. Argon gas was purged for 15 min then Xantphos (133.7 mg, 0.234 mmol, 0.2 eq) and Pd$_2$(dba)$_3$ (105.8 mg, 0.115 mmol, 0.1 eq) were added under argon atmosphere. Sealed tube cap was tightly closed and the resultant reaction mixture was heated to 100° C. for 16 h. The reaction was monitored by crude LCMS/TLC; after completion of the reaction, the mixture was quenched with saturated NH$_4$Cl (10 mL), filtered through celite bed and washed with EtOAc (10 mL). The mixture was extracted with EtOAc (2×10 mL), combined organic extracts were washed with brine (10 mL), dried over sodium sulfate, filtered and concentrated in vacuo to obtain the crude. The crude was purified through silica gel column chromatography using 70% EtOAc/heptanes, afforded Int-1 (220 mg, 56.4%). MS: m/z=338.1 [M+H]$^+$.

Step-2: Synthesis of 1-(pyrazin-2-yl)-2-(trifluoromethyl)-1,2,3,4-tetrahydroquinoline-6-carboxylic acid (Int-2): Int-1 (220 mg, 0.652 mmol, 1 eq) in methanol: water (1:1, 10 mL) was subjected to the general procedure for ester hydrolysis with NaOH to afford Int-2 (120 mg, 57.1%), as a brown solid. MS: m/z=324.2 [M+H]$^+$.

Step-3: Synthesis of (4-fluoropiperidin-1-yl)(1-(pyrazin-2-yl)-2-(trifluoromethyl)-1,2,3,4-tetrahydroquinolin-6-yl)methanone (MF-DH-161): A stirred solution of Int-2 (120 mg, 0.372 mmol, 1 eq) in DMF (5 v) was subjected to the general procedure for amide coupling using HATU to afford MF-DH-161 (17.0% yield) as a semi solid.

Synthesis of (4,4-dimethyl-1-(pyrazin-2-yl)-1,2,3,4-tetrahydroquinolin-6-yl)(4-fluoropiperidin-1-yl)methanone MF-DH-160; ((4-fluoropiperidin-1-yl)(4-methyl-1-(pyrazin-2-yl)-1,2,3,4-tetrahydroquinolin-6-yl)methanone MF-DH-162; and ((4-fluoropiperidin-1-yl)(1-(pyrimidin-5-yl)-1,2,3,4-tetrahydroquinolin-6-yl)methanone MF-DH-164

Provided below is an exemplary scheme to synthesize (4,4-dimethyl-1-(pyrazin-2-yl)-1,2,3,4-tetrahydroquinolin-6-yl)(4-fluoropiperidin-1-yl)methanone, (MF-DH-160); ((4-fluoropiperidin-1-yl)(4-methyl-1-(pyrazin-2-yl)-1,2,3,4-tetrahydroquinolin-6-yl)methanone, (MF-DH-162); and ((4-fluoropiperidin-1-yl)(1-(pyrimidin-5-yl)-1,2,3,4-tetrahydroquinolin-6-yl)methanone, (MF-DH-164), which are inhibitors of hydroxyprostaglandin dehydrogenase.

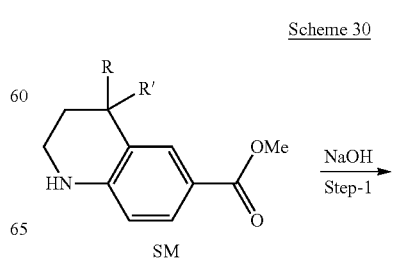

-continued

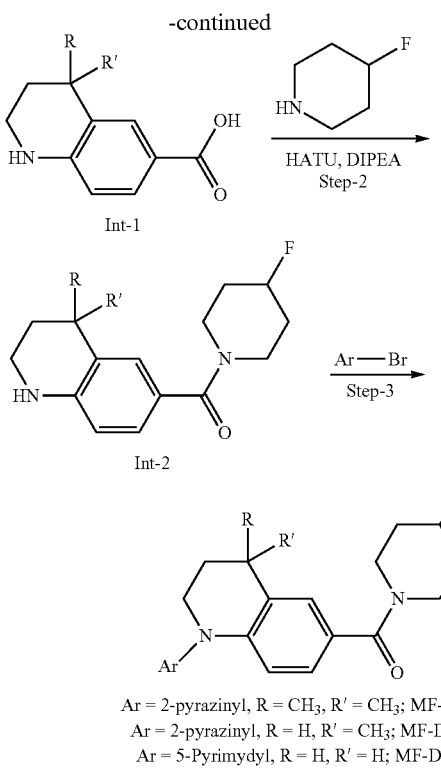

Ar = 2-pyrazinyl, R = CH₃, R' = CH₃; MF-DH-160
Ar = 2-pyrazinyl, R = H, R' = CH₃; MF-DH-162
Ar = 5-Pyrimydyl, R = H, R' = H; MF-DH-164

Step-1: Synthesis of Int-1: SM (1 g, 5.00 mmol, 1 eq) in methanol: water (1:1, 10 mL) was subjected to the general procedure for ester hydrolysis with NaOH to Int-1a (R, $R^8$=CH₃, 86.9% yield, MS: 206.1 [M+H]⁺), Int-1b (R=H, $R^8$=CH₃, 74.0% yield, MS: 192.1 [M+H]⁺) and Int-1c (R, R'=H, 73.4% yield, MS: 176.1 [M−H]−.

Step-2: Synthesis of (Int-2): A stirred solution of Int-1 (1.563 mmol, 1 eq) in DMF (10 mL) was subjected to the general procedure for amide coupling using HATU to afford Int-2a (R, $R^8$=CH₃, 800 mg, 86.9% yield, MS: 291.1 [M+H]⁺), Int-2b (R=H, $R^8$=CH₃, 650 mg, 75.9% yield, MS: 277.1 [M+H]⁺) and Int-2c (R, $R^8$=H, 73.4% yield, MS: 263.1 [M−H]−) as colorless liquids.

Step-3: Synthesis of MF-DH-160, MF-DH-162 and MF-DH-164 (general procedure for Buchwald coupling): To a stirring solution of Int-2a/2b/2c (1.26 mmol, 1 eq.), 2-bromo pyrazine/5-bromopyridine (1.2 eq.) in 1,4-dioxane (4 mL), Cs₂CO₃ (3 eq) was added and then purged with argon for 15 min. To this solution, Pd₂(dba)₃ (0.1 eq) and xantphos (0.1 eq) was added and purged with Argon for another 10 min. The resulting reaction mixture was stirred at 90° C. for 16 h. An extractive workup led to the crude which was purified by column chromatography followed by prep-HPLC to afford MF-DH-160 (16.7% yield), MF-DH-162 (7.5% yield), and MF-DH-164 (18.6% yield) as off-white solid/semi solids.

Synthesis of (3-chloro-1-(5-methylpyrazin-2-yl)-1H-pyrrolo[2,3-b]pyridin-5-yl)(4-fluoropiperidin-1-yl) methanone MF-DH-167; (3-chloro-1-(3-methylpyrazin-2-yl)-1H-pyrrolo[2,3-b]pyridin-5-yl)(4-fluoropiperidin-1-yl)methanone MF-DH-168; and (3-chloro-1-(4-methoxyphenyl)-1H-pyrrolo[2,3-b]pyridin-5-yl)(4-fluoropiperidin-1-yl)methanone MF-DH-191

Provided below is an exemplary scheme to synthesize (3-chloro-1-(5-methylpyrazin-2-yl)-1H-pyrrolo[2,3-b]pyridin-5-yl)(4-fluoropiperidin-1-yl)methanone, MF-DH-167; (3-chloro-1-(3-methylpyrazin-2-yl)-1H-pyrrolo[2,3-b]pyridin-5-yl)(4-fluoropiperidin-1-yl)methanone, MF-DH-168; and (3-chloro-1-(4-methoxyphenyl)-1H-pyrrolo[2,3-b]pyridin-5-yl)(4-fluoropiperidin-1-yl)methanone, MF-DH-191, which are inhibitors of hydroxyprostaglandin dehydrogenase.

Scheme 31

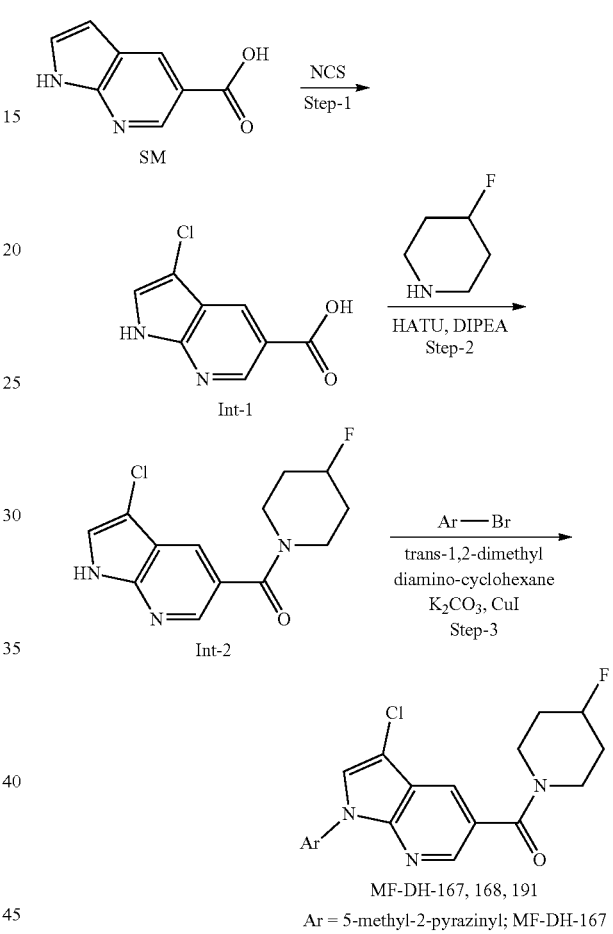

Ar = 5-methyl-2-pyrazinyl; MF-DH-167
Ar = 3-methyl-2-pyrazinyl; MF-DH-168
Ar = 4-methoxyphenyl; MF-DH-191

Step-1: Synthesis of Int-1: 1H-pyrrolo[2,3-b]pyridine-5-carboxylic acid (1 g, 6.16 mmol, 1 eq) was converted to Int-1 (850 mg; Yield: 70.1%)) as light yellow solid using the general procedure for chlorination with NCS. MS: m/z=197.01 [M+H]⁺.

Step-2: Synthesis of Int-2: A stirring solution of SM/Int-1 (1 g, 5.12 mmol, 1 eq) in DMF (10 mL) was subjected to the general procedure for amide coupling using HATU to afford Int-2 (1.1 g, 76%) as a brown solid. MS: m/z=282.2 [M+H]⁺.

Step-3: General procedure for Synthesis of MF-DH-167 and MF-DH-168, MF-DH-191: To a stirred solution of Int-2 (1 eq) in dioxane (10 mL), 5-methyl-2-bromopyrazine/3-methyl-2-bromopyrazine/4-bromo anisole (1.2 mmol, 1.2 eq), K₃PO₄ (630 mg, 3 mmol, 3 eq) were added at room temperature. The reaction mixture was purged with argon gas for 15 min. To this stirred solution CuI (38.1 mg, 0.2 mmol, 0.2 eq), and trans-dimethyl cyclohexane-1,2-diamine (28.44 mg, 0.2 mmol, 0.2 eq) was added and then continued stirring at 100° C. for 16 h. The reaction was monitored by TLC and after complete consumption of starting material, quenched with sat. NH₄Cl solution (10 mL) filtered, washed with EtOAc. This was extracted with EtOAc, washed with ice water (2×30 mL) and brine (50 mL) and the organic phases dried over sodium sulfate, filtered and concentrated under reduced pressure to obtain the crude. This was further purified by prep-HPLC to afford MF-DH-167 (16.5% yield), MF-DH-168 (9.5% yield), and MF-DH-191 (16.9% yield) as off-white solids.

Synthesis of (4-fluoropiperidin-1-yl)(4-(pyrazin-2-yl)-3,4-dihydro-2H-benzo[b][1,4]oxazin-7-yl)methanone MF-DH-159; (4-(benzo[d][1,3]dioxol-5-yl)-3,4-dihydro-2H-benzo[b][1,4]oxazin-7-yl)(piperidin-1-yl)methanone MF-DH-207; and (4-(4-methoxyphenyl)-3,4-dihydro-2H-benzo[b][1,4]oxazin-7-yl)(piperidin-1-yl)methanone MF-DH-209

Provided below is an exemplary scheme to synthesize (4-fluoropiperidin-1-yl)(4-(pyrazin-2-yl)-3,4-dihydro-2H-benzo[b][1,4]oxazin-7-yl)methanone, MF-DH-159; (4-(benzo[d][1,3]dioxol-5-yl)-3,4-dihydro-2H-benzo[b][1,4]oxazin-7-yl)(piperidin-1-yl)methanone, MF-DH-207; and (4-(4-methoxyphenyl)-3,4-dihydro-2H-benzo[b][1,4]oxazin-7-yl)(piperidin-1-yl)methanone, MF-DH-209, which are inhibitors of hydroxyprostaglandin dehydrogenase.

Step-1: Synthesis of 3,4-dihydro-2H-benzo[b][1,4]oxazine-7-carboxylic acid (Int-1): Methyl 3,4-dihydro-2H-benzo[b][1,4]oxazine-7-carboxylate (500 mg, 2.59 mmol, 1 eq) in THF:water (1:1, 10 mL) was subjected to the general procedure for ester hydrolysis with NaOH to afford Int-1 (300 mg, 64.7%) as a brown solid. Same reaction was repeated on 500 mg scale afforded 310 mg of Int-1. MS: m/z=179.9 [M+H]⁺.

Step-2: Synthesis of (3,4-dihydro-2H-benzo[b][1,4]oxazin-7-yl)(piperidin-1-yl)methanone/(3,4-dihydro-2H-benzo[b][1,4]oxazin-7-yl)(4-fluoropiperidin-1-yl)methanone (Int-2): A stirred solution of Int-1 (1.67 mmol, 1 eq) in DMF (10 mL) was subjected to the general procedure for amide coupling using HATU to afford the crude. The crude was purified through silica gel column chromatography to obtain Int-2a (X=H, 95% yield, MS: m/z=247.1 [M+H]⁺) and Int-2b (X=F, 63.3% yield, MS; m/z=265.1 [M+H]⁺).

Step-3: Synthesis of (1-(3-chlorophenyl)-1,2,3,4-tetrahydroquinolin-6-yl)(piperidin-1-yl)methanone, MF-DH-159, MF-DH-207, and MF-DH-209: Using the general procedure for Buchwald coupling, Int-2 (0.56 mmol, 1 eq.) and 2-bromopyrazine/5-Bromobenzo[d][1,3]dioxole/4-bromoanisole (1.2 eq.) were converted to MF-DH-159 (5.48% yield), MF-DH-207 (30.3% yield), and MF-DH-209 (2.2% yield) which were isolated after purification as off-white solids.

Synthesis of (1-(tert-butyl)-1H-benzo[d]imidazol-5-yl)(4-fluoropiperidin-1-yl)methanone (MF-DH-203)

Provided below is an exemplary scheme to synthesize (1-(tert-butyl)-1H-benzo[d]imidazol-5-yl)(4-fluoropiperidin-1-yl)methanone, MF-DH-203, that is an inhibitor of hydroxyprostaglandin dehydrogenase.

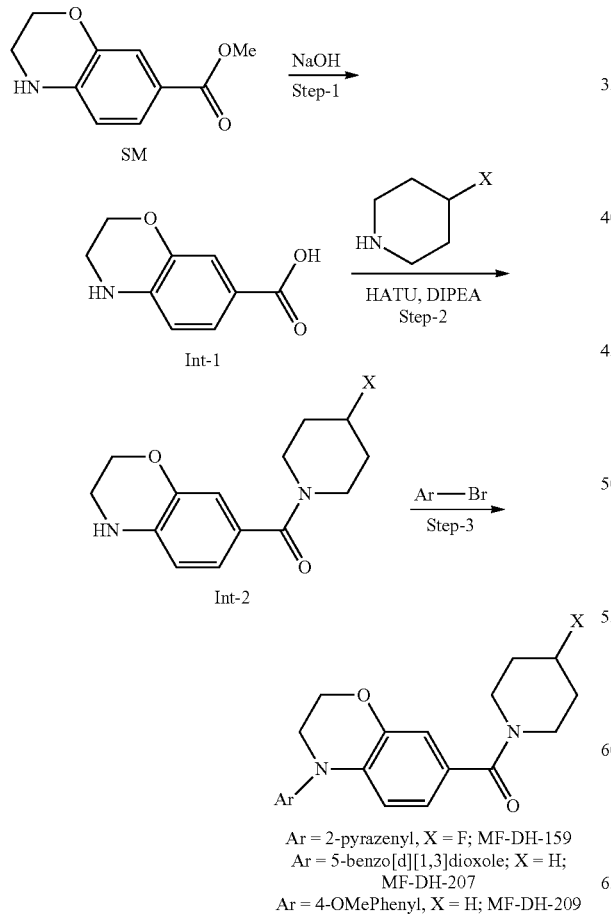

Ar = 2-pyrazenyl, X = F; MF-DH-159
Ar = 5-benzo[d][1,3]dioxole; X = H; MF-DH-207
Ar = 4-OMePhenyl, X = H; MF-DH-209

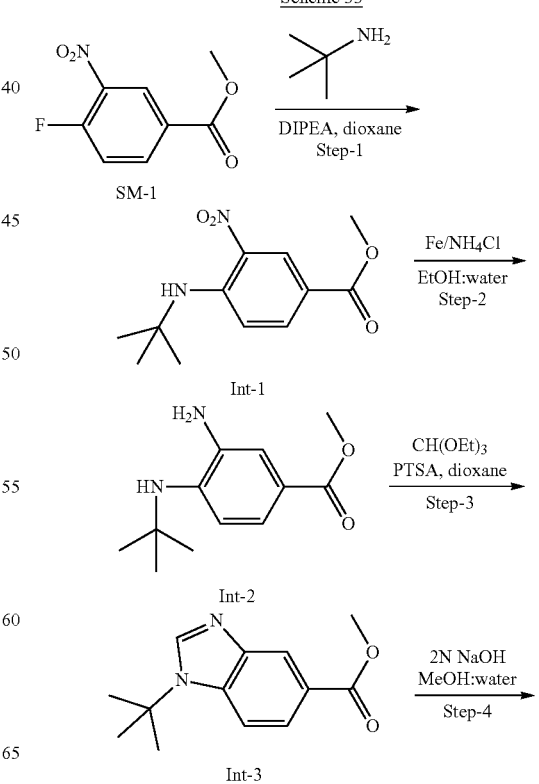

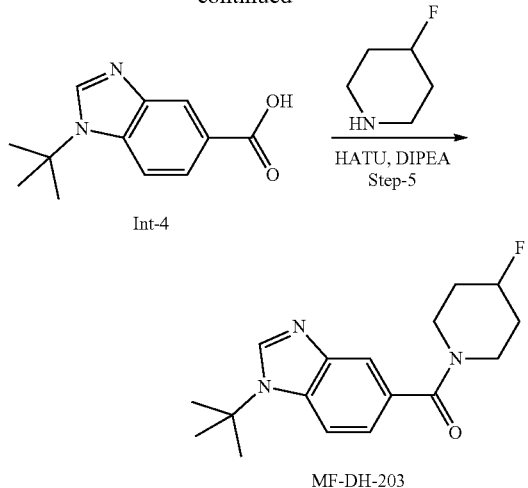

Step-1: Synthesis of methyl 4-(tert-butylamino)-3-nitrobenzoate (Int-1): To a stirred solution of methyl 4-fluoro-3-nitrobenzoate (2.5 g, 12.56 mmol, 1 eq) in EtOH (100 mL), t-Butylamine (918 mg, 12.56 mmol, 1 eq) was added at room temperature in a steel bomb. The cap was tightly closed and the resultant reaction mixture was heated to 100° C. for 16 h. The reaction was monitored by LCMS/TLC and after completion of the reaction, was cooled to room temperature. The volatiles were evaporated, quenched with sat.NH$_4$Cl (100 mL), extracted with EtOAc (3×50 mL) and combined organic extracts were washed with brine (50 mL), dried over sodium sulfate, filtered and concentrated in vacuo to get the crude. Trituration with diethyl ether (100 mL) led to methyl 4-(tert-butylamino)-3-nitrobenzoate (Int-1, 1.2 g, 38.10%) as a yellow solid. MS: m/z=253.1 [M+H]$^+$.

Step-2: Synthesis of methyl 3-amino-4-(tert-butylamino) benzoate (Int-2): To a stirred solution of Int-1 (1.2 g, 4.70 mmol, 1 eq) in EtOH/water (1:1, 50 mL), Iron powder (1.33 g, 23.8 mmol, 5 eq), NH$_4$Cl (1.27 g, 23.8 mmol, 5 eq) were added at room temperature. The resultant reaction mixture was heated to 100° C. for 16 h. The reaction was monitored by LCMS/TLC and after completion of the reaction, the mixture was filtered through a celite bed and washed with EtOAc (1×30 mL). Volatiles were evaporated, quenched with sat. NaHCO$_3$ (20 mL), extracted with EtOAc (3×30 mL); the combined organic extracts were washed with brine (30 mL), dried over sodium sulfate, filtered and concentrated in vacuo to obtain the crude. The crude was purified through silica gel column chromatography using 50% EtOAc/heptane to obtain methyl 3-amino-4-(tert-butylamino)benzoate (Int-2, 1.0 g, 95.07%) as a gummy liquid. MS: m/z=223.1 [M+H]$^+$.

Step-3: Synthesis of methyl 1-(tert-butyl)-1H-benzo[d] imidazole-5-carboxylate (Int-3): To a stirred solution of Int-2 (1 g, 4.23 mmol, 1 eq) and triethyl orthoformate (3.1 g, 21.18 mmol, 5 eq) in 1,4-Dioxane (80 mL) PTSA (145 mg, 0.84 mmol, 0.2 eq) was added at room temperature. The resulting reaction mixture was heated to 100° C. for 16 h until consumption of SM by crude LCMS/TLC. Volatiles were evaporated, washed with sat. NaHCO$_3$ (50 mL) and extracted with EtOAc (3×30 mL); combined organic extracts was washed with brine (50 mL), dried over sodium sulfate, filtered and concentrated in vacuo to obtain the crude. The crude was purified through silica gel column chromatography using 50% EtOAc/heptane to obtained methyl 1-(tert-butyl)-1H-benzo[d]imidazole-5-carboxylate (Int-3, 600 mg, 61.1% yield, MS: m/z=233.1 [M+H]$^+$) as a pale brown solid.

Step-4: Synthesis of 1-(tert-butyl)-1H-benzo[d]imidazole-5-carboxylic acid (Int-4): Int-3 (600 mg, 2.43 mmol, 1 eq) in THF/water (8:2, 20 mL) was subjected to the general procedure for ester hydrolysis with NaOH to afford 1-(tert-butyl)-1H-benzo[d]imidazole-5-carboxylic acid (Int-4, 320 mg, 60.2%, MS: m/z=219.2 [M+H]$^+$) as a pale brown sticky solid.

Step-5: Synthesis of (1-(tert-butyl)-1H-benzo[d]imidazol-5-yl)(4-fluoropiperidin-1-yl)methanone (MF-DH-203): A stirred solution of 1-(tert-butyl)-1H-benzo[d]imidazole-5-carboxylic acid (320 mg, 1.46 mmol, 1 eq) in DMF (10 v) was subjected to the general procedure for amide coupling using HATU to afford MF-DH-203 (20.4% yield) as an off white solid.

Synthesis of (4-fluoropiperidin-1-yl)(1-(pyrazin-2-yl)indolin-5-yl)methanone MF-DH-165

Provided below is an exemplary scheme to synthesize (4-fluoropiperidin-1-yl)(1-(pyrazin-2-yl)indolin-5-yl) methanone, MF-DH-165, that is an inhibitor of hydroxyprostaglandin dehydrogenase.

Scheme 34

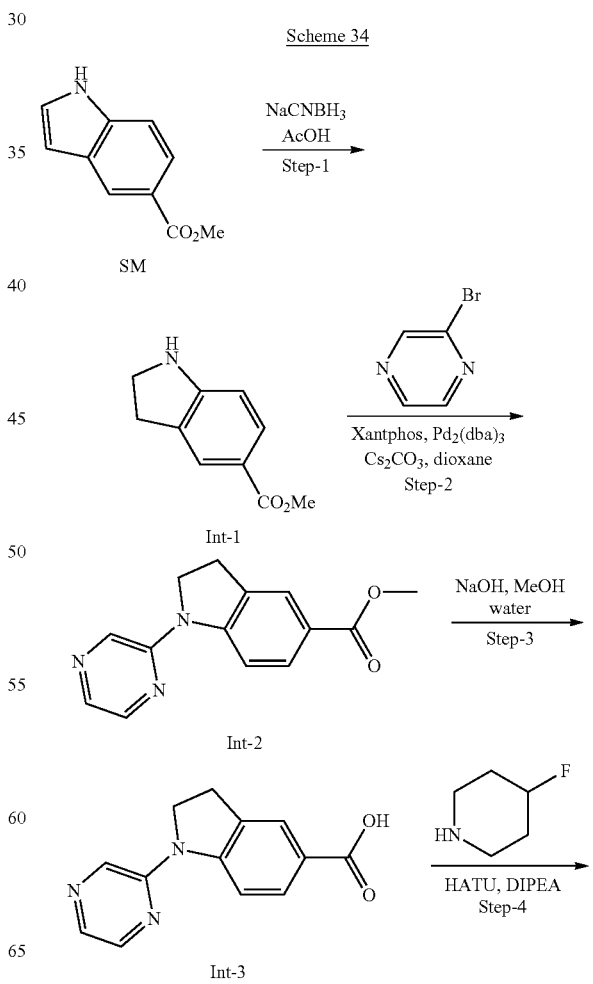

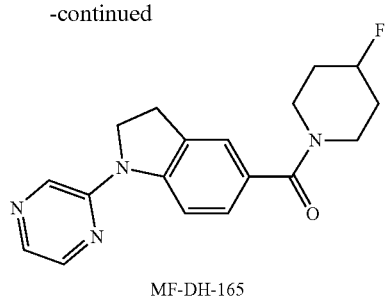

MF-DH-165

Step-1: Synthesis of methyl indoline-5-carboxylate (Int-1): To a stirred solution of SM (2 g, 11.42 mmol, 1 eq) in acetic acid (20 mL), NaCNBH$_3$ (2.15 g, 34.27 mmol, 3 eq) was added at 0° C. over 15 min. The resulting reaction mixture was stirred at room temperature for 12 h. Volatiles were evaporated, neutralized with NaHCO$_3$ to pH=7. The mixture was extracted with EtOAc (2×20 mL). The combined organic extracts were washed with brine (10 mL), dried over sodium sulfate, filtered and concentrated in vacuo to obtain the crude. The crude was purified through silica gel column chromatography to afford methyl indoline-5-carboxylate, Int-1 (1.65 g, 81.6%), as a brown solid. LCMS: 97.65%, m/z=178.2 [M+H]$^+$.

Step-2: Synthesis of methyl 1-(pyrazin-2-yl)indoline-5-carboxylate (Int-2): Using the general procedure for Buchwald coupling, methyl indoline-5-carboxylate (Int-1) (500 mg, 2.83 mmol, 1 eq) and 2-chloro pyrazine (355 mg, 3.10 mmol, 1.2 eq) were converted to Int-2 (310 mg, 42.9%). LCMS: 95.10%, m/z=257.1[M+H]$^+$.

Step-3: Synthesis of 1-(pyrazin-2-yl)indoline-5-carboxylic acid (Int-3): Methyl 1-(pyrazin-2-yl)indoline-5-carboxylate (110 mg, 0.43 mmol, 1 eq) in MeOH/water (8:2, 10 mL) was subjected to the general procedure for ester hydrolysis with NaOH to afford 1-(pyrazin-2-yl)indoline-5-carboxylic acid (80 mg, 77.2%) as a pale brown sticky solid. MS: m/z=242.2[M+H]$^+$.

Step-4: Synthesis of ((4-fluoropiperidin-1-yl)(1-(pyrazin-2-yl)indolin-5-yl)methanone (MF-DH-165) (General procedure for amide coupling with EDCI): To a stirred solution of 1-(pyrazin-2-yl)indoline-5-carboxylic acid (80 mg, 0.32 mmol, 1 eq) in DCM (10 v) under inert atmosphere were added EDCI (92 mg, 0.48 mmol, 1.5 eq) and HOBt (52 mg, 0.38 mmol, 1.2 eq). The mixture was cooled to 0° C. and 4-fluoro piperidine (44 mg, 0.32 mmol, 1.0 eq) was added. To this stirred solution N,N'-diisopropylethylamine (0.13 mL, 0.96 mmol, 3 eq), DMAP (5 mg) was added at 0° C. and then the mixture was warmed and stirred at room temperature for 16 h. The reaction mixture was quenched with ice water (10 mL) and extracted with EtOAc (2×15 mL). The combined organic extracts were washed with ice water (2×10 mL) and brine (10 mL), dried over sodium sulfate, filtered and concentrated in vacuo to obtain the crude. The crude was purified through silica gel column chromatography followed by prep-HPLC to afford MF-DH-165 (7.2% yield) as an off white solid.

Synthesis of Pyrrolopyridine-5-Carboxyamide Analogs with Amide/Aryl Variation

Provided below is an exemplary scheme to synthesize pyrrolopyridine-5-carboxyamide analogs with amide/Aryl variations that are inhibitors of hydroxyprostaglandin dehydrogenase.

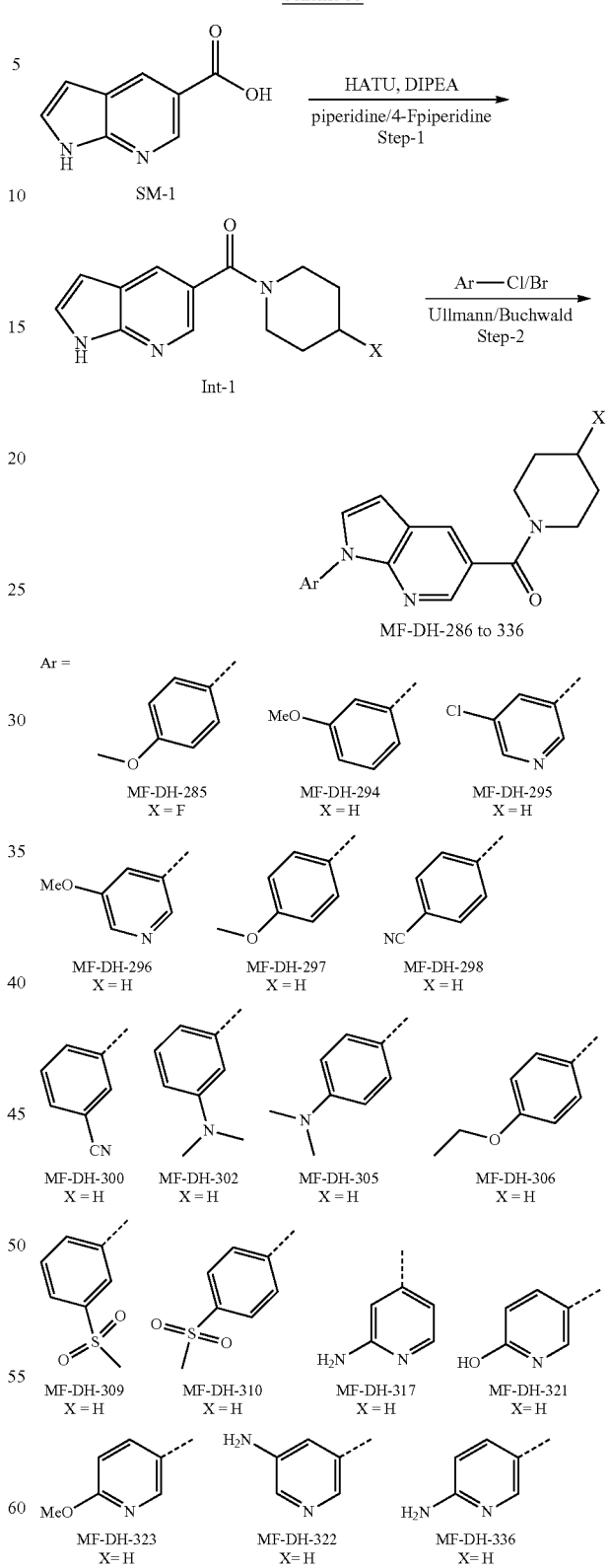

Step-1: Synthesis of Int-1a (X=H) and Int-1b (X=F): The synthesis of Int-1a and Int-1b is described in Schemes 9 and 10.

Step-2: General procedure for Ullmann reaction: synthesis of MF-DH-239, 285, 294, 295, 296, 297, 298, 300, 302, 305, 306, 309, 310, 317, 321, 322 and MF-DH-336: Int-1a and Int-1b were subjected to the general procedure for Ullmann coupling with the appropriate aryl bromides. The crude products were purified by flash chromatography to afford MF-DH-285, MF-DH-294, MF-DH-295, MF-DH-296, MF-DH-297, MF-DH-298, MF-DH-300, MF-DH-302, MF-DH-305, MF-DH-306, MF-DH-309, MF-DH-310, MF-DH-317, MF-DH-321, MF-DH-322 and MF-DH-336.

Synthesis of Pyrrolopyridine-5-Carboxyamide Analogs with N-Aryl Variation

Provided below is an exemplary scheme to synthesize pyrrolopyridine-5-carboxyamide analogs with N-Aryl variations that are inhibitors of hydroxyprostaglandin dehydrogenase.

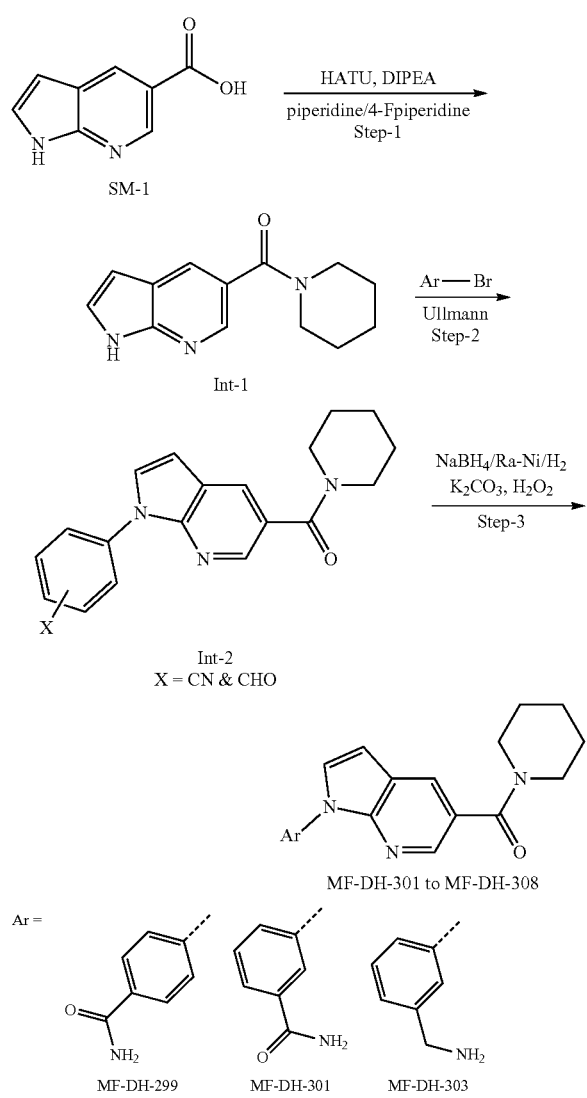

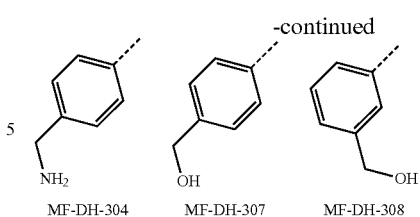

General Procedure for the Oxidation of Nitriles (MF-DH-299 and MF-DH-301)

To a stirred solution of Int-2 (0.5 mmol, 1 eq) in DMSO (10 mL), $K_2CO_3$ (2.0 eq), $H_2O_2$ (2 eq) was added at room temperature under aerobic conditions. Reaction mixture was heated to 80° C. for 16 h. The reaction was monitored by LCMS/TLC and, after completion of the reaction, quenched with ice water (20 mL), filtered through Celite® bed, and washed with EtOAc (20 ml). The organic phase was separated and the aqueous phase was extracted with ethyl acetate (2×10 mL). The combined organic extracts were washed with brine (20 mL), dried over sodium sulfate, filtered, and concentrated under reduced pressure to obtain the crude product, which was further purified by flash chromatography to afford MF-DH-299 and MF-DH-301.

General Procedure for Reduction of Nitriles (MF-DH-303 and MF-DH-304)

To a stirred solution of nitrile Int-2 (0.5 mmol, 1 eq) in MeOH (15 mL), Ra—Ni (20 mol %) was added at room temperature under nitrogen atmosphere. The reaction mixture was stirred for 16 h under hydrogen balloon atmosphere. The reaction was monitored by LCMS/TLC; upon completion of the reaction, the solids were filtered through a Celite® bed, washed with EtOAc (20 mL), and the volatiles were evaporated. The aqueous phase was extracted with ethyl acetate (2×10 mL) and the combined organic extracts were washed with a brine solution (20 mL), dried over sodium sulfate, filtered, and concentrated under reduced pressure to afford the crude product, which was further purified by flash chromatography to afford MF-DH-303 and MF-DH-304.

General Procedure for Reduction of Aldehydes (MF-DH-307 and MF-DH-308)

To a stirred solution of aldehyde Int-2 (0.5 mmol, 1 eq) in MeOH (15 mL), $NaBH_4$ (5 eq) was added portion wise at 0° C. for 15 min. The reaction mixture was stirred for 6 h at room temperature. The reaction was monitored by LCMS/TLC; upon completion, the reaction mixture was quenched with satd. $NH_4Cl$ (20 mL) and the volatiles were evaporated. The aqueous phase was extracted with ethyl acetate (2×20 mL) and the combined organic extracts were washed with brine solution (20 mL), dried over sodium sulfate, filtered, and concentrated under reduced pressure to afford the crude product, which was further purified by flash chromatography afforded MF-DH-307 and MF-DH-308.

Synthesis of 3-Chloro-Pyrrolopyridine-5-Carboxyamide Analogs with Amide/Aryl/Heteroaryl Variation Provided below is an exemplary scheme to synthesize 3-chloro-pyrrolopyridine-5-carboxyamide analogs with amide/aryl/heteroaryl variations that are inhibitors of hydroxyprostaglandin dehydrogenase.

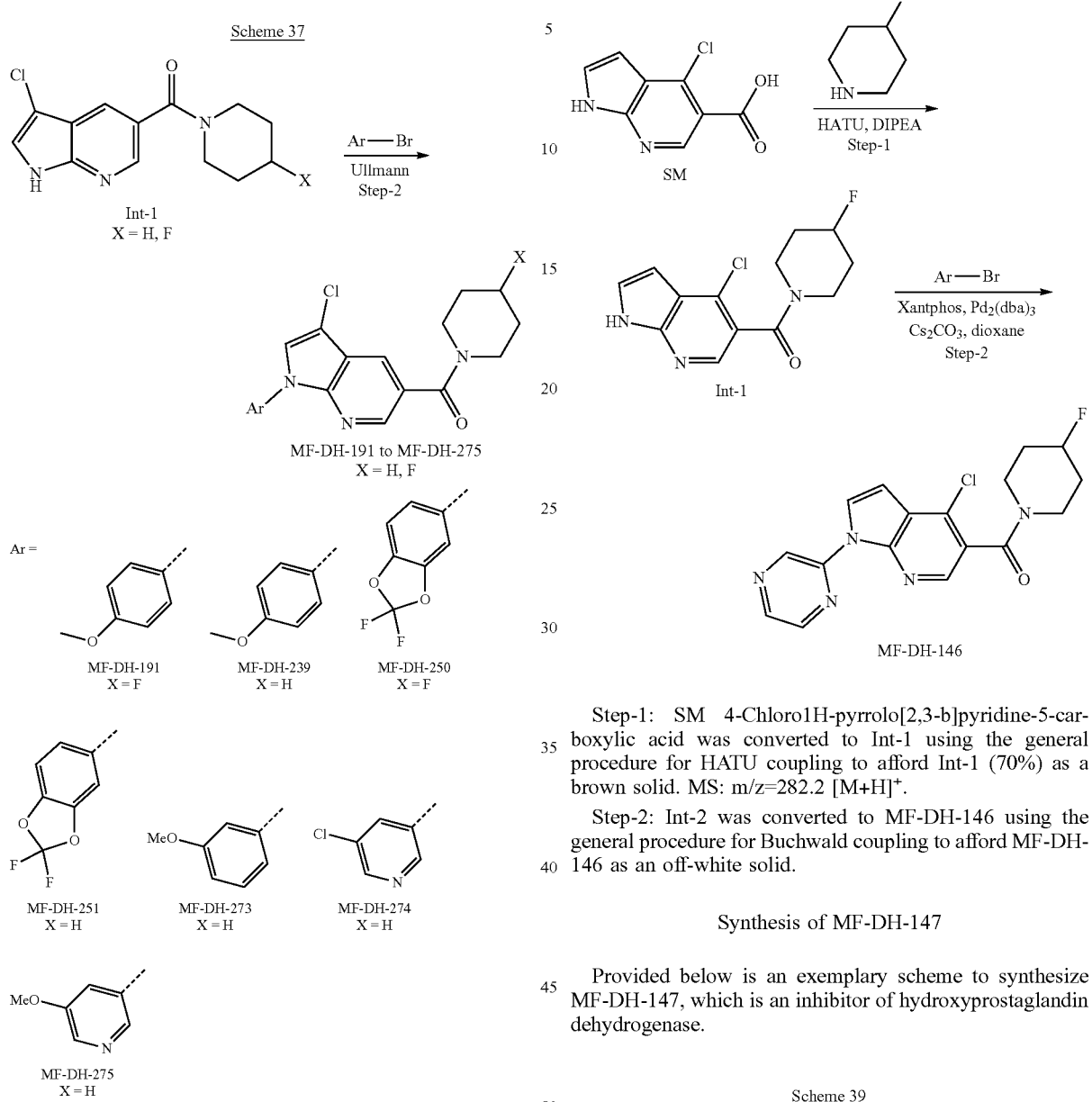

The synthesis of Int-1a (X=H) is described in Scheme 9. The synthesis of Int-1b (X=F) is described in Scheme 31.

Step-1: Synthesis of MF-DH-191, MF-DH-250, MF-DH-251, MF-DH-273, MF-DH-274 and MF-DH-273: Int-1 was converted to the title compounds according to the general procedure for Ullmann coupling with the appropriate aryl bromides.

Synthesis of MF-DH-146

Provided below is an exemplary scheme to synthesize MF-DH-146, which is an inhibitor of hydroxyprostaglandin dehydrogenase.

Step-1: SM 4-Chloro1H-pyrrolo[2,3-b]pyridine-5-carboxylic acid was converted to Int-1 using the general procedure for HATU coupling to afford Int-1 (70%) as a brown solid. MS: m/z=282.2 [M+H]$^+$.

Step-2: Int-2 was converted to MF-DH-146 using the general procedure for Buchwald coupling to afford MF-DH-146 as an off-white solid.

Synthesis of MF-DH-147

Provided below is an exemplary scheme to synthesize MF-DH-147, which is an inhibitor of hydroxyprostaglandin dehydrogenase.

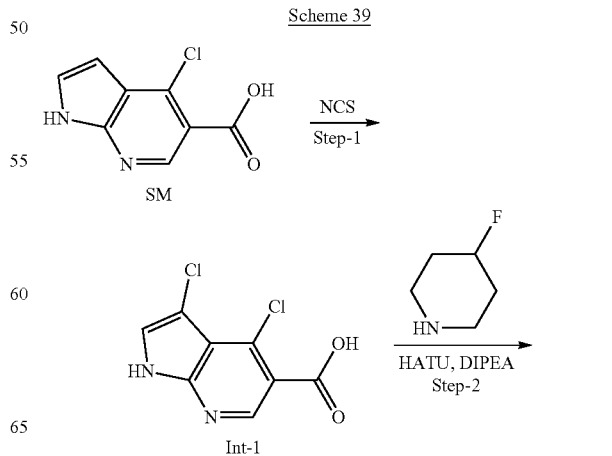

-continued

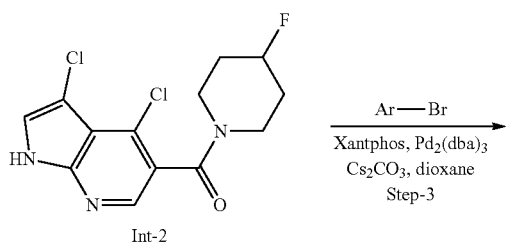

Int-2

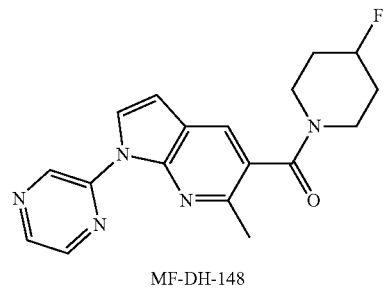

MF-DH-148

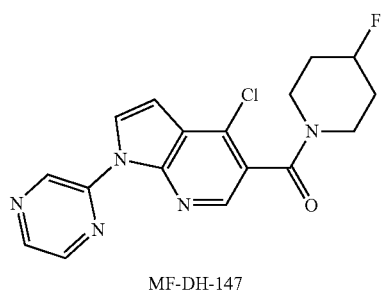

MF-DH-147

Step-1: SM 6-methyl-1H-pyrrolo[2,3-b]pyridine-5-carboxylic acid was converted to Int-1 using the general procedure for HATU coupling to afford Int-1 (60%) as a brown liquid. MS: m/z=262.1 [M+H]$^+$.

Step-2: Synthesis of MF-DH-148: Int-1 (0.95 mmol, 1 eq) and 2-bromopyrazine (183 mg, 1.14 mmol, 1.2 eq) were reacted using the general procedure for Buchwald coupling to afford the crude product, which was purified through silica gel column chromatography using 70% EtOAc/heptanes followed by Prep-HPLC purification to afford MF-DH-148.

Step-1: SM was converted to Int-1 using the general procedure for chlorination with NCS to afford Int-1 (334 mg; Yield: 70.1%) as a light yellow solid. MS: m/z=231.10 [M+H]$^+$.

Step-2: Int-1 was converted to Int-2 using the general procedure for HATU coupling to afford Int-2 (323 mg, 76%) as a brown solid. MS: m/z=299.2 [M+2H]$^+$.

Step-3: Int-2 was converted to MF-DH-147 using the general procedure for Buchwald coupling to afford MF-DH-147 as an off-white solid.

Synthesis of MF-DH-148

Provided below is an exemplary scheme to synthesize MF-DH-148, which is an inhibitor of hydroxyprostaglandin dehydrogenase.

Synthesis of MF-DH-149

Provided below is an exemplary scheme to synthesize MF-DH-149, which is an inhibitor of hydroxyprostaglandin dehydrogenase.

Scheme 41

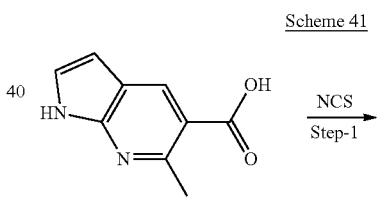

SM

Scheme 40

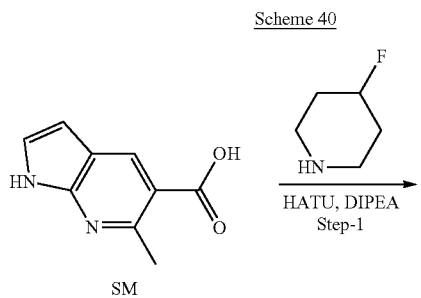

SM

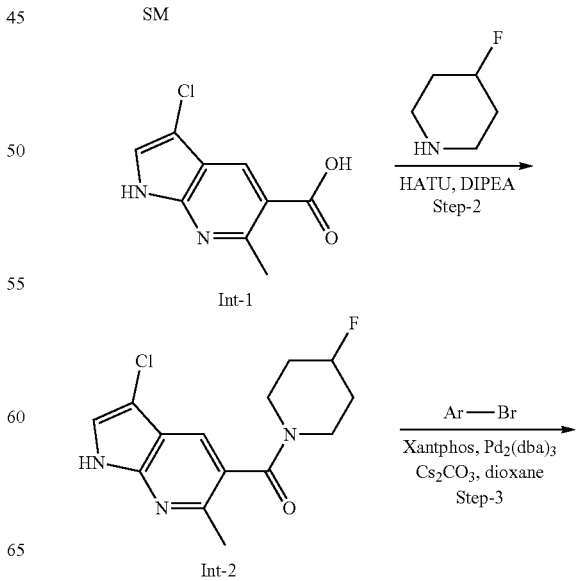

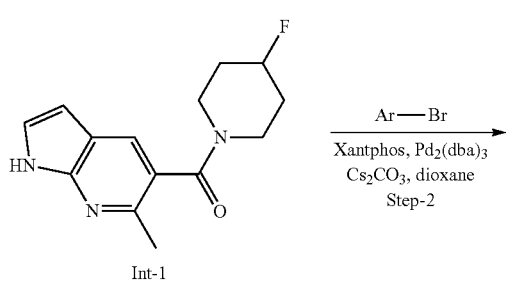

Int-1

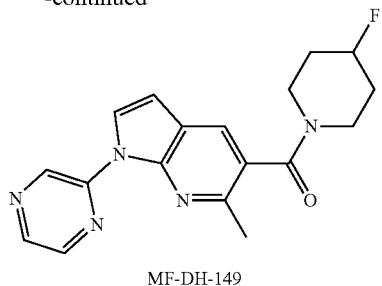

MF-DH-149

Step-1: 6-methyl-1H-pyrrolo[2,3-b]pyridine-5-carboxylic acid (SM) was converted to Int-1 using the general procedure for chlorination with NCS to afford Int-1 (300 mg; Yield: 84.2%) as a gummy liquid. MS: m/z=211.2 [M+H]$^+$, 212.2 [M+2H]$^+$.

Step-2: Int-1 was converted to Int-2 using the general procedure for HATU coupling to afford Int-2 (259 mg/168 mg, 63%) as a brown liquid. MS: m/z=278.1 [M+H]$^+$.

Step-3: Synthesis of MF-DH-149: Int-2 (0.95 mmol, 1 eq) and 2-bromopyrazine were reacted using the general procedure for Buchwald coupling to afford the crude product, which was purified through silica gel column chromatography using 70% EtOAc/heptanes followed by Prep-HPLC purification to afford MF-DH-149.

Synthesis of (1-(methylsulfonyl)-1H-pyrrolo[2,3-b]pyridin-5-yl)(piperidin-1-yl)methanone (MF-DH-311) and piperidin-1-yl(1-tosyl-1H-pyrrolo[2,3-b]pyridin-5-yl)methanone (MF-DH-312)

Provided below is an exemplary scheme to synthesize (1-(methylsulfonyl)-1H-pyrrolo[2,3-b]pyridin-5-yl)(piperidin-1-yl)methanone, MF-DH-311, and piperidin-1-yl(1-tosyl-1H-pyrrolo[2,3-b]pyridin-5-yl)methanone, MF-DH-312, which are inhibitors of hydroxyprostaglandin dehydrogenase.

The synthesis of Int-1 is described in Scheme 9.

Step-1: Synthesis of MF-DH-311 and MF-DH-312: Sodium hydride (60% in mineral oil) (100 mg, 1.5 mmol, 1.52 eq) was added to a stirred solution of piperidin-1-yl (1H-pyrrolo[2,3-b]pyridin-5-yl)methanone (230 mg, 1 mmol) in DMF (15 mL) at 0° C. and the resulting suspension was warmed to room temperature and stirred for 1 h. Difluorocyclohexyl 4-methylbenzenesulfonate, tosyl chloride, and mesyl chloride (1.2 eq each) were added and the resulting reaction mixture was stirred for 6 h. The reaction was monitored by crude LCMS/TLC; after complete consumption of the starting material, the reaction mixture was quenched with sat. NH$_4$Cl (10 ml) and extracted with EtOAc (2×50 mL). The combined organic extracts were washed with brine (20 mL), dried over sodium sulfate, filtered, and concentrated in vacuo to obtain the crude product. The crude product was purified through silica gel column chromatography using 60% EtOAc/heptane to afford (1-(methylsulfonyl)-1H-pyrrolo[2,3-b]pyridin-5-yl)(piperidin-1-yl)methanone (MF-DH-311) and piperidin-1-yl(1-tosyl-1H-pyrrolo[2,3-b]pyridin-5-yl)methanone (MF-DH-312) as off-white solids.

Synthesis of Pyrrolopyridine-5-Carboxyamide Analogs with Amide/Aryl Variation

Provided below is an exemplary scheme to synthesize MF-DH-318, MF-DH-320, MF-DH-322, MF-DH-342, MF-DH-344, MF-DH-346, MF-DH-366, MF-DH-389, and MF-DH-397, which are inhibitors of hydroxyprostaglandin dehydrogenase.

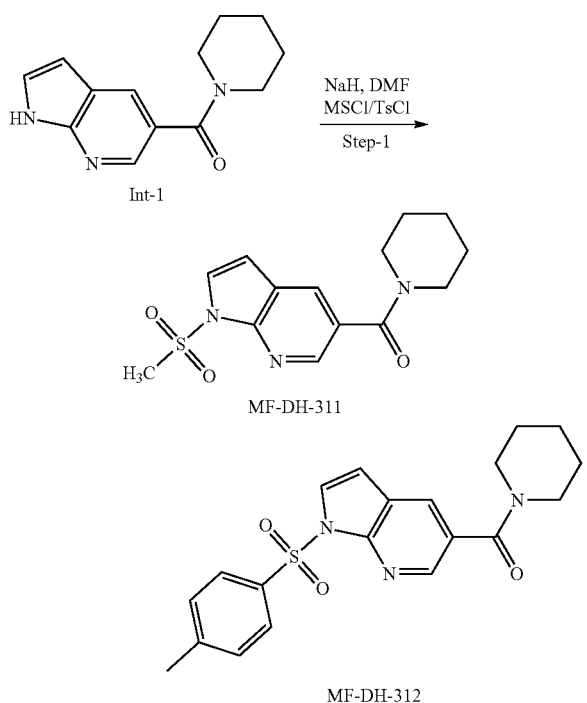

Scheme 42

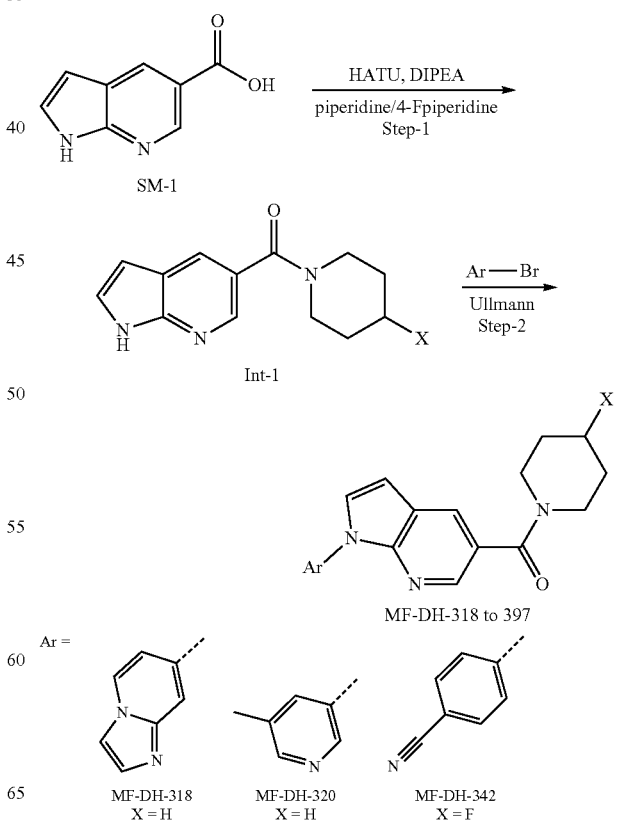

Scheme 43

449

-continued

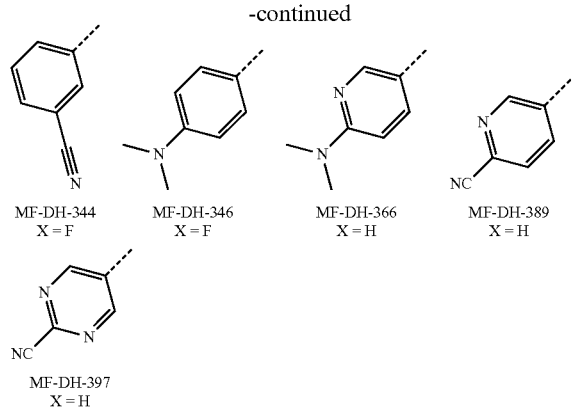

MF-DH-344  
X = F

MF-DH-346  
X = F

MF-DH-366  
X = H

MF-DH-389  
X = H

MF-DH-397  
X = H

Step-1: Synthesis of Int-1a (X=H) and Int-1b (X=F): The synthesis of Int-1a and Int-1b is described in Scheme 9.

Int-1a was converted to MF-DH-318 using the general procedure for Ullmann coupling using 7-bromoimidazo[1,2-a]pyridine to afford MW-DH-318 as a sticky solid.

Int-1a was converted to MF-DH-320 using the general procedure for Ullmann coupling using 3-bromo-5-methyl pyridine with Int-1 to afford MF-DH-320 as an off-white solid.

Int-1a was converted to MF-DH-322 using the general procedure for Ullmann coupling using 5-bromopyridin-3-amine to afford MF-DH-322 as an off-white solid.

Int-1b was converted to MF-DH-342 using the general procedure for Ullmann coupling using 4-bromobenzo nitrile to afford MF-DH-342 as an off-white solid.

Int-1b was converted to MF-DH-344 using the general procedure for Ullmann coupling using 3-bromobenzo nitrile to afford MF-DH-344 as an off-white solid.

Int-1b was converted to MF-DH-346 using the general procedure for Ullmann coupling using 4-bromo-N,N-dimethylaniline to afford MF-DH-346 as an off-white solid.

Int-1a was converted to MF-DH-366 using the general procedure for Ullmann coupling using 5-bromo-N,N-dimethylpyridin-2-amine to afford MF-DH-346 as an off-white solid.

Int-1a was converted to MF-DH-389 using the general procedure for Ullmann coupling using 5-bromopicolinonitrile to afford MW-DH-389 as an off-white solid.

Int-1a was converted to MF-DH-397 using the general procedure for Ullmann coupling using 5-bromopyrimidine-2-carbonitrile to afford MF-DH-397 as an off-white solid.

Synthesis of (1-(1H-indazol-5-yl)-1H-pyrrolo[2,3-b]pyridin-5-yl)(piperidin-1-yl)methanone (MF-DH-319)

Provided below is an exemplary scheme to synthesize (1-(1H-indazol-5-yl)-1H-pyrrolo[2,3-b]pyridin-5-yl)(piperidin-1-yl)methanone, MF-DH-319, that is an inhibitor of hydroxyprostaglandin dehydrogenase.

Scheme 44

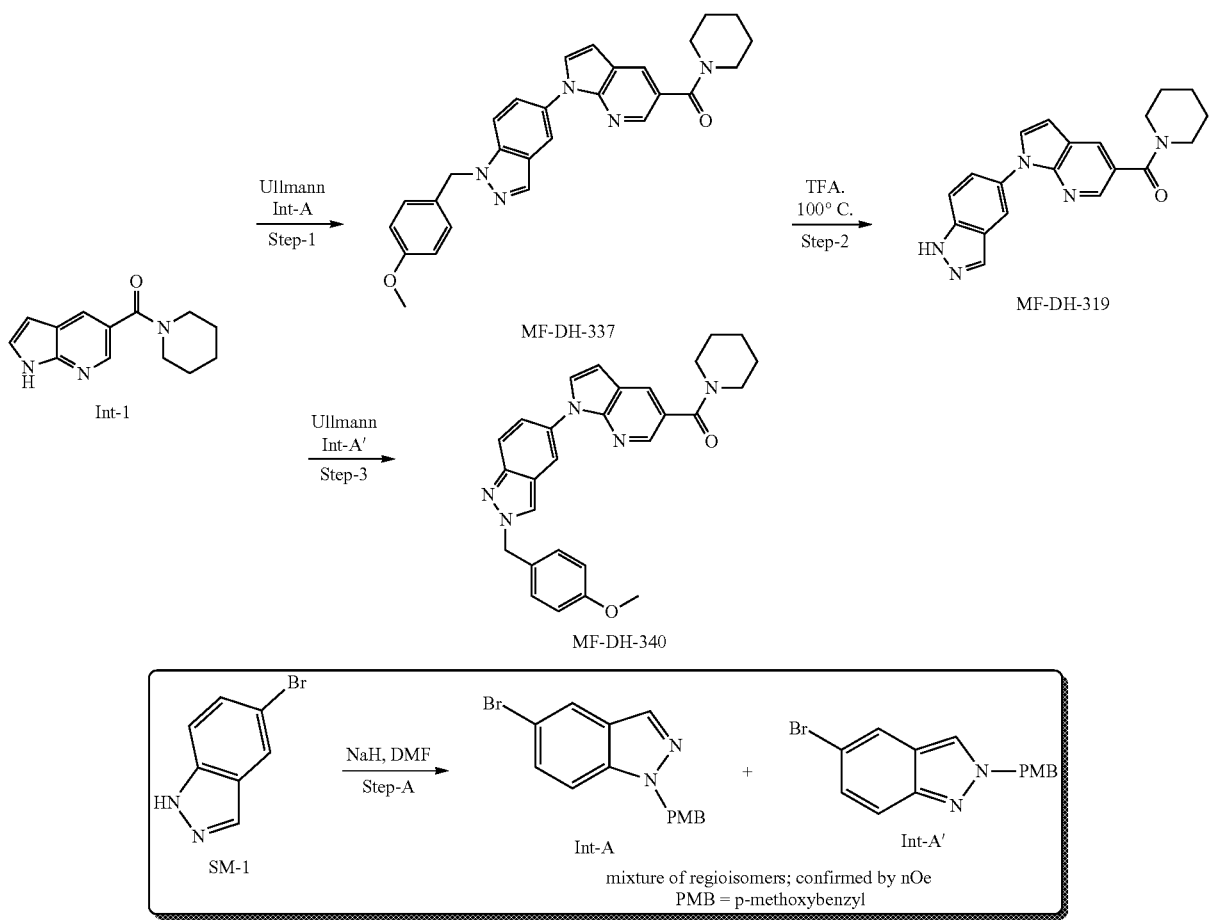

451

Step-A: Synthesis of 5-bromo-1-(4-methoxybenzyl)-1H-indazole (Int-A) and 5-bromo-1-(4-methoxybenzyl)-2H-indazole (Int-A'): To a stirred solution of 6-bromoindazole (1 g, 5.07 mmol, 1 eq) in DMF (15 mL), NaH (60% in mineral oil) (0.24 g, 6.08 mmol, 1.2 eq) was added at 0° C. to room temperature for 1 h. To this stirred suspension of PMBCl (1.18 g, 7.60 mmol, 1.5 eq) was added and then the resulting reaction mixture was stirred for 4 h. The reaction was monitored by crude LCMS/TLC; after complete consumption of the starting material, the reaction mixture was quenched with sat. $NH_4Cl$ (10 ml) and extracted with EtOAc (2×50 mL). Combined organic extracts were washed with brine (20 mL), dried over sodium sulfate, filtered and concentrated in vacuo to obtain the crude. The crude was purified through silica gel column chromatography using 40% EtOAc/heptane to afford 5-bromo-1-(4-methoxybenzyl)-1H-indazole, Int-A (0.81 g, 50.06%) and 5-bromo-1-(4-methoxybenzyl)-2H-indazole, Int-A' (0.55 g, 34.3%) as off-white solids. LCMS: 98.3%, m/z=318.1[M+2H]$^+$.

Step-1: The synthesis of Int-1 is described in Scheme 9. Int-1 was converted to MF-DH-337 using the general procedure for Ullmann coupling using 5-bromo-1-(4-methoxybenzyl)-1H-indazole (Int-A) with Int-1 to afford MF-DH-337 as sticky solid.

Step-3: Int-1 was converted to MF-DH-340 using the general procedure for Ullmann coupling using 5-bromo-1-(4-methoxybenzyl)-2H-indazole (Int-A') with Int-1 to afford MF-DH-340 as an off-white solid.

Step-2: Synthesis of 5 (1-(1H-indazol-5-yl)-1H-pyrrolo[2,3-b]pyridin-5-yl)(piperidin-1-yl)methanone (MF-DH-319): To a stirred solution of MF-DH-337 (120 mg, 0.257 mmol, 1 eq) in DCE (15 mL), TFA (4 mL) was added at 0° C. and stirred at room temperature for 1 h and then heated to 80° C. for 16 h. The reaction was monitored by crude LCMS/TLC; after complete consumption of the starting material, the reaction mixture was quenched with satd. $NaHCO_3$ (10 ml) and extracted with EtOAc (2×50 mL). Combined organic extracts were washed with brine (20 mL); dried over sodium sulfate, filtered and concentrated in vacuo to obtain the crude. The crude was purified through silica gel column chromatography using 40% EtOAc/heptane to afford 5 (1-(1H-indazol-5-yl)-1H-pyrrolo[2,3-b]pyridin-5-yl)(piperidin-1-yl)methanone (MF-DH-319) as a sticky liquid.

Synthesis of Pyrrolopyridine-5-Carboxyamide Analogs with Amide/Aryl Variation

Provided below is an exemplary scheme to synthesize pyrrolopyridine-5-carboxyamide analogs with amide/Aryl variations that are inhibitors of hydroxyprostaglandin dehydrogenase.

Scheme 45

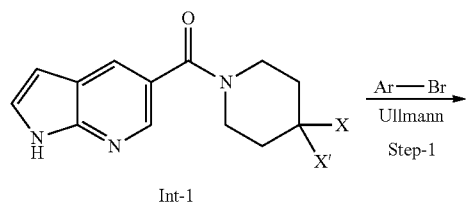

Int-1

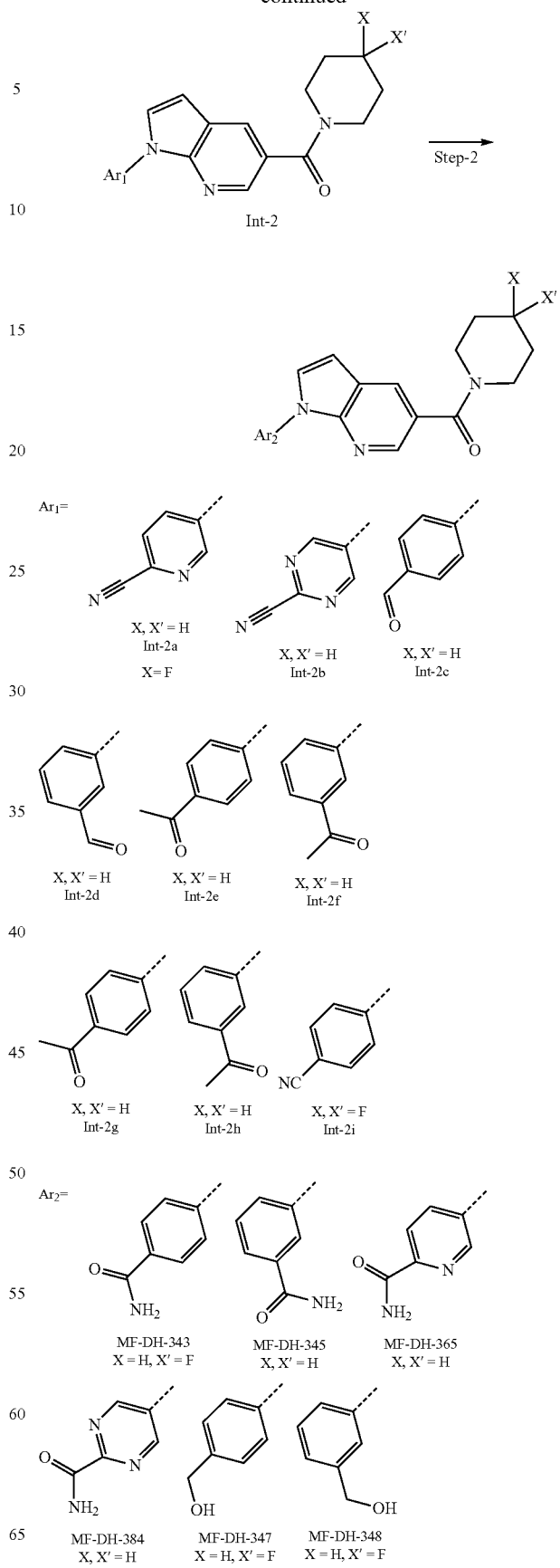

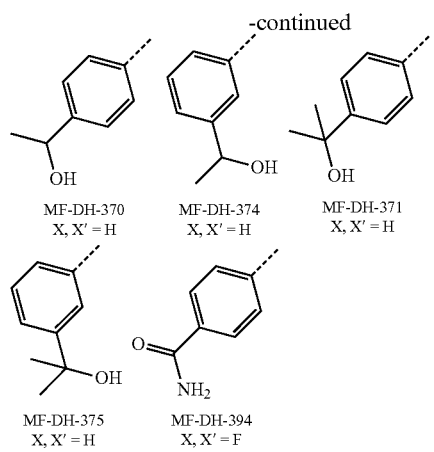

MF-DH-370
X, X' = H

MF-DH-374
X, X' = H

MF-DH-371
X, X' = H

MF-DH-375
X, X' = H

MF-DH-394
X, X' = F

The synthesis of Int-1a (X, X'=H) and Int-1b (X=H, X'=F) is described in Scheme 9.

Synthesis of Int-1c (X, X'=F): To a stirred solution of 11H-pyrrolo[2,3-b]pyridine-5-carboxylic acid (30 g, 185.1 mmol, 1 eq) in DMF (5 v) under inert atmosphere were added HATU (84.44 g, 222.2 mmol, 1.3 eq) and 4,4-difluoropiperidine (31.98 g, 203.7 mmol, 1.1 eq) was added at 0° C. To this stirred solution N,N'-diisopropylethylamine (119.6 g, 925.9 mmol, 5 eq) was added at 0° C. and then continued for stirring at RT for 16 h. The reaction mixture was quenched with ice water (200 mL), extracted with EtOAc (3×200 mL). The combined organic extracts were washed with ice water (2×100 mL) and brine (100 mL); dried over sodium sulphate, filtered and concentrated in vacuo to obtain the crude. The crude was purified through flash column chromatography to afford 32.5 g of Int-1c (66.2% yield). $^1$HNMR (400 MHz, DMSO-d6): δ 11.89 (s, 1H), 8.31 (d, J=2.0 Hz, 1H), 8.08 (d, J=1.6 Hz, 1H), 7.56 (t, J=2.8 Hz, 1H), 6.52 (dd, J=1.6, 3.2 Hz, 1H), 3.64-3.58 (m, 4H), 2.09-2.01 (m, 4H). LCMS: 97.17%; MS: 266 [M+H]$^+$.

Step-1: Int-1a, Int-1b, and Int-1c were converted to Int-2a: (Ar$_1$=Pyridine-2-CN; X, X'=H) 30% yield, MS: m/z=332.2 [M+H]$^+$; Int-2b: (Ar$_1$=Pyrazine-2-CN; X, X'=H) 68% yield, MS: m/z=333.2 [M+H]$^+$; Int-2c: (Ar$_1$=4-CHO-Ph; X, X'=H) 83% yield, MS: m/z=334.1 [M+H]$^+$; Int-2d: (Ar$_1$=3-CHO-Ph; X, X'=H) 53% yield, MS: m/z=334.1 [M+H]$^+$, Int-2e: (Ar$_1$=4-CH$_3$C=O-Ph; X, X'=H) 62% yield, MS: m/z=348.1 [M+H]$^+$; Int-2f: (Ar$_1$=3-CH$_3$C=O-Ph; X, X'=H) 60% yield, MS: m/z=348.1 [M+H]$^+$, Int-2 g: (Ar$_1$=4-CHO-Ph; X=H, X'=F) 58% yield, MS: m/z=353.1 [M+H]$^+$; Int-2 h: (Ar$_1$=3-CHO-Ph, X=H, X'=F) 78% yield, MS: m/z=353.1 [M+H]$^+$, and Int-2i: (Ar$_1$=4-CN-Ph, X=H, X'=F) 43% yield, MS: m/z=349.2 [M+H]$^+$.

Step 2: Using the general procedure for the oxidation of nitriles, MF-DH-342 (synthesis described in Scheme 43), MF-DH-344 (synthesis described in Scheme 43), Int-2a, Int-2b, and Int-2i were converted to MF-DH-343, MF-DH-345, MF-DH-365, MF-DH-384, and MF-DH-394, which were isolated as off-white solids.

Using the general procedure for reduction of aldehydes/ketones, MF-DH-347, MF-DH-348, MF-DH-347, and MF-DH-348 were obtained as sticky liquids.

General Procedure for Aldehyde/Ketone Alkylation

To a stirred solution of aldehyde/ketone Int-2c, Int-2e, Int-2d, and Int-2f (0.5 mmol, 1 eq) in THF (15 mL), MeMgBr (2M in THF, 2 eq) was added portion wise at 0° C. for 15 min. The reaction mixture was stirred for 5 h at room temperatures. The reaction was monitored by LCMS/TLC. Upon completion, the reaction mixture was quenched with satd. NH$_4$Cl (20 mL), extracted with EtOAc (2×20 mL), and the combined organic extracts were washed with brine solution (20 mL), dried over sodium sulfate, filtered, and concentrated under reduced pressure to afford the crude product, which was further purified by flash chromatography to afford MF-DH-370, MF-DH-374, MF-DH-371, and MF-DH-375 as off-white solids and sticky liquids.

General Procedure for Aldehyde Reduction: To a stirred solution of aldehyde/ketone Int-2 g/Int-2 h (0.5 mmol, 1 eq) in MeOH (15 mL), NaBH$_4$ (4 eq.) was added portion wise at 0° C. for 15 min. The reaction mixture was stirred for 2 h at room temperature. Upon completion, the reaction mixture was concentrated under vacuum, diluted with water, and extracted with EtOAc (2×20 mL). The combined organic extracts were washed with brine solution (20 mL), dried over sodium sulfate, filtered, and concentrated under reduced pressure to afford the crude product, which was further purified by flash chromatography to afford MF-DH-347 and MF-DH-348 as off white solids.

Synthesis of Pyrrolopyridine-5-Carboxyamide Analogs with Amide/Aryl Variation (MF-DH-324, MF-DH-325, MF-DH-326, MF-DH-327, MF-DH-328, MF-DH-329)

Provided below is an exemplary scheme to synthesize pyrrolopyridine-5-carboxyamide analogs with amide/Aryl variations that are inhibitors of hydroxyprostaglandin dehydrogenase.

Scheme 46

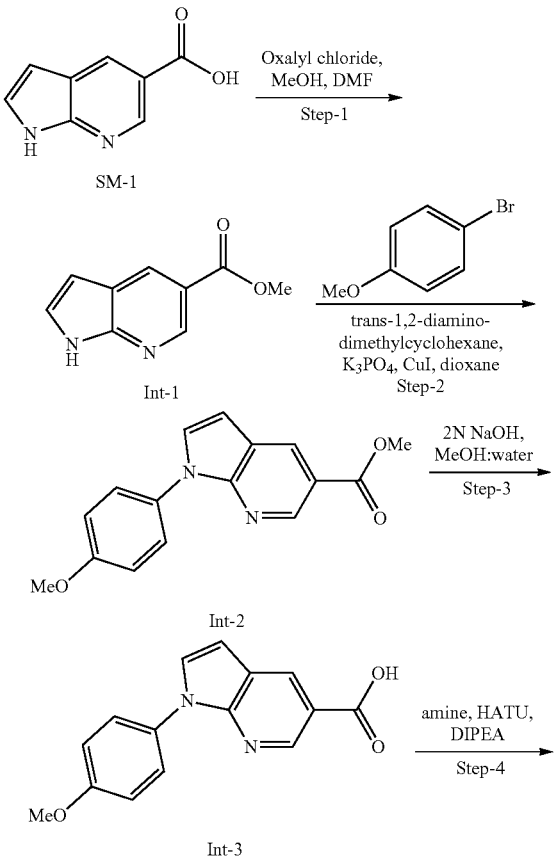

455

-continued

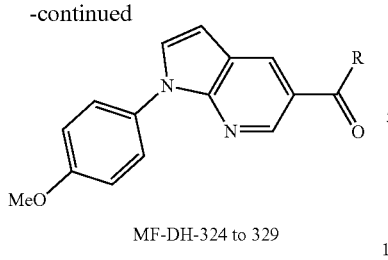

MF-DH-324 to 329

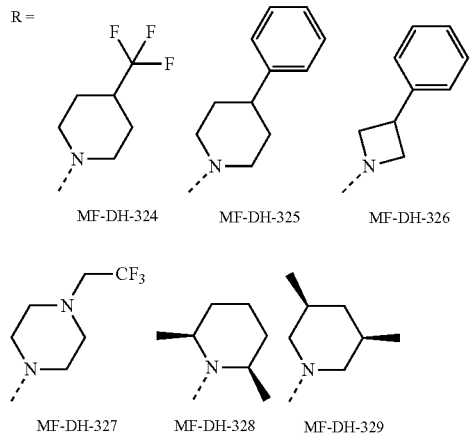

Step-1: Synthesis of methyl 1H-pyrrolo[2,3-b]pyridine-5-carboxylate (Int-1): To a stirred solution of 1H-pyrrolo[2,3-b]pyridine-5-carboxylic acid (5 g, 30.08 mmol, 1 eq) in DCM (100 mL) were added oxalylchloride (5.3 mL, 61.60 mmol, 2 eq) followed by DMF (0.5 mL) at 0° C. for 30 min and then was stirred at room temperature for 1 h. The reaction was monitored by TLC, after completion of the reaction, quenched with methanol (20 mL), and stirred at room temperature for 12 h. Then solvent was evaporated under reduced pressure and diluted with ethyl acetate (100 mL), washed with sat. NaHCO$_3$ solution (50 mL), and brine (50 mL) and the organic phases were dried over sodium sulfate, filtered, and concentrated under reduced pressure to obtain methyl 1H-pyrrolo[2,3-b]pyridine-5-carboxylate, Int-1 (5.38 g, 99%) as an off-white solid. LCMS: 96.42%, m/z=177.1[M+H]$^+$. $^1$H NMR (DMSO-d6, 400 MHz): δ 12.08 (br s, 1H), 8.78 (s, 1H), 8.50 (s, 1H), 7.56 (s, 1H), 6.57 (s, 1H), 3.81 (s, 3H).

Step-2 Synthesis of methyl 1-(4-methoxyphenyl)-1H-pyrrolo[2,3-b]pyridine-5-carboxylate (Int-2): Using the general procedure for Ullmann reaction Int-1 (2.5 g, 14.1 mmol) was converted to Int-2 (2.51 g, 62.5%) which was isolated as an off-white solid. LCMS: 99.12%, m/z=283.1[M+H]$^+$.

Step-3: Synthesis of 1-(4-methoxyphenyl)-1H-pyrrolo[2,3-b]pyridine-5-carboxylic acid (Int-3): Methyl 1-(4-methoxyphenyl)-1H-pyrrolo[2,3-b]pyridine-5-carboxylate (2.5 g, 8 mmol, 1 eq) in MeOH: water (8:2, 30 mL) was subjected to the general procedure for ester hydrolysis with NaOH to afford Int-3 (1.5 g, 65.21%) as a pale brown sticky solid. LCMS: 96.35 m/z=269.1[M+H]$^+$.

Step-4: Synthesis of MF-DH-324, MF-DH-325, MF-DH-326, MF-DH-327, MF-DH-328, and MF-DH-329: Using the general procedure for HATU coupling, Int-3 was converted to MF-DH-MF-DH-324, MF-DH-325, MF-DH-326, MF-DH-327, MF-DH-328, and MF-DH-329 which were isolated after purification as off white solid/sticky solids.

456

Synthesis of Pyrrolopyridine-5-Carboxyamide Analogs with Amide/Aryl Variation

Provided below is an exemplary scheme to synthesize pyrrolopyridine-5-carboxyamide analogs with amide/Aryl variations that are inhibitors of hydroxyprostaglandin dehydrogenase.

Scheme 47

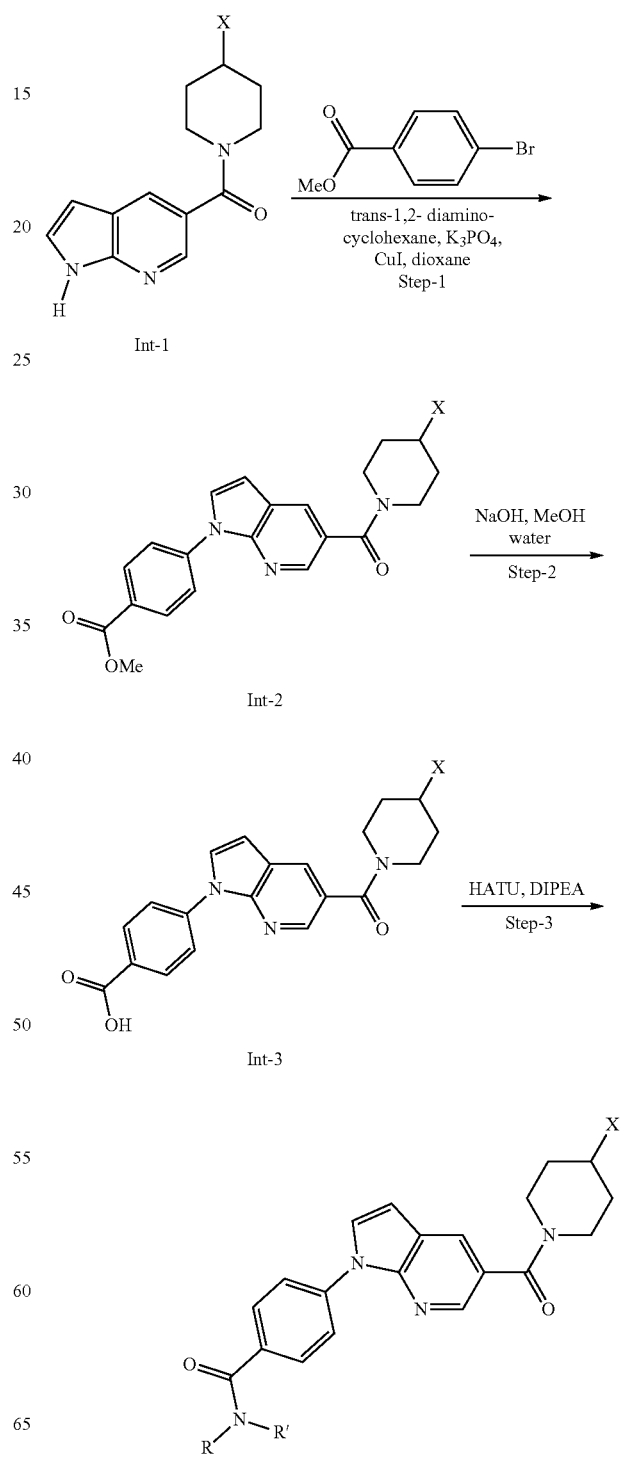

-continued

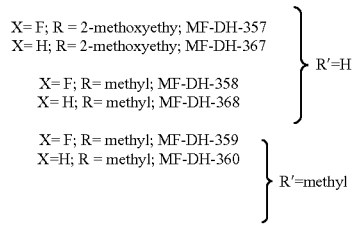

X= F; R = 2-methoxyethy; MF-DH-357
X= H; R = 2-methoxyethy; MF-DH-367  } R'=H

X= F; R= methyl; MF-DH-358
X= H; R= methyl; MF-DH-368  }

X= F; R= methyl; MF-DH-359
X=H; R = methyl; MF-DH-360  } R'=methyl

The synthesis of Int-1a (X=H) and Int-1b (X=F) is described in Scheme 9.

Step-1: Int-1a/1b was converted to Int-2a/2b using the general procedure for Ullmann coupling with 4-bromobenzoate to afford Int-2a (X=H, 55% yield, MS: m/z=364.1 [M+1]$^+$) and Int-2b (X=F, 60.74% yield, MS: m/z=382.1 [M+1]$^+$) as off-white solids.

Step-2: Int-2 was converted to Int-3a (X=H, 8600 yield, m/z=350.1 [M+1]$^+$) and Int-3b (X=F, 89% o yield, MS: m/z=366.1 [M–H]–) using the general procedure for ester hydrolysis with NaOH. The crudes were taken to the next stage without purification.

Step-3: Int-3 was subjected to the general procedure for amide couplings with HATU to afford MF-DH-357, MF-DH-367, MF-DH-358, MF-DH-368, MF-DH-359, and MF-DH-360.

Synthesis of Azabenzimidazole Analogs with Aryl/Amide Variation

Provided below is an exemplary scheme to synthesize azabenzimidazole analogs with amide/Aryl variations that are inhibitors of hydroxyprostaglandin dehydrogenase.

Scheme 48

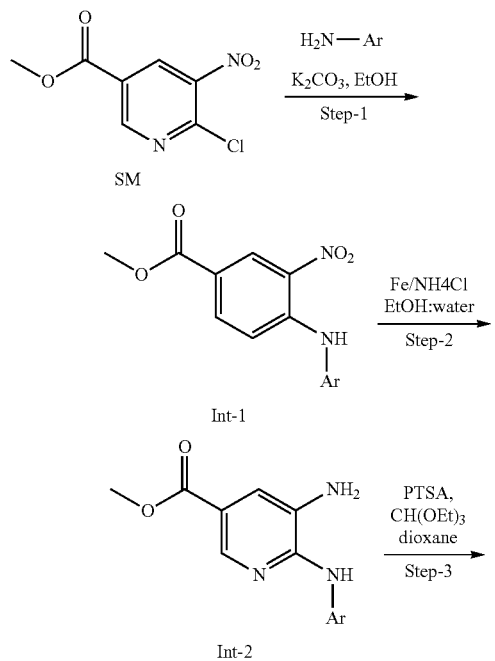

-continued

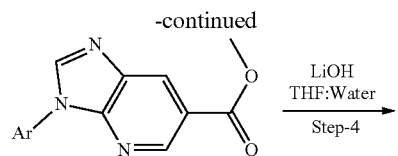

Int-3

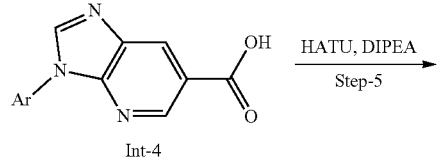

Int-4

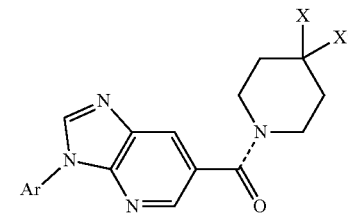

Structures below

Ar =

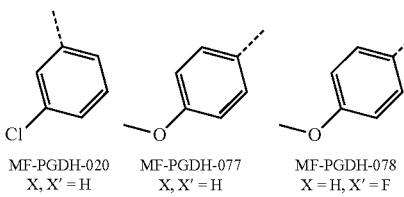

MF-PGDH-020    MF-PGDH-077    MF-PGDH-078
X, X' = H        X, X' = H       X = H, X' = F

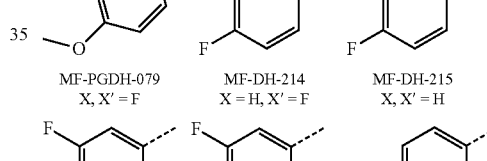

MF-PGDH-079    MF-DH-214       MF-DH-215
X, X' = F       X = H, X' = F    X, X' = H

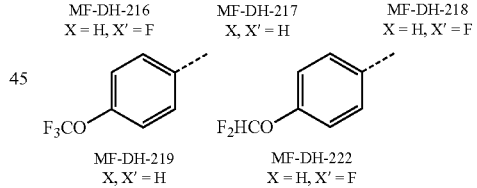

MF-DH-216       MF-DH-217       MF-DH-218
X = H, X' = F    X, X' = H       X = H, X' = F

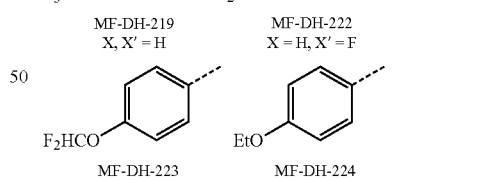

MF-DH-219       MF-DH-222
X, X' = H       X = H, X' = F

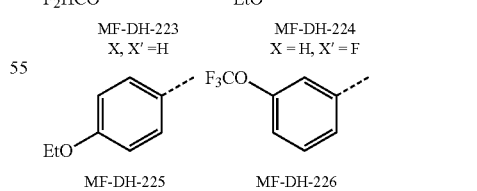

MF-DH-223       MF-DH-224
X, X' =H        X = H, X' = F

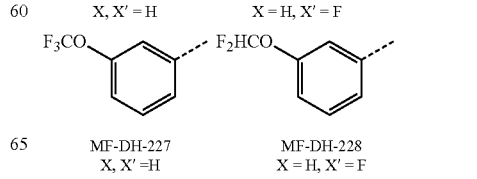

MF-DH-225       MF-DH-226
X, X' = H       X = H, X' = F

MF-DH-227       MF-DH-228
X, X' =H        X = H, X' = F

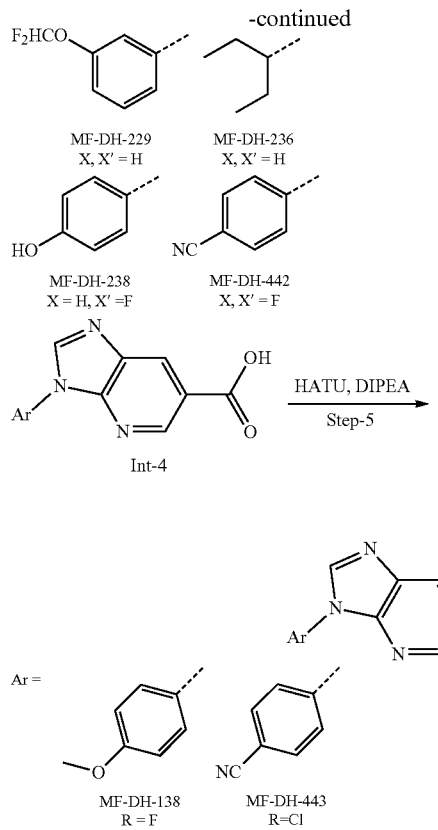

Step-1: Synthesis of Int-1 general procedure: In a sealed bomb, methyl 6-chloro-5-nitronicotinate (7 g, 32.31 mmol, 1 eq), Arylamines (Ar—NH$_2$, 1 eq) were dissolved in EtOH (70 mL). To this stirring solution K$_2$CO$_3$ (1 eq) was added at room temperature. Steel bomb cap was tightly closed then resultant reaction mixture was heated to 100° C. for 16 h. The reaction was monitored by crude LCMS/TLC; after completion of the reaction; cooled to room temperature and then filtered, washed with EtOAc (50 mL). Volatiles were evaporated, quenched with satd. NH$_4$Cl (100 mL), extracted with EtOAc (3×50 mL) and combined organic extracts were washed with brine (50 mL). Dried over sodium sulfate, filtered and concentrated in vacuo to obtain the yellow solid, trituration with DEE (100 mL) afforded Int-1a (Ar=3-Cl phenyl, 64% yield, MS: m/z=307.2 [M+H]$^+$); Int-1b (Ar=4-OMePh, 87% yield, MS: m/z=318.2 [M+H]$^+$); Int-1c (Ar=4-F-Ph, 70% yield, MS: [M+H]$^+$); Int-1d (Ar=3,4 Di Fluo-roPh, 96% yield); Int-1e (Ar=4-OCF$_3$Ph, 96% yield, MS: m/z=328.2); Int-1f (Ar=4-OCHF$_2$Ph, 66% yield, MS: m/z=338.2 [M+H]$^+$); Int-1 g (Ar=4-OEtPh, 62% yield, MS: m/z=317.2 [M+H]$^+$); Int-1 h (Ar=3-OCF$_3$Ph, 72% yield, MS: m/z=326.2 [M+H]$^+$); Int-1i (Ar=3-OCHF$_2$Ph, 62% yield, MS: m/z=309.2 [M+H]$^+$); Int-1j (Ar=3-pentyl, 83% yield, MS: m/z=254.1 [M+H]$^+$); Int-1k (Ar=4-OHPh, 76% yield, MS: m/z=290.1 [M+H]$^+$); and Int-11 (Ar=4-CNPh, crude, m/z=299.1 [M+H]$^+$).

Step-2: Synthesis of Int-2: Int-1 (2 g, 1 eq) was subjected to the general procedure for aryl nitro reduction using Fe. The crude was purified through silica gel column chromatography using 60% to 70% EtOAc/heptane to afford Int-2a (Ar=3-ClPh, 20% yield, MS: m/z=291.0 [M+H]$^+$); Int-2b (Ar=4-OMePh, crude, MS: m/z=288.2 [M+H]$^+$); Int-2c (Ar=4-FPh, crude, MS: m/z=261.2 [M+H]$^+$); Int-2d (Ar=3, 4-Di FluoroPh, 96% yield, MS: m/z=280.2 [M+H]$^+$); Int-2e (Ar=4-OCF$_3$Ph, 96% yield, MS: m/z=328.2); Int-2f (Ar=4-OCHF$_2$Ph, 71.4% yield, MS: m/z=324.2 [M+1]$^+$); Int-2 g (Ar=4-OEtPh, 93% yield, MS: m/z=286.2 [M+H]$^+$); Int-2 h (Ar-3-OCF$_3$Ph, 68% yield, MS: m/z=338.1 [M+H]$^+$); Int-2i (Ar=3-OCHF$_2$Ph, 57% yield, MS: m/z=310.2 [M+1H]$^+$); Int-2j (Ar=3-pentyl, 84% yield, MS: m/z=252.1 [M+H]$^+$); Int 2k (Ar=4-OHPh, 76% yield, MS: m/z=290.1 [M+H]$^+$); and Int-21 (Ar=4-CNPh, crude, MS: m/z=269.2 [M+H]$^+$).

Step-3: Synthesis of Int-3 general procedure: To a stirred solution of Int-2 (1.5 g, 1 eq) and triethyl orthoformate (5 eq) in dioxane (20 mL), PTSA (0.2 eq) was added at room temperature. The resulting reaction mixture was heated to 100° C. for 16 h. The reaction was monitored by crude LCMS/TLC; after complete consumption of the starting material, the reaction mixture was quenched with sat. NaHCO$_3$ solution (20 mL), extracted with EtOAc (3×50 mL); the combined organic extracts were washed with brine (20 mL), dried over sodium sulfate, filtered and concentrated in vacuo to obtain the crude. The crude was purified by silica gel column chromatography using 50% EtOAc/heptane to obtain Int-3a (Ar=3-ClPh, 20% yield, MS: m/z=291.0 [M+H]$^+$); Int-3b (Ar=4-OMePh, 58% yield, MS: m/z=298.2 [M+1]$^+$), Int-3c (Ar=4-FPh, crude, MS: m/z=271.2 [M+H]$^+$); Int-3d (Ar=3,4-Di FluoroPh, crude, MS: m/z=290.1 [M+H]$^+$); Int-3e (Ar=4-OCF$_3$Ph, 81% yield, MS: m/z=338.1); Int-3f (Ar=4-OCHF$_2$Ph, 97.1% yield, MS: m/z=334.1 [M+H]$^+$); Int-3 g (Ar=4-OEtPh, 56% yield, MS: m/z=297.2 [M+H]$^+$); Int-3 h (Ar=3-OCF$_3$Ph, 67% yield, MS: m/z=276.1 [M+H]$^+$); Int-3i (Ar=3-OCHF$_2$Ph, 65% yield, MS: m/z=309.2 [M+H]$^+$); Int-3j (Ar=3-pentyl, 84% yield, MS: m/z=262.2 [M+H]$^+$); Int 3k (Ar=4-OHPh, 58% yield, MS: m/z=269.2 [M+H]$^+$); and Int-31 (Ar=4-CNPh, 56.6% yield, MS: m/z=279.1 [M+H]$^+$).

Step-4: Synthesis of Int-4: Int-3 (1.2 g, 1 eq) in MeOH: water (1:1, 20 mL) was subjected to the general procedure for ester hydrolysis with LiOH to afford Int-4a (Ar=3-ClPh, 82% yield, MS: m/z=291.0 [M+H]$^+$); Int-4b (Ar=4-OMePh, 82% yield, MS: m/z=270.1 [M+H]$^+$); Int-4c (Ar=4-FPh, 19% yield), Int-4d (Ar=3,4 DiFluoroPh, 56% yield, MS: m/z=376.1 [M+H]$^+$); Int-4e (Ar=4-OCF$_3$Ph, 90% yield, MS: m/z=324.1 [M+H]$^+$); Int-4f (Ar=4-OCHF$_2$Ph, 43.4% yield, MS: m/z=306.1 [M+H]$^+$); Int-4 g (Ar=4-OEtPh, 85.2% yield, MS: m/z=282.1 [M−H]−); Int-4 h (Ar=3-OCF$_3$Ph, 52.2% yield, MS: m/z=338.2 [M+H]$^+$); Int-4i (Ar=3-OCHF$_2$Ph, 78% yield, MS: m/z=306.1 [M+H]$^+$), Int-4j (Ar=3-pentyl, 81% yield, MS: m/z=234.1[M+H]$^+$); Int 4k (Ar=4-OHPh, 85% yield, MS: m/z=256.1 [M+H]$^+$); and Int-41 (Ar=4-CNPh, 90% yield, MS: m/z=263.1 [M−H]−).

Step-5: Synthesis of MF-DH-214, MF-DH-215, MF-DH-216, MF-DH-217, MF-DH-218, MF-DH-219, MF-DH-222, MF-DH-223, MF-DH-224, MF-DH-225, MF-DH-226, MF-DH-227, MF-DH-228, MF-DH-229, MF-DH-236, MF-DH-238, MF-DH-442, MF-DH-138, and MF-DH-443: Int-4 (1 eq) and piperidine/4-fluoro piperidine/4,4-difluoropiperidine/3-fluoroazetidine/3-chloroazetidine (1.2 eq) were subjected to the general procedure for amide coupling with HATU. The crudes were purified by flash silica gel column chromatography using 60% EtOAc: heptane or by Prep-HPLC purification to afford MF-DH-214, MF-DH-215, MF-DH-216, MF-DH-217, MF-DH-218, MF-DH-219, MF-DH-222, MF-DH-223, MF-DH-224, MF-DH-225, MF-DH-226, MF-DH-227, MF-DH-228, MF-DH-229, MF-DH-236, MF-DH-238, MF-DH-442, MF-DH-138, and MF-DH-443 as off-white solids/gummy liquids.

Synthesis of MF-DH-464: MF-DH-442 was subjected to the general procedure for oxidation of nitriles. The crude was purified by flash chromatography to afford MF-DH-464 as an off-white solid.

Synthesis of MF-DH-176 and MF-DH-205

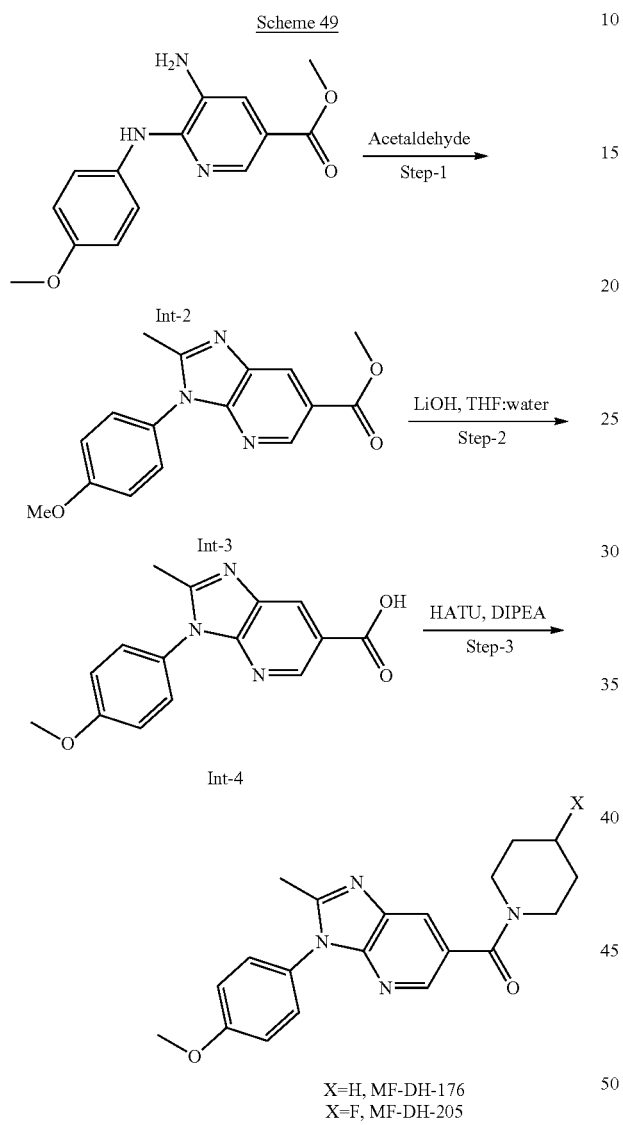

The synthesis of Int-2 is described in Scheme 48.

Step-1: Synthesis of methyl 3-(4-methoxyphenyl)-2-methyl-3H-imidazo[4,5-b]pyridine-6-carboxylate (Int-3): To a stirred solution 5-amino-6-((4-methoxyphenyl)amino)nicotinate (300 mg, 1.09 mmol, 1.0 eq) in DMF (2 mL) was added acetaldehyde (74 mg, 3.27 mmol, 3.0 eq) and sodium sulfate (3.09 mg, 2.18 mmol, 2.0 eq) at room temperature. The reaction was heated to 80° C. for 12 h. The reaction was monitored by crude LCMS/TLC; after complete consumption of the starting material, the reaction mixture was quenched with ice water (20 mL), extracted with EtOAc (2×15 mL). The combined organic extracts were washed with ice water (2×10 mL) and brine (10 mL), dried over sodium sulfate, filtered and concentrated in vacuo to obtain the crude. The crude was purified by silica gel column chromatography using 50% EtOAc/Hexane to obtain methyl 3-(4-methoxyphenyl)-2-methyl-3H-imidazo[4,5-b]pyridine-6-carboxylate (210 mg, 64.4%) as an off-white solid. MS: m/z=311.1 [M+H]$^+$.

Step-2: Synthesis of 3-(4-methoxyphenyl)-2-methyl-3H-imidazo[4,5-b]pyridine-6-carboxylic acid (Int-4) Using the general procedure for ester hydrolysis with LiOH, methyl 3-(4-methoxyphenyl)-2-methyl-3H-imidazo[4,5-b]pyridine-6-carboxylate (Int-3) (210 mg) was converted to 3-(4-methoxyphenyl)-2-methyl-3H-imidazo[4,5-b]pyridine-6-carboxylic acid (Int-4, 160 mg, 79.2%) which was isolated as an off-white solid MS: m/z=284.1 [M+H]$^+$.

Step-3: Synthesis of MF-DH-176 and MF-DH-205: 3-(4-methoxyphenyl)-2-methyl-3H-imidazo[4,5-b]pyridine-6-carboxylic acid (Int-4) was converted to MF-DH-176 and MF-DH-205 using the general procedure for amide coupling using HATU.

Synthesis of MF-DH-117 and MF-DH-130

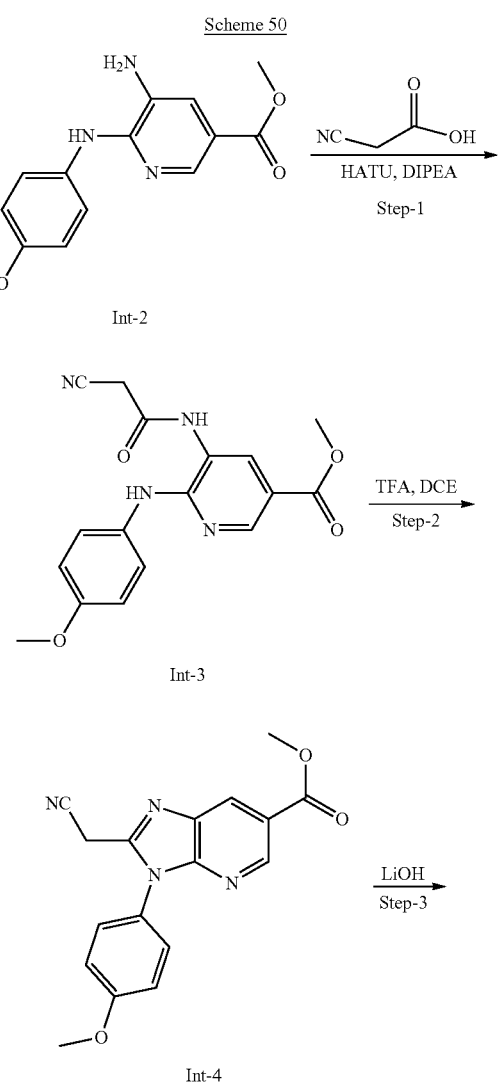

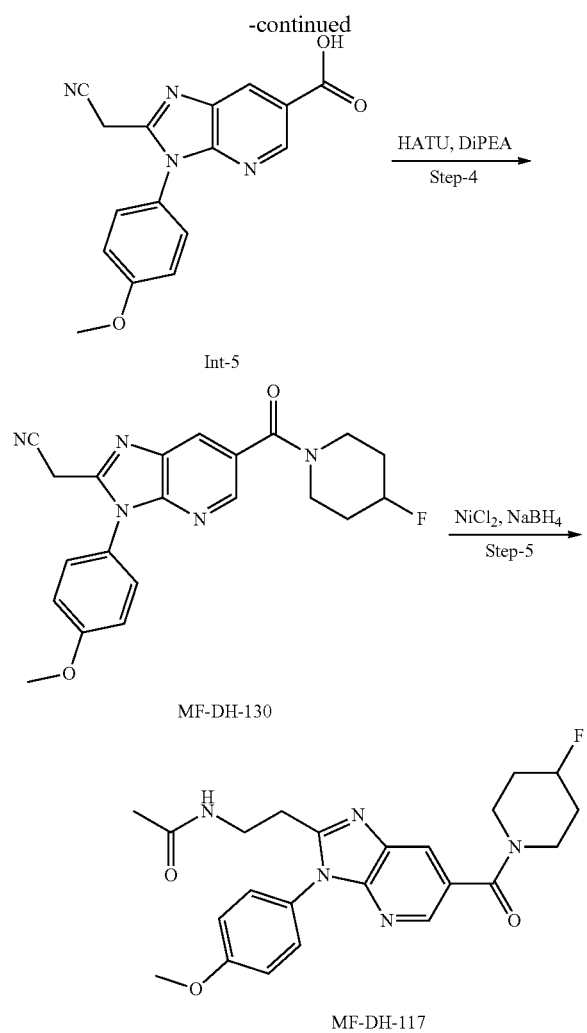

Int-5

MF-DH-130

MF-DH-117

The synthesis of Int-2 is described in Scheme 48.

Step-1: Synthesis of methyl 5-(2-cyanoacetamido)-6-((4-methoxyphenyl)amino)nicotinate (Int-3): Using the general procedure for amide coupling with HATU, methyl 5-amino-6-((4-methoxyphenyl)amino)nicotinate Int-2 (2 g) was converted to methyl 5-(2-cyanoacetamido)-6-((4-methoxyphenyl)amino)nicotinate (Int-3) which was isolated as an off-white solid. MS: m/z=355.0 [M+H]$^+$.

Step-2: Synthesis of methyl 2-(cyanomethyl)-3-(4-methoxyphenyl)-3H-imidazo[4,5-b]pyridine-6-carboxylate (Int-4): To a stirred solution of methyl 5-(2-cyanoacetamido)-6-((4-methoxyphenyl)amino)nicotinate (Int-3) (2 g, 5.89 mmol. 1.0 eq) in DCE (20 mL) at 0° C., was added trifluoroacetic acid (5 mL). The reaction mixture was slowly brought to room temperature and heated to 80° C., for 16 h. The reaction was monitored by crude LCMS/TLC; after complete consumption of the starting material, the reaction mixture was made neutral with saturated sodium bicarbonate (50 mL) and extracted with EtOAc (2×50 mL). The combined organic extracts were washed with water (2×10 mL) and brine (10 mL), dried over sodium sulfate, filtered and concentrated in vacuo to obtain the crude. The crude was used in the next step without further purification to obtain methyl 2-(cyanomethyl)-3-(4-methoxyphenyl)-3H-imidazo[4,5-b]pyridine-6-carboxylate (Int-4) (1.8 g, 94% yield) as an off-white solid. MS: m/z=323.2 [M+H]$^+$.

Step-3: Synthesis of 2-(cyanomethyl)-3-(4-methoxyphenyl)-3H-imidazo[4,5-b]pyridine-6-carboxylic acid (Int-5) Using the general procedure for ester hydrolysis with LiOH, methyl 2-(cyanomethyl)-3-(4-methoxyphenyl)-3H-imidazo[4,5-b]pyridine-6-carboxylate (Int-4) (700 mg) was converted to 2-(cyanomethyl)-3-(4-methoxyphenyl)-3H-imidazo[4,5-b]pyridine-6-carboxylic acid (Int-5) (320 mg, 47.2%) isolated as an off-white solid. MS: m/z=307.0 [M−H]−.

Step-4: Synthesis of MF-DH-117 and MF-DH-130: Using the general procedure for amide coupling with HATU, 2-(cyanomethyl)-3-(4-methoxyphenyl)-3H-imidazo[4,5-b]pyridine-6-carboxylic acid (Int-5) (1 eq) was converted to MF-DH-130. The crude was purified by silica gel column chromatography using 2-3% MeOH: CH$_2$C$_2$ followed by Prep-HPLC purification to obtain MF-DH-130 as an off-white solid.

General procedure for reduction of nitriles and acetylation for the synthesis of MW-DH-117: Step-5: To a stirred solution of MF-DH-130 (0.5 mmol, 1 eq) in MeOH (15 mL), NiCl2.6H2O (1 eq %) followed by NaBH$_4$ (5 eq) was added at 0° C. then warmed to room temperature for 30 min under hydrogen/nitrogen atmosphere. To this cooled reaction mixture, added Ac$_2$O (2 eq) and then the reaction mixture was stirred for 16 h. The reaction was monitored by LCMS/TLC, after completion of the reaction, quenched with ice water (20 mL) filtered through celite bed and volatiles were evaporated. The mixture was extracted with EtOAc (2×20 ml), and combined organic extracts were washed with brine (20 mL), dried over sodium sulfate, filtered and concentrated under reduced pressure to obtain the crude. This was further purified by flash chromatography to afford MF-DH-117 as an off-white solid.

Synthesis of MF-DH-184, MF-DH-185, MF-DH-195, MF-DH-267 and MF-DH-268

Scheme 51

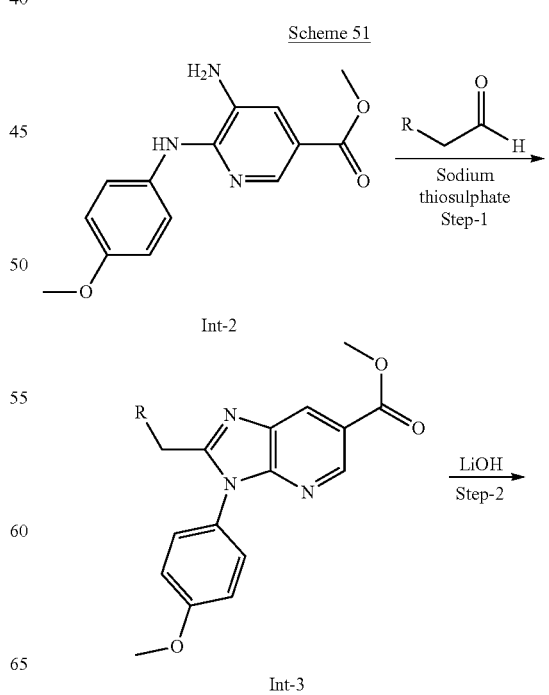

Int-2

Int-3

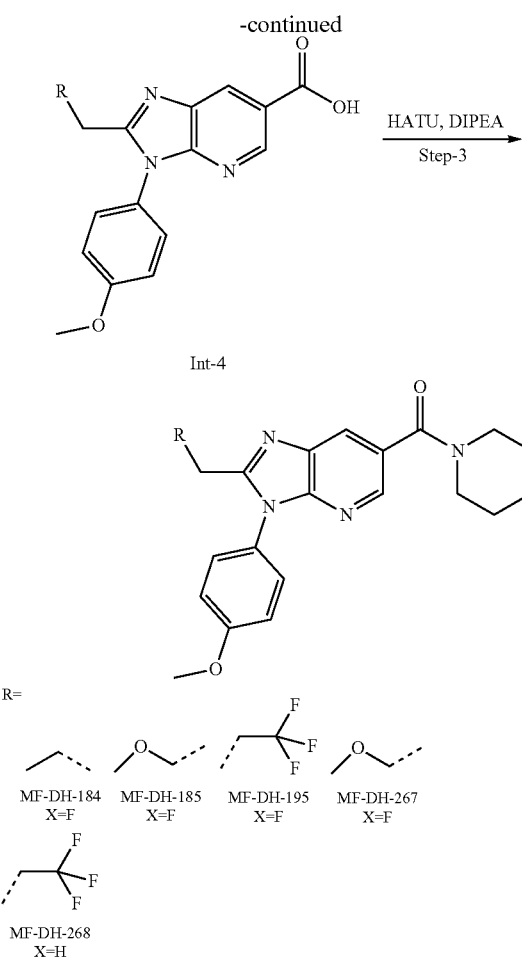

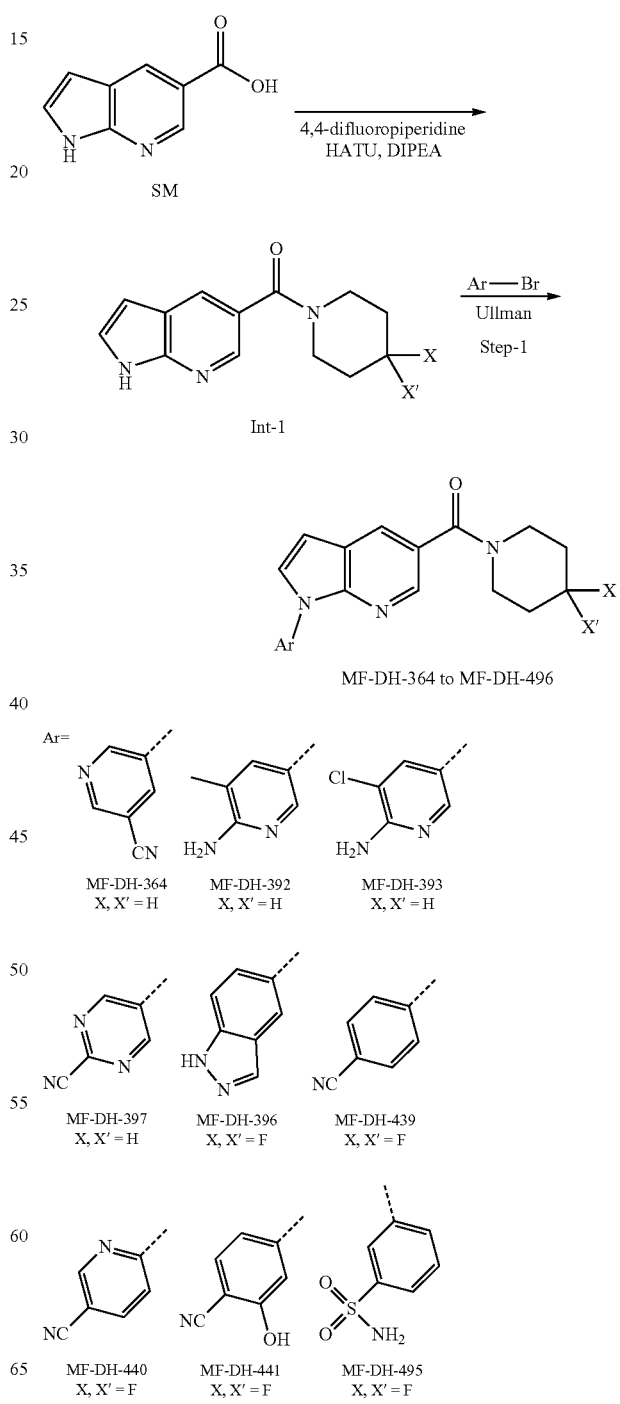

Synthesis of 5-(5-(piperidine-1-carbonyl/4-fluoropiperidine-1-carbonyl/-fluoropiperidine-1-carbonyl)-1H-pyrrolo[2,3-b]pyridin-1-yl) carboxamide Analogs with aryl/amide Variation Provided below is an exemplary scheme to synthesize 5-(5-(piperidine-1-carbonyl/4-fluoropiperidine-1-carbonyl/-fluoropiperidine-1-carbonyl)-1H-pyrrolo[2,3-b]pyridin-1-yl) carboxamide analogs with aryl/amide variations that are inhibitors of hydroxyprostaglandin dehydrogenase.

The synthesis of Int-2 is described in Scheme 48.

Step-1: Synthesis of Int-3, general procedure: To a stirred solution of methyl 5-amino-6-((4-methoxyphenyl)amino) nicotinate Int-2 in DMF (10 V) was added respective aldehydes (4.0 eq), sodium thiosulfate (1.0 eq) was added and then heated to 70-80° C. for 16 h. The reaction was monitored by crude LCMS/TLC; after complete consumption of the starting material, the reaction mixture was quenched with ice water (20 mL) and extracted with EtOAc (2×30 mL). The combined organic extracts were washed with water (2×10 mL) and brine (10 mL), dried over sodium sulfate, filtered and concentrated in vacuo to obtain the crude as a thick syrup. The crude was used in the next step without further purification.

Step-2: Synthesis of Int-4: Using the general procedure for ester hydrolysis with LiOH, Int-3 was converted to Int-4a (R=Methyl, 39% yield, MS: m/z=298.0 [M+H]$^+$); Int-4b (R=Methoxy methyl, 65.2% yield, MS: m/z=326.0 [M−H]−); and Int-4c (R=trifluoroethyl, 77% yield, MS: m/z=366.1 [M+H]$^+$), which were isolated as off-white solids.

Step-3: Synthesis of MF-DH-184, MF-DH-185, MF-DH-195, MF-DH-267 and MF-DH-268 general procedure: Using the general procedure for amide coupling with HATU, Int-5 was converted to crude products. The crude was purified through silica gel column chromatography using 2-3% MeOH: CH$_2$C$_2$ followed by Prep-HPLC purification to obtain MF-DH-184, MF-DH-185, MF-DH-195, MF-DH-267 and MF-DH-268 as off-white solids/gummy liquids.

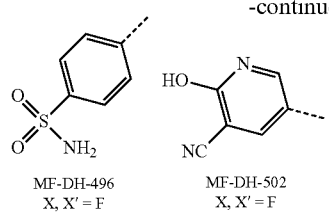

MF-DH-496
X, X' = F

MF-DH-502
X, X' = F

The synthesis of Int-1a (X, X'=H) is described in Scheme 9.

The synthesis of Int-1b (X, X'=F) is described in Scheme 45.

Step-1: Synthesis of MF-DH-364, MF-DH-392, MF-DH-393, MF-DH-397, MF-DH-396, MF-DH-439, MF-DH-440, MF-DH-441, MF-DH-495, MF-DH-496 and MF-DH-502: Using the general procedure for Ullmann coupling with the corresponding aryl bromides, Int-1a and Int-1b were converted to the title compounds after the crude was purified by flash column/Prep-HPLC purification.

Synthesis of (1-(4-(1-aminoethyl)phenyl)-1H-pyrrolo[2,3-b]pyridin-5-yl)(piperidin-1-yl)methanone/ (1-(3-(1-aminoethyl)phenyl)-1H-pyrrolo[2,3-b]pyridin-5-yl)(piperidin-1-yl)methanone (MF-DH-372 and MF-DH-376)

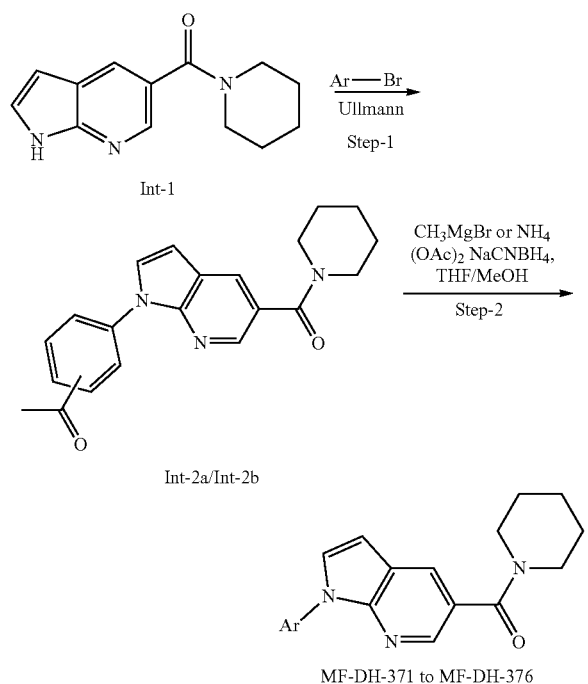

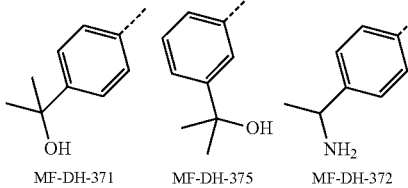

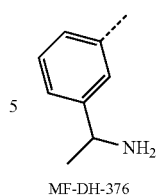

MF-DH-376

Step-1: General procedure for synthesis of 1-(4/3-(5-(piperidine-1-carbonyl)-1H-pyrrolo[2,3-b]pyridin-1-yl)phenyl)ethan-1-one/4/3-(5-(piperidine-1-carbonyl)-1H-pyrrolo[2,3-b]pyridin-1-yl)benzaldehyde (Int-2): Piperidin-1-yl (1H-pyrrolo[2,3-b]pyridin-5-yl)methanone (Int-1) was converted to 1-(3-(5-(piperidine-1-carbonyl)-1H-pyrrolo[2,3-b]pyridin-1-yl)phenyl)ethan-1-one (Int-2a) and 1-(4-(5-(piperidine-1-carbonyl)-1H-pyrrolo[2,3-b]pyridin-1-yl)phenyl)ethan-1-one (Int-2b) using the general procedure for Ullmann coupling with respective 3/4-bromobenzophenone to afford Int-2a (33% yield, MS: m/z=348.2 [M+H]$^+$) and Int-2b (54% yield, MS: m/z=348.2 [M+H]$^+$).

Step-2: General procedure for the synthesis of (1-(4/3-(2-hydroxypropan-2-yl)phenyl)-1H-pyrrolo[2,3-b]pyridin-5-yl)(piperidin-1-yl)methanone (MF-DH-371 and MF-DH-375): To a stirred solution of ketone (Int-2a/Int-2b) (0.5 mmol, 1 eq) in THF (15 mL), methyl magnesium bromide (1.5 eq) was added at 0° C. under nitrogen atmosphere and then stirred for 4 h at room temperature. The reaction was monitored by LCMS/TLC, after completion of the reaction, quenched with satd. NH$_4$Cl (15 ml); the aqueous phase was extracted with ethyl acetate (2×10 mL) and combined organic extracts were washed with brine (20 mL), dried over sodium sulfate, filtered and concentrated under reduced pressure to obtain the crude. This was further purified by flash chromatography to afford MF-DH-371 and MF-DH-375 as an off-white solid/sticky liquid.

Step-2: Synthesis of (1-(3/4-(1-aminoethyl) phenyl)-1H-pyrrolo[2,3-b]pyridin-5-yl)(piperidin-1-yl)methanone (MF-DH-372 and MF-DH-376): To a stirred solution of Int-2a/Int-2b in methanol (10 vol), ammonium acetate (5.0 eq) was added at room temperature. The reaction was heated to 50° C., for 5 h. The reaction mixture was cooled to 0° C., sodium cyanoborohydride (3.0 eq) was added and stirred at room temperature for 16 h. The reaction was monitored by TLC, after completion of the reaction, the reaction mixture was diluted with water and extracted with DCM. The organic phases were dried over sodium sulfate, filtered and concentrated under reduced pressure to afford the crude. This was further purified by Prep-HPLC to afford MF-DH-372 and MF-DH-376 as sticky liquids.

Synthesis of 2-(4-(5-(4,4-difluoropiperidine-1-carbonyl)-1H-pyrrolo[2,3-b]pyridin-1-yl)phenyl)acetic acid/1-(4-(5-(4,4-difluoropiperidine-1-carbonyl)-1H-pyrrolo[2,3-b]pyridin-1-yl)phenyl)cyclopropane-1-carboxylic acid/4-(5-(piperidine-1-carbonyl)-1H-pyrrolo[2,3-b]pyridin-1-yl)benzoic acid (MF-DH-426, 427 and MF-DH-433)

Scheme 54

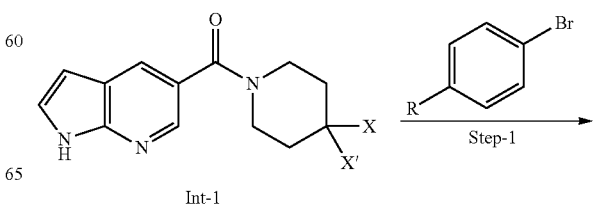

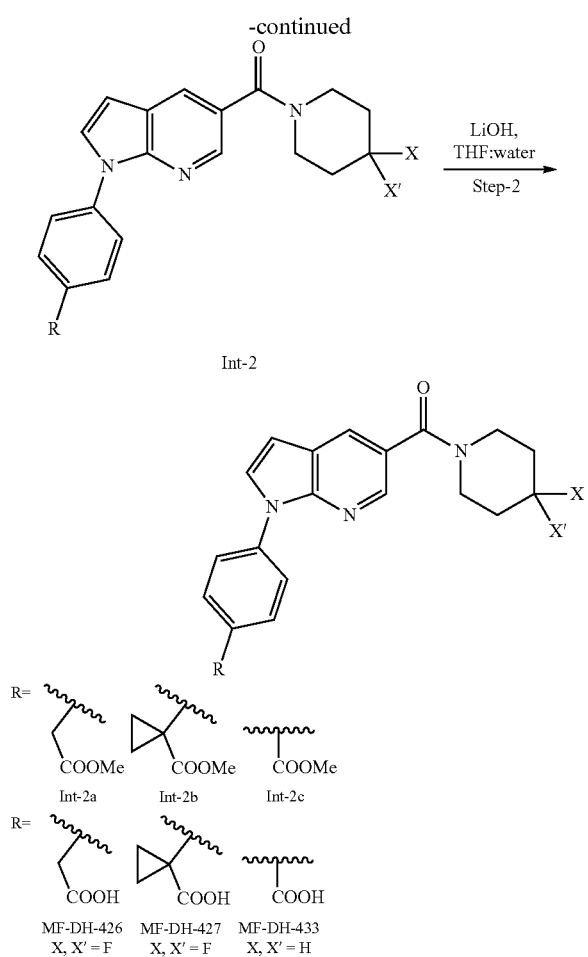

The synthesis of Int-1a (X, X'=F) is described in Scheme 45. The synthesis of Int-1b (X, X'=H) is described in Scheme 9.

Step-1: Synthesis of methyl 2-(4-(5-(4,4-difluoropiperidine-1-carbonyl)-1H-pyrrolo[2,3-b]pyridin-1-yl)phenyl)acetate/methyl 1-(4-(5-(4,4-difluoropiperidine-1-carbonyl)-1H-pyrrolo[2,3-b]pyridin-1-yl)phenyl)cyclopropane-1-carboxylate/(methyl 4-(5-(piperidine-1-carbonyl)-1H-pyrrolo[2,3-b]pyridin-1-yl) (Int-2): (4,4-difluoropiperidin-1-yl)(1H-pyrrolo[2,3-b]pyridin-5-yl)methanone/piperidin-1-yl(1H-pyrrolo[2,3-b]pyridin-5-yl)methanone (Int-1) was converted to Int-2a (64.2% yield, MS: m/z=414.2 [M+H]$^+$); Int-2b (60.4% yield, MS: m/z=440.2 [M+H]$^+$); and Int-2c (80% yield, MS: m/z=364.2 [M+H]$^+$) using the general procedure for Ullmann coupling.

Step-2: General procedure for synthesis of 2-(4-(5-(4,4-difluoropiperidine-1-carbonyl)-1H-pyrrolo[2,3-b]pyridin-1-yl)phenyl)acetic acid/1-(4-(5-(4,4-difluoropiperidine-1-carbonyl)-1H/-pyrrolo[2,3-b]pyridin-1-yl)phenyl)cyclopropane-1-carboxylic acid/4-(5-(piperidine-1-carbonyl)-1H-pyrrolo[2,3-b]pyridin-1-yl)benzoic acid (de-DH-426, 427 and MF-DH-433): Int-2a, Int-2b, and Int-2c were converted to MF-DH-426, MF-DH-427 and MF-DH-433 using the general procedure for ester hydrolysis with LiOH.

Synthesis of pyrrolopyridine-4,4-difluoropiperidine-5-carboxyamide analogs with 4-benzamide Variation (MF-DH-404, 412, 413, 418, 421, 451, 431, 411, 409, 403, 419, 420, 428, 429, 432 and MF-DH-450)

Provided below is an exemplary scheme to synthesize pyrrolopyridine-4,4-difluoropiperidine-5-carboxyamide analogs with 4-benzamide variations that are inhibitors of hydroxyprostaglandin dehydrogenase.

Scheme 55

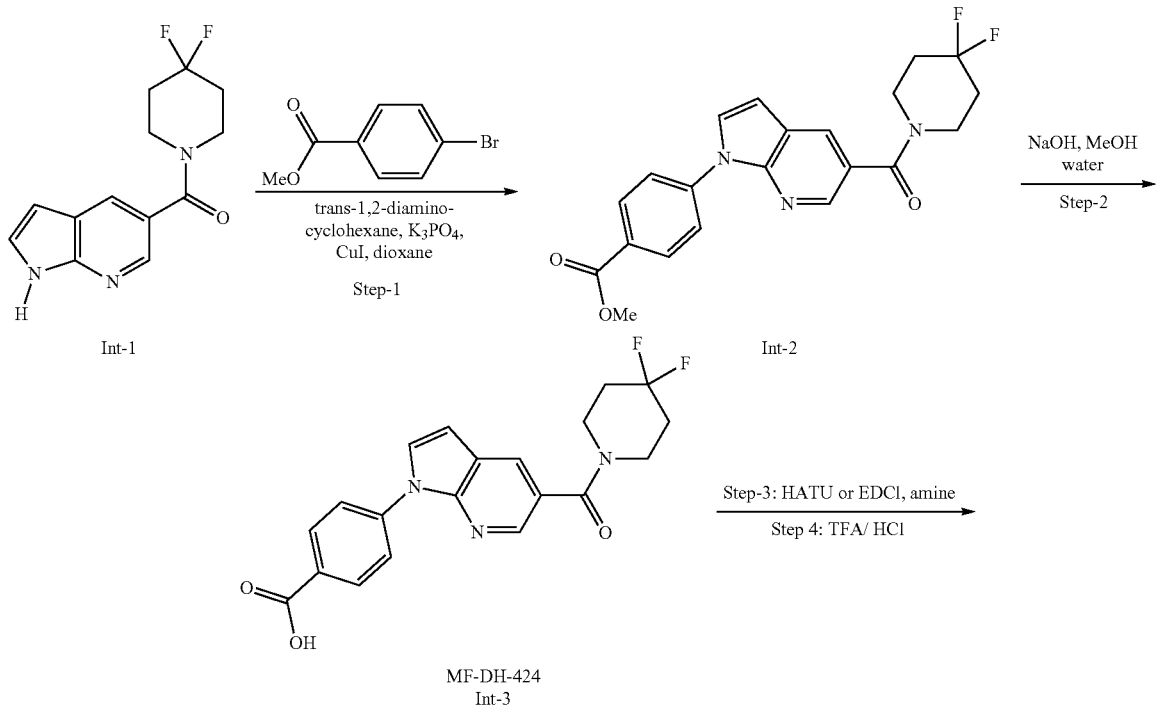

-continued

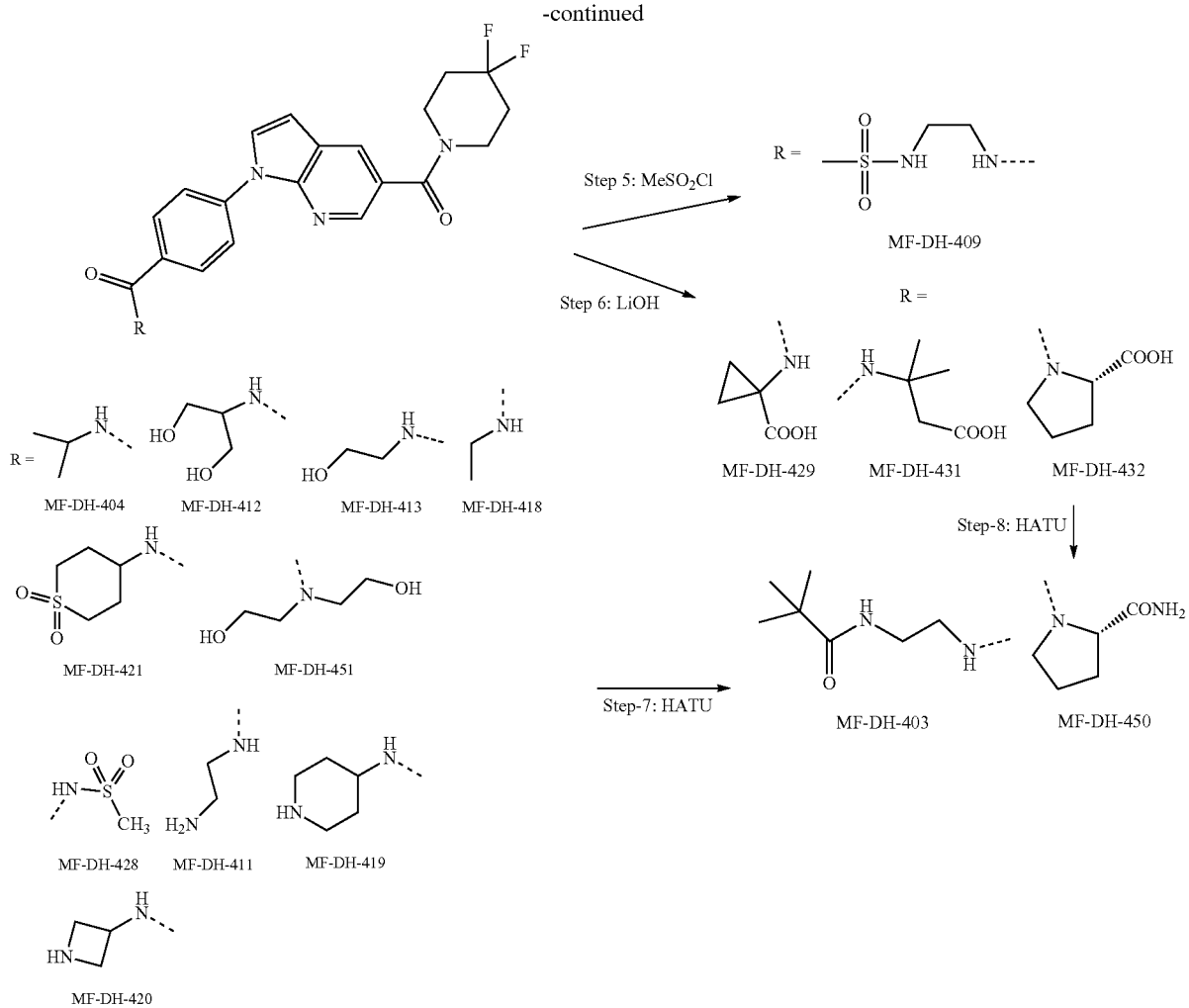

The synthesis of Int-1 is described in Scheme 45.

Step-1: Synthesis of methyl 4-(5-(4,4-difluoropiperidine-1-carbonyl)-1H-pyrrolo[2,3-b]pyridin-1-yl)benzoate (Int-2): (4,4-difluoropiperidin-1-yl)(1H-pyrrolo[2,3-b]pyridin-5-yl)methanone (3 g, 11.3 mmol, 1.0 eq) was converted to methyl 4-(5-(4,4-difluoropiperidine-1-carbonyl)-1H-pyrrolo[2,3-b]pyridin-1-yl)benzoate (Int-2) using the general procedure for Ullmann coupling to afford 3.05 g (65%) of the product as an off-white solid. MS: 399.1 (M+1).

Step-2: synthesis of 4-(5-(4,4-difluoropiperidine-1-carbonyl)-1H-pyrrolo[2,3-b]pyridin-1-yl)benzoic acid (Int-3): methyl 4-(5-(4,4-difluoropiperidine-1-carbonyl)-1H-pyrrolo[2,3-b]pyridin-1-yl)benzoate (3.0 g, 7.5 mmol) was converted to 4-(5-(4,4-difluoropiperidine-1-carbonyl)-1H-pyrrolo[2,3-b]pyridin-1-yl)benzoic acid using the general procedure for ester hydrolysis with LiOH. Int-3 (MF-DH-424) was isolated as an off-white solid (1.64 g, Yield 57%), LCMS 386.1 [M+H]+; HPLC purity 99.34%.

Step-3: Synthesis of 4-(5-(4,4-difluoropiperidine-1-carbonyl)-1H-pyrrolo[2,3-b]pyridin-1-yl)-N-(methylsulfonyl)benzamide (MF-DH-428): 4-(5-(4,4-difluoropiperidine-1-carbonyl)-1H-pyrrolo[2,3-b]pyridin-1-yl)benzoic acid (Int-3) was converted to 4-(5-(4,4-difluoropiperidine-1-carbonyl)-1H-pyrrolo[2,3-b]pyridin-1-yl)-N-(methylsulfonyl)benzamide (MF-DH-428) using the general procedure for amide coupling with EDCI (1.5 eq), DMAP (1 eq). 4-(5-(4,4-difluoropiperidine-1-carbonyl)-1H-pyrrolo[2,3-b]pyridin-1-yl)-N-(methylsulfonyl)benzamide was isolated as an off white solid.

Step-3 and 4: Synthesis of MF-DH-411, MF-DH-419 and MF-DH-420: 4-(5-(4,4-difluoropiperidine-1-carbonyl)-1H-pyrrolo[2,3-b]pyridin-1-yl)benzoic acid (Int-3) was converted to MF-DH-404, MF-DH-412, MF-DH-413, MF-DH-418, MF-DH-421, MW-DH-451 and the N-Boc amides of MF-DH-411, 419 and MF-DH-420 using the general procedure for amide coupling with HATU and the respective amines. Subsequent deprotection of the Boc-protected amines with 4M dioxane HCl/TFA followed by neutralization with NaHCO₃ and a normal extractive work-up afforded MF-DH-411, MF-DH-419, and MF-DH-420) as off-white solids/gummy liquids.

Step-5: Synthesis of 4-(5-(4,4-difluoropiperidine-1-carbonyl)-1H-pyrrolo[2,3-b]pyridin-1-yl)-N-(2-(methylsulfonamido)ethyl)benzamide (MF-DH-409): N-(2-aminoethyl)-4-(5-(4,4-difluoropiperidine-1-carbonyl)-1H-pyrrolo[2,3-b]pyridin-1-yl)benzamide (MF-DH-411) was converted to MF-DH-409 using NaH (1 eq) methane sulfonyl chloride (1.3 eq) in DMF (5V) followed by a normal extractive workup and purification to afford the final compound as an off white solid.

Step-3 and 6: Synthesis of MF-DH-429, MF-DH-431, and MF-DH-432: Int-3 was converted to methyl esters of MF- DH-429, MF-DH-431, and MF-DH-432 using the general procedure for amide coupling with HATU an L-Proline methyl ester/methyl 1-aminocyclopropane-1-carboxylate/3-amino-3-methylbutanoic acid (1 eq) followed by hydrolysis under general procedure of ester hydrolysis with LiOH to afford final compounds MF-DH-429, MF-DH-431, and MF-DH-432 as off white solids/gummy liquids.

Step-7: Synthesis of 4-(5-(4,4-difluoropiperidine-1-carbonyl)-1H-pyrrolo[2,3-b]pyridin-1-yl)-N-(2-pivalamidoethyl)benzamide (MF-DH-403): N-(2-aminoethyl)-4-(5-(4,4-difluoropiperidine-1-carbonyl)-1H-pyrrolo[2,3-b]pyridin-1-yl)benzamide was converted to 4-(5-(4,4-difluoropiperidine-1-carbonyl)-1H-pyrrolo[2,3-b]pyridin-1-yl)-N-(2-pivalamidoethyl)benzamide (MF-DH-403) using the general procedure for amide coupling with HATU. This afforded the final compound as an off white solid.

Step-8: Synthesis of (S)-1-(4-(5-(4,4-difluoropiperidine-1-carbonyl)-1H-pyrrolo[2,3-b]pyridin-1-yl)benzoyl)pyrrolidine-2-carboxamide (MF-DH-450): MF-DH-432 was converted to (S)-1-(4-(5-(4,4-difluoropiperidine-1-carbonyl)-1H-pyrrolo[2,3-b]pyridin-1-yl)benzoyl)pyrrolidine-2-carboxamide (MF-DH-450) using general procedure for amide coupling with HATU and $NH_4Cl$ to afford MF-DH-450 as an off white solid.

Synthesis of Pyrrolopyridine-4,4-difluoropiperidine-5-carboxyamide Analogs with 3-benzamide Variation (MF-DH-467, MF-DH-468, MF-DH-480, MF-DH-486, MF-DH-489, MF-DH-498, and MF-DH-499)

Provided below is an exemplary scheme to synthesize Pyrrolopyridine-4,4-difluoropiperidine-5-carboxyamide analogs with 3-benzamide variations that are inhibitors of hydroxyprostaglandin dehydrogenase.

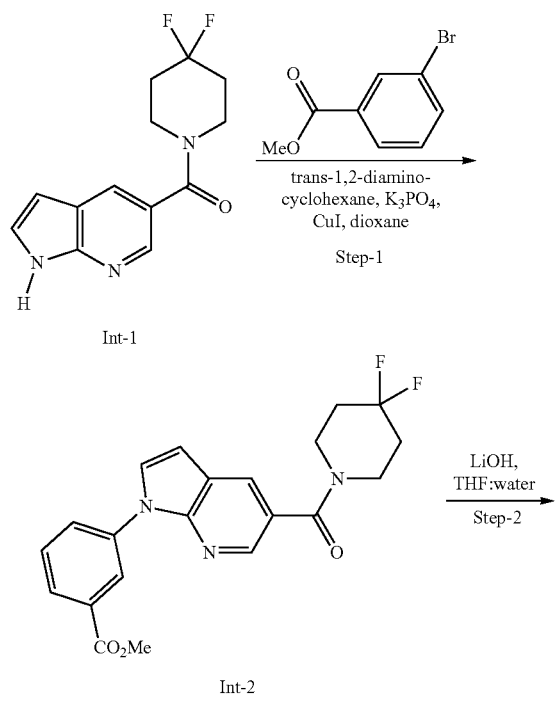

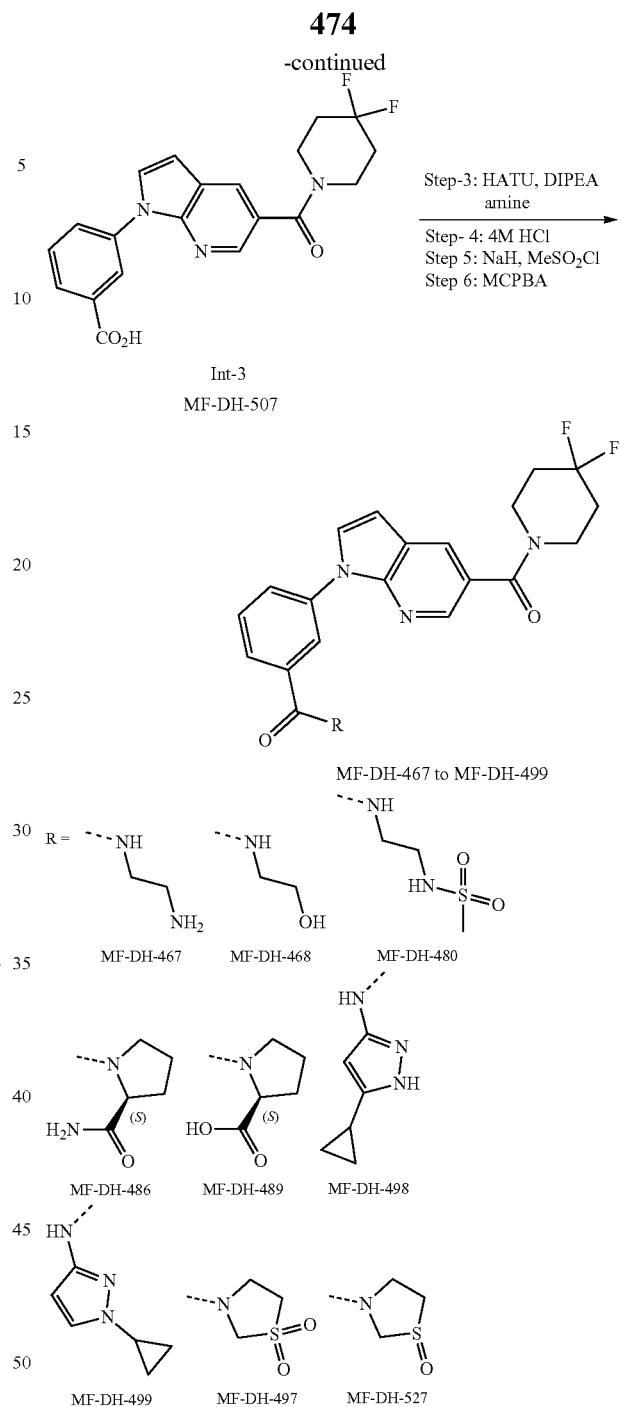

The synthesis of Int-1 is described in Scheme 45.

Step-1: Synthesis of methyl 3-(5-(4,4-difluoropiperidine-1-carbonyl)-1H-pyrrolo[2,3-b]pyridin-1-yl)benzoate (Int-2): (4,4-difluoropiperidin-1-yl)(1H-pyrrolo[2,3-b]pyridin-5-yl)methanone (2 g, 7.48 mmol, 1.0 eq) was converted to methyl 3-(5-(4,4-difluoropiperidine-1-carbonyl)-1H-pyrrolo[2,3-b]pyridin-1-yl)benzoate (Int-2) using the general procedure for Ullmann coupling with methyl 3-bromo benzoate (2.412 g, 1.5 eq) to afford 1.77 g (59%) of product as an off-white solid. LCMS 399.1 (M+1).

Step-2: Synthesis of 3-(5-(4,4-difluoropiperidine-1-carbonyl)-1H-pyrrolo[2,3-b]pyridin-1-yl)benzoic acid (Int-3): methyl 3-(5-(4,4-difluoropiperidine-1-carbonyl)-1H-pyrrolo[2,3-b]pyridin-1-yl)benzoate (1.75 g, 4.39 mmol) was converted to 3-(5-(4,4-difluoropiperidine-1-carbonyl)-1H-pyrrolo[2,3-b]pyridin-1-yl)benzoic acid using the general procedure for ester hydrolysis with LiOH. MF-DH-507 (Int-3) was isolated as an off-white solid (0.87 g, Yield 52%), LCMS 386.1 (M+1); HPLC purity 97.07%.

Step-3: Synthesis of 3-(5-(4,4-difluoropiperidine-1-carbonyl)-1H-pyrrolo[2,3-b]pyridin-1-yl)-N-(2-hydroxyethyl)benzamide (MF-DH-468)/(3-(5-(4,4-difluoropiperidine-1-carbonyl)-1H-pyrrolo[2,3-b]pyridin-1-yl)benzoyl)-L-proline (MF-DH-489)/N-(5-cyclopropyl-1H-pyrazol-3-yl)-3-(5-(4,4-difluoropiperidine-1-carbonyl)-1H-pyrrolo[2,3-b]pyridin-1-yl)benzamide (MF-DH-498)/N-(1-cyclopropyl-1H-pyrazol-3-yl)-3-(5-(4,4-difluoropiperidine-1-carbonyl)-1H-pyrrolo[2,3-b]pyridin-1-yl)benzamide (MF-DH-499): 4-(5-(4,4-difluoropiperidine-1-carbonyl)-1H-pyrrolo[2,3-b]pyridin-1-yl)benzoic acid was converted to 3-(5-(4,4-difluoropiperidine-1-carbonyl)-1H-pyrrolo[2,3-b]pyridin-1-yl)-N-(2-hydroxyethyl)benzamide/(3-(5-(4,4-difluoropiperidine-1-carbonyl)-1H-pyrrolo[2,3-b]pyridin-1-yl)benzoyl)-L-proline/N-(5-cyclopropyl-1H-pyrazol-3-yl)-3-(5-(4,4-difluoropiperidine-1-carbonyl)-1H-pyrrolo[2,3-b]pyridin-1-yl)benzamide/N-(1-cyclopropyl-1H-pyrazol-3-yl)-3-(5-(4,4-difluoropiperidine-1-carbonyl)-1H-pyrrolo[2,3-b]pyridin-1-yl) benzamide using general procedure for amide coupling with HATU.

Step-3 and 4: Synthesis of N-(2-aminoethyl)-3-(5-(4,4-difluoropiperidine-1-carbonyl)-1H-pyrrolo[2,3-b]pyridin-1-yl)benzamide: 3-(5-(4,4-difluoropiperidine-1-carbonyl)-1H-pyrrolo[2,3-b]pyridin-1-yl)benzoic acid (Int-3) was converted to tert-butyl (2-(3-(5-(4,4-difluoropiperidine-1-carbonyl)-1H-pyrrolo[2,3-b]pyridin-1-yl)benzamido)ethyl)carbamate (54.94% yield, MS: m/z=528.2 [M+H]$^+$) using the general procedure for amide coupling with HATU with N-Boc diaminoethane. tert-butyl (2-(3-(5-(4,4-difluoropiperidine-1-carbonyl)-1H-pyrrolo[2,3-b]pyridin-1-yl)benzamido)ethyl)carbamate was subjected to deprotection with 4M HCl in dioxane. Organics were neutralized with satd. NaHCO$_3$ solution and worked up to afford N-(2-aminoethyl)-3-(5-(4,4-difluoropiperidine-1-carbonyl)-1H-pyrrolo[2,3-b]pyridin-1-yl) benzamide (MF-DH-467) as an off white solid.

Step-5: Synthesis of 3-(5-(4,4-difluoropiperidine-1-carbonyl)-1H-pyrrolo[2,3-b]pyridin-1-yl)-N-(2-(methylsulfonamido)ethyl)benzamide (MF-DH-480): N-(2-aminoethyl)-3-(5-(4,4-difluoropiperidine-1-carbonyl)-1H-pyrrolo[2,3-b]pyridin-1-yl)benzamide (MF-DH-467) was converted to MF-DH-480 using NaH (1 eq) methane sulfonyl chloride (1.3 eq) in DMF (5V). An extractive workup and purification afforded the final compound as an off white solid.

Step-3: Synthesis of (S)-1-(4-(5-(4,4-difluoropiperidine-1-carbonyl)-1H-pyrrolo[2,3-b]pyridin-1-yl)benzoyl)pyrrolidine-2-carboxamide (MF-DH-486): (3-(5-(4,4-difluoropiperidine-1-carbonyl)-1H-pyrrolo[2,3-b]pyridin-1-yl)benzoyl)-L-proline (MF-DH-489) was converted to (S)-1-(3-(5-(4,4-difluoropiperidine-1-carbonyl)-1H-pyrrolo[2,3-b]pyridin-1-yl)benzoyl)pyrrolidine-2-carboxamide (MF-DH-486) using general procedure for amide coupling with HATU and NH$_4$Cl to afford (S)-1-(4-(5-(4,4-difluoropiperidine-1-carbonyl)-1H-pyrrolo[2,3-b]pyridin-1-yl)benzoyl)pyrrolidine-2-carboxamide as an off white solid.

Step-3 and 6: (4,4-difluoropiperidin-1-yl)(1-(3-(1,1-dioxidothiazolidine-3-carbonyl)phenyl)-1H-pyrrolo[2,3-b]pyridin-5-yl)methanone and (4,4-difluoropiperidin-1-yl)(1-(3-(1-oxidothiazolidine-3-carbonyl)phenyl)-1H-pyrrolo[2,3-b]pyridin-5-yl)methanone (NW-DH-497) and (MF-DH-527): 3-(5-(4,4-difluoropiperidine-1-carbonyl)-1H-pyrrolo[2,3-b]pyridin-1-yl)benzoic acid (Int-3) was converted to (4,4-difluoropiperidin-1-yl)(1-(3-(thiazolidine-3-carbonyl)phenyl)-1H-pyrrolo[2,3-b]pyridin-5-yl)methanone using general procedure for amide coupling with HATU. The resulting product, (4,4-difluoropiperidin-1-yl)(1-(3-(thiazolidine-3-carbonyl)phenyl)-1H-pyrrolo[2,3-b]pyridin-5-yl)methanone (95.13% yield, MS: m/z=457.3 [M+1]), was oxidized with m-CPBA (1.5 eq) purified via prep-HPLC to afford (4,4-difluoropiperidin-1-yl)(1-(3-(1,1-dioxidothiazolidine-3-carbonyl)phenyl)-1H-pyrrolo[2,3-b]pyridin-5-yl)methanone (MF-DH-497) and (4,4-difluoropiperidin-1-yl)(1-(3-(1-oxidothiazolidine-3-carbonyl)phenyl)-1H-pyrrolo[2,3-b]pyridin-5-yl)methanone (MF-DH-527) as off white solids.

Synthesis of 5-(5-(4,4-difluoropiperidine-1-carbonyl)-1H-pyrrolo[2,3-b]pyridin-1-yl)nicotinamide with amide variation (MF-DH-405, 407, 448, 459, 477, 500 and NW-DH-501)

Provided below is an exemplary scheme to synthesize 5-(5-(4,4-difluoropiperidine-1-carbonyl)-1H-pyrrolo[2,3-b]pyridin-1-yl)nicotinamide with amide variations that are inhibitors of hydroxyprostaglandin dehydrogenase.

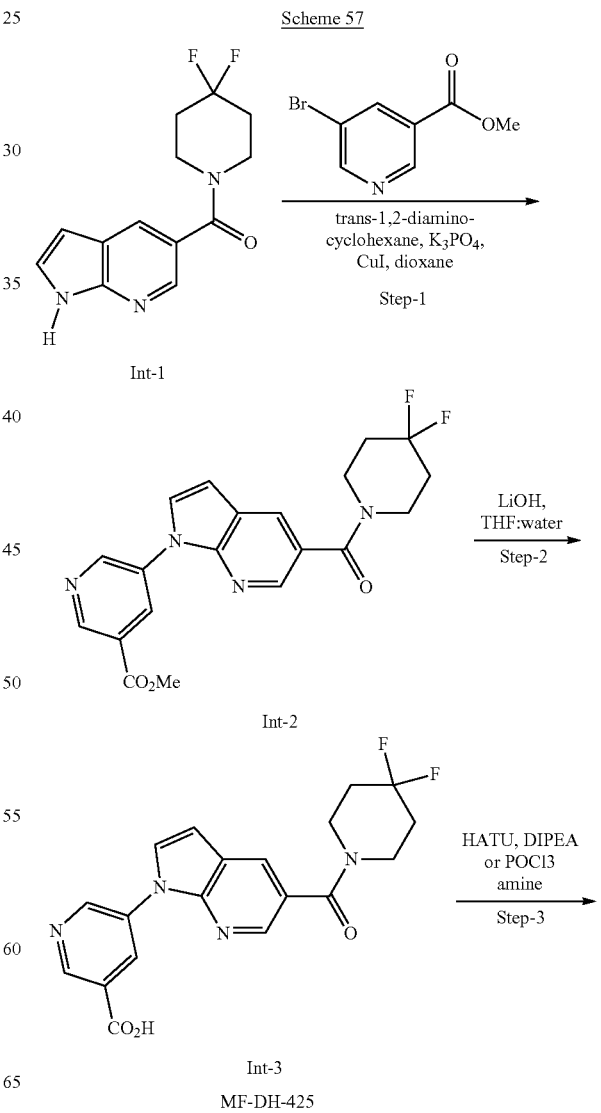

Scheme 57

-continued

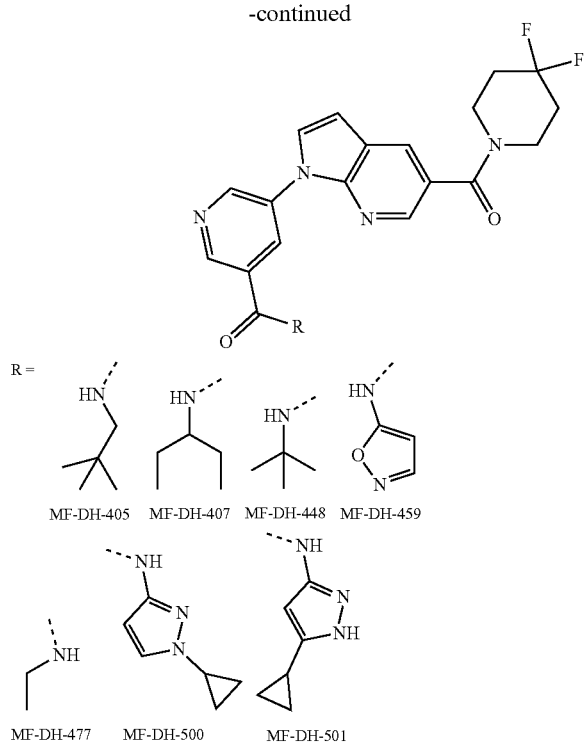

MF-DH-405  MF-DH-407  MF-DH-448  MF-DH-459

MF-DH-477  MF-DH-500  MF-DH-501

The synthesis of Int-1 is described in Scheme 45.

Step-1: Synthesis of methyl 5-(5-(4,4-difluoropiperidine-1-carbonyl)-1H-pyrrolo[2,3-b]pyridin-1-yl)nicotinate (Int-2): (4,4-difluoropiperidin-1-yl)(1H-pyrrolo[2,3-b]pyridin-5-yl)methanone (2 g, 7.02 mmol, 1.0 eq) was converted to methyl 5-(5-(4,4-difluoropiperidine-1-carbonyl)-1H-pyrrolo[2,3-b]pyridin-1-yl)nicotinate using the general procedure for Ullmann coupling with methyl 5-bromo nicotinate (2.412 g, 1.5 eq) and K3PO4 (2 eq). The product was obtained (1.31 g, 45.8%) as an off-white solid; LCMS 401.2 [M+H]f.

Step-2: synthesis of 5-(5-(4,4-difluoropiperidine-1-carbonyl)-1H-pyrrolo[2,3-b]pyridin-1-yl)nicotinic acid (Int-3): methyl 5-(5-(4,4-difluoropiperidine-1-carbonyl)-1H-pyrrolo[2,3-b]pyridin-1-yl) nicotinate (1.30 g, 3.24 mmol) was converted to 5-(5-(4,4-difluoropiperidine-1-carbonyl)-1H-pyrrolo[2,3-b]pyridin-1-yl) nicotinic acid using the general procedure for ester hydrolysis with LiOH. MF-DH-425 (Int-3) was isolated as an off-white solid (0.78 g, Yield 61%), m/z=386.2 [M+H]$^+$; HPLC purity 97.07%.

Step-3: Synthesis of 5-(5-(4,4-difluoropiperidine-1-carbonyl)-1H-pyrrolo[2,3-b]pyridin-1-yl)-N-neopentylnicotinamide/5-(5-(4,4-difluoropiperidine-1-carbonyl)-1H-pyrrolo[2,3-b]pyridin-1-yl)-N-(pentan-3-yl)nicotinamide/N-(tert-butyl)-5-(5-(4,4-difluoropiperidine-1-carbonyl)-1H-pyrrolo[2,3-b]pyridin-1-yl)nicotinamide/6-(5-(4,4-difluoropiperidine-1-carbonyl)-1H-pyrrolo[2,3-b]pyridin-1-yl)-N-ethylnicotinamide/N-(1-cyclopropyl-1H-pyrazol-3-yl)-5-(5-(4,4-difluoropiperidine-1-carbonyl)-1H-pyrrolo[2,3-b]pyridin-1-yl)nicotinamide/N-(5-cyclopropyl-1H-pyrazol-3-yl)-5-(5-(4,4-difluoropiperidine-1-carbonyl)-1H-pyrrolo[2,3-b]pyridin-1-yl)nicotinamide (MF-DH-405, 407, 448, 459, 477, 500 and MF-DH-501): 5-(5-(4,4-difluoropiperidine-1-carbonyl)-1H-pyrrolo[2,3-b]pyridin-1-yl)nicotinic acid was converted to the title compounds using general procedure for amide coupling with HATU. This afforded final compounds as off-white solids.

Step-3: Synthesis of 5-(5-(4,4-difluoropiperidine-1-carbonyl)-1H-pyrrolo[2,3-b]pyridin-1-yl)-N-(isoxazol-5-yl)nicotinamide (MF-DH-459); General procedure for amide coupling with POCl3/pyridine: To the stirred solution of 5-(5-(4,4-difluoropiperidine-1-carbonyl)-1H-pyrrolo[2,3-b]pyridin-1-yl)nicotinic acid (150 mg, 0.3 mmol) in pyridine (5 mL), POCl3 (0.2 ml) was added at 0° C. followed by isoxazol-5-amine (1.1 eq). The resulting reaction mixture was stirred for 30 min at room temperature. After complete consumption of starting material, the mixture was poured into crushed ice, the precipitate was filtered and washed with ether (50 mL). The crude was then purified by flash column chorography using 10% MeOH:CH2Cl2 to afford the title compound as an off white solid.

Synthesis of pyrrolopyridine-5-carboxyamide Analogs with amide/Aryl Variation (MF-DH-406, 422, 430, 437, 438, 429, and MF-DH-460)

Provided below is an exemplary scheme to synthesize pyrrolopyridine-5-carboxyamide analogs with amide/Aryl variations that are inhibitors of hydroxyprostaglandin dehydrogenase.

Scheme 58

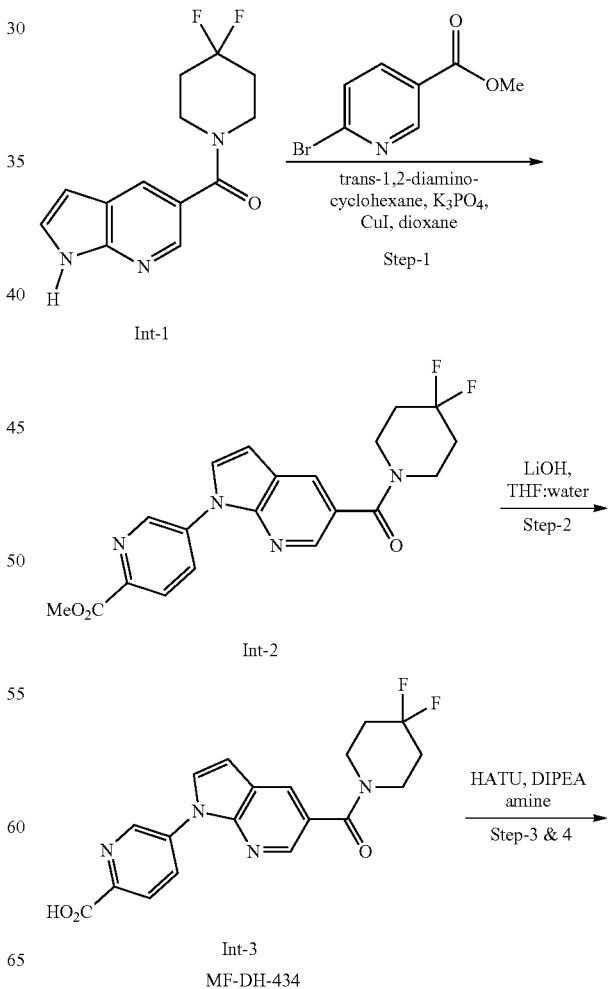

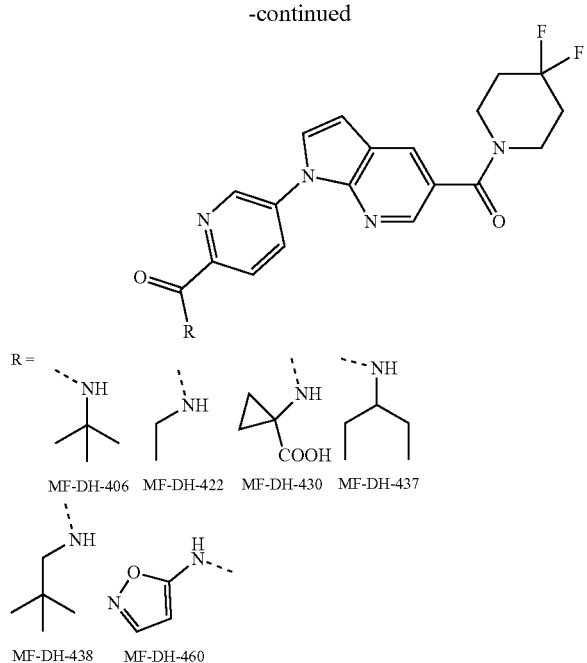

MF-DH-406  MF-DH-422  MF-DH-430  MF-DH-437

MF-DH-438  MF-DH-460

The synthesis of Int-1 is described in Scheme 45.

Step-1: Synthesis of methyl 5-(5-(4,4-difluoropiperidine-1-carbonyl)-1H-pyrrolo[2,3-b]pyridin-1-yl)picolinate (Int-2): (4,4-difluoropiperidin-1-yl)(1H-pyrrolo[2,3-b]pyridin-5-yl)methanone (2 g, 7.02 mmol, 1.0 eq) was converted to methyl 5-(5-(4,4-difluoropiperidine-1-carbonyl)-1H-pyrrolo[2,3-b]pyridin-1-yl) picolinate using the general procedure for Ullmann coupling. Int-2 was obtained (2.33 g, 77%) as an off-white solid; LCMS 401.2 [M+H]+.

Step-2: Synthesis of 5-(5-(4,4-difluoropiperidine-1-carbonyl)-1H-pyrrolo[2,3-b]pyridin-1-yl)picolinic acid (MF-DH-434, Int-3): Methyl 5-(5-(4,4-difluoropiperidine-1-carbonyl)-1H-pyrrolo[2,3-b]pyridin-1-yl)picolinate (2.30 g, 5.75 mmol) was converted to 5-(5-(4,4-difluoropiperidine-1-carbonyl)-1H-pyrrolo[2,3-b]pyridin-1-yl) nicotinic acid using the general procedure for ester hydrolysis with LiOH. This afforded MF-DH-434 (Int-3) as an off-white solid (1.40 g, Yield 63%), LCMS 386.2 [M+H]+; HPLC purity 99.07%.

Step-3: Synthesis of N-(tert-butyl)-5-(5-(4,4-difluoropiperidine-1-carbonyl)-1H-pyrrolo[2,3-b]pyridin-1-yl)picolinamide/6-(5-(4,4-difluoropiperidine-1-carbonyl)-1H-pyrrolo[2,3-b]pyridin-1-yl)-N-ethylpicolinamide/5-(5-(4,4-difluoropiperidine-1-carbonyl)-1H-pyrrolo[2,3-b]pyridin-1-yl)-N-(pentan-3-yl) picolinamide/5-(5-(4,4-difluoropiperidine-1-carbonyl)-1H-pyrrolo[2,3-b]pyridin-1-yl)-N-neopentylpicolinamide (MF-DH-406, MF-DH-422, MF-DH-437, and MF-DH-438): 5-(5-(4,4-difluoropiperidine-1-carbonyl)-1H-pyrrolo[2,3-b]pyridin-1-yl) picolinic acid was converted to the title compounds using the general procedure for amide coupling with HATU and corresponding t-Butylamine/ethylamine/3-aminopentane/neopentylamine (1.2 eq). This afforded final compounds as off white solids.

Step-3: Synthesis of 1-(5-(5-(4,4-difluoropiperidine-1-carbonyl)-1H-pyrrolo[2,3-b]pyridin-1-yl)picolinamido)cyclopropane-1-carboxylic acid (MF-DH-460): 5-(5-(4,4-difluoropiperidine-1-carbonyl)-1H-pyrrolo[2,3-b]pyridin-1-yl) picolic acid (150 mg, 0.3 mmol) was subjected to the general procedure for amide coupling with POCl3/pyridine with isoxazol-5-amine (1.1 eq). The crude was purified by flash column chromatography using 10% MeOH:CH2Cl2 to afford the desired compound as an off white solid.

Step-3 and 4: Synthesis of 1-(5-(5-(4,4-difluoropiperidine-1-carbonyl)-1H-pyrrolo[2,3-b]pyridin-1-yl)picolinamido)cyclopropane-1-carboxylic acid (MF-DH-430): 4-(5-(4,4-difluoropiperidine-1-carbonyl)-1H-pyrrolo[2,3-b]pyridin-1-yl)picolic acid (Int-3) was converted to methyl ester of MF-DH-430 using the general procedure for amide coupling with HATU followed by hydrolysis under general procedure for ester hydrolysis with LiOH to afford final compound MF-DH-430 as an off white solid.

Synthesis of Pyrrolopyridine-5-Carboxyamide Analogs with Amide/Aryl Variation (MF-DH-473, MF-DH-478, MF-DH-457, MF-DH-472 and MF-DH-479)

Provided below is an exemplary scheme to synthesize pyrrolopyridine-5-carboxyamide analogs with amide/Aryl variations that are inhibitors of hydroxyprostaglandin dehydrogenase.

Scheme 59

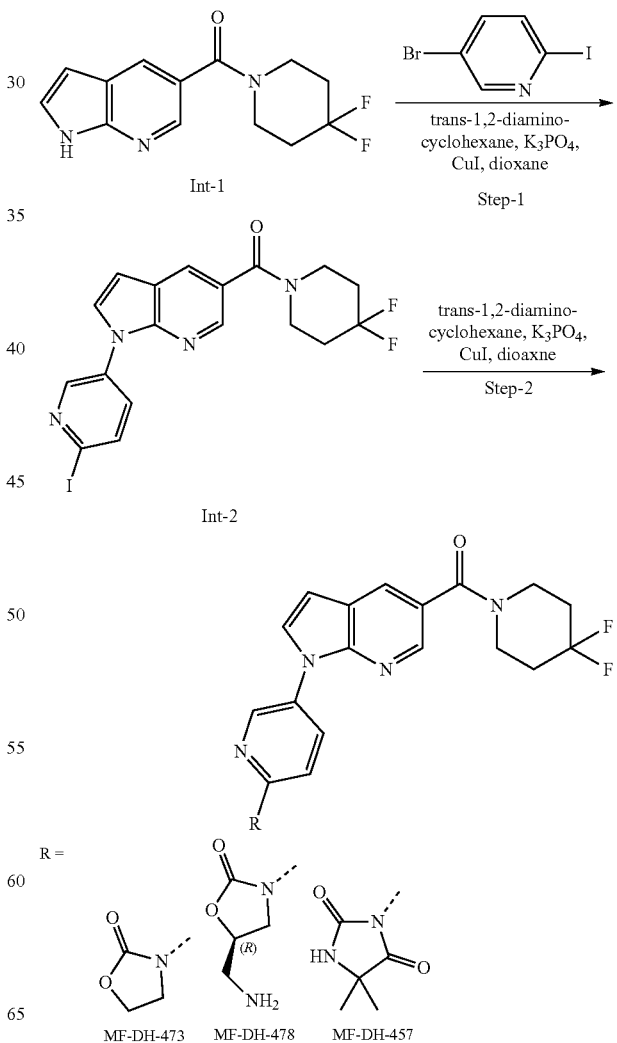

MF-DH-473  MF-DH-478  MF-DH-457

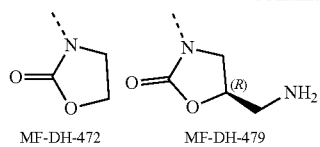

MF-DH-472    MF-DH-479

The synthesis of Int-1 is described in Scheme 45.

Step-1: Synthesis of (4,4-difluoropiperidin-1-yl)(1-(6-iodopyridin-3-yl)-1H-pyrrolo[2,3-b]pyridin-5-yl)methanone (Int-2): (4,4-difluoropiperidin-1-yl)(1H-pyrrolo[2,3-b]pyridin-5-yl)methanone (Int-1) (5 g, 13.2 mmol, 1.0 eq) was converted to (4,4-difluoropiperidin-1-yl)(1-(6-iodopyridin-3-yl)-1H-pyrrolo[2,3-b]pyridin-5-yl)methanone (Int-2) with 5-bromo-2-iodopyridine (5.87 g, 20.7 mmol, 1.1 eq) using the general Ullmann coupling conditions to afford (Int-2) (3.49 g, 56.47% yield) as an off-white solid. LCMS: 68.13%; MS: m/z=469.0 [M+H]$^+$.

Step-2: Synthesis of MF-DH-473, MF-DH-478, MF-DH-457, MF-DH-472 and MF-DH-479: (4,4-difluoropiperidin-1-yl)(1-(6-iodopyridin-3-yl)-1H-pyrrolo[2,3-b]pyridin-5-yl)methanone (Int-2) was converted to the title compounds by using the general procedure for Ullmann coupling.

Synthesis of Pyrrolopyridine-5-Carboxyamide Analogs with Amide/Aryl Variation

Provided below is an exemplary scheme to synthesize pyrrolopyridine-5-carboxyamide analogs with amide/Aryl variations that are inhibitors of hydroxyprostaglandin dehydrogenase.

Scheme 60

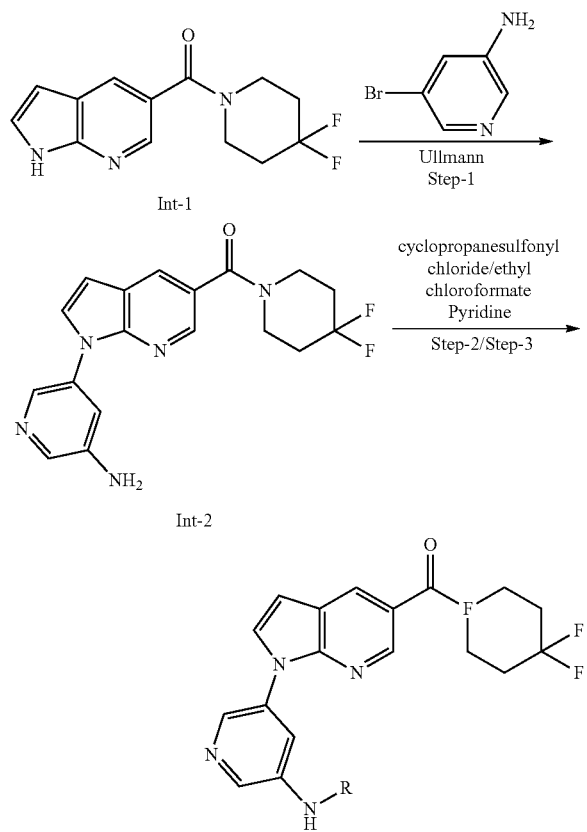

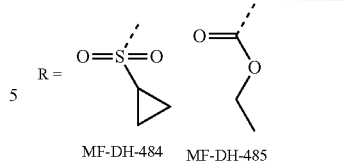

MF-DH-484    MF-DH-485

The synthesis of Int-1 is described in Scheme 45.

Step-1: Synthesis of (1-(5-aminopyridin-3-yl)-1H-pyrrolo[2,3-b]pyridin-5-yl)(4,4-difluoropiperidin-1-yl)methanone (Int-2): (4,4-difluoropiperidin-1-yl)(1H-pyrrolo[2,3-b]pyridin-5-yl)methanone (Int-1) was converted to Int-2 with 5-bromo-3-aminopyridine using the general Ullmann coupling conditions to afford the desired product (75.41%) as light brown solid. LCMS: 92.50%; MS: m/z=358.1 [M+H]$^+$.

Step-2: Synthesis of N-(5-(5-(4,4-difluoropiperidine-1-carbonyl)-1H-pyrrolo[2,3-b]pyridin-1-yl)pyridin-3-yl)cyclopropanesulfonamide (MF-DH-484): To a stirred solution of (1-(5-aminopyridin-3-yl)-1H-pyrrolo[2,3-b]pyridin-5-yl)(4,4-difluoropiperidin-1-yl)methanone (Int-2) (100 mg, 0.28 mmol, 1.0 eq) in pyridine (2 mL) at 0° C. was added cyclopropanesulfonyl chloride (47 mg, 0.33 mmol, 1.2 eq) and then stirred at room temperature for 16 h. The progress of the reaction was monitored with TLC and LCMS. The reaction was concentrated under reduced pressure. The crude was purified using flash chromatography to obtain MF-DH-484 (45.1 mg) as an off-white solid.

Step-3: Synthesis of ethyl (5-(5-(4,4-difluoropiperidine-1-carbonyl)-1H-pyrrolo[2,3-b]pyridin-1-yl)pyridin-3-yl)carbamate (MF-DH-485): To a stirred solution of Int-2 (150 mg, 0.4 mmol, 1.0 eq) in DCM (5 mL) at 0° C., ethyl chloroformate (68 mg, 0.6 mmol, 1.5 eq), pyridine (66 mg, 0.8 mmol, 2.0 eq) and DMAP (10 mg, catalytic) were added sequentially and then stirred at room temperature for 16 h. The progress of the reaction was monitored with TLC and LCMS. The reaction mixture was diluted with water and extracted with DCM (2×30 mL). The combined organic phases were dried over sodium sulfate, filtered and concentrated. The crude was purified using flash chromatography affording MF-DH-485 (116 mg, 64.6% yield) as an off-white solid.

Synthesis of Pyrrolopyridine-5-Carboxyamide Analogs with Amide/Aryl Variation

Provided below is an exemplary scheme to synthesize pyrrolopyridine-5-carboxyamide analogs with amide/Aryl variations that are inhibitors of hydroxyprostaglandin dehydrogenase.

Scheme 61

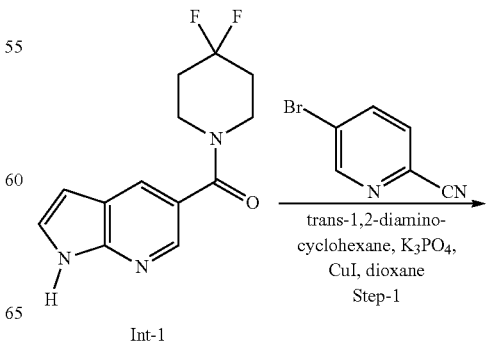

trans-1,2-diamino-cyclohexane, K$_3$PO$_4$, CuI, dioxane
Step-1

Int-1

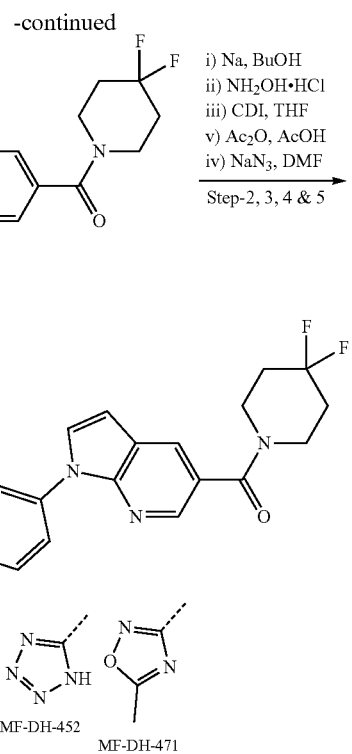

The synthesis of Int-1 is described in Scheme 45.

Step-1: Synthesis 5-(5-(4,4-difluoropiperidine-1-carbonyl)-1H-pyrrolo[2,3-b]pyridin-1-yl)picolinonitrile (Int-2): 4,4-difluoropiperidin-1-yl)(1H-pyrrolo[2,3-b]pyridin-5-yl)methanone (Int-1) (5 g, 18.8 mmol, 1.0 eq) was converted to 5-(5-(4,4-difluoropiperidine-1-carbonyl)-1H-pyrrolo[2,3-b]pyridin-1-yl)picolinonitrile (Int-2) using the general procedure for Ullmann coupling to afford 3 g of Int-2 (43.47%) as an off-white solid. LCMS: 92.4% MS: m/z=368.2 [M+H]⁺.

Step-2: Synthesis of (1-(6-(1H-tetrazol-5-yl)pyridin-3-yl)-1H-pyrrolo[2,3-b]pyridin-5-yl)(4,4-difluoropiperidin-1-yl)methanone (MF-DH-455) (General procedure for preparation of triazoles from nitriles): To a stirred solution of 5-(5-(4,4-difluoropiperidine-1-carbonyl)-1H-pyrrolo[2,3-b]pyridin-1-yl)picolinonitrile (0.15 g, 0.4 mmol, 1.0 eq) in n-Butanol (2 mL) at 0° C. was added sodium methoxide (22 mg, 0.4 mmol, 1.0 eq) after 10 min, formyl hydrazine (24 mg, 0.4 mmol, 1.0 eq) was added and heated to 120° C. for 16 h. The progress of the reaction was monitored with TLC and LCMS. The reaction mixture was concentrated under reduced pressure, diluted with water and extracted with EtOAc (2×20 mL). The combined extracts were dried over sodium sulfate, filtered and concentrated under reduced pressure. The crude was purified using prep HPLC to NW-DH-455 (10 mg, 5.80% yield) as an off-white solid.

Step-3: Synthesis of (Z)-5-(5-(4,4-difluoropiperidine-1-carbonyl)-1H-pyrrolo[2,3-b]pyridin-1-yl)-N'-hydroxypicolinimidamide (Int-3) (General procedure for the synthesis of 1,2,4-oxadiazol-5(4H)-one from nitrile): To a stirred solution of 5-(5-(4,4-difluoropiperidine-1-carbonyl)-1H-pyrrolo[2,3-b]pyridin-1-yl)picolinonitrile (130 mg, 0.35 mmol, 1.0 eq) in EtOH (5 mL) was added NH$_2$OH.HCl (65 m, 0.9 mmol, 1.5 eq) and heated to 80° C. for 16 h. The progress of the reaction was monitored with TLC and LCMS. The reaction was concentrated under reduced pressure, diluted with EtOAc (20 mL), washed with water (10 mL), then organic phase was dried over sodium sulfate, filtered and concentrated to afford (Z)-5-(5-(4,4-difluoropiperidine-1-carbonyl)-1H-pyrrolo[2,3-b]pyridin-1-yl)-N'-hydroxypicolinimidamide (Int-3, 100 mg, 70.9% yield) The crude was used in the next step without further purification.

Synthesis of 3-(5-(5-(4,4-difluoropiperidine-1-carbonyl)-1H-pyrrolo[2,3-b]pyridin-1-yl)pyridin-2-yl)-1,2,4-oxadiazol-5(4H)-one (MF-DH-456): To a stirred solution of (Z)-5-(5-(4,4-difluoropiperidine-1-carbonyl)-1H-pyrrolo[2,3-b]pyridin-1-yl)-N'-hydroxypicolinimidamide (Int-3, 50 mg, 0.12 mmol, 1.0 eq) in DCM (10 mL) at 0° C., was added CDI (24 mg, 0.14 mmol, 1.5 eq) and TEA (0.01 mL, 0.15 mmol, 1.5 eq) was added and stirred at room temperature for 16 h. The progress of the reaction was monitored with TLC and LCMS. The reaction mixture was concentrated under reduced pressure, diluted with water and extracted with EtOAc (10 mL). The combine extracts were dried over sodium sulfate, filtered and concentrated. The crude was purified using prep HPLC, to obtain 3-(5-(5-(4,4-difluoropiperidine-1-carbonyl)-1H-pyrrolo[2,3-b]pyridin-1-yl)pyridin-2-yl)-1,2,4-oxadiazol-5(4H)-one (MF-DH-456) (5 mg, 9.4% yield) as an off-white solid.

Step-4: Synthesis of (4,4-difluoropiperidin-1-yl)(1-(6-(5-methyl-1,2,4-oxadiazol-3-yl)pyridin-3-yl)-1H-pyrrolo[2,3-b]pyridin-5-yl)methanone (MF-DH-471), (General procedure for the synthesis of 5-methyl-1,2,4-oxadiazole from nitrile): To a stirred solution of ((Z)-5-(5-(4,4-difluoropiperidine-1-carbonyl)-1H-pyrrolo[2,3-b]pyridin-1-yl)-N'-hydroxypicolinimidamide (Int-3) (200 mg, 0.53 mmol, 1.0 eq) in acetic acid (10 mL), acetic anhydride was added and heated to 100° C., for 16 h. The reaction mixture was concentrated under reduced pressure, diluted with water and extracted with ethyl acetate. The combined extracts were washed with NaHCO$_3$ solution, water and dried over sodium sulfate, filtered and concentrated. The crude was purified by prep HPLC to obtain (4,4-difluoropiperidin-1-yl)(1-(6-(5-methyl-1,2,4-oxadiazol-3-yl)pyridin-3-yl)-1H-pyrrolo[2,3-b]pyridin-5-yl)methanone (MF-DH-471) (50 mg, 22.52% yield) as an off-white solid.

Step-5: Synthesis of (1-(6-(1H-tetrazol-5-yl)pyridin-3-yl)-1H-pyrrolo[2,3-b]pyridin-5-yl)(4,4-difluoropiperidin-1-yl)methanone (MF-DH-452) (General procedure for preparation of tetrazole from nitriles): To a suspension of 5-(5-(4,4-difluoropiperidine-1-carbonyl)-1H-pyrrolo[2,3-b]pyridin-1-yl) picolinonitrile (50 mg, 0.7 mmol, 1.0 eq) in DMF: water (5 mL), NaN$_3$ (22 mg, 1.4 mg, 2.0 eq) was added and stirred at 100° C. for 16 h. This was extracted with EtOAc, concentrated, filtered and washed with ACN and methanol affording (1-(6-(1H-tetrazol-5-yl)pyridin-3-yl)-1H-pyrrolo[2,3-b]pyridin-5-yl)(4,4-difluoropiperidin-1-yl) methanone (MF-DH-452, 42 mg, 45.3% yield) as an off-white solid.

Synthesis of (1-(5-(1H-tetrazol-5-yl)pyridin-3-yl)-1H-pyrrolo[2,3-b]pyridin-5-yl)(4,4-difluoropiperidin-1-yl)methanone/3-(5-(5-(4,4-difluoropiperidine-1-carbonyl)-1H-pyrrolo[2,3-b]pyridin-1-yl)pyridin-3-yl)-1,2,4-oxadiazol-5(4H)-one/(4,4-difluoropiperidin-1-yl)(1-(5-(5-methyl-1,2,4-oxadiazol-3-yl)pyridin-3-yl)-1H-pyrrolo[2,3-b]pyridin-5-yl)methanone Scheme 62

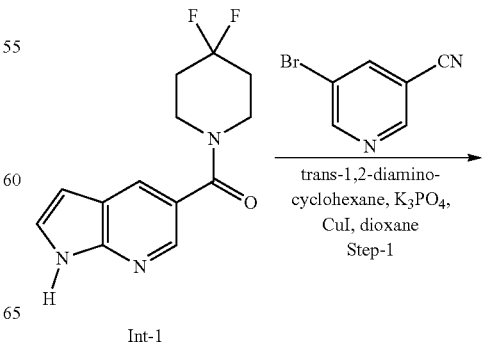

-continued

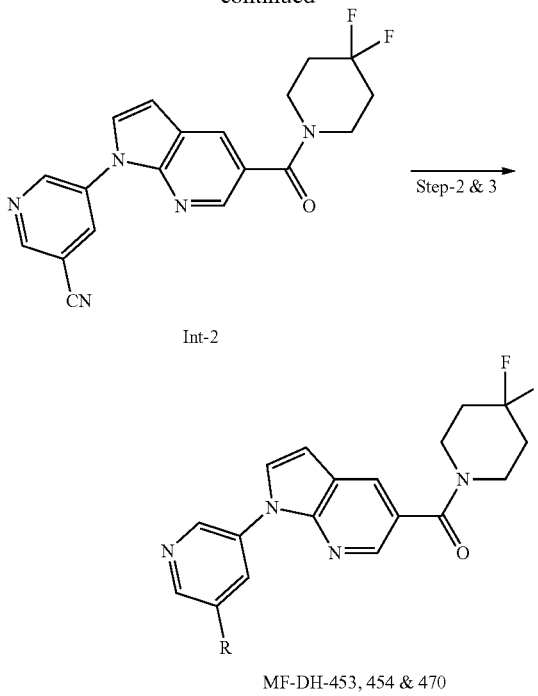

Int-2

MF-DH-453, 454 & 470

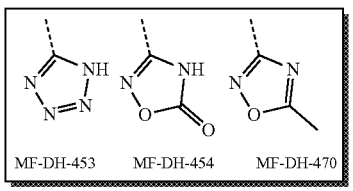

MF-DH-453   MF-DH-454   MF-DH-470

The synthesis of Int-1 is described in Scheme 45.

Step-1: Synthesis of 5-(5-(4,4-difluoropiperidine-1-carbonyl)-1H-pyrrolo[2,3-b]pyridin-1-yl)nicotinonitrile (Int-2): 4,4-difluoropiperidin-1-yl)(1H-pyrrolo[2,3-b]pyridin-5-yl)methanone (Int-1) (1.6 g, 6.0 mmol, 1.0 eq) was converted to 5-(5-(4,4-difluoropiperidine-1-carbonyl)-1H-pyrrolo[2,3-b]pyridin-1-yl)nicotinonitrile using general procedure for Ullmann coupling to afford 3 g of Int-2 (1.52 g, 72%) as an off-white solid. LCMS: 96.3%; MS: m/z=368.2 [M+H]⁺.

Step-2: Synthesis of (1-(5-(1H-tetrazol-5-yl)pyridin-3-yl)-1H-pyrrolo[2,3-b]pyridin-5-yl)(4,4-difluoropiperidin-1-yl)methanone (MF-DH-453): 5-(5-(4,4-difluoropiperidine-1-carbonyl)-1H-pyrrolo[2,3-b]pyridin-1-yl)nicotinonitrile was converted to (1-(5-(1H-tetrazol-5-yl)pyridin-3-yl)-1H-pyrrolo[2,3-b]pyridin-5-yl)(4,4-difluoropiperidin-1-yl) methanone using the general procedure to prepare tetrazole from nitriles to afford an off-white solid.

Step-2 and 3: Synthesis of 3-(5-(5-(4,4-difluoropiperidine-1-carbonyl)-1H-pyrrolo[2,3-b]pyridin-1-yl)pyridin-2-yl)-1,2,4-oxadiazol-5(4H)-one (MF-DH-454): 5-(5-(4,4-difluoropiperidine-1-carbonyl)-1H-pyrrolo[2,3-b]pyridin-1-yl) nicotinonitrile was converted to ((Z)-5-(5-(4,4-difluoropiperidine-1-carbonyl)-1H-pyrrolo[2,3-b]pyridin-1-yl)-N'-hydroxynicotinamide using the general procedure to make 1,2,4-oxadiazol-5(4H)-one from nitrile to afford an off-white solid.

Step-2 and 3: Synthesis of (4,4-difluoropiperidin-1-yl)(1-(5-(5-methyl-1,2,4-oxadiazol-3-yl)pyridin-3-yl)-1H-pyrrolo[2,3-b]pyridin-5-yl)methanone (MF-DH-470): 5-(5-(4,4-difluoropiperidine-1-carbonyl)-1H-pyrrolo[2,3-b]pyridin-1-yl)nicitinonitrile was converted to ((Z)-5-(5-(4,4-difluoropiperidine-1-carbonyl)-1H-pyrrolo[2,3-b]pyridin-1-yl)-N'-hydroxynicotinamide using the general procedure to make 5-methyl-1,2,4-oxadiazole from nitrile to afford MF-DH-470 as an off-white solid.

Synthesis of Pyrrolopyridine-5-Carboxyamide Analogs with Amide/Aryl Variation

Provided below is an exemplary scheme to synthesize pyrrolopyridine-5-carboxyamide analogs with amide/Aryl variations that are inhibitors of hydroxyprostaglandin dehydrogenase.

Scheme 63

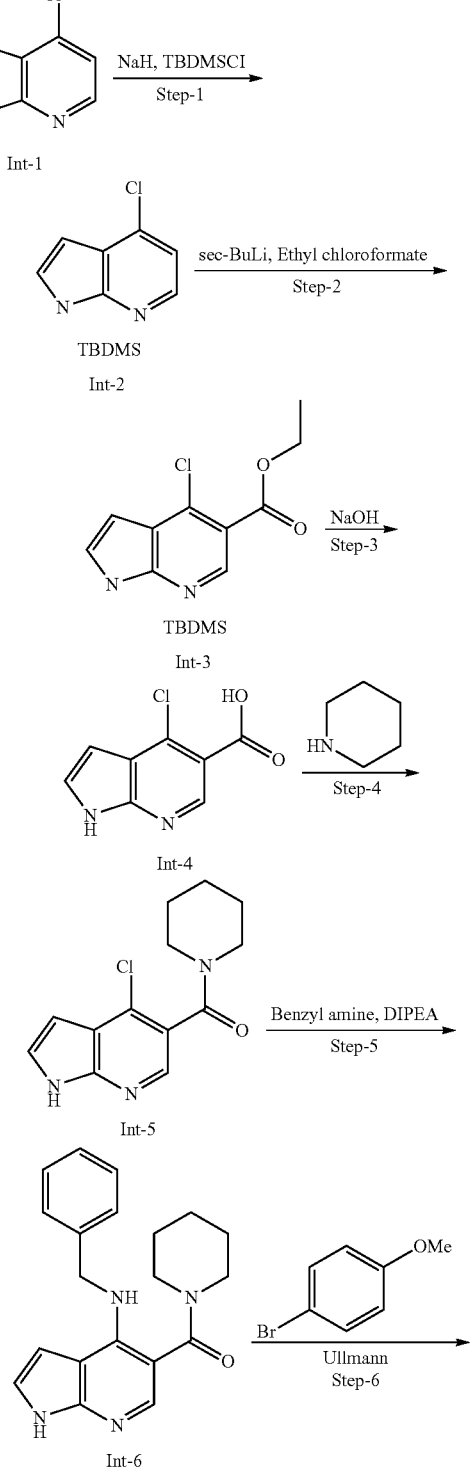

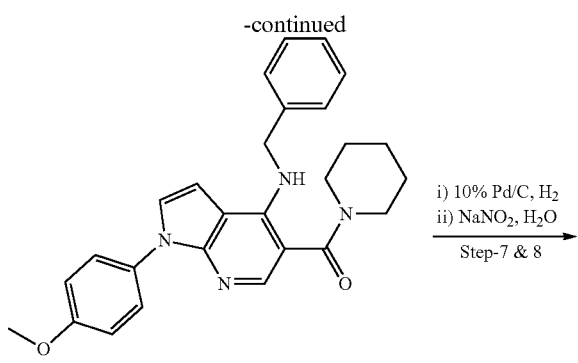

MF-DH-385

X = OH, MF-DH-288
X = NH₂, MF-DH-290

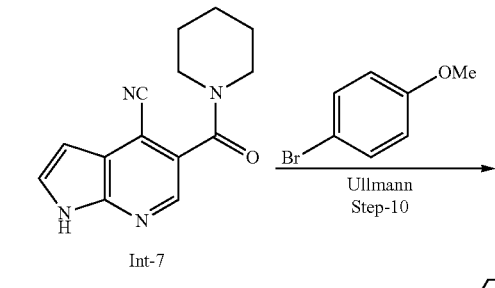

MF-DH-289

Step-1: Synthesis of 1-(tert-butyldimethylsilyl)-4-chloro-1H-pyrrolo[2,3-b]pyridine (Int-2): To a stirred solution of 4-chloro-1H-pyrrolo[2,3-b]pyridine (Int-1) (10 g, 65.7 mmol, 1.0 eq) in dry THE (100 mL) at 0° C., NaH (50% in paraffin oil, 3.1 g, 131.5 mmol, 2.0 eq) was added. After 10 min, TBDMSCl (15 g, 98.5 mmol, 1.5 eq) was added and stirred at room temperature for 16 h. The progress of the reaction was monitored with TLC and LCMS; after the consumption of starting material, the reaction mixture was quenched with ice water and extracted with EtOAc (2×50 mL). The combined organic phases were washed with water and brine. The organics were dried over sodium sulfate, filtered and concentrated to obtain a sticky liquid. The crude 10 g was used in the next step without further purification.

Note: The Int-2 is not stable at room temperature and was used immediately in the next step.

Step-2: Synthesis of ethyl 1-(tert-butyldimethylsilyl)-4-chloro-1H-pyrrolo[2,3-b]pyridine-5-carboxylate (Int-3): To a stirred solution of 1-(tert-butyldimethylsilyl)-4-chloro-1H-pyrrolo[2,3-b]pyridine Int-2 (8.2 g, 36.67 mmol, 1.0 eq) in dry THE (100 mL) at −78° C., sec-BuLi (1.6M in cyclohexane, 2.0 eq) was added dropwise and stirred for 30 min. Ethyl chloroformate (6.08 g, 55 mmol, 1.5 eq) in THE (20 mL) was added at −78° C. and stirred for 2 h. The progress of the reaction was monitored with TLC. The reaction was quenched with saturated ammonium chloride and extracted with EtOAc (2×20 mL). The combined extracts were washed with water and brine, dried over sodium sulfate and concentrated to afford Int-3 (7.15 g) as a sticky liquid which was used in the next step without further purification.

Step-3: Synthesis of 4-chloro-1H-pyrrolo[2,3-b]pyridine-5-carboxylic acid (Int-4): Int-3 (7 g, 20.3 mmol, 1.0 eq) was converted to Int-4 using the general procedure for ester hydrolysis with NaOH to afford (4-chloro-1H-pyrrolo[2,3-b]pyridine-5-carboxylic acid (Int-4) as a pale yellow solid. (3.1 g, 73% yield) MS: m/z=197.1 [M+H]⁺, 198.1 [M+H]⁺.

Step-4: Synthesis of (4-chloro-1H-pyrrolo[2,3-b]pyridin-5-yl)(piperidin-1-yl)methanone (Int-5): 4-chloro-1H-pyrrolo[2,3-b]pyridine-5-carboxylic acid (Int-4) (3.01, 15.3 mmol, 1.0 eq) was converted to (4-chloro-1H-pyrrolo[2,3-b]pyridin-5-yl)(piperidin-1-yl)methanone using the general procedure for amide coupling with HATU to afford Int-5 as an off-white solid. MS: m/z=265.1 [M+2H]⁺.

Step-5: Synthesis of (4-(benzylamino)-1H-pyrrolo[2,3-b]pyridin-5-yl)(piperidin-1-yl)methanone Int-6: In a microwave vial, to a solution of (4-chloro-1H-pyrrolo[2,3-b]pyridin-5-yl)(piperidin-1-yl)methanone (Int-5) (200 mg×5, 0.76 mmol, 1.0 eq) in n-BuOH (5 mL) was added benzyl amine (89 mg×7, 0.83 mmol, 1.1 eq) and DIPEA (190 mg×7, 1.52 mmol, 2.0 eq). The reaction was irradiated in microwave for 2 h at 150° C. Progress of the reaction was monitored with TLC and LCMS. The reaction was concentrated under reduced pressure. The crude was purified using combi flash to afford (4-(benzylamino)-1H-pyrrolo[2,3-b]pyridin-5-yl)(piperidin-1-yl)methanone (Int-6) (640 mg, 51% yield) as a yellow solid. MS: m/z=335.2 [M+H]⁺.

Step-6: Synthesis of (4-(benzylamino)-1-(4-methoxyphenyl)-1H-pyrrolo[2,3-b]pyridin-5-yl) (piperidin-1-yl) methanone (MF-DH-385): Int-6 was converted to MF-DH-385 with 4-bromo anisole (840 mg, 0.35 mmol, 1.2 eq) using the general procedure for Ullmann coupling to afford the desired product (550 mg, 45.8% yield) as an off-white sticky solid.

Step-7: Synthesis of (4-amino-1-(4-methoxyphenyl)-1H-pyrrolo[2,3-b]pyridin-5-yl)(piperidin-1-yl)methanone (MF-DH-290) (General procedure for debenzylation): To a solution of (4-(benzylamino)-1-(4-methoxyphenyl)-1H-pyrrolo[2,3-b]pyridin-5-yl) (piperidin-1-yl) methanone (MF-DH-385) (100 mg, 0.22 mmol, 1.0 eq) in THF: MeOH (1:1, 10 mL), 10% Pd/C (10 mg) was added and stirred under Hydrogen (balloon pressure) for 12 h. The progress of the reaction was monitored with TLC and LCMS. The reaction mixture was filtered through a celite bed and concentrated and then purified using flash chromatography to afford MF-DH-290 as a sticky liquid (24 mg, 30% yield).

Step-8: Synthesis of (4-amino-1-(4-methoxyphenyl)-1H-pyrrolo[2,3-b]pyridin-5-yl)(piperidin-1-yl)methanone (MF-DH-288) (General procedure for conversion of aryl amines to hydroxyl amines via diazotization): To a stirred solution of 4-amino-1-(4-methoxyphenyl)-1H-pyrrolo[2,3-b]pyridin-5-yl)(piperidin-1-yl)methanone, MF-DH-290 (100 mg, 0.28 mmol, 1.0 eq) in acetic acid/water (1:1, 5 mL) at 0° C. was added NaNO₂ (48 mg, 0.56 mmol, 2.0 eq) and heated to 100° C. for 16 h. The progress of the reaction was monitored with LCMS, NaHCO₃ was added and the mixture extracted with 10% MeOH/DCM. The organic phase was dried over sodium sulfate, filtered and concentrated. The crude was purified using Prep-HPLC to afford MF-DH-288 as sticky liquid.

Step-9: Synthesis of 5-(piperidine-1-carbonyl)-1H-pyrrolo[2,3-b]pyridine-4-carbonitrile (Int-7): To a stirred solution of (4-chloro-1H-pyrrolo[2,3-b]pyridin-5-yl)(piperidin-1-yl)methanone (Int-5) (340 mg, 1.29 mmol, 1.0 eq) in dry DMA (10 mL), Pd₂(dba)₃ (0.1 eq), Zn (1.2 eq), Zn (CN)₂ (1.2 eq) were added under argon atmosphere and then purged for 10 min. The resulting reaction mixture was heated to 100° C. for 16 h. The progress of the reaction was monitored with TLC and LCMS; after the consumption of starting material, the reaction mixture was quenched with ice water and extracted with EtOAc (2×50 mL). The combined organic phases were washed with water and brine, dried over sodium sulfate, filtered and concentrated and then flash column purification afforded 135 mg of Int-7. MS: m/z=255.1 [M+H]⁺.

Step-10: Synthesis of 1-(4-methoxyphenyl)-5-(piperidine-1-carbonyl)-1H-pyrrolo[2,3-b]pyridine-4-carbonitrile (MF-DH-289): 5-(piperidine-1-carbonyl)-1H-pyrrolo[2,3-b]pyridine-4-carbonitrile (130 mg, 0.51 mmol) was converted to 1-(4-methoxyphenyl)-5-(piperidine-1-carbonyl)-1H-pyrrolo[2,3-b]pyridine-4-carbonitrile using the general procedure for Ullmann coupling to afford MF-DH-289.

Synthesis of 4-(5-(4-fluoropiperidine-1-carbonyl)-1H-pyrrolo[3,2-b]pyridin-1-yl)benzonitrile/4-(5-(4-fluoropiperidine-1-carbonyl)-1H-pyrrolo[2,3-c]pyridin-1-yl)benzonitrile Scheme 64

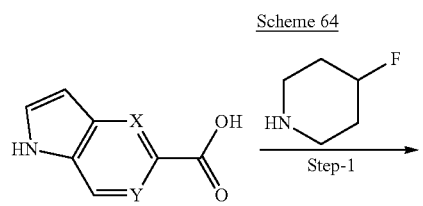

Int-1a: X = N, Y = CH
Int-1b: X = CH, Y = N

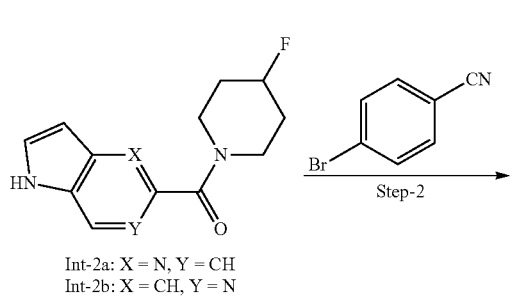

Int-2a: X = N, Y = CH
Int-2b: X = CH, Y = N

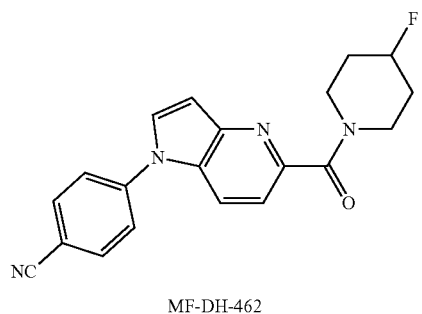

MF-DH-462

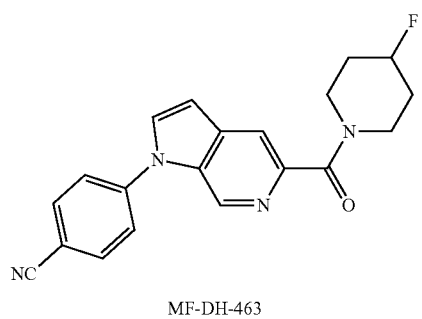

MF-DH-463

Step-1: Synthesis of (4-fluoropiperidin-1-yl)(1H-pyrrolo[3,2-b]pyridin-5-yl)methanone/(4-fluoropiperidin-1-yl)(1H-pyrrolo[2,3-c]pyridin-5-yl)methanone (Int-2): Int-1 was converted to Int-2 using the general method for acid/amine coupling with HATU to afford the desired product.

Step-2: Synthesis of MF-DH-462 and MF-DH-463: Int-2 was converted to MF-DH-462 and MF-DH-463 using the general procedure for Ullmann coupling described previously.

Synthesis of ((2R,6S)-2,6-dimethylpiperidin-1-yl)(1-(4-methoxyphenyl)-1H-pyrrolo[2,3-b]pyridin-5-yl)methanone/((3R,5S)-3,5-dimethylpiperidin-1-yl)(1-(4-methoxyphenyl)-1H-pyrrolo[2,3-b]pyridin-5-yl)methanone/4-(5-((3R,5S)-3,5-difluoropiperidine-1-carbonyl)-1H-pyrrolo[2,3-b]pyridin-1-yl)benzonitrile/4-(5-((3R,5S)-3,5-dimethylpiperidine-1-carbonyl)-1H-pyrrolo[2,3-b]pyridin-1-yl)benzamide Scheme 65

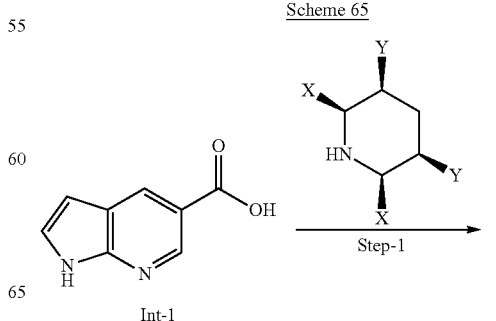

Int-1

491

-continued

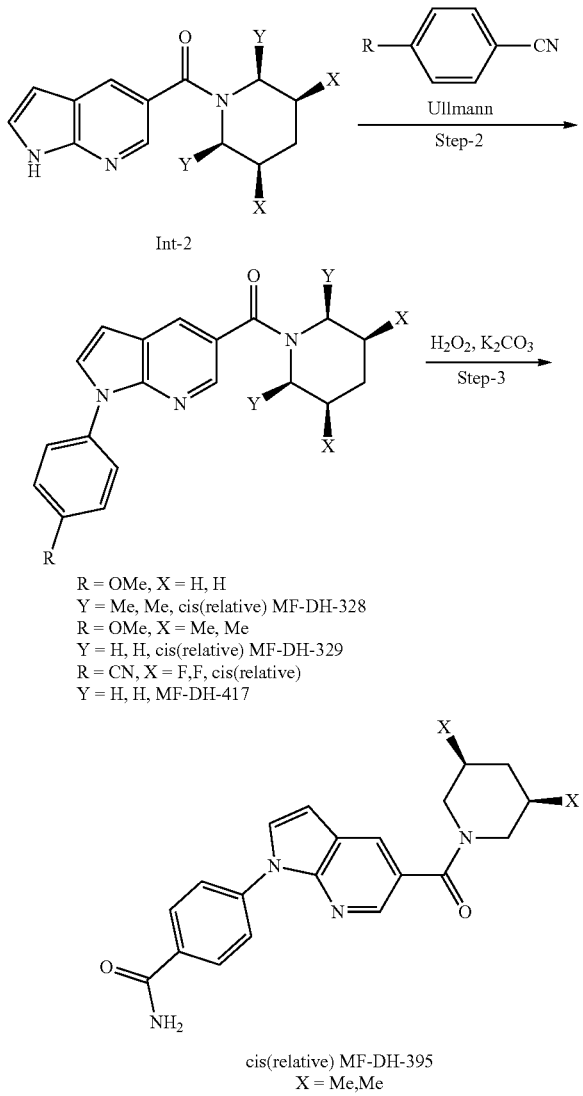

Int-2

R = OMe, X = H, H
Y = Me, Me, cis(relative) MF-DH-328
R = OMe, X = Me, Me
Y = H, H, cis(relative) MF-DH-329
R = CN, X = F,F, cis(relative)
Y = H, H, MF-DH-417 cis(relative) MF-DH-395
X = Me,Me

Step-1: Synthesis of (Int-2): 1H-pyrrolo[2,3-b]pyridine-5-carboxylic acid was converted to Int-2 using general procedure for amide coupling with HATU and the appropriate piperidine to afford Int-2 as an off-white solid.

Step-2: Synthesis of ((2R,6S)-2,6-dimethylpiperidin-1-yl)(1-(4-methoxyphenyl)-1H-pyrrolo[2,3-b]pyridin-5-yl)methanone/((3R,5S)-3,5-dimethylpiperidin-1-yl)(1-(4-methoxyphenyl)-1H-pyrrolo[2,3-b]pyridin-5-yl)methanone/4-(5-((3R,5S)-3,5-difluoropiperidine-1-carbonyl)-1H-pyrrolo[2,3-b]pyridin-1-yl)benzonitrile: Int-2 was converted to the title compounds using the general procedure for Ullmann coupling to afford MF-DH-328, MF-DH-329 and MF-DH-417 after purification.

Step-3: Synthesis of 4-(5-((3R,5S)-3,5-dimethylpiperidine-1-carbonyl)-1H-pyrrolo[2,3-b]pyridin-1-yl)benzamide (MF-DH-395): 4-(5-((3R,5S)-3,5-difluoropiperidine-1-carbonyl)-1H-pyrrolo[2,3-b]pyridin-1-yl)benzonitrile was converted to 4-(5-((3R,5S)-3,5-dimethylpiperidine-1-carbonyl)-1H-pyrrolo[2,3-b]pyridin-1-yl)benzamide using the general procedure for oxidation of nitriles to amides to afford MF-DH-395 as sticky solid.

492

Synthesis of 4-(5-(4,4-difluoropiperidine-1-carbonothioyl)-1H-pyrrolo[2,3-b]pyridin-1-yl)benzonitrile (MF-DH-449)

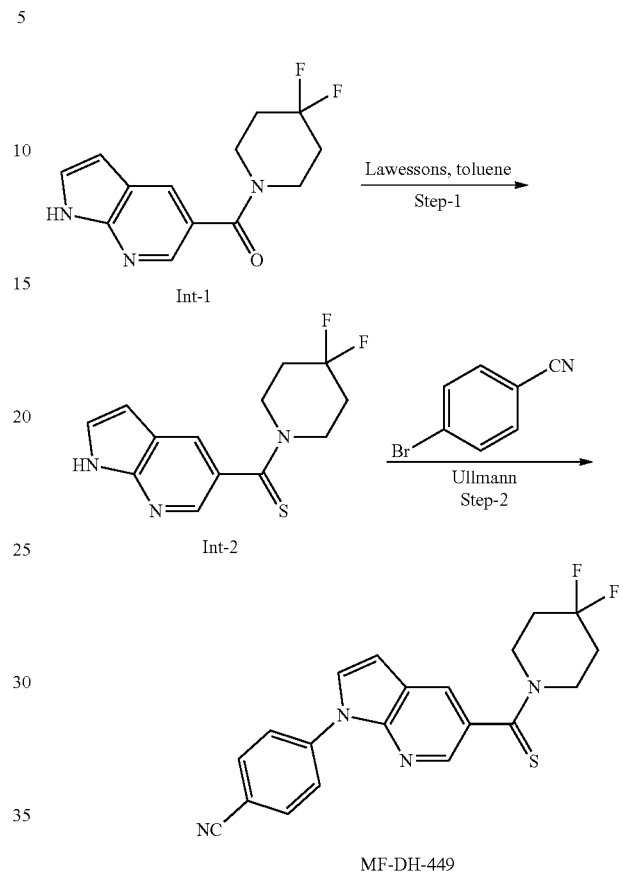

The synthesis of Int-1 is described previously under Scheme 45.

Step-1: Synthesis of (4,4-difluoropiperidin-1-yl)(1H-pyrrolo[2,3-b]pyridin-5-yl)methanethione (4,4-difluoropiperidin-1-yl) (Int-2): To a stirred solution of (4,4-difluoropiperidin-1-yl)(1H-pyrrolo[2,3-b]pyridin-5-yl)methanone (Int-1) (400 mg, 1.5 mmol, 1.0 eq) in toluene (8 mL), Lawesson's reagent (1.21 g, 3.0 mmol, 2.0 eq) was added and heated to 120° C. for 4 h. The progress of the reaction was monitored with TLC and LCMS. The reaction mixture was diluted with water (20 mL) and EtOAc (50 mL). The EtOAc layer was separated, washed with water and brine. The organic phase was dried over sodium sulfate, filtered and concentrated. The crude was purified using combi-flash to afford (4,4-difluoropiperidin-1-yl)(1H-pyrrolo[2,3-b]pyridin-5-yl)methanethione (4,4-difluoropiperidin-1-yl) (Int-2) (220 mg, 63% yield) as an off-white solid. LCMS: 94.2%; MS: m/z=282.1 [M+H]$^+$.

Step-2: Synthesis of 4-(5-(4,4-difluoropiperidine-1-carbonothioyl)-1H-pyrrolo[2,3-b]pyridin-1-yl)benzonitrile (MF-DH-449): (4,4-difluoropiperidin-1-yl)(1H-pyrrolo[2,3-b]pyridin-5-yl)methanethione (4,4-difluoropiperidin-1-yl) (Int-2) (30 mg, 0.1 mmol, 1.0 eq) was converted to 4-(5-(4,4-difluoropiperidine-1-carbonothioyl)-1H-pyrrolo[2,3-b]pyridin-1-yl)benzonitrile by using the general procedure for Ullmann coupling to afford MF-DH-449 (5.0 mg, 12.8% yield) as an off-white solid.

493

Synthesis of (1-(3-chloro-5-(1,1-dioxidothiomorpholine-4-carbonyl)phenyl)-1H-pyrrolo[2,3-b]pyridin-5-yl)(4,4-difluoropiperidin-1-yl)methanone/3-chloro-5-(5-(4,4-difluoropiperidine-1-carbonyl)-1H-pyrrolo[2,3-b]pyridin-1-yl)-N-(1,1-dioxidotetrahydro-2H-thiopyran-4-yl)benzamide Scheme 67

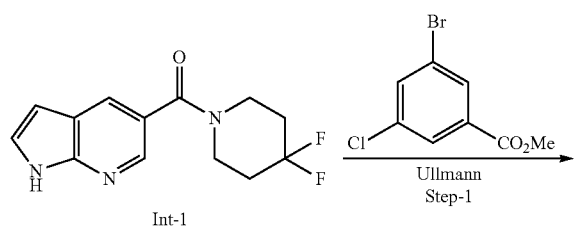

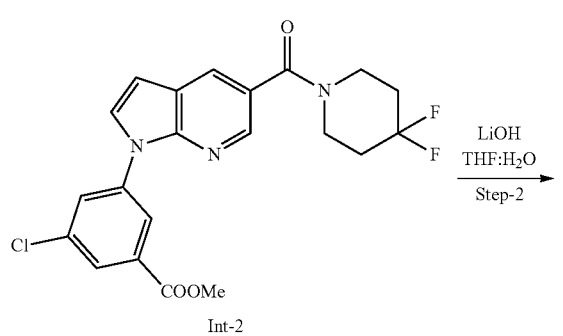

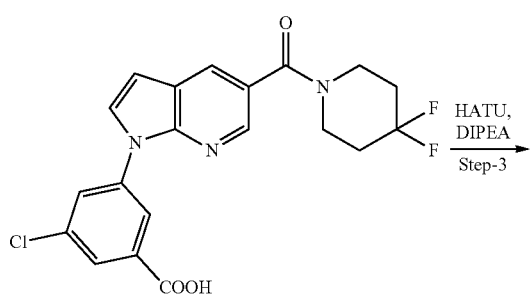

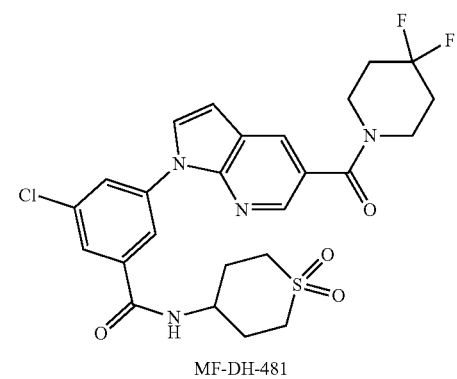

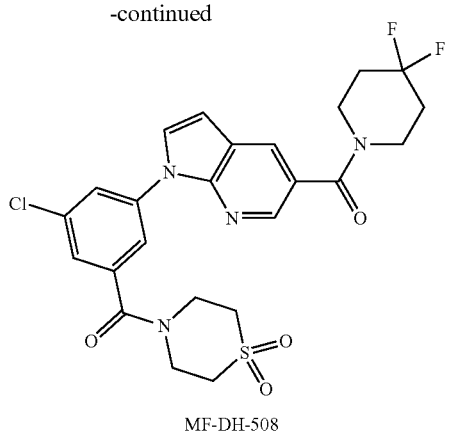

MF-DH-508

The synthesis of Int-1 is described in Scheme 45.

Step-1: Synthesis of methyl 3-chloro-5-(5-(4,4-difluoropiperidine-1-carbonyl)-1H-pyrrolo[2,3-b]pyridin-1-yl)benzoate (Int-2): (4,4-difluoropiperidin-1-yl)(1H-pyrrolo[2,3-b]pyridin-5-yl)methanone (400 mg, 1.4 mmol) was converted to methyl 3-chloro-5-(5-(4,4-difluoropiperidine-1-carbonyl)-1H-pyrrolo[2,3-b]pyridin-1-yl)benzoate (Int-2) using the general procedure for Ullmann coupling to obtain Int-2 (210 mg, 32%) as an off-white solid/sticky liquid. MS: m/z=435.1 [M+2H]$^+$.

Step-2 and 3: Synthesis of ((1-(3-chloro-5-(1,1-dioxidothiomorpholine-4-carbonyl)phenyl)-1H-pyrrolo[2,3-b]pyridin-5-yl)(4,4-difluoropiperidin-1-yl)methanone/3-chloro-5-(5-(4,4-difluoropiperidine-1-carbonyl)-1H-pyrrolo[2,3-b]pyridin-1-yl)-N-(1,1-dioxidotetrahydro-2H-thiopyran-4-yl)benzamide (MF-DH-481 and MF-DH-508): methyl 3-chloro-5-(5-(4,4-difluoropiperidine-1-carbonyl)-1H-pyrrolo[2,3-b]pyridin-1-yl)benzoate (Int-2) was subjected to the general procedure for ester hydrolysis using LiOH, followed by the general procedure for amide coupling with HATU to obtain MF-DH-481 and MF-DH-508 as off white solids.

Synthesis of 2-(5-(5-(4,4-difluoropiperidine-1-carbonyl)-1H-pyrrolo[2,3-b]pyridin-1-yl)pyridin-3-yl)-2-methylpropanenitrile and 2-(5-(5-(4,4-difluoropiperidine-1-carbonyl)-1H-pyrrolo[2,3-b]pyridin-1-yl)pyridin-3-yl)-2-methylpropanamide (MF-DH-509 and MF-DH-487)

Scheme 68

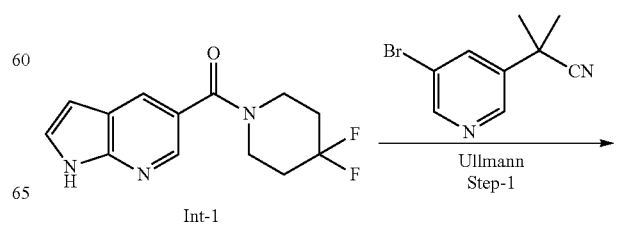

496

Synthesis of 4-(5-(4-fluoropiperidine-1-carbonyl)-4-methyl-1H-pyrrolo[2,3-b]pyridin-1-yl)benzamide (MF-DH-380)

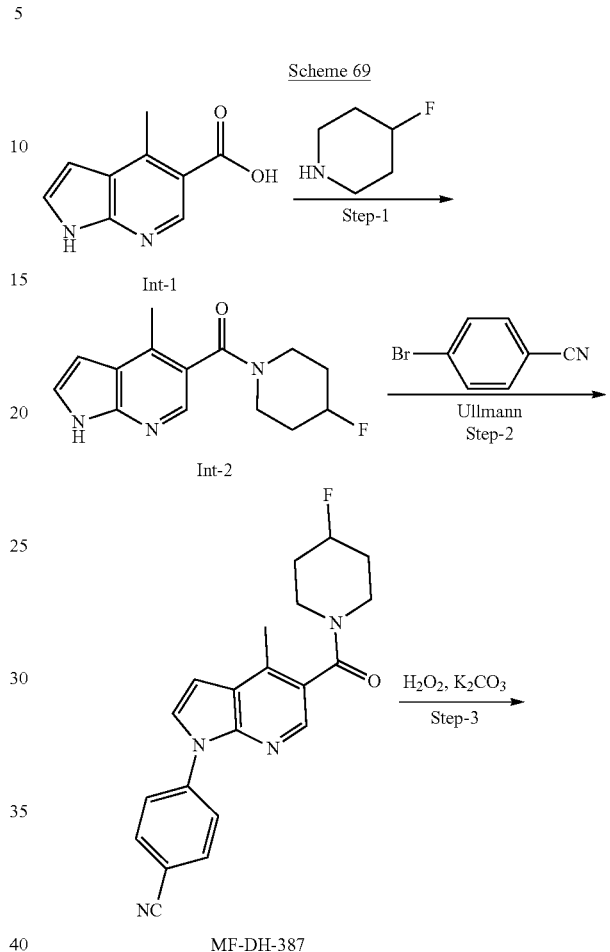

The synthesis of Int-1 is described in Scheme 45.

Step-1: Synthesis of 2-(5-(5-(4,4-difluoropiperidine-1-carbonyl)-1H-pyrrolo[2,3-b]pyridin-1-yl)pyridin-3-yl)-2-methylpropanenitrile (MF-DH-509): (4,4-difluoropiperidin-1-yl)(1H-pyrrolo[2,3-b]pyridin-5-yl) (Int-1) was converted to 2-(5-(5-(4,4-difluoropiperidine-1-carbonyl)-1H-pyrrolo[2,3-b]pyridin-1-yl)pyridin-3-yl)-2-methylpropanenitrile (MF-DH-509) by reacting with 2-(5-bromopyridin-3-yl)-2-methylpropanenitrile using the general procedure for Ullmann coupling to afford MF-DH-509 (54.6% yield) as an off-white sticky solid.

Step-2: Synthesis 2-(5-(5-(4,4-difluoropiperidine-1-carbonyl)-1H-pyrrolo[2,3-b]pyridin-1-yl)pyridin-3-yl)-2-methylpropanamide (MF-DH-487): 2-(5-(5-(4,4-difluoropiperidine-1-carbonyl)-1H-pyrrolo[2,3-b]pyridin-1-yl)pyridin-3-yl)-2-methylpropanenitrile was converted to 2-(5-(5-(4,4-difluoropiperidine-1-carbonyl)-1H-pyrrolo[2,3-b]pyridin-1-yl)pyridin-3-yl)-2-methylpropanamide using the general procedure for oxidation of nitrile to amide to afford MF-DH-487 as off-white solid.

Step-1: Synthesis of (4-fluoropiperidin-1-yl)(4-methyl-1H-pyrrolo[2,3-b]pyridin-5-yl)methanone (Int-2): Int-1 was converted to (4-fluoropiperidin-1-yl)(4-methyl-1H-pyrrolo[2,3-b]pyridin-5-yl)methanone using the general procedure for HATU acid/amine coupling described above to afford Int-2 (63%) as a brown sticky solid. MS: m/z=262.2 [M+H]$^+$.

Step-2: Synthesis of 4-(5-(4-fluoropiperidine-1-carbonyl)-4-methyl-1H-pyrrolo[2,3-b]pyridin-1-yl)benzonitrile (MF-DH-387): (4-fluoropiperidin-1-yl)(4-methyl-1H-pyrrolo[2,3-b]pyridin-5-yl)methanone was converted to 4-(5-(4-fluoropiperidine-1-carbonyl)-4-methyl-1H-pyrrolo[2,3-b]pyridin-1-yl)benzonitrile using the general procedure for Ullmann coupling to afford MF-DH-387 as an off-white solid.

Step-3: Synthesis 4-(5-(4-fluoropiperidine-1-carbonyl)-4-methyl-1H-pyrrolo[2,3-b]pyridin-1-yl)benzamide (MF-DH-380): 4-(5-(4-fluoropiperidine-1-carbonyl)-4-methyl-1H-pyrrolo[2,3-b]pyridin-1-yl)benzonitrile was converted to 4-(5-(4-fluoropiperidine-1-carbonyl)-4-methyl-1H-pyrrolo[2,3-b]pyridin-1-yl)benzamide using the general procedure for oxidation of nitrile to amide affording MF-DH-380 as an off-white solid.

Synthesis of 4-(3-chloro-5-(4-fluoropiperidine-1-carbonyl)-1H-pyrrolo[2,3-b]pyridin-1-yl)benzamide/ 4-(3-chloro-5-(4-fluoropiperidine-1-carbonyl)-1H-pyrrolo[2,3-b]pyridin-1-yl)benzamide/4-(3-chloro-5-(piperidine-1-carbonyl)-1H-pyrrolo[2,3-b]pyridin-1-yl)benzamide (MF-DH-382 and MF-DH-383)

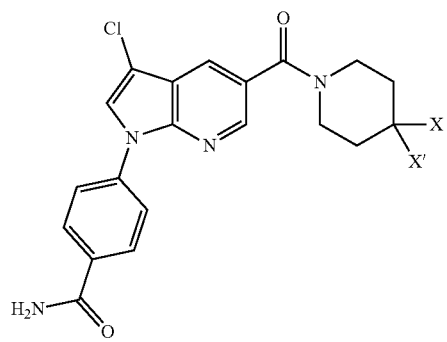

MF-DH-382  MF-DH-383
X = H, X' = F   X, X' = H

Steps 1 and 2 leading to Int-3 are described in Scheme 20 (X, X'=H) and Scheme 31 (X=H, X'=F).

Steps 3 and 4: Int-3 was subjected to the general procedure for Ullmann coupling to afford Int-4 (62% yield; MS: m/z=365.1 [M+H]⁺) and MF-DH-388 (57% yield; MS: m/z=383.2 [M+H]⁺). Int-4 and MF-DH-388 were subjected to the general procedure for oxidation of the nitrile to amide to afford the title compounds MF-DH-383 and MF-DH-382.

Synthesis of (3-chloro-1-(6-methylpyrazin-2-yl)-1H-pyrrolo[2,3-b]pyridin-5-yl)(4-fluoropiperidin-1-yl)methanone/(3-chloro-1-(2-methylpyrimidin-5-yl)-1H-pyrrolo[2,3-b]pyridin-5-yl)(4-fluoropiperidin-1-yl)methanone

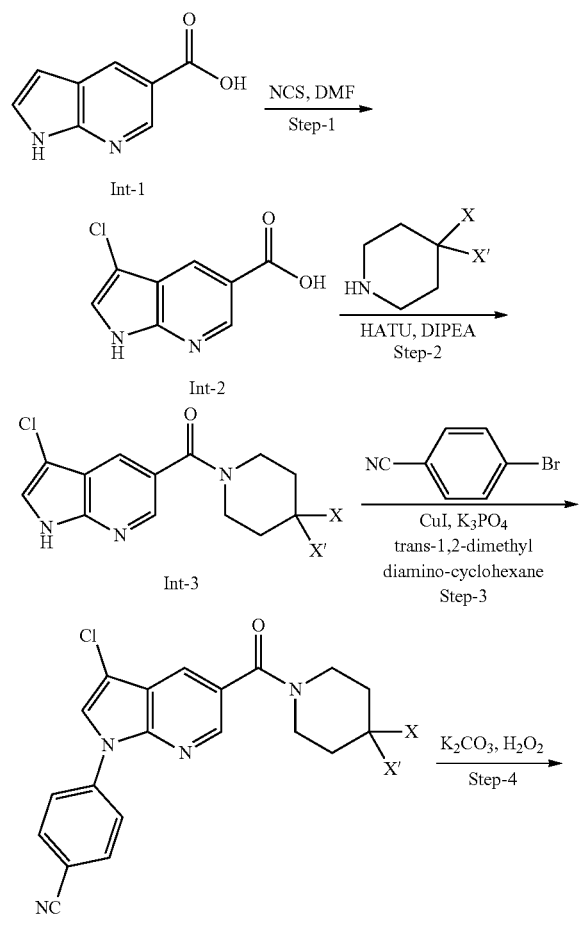

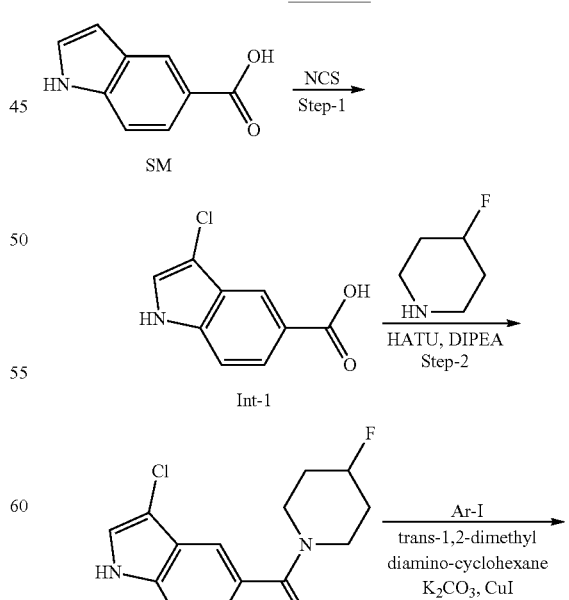

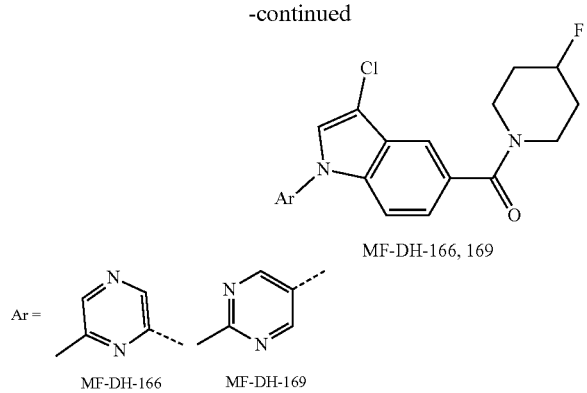

MF-DH-166, 169

Ar = MF-DH-166, MF-DH-169

Step-1: The synthesis of Int-1 is described in Scheme 20.

Step-2: Int-1 was converted to Int-2 using the general procedure for HATU acid-amine coupling affording Int-2 as an off-white solid. MS: m/z=281.1 [M+H]$^+$.

Step-3: Int-2 was converted to MF-DH-166 and MF-DH-169 using the general procedure for Ullmann coupling afforded the desired products as off-white solids.

Synthesis of (4-fluoropiperidin-1-yl)(3-methyl-1-(pyrazin-2-yl)-1H-indol-5-yl)methanone/(4-fluoropiperidin-1-yl)(3-methyl-1-(pyrimidin-5-yl)-1H-indol-5-yl)methanone/(4-fluoropiperidin-1-yl)(1-(4-methoxyphenyl)-3-methyl-1H-indol-5-yl)methanone Scheme 72

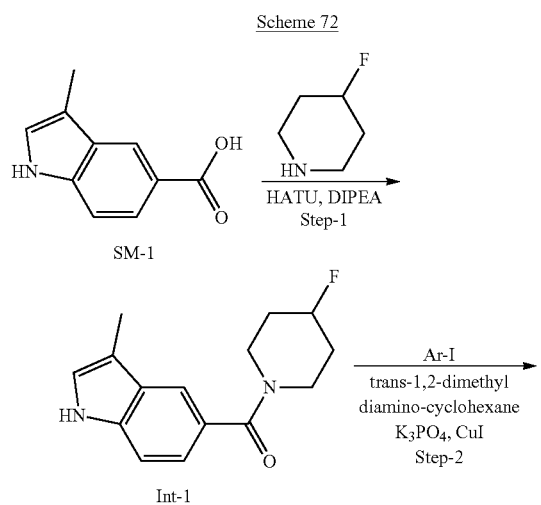

SM-1

Int-1

MF-DH-178, 180, 190

Ar = 5-Pyrimidinyl, MF-DH-178
Ar = 2-Pyrizenyl, MF-DH-180
Ar = 4-OMephenyl, MF-DH-190

Step-1: Synthesis of (3-methyl-1H-indol-5-yl)(piperidin-1-yl)methanone (Int-1): 3-methyl-1H-indole-5-carboxylic acid (SM-1) was converted to Int-1 using the general procedure for HATU acid-amine coupling described earlier using 4-fluoro piperidine affording Int-2 as an off white solid. (68.1% yield, MS: m/z=261.1 [M+H]$^+$).

Step-2: Synthesis of (4-fluoropiperidin-1-yl)(3-methyl-1-(pyrimidin-5-yl)-1H-indol-5-yl)methanone/(4-fluoropiperidin-1-yl)(3-methyl-1-(pyrazin-2-yl)-1H-indol-5-yl)methanone/(4-fluoropiperidin-1-yl)(1-(4-methoxyphenyl)-3-methyl-1H-indol-5-yl)methanone: Int-1was converted to MF-DH-178, MF-DH-180, MF-DH-190 using the general procedure for Ullmann coupling described earlier using 5-iodopyrimidine, 2-iodopyrazine and 1-iodo-4-methoxybenzene affording MF-DH-178, MF-DH-180, MF-DH-190 respectively as off-white solids.

Synthesis of (4-fluoropiperidin-1-yl)(3-(4-methoxyphenyl)-1-methyl-1H-pyrrolo[3,2-b]pyridin-6-yl)methanone/(4-fluoropiperidin-1-yl)(3-(3-methoxyphenyl)-1-methyl-1H-pyrrolo[3,2-b]pyridin-6-yl)methanone/(4-fluoropiperidin-1-yl)(3-(2-methoxyphenyl)-1-methyl-1H-pyrrolo[3,2-b]pyridin-6-yl)methanone (4-fluoropiperidin-1-yl)(3-(4-methoxyphenyl)-1H-pyrrolo[3,2-b]pyridin-6-yl)methanone Scheme 73

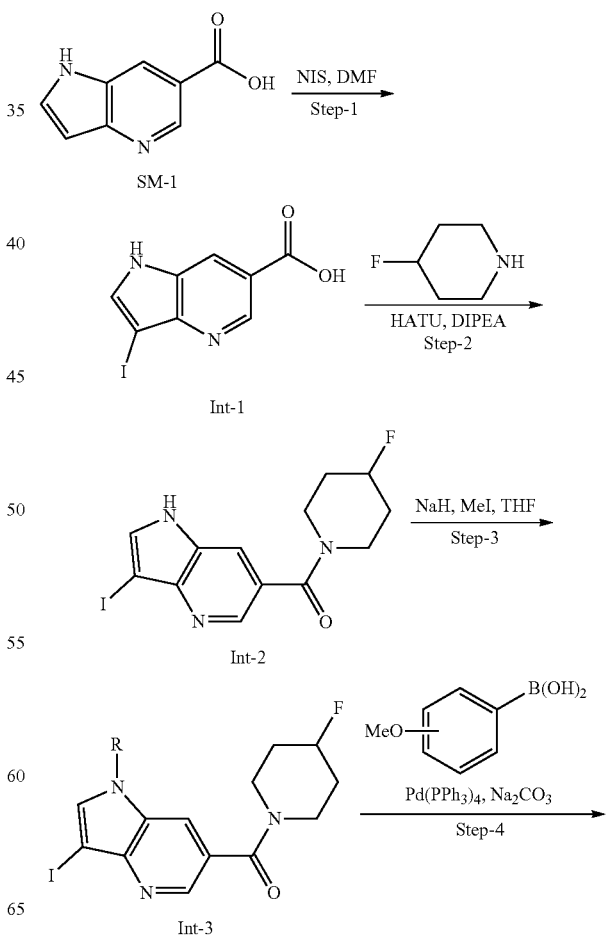

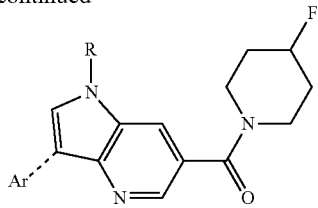

MF-DH-181, 199, 200, 204

Ar = 4-OMe phenyl, R = Me, MF-DH-181
Ar = 3-OMe phenyl, R = Me, MF-DH-199
Ar = 2-OMe phenyl, R = Me, MF-DH-200
Ar = 4-OMe phenyl, R = H, MF-DH-204

Step-1: Synthesis of 3-iodo-1H-pyrrolo[3,2-b]pyridine-6-carboxylic acid (Int-1): To a preheated solution (40° C.) of 1H-pyrrolo[3,2-b]pyridine-6-carboxylic acid (1 g, 6.16 mmol, 1 eq) in DMF (10 mL), N-Iodosuccinimide (1.66 g, 7.4 mmol, 1.2 eq) was added at room temperature and the reaction mixture was heated at 60° C. for 3 h; after consumption of starting material, the reaction mixture was allowed to sit for 12 h without stirring. The mixture was quenched with ice water (30 mL) and extracted with DCM (2×30 mL). The combined organic extracts were washed with ice water (2×20 mL) and brine (10 mL), dried over sodium sulfate, filtered and concentrated in vacuo to obtain Int-1 (1.3 g; Yield: 73%) as a light-yellow solid. MS: m/z=286.8 [M−H]$^+$.

Step-2: Synthesis of (4-fluoropiperidin-1-yl)(3-iodo-1H-pyrrolo[3,2-b]pyridin-6-yl)methanone (Int-2): 3-Iodo-1H-pyrrolo[3,2-b]pyridine-6-carboxylic acid (Int-1) (1 eq.) was converted to (4-fluoropiperidin-1-yl)(3-iodo-1H-pyrrolo[3,2-b]pyridin-6-yl)methanone using the general procedure for acid-amine coupling with HATU to afford (Int-2) as an off-white solid. MS: m/z=373.9 [M+H]$^+$.

Step-3: Synthesis of (4-fluoropiperidin-1-yl)(3-iodo-1-methyl-1H-pyrrolo[3,2-b]pyridin-6-yl)methanone (Int-3): To a stirred solution of (4-fluoropiperidin-1-yl)(3-iodo-1H-pyrrolo[3,2-b]pyridin-6-yl)methanone (1 eq.) in THE at 0° C., NaH (1.5 eq) was added and stirred for 10 minutes followed by the addition of methyl iodide (1.5 eq.) drop wise at the same temperature. The reaction mixture was then stirred for 2 h. After complete consumption of the starting material, the reaction mixture was quenched with ice water and extracted with EtOAc. The combined organic extracts were washed with ice water and brine; dried over sodium sulfate, filtered and concentrated in vacuo to obtain the crude. The crude was purified through silica gel column chromatography affording (4-fluoropiperidin-1-yl)(3-iodo-1-methyl-1H-pyrrolo[3,2-b]pyridin-6-yl)methanone (Int-3) as off-white solid. MS: m/z=388.1 [M+H]$^+$.

Step-4: Synthesis of (4-fluoropiperidin-1-yl)(3-(4-methoxyphenyl)-1-methyl-1H-pyrrolo[3,2-b]pyridin-6-yl)methanone/(4-fluoropiperidin-1-yl)(3-(3-methoxyphenyl)-1-methyl-1H-pyrrolo[3,2-b]pyridin-6-yl)methanone/(4-fluoropiperidin-1-yl)(3-(2-methoxyphenyl)-1-methyl-1H-pyrrolo[3,2-b]pyridin-6-yl)methanone (MF-DH-181, MF-DH-199 and MF-DH-200): (4-Fluoropiperidin-1-yl)(3-iodo-1-methyl-1H-pyrrolo[3,2-b]pyridin-6-yl)methanone (Int-3) was subjected to the general procedure for Suzuki coupling with the appropriate phenyl boronic acids. The crudes were purified through silica gel column chromatography to obtain the desired products.

Synthesis of ((4-fluoropiperidin-1-yl)/((piperidin-1-yl)/(1H-benzo[d][1,2,3]triazol-5-yl) Analogs with aryl/amide Variation Provided below is an exemplary scheme to synthesize ((4-fluoropiperidin-1-yl)/((piperidin-1-yl)/(1H-benzo[d][1,2,3]triazol-5-yl) analogs with aryl/amide variations that are inhibitors of hydroxyprostaglandin dehydrogenase.

Scheme 74

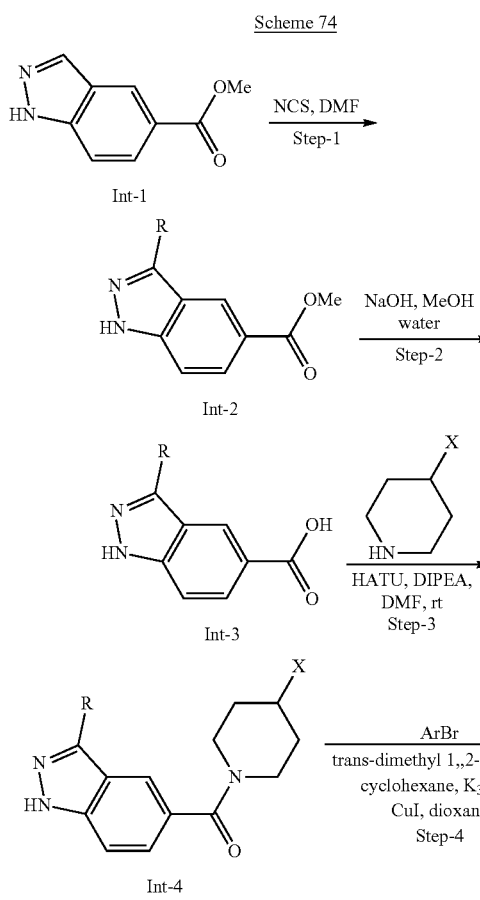

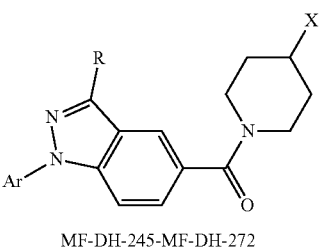

MF-DH-245-MF-DH-272

-continued

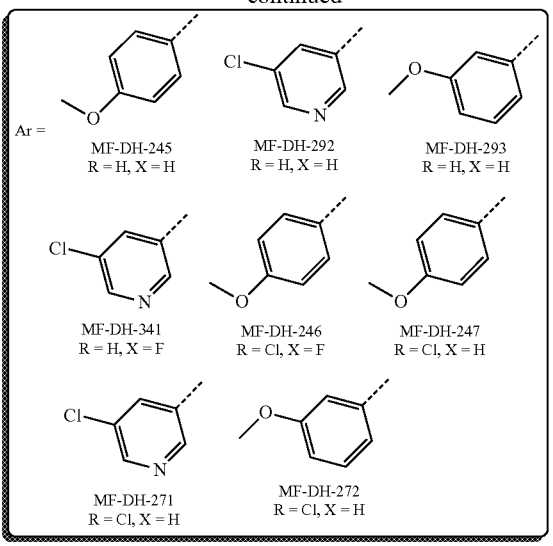

-continued

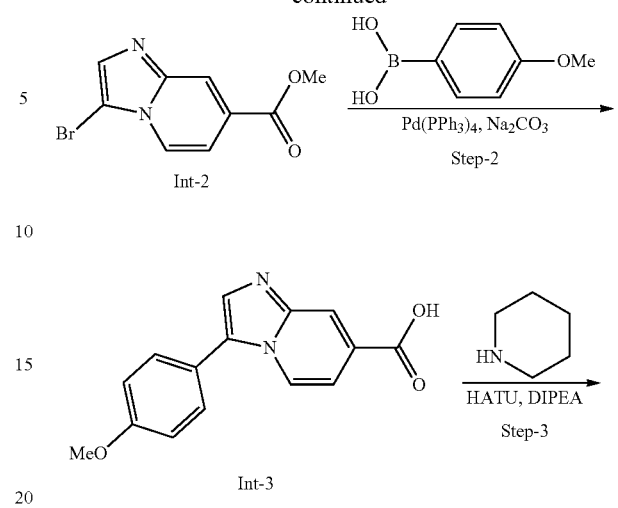

Step-1: Synthesis of Int-2: methyl 1H-indazole-5-carboxylate (1 eq) was converted to methyl 3-chloro-1H-indazole-5-carboxylate using the general procedure for chlorination with NCS affording Int-2 (43.2% yield, MS: m/z=212.2 [M+2a]$^+$).

Step-2: Synthesis of Int-3a and Int-3b: Methyl 1H-indazole-5-carboxylate/methyl 3-chloro-1H-indazole-5-carboxylate were converted to Int-3a (R=H)/Int-3b (R=Cl) using the general procedure for ester hydrolysis with NaOH to afford Int-3a (73.0% yield, MS: m/z=163.1 [M+H]$^+$) and Int-3b (69.6% yield, MS: m/z=198.1 [M+2H]$^+$).

Step-3: 1H-indazole-5-carboxylic acid (Int-3a)/3-chloro-1H-indazole-5-carboxylic acid (Int-3b) was converted to Int-4a (R=H, X=H)/Int-4b (R=Cl, X=H)/Int-4c (R=H, X=F)/Int-4d (R=Cl, X=F) using the general procedure of amide coupling with HATU to afford Int-4a (72.3% yield, MS: m/z=230.1 [M+H]$^+$), Int-4b (68.0% yield, MS: m/z=265.1 [M+2H]$^+$), Int-4c (72.0% yield, MS: m/z=248.2 [M+H]$^+$), and Int-4d (67.2% yield MS: m/z=283.2 [M+2H]$^+$) as off-white solids.

Step-4: Synthesis of MF-DH-245, MF-DH-292, MF-DH-293, MF-DH-341, MF-DH-246, MF-DH-247, MF-DH-271, MF-DH-272: Int-4 was converted to MF-DH-245, MF-DH-392, MF-DH-293, MF-DH-341, MF-DH-246, MF-DH-247, MF-DH-271, MF-DH-272 using the general procedure for Ullmann coupling.

Synthesis of (3-(4-methoxyphenyl)imidazo[1,2-a]pyridin-7-yl)(piperidin-1-yl)methanone (MF-DH-241)

Scheme 75

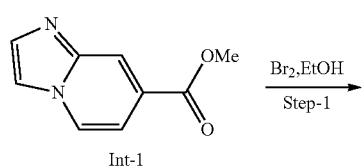

Step-1: Synthesis of methyl 3-bromoimidazo[1,2-a]pyridine-7-carboxylate (Int-2): To a stirred solution of methyl imidazo[1,2-a]pyridine-7-carboxylate (1 eq.) in EtOAc (10 v), bromine (1.1 eq.) was added at 0° C. The reaction mixture was stirred for 1 h at 0° C. After complete consumption of the starting material, the reaction mixture was quenched with sodium bisulfite and extracted with EtOAc (2×20 mL). The combined organic extracts were washed with ice water and brine, dried over sodium sulfate, filtered and concentrated in vacuo to obtain the crude. The crude was purified through silica gel column chromatography affording methyl 3-bromoimidazo[1,2-a]pyridine-7-carboxylate (Int-2) as an off-white solid. MS: m/z=256.1 [M+2H]$^+$.

Step-2: Synthesis of 3-(4-methoxyphenyl)imidazo[1,2-a]pyridine-7-carboxylic acid (Int-3): Methyl 3-bromoimidazo[1,2-a]pyridine-7-carboxylate (Int-2) was converted to 3-(4-methoxyphenyl)imidazo[1,2-a]pyridine-7-carboxylic acid using general procedure for Suzuki coupling to afford Int-3 as an off white solid. MS: m/z=269.1 [M+H]$^+$.

Step-3: Synthesis of (3-(4-methoxyphenyl)imidazo[1,2-a]pyridin-7-yl)(piperidin-1-yl)methanone (MF-DH-241): 3-(4-methoxyphenyl)imidazo[1,2-a]pyridine-7-carboxylic acid (Int-3) was converted to (3-(4-methoxyphenyl)imidazo[1,2-a]pyridin-7-yl)(piperidin-1-yl)methanone (MF-DH-241) using general procedure for HATU acid-amine coupling affording the desired product as an off-white solid.

505

Synthesis of (4-fluoropiperidin-1-yl)(1-(4-methoxyphenyl)-1H-benzo[d][1,2,3]triazol-5-yl)methanone/(1-(4-methoxyphenyl)-1H-benzo[d][1,2,3]triazol-5-yl)(piperidin-1-yl)methanone

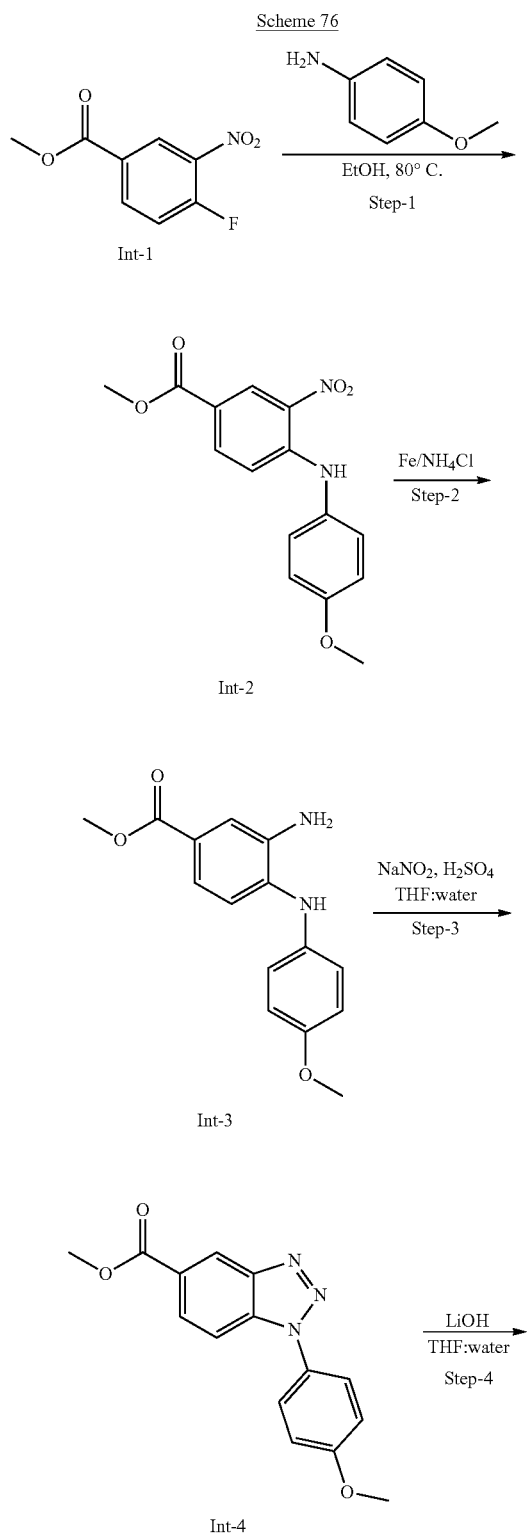

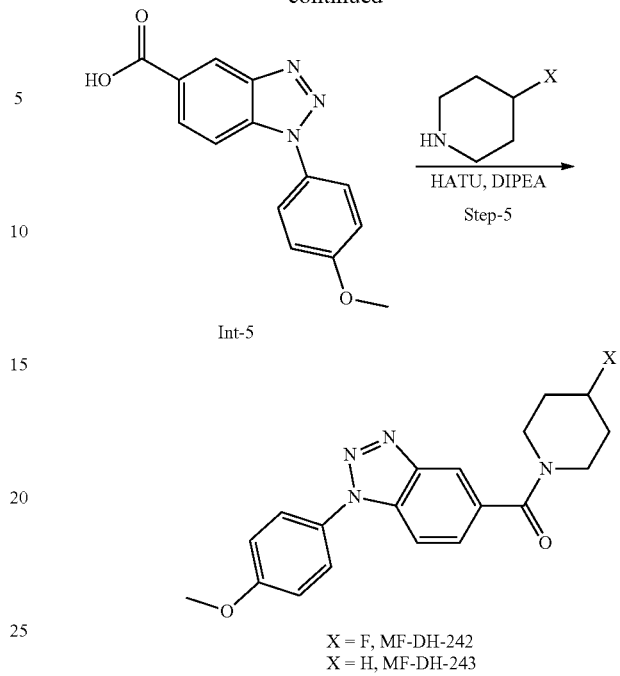

X = F, MF-DH-242
X = H, MF-DH-243

The synthesis of Int-3 is described in Scheme 7.

Step-3: Synthesis of methyl 1-(4-methoxyphenyl)-1H-benzo[d][1,2,3]triazole-5-carboxylate (Int-4): methyl 3-amino-4-((4-methoxyphenyl)amino)benzoate (Int-3) (1.0 eq) was converted to methyl 1-(4-methoxyphenyl)-1H-benzo[d][1,2,3]triazole-5-carboxylate using aqueous solution of $NaNO_2$ (2.0 eq) and Conc. HCl (1 mL) at −5° C. for 12 h to afford Int-4 (51.0% yield, MS: m/z=284.1 [M+H]$^+$).

Step-4: Synthesis of 1-(4-methoxyphenyl)-1H-benzo[d][1,2,3]triazole-5-carboxylic acid (Int-5): Methyl 3-chloro-5-(5-(4,4-difluoropiperidine-1-carbonyl)-1H-pyrrolo[2,3-b]pyridin-1-yl)benzoate (Int-4) was converted to 1-(4-methoxyphenyl)-1H-benzo[d][1,2,3]triazole-5-carboxylic acid using general ester hydrolysis procedures with LiOH affording Int-5 (73.0% yield, MS: m/z=270.3 [M+H]$^+$) as an off white solid.

Step-5: Synthesis of MF-DH-242 and 243: 1-(4-methoxyphenyl)-1H-benzo[d][1,2,3]triazole-5-carboxylic acid was converted to MF-DH-242 and 243 using the general procedure for acid-amine coupling with HATU.

Synthesis of (2-(3-hydroxy-3-methylbutyl)-1-(4-methoxyphenyl)-1H-pyrrolo[2,3-b]pyridin-5-yl)(piperidin-1-yl)methanone/4-(5-(4,4-difluoropiperidine-1-carbonyl)-2-(3-hydroxy-3-methylbutyl)-1H-pyrrolo[2,3-b]pyridin-1-yl)benzonitrile/3-(1-(4-cyanophenyl)-5-(4,4-difluoropiperidine-1-carbonyl)-1H-pyrrolo[2,3-b]pyridin-2-yl)propanamide

Scheme 77

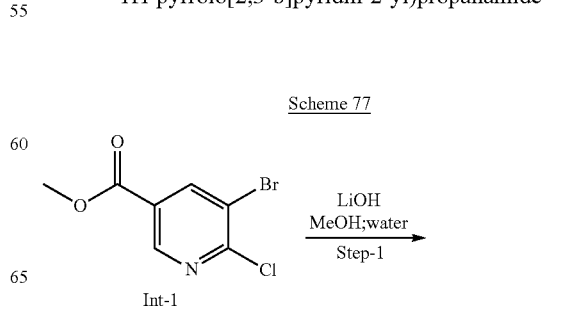

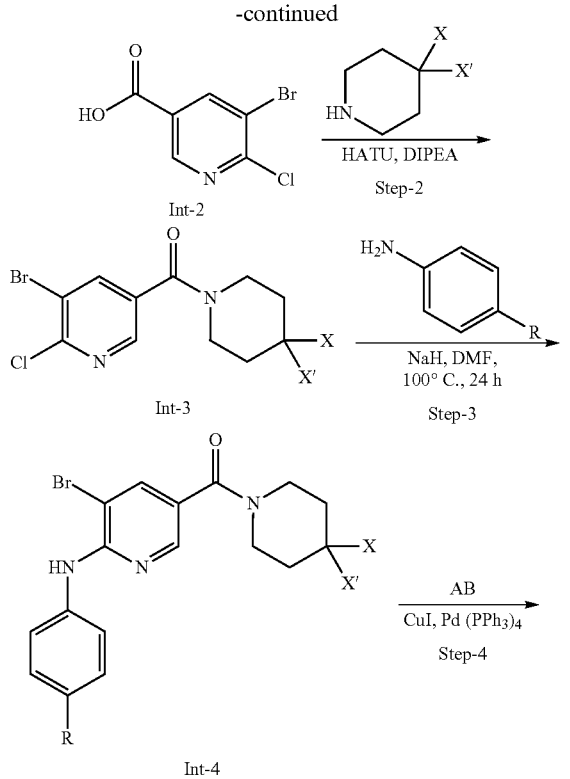

R = OMe; X, X' = H; R₁ = (CH₃)₂CHOH MF-DH-330
R = CN; X, X' = F; R₁ = (CH₃)₂CHOH MF-DH-444
R = CN; X, X' = F; R₁ = CONH₂ MF-DH-446

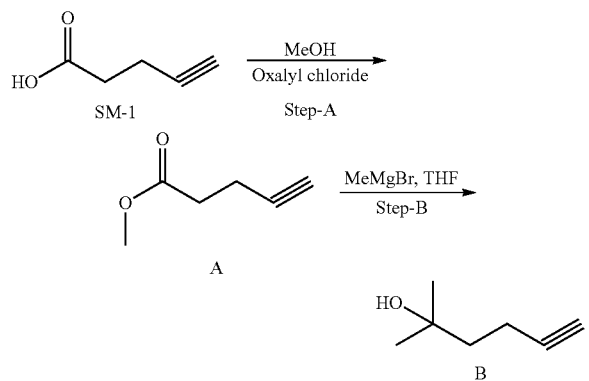

Step-A: Synthesis of methyl pent-4-ynoate (Int-A): To the stirred solution of pent-4-ynoic acid (SM-1) (5 g, 50.9 mmol) in DCM (45 mL) was added oxalyl chloride (6.1 g, 50.9 mmol, 1 eq) dropwise at 0° C., and the reaction mixture was stirred at 0° C. for 1 h. The reaction was monitored by TLC; upon completion, the reaction was cooled to room temperature and the volatiles were evaporated. The mixture was redissolved in DCM (45 mL). MeOH (5 eq) was added and the reaction mixture was stirred at room temperature for 5 h. The mixture was concentrated in vacuo to obtain the crude. The crude was purified through silica gel column chromatography using 10% EtOAc:Hex to obtain methyl pent-4-ynoate (Int-A, 5.08 g, 89%) as a yellow liquid.

Step-B: Synthesis of 2-methylhex-5-yn-2-ol (Int-B): To a stirred solution of methyl pent-4-ynoate (Int-A, 3.36 g, 10 mmol, 1 eq) in THF (15 mL) was added MeMgBr (2M in THF, 3 eq) portionwise at 0° C. over 15 min. The reaction mixture was stirred for 5 h at room temperature. The reaction was monitored by LCMS/TLC; upon completion, the reaction mixture was quenched with saturated NH₄Cl solution (20 mL) and extracted with EtOAc (2×20 mL). The combined organic extracts were washed with brine solution (20 mL), dried over sodium sulfate, filtered, and concentrated under reduced pressure to afford the crude. The crude was further purified by flash chromatography using 30% EtOAc: Hex to afford 2-methylhex-5-yn-2-ol (Int-B, 1.93 g, 57.6%) as a light brown liquid.

Step-1: Synthesis of methyl 5-bromo-6-chloronicotinate (Int-2): Methyl 5-bromo-6-chloronicotinate (1 g, 1 eq) was converted to 5-bromo-6-chloronicotinic acid (Int-2) using general procedure for ester hydrolysis with LiOH affording Int-2 (66.3% yield; MS: m/z=236.1[M+H]⁺) as an off-white solid.

Step-2: Synthesis of (5-bromo-6-chloropyridin-3-yl)(piperidin-1-yl)methanone (Int-3a, X, X'=H) and (5-bromo-6-chloropyridin-3-yl)(4,4-difluoropiperidin-1-yl)methanone (Int-3b, X, X'=F): 5-bromo-6-chloronicotinic acid (Int-2) was converted to Int-3a (X, X'=H, 53% yield, MS: m/z=304.1[M+2H]⁺) and Int-3b (X, X'=F, 46.5% yield, MS: m/z=339.1[M+H]⁺, 340.1[M+2H]⁺) using general procedure for HATU acid-amine coupling.

Step-3: Synthesis of (5-bromo-6-((4-methoxyphenyl)amino)pyridin-3-yl)(piperidin-1-yl)methanone (Int-4a) and 4-((3-bromo-5-(4,4-difluoropiperidine-1-carbonyl)pyridin-2-yl)amino)benzonitrile (Int-4b); general procedure for SNAr #3: To a stirred solution of 4-amino benzonitrile (1 eq.) in DMF (10 v), NaH (1.5 eq.) was added portion wise at 0° C. and the reaction was stirred for 10 mins followed by addition of (5-bromo-6-chloropyridin-3-yl)(4,4-difluoropiperidin-1yl)methanone (Int-3) at 0° C. The reaction mixture was then stirred at 100° C. for 24 h. The progress of the reaction was monitored by crude LCMS/TLC; after complete consumption of the starting material, reaction mixture was quenched with ice water (30 mL) and extracted with EtOAc (2×30 mL). The combined organic extracts were washed with ice water (2×20 mL) and brine (10 mL), dried over sodium sulfate, filtered and concentrated in vacuo to afford Int-4a (X, X'=H, 41.5% yield, MS: m/z=390.1[M+H]⁺) and Int-4b (X, X'=F, 32.5% yield, MS: m/z=421.1[M+2H]⁺).

Step-4: Synthesis of (2-(3-hydroxy-3-methylbutyl)-1-(4-methoxyphenyl)-1H-pyrrolo[2,3-b]pyridin-5-yl)(piperidin-1-yl)methanone/4-(5-(4,4-difluoropiperidine-1-carbonyl)-2-(3-hydroxy-3-methylbutyl)-1H-pyrrolo[2,3-b]pyridin-1-yl)benzonitrile (MF-DH-330, MF-DH-44) (General procedure for Sonogashira coupling): (5-bromo-6-((4-methoxyphenyl)amino)pyridin-3-yl)(piperidin-1-yl)methanone (Int-4a)/4-((3-bromo-5-(4,4-difluoropiperidine-1-carbonyl)pyridin-2-yl)amino)benzonitrile (Int-4b) was subjected to Sonogashira coupling with 1 eq. alkyne (B/A), Pd(PPh₃)₄ (0.1 eq), CuI (0.2 eq) and TEA (3 eq) in dioxane (5 v) at 100° C. for 12 h affording NW-DH-330, MF-DH-444 and methyl 3-(1-(4-cyanophenyl)-5-(4,4-difluoropiperidine-1-carbonyl)-1H-pyrrolo[2,3-b]pyridin-2-yl)propanoate.

Synthesis of 3-(1-(4-cyanophenyl)-5-(4,4-difluoropiperidine-1-carbonyl)-1H-pyrrolo[2,3-b]pyridin-2-yl)propanamide (MF-DH-446): methyl 3-(1-(4-cyanophenyl)-5-(4,4-difluoropiperidine-1-carbonyl)-1H-pyrrolo[2,3-b]pyridin-2-yl)propanoate was converted to 3-(1-(4-cyanophenyl)-5-(4,4-difluoropiperidine-1-carbonyl)-1H-pyrrolo[2,3-b]pyridin-2-yl)propanoic acid using general procedure for ester hydrolysis with LiOH afforded acid; the acid was then converted to 3-(1-(4-cyanophenyl)-5-(4,4-difluoropiperidine-1-carbonyl)-1H-pyrrolo[2,3-b]pyridin-2-yl)propanamide (MF-DH-446) by using acid-amine (NH$_4$Cl) coupling with HATU affording MF-DH-446.

Synthesis of (4,4-difluoropiperidin-1-yl)(1-(6-(3-methyl-3-(methylsulfonyl)but-1-yn-1-yl)pyridin-3-yl)-1H-pyrrolo[2,3-b]pyridin-5-yl)methanone (MF-DH-465)

Step-1: Synthesis of Int-2: Int-2 was synthesized by using the general Ullmann coupling condition of Int-1 with 5-bromo-2-iodopyridine followed by purification to afford Int-2 (2.95 g) as an off-white solid. MS: m/z=469.0 (M+H).

Step-2: Synthesis of MF-DH-465: (4,4-difluoropiperidin-1-yl)(1-(6-iodopyridin-3-yl)-1H-pyrrolo[2,3-b]pyridin-5-yl)methanone was converted to (4,4-difluoropiperidin-1-yl)(1-(6-(3-methyl-3-(methylsulfonyl)but-1-yn-1-yl)pyridin-3-yl)-1H-pyrrolo[2,3-b]pyridin-5-yl)methanone using the general procedure for Sonogashira coupling to afford MF-DH-465.

Step-3: Synthesis of 3-methyl-3-(methylsulfonyl)but-1-yne (Int-3): To a stirred solution of 3-chloro-3-methylbut-1-yne (5 g, 48.73 mmol, 1.0 eq) in DMF (25 mL) was added sodium methane sulfonate (6 g, 58.47 mmol, 1.2 eq) and Cu(I) Cl (0.48 g, 4.87 mmol, 0.1 eq) at 0° C. The reaction of was stirred at 50° C., for 16 h. Workup and then flash column purification afforded Int-3.

Synthesis of Pyrrolopyridine-5-Carboxyamide Analogs with Amide/Aryl Variation

Provided below is an exemplary scheme to synthesize pyrrolopyridine-5-carboxyamide analogs with amide/Aryl variations that are inhibitors of hydroxyprostaglandin dehydrogenase.

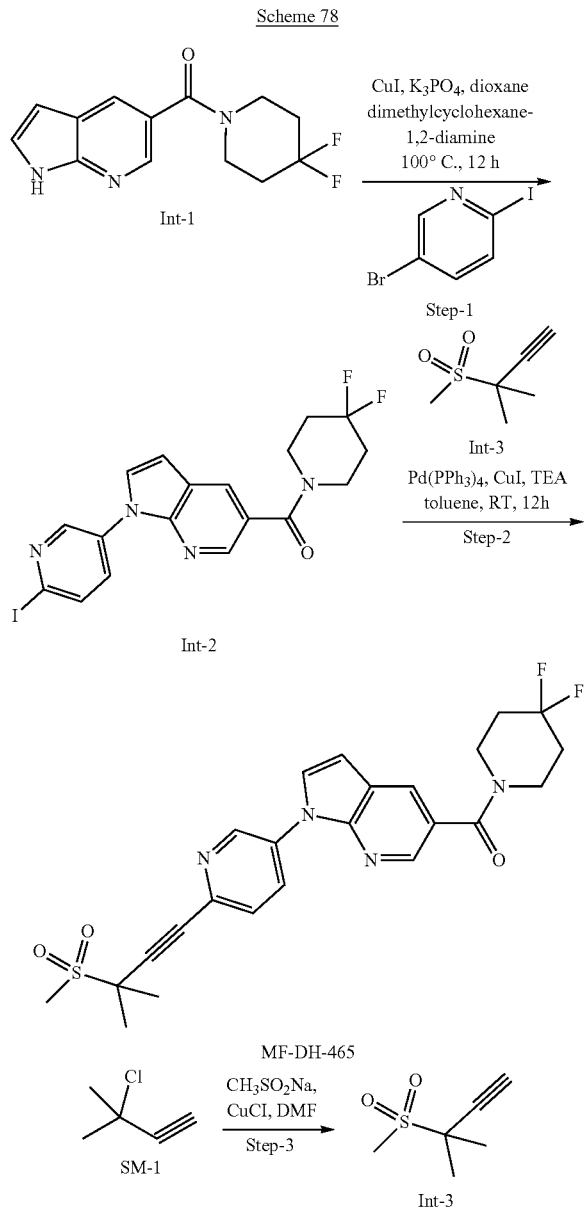

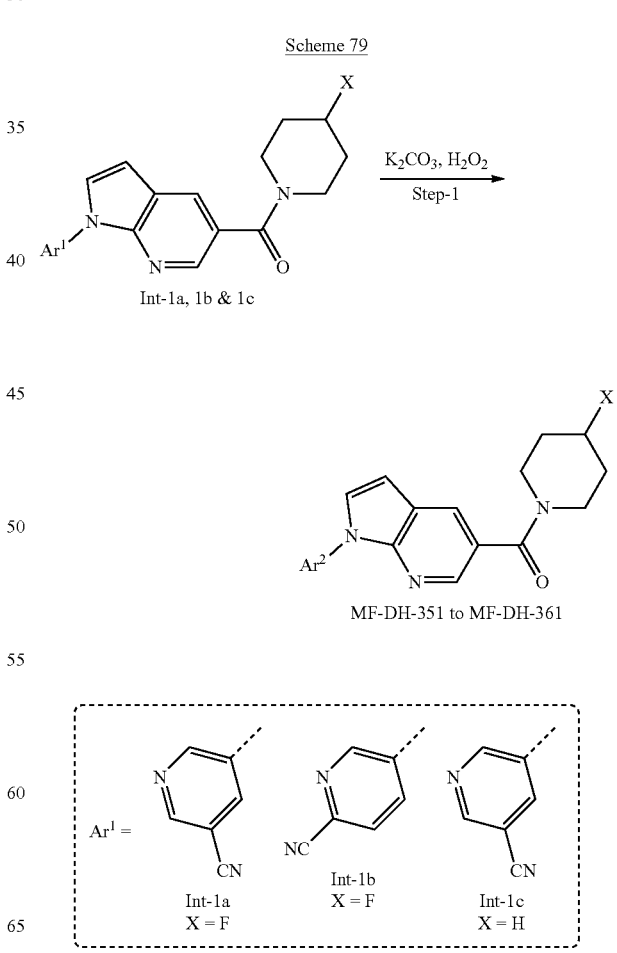

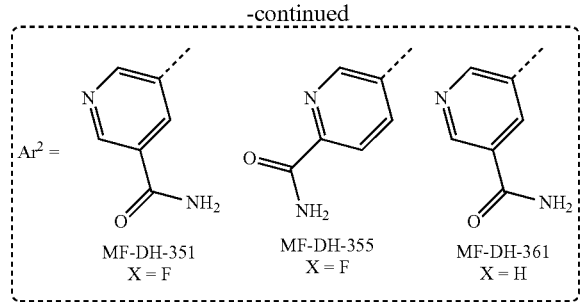

Int-1a, Int-1b, and Int-1c were prepared by subjecting piperidin-1-yl(1H-pyrrolo[2,3-b]pyridin-5-yl)methanone/(4-fluoropiperidin-1-yl)(1H-pyrrolo[2,3-b]pyridin-5-yl) methanone to the general procedure for Ullmann coupling to afford Int-1a (64% yield, MS: m/z 350.1 [M+H]$^+$); Int-1b (53% yield, MS: m/z 350.2 [M+H]$^+$); and Int-1c (63% yield, MS: m/z 332.2 [M+H]$^+$).

Step-1: Synthesis of MF-DH-351, MF-DH-355 and MF-DH-361: Int-1 was converted to 4-(5-(4-fluoropiperidine-1-carbonyl)-1H-pyrrolo[2,3-b]pyridin-1-yl)benzamide/3-(5-(4-fluoropiperidine-1-carbonyl)-1H-pyrrolo[2,3-b]pyridin-1-yl)benzamide 4-(5-(4-fluoropiperidine-1-carbonyl)-4-methyl-1H-pyrrolo[2,3-b]pyridin-1-yl)benzamide/5-(5-(4-fluoropiperidine-1-carbonyl)-1H-pyrrolo[2,3-b]pyridin-1-yl)nicotinamide/3-(5-(4-fluoropiperidine-1-carbonyl)-1H-pyrrolo[2,3-b]pyridin-1-yl)benzamide/5-(5-(piperidine-1-carbonyl)-1H-pyrrolo[2,3-b]pyridin-1-yl)nicotinamide using general procedure for oxidation of nitrile to amide affording MF-DH-343, 345, 351, 355 and MF-DH-361 as off-white solids.

Synthesis of Pyrrolopyridine-5-Carboxyamide Analogs with Amide/Aryl Variation Provided below is an exemplary scheme to synthesize pyrrolopyridine-5-carboxyamide analogs with amide/Aryl variations that are inhibitors of hydroxyprostaglandin dehydrogenase.

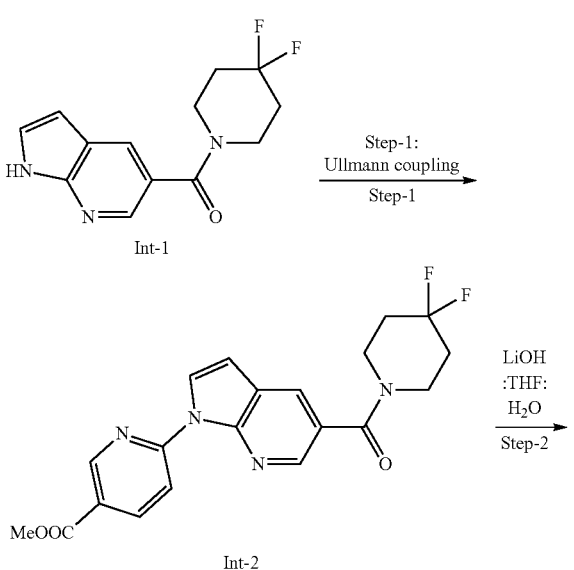

Scheme 80

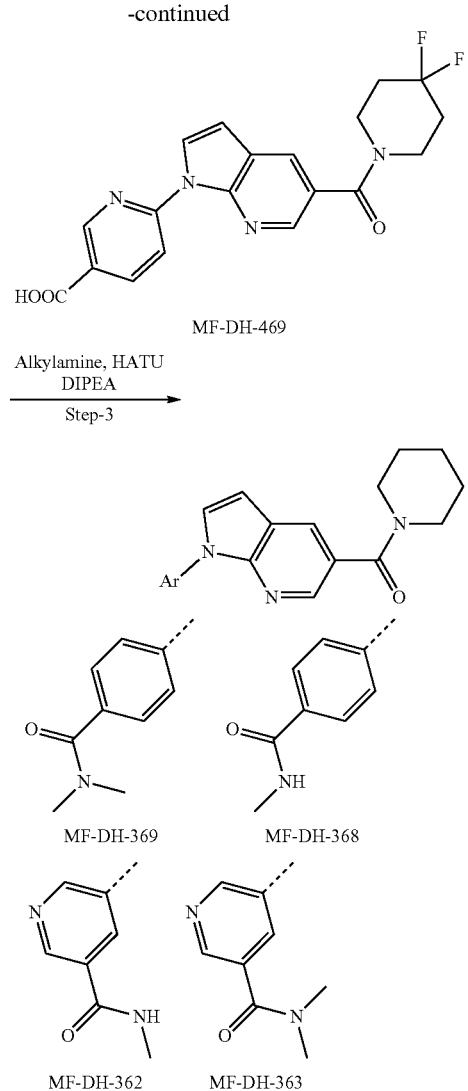

The synthesis of Int-1 is described in Scheme 45.

Step-1: Int-1 was converted to Int-2 using the general procedure for Ullmann coupling with the appropriate aryl bromide (48.3% yield, MS: m/z=410.1[M+H]$^+$).

Step-2: Int-2 was subjected to the general procedure for ester hydrolysis with LiOH to afford MF-DH-469.

Step-3: Synthesis of MF-DH-362, MF-DH-363, MF-DH-368, and MF-DH-369: MF-DH-425 (synthesis described in Scheme 57) and MF-DH-433 (synthesis described in Scheme 54) were converted to final compounds using general procedure for HATU acid-amine coupling affording MF-DH-362, MF-DH-363, MF-DH-368, MF-DH-369 as off-white solids.

Synthesis of pyrrolopyridine-5-carboxyamide Analogs with amide/Aryl Variation Provided below is an exemplary scheme to synthesize pyrrolopyridine-5-carboxyamide analogs with amide/Aryl variations that are inhibitors of hydroxyprostaglandin dehydrogenase.

Scheme 81

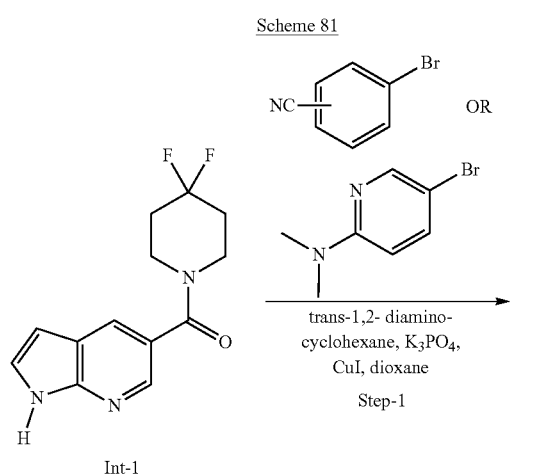

Int-1

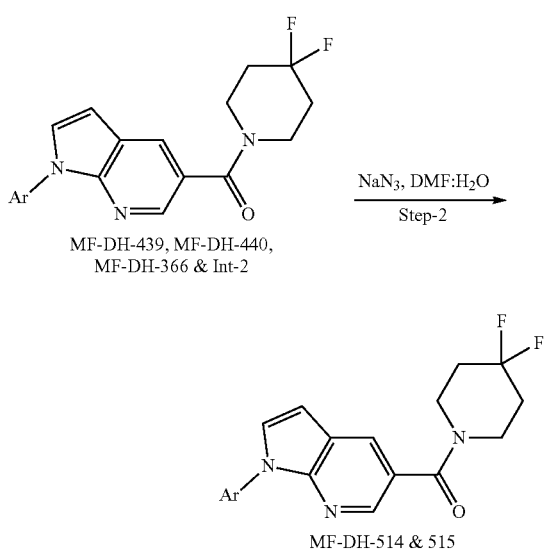

MF-DH-439, MF-DH-440, MF-DH-366 & Int-2

MF-DH-514 & 515

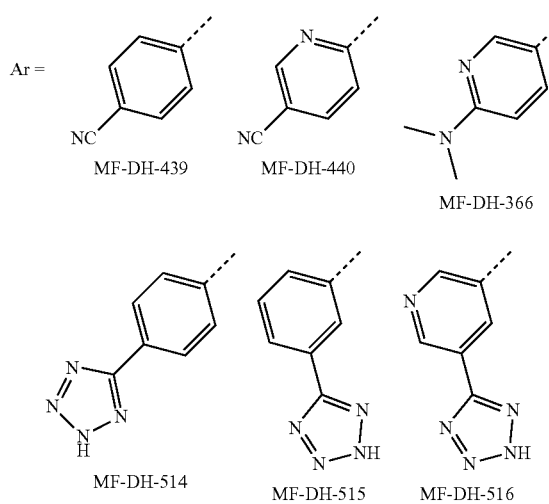

was subjected to the general procedure for Ullmann coupling with 4-bromo benzonitrile/6-bromonicotinonitrile/5-Bromo-N,N-dimethyl-Pyridine-2-amine/3-bromobenzonitrile to afford the title compounds (MF-DH-439, MF-DH-440, MF-DH-366) and 3-(5-(4,4-difluoropiperidine-1-carbonyl)-1H-pyrrolo[2,3-b]pyridin-1-yl)benzonitrile (Int-2) as off-white solids.

Step-2: Synthesis of (1-(4-(2H-tetrazol-5-yl)phenyl)-1H-pyrrolo[2,3-b]pyridin-5-yl)(4,4-difluoropiperidin-1-yl) methanone/(1-(3-(2H-tetrazol-5-yl) phenyl)-1H-pyrrolo[2,3-b]pyridin-5-yl)(4,4-difluoropiperidin-1-yl)methanone (MF-DH-514 and MF-DH-515): 4-(5-(4,4-difluoropiperidine-1-carbonyl)-1H-pyrrolo[2,3-b]pyridin-1-yl)benzonitrile/3-(5-(4,4-difluoropiperidine-1-carbonyl)-1H-pyrrolo[2,3-b]pyridin-1-yl)benzonitrile (Int-2) was converted to (1-(4-(2H-tetrazol-5-yl)phenyl)-1H-pyrrolo[2,3-b]pyridin-5-yl)(4,4-difluoropiperidin-1-yl)methanone/(1-(3-(2H-tetrazol-5-yl) phenyl)-1H-pyrrolo[2,3-b]pyridin-5-yl)(4,4-difluoropiperidin-1-yl)methanone by using the general procedure for the synthesis of tetrazole from a nitrile to afford MF-DH-514 and MF-DH-515 as off white solids.

Step-2: Synthesis of (1-(5-(1H-1,2,4-triazol-3-yl)pyridin-3-yl)-1H-pyrrolo[2,3-b]pyridin-5-yl)(4,4-difluoropiperidin-1-yl)methanone (MF-DH-516): 5-(5-(4,4-difluoropiperidine-1-carbonyl)-1H-pyrrolo[2,3-b]pyridin-1-yl) nicotinonitrile was converted to (1-(5-(1H-1,2,4-triazol-3-yl)pyridin-3-yl)-1H-pyrrolo[2,3-b]pyridin-5-yl)(4,4-difluoropiperidin-1-yl)methanone by using general procedure for the synthesis of triazoles from nitrile affording MF-DH-516 as an off white solid.

Synthesis of (4,4-Difluoropiperidin-1-yl)(1-(6-(5-(trifluoromethyl)-4H-1,2,4-triazol-3-yl)pyridin-3-yl)-1H-pyrrolo[2,3-b]pyridin-5-yl)methanone (MF-DH-519)

Scheme 82

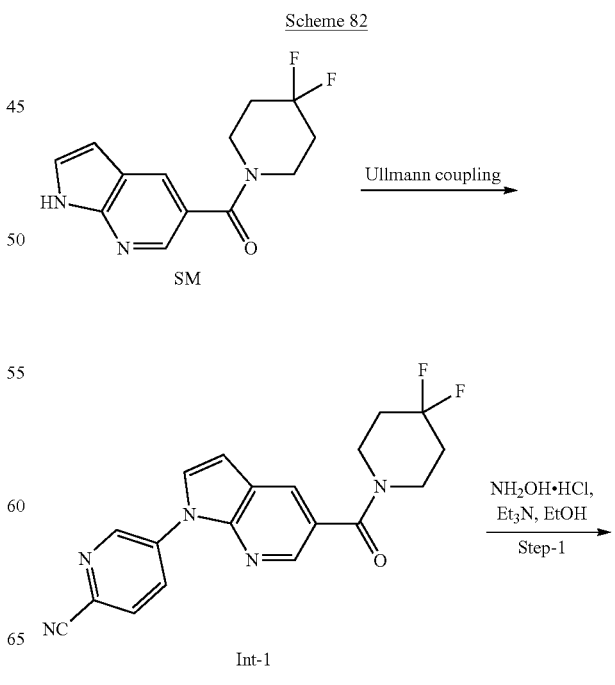

The synthesis of Int-1 is described in Scheme 45.

Step-1: Synthesis of MF-DH-366, MF-DH-440, MF-DH-439 and Int-2: 4,4-difluoropiperidin-1-yl)(1H-pyrrolo[2,3-b]pyridin-5-yl)methanone (Int-1, 1.6 g, 6.0 mmol, 1.0 eq)

-continued

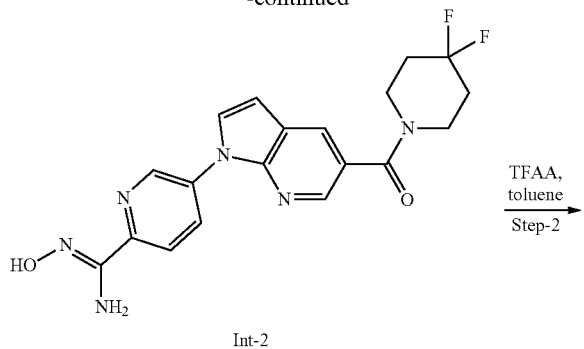

Int-2

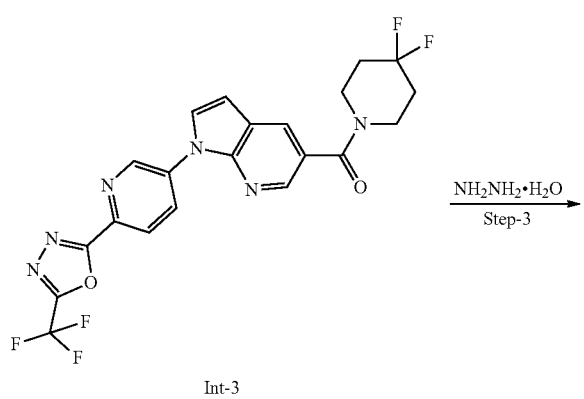

Int-3

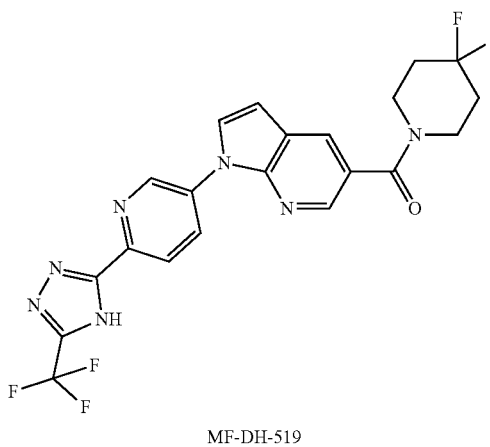

MF-DH-519

The SM (synthesis described in Scheme 45) was converted to Int-1 using the general procedure for Ullmann coupling with the appropriate heteroaryl bromide.

Step-1: Synthesis of (Z)-5-(5-(4,4-difluoropiperidine-1-carbonyl)-1H-pyrrolo[2,3-b]pyridin-1-yl)-N'-hydroxypicolinimidamide (Int-2): 5-(5-(4,4-difluoropiperidine-1-carbonyl)-1H-pyrrolo[2,3-b]pyridin-1-yl)picolinonitrile (Int-1) (200 mg, 0.54 mmol, 1.0 eq.) was converted to (Z)-5-(5-(4,4-difluoropiperidine-1-carbonyl)-1H-pyrrolo[2,3-b]pyridin-1-yl)-N'-hydroxypicolinimidamide as described in the general procedure for the synthesis of 1,2,4-oxadiazol-5(4H)-one from nitrile to afford 150 mg of (Z)-5-(5-(4,4-difluoropiperidine-1-carbonyl)-1H-pyrrolo[2,3-b]pyridin-1-yl)-N'-hydroxypicolinimidamide, Int-2. LCMS: 87.94%, MS: m/z=401.2 [M+H]$^+$.

Step-2: Synthesis of (4,4-difluoropiperidin-1-yl)(1-(6-(5-(trifluoromethyl)-1,3,4-oxadiazol-2-yl)pyridin-3-yl)-1H-pyrrolo[2,3-b]pyridin-5-yl)methanone (Int-3): To a stirred solution of (Z)-5-(5-(4,4-difluoropiperidine-1-carbonyl)-1H-pyrrolo[2,3-b]pyridin-1-yl)-N' hydroxypicolinimidamide (Int-2) (150 mg, 0.3 mmol, 1.0 eq.) in toluene (3 mL) was added trifluoro acetic anhydride (0.1 ml, 0.75 mmol, 1 eq.) at 0° C. The reaction mixture was then heated to reflux for 16 h. The reaction was monitored by crude LCMS/TLC; after complete consumption of the starting material, the reaction mixture was extracted with EtOAc. The combined organic extracts were washed with water (2×10 mL) and brine (10 mL), dried over sodium sulfate, filtered, and concentrated in vacuo to afford 150 mg of (4,4-difluoropiperidin-1-yl)(1-(6-(5-(trifluoromethyl)-1,3,4-oxadiazol-2-yl)pyridin-3-yl)-1H-pyrrolo[2,3-b]pyridin-5-yl)methanone (Int-3) which was directly used for the next step. MS: m/z=479.1 [M+H]$^+$.

Step-3: Synthesis of (4,4-difluoropiperidin-1-yl)(1-(6-(5-(trifluoromethyl)-4H-1,2,4-triazol-3-yl)pyridin-3-yl)-1H-pyrrolo[2,3-b]pyridin-5-yl)methanone (MF-DH-519): To a stirred solution of (4,4-difluoropiperidin-1-yl)(1-(6-(5-(trifluoromethyl)-1,3,4-oxadiazol-2-yl)pyridin-3-yl)-1H-pyrrolo[2,3-b]pyridin-5-yl)methanone (Int-3) (150 mg, 0.31 mmol, 1.0 eq.) in methanol (2 mL), hydrazine hydrate (0.15 mg, 0.93 mmol, 3 eq.) was added at 0° C. The reaction mixture was stirred at room temperature for 16 h. The reaction was monitored by crude LCMS/TLC; after complete consumption of the starting material, the reaction mixture was concentrated in vacuo and extracted with EtOAc. The combined organic extracts were washed with ice water (2×10 mL) and brine (10 mL), dried over sodium sulfate, filtered, and concentrated in vacuo to obtain the crude. The crude was purified through silica gel column chromatography using 50% EtOAc/heptane to afford (4,4-difluoropiperidin-1-yl)(1-(6-(5-(trifluoromethyl)-4H-1,2,4-triazol-3-yl)pyridin-3-yl)-1H-pyrrolo[2,3-b]pyridin-5yl) methanone, MF-DH-519 as brown solid (12 mg, 8% yield). LCMS: 90.27%, MS: m/z=479.1 [M+H]$^+$.

Synthesis of (1-(5-(5-cyclopropyl-1H-1,2,4-triazol-3-yl)pyridin-3-yl)-1H-pyrrolo[2,3-b]pyridin-5-yl)(4,4-difluoropiperidin-1-yl)methanone/(1-(6-(5-cyclopropyl-1H-1,2,4-triazol-3-yl)pyridin-3-yl)-1H-pyrrolo[2,3-b]pyridin-5-yl)(4,4-difluoropiperidin-1-yl)methanone (NW-DH-517 and MF-DH-518)
Scheme 83
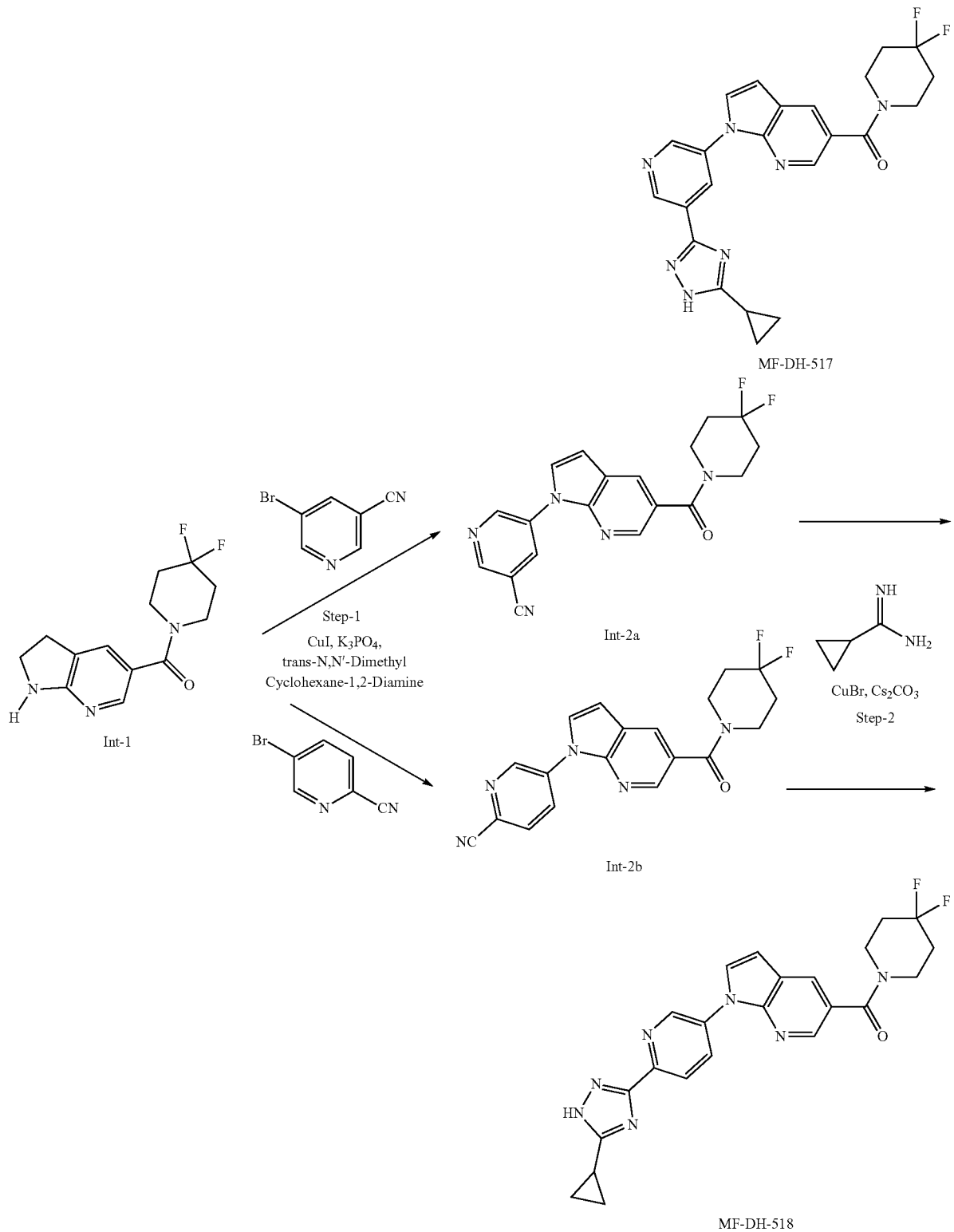

The synthesis of Int-1 is described in Scheme 45.

Step-1: Synthesis of 5-(5-(4,4-difluoropiperidine-1-carbonyl)-1H-pyrrolo[2,3-b]pyridin-1-yl)nicotinonitrile/5-(5-(4,4-difluoropiperidine-1-carbonyl)-1H-pyrrolo[2,3-b]pyridin-1-yl)picolinonitrile (Int-2): (4,4-difluoropiperidin-1-yl)(1H-pyrrolo[2,3-b]pyridin-5-yl)methanone (Int-1) was converted to 5-(5-(4,4-difluoropiperidine-1-carbonyl)-1H-pyrrolo[2,3-b]pyridin-1-yl)nicotinonitrile/5-(5-(4,4-difluoropiperidine-1-carbonyl)-1H-pyrrolo[2,3-b]pyridin-1-yl)picolinonitrile (Int-2) using the general procedure for Ullmann reaction described earlier using 5-bromonicotinonitrile/5-bromopicolinonitrile to afford Int-2a (57% yield; LCMS: 96.3%; MS: m/z=368.2 [M+H]$^+$) and Int-2b (51% yield; LCMS: 92.4% MS: m/z=368.2 [M+H]$^+$) as off white solids.

Step-2: Synthesis of (1-(5-(5-cyclopropyl-1H-1,2,4-triazol-3-yl)pyridin-3-yl)-1H-pyrrolo[2,3-b]pyridin-5-yl)(4,4-difluoropiperidin-1-yl)methanone/(1-(6-(5-cyclopropyl-1H-1,2,4-triazol-3-yl)pyridin-3-yl)-1H-pyrrolo[2,3-b]pyridin-5-yl)(4,4-difluoropiperidin-1-yl)methanone (MF-DH-517 and MF-DH-518) (General procedure for synthesis of 5-cyclopropyl-1,2,4-triazoles from nitriles): To a solution of 5-(5-(4,4-difluoropiperidine-1-carbonyl)-1H-pyrrolo[2,3-b]pyridin-1-yl)nicotinonitrile/5-(5-(4,4-difluoropiperidine-1-carbonyl)-1H-pyrrolo[2,3-b]pyridin-1-yl)picolinonitrile (Int-2) (150 mg, 0.40 mmol, 1.0 eq.) in DMSO (5 mL), Cs$_2$CO$_3$ (400 mg, 1.22 mmol, 3 eq.), CuBr (38 mg, 0.1 eq) was added and the reaction mixture was then heated at 120° C. for 16 h under aerobic conditions. The reaction was monitored by crude LCMS/TLC; after complete consumption of the starting material, the reaction mixture was cooled to room temperature, quenched with ice water (10 mL), and extracted with EtOAc. The organic extracts were washed with ice water (2×10 mL) and brine (10 mL), dried over sodium sulfate, filtered, and concentrated in vacuo to obtain the crude. The crude was purified through silica gel column chromatography followed by Prep-HPLC purification to afford MF-DH-517 (8%) and MF-DH-518 (12%) as off-white solids.

Synthesis of (S)-4-(5-(3-methylpiperidine-1-carbonyl)-1H-pyrrolo[2,3-b]pyridin-1-yl)benzoic acid (MF-DH-562)

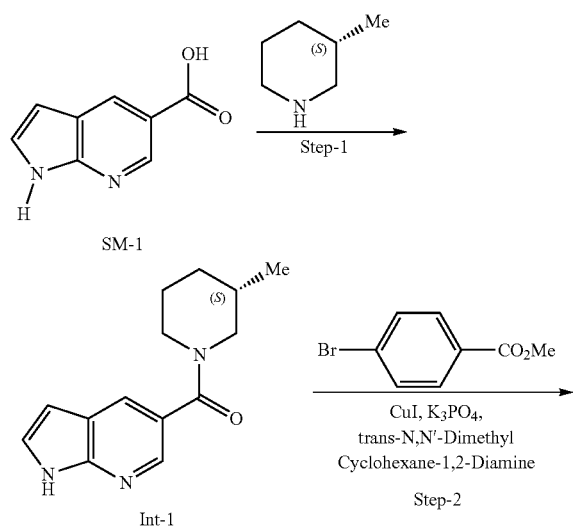

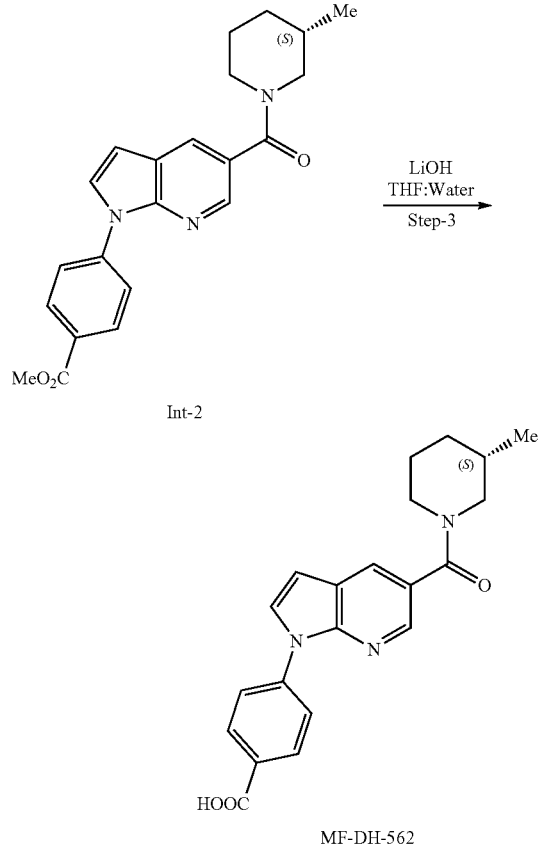

Step-1: Synthesis of (S)-(3-methylpiperidin-1-yl)(1H-pyrrolo[2,3-b]pyridin-5-yl)methanone (Int-1): 1H-pyrrolo[2,3-b]pyridine-5-carboxylic acid (100 mg, 0.62 mmol, 1.0 eq.) was converted to (S)-(3-methylpiperidin-1-yl)(1H-pyrrolo[2,3-b]pyridin-5-yl)methanone using general procedure for acid-amine coupling using HATU (354 mg, 0.93 mmol, 1.5 eq), (S)-3-methylpiperidine HCl (101 mg, 1.2 mmol, 1.2 eq) to afford (S)-(3-methylpiperidin-1-yl) (1H-pyrrolo[2,3-b]pyridin-5-yl)methanone (Int-1, 100 mg, 66.23%) as a brown liquid. MS: m/z=244.1 [M+H]$^+$.

Step-2: Synthesis of methyl (S)-4-(5-(3-methylpiperidine-1-carbonyl)-1H-pyrrolo[2,3-b]pyridin-1-yl)benzoate (Int-2): (S)-(3-methylpiperidin-1-yl)(1H-pyrrolo[2,3-b]pyridin-5-yl)methanone (Int-1) (100 mg, 0.41 mmol, 1.0 eq.) was converted to methyl (S)-4-(5-(3-methylpiperidine-1-carbonyl)-1H-pyrrolo[2,3-b]pyridin-1-yl)benzoate (Int-2) using the general procedure for Ullmann reaction described earlier using methyl 4-bromobenzoate to afford Int-2 after purification (95 mg; 61.29% yield) as an off white solid. LCMS: 99.07%, MS: m/z=378.2 [M+H]$^+$.

Step-3: Synthesis of (S)-4-(5-(3-methylpiperidine-1-carbonyl)-1H-pyrrolo[2,3-b]pyridin-1-yl)benzoic acid (MF-DH-562): Methyl (S)-4-(5-(3-methylpiperidine-1-carbonyl)-1H-pyrrolo[2,3-b]pyridin-1-yl)benzoate (Int-2) was converted to (S)-4-(5-(3-methylpiperidine-1-carbonyl)-1H-pyrrolo[2,3-b]pyridin-1-yl)benzoic acid using general procedure for ester hydrolysis using LiOH to afford (S)-4-(5-(3-methylpiperidine-1-carbonyl)-1H-pyrrolo[2,3-b]pyridin-1-yl)benzoic acid (MF-DH-562, 43 mg, 49.3% yield) as an off white solid. LCMS: 92.02%, MS: m/z=364.2 [M+H]$^+$.

521

Synthesis of (S)-4-(5-(3-fluoropyrrolidine-1-carbonyl)-1H-pyrrolo[2,3-b]pyridin-1-yl)benzonitrile/(R)-4-(5-(3-fluoropyrrolidine-1-carbonyl)-1H-pyrrolo[2,3-b]pyridin-1-yl)benzonitrile (MF-DH-574 and MF-DH-575)

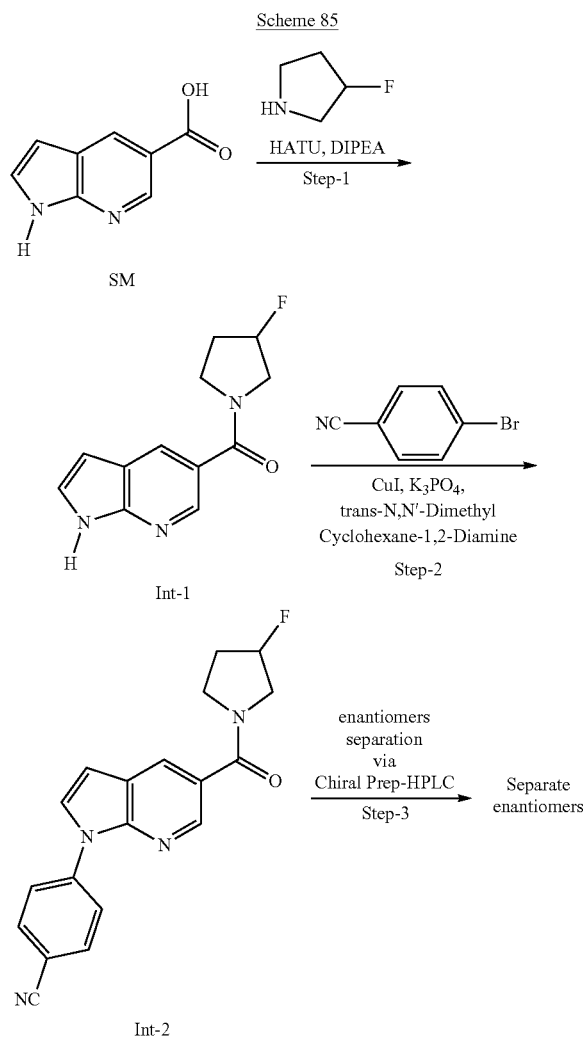

522

HPLC purification to get both the enantiomers separately, MF-DH-574 and MF-DH-575.

Synthesis of 4-(5-(4,4-difluoropiperidine-1-carbonyl)-2-(3-hydroxy-3-methylbutyl)-1H-pyrrolo[2,3-b]pyridin-1-yl)benzoic acid (MF-DH-538)

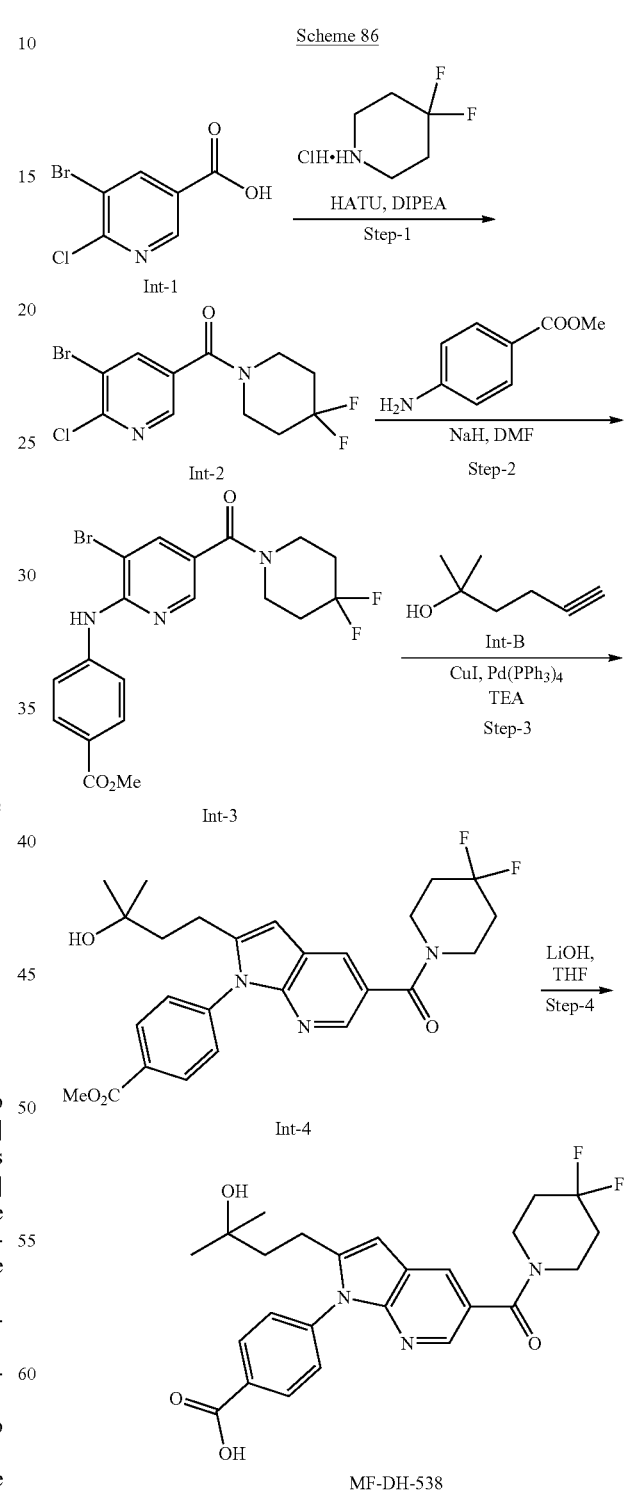

Step-1: Synthesis of (3-fluoropyrrolidin-1-yl)(1H-pyrrolo[2,3-b]pyridin-5-yl)methanone (Int-1): 1H-pyrrolo[2,3-b]pyridine-5-carboxylic acid (500 mg, 3.085 mmol, 1 eq.) was converted to (3-fluoropyrrolidin-1-yl)(1H-pyrrolo[2,3-b]pyridin-5-yl)methanone (Int-1) using the general procedure for acid-amine coupling with HATU and 3-fluoropyrrolidine.HCl to afford Int-1 (500 mg; 71.5%) as an off white solid; LCMS: 99.93%, MS: m/z=234.1 [M+H]⁺.

Step-2 and 3: Synthesis of both enantiomers of 4-(5-(3-fluoropyrrolidine-1-carbonyl)-1H-pyrrolo[2,3-b]pyridin-1-yl)benzonitrile (MF-DH-574 and MF-DH-575): (3-Fluoropyrrolidin-1-yl)(1H-pyrrolo[2,3-b]pyridin-5-yl)methanone (Int-1) (430 mg, 1.8 mmol, 1.0 eq.) was converted to 4-(5-(3-fluoropyrrolidine-1-carbonyl)-1H-pyrrolo[2,3-b]pyridin-1-yl)benzonitrile (Int-2) using the general procedure for Ullmann reaction using 4-bromo benzonitrile to afford racemic Int-2 (220 mg; 36.5% yield) as an off white solid. The racemic product (Int-2) was separated via Chiral Prep- Step-1: Synthesis of (5-bromo-6-chloropyridin-3-yl)(4,4-difluoropiperidin-1-yl)methanone (Int-2): 5-bromo-6-chloronicotinic acid (Int-1) (2.0 g, 8.54 mmol, 1.0 eq.) was converted to (5-bromo-6-chloropyridin-3-yl)(4,4-difluoropiperidin-1-yl)methanone (Int-2) using the general procedure for amide coupling with HATU to afford 5-bromo-6-chloropyridin-3-yl)(4,4-difluoropiperidin-1-yl)methanone, Int-2 (1.8 g, 60% yield) as an off white solid. MS: m/z=338.2 [M+H]⁺, 339.0 [M+2H]⁺.

Step-2: Synthesis of methyl 4-((3-bromo-5-(4,4-difluoropiperidine-1-carbonyl)pyridin-2-yl)amino)benzoate (Int-3): (5-bromo-6-chloropyridin-3-yl)(4,4-difluoropiperidin-1-yl)methanone (Int-2) (400 mg, 1.55 mmol, 1.0 eq.) was subjected to the general procedure for SNAr reaction #3 to afford methyl 4-((3-bromo-5-(4,4-difluoropiperidine-1-carbonyl)pyridin-2-yl)amino)benzoate (Int-3) (200 mg, 37% yield). MS: m/z=454.1 [M+H]⁺, 455.0 [M+2H]⁺.

Step-3: Synthesis of methyl 4-(2-(3-hydroxy-3-methylbutyl)-5-(piperidine-1-carbonyl)-1H-pyrrolo[2,3-b]pyridin-1-yl)benzoate (Int-4): methyl 4-((3-bromo-5-(4,4-difluoropiperidine-1-carbonyl)pyridin-2-yl)amino)benzoate (Int-3) (200 mg, 0.44 mmol, 1.0 eq.) was converted to methyl 4-(2-(3-hydroxy-3-methylbutyl)-5-(piperidine-1-carbonyl)-1H-pyrrolo[2,3-b]pyridin-1-yl)benzoate using general procedure for Sonogashira coupling using 2-methylhex-5-yn-2-ol (Int-B, previously described in the synthesis of MF-DH-330) (148 mg, 1.32 mmol, 3.0 eq) to afford methyl 4-(2-(3-hydroxy-3-methylbutyl)-5-(piperidine-1-carbonyl)-1H-pyrrolo[2,3-b]pyridin-1-yl)benzoate (Int-4, 70 mg, 35% yield) as a sticky liquid. MS: m/z=486 [M+H]⁺.

Step-4: Synthesis of 4-(5-(4,4-difluoropiperidine-1-carbonyl)-2-(3-hydroxy-3-methylbutyl)-1H-pyrrolo[2,3-b]pyridin-1-yl)benzoic acid (MF-DH-538): Methyl 4-(2-(3-hydroxy-3-methylbutyl)-5-(piperidine-1-carbonyl)-1H-pyrrolo[2,3-b]pyridin-1-yl)benzoate (Int-4) (70 mg, 0.14 mmol, 1.0 eq.) was converted to 4-(5-(4,4-difluoropiperidine-1-carbonyl)-2-(3-hydroxy-3-methylbutyl)-1H-pyrrolo[2,3-b]pyridin-1-yl)benzoic acid using general procedure for ester hydrolysis with LiOH to afford MF-DH-538 (28.4 mg, 43.0% yield) as a sticky liquid. MS: m/z=472.2 [M+H]⁺.

Synthesis of 4-(6-(4,4-difluoropiperidine-1-carbonyl)-2-(3-hydroxy-3-methylbut-1-yn-1-yl)-3H-imidazo[4,5-b]pyridin-3-yl)benzonitrile/4-(6-(4,4-difluoropiperidine-1-carbonyl)-2-(5-hydroxy-5-methylhex-1-yn-1-yl)-3H-imidazo[4,5-b]pyridin-3-yl)benzonitrile (MF-DH-476 and MF-DH-544)

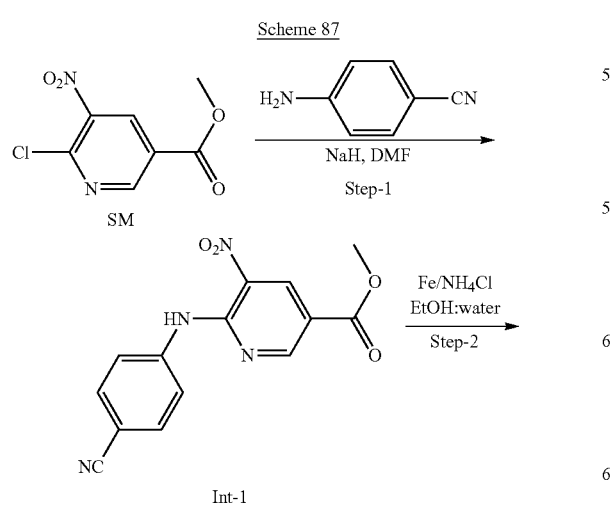

Scheme 87

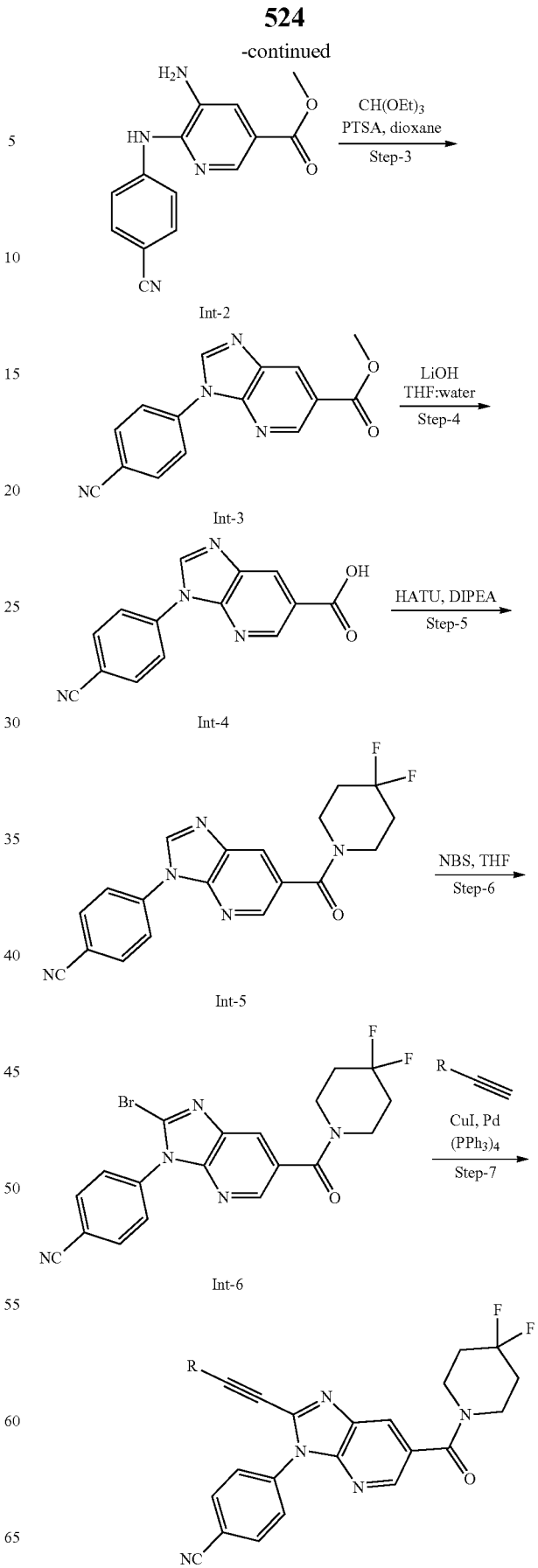

R = 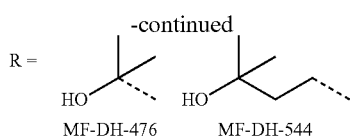

MF-DH-476    MF-DH-544

Step-1: Synthesis of methyl 6-((4-cyanophenyl)amino)-5-nitronicotinate (Int-1): methyl 6-chloro-5-nitronicotinate (SM) (2 g, 9.23 mmol, 1.0 eq.) was converted to methyl 6-((4-cyanophenyl)amino)-5-nitronicotinate (Int-1) using the general procedure for SNAr #3 reaction with NaH and 4-aminobenzonitrile (1.63 g, 13.85 mmol, 1.5 eq.) to obtain methyl 6-((4-cyanophenyl)amino)-5-nitronicotinate (Int-1, 2.0 g, 72.4% yield). The crude was used in the next step without further purification. MS: m/z=299.1 [M+H]$^+$.

Step-2: Synthesis of methyl 5-amino-6-((4-cyanophenyl)amino)nicotinate (Int-2): methyl 6-((4-cyanophenyl)amino)-5-nitronicotinate (Int-1) (2 g, 6.71 mmol, 1.0 eq) was converted to 5-amino-6-((4-cyanophenyl)amino)nicotinate (Int-2) using the general procedure for reduction of nitro compounds using Fe to obtain 5-amino-6-((4-cyanophenyl)amino)nicotinate (Int-2, 350 mg, 14% yield after two steps) as a gummy liquid/semi solid. MS: m/z=269.2 [M+H]$^+$.

Step-3: Synthesis of methyl 3-(4-cyanophenyl)-3H-imidazo[4,5-b]pyridine-6-carboxylate (Int-3): methyl 5-amino-6-((4-cyanophenyl)amino)nicotinate (Int-2) (350 mg, 1.5 mmol, 1.0 eq) was converted to methyl 3-(4-cyanophenyl)-3H-imidazo[4,5-b]pyridine-6-carboxylate by using the general procedure for imidazole cyclisation with PTSA described for MF-PGDH-023 to obtain methyl 3-(4-cyanophenyl)-3H-imidazo[4,5-b]pyridine-6-carboxylate (Int-3, 300 mg, 84% yield) as a pale brown solid. MS: m/z=279.1 [M+H]$^+$.

Step-4: Synthesis of 3-(4-cyanophenyl)-3H-imidazo[4,5-b]pyridine-6-carboxylic acid (Int-4): 3-(4-cyanophenyl)-3H-imidazo[4,5-b]pyridine-6-carboxylate (Int-3) (250 mg, 0.919 mmol, 1.0 eq) was converted to 3-(4-cyanophenyl)-3H-imidazo[4,5-b]pyridine-6-carboxylic acid (Int-4) using the general procedure for ester hydrolysis with LiOH to obtain 4-cyanophenyl-3H-imidazo[4,5-b]pyridine-6-carboxylic acid (Int-4, 200 mg, 84% yield) as an off white solid. MS: m/z=262.1 [M–H]–.

Step-5: Synthesis of 4-(6-(4,4-difluoropiperidine-1-carbonyl)-3H-imidazo[4,5-b]pyridin-3-yl)benzonitrile (Int-5): 4-cyanophenyl-3H-imidazo[4,5-b]pyridine-6-carboxylic acid (Int-4, 200 mg, 0.77 mmol, 1.0 eq) was converted to 4-(6-(4,4-difluoropiperidine-1-carbonyl)-3H-imidazo[4,5-b]pyridin-3-yl)benzonitrile (Int-5) using the general acid-amine coupling using HATU to obtain 4-(6-(4,4-difluoropiperidine-1-carbonyl)-3H-imidazo[4,5-b]pyridin-3-yl)benzonitrile (Int-5, 250 mg, 89.9% yield) as an off white solid. MS: m/z=368.2 [M+H]$^+$.

Step-6: Synthesis of 4-(2-bromo-6-(4,4-difluoropiperidine-1-carbonyl)-3H-imidazo[4,5-b]pyridin-3-yl)benzonitrile (Int-6): To a stirred solution of 4-(6-(4,4-difluoropiperidine-1-carbonyl)-3H-imidazo[4,5-b]pyridin-3-yl)benzonitrile (Int-5) (220 mg, 0.59 mmol, 1.0 eq) in THF (10 v) at room temperature, NBS (320 mg, 1.79 mmol, 3.0 eq) was added and then heated to 60° C. for 3 h. The progress of the reaction was monitored by TLC and LCMS. After consumption of SM, the reaction was diluted with water (20 ml) and extracted with EtOAc (2×30 mL). The combined extracts were washed with sodium thiosulfate solution (20 mL), dried over sodium sulfate, filtered, and concentrated. The crude was purified by combi-flash chromatography to afford 4-(2-bromo-6-(4,4-difluoropiperidine-1-carbonyl)-3H-imidazo[4,5-b]pyridin-3-yl)benzonitrile (Int-6, 90 mg, 33% yield, MS: m/z=447.1 [M+H]$^+$, 448.1 [M+2H]$^+$) as a brown solid.

Step-7: Synthesis of 4-(6-(4,4-difluoropiperidine-1-carbonyl)-2-(3-hydroxy-3-methylbut-1-yn-1-yl)-3H-imidazo[4,5-b]pyridin-3-yl)benzonitrile/4-(6-(4,4-difluoropiperidine-1-carbonyl)-2-(5-hydroxy-5-methylhex-1-yn-1-yl)-3H-imidazo[4,5-b]pyridin-3-yl)benzonitrile (MF-DH-476 and MF-DH-544): 4-(2-bromo-6-(4,4-difluoropiperidine-1-carbonyl)-3H-imidazo[4,5-b]pyridin-3-yl)benzonitrile (Int-6, 80 mg, 0.18 mmol, 1.0 eq.) was converted to 4-(6-(4,4-difluoropiperidine-1-carbonyl)-2-(3-hydroxy-3-methylbut-1-yn-1-yl)-3H-imidazo[4,5-b]pyridin-3-yl)benzonitrile/4-(6-(4,4-difluoropiperidine-1-carbonyl)-2-(5-hydroxy-5-methylhex-1-yn-1-yl)-3H-imidazo[4,5-b]pyridin-3-yl)benzonitrile using the general procedure for Sonogashira coupling with 2-methylbut-3-yn-2-ol/Int-B (previously described in the synthesis of MF-DH-330) to afford MF-DH-476 and MF-DH-544 as off white solids.

Synthesis of (4,4-difluoropiperidin-1-yl)(2-(3-hydroxy-3-methylbutyl)-1-(4-(5-methyl-1,2,4-oxadiazol-3-yl)phenyl)-1H-pyrrolo[2,3-b]pyridin-5-yl)methanone (MF-DH-542)

Scheme 88

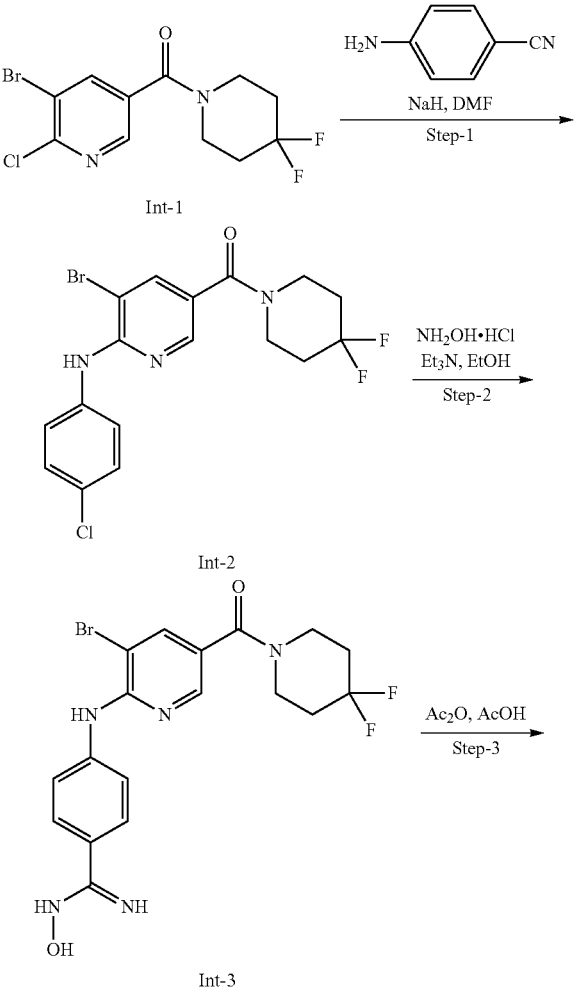

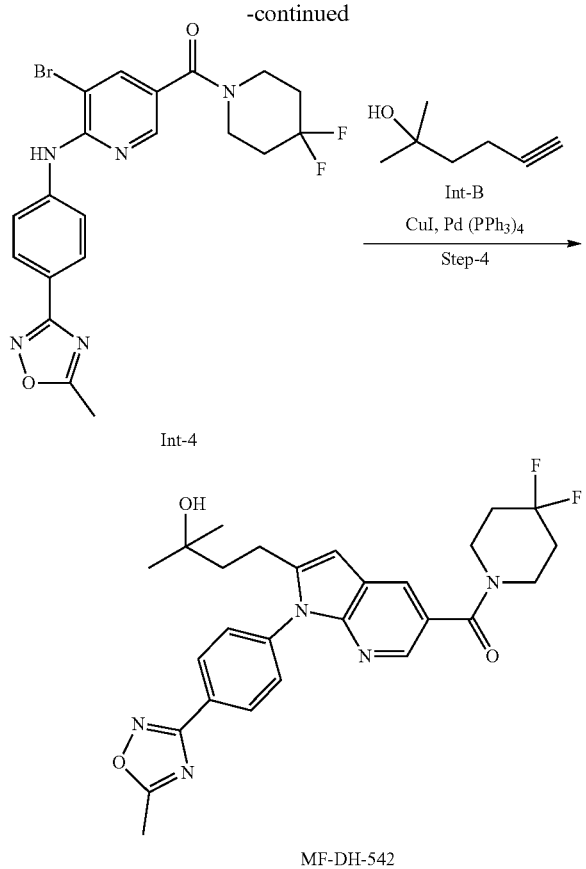

MF-DH-542

Step-1: Synthesis of 4-((3-bromo-5-(4,4-difluoropiperidine-1-carbonyl)pyridin-2-yl)amino)benzonitrile (Int-2): 5-bromo-6-chloropyridin-3-yl)(4,4-difluoropiperidin-1-yl)methanone (Int-1) (1 g, 2.8 mmol) was converted to 4-((3-bromo-5-(4,4-difluoropiperidine-1-carbonyl)pyridin-2-yl)amino)benzonitrile (Int-2) using the general procedure for SNAr #3 reaction described earlier using 4-aminobenzonitrile to afford 4-((3-bromo-5-(4,4-difluoropiperidine-1-carbonyl)pyridin-2-yl)amino)benzonitrile (Int-2, 510 mg; 43% yield, MS: m/z=422.2 [M+H]$^+$, 423.1 [M+2H]$^+$) as an off white solid.

Step-2: Synthesis of 4-((3-bromo-5-(4,4-difluoropiperidine-1-carbonyl)pyridin-2-yl)amino)-N-hydroxybenzimidamide (Int-3): 4-((3-bromo-5-(4,4-difluoropiperidine-1-carbonyl)pyridin-2-yl)amino)benzonitrile (Int-2, 500 mg, 1.18 mmol, 1.0 eq.) was converted to 4-((3-bromo-5-(4,4-difluoropiperidine-1-carbonyl)pyridin-2-yl)amino)-N-hydroxybenzimidamide as described in the general procedure for the synthesis of 1,2,4-oxadiazol-5(4H)-one from nitrile to afford Int-3 (400 mg, crude). The obtained crude of Int-3 was directly used for the next step. MS: m/z=455.1 [M+H]$^+$, 456.2 [M+2H]$^+$.

Step-3: Synthesis of (5-bromo-6-((4-(5-methyl-1,2,4-oxadiazol-3-yl)phenyl)amino)pyridin-3-yl)(4,4-difluoropiperidin-1-yl)methanone (Int-4): To a stirred solution of 4-((3-bromo-5-(4,4-difluoropiperidine-1-carbonyl)pyridin-2-yl)amino)-N-hydroxybenzimidamide (Int-3, 400 mg, 0.88 mmol, 1 eq.) in acetic acid (20 mL) was added acetic anhydride (180 mg, 1.76 mmol, 1.0 eq.) at 0° C. The reaction mixture was then heated to reflux for 16 h. The reaction was monitored by crude LCMS/TLC; after completion of the starting material, the reaction mixture was extracted with EtOAc. The combined organic extracts were washed with water (2×10 mL) and brine (10 mL), dried over sodium sulfate, filtered, and concentrated in vacuo. The crude was purified over combi-flash to afford to 5-bromo-6-((4-(5-methyl-1,2,4-oxadiazol-3-yl)phenyl)amino)pyridin-3-yl)(4,4-difluoropiperidin-1-yl)methanone (Int-4, 150 mg, 35.7% yield, MS: m/z=478.0 [M+H]$^+$, 479.1 [M+2H]$^+$).

Step-4: Synthesis of (4,4-difluoropiperidin-1-yl)(2-(3-hydroxy-3-methylbutyl)-1-(4-(5-methyl-1,2,4-oxadiazol-3-yl)phenyl)-1H-pyrrolo[2,3-b]pyridin-5-yl)methanone (MF-DH-542): (5-bromo-6-((4-(5-methyl-1,2,4-oxadiazol-3-yl)phenyl)amino)pyridin-3-yl)(4,4-difluoropiperidin-1-yl)methanone (Int-4, 130 mg, 0.27 mmol, 1.0 eq.) was converted to (4,4-difluoropiperidin-1-yl)(2-(3-hydroxy-3-methylbutyl)-1-(4-(5-methyl-1,2,4-oxadiazol-3-yl)phenyl)-1H-pyrrolo[2,3-b]pyridin-5-yl)methanone using general procedure for Sonogashira coupling with 2-methylhex-5-yn-2-ol (Int-B, previously described in the synthesis of MF-DH-330) (92 mg, 0.82 mmol, 2.0 eq) to afford (4,4-difluoropiperidin-1-yl)(2-(3-hydroxy-3-methylbutyl)-1-(4-(5-methyl-1,2,4-oxadiazol-3-yl)phenyl)-1H-pyrrolo[2,3-b]pyridin-5-yl)methanone (MF-DH-542, 30 mg, 35% yield, LCMS: 96.8%, MS: m/z=510.1 [M+H]$^+$) as a white solid.

Synthesis of N-(6-(tert-butyl)pyridin-3-yl)-5-(5-(4,4-difluoropiperidine-1-carbonyl)-1H-pyrrolo[2,3-b]pyridin-1-yl)nicotinamide (MF-DH-520)

Scheme 89

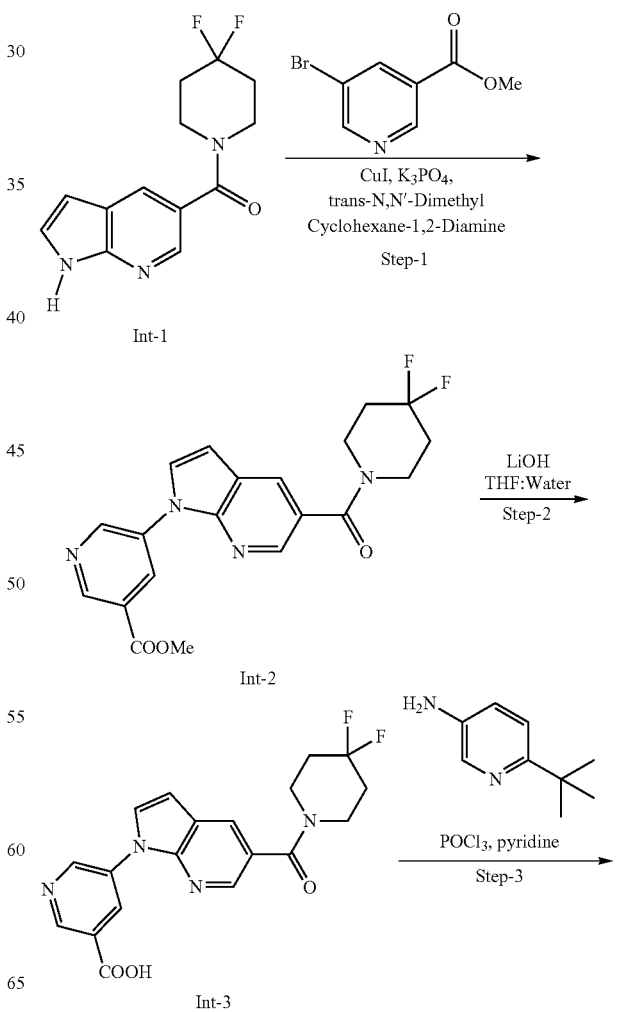

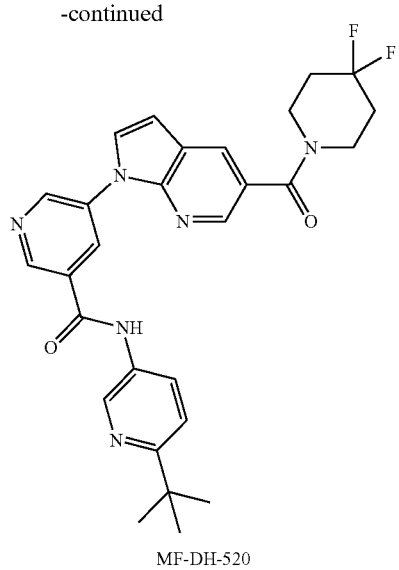

MF-DH-520

The synthesis of Int-1 is described in Scheme 45.

Step-1: Synthesis of methyl 5-(5-(4,4-difluoropiperidine-1-carbonyl)-1H-pyrrolo[2,3-b]pyridin-1-yl)nicotinate (Int-2): (4,4-difluoropiperidin-1-yl)(1H-pyrrolo[2,3-b]pyridin-5-yl)methanone (Int-1, 500 mg, 1.8 mmol, 1.0 eq.) was converted to methyl 5-(5-(4,4-difluoropiperidine-1-carbonyl)-1H-pyrrolo[2,3-b]pyridin-1-yl)nicotinate (Int-2) using the general procedure for Ullmann reaction described earlier, using methyl 5-bromonicotinate to afford methyl 5-(5-(4,4-difluoropiperidine-1-carbonyl)-1H-pyrrolo[2,3-b]pyridin-1-yl)nicotinate (Int-2, 200 mg, 27.47% yield, MS: m/z=387.1 [M+H]$^+$) as white solid.

Step-2: Synthesis of 5-(5-(4,4-difluoropiperidine-1-carbonyl)-1H-pyrrolo[2,3-b]pyridin-1-yl)nicotinic acid (Int-3): Methyl 5-(5-(4,4-difluoropiperidine-1-carbonyl)-1H-pyrrolo[2,3-b]pyridin-1-yl)nicotinate (Int-2, 200 mg, 0.58 mmol, 1.0 eq) was converted to 5-(5-(4,4-difluoropiperidine-1-carbonyl)-1H-pyrrolo[2,3-b]pyridin-1-yl)nicotinic acid using general procedure for ester hydrolysis with LiOH to afford 5-(5-(4,4-difluoropiperidine-1-carbonyl)-1H-pyrrolo[2,3-b]pyridin-1-yl)nicotinic acid (Int-3, 100 mg, 50.2% yield, MS: m/z=387.1 [M+H]$^+$) as off white solid.

Step-3: Synthesis of N-(6-(tert-butyl)pyridin-3-yl)-5-(5-(4,4-difluoropiperidine-1-carbonyl)-1H-pyrrolo[2,3-b]pyridin-1-yl)nicotinamide (MF-DH-520): 5-(5-(4,4-difluoropiperidine-1-carbonyl)-1H-pyrrolo[2,3-b]pyridin-1-yl) nicotinic acid (Int-3, 100 mg, 0.25 mmol, 1.0 eq.) was converted to N-(6-(tert-butyl)pyridin-3-yl)-5-(5-(4,4-difluoropiperidine-1-carbonyl)-1H-pyrrolo[2,3-b]pyridin-1-yl) nicotinamide using the general procedure of acid-amine coupling using POCl$_3$/pyridine to afford to N-(6-(tert-butyl) pyridin-3-yl)-5-(5-(4,4-difluoropiperidine-1-carbonyl)-1H-pyrrolo[2,3-b]pyridin-1-yl)nicotinamide (MF-DH-520, 18 mg, 13.4% yield, LCMS: 99.1%. MS: m/z=519.2 [M+H]$^+$).

Example 2: hPGDH Inhibitor Screening Biochemical Assay

A hydroxyprostaglandin dehydrogenase inhibition screening biochemical assay can be performed to assess the synthesized inhibitors provided herein. Provided herein is an exemplary biochemical assay for hPGDH inhibitor screening.

The in vitro biochemical assay can be performed in white, 384 plates in total 20 μl reaction volume consisting of 10 nM of 15-PGDH/HPGD (R&D System #5660-DH), 15 μM Prostaglandin E2 (Sigma, Cat #P5640-10MG) and 0.25 mM β-Nicotinamide adenine dinucleotide sodium salt (Sigma, Cat #N0632-5G) made in reaction buffer (50 mM Tris-HCl, pH 7.5, 0.01% Tween 20) at 10-point dose response curve for test/tool compounds. Briefly, 5 μl (4×) of compounds solution and 5 μl (final concentration, 10 nM) of enzyme solution is added to white 384 well plates and incubated for 10 mins at 37° C. 5 μl (4×) of Prostaglandin E2 and 5 μl (4×) of β-Nicotinamide adenine dinucleotide sodium salt is added to the wells and incubated for 10 mins at room temperature. Fluorescence is recorded at ex/em=340 nm/485 nm. The percentage (%) inhibition of enzyme activity was determined relative to positive control (1% DMSO) and IC50 was calculated using GraphPad prism software (four parameter-variable slope equation). Exemplary data are shown in Table 4.

TABLE 4

| hPGDH inhibition potency | | | |
|---|---|---|---|
| Molecule Name | hPGDH: Average IC$_{50}$ (μM) | Molecule Name | hPGDH: Average IC$_{50}$ (μM) |
| MF-DH-133 | A | MF-PGDH-047 | C |
| MF-DH-145 | A | MF-PGDH-050 | C |
| MF-DH-140 | A | MF-PGDH-035 | A |
| MF-DH-135 | A | MF-PGDH-024 | A |
| MF-DH-132 | B | MF-PGDH-088 | B |
| MF-DH-157 | A | MF-PGDH-048 | B |
| MF-DH-121 | C | MF-PGDH-090 | C |
| MF-DH-139 | A | MF-PGDH-091 | A |
| MF-DH-138 | B | MF-PGDH-049 | A |
| MF-DH-134 | A | MF-PGDH-046 | B |
| MF-DH-131 | A | MF-PGDH-032 | B |
| MF-DH-116 | C | MF-PGDH-064 | C |
| MF-DH-141 | A | MF-PGDH-065 | C |
| MF-DH-115 | B | MF-PGDH-063 | B |
| MF-DH-128 | B | MF-PGDH-052 | B |
| MF-DH-123 | A | MF-PGDH-045 | B |
| MF-PGDH-075 | A | MF-PGDH-034 | A |
| MF-PGDH-069 | A | MF-PGDH-033 | A |
| MF-PGDH-057 | A | MF-PGDH-007 | A |
| MF-DH-129 | B | MF-PGDH-040 | B |
| MF-DH-118 | B | MF-PGDH-039 | A |
| MF-PGDH-105 | B | MF-PGDH-038 | A |
| MF-PGDH-096 | A | MF-PGDH-030 | A |
| MF-PGDH-022 | A | MF-PGDH-042 | C |
| MF-PGDH-097 | A | MF-PGDH-027 | A |
| MF-PGDH-095 | A | MF-PGDH-037 | A |
| MF-PGDH-106 | A | MF-PGDH-041 | A |
| MF-PGDH-107 | A | MF-PGDH-043 | B |
| MF-PGDH-076 | A | MF-PGDH-036 | A |
| MF-PGDH-062 | A | MF-PGDH-026 | A |
| MF-PGDH-058 | B | MF-PGDH-018 | A |
| MF-PGDH-087 | B | MF-PGDH-023 | A |
| MF-PGDH-074 | A | MF-PGDH-019 | A |
| MF-PGDH-073 | B | MF-PGDH-017 | B |
| MF-PGDH-070 | A | MF-PGDH-016 | A |
| MF-PGDH-067 | A | MF-PGDH-015 | A |
| MF-PGDH-054 | A | MF-PGDH-014 | A |
| MF-PGDH-104 | B | MF-PGDH-005 | A |
| MF-PGDH-068 | A | MF-PGDH-021 | B |
| MF-PGDH-053 | A | MF-PGDH-020 | A |
| MF-PGDH-089 | B | MF-PGDH-012 | A |
| MF-PGDH-079 | A | MF-PGDH-011 | A |
| MF-PGDH-078 | A | MF-PGDH-009 | A |
| MF-PGDH-077 | A | MF-PGDH-008 | A |
| MF-PGDH-071 | A | MF-PGDH-006 | A |
| MF-PGDH-061 | A | MF-PGDH-004 | A |
| MF-PGDH-098 | C | MF-DH-146 | A |
| MF-DH-158 | A | MF-DH-160 | B |
| MF-DH-178 | B | MF-DH-130 | B |

TABLE 4-continued hPGDH inhibition potency

| Molecule Name | hPGDH: Average IC$_{50}$ (μM) | Molecule Name | hPGDH: Average IC$_{50}$ (μM) |
|---|---|---|---|
| MF-DH-180 | B | MF-DH-124 | A |
| MF-DH-169 | A | MF-DH-150 | A |
| MF-DH-166 | A | MF-DH-397 | A |
| MF-DH-384 | A | MF-DH-367 | A |
| MF-DH-365 | A | MF-DH-389 | A |
| MF-DH-374 | A | MF-DH-370 | A |
| MF-DH-369 | A | MF-DH-368 | A |
| MF-DH-347 | A | MF-DH-348 | A |
| MF-DH-345 | A | MF-DH-344 | A |
| MF-DH-343 | A | MF-DH-342 | A |
| MF-DH-329 | A | MF-DH-327 | C |
| MF-DH-319 | A | MF-DH-340 | A |
| MF-DH-328 | B | MF-DH-326 | C |
| MF-DH-317 | A | MF-DH-310 | A |
| MF-DH-309 | A | MF-DH-304 | A |
| MF-DH-303 | B | MF-DH-337 | A |
| MF-DH-336 | A | MF-DH-325 | C |
| MF-DH-324 | B | MF-DH-323 | A |
| MF-DH-322 | A | MF-DH-427 | A |
| MF-DH-318 | A | MF-DH-306 | A |
| MF-DH-302 | A | MF-DH-321 | A |
| MF-DH-312 | C | MF-DH-307 | A |
| MF-DH-308 | A | MF-DH-305 | A |
| MF-DH-301 | A | MF-DH-300 | A |
| MF-DH-299 | A | MF-DH-298 | A |
| MF-DH-311 | C | MF-DH-297 | A |
| MF-DH-296 | A | MF-DH-295 | A |
| MF-DH-294 | A | MF-DH-285 | A |
| MF-DH-274 | A | MF-DH-275 | A |
| MF-DH-273 | A | MF-DH-250 | A |
| MF-DH-251 | A | MF-DH-239 | A |
| MF-DH-191 | A | MF-DH-147 | A |
| MF-DH-149 | C | MF-DH-148 | C |
| MF-DH-394 | A | MF-DH-375 | B |
| MF-DH-371 | A | MF-DH-366 | A |
| MF-DH-462 | C | MF-DH-449 | C |
| MF-DH-448 | A | MF-DH-445 | A |
| MF-DH-439 | A | MF-DH-417 | A |
| MF-DH-406 | A | MF-DH-438 | A |
| MF-DH-437 | A | MF-DH-420 | A |
| MF-DH-433 | A | MF-DH-422 | A |
| MF-DH-419 | A | MF-DH-412 | A |
| MF-DH-411 | A | MF-DH-402 | A |
| MF-DH-270 | A | MF-DH-425 | A |
| MF-DH-424 | A | MF-DH-418 | A |
| MF-DH-416 | A | MF-DH-413 | A |
| MF-DH-405 | A | MF-DH-376 | B |
| MF-DH-364 | A | MF-DH-409 | A |
| MF-DH-407 | A | MF-DH-403 | A |
| MF-DH-396 | A | MF-DH-393 | A |
| MF-DH-355 | A | MF-DH-339 | A |
| MF-DH-330 | A | MF-DH-288 | C |
| MF-DH-404 | A | MF-DH-392 | A |
| MF-DH-378 | A | MF-DH-362 | A |
| MF-DH-359 | A | MF-DH-358 | A |
| MF-DH-357 | A | MF-DH-351 | A |
| MF-DH-400 | A | MF-DH-484 | A |
| MF-DH-395 | A | MF-DH-394 | A |
| MF-DH-390 | A | MF-DH-375 | B |
| MF-DH-371 | A | MF-DH-366 | A |
| MF-DH-363 | A | MF-DH-361 | A |
| MF-DH-341 | B | MF-DH-386 | A |
| MF-DH-290 | A | MF-DH-289 | A |
| MF-DH-388 | A | MF-DH-387 | A |
| MF-DH-385 | A | MF-DH-527 | A |
| MF-PGDH-020 | A | MF-DH-393 | A |
| MF-PGDH-077 | A | MF-DH-396 | A |
| MF-PGDH-078 | A | MF-DH-403 | A |
| MF-PGDH-079 | A | MF-DH-407 | A |
| MF-DH-544 | B | MF-DH-409 | A |
| MF-DH-124 | A | MF-DH-364 | A |
| MF-DH-130 | B | MF-DH-376 | B |
| MF-DH-166 | A | MF-DH-405 | A |
| MF-DH-169 | A | MF-DH-413 | A |
| MF-DH-180 | B | MF-DH-418 | A |
| MF-DH-178 | B | MF-DH-402 | A |
| MF-DH-176 | B | MF-DH-411 | A |
| MF-DH-117 | C | MF-DH-412 | A |
| MF-DH-175 | A | MF-DH-419 | A |
| MF-DH-184 | B | MF-DH-422 | A |
| MF-DH-186 | B | MF-DH-433 | A |
| MF-DH-187 | A | MF-DH-434 | A |
| MF-DH-189 | A | MF-DH-437 | A |
| MF-DH-193 | A | MF-DH-438 | A |
| MF-DH-195 | B | MF-DH-406 | A |
| MF-DH-199 | B | MF-DH-417 | B |
| MF-DH-200 | C | MF-DH-439 | A |
| MF-DH-204 | B | MF-DH-448 | A |
| MF-DH-205 | A | MF-DH-449 | C |
| MF-DH-181 | B | MF-DH-462 | C |
| MF-DH-185 | C | MF-DH-421 | A |
| MF-DH-190 | A | MF-DH-426 | A |
| MF-DH-206 | A | MF-DH-427 | B |
| MF-DH-201 | C | MF-DH-429 | A |
| MF-DH-237 | A | MF-DH-450 | A |
| MF-DH-218 | B | MF-DH-451 | A |
| MF-DH-219 | A | MF-DH-463 | C |
| MF-DH-224 | B | MF-DH-431 | A |
| MF-DH-236 | B | MF-DH-432 | A |
| MF-DH-238 | B | MF-DH-440 | B |
| MF-DH-214 | B | MF-DH-441 | A |
| MF-DH-215 | A | MF-DH-453 | A |
| MF-DH-216 | B | MF-DH-454 | A |
| MF-DH-217 | A | MF-DH-458 | A |
| MF-DH-225 | A | MF-DH-467 | B |
| MF-DH-242 | A | MF-DH-430 | A |
| MF-DH-243 | A | MF-DH-442 | A |
| MF-DH-222 | B | MF-DH-443 | A |
| MF-DH-223 | A | MF-DH-452 | A |
| MF-DH-228 | B | MF-DH-457 | A |
| MF-DH-267 | B | MF-DH-459 | A |
| MF-DH-268 | B | MF-DH-468 | A |
| MF-DH-226 | B | MF-DH-469 | A |
| MF-DH-227 | B | MF-DH-420 | A |
| MF-DH-229 | B | MF-DH-455 | A |
| MF-DH-246 | B | MF-DH-456 | A |
| MF-DH-247 | B | MF-DH-464 | A |
| MF-DH-249 | A | MF-DH-465 | B |
| MF-DH-245 | A | MF-DH-471 | A |
| MF-DH-272 | B | MF-DH-472 | A |
| MF-DH-271 | B | MF-DH-477 | A |
| MF-DH-287 | A | MF-DH-428 | A |
| MF-DH-284 | C | MF-DH-460 | A |
| MF-DH-292 | A | MF-DH-470 | A |
| MF-DH-337 | A | MF-DH-480 | A |
| MF-DH-340 | A | MF-DH-482 | A |
| MF-DH-346 | A | MF-DH-485 | A |
| MF-DH-380 | A | MF-DH-478 | A |
| MF-DH-385 | B | MF-DH-479 | A |
| MF-DH-387 | A | MF-DH-481 | A |
| MF-DH-388 | A | MF-DH-484 | A |
| MF-DH-389 | A | MF-DH-486 | A |
| MF-DH-289 | A | MF-DH-489 | B |
| MF-DH-290 | A | MF-DH-496 | A |
| MF-DH-365 | A | MF-DH-498 | A |
| MF-DH-382 | A | MF-DH-499 | A |
| MF-DH-383 | A | MF-DH-500 | A |
| MF-DH-397 | A | MF-DH-501 | A |
| MF-DH-361 | A | MF-DH-487 | A |
| MF-DH-363 | A | MF-DH-491 | A |
| MF-DH-366 | A | MF-DH-507 | A |
| MF-DH-395 | A | MF-DH-508 | A |
| MF-DH-399 | A | MF-DH-509 | A |
| MF-DH-400 | A | MF-DH-515 | A |
| MF-DH-351 | A | MF-DH-444 | A |
| MF-DH-362 | A | MF-DH-495 | A |
| MF-DH-392 | A | MF-DH-514 | A |
| MF-DH-404 | A | MF-DH-521 | A |

TABLE 4-continued hPGDH inhibition potency

| Molecule Name | hPGDH: Average IC$_{50}$ (μM) | Molecule Name | hPGDH: Average IC$_{50}$ (μM) |
|---|---|---|---|
| MF-DH-288 | B | MF-DH-446 | B |
| MF-DH-330 | A | MF-DH-497 | A |
| MF-DH-355 | A | MF-DH-502 | A |
| MF-DH-424 | A | MF-DH-516 | A |
| MF-DH-425 | A | MF-DH-575 | A |
| MF-DH-574 | A | MF-DH-562 | A |
| MF-DH-476 | B | MF-DH-542 | A |
| MF-DH-519 | A | MF-DH-518 | A |
| MF-DH-538 | A | MF-DH-520 | A |
| MF-DH-517 | A | | |

A < 0.1 μM; 0.1 μM ≤ B < 1 μM; 1 μM ≤ C

Example 3: Liver Microsome Stability Assay

A microsomal mixture (microsomes and Kphos buffer) was prepared at a concentration of 1.428 mg/mL in 2 mL tubes. To this microsomal mixture 1.6 μL (1 mM) of test compound and positive control were spiked; from this mixture, 70 μL was transferred to 96 well plate and pre-incubated at 37° C. for 5 min. After pre-incubation, the zero minute time point reaction was stopped using 100 μL of ice-cold acetonitrile containing internal standard and μL of NADPH (3.33 mM in Kphos buffer) was added. The 45 minute time point reaction was initiated by addition of 30 μL of NADPH (3.33 mM in Kphos buffer) and incubated at 37° C. for 15 and 45 min. Reactions without NADPH and buffer controls (minus NADPH) at 0, 15, and 45 minutes were also incubated to rule out non-NADPH metabolism or chemical instability in the incubation buffer. Incubation reactions were stopped with 100 μL of ice-cold acetonitrile containing internal standard. The plates were centrifuged at 4000 RPM for 15 min and 100 μL aliquots were submitted for analysis by LC-MS/MS. (Verapamil in human liver microsomes (HLM) and rat liver microsomes (RLM) was used as positive controls. Imipramine in mouse liver microsomes (MLM) was used as a positive control.) Samples were monitored for parent compound disappearance in MRM mode (multiple reaction monitoring) using LC-MS/MS. The peak area ratios of analyte versus internal standard were used to calculate the % remaining at the end of 45 minutes in the presence of NADPH.

Exemplary data are shown in Table 5.

TABLE 5

| | Liver Microsome Stability | | | |
|---|---|---|---|---|
| Molecule Name | HLM + NADPH (% remaining at 45 min) | MLM + NADPH (% remaining at 45 min) | RLM + NADPH (% remaining at 45 min) | Solubility: Solubility at pH 7.4 (μM) |
| MF-PGDH-020 | 87 | 30 | 23 | 150 |
| MF-PGDH-077 | 97 | | 84 | 160 |
| MF-PGDH-078 | 96 | | 89 | 140 |
| MF-PGDH-079 | 100 | | 87 | 140 |
| MF-DH-124 | 48 | | 34 | |
| MF-DH-130 | 68 | | 74 | |
| MF-DH-166 | 47 | | 33 | |
| MF-DH-169 | 71 | | 69 | |
| MF-DH-175 | 117 | | 45 | |
| MF-DH-187 | | | 17 | |
| MF-DH-189 | | | 23 | |
| MF-DH-193 | | | 0 | |
| MF-DH-205 | | | 78 | |
| MF-DH-190 | | | 29 | |
| MF-DH-206 | | | 9 | |
| MF-DH-201 | | | 48 | |
| MF-DH-237 | | | 0 | |
| MF-DH-218 | | | 34 | |
| MF-DH-219 | | | 26 | |
| MF-DH-224 | | | 38 | |
| MF-DH-214 | | | 60 | |
| MF-DH-215 | | | 45 | |
| MF-DH-216 | | | 64 | |
| MF-DH-217 | | | 34 | |
| MF-DH-225 | | | 40 | |
| MF-DH-242 | | | 51 | |
| MF-DH-243 | | | 34 | |
| MF-DH-223 | | | 74 | |
| MF-DH-228 | | | 69 | |
| MF-DH-267 | | | 67 | |
| MF-DH-268 | | | 60 | |
| MF-DH-227 | | | 48 | |
| MF-DH-229 | | | 39 | |
| MF-DH-246 | | | 46 | |
| MF-DH-247 | | | 22 | |
| MF-DH-249 | | | 29 | |
| MF-DH-245 | | | 16 | |
| MF-DH-287 | | | 44 | |
| MF-DH-292 | | | 27 | 69 |
| MF-DH-337 | | | 1 | <5.0 |
| MF-DH-380 | 89 | | | 75 |
| MF-DH-387 | 72 | | | |
| MF-DH-365 | 41 | | | |
| MF-DH-382 | 26 | | | |
| MF-DH-383 | 12 | | | |
| MF-DH-395 | 8 | | | 80 |
| MF-DH-399 | 6 | | | |
| MF-DH-400 | 0 | | | |
| MF-DH-404 | 101 | | | <5.0 |
| MF-DH-396 | 4 | | | |
| MF-DH-403 | 45 | | | |
| MF-DH-407 | 51 | | | |
| MF-DH-409 | 78 | | | |
| MF-DH-405 | 86 | | | |
| MF-DH-413 | 94 | | | |
| MF-DH-411 | 87 | | | |
| MF-DH-412 | 97 | | | |
| MF-DH-422 | 87 | | | |
| MF-DH-434 | 94 | | | |
| MF-DH-437 | 25 | | | |
| MF-DH-438 | 63 | | | |
| MF-DH-406 | 66 | | | |
| MF-DH-448 | 79 | | | |
| MF-DH-429 | 97 | | | |
| MF-DH-453 | 116 | | | >100 |
| MF-DH-454 | 92 | | | >100 |
| MF-DH-458 | 68 | | | 62 |
| MF-DH-467 | 90 | | | |
| MF-DH-452 | 90 | | | |
| MF-DH-457 | 87 | | | |
| MF-DH-459 | 31 | | | |
| MF-DH-455 | 86 | | | |
| MF-DH-464 | 100 | | | |
| MF-DH-471 | 99 | | | |
| MF-DH-472 | 83 | | | |
| MF-DH-428 | 97 | | | |
| MF-DH-470 | 74 | | | |
| MF-DH-482 | 103 | | | |
| MF-DH-485 | 80 | | | |
| MF-DH-481 | 81 | | | |
| MF-DH-498 | 0 | | | |
| MF-DH-499 | 15 | | | |
| MF-DH-500 | 60 | | | |
| MF-DH-507 | 97 | | | |
| MF-DH-508 | 37 | | | |
| MF-DH-515 | 103 | | | |
| MF-DH-514 | 110 | | | |

TABLE 5-continued

| Molecule Name | Liver Microsome Stability | | | Solubility: Solubility at pH 7.4 (μM) |
|---|---|---|---|---|
| | HLM + NADPH (% remaining at 45 min) | MLM + NADPH (% remaining at 45 min) | RLM + NADPH (% remaining at 45 min) | |
| MF-DH-521 | | 84 | | |
| MF-DH-516 | | 88 | | |
| MF-DH-424 | | 96 | | 156 |
| MF-DH-542 | | 68 | | |
| MF-DH-519 | | 89 | | |
| MF-DH-518 | | 92 | | |
| MF-DH-538 | | 91 | | |
| MF-DH-520 | | 38 | | |
| MF-DH-517 | | 47 | | |

HLM = human liver microsomes; MLM = mouse liver microsomes, RLM = rat liver microsomes Example 4: A549 Cell-Based Assay 30,000 A549 cells per well were seeded into a tissue culture treated flat bottom 96 well plate, and incubated for 24 hours in a 37° C., 500 $CO_2$ incubator. After 24 hours of incubation, complete media were replaced with 100 μL of low serum (F12K+1% FBS) media and the plate was incubated for 24 hours in a 37° C., 5% $CO_2$ incubator. After 24 hours of incubation, low serum media was replaced with 80 μL of complete medium (F12K+10% FBS) and 10 μL (10× concentration) of compounds were added and incubated at 37° C. for 30 minutes followed by stimulation of 10 μL (10× concentration) of IL-1b (Final concentration 0.25 ng/mL) overnight in a 37° C., 500 $CO_2$ incubator. After 24 hours of incubation, the supernatant was collected and the $PGE_2$ level was detected by using Cisbio HTRF kit (Catalog #62P2APEH). Briefly, 5 μL of sample (100-Fold diluted) was dispensed into each sample well. 5 μL of each Prostaglandin E2 standard (Std 0-Std 7) was dispensed into each standard well. 2.5 μL of Prostaglandin E2-d2 working solution was added to all wells except negative controls and 2.5 μL of Anti-Prostaglandin $E_2$-Eu3+ Cryptate working solution was added to all wells. The plate was sealed and incubated for 5 hours at room temperature. After 5 hours of incubation, the plate sealer was removed and the plate was read on a HTRF® compatible reader. Delta F and $PGE_2$ level were calculated as per kit instructions. % Fold change was calculated with respect to DMSO control wells.

The cell-based assay was considered a positive response when treated cells had >1.5-fold the level of $PGE_2$ in the vehicle treated cells when normalized as described above. Selected compounds which had >1.5 fold induction of $PGE_2$ over the positive control when tested at 1 μM include MF-DH-455, MF-DH-343, MF-DH-458, MF-DH-519, MF-DH-459, MF-DH-319, MF-DH-516, MF-DH-296, MF-DH-456, MF-DH-520, MF-PGDH-068, MF-DH-357, MF-DH-485, MF-DH-380, MF-PGDH-070, MF-DH-368, MF-DH-135, MF-DH-472, MF-DH-469, MF-DH-393, MF-DH-419, MF-DH-301, MF-DH-517, MF-PGDH-062, MF-DH-518, MF-DH-358, MF-DH-300, MF-DH-387, MF-DH-522, MF-DH-342, MF-DH-384, MF-DH-275, MF-DH-473, MF-PGDH-071, MF-DH-404, MF-DH-482, MF-PGDH-004, MF-DH-470, MF-DH-295, MF-DH-369, MF-DH-413, MF-DH-424, MF-DH-307, MF-PGDH-008, MF-DH-406, MF-DH-403, MF-DH-418, MF-DH-297, MF-PGDH-076, MF-DH-239, MF-PGDH-006, MF-DH-471, MF-DH-298, MF-DH-521, MF-DH-345, MF-PGDH-035, MF-DH-336, MF-DH-400, MF-DH-361, MF-DH-514, MF-DH-394, MF-DH-299, MF-DH-242, MF-DH-407, MF-DH-396, MF-DH-481, MF-DH-434, MF-DH-359, MF-DH-243, MF-DH-542, MF-DH-430, MF-DH-444, MF-DH-448, MF-DH-422, MF-DH-367, MF-DH-409, MF-DH-157, MF-DH-370, MF-DH-451, MF-DH-405, MF-DH-495, MF-DH-478, and MF-DH-355.

As an example, data for MF-DH-191, MF-DH-342, MF-DH-357, and MF-DH-358 are shown in FIG. 1; MF-DH-342, MF-DH-357, and MF-DH-358 displayed activity in this assay.

What is claimed is:

1. A compound having the structure of Formula IIq:

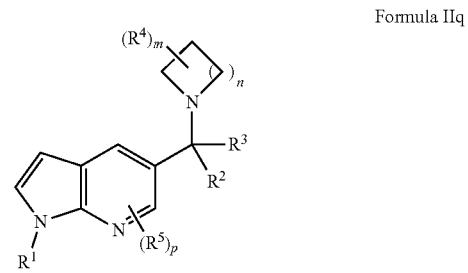

Formula IIq or a pharmaceutically acceptable salt thereof, wherein:
$R^1$ is selected from $C_{6-10}$aryl and 5- to 10-membered heteroaryl; wherein said aryl or heteroaryl is optionally substituted with 1 to 3 substituents each independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^1SO_2R^8$, —$NR^{10}SO_2NR^6R^7$, $C_{1-6}$alkyl, $C_{1-6}$haloalkyl, $C_{3-10}$cycloalkyl, and 5- to 10-membered heteroaryl;
$R^2$ is H and $R^3$ is —$CF_3$; or
$R^2$ and $R^3$ are taken together to form oxo;
each $R^4$ is independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$haloalkyl, $C_{3-10}$cycloalkyl, $C_{6-10}$aryl, and 5- to 10-membered heteroaryl; or
two $R^4$'s are taken together with the carbon atoms to which they are attached and any intervening atoms to form a $C_{3-10}$cycloalkyl, and any remaining $R^4$'s are independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$haloalkyl, $C_{3-10}$cycloalkyl, $C_{6-10}$aryl, and 5- to 10-membered heteroaryl;
each $R^5$ is selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}SO_2R^8$, $C_{1-6}$alkyl, and $C_{1-6}$haloalkyl;
$R^6$ and $R^7$ are independently selected at each occurrence from H, $C_{1-6}$alkyl, $C_{1-6}$haloalkyl, and $C_{3-10}$cycloalkyl;
each $R^8$ is independently selected from H, $C_{1-6}$alkyl, $C_{1-6}$haloalkyl, $C_{3-10}$cycloalkyl, $C_{6-10}$aryl, and 5- to 10-membered heteroaryl;
each $R^9$ is independently selected from $C_{1-6}$alkyl, $C_{1-6}$haloalkyl, $C_{3-10}$cycloalkyl, $C_{6-10}$aryl, and 5- to 10-membered heteroaryl;
each $R^{10}$ is independently selected from H, $C_{1-6}$alkyl, $C_{1-6}$haloalkyl, and $C_{3-10}$cycloalkyl;

n is 1, 2, 3, or 4;
m is 0, 1, 2, 3, 4, 5, 6, 7, 8, 9, or 10; and
p is 0, 1, 2, or 3.

2. The compound of claim 1, or a pharmaceutically acceptable salt thereof, wherein $R^2$ and $R^3$ are taken together to form oxo.

3. The compound of claim 1, or a pharmaceutically acceptable salt thereof, wherein $R^2$ is H and $R^3$ is —$CF_3$.

4. The compound of claim 1, or a pharmaceutically acceptable salt thereof, wherein each $R^4$ is independently selected from halo, —$NR^6R^7$, —$OR^8$, —$C(O)R^8$, —$C(O)OR^8$, and —$C(O)NR^6R^7$.

5. The compound of claim 1, or a pharmaceutically acceptable salt thereof, wherein each $R^4$ is halo.

6. The compound of claim 1, or a pharmaceutically acceptable salt thereof, wherein two $R^4$'s are taken together with the carbon atoms to which they are attached and any intervening atoms to form a $C_{3-10}$cycloalkyl, and any remaining $R^4$'s are each independently selected from halo, —$NR^6R^7$, —$OR^8$, —$C(O)R^8$, —$C(O)OR^8$, and —$C(O)NR^6R^7$.

7. The compound of claim 1, or a pharmaceutically acceptable salt thereof, wherein m is 0, 1, or 2.

8. The compound of claim 1, or a pharmaceutically acceptable salt thereof, wherein n is 2 or 3.

9. The compound of claim 1, or a pharmaceutically acceptable salt thereof, wherein each $R^5$ is selected from halo, —$NR^6R^7$, —$OR^8$, $C_{1-6}$alkyl, and $C_{1-6}$haloalkyl.

10. The compound of claim 1, or a pharmaceutically acceptable salt thereof, wherein p is 0.

11. The compound of claim 1, or a pharmaceutically acceptable salt thereof, wherein $R^1$ is selected from $C_{6-10}$aryl and 5- to 10-membered heteroaryl; wherein said aryl or heteroaryl is optionally substituted with 1 to 3 substituents independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, $C_{1-6}$alkyl, $C_{1-6}$haloalkyl, $C_{3-10}$cycloalkyl, and 5- to 10-membered heteroaryl.

12. The compound of claim 11, or a pharmaceutically acceptable salt thereof, wherein $R^1$ is selected from $C_{6-10}$aryl and 5- to 10-membered heteroaryl; wherein said aryl or heteroaryl is optionally substituted with 1 to 3 substituents each independently selected from halo, —$NR^6R^7$, —$OR^8$, —$C(O)R^8$, —$C(O)OR^8$, and —$C(O)NR^6R^7$.

13. The compound of claim 11, or a pharmaceutically acceptable salt thereof, wherein $R^1$ is $C_{6-10}$aryl.

14. The compound of claim 13, or a pharmaceutically acceptable salt thereof, wherein the aryl is phenyl.

15. The compound of claim 11, or a pharmaceutically acceptable salt thereof, wherein $R^1$ is 5- to 10-membered heteroaryl.

16. The compound of claim 15, or a pharmaceutically acceptable salt thereof, wherein the heteroaryl is selected from isothiazolyl, imidazolyl, indazolyl, indolyl, indazolyl, isoindolyl, indolinyl, isoindolinyl, isoquinolyl, indolizinyl, isoxazolyl, purinyl, pyrrolyl, pyrazolyl, pyridinyl, pyrazinyl, pyrimidinyl, pyridazinyl, pyrrolyl, thiazolyl, thiadiazolyl, triazolyl, tetrazolyl, triazinyl, and thiophenyl.

17. The compound of claim 1, or a pharmaceutically acceptable salt thereof, wherein:
$R^1$ is selected from $C_{6-10}$aryl and 5- to 10-membered heteroaryl, substituted with a substituent independently selected from halo, —$NR^6R^7$, —$OR^8$, —$C(O)R^8$, —$C(O)OR^8$, —$C(O)NR^6R^7$, —$SOR^9$, —$SO_2R^9$, —$SO_2NR^6R^7$, —$NR^{10}C(O)R^8$, —$NR^{10}C(O)NR^6R^7$, —$NR^{10}SO_2R^8$, —$NR^{10}SO_2NR^6R^7$, $C_{1-6}$alkyl, $C_{1-6}$haloalkyl, $C_{3-10}$cycloalkyl, and 5- to 10-membered heteroaryl;

$R^2$ and $R^3$ are taken together to form oxo;

each $R^4$ is independently selected from halo, $C_{1-6}$alkyl, and $C_{1-6}$haloalkyl; and n is 3, m is 0, 1, or 2, and p is 0.

18. The compound of claim 1, or a pharmaceutically acceptable salt thereof, wherein the compound is selected from the group consisting of:

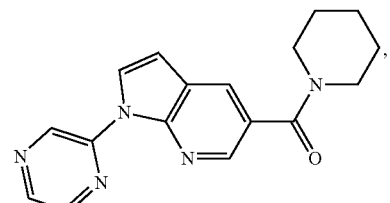

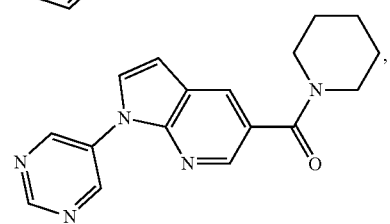

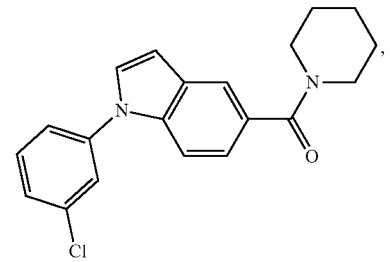

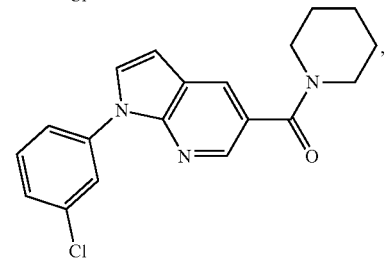

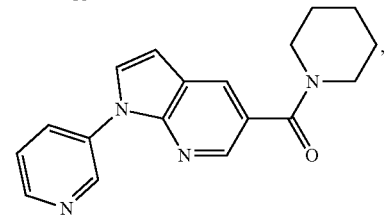

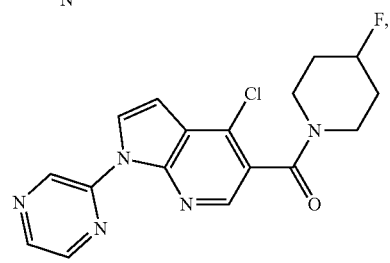

539
-continued
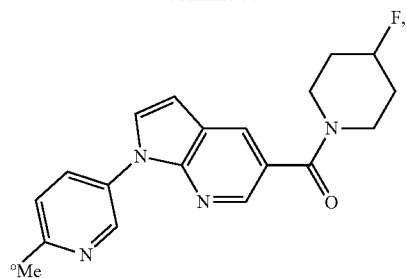
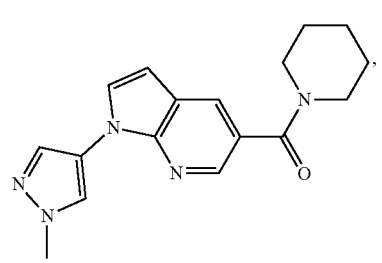
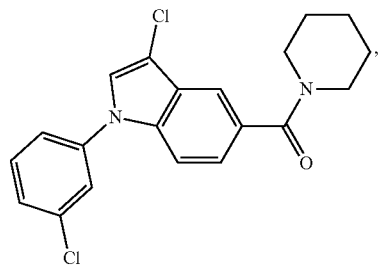
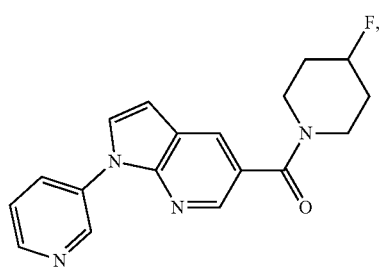
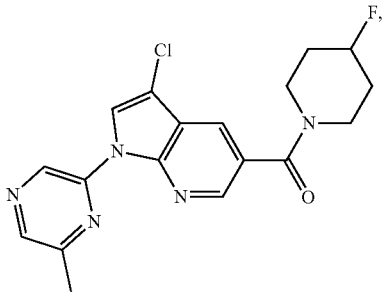
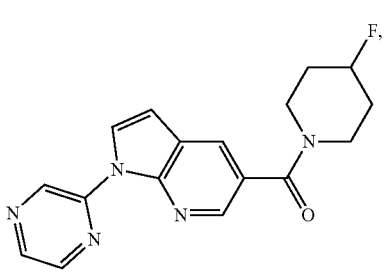
540
-continued
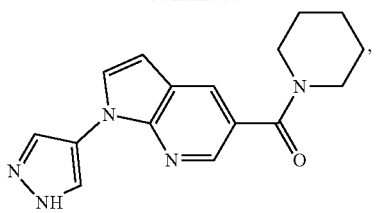
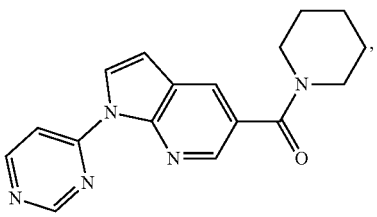
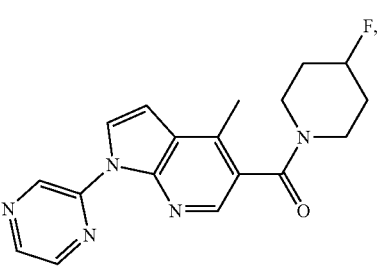
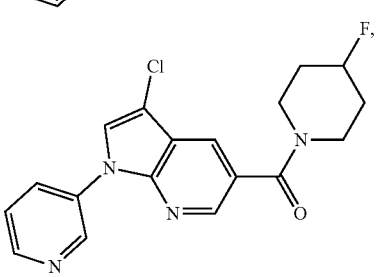
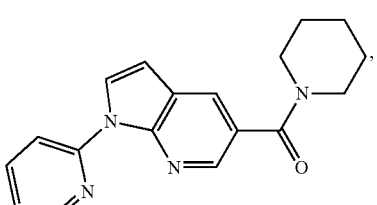
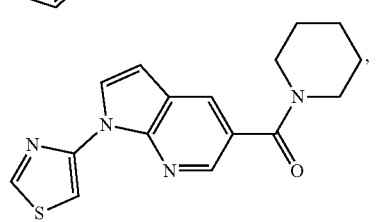
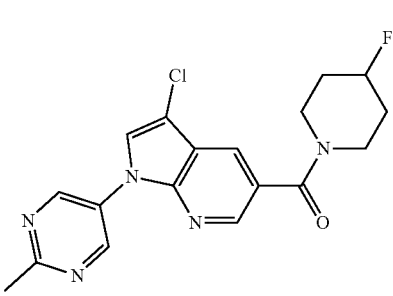

541
-continued
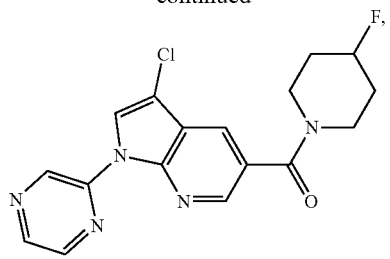
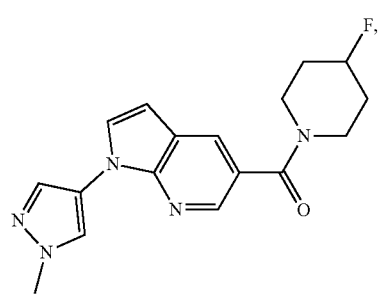
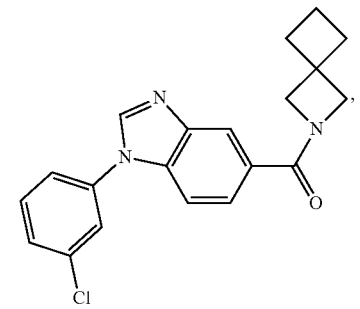
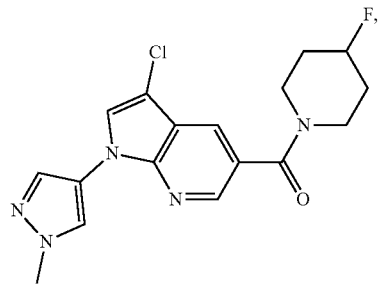
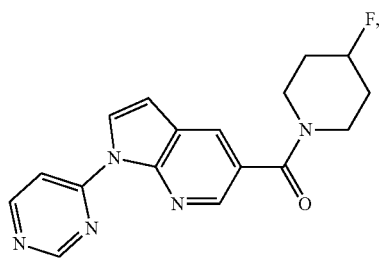
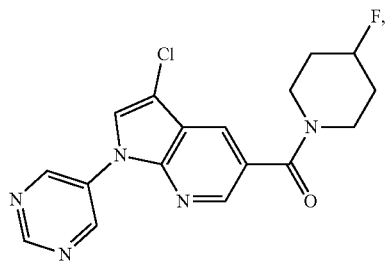
542
-continued
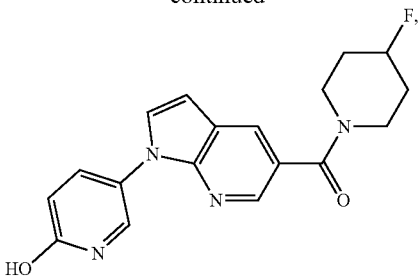
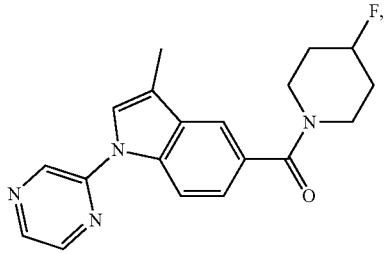
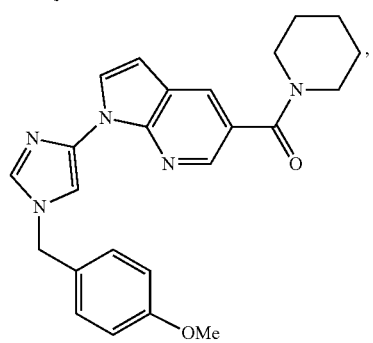
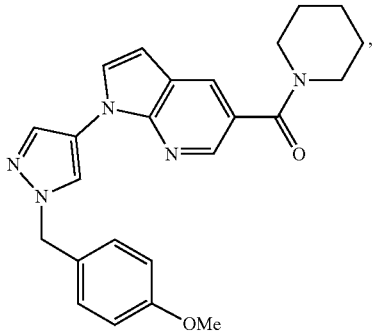
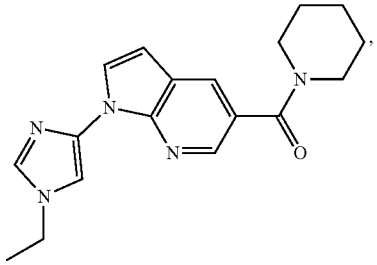
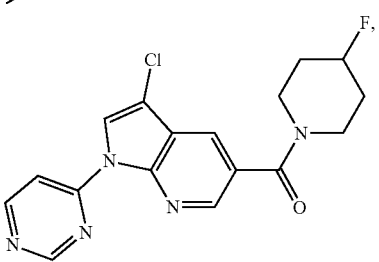

543
-continued
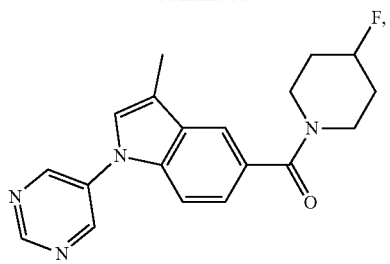
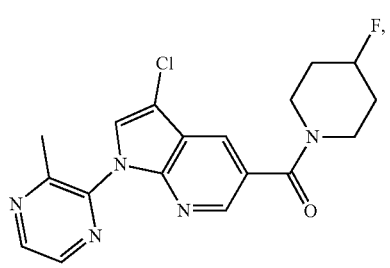
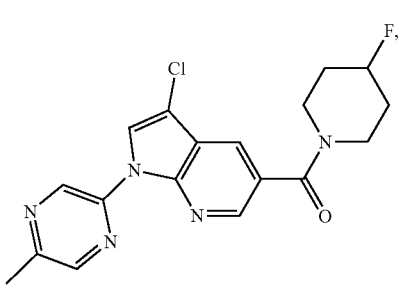
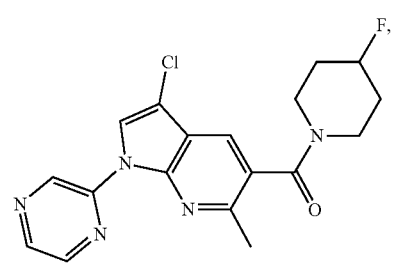
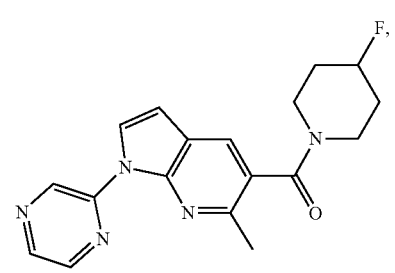
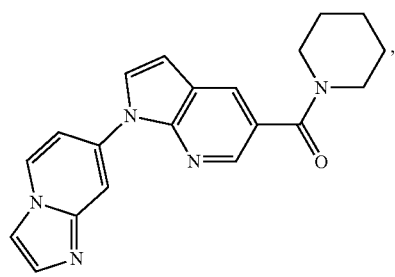
544
-continued
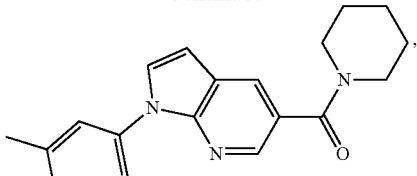
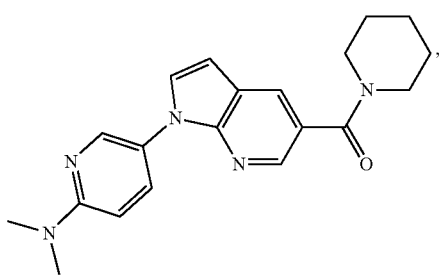
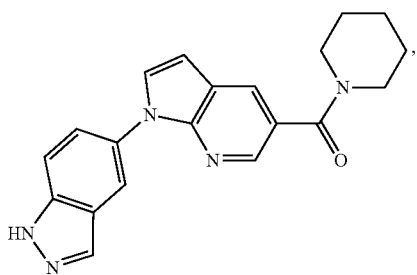
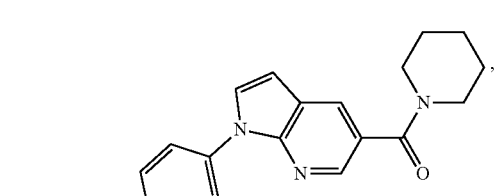
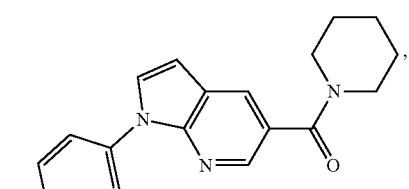
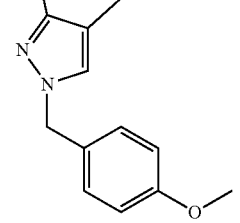

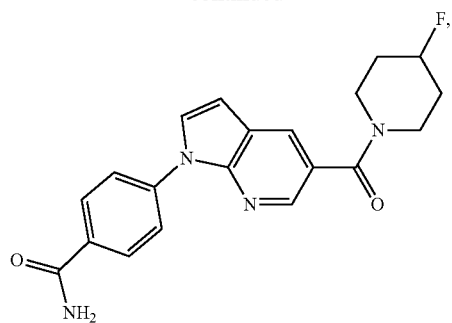
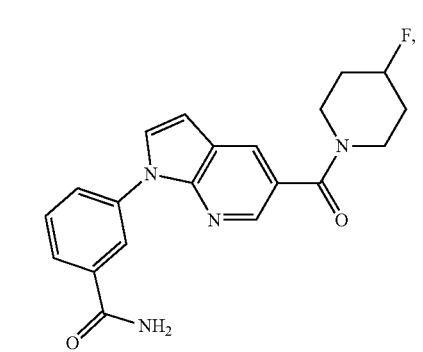
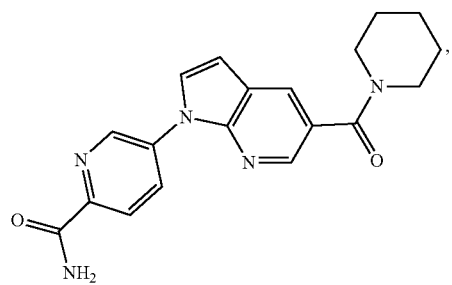
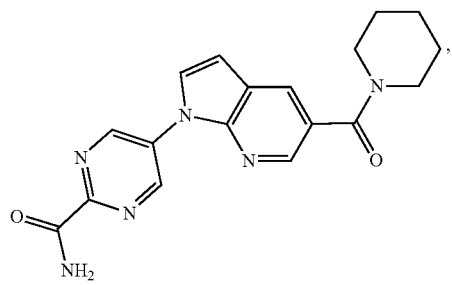
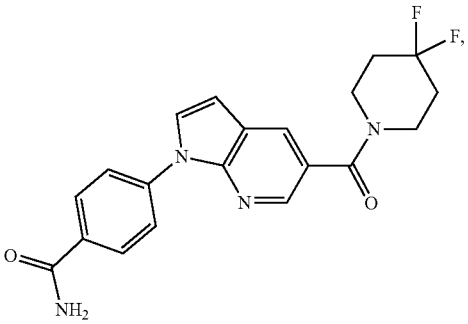
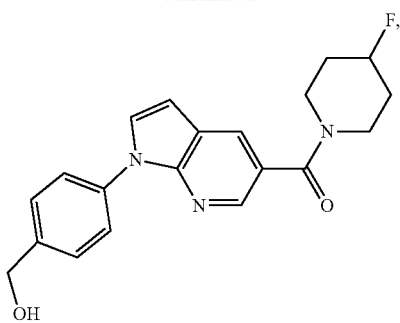
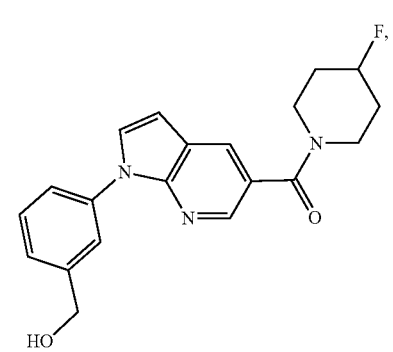
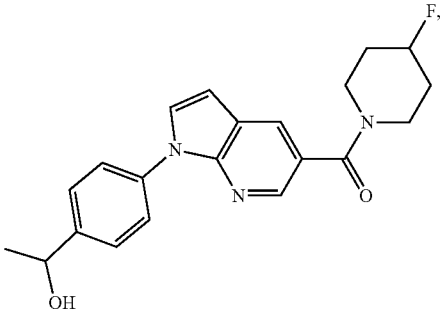
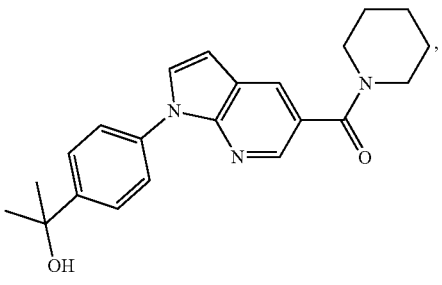
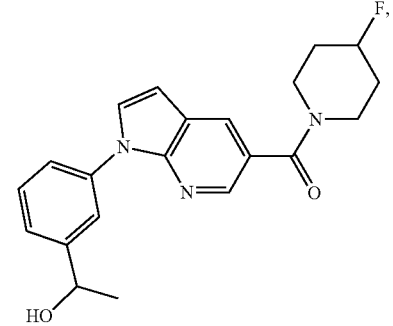

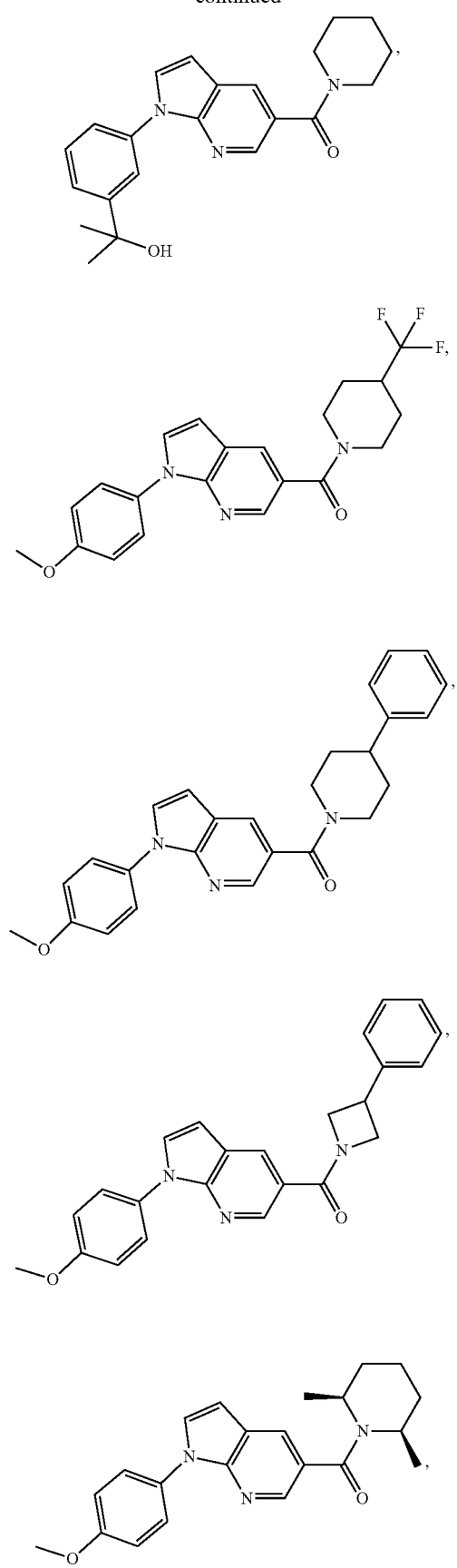

549
-continued
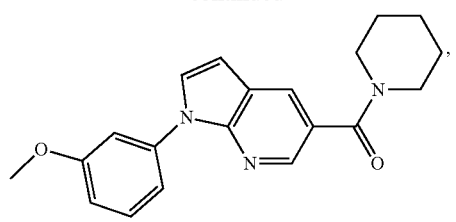
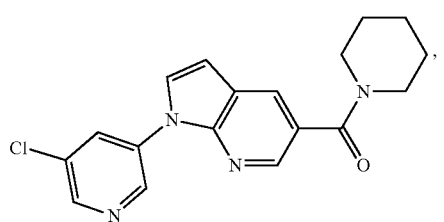
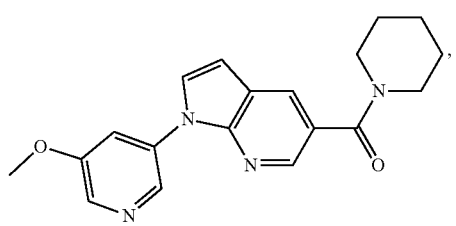
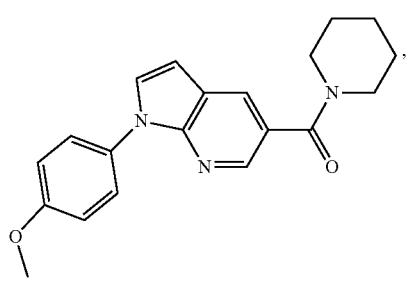
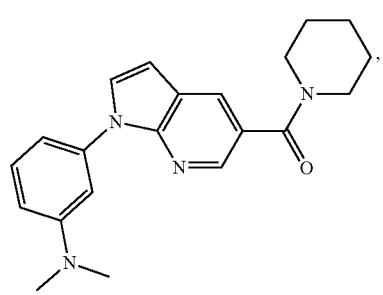
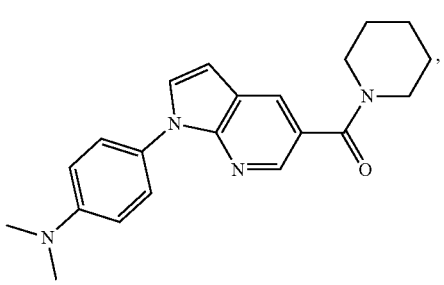
550
-continued
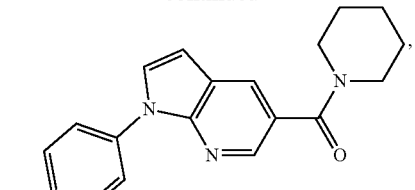
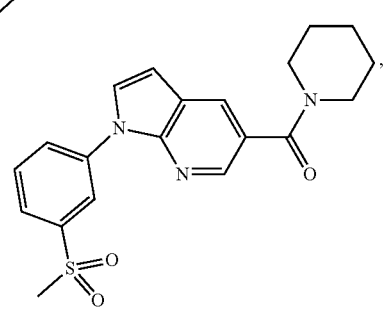
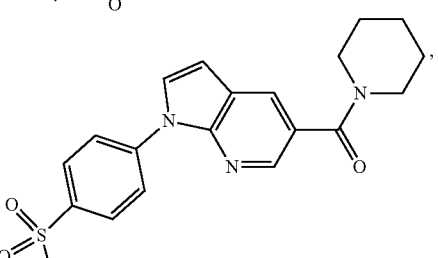
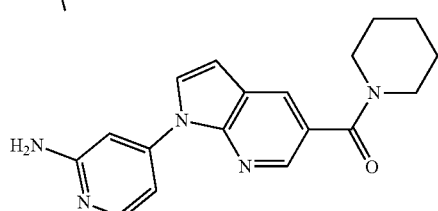
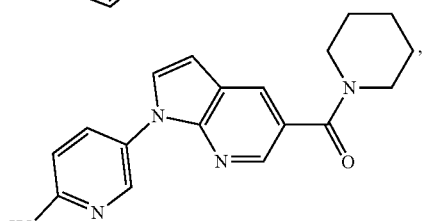
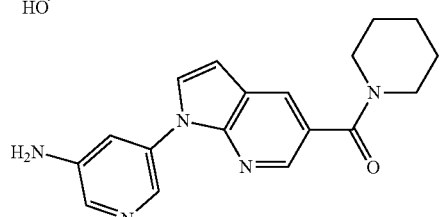
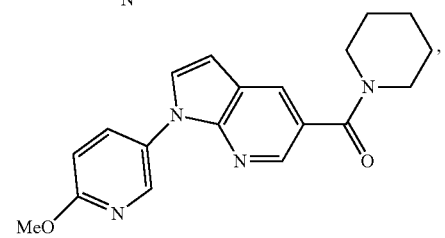

551
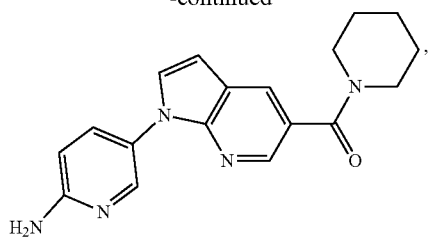
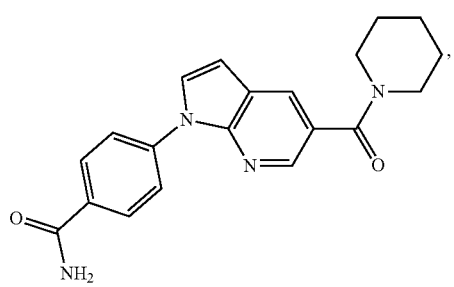
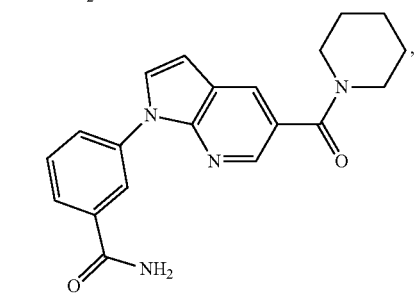
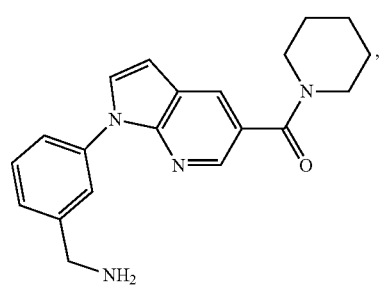
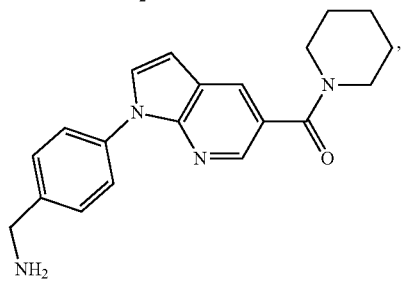
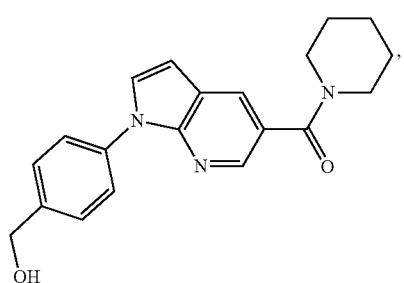
552
-continued
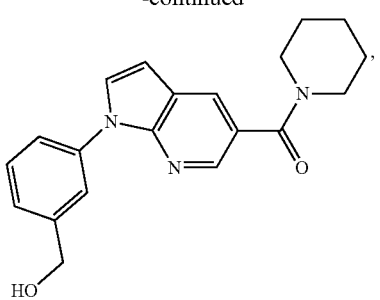
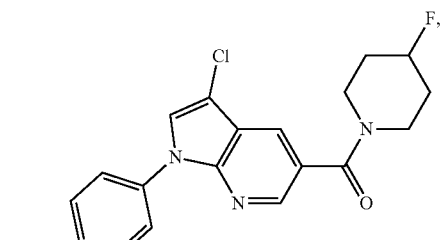
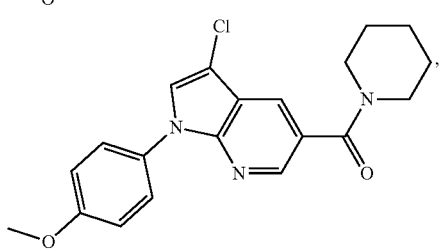
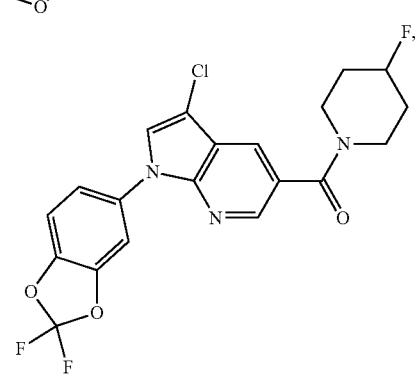
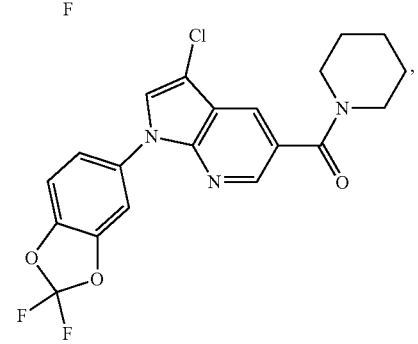
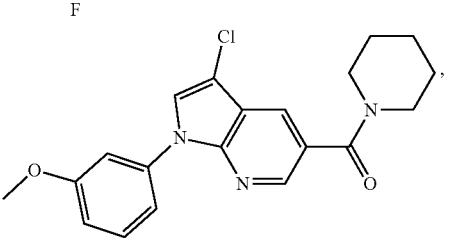

553
-continued
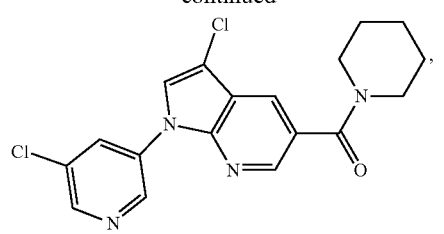
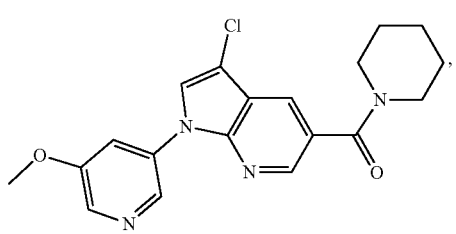
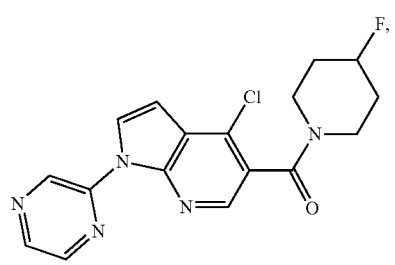
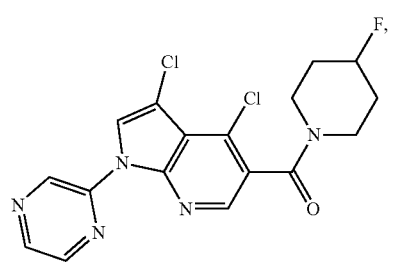
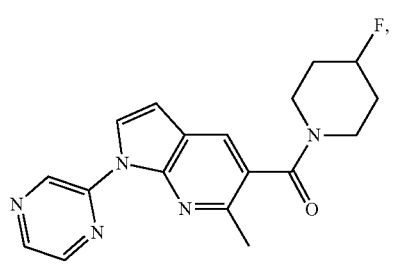
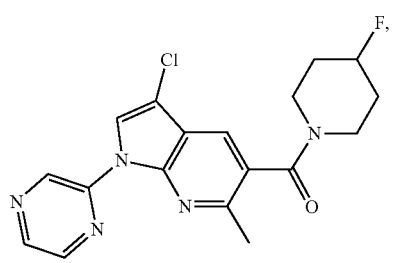
554
-continued
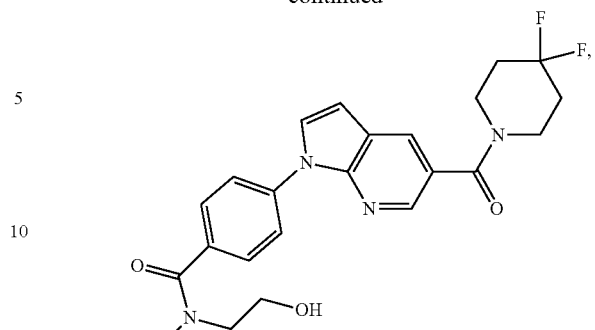
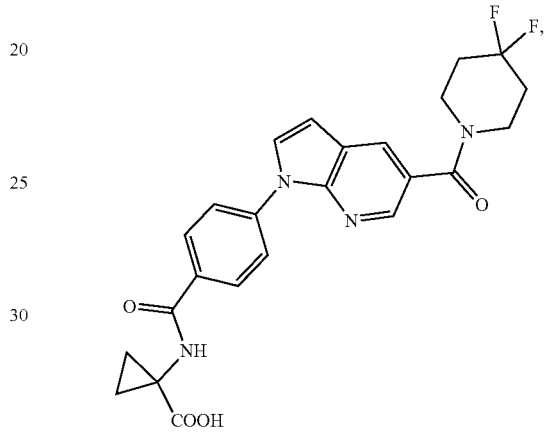
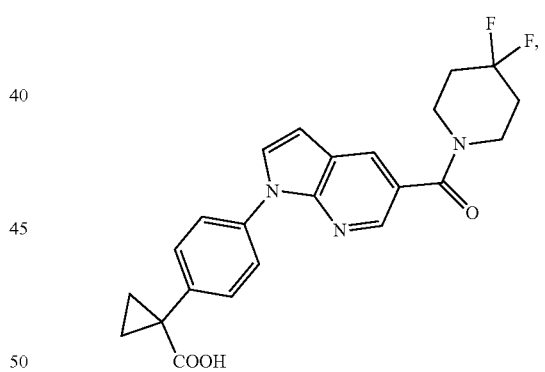
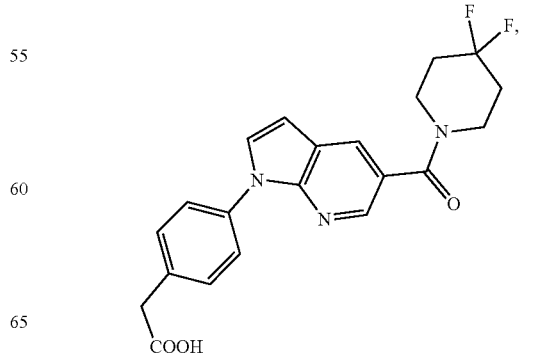

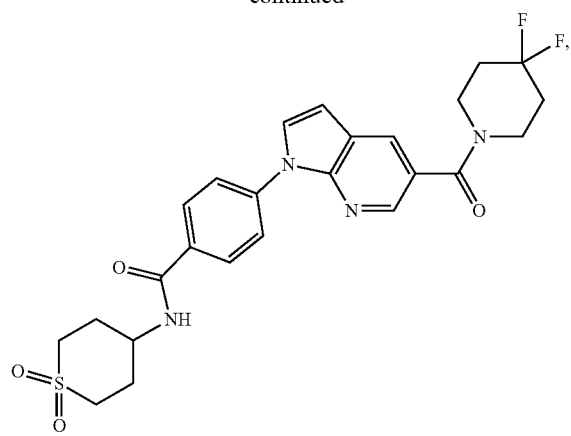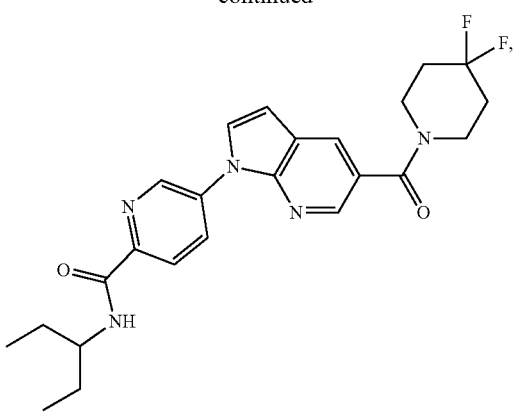

557
-continued
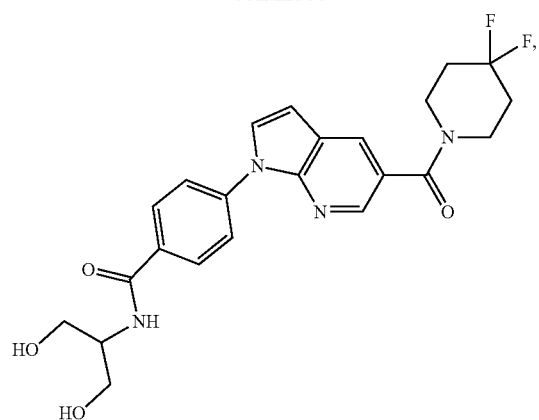
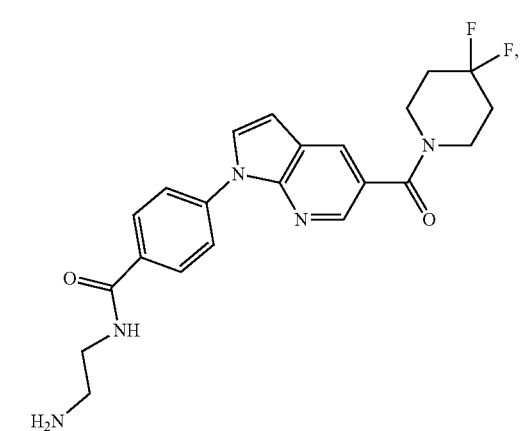
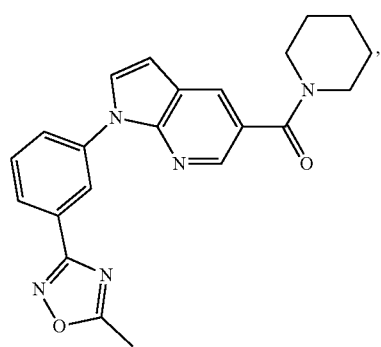
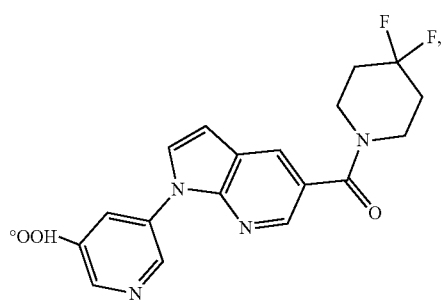
558
-continued
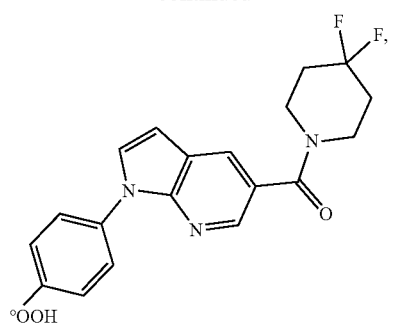
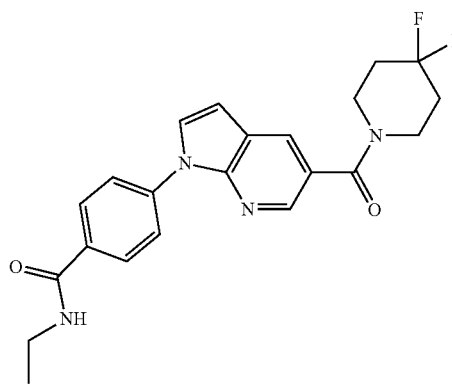
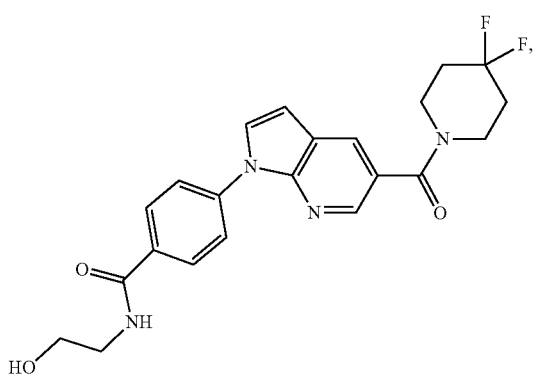
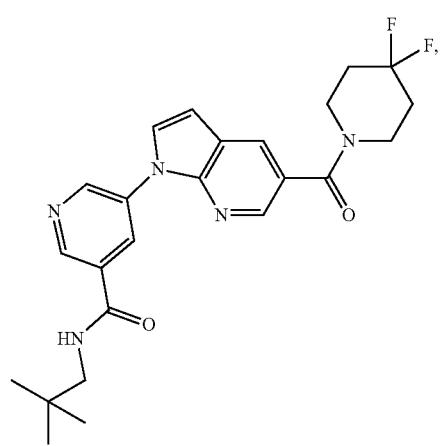

559
-continued
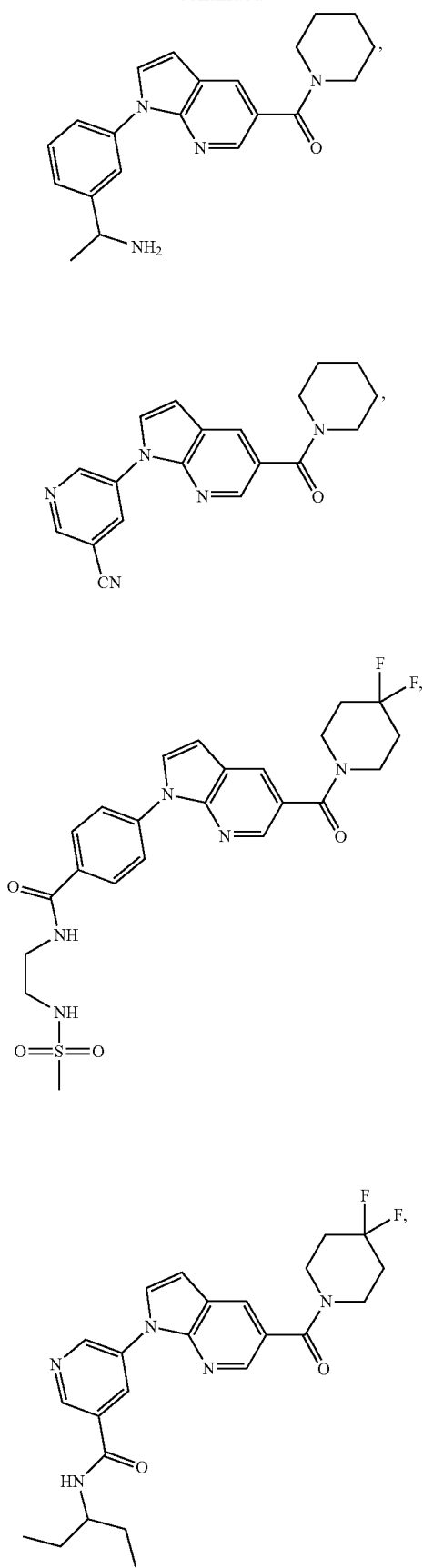
560
-continued
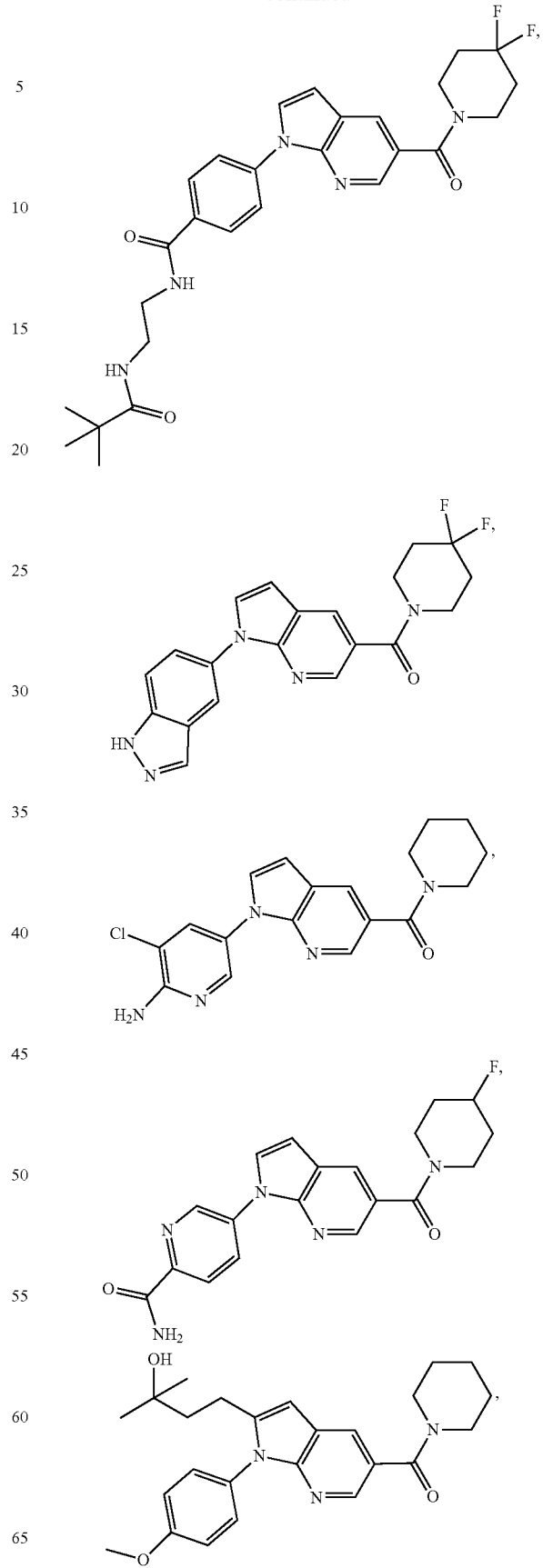

561-continued
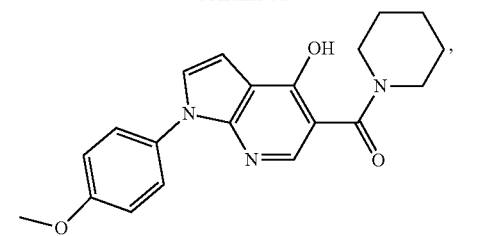
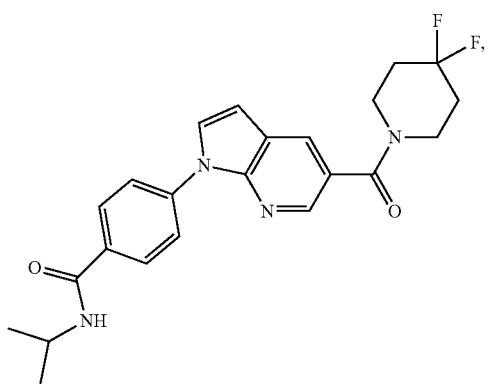
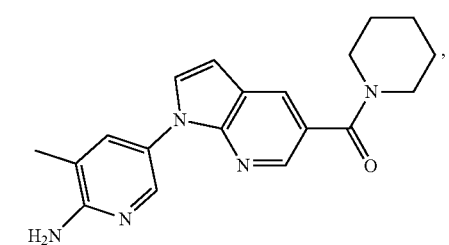
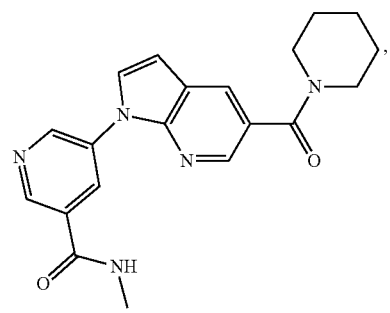
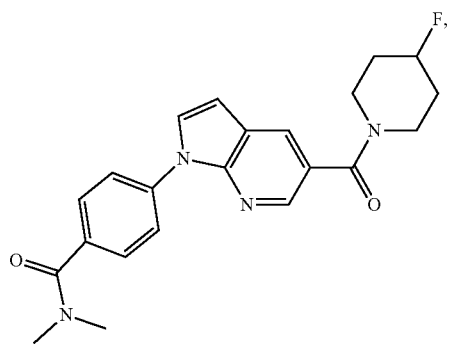
562-continued
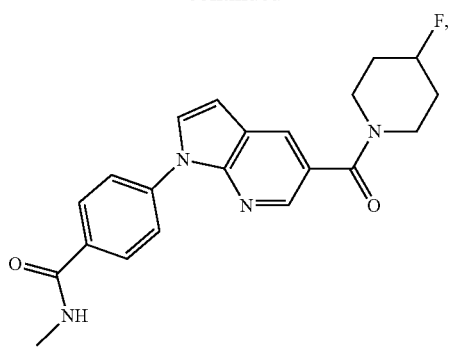
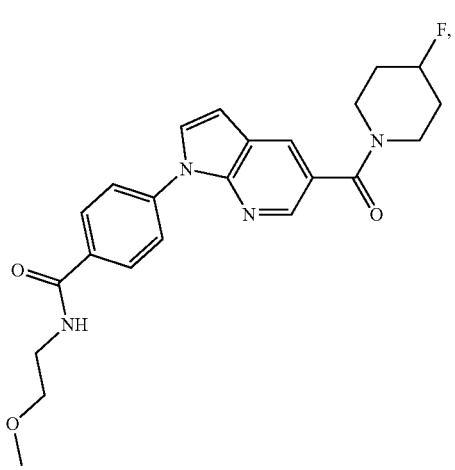
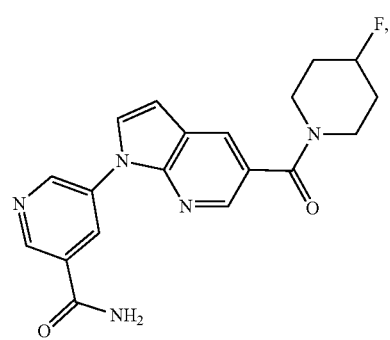
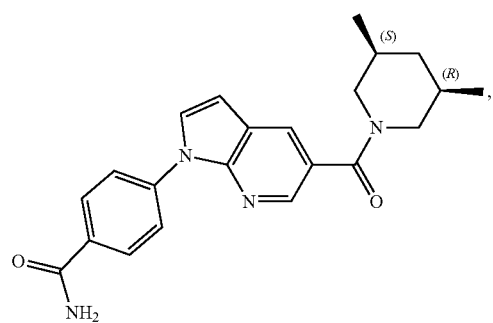

563
-continued
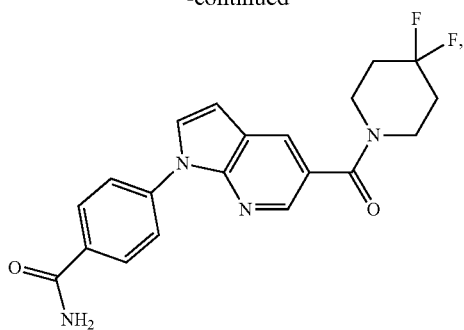
564
-continued
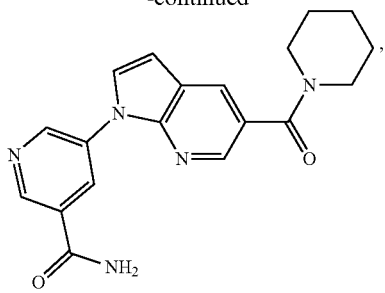
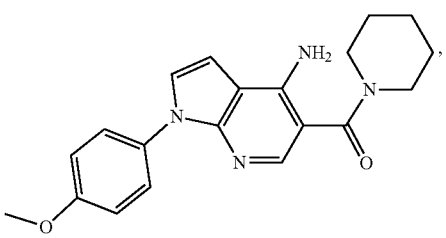
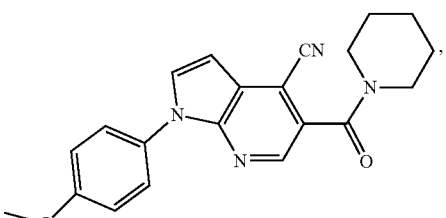
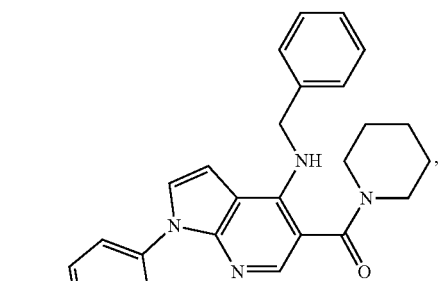
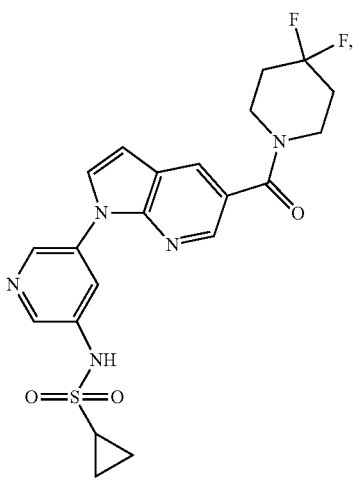

565
-continued
566
-continued
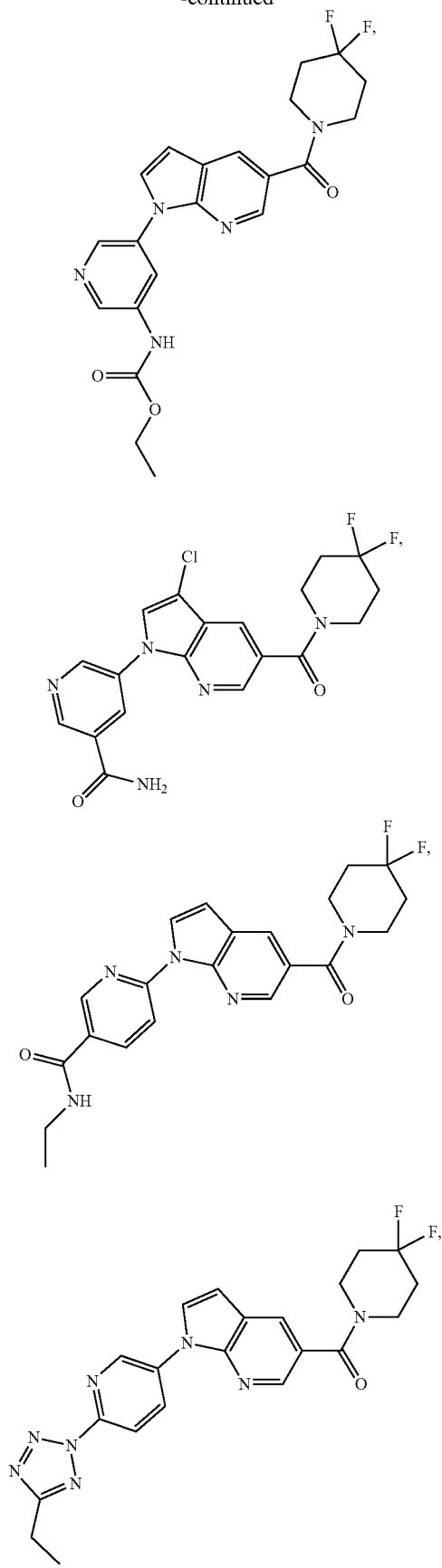
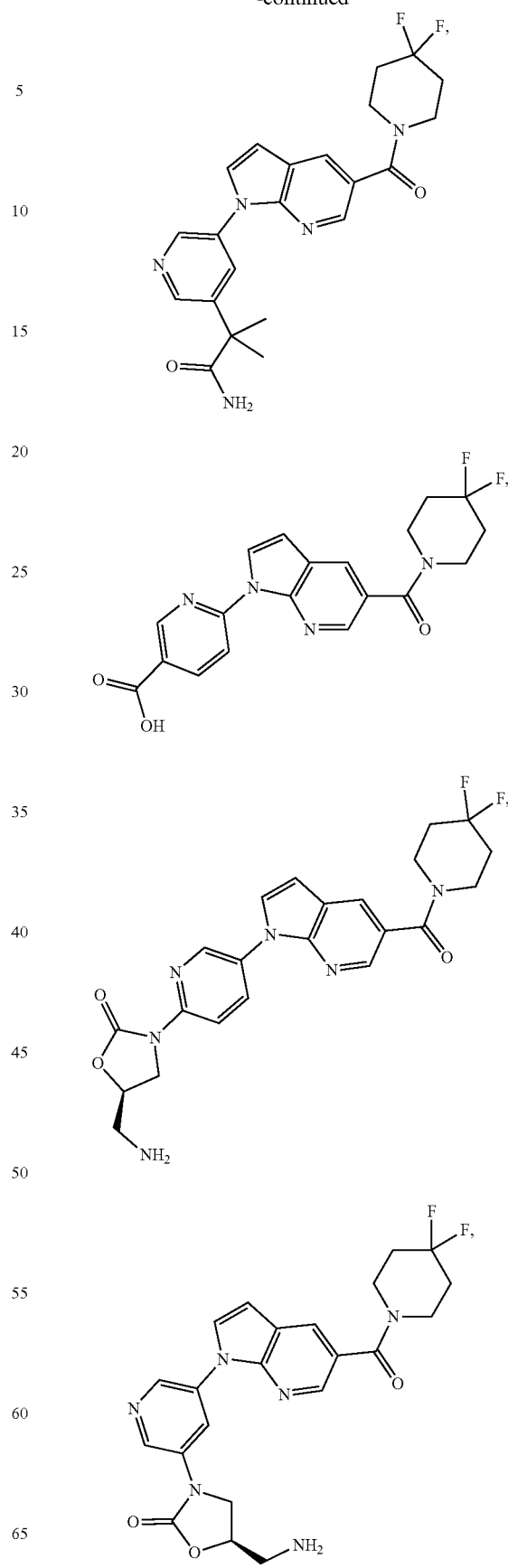

567
-continued
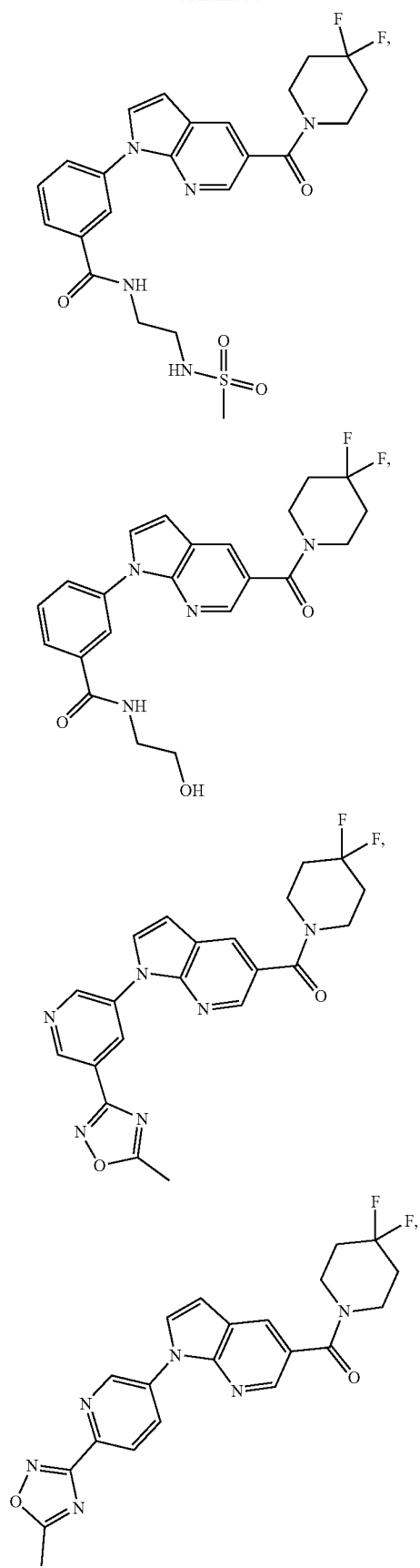
568
-continued
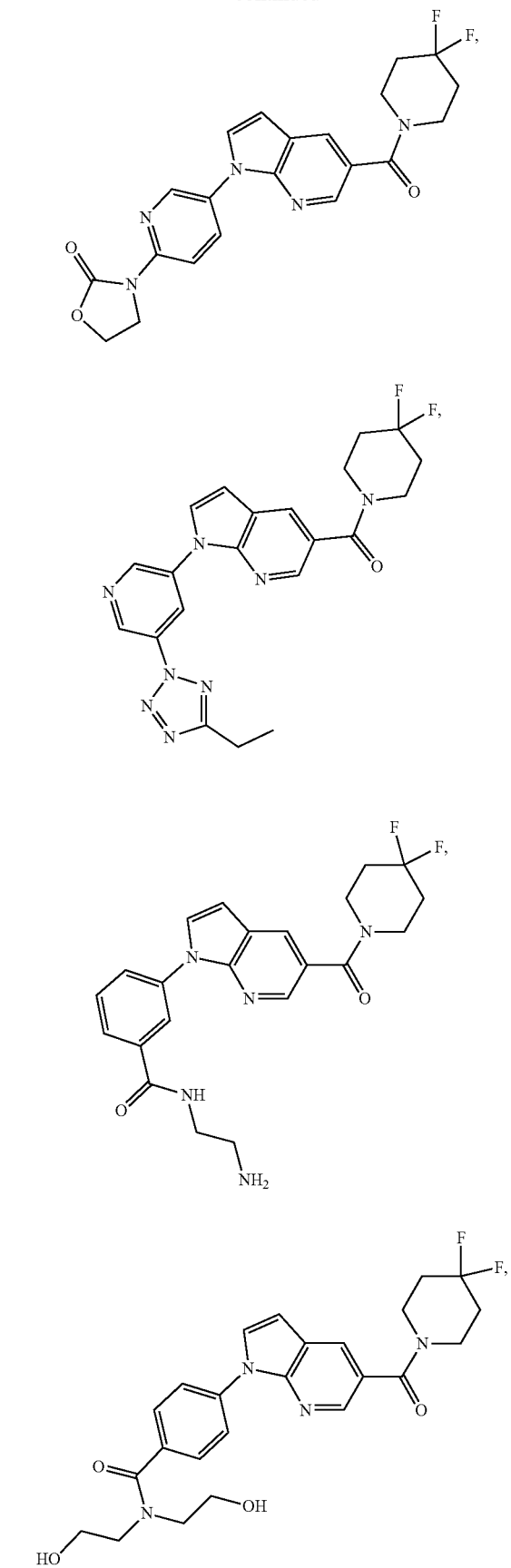

569
-continued
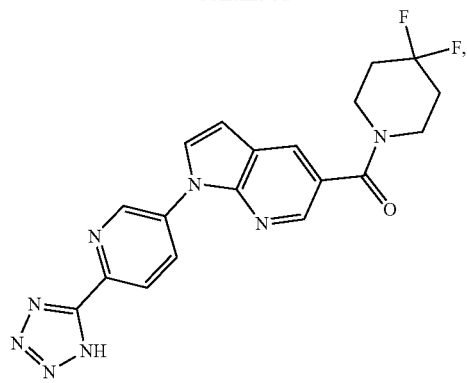
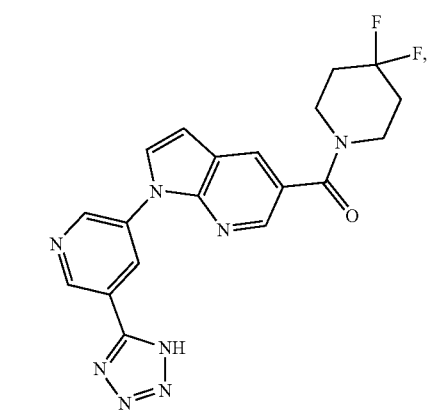
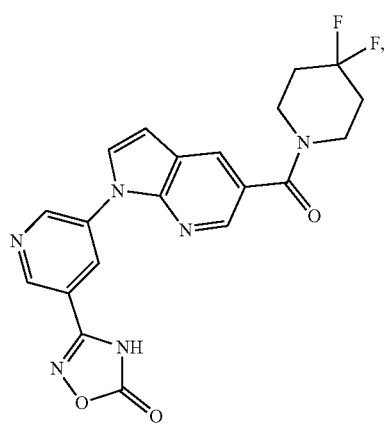
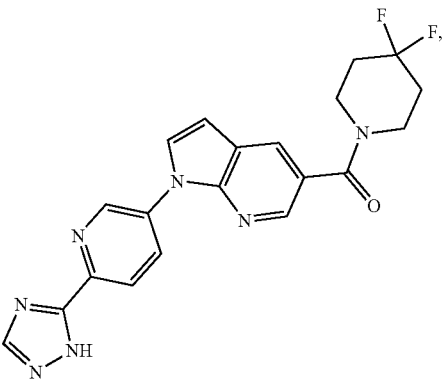
570
-continued
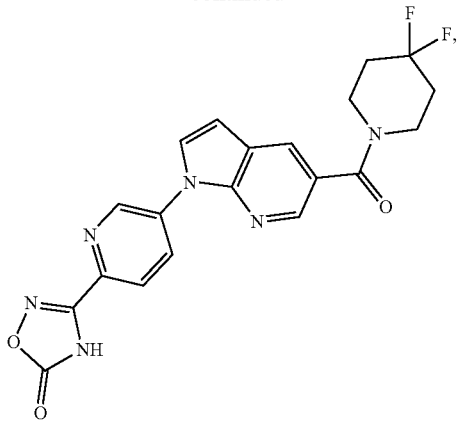
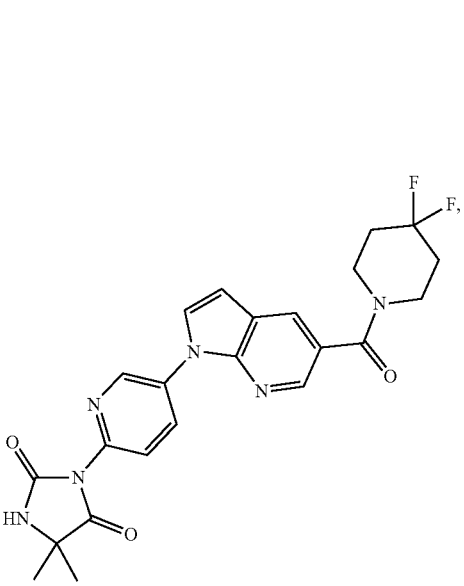
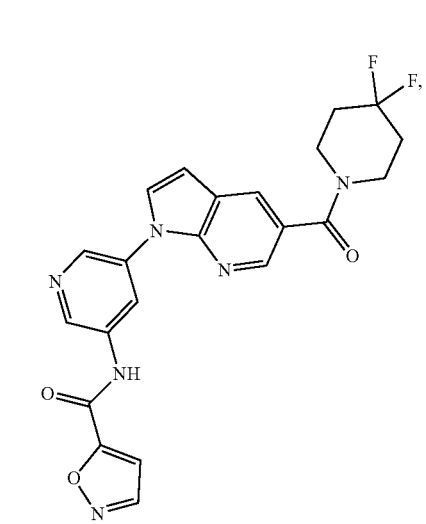

571
-continued
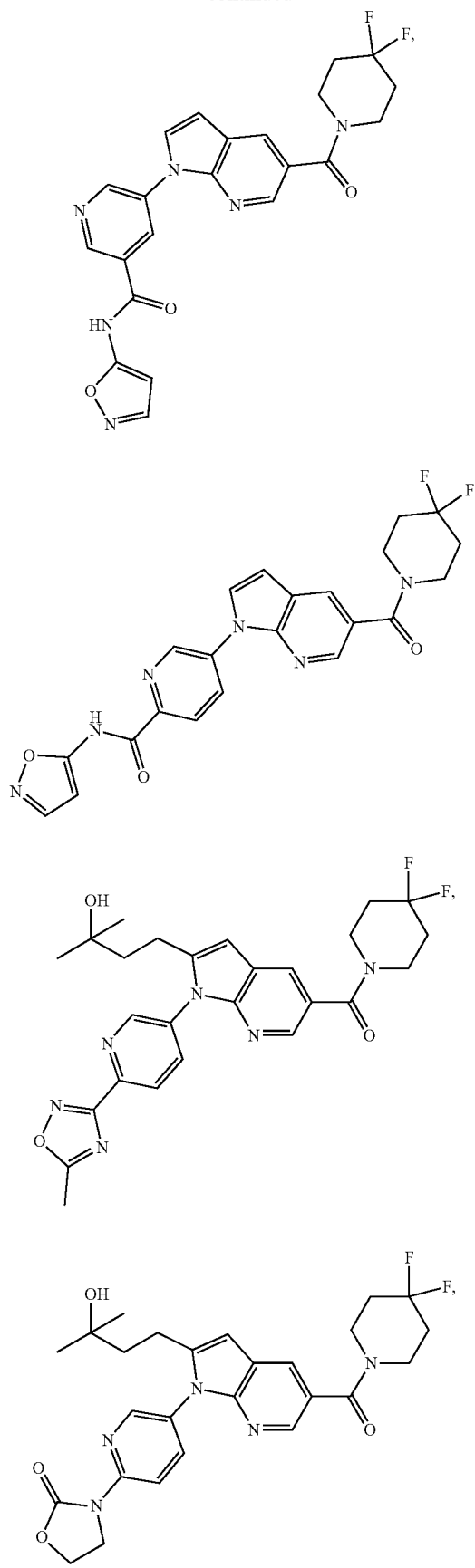
572
-continued
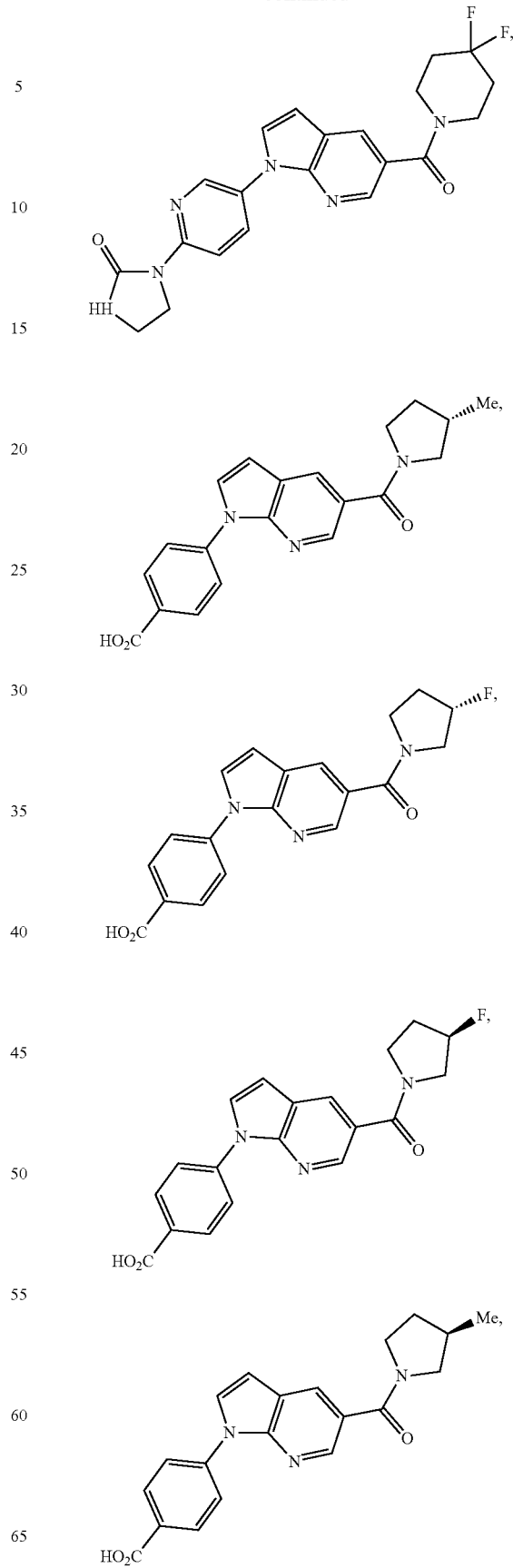

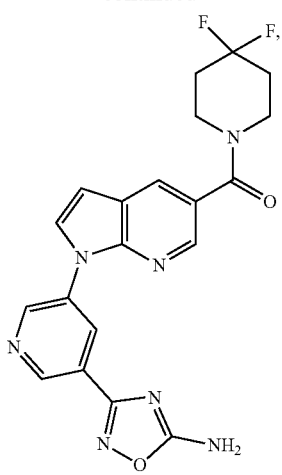

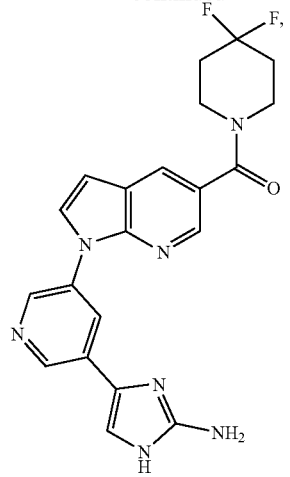

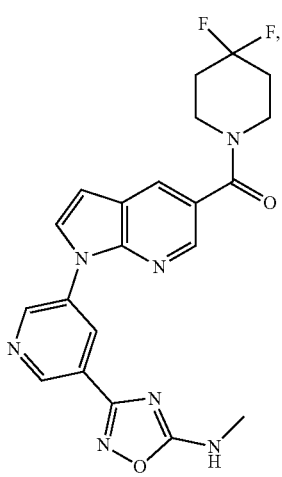

19. A pharmaceutical composition comprising the compound or pharmaceutically acceptable salt thereof of claim 1, and a pharmaceutically acceptable excipient.

20. A method of inhibiting 15-hydroxyprostaglandin dehydrogenase (15-PGDH) in a subject in need thereof, comprising administering to the subject a therapeutically effective amount of the compound or pharmaceutically acceptable salt thereof of claim 1.

* * * * *